US011168326B2

(12) United States Patent
Thanos et al.

(10) Patent No.: US 11,168,326 B2
(45) Date of Patent: Nov. 9, 2021

(54) ENGINEERED IMMUNOSTIMULATORY BACTERIAL STRAINS AND USES THEREOF

(71) Applicant: Actym Therapeutics, Inc., Berkeley, CA (US)

(72) Inventors: Christopher D. Thanos, Tiburon, CA (US); Laura Hix Glickman, Oakland, CA (US); Justin Skoble, Berkeley, CA (US)

(73) Assignee: Actym Therapeutics, Inc., Berkeley, CA (US)

( * ) Notice: Subject to any disclaimer, the term of this patent is extended or adjusted under 35 U.S.C. 154(b) by 0 days.

(21) Appl. No.: 16/033,187

(22) Filed: Jul. 11, 2018

(65) Prior Publication Data

US 2019/0017050 A1 Jan. 17, 2019

Related U.S. Application Data

(60) Provisional application No. 62/531,327, filed on Jul. 11, 2017, provisional application No. 62/648,380, filed on Mar. 26, 2018.

(51) Int. Cl.

| | |
|---|---|
| ***A61K 39/00*** | (2006.01) |
| ***A61K 39/02*** | (2006.01) |
| ***C12N 15/113*** | (2010.01) |
| ***C12N 1/20*** | (2006.01) |
| ***A61P 35/00*** | (2006.01) |
| ***C12N 1/36*** | (2006.01) |
| ***C12N 15/74*** | (2006.01) |
| *C12R 1/42* | (2006.01) |

(52) U.S. Cl.

CPC .......... *C12N 15/1135* (2013.01); *A61P 35/00* (2018.01); *C12N 1/205* (2021.05); *C12N 1/36* (2013.01); *C12N 15/113* (2013.01); *C12N 15/74* (2013.01); *C12N 2310/14* (2013.01); *C12N 2310/141* (2013.01); *C12N 2310/17* (2013.01); *C12N 2310/531* (2013.01); *C12N 2320/32* (2013.01); *C12R 2001/42* (2021.05)

(58) Field of Classification Search

CPC ..... A61K 39/00; A61K 39/02; A61K 39/0275
USPC .... 424/93.1, 93.2, 93.4, 184.1, 234.1, 258.1
See application file for complete search history.

(56) References Cited

U.S. PATENT DOCUMENTS

| | | | | |
|---|---|---|---|---|
| 3,536,809 | A | 10/1970 | Applezweig | 424/28 |
| 3,598,123 | A | 8/1971 | Zaffaroni | 128/268 |
| 3,630,200 | A | 12/1971 | Higuchi | 128/260 |
| 3,710,795 | A | 1/1973 | Higuchi et al. | 128/260 |
| 3,845,770 | A | 11/1974 | Theeuwes et al. | 128/260 |
| 3,847,770 | A | 11/1974 | Radlowe et al. | 204/159.23 |
| 3,916,899 | A | 11/1975 | Theeuwes et al. | 128/260 |
| 3,936,354 | A | 2/1976 | LaPointe et al. | 195/79 |
| 4,008,719 | A | 2/1977 | Theeuwes et al. | 128/260 |
| 4,044,126 | A | 8/1977 | Cook et al. | 424/243 |
| 4,364,923 | A | 12/1982 | Cook et al. | 424/46 |
| 4,414,209 | A | 11/1983 | Cook et al. | 424/243 |
| 4,687,660 | A | 8/1987 | Baker et al. | 424/465 |
| 4,769,027 | A | 9/1988 | Baker et al. | 424/493 |
| 5,033,252 | A | 7/1991 | Carter | 53/425 |
| 5,052,558 | A | 10/1991 | Carter | 206/439 |
| 5,059,595 | A | 10/1991 | Le Grazie | 424/468 |
| 5,073,543 | A | 12/1991 | Marshall et al. | 514/21 |
| 5,120,548 | A | 6/1992 | McClelland et al. | 424/473 |
| 5,323,907 | A | 6/1994 | Kalvelage | 206/531 |
| 5,354,556 | A | 10/1994 | Sparks et al. | 424/419 |
| 5,591,767 | A | 1/1997 | Mohr et al. | 514/413 |
| 5,639,476 | A | 6/1997 | Oshiack et al. | 424/468 |
| 5,674,533 | A | 10/1997 | Santus et al. | 424/493 |
| 5,733,566 | A | 3/1998 | Lewis | 424/426 |
| 5,997,881 | A | 12/1999 | Powell et al. | 424/234.1 |
| 6,024,961 | A | 2/2000 | Curtiss, III et al. | 424/200.1 |
| 6,080,849 | A | 6/2000 | Bermudes et al. | 536/23.7 |
| 6,190,657 | B1 | 2/2001 | Pawelek et al. | 424/93.1 |
| 6,383,496 | B1 | 5/2002 | Curtiss, III et al. | 424/200.1 |
| 6,447,784 | B1 | 9/2002 | Bermudes et al. | 424/235.1 |

(Continued)

FOREIGN PATENT DOCUMENTS

| | | |
|---|---|---|
| AU | 2005316458 | 6/2006 |
| AU | 2015202068 B2 | 5/2015 |

(Continued)

OTHER PUBLICATIONS

Low et al. "Construction of VNP20009", in, Springer C.J. (Eds.) Suicide Gene Therapy. Methods in Molecular medicine, vol. 90, pp. 47-59, 2004.*

(Continued)

*Primary Examiner* — Rodney P Swartz
(74) *Attorney, Agent, or Firm* — Dentons US LLP; Stephanie Seidman

(57) ABSTRACT

Provided are immunostimulatory bacteria and pharmaceutical compositions containing the bacteria. The immunostimulatory bacteria provided herein contain one or more modalities that enhance the anti-tumor activity of the immunostimulatory bacteria. Among the immunostimulatory bacteria provided are bacteria, such as *Salmonella* species, which are modified to be auxotrophic or are auxotrophic for adenosine and/or contain plasmids encoding RNAi, such as shRNA and microRNA, that mediate gene disruption and/or expression of immune checkpoints, such as TREX1, VISTA, PD-L1 and, genes that influence the immune system. The bacteria contain additional modifications to enhance their anti-tumor activity. Also provided are methods of inhibiting the growth or reducing the volume of a solid tumor by administering the pharmaceutical compositions.

38 Claims, 53 Drawing Sheets

Specification includes a Sequence Listing.

(56) References Cited

U.S. PATENT DOCUMENTS

| | | | | |
|---|---|---|---|---|
| 6,475,482 | B1 | 11/2002 | Bermudes et al. | 424/93.4 |
| 6,548,287 | B1 | 4/2003 | Powell et al. | 435/69.1 |
| 6,863,894 | B2 | 3/2005 | Bermudes et al. | 424/235 |
| 6,923,972 | B2 | 8/2005 | Bermudes et al. | 424/235.1 |
| 6,962,696 | B1 | 11/2005 | Bermudes et al. | 424/93.4 |
| 7,083,794 | B2 | 8/2006 | Curtiss, III et al. | 424/200.1 |
| 7,115,269 | B2 | 10/2006 | Darji et al. | 424/200.1 |
| 7,195,757 | B2 | 3/2007 | Curtiss, III et al. | 424/93.48 |
| 7,344,710 | B2 | 3/2008 | Dang et al. | 424/93.1 |
| 7,354,592 | B2 | 4/2008 | Bermudes et al. | 424/93.2 |
| 7,390,646 | B2 | 6/2008 | Andino-Pavlovsky et al. | 435/252.33 |
| 7,452,531 | B2 | 11/2008 | Bermudes et al. | 424/93.4 |
| 7,514,089 | B2 | 4/2009 | Bermudes et al. | 369/30.31 |
| 7,732,417 | B2 | 6/2010 | Beach et al. | 514/44 |
| 7,892,740 | B2 | 2/2011 | Weichselbaum et al. | 435/6 |
| 7,998,461 | B2 | 8/2011 | Forbes et al. | 424/9.2 |
| 8,093,025 | B2 | 1/2012 | Loessner et al. | 435/69.5 |
| 8,202,846 | B2 | 6/2012 | Hannon et al. | 514/44 |
| 8,221,739 | B2 | 7/2012 | Leonard et al. | 424/93.2 |
| 8,232,259 | B2 | 7/2012 | Klinman et al. | 514/44 |
| 8,241,844 | B2 | 8/2012 | Bulla, Jr. et al. | 435/5 |
| 8,383,599 | B2 | 2/2013 | Hannon et al. | 514/44 |
| 8,426,375 | B2 | 4/2013 | Kandimalla et al. | 514/44 |
| 8,426,675 | B2 | 4/2013 | Dickins et al. | 800/14 |
| 8,440,207 | B2 | 5/2013 | Bermudes | 424/200.1 |
| 8,524,220 | B1 | 9/2013 | Bermudes | 424/93.2 |
| 8,524,224 | B2 | 9/2013 | Henson et al. | 424/93.5 |
| 8,580,757 | B2 | 11/2013 | Federov et al. | 514/44 A |
| 8,647,618 | B2 | 2/2014 | Leonard et al. | 424/93.48 |
| 8,647,642 | B2 | 2/2014 | Bermudes | 424/258.1 |
| 8,679,473 | B2 | 3/2014 | Fensterle et al. | 424/93.1 |
| 8,822,194 | B2 | 9/2014 | Zhao et al. | 435/252.3 |
| 8,829,254 | B2 | 9/2014 | Nair et al. | 570/155 |
| 9,068,187 | B1 | 6/2015 | Bermudes | 424/93.2 |
| 9,181,546 | B2 | 11/2015 | Li et al. | 424/93.1 |
| 9,242,000 | B2 | 1/2016 | Cheresh et al. | 514/44 R |
| 9,265,804 | B2 | 2/2016 | Newman | 424/93.48 |
| 9,315,817 | B2 | 4/2016 | Bermudes | 435/252.3 |
| 9,320,787 | B2 | 4/2016 | Gunn | 424/257.1 |
| 9,415,098 | B2 | 8/2016 | Lubenau | 424/258.1 |
| 9,421,252 | B2 | 8/2016 | Bermudes | 424/258.1 |
| 9,453,227 | B2 | 9/2016 | Diamond et al. | 424/258.1 |
| 9,511,129 | B2 | 12/2016 | Hanson et al. | 435/821 |
| 9,616,114 | B1 | 4/2017 | Bermudes | 424/258.1 |
| 9,624,494 | B2 | 4/2017 | Hannon et al. | 514/44 A |
| 9,731,011 | B2 | 8/2017 | Brahmbhatt et al. | 424/197.11 |
| 9,790,504 | B2 | 10/2017 | Khodarev et al. | 514/44 A |
| 9,878,023 | B1 | 1/2018 | Bermudes | 424/93.2 |
| 10,052,371 | B2 | 8/2018 | Newman | 424/93.48 |
| 10,087,451 | B2 | 10/2018 | Bermudes | 424/258.1 |
| 10,100,314 | B2 | 10/2018 | Diamond et al. | 424/258.1 |
| 10,188,722 | B2 | 1/2019 | Bermudes | 424/258.1 |
| 10,195,259 | B2 | 2/2019 | Newman | 530/388.4 |
| 10,286,051 | B1 | 5/2019 | Bermudes | 424/258.1 |
| 10,293,037 | B2 | 5/2019 | Lubenau | 424/185.1 |
| 10,421,971 | B2 | 9/2019 | Deng et al. | 514/44 R |
| 10,449,237 | B1 | 10/2019 | Bermudes | 424/258.1 |
| 10,500,277 | B2 | 12/2019 | Brahmbhatt et al. | 424/197.11 |
| 10,525,082 | B2 | 1/2020 | Crane et al. | 424/130.1 |
| 10,584,339 | B2 | 3/2020 | Diamond et al. | 424/93.2 |
| 10,626,403 | B2 | 4/2020 | Bermudes | 424/258.1 |
| 10,729,731 | B1 | 8/2020 | Bermudes | 424/200.1 |
| 10,821,163 | B2 | 11/2020 | Lubenau | 424/186.1 |
| 10,828,356 | B1 | 11/2020 | Bermudes | 424/200.1 |
| 10,961,538 | B2 | 3/2021 | Diamond et al. | 424/258.1 |
| 2002/0026655 | A1 | 2/2002 | Bermudes et al. | 424/235.1 |
| 2003/0031683 | A1 | 2/2003 | Curtiss, III et al. | 424/200.1 |
| 2003/0109026 | A1 | 6/2003 | Bermudes et al. | 435/252.3 |
| 2003/0170276 | A1 | 9/2003 | Bermudes et al. | 424/258.1 |
| 2003/0175297 | A1 | 9/2003 | Urashima | 424/200.1 |
| 2003/0180320 | A1 | 9/2003 | Darji et al. | 424/200.1 |
| 2004/0120962 | A1 | 6/2004 | Curtiss, III et al. | 424/184.1 |
| 2004/0229338 | A1 | 11/2004 | King | 435/252.3 |
| 2005/0118193 | A1 | 6/2005 | Andino-Pavlovsky et al. | 435/252.339 |
| 2005/0244375 | A1 | 11/2005 | Leonard et al. | 424/93.2 |
| 2005/0249706 | A1 | 11/2005 | Bermudes et al. | 424/93.4 |
| 2005/0255088 | A1 | 11/2005 | Bermudes et al. | 424/93.2 |
| 2006/0051380 | A1 | 3/2006 | Schulick et al. | 424/277.1 |
| 2007/0009489 | A1 | 1/2007 | Bermudes et al. | 369/30.31 |
| 2007/0298012 | A1 | 12/2007 | King et al. | 424/93.2 |
| 2008/0091375 | A1 | 4/2008 | Brunell | 702/107 |
| 2008/0112928 | A1 | 5/2008 | Loessner et al. | 435/69.5 |
| 2008/0124355 | A1 | 5/2008 | Bermudes | 424/200.1 |
| 2009/0011439 | A1 | 1/2009 | Weichselbaum et al. | 435/6 |
| 2009/0111762 | A1 | 4/2009 | Roth et al. | 514/44 |
| 2009/0123426 | A1 | 5/2009 | Li et al. | 424/93.1 |
| 2009/0169517 | A1 | 7/2009 | Bermudes et al. | 424/93.4 |
| 2009/0175829 | A1 | 7/2009 | Forbes et al. | 424/9.2 |
| 2009/0208534 | A1 | 8/2009 | Xu et al. | 424/258.1 |
| 2009/0220459 | A1 | 9/2009 | Fensterle et al. | 424/93.2 |
| 2010/0098665 | A1 | 4/2010 | Leonard et al. | 424/93.2 |
| 2010/0135961 | A1 | 6/2010 | Bermudes | 424/258.1 |
| 2011/0200998 | A1 | 8/2011 | Weichselbaum et al. | 435/6 |
| 2012/0009153 | A1 | 1/2012 | Guo et al. | 424/93.2 |
| 2012/0093773 | A1 | 4/2012 | Li et al. | 424/93.1 |
| 2012/0142080 | A1 | 6/2012 | Bermudes | 424/200.1 |
| 2012/0171159 | A1 | 7/2012 | Fensterle et al. | 424/93.1 |
| 2012/0294929 | A1 | 11/2012 | Roth et al. | 424/450 |
| 2013/0045525 | A1 | 2/2013 | Leonard et al. | 424/93.48 |
| 2013/0142786 | A1 | 6/2013 | Liu et al. | 424/133.1 |
| 2013/0150258 | A1 | 6/2013 | Weichselbaum et al. | 435/6 |
| 2014/0127284 | A1 | 5/2014 | Cheresh et al. | 424/450 |
| 2014/0127816 | A1 | 5/2014 | Hanson et al. | 435/821 |
| 2014/0178341 | A1 | 6/2014 | Zhao et al. | 424/93.2 |
| 2014/0002123 | A1 | 7/2014 | Newman | 424/93.48 |
| 2014/0186401 | A1 | 7/2014 | Diamond et al. | 424/258.1 |
| 2014/0220661 | A1 | 8/2014 | Bermudes | 435/252.3 |
| 2014/0242095 | A1 | 8/2014 | Wang et al. | 424/174.1 |
| 2015/0017204 | A1 | 1/2015 | Bermudes | 424/258.1 |
| 2015/0071873 | A1 | 3/2015 | Biot et al. | 424/85.1 |
| 2015/0098897 | A1 | 4/2015 | Brahmbhatt et al. | 424/197.11 |
| 2015/0147315 | A1 | 5/2015 | Wei | 435/7.32 |
| 2015/0165011 | A1 | 6/2015 | Lubenau | 424/258.1 |
| 2015/0224151 | A1 | 8/2015 | Julian Gomez et al. | 424/93.4 |
| 2016/0184456 | A1 | 6/2016 | Diamond et al. | 424/93.48 |
| 2016/0199422 | A1 | 7/2016 | Newman | 424/93.48 |
| 2016/0002223 | A1 | 8/2016 | Bermudes | 424/258.1 |
| 2016/0222387 | A1 | 8/2016 | Khodarev et al. | 514/44 A |
| 2016/0228523 | A1 | 8/2016 | Newman | 530/388.4 |
| 2016/0250311 | A1 | 9/2016 | Lubenau | 424/258.1 |
| 2016/0333355 | A1 | 11/2016 | Deng et al. | 514/44 R |
| 2016/0369282 | A1 | 12/2016 | Li et al. | 424/93.1 |
| 2017/0020931 | A1 | 1/2017 | Zhou et al. | 424/144.1 |
| 2017/0081671 | A1 | 3/2017 | Diamond et al. | 424/258.1 |
| 2017/0081673 | A1 | 3/2017 | Hanson et al. | 435/821 |
| 2017/0087185 | A1 | 3/2017 | Crane et al. | 424/130.1 |
| 2017/0157239 | A1 | 6/2017 | Bermudes | 424/258.1 |
| 2017/0298362 | A1 | 10/2017 | Khodarev et al. | 514/44 A |
| 2017/0326235 | A1 | 11/2017 | Brahmbhatt et al. | 424/197.11 |
| 2017/0333490 | A1 | 11/2017 | Forbes et al. | 424/93.2 |
| 2018/0104320 | A1 | 4/2018 | Gravekamp | 424/236.1 |
| 2018/0148729 | A1 | 5/2018 | Hasty et al. | 424/184.1 |
| 2018/0311343 | A1 | 11/2018 | Huang et al. | 514/44 R |
| 2019/0008936 | A1 | 1/2019 | Lubenau | 424/185.1 |
| 2019/0017057 | A1 | 1/2019 | Bermudes | 424/258.1 |
| 2019/0071679 | A1 | 3/2019 | Khodarev et al. | 514/44 A |
| 2019/0153452 | A1 | 5/2019 | Diamond et al. | 424/93.2 |
| 2019/0160115 | A1 | 5/2019 | Falb et al. | 424/93.2 |
| 2019/0183996 | A1 | 6/2019 | Lubenau | 424/186.1 |
| 2019/0307869 | A1 | 10/2019 | Newman | 530/388.4 |
| 2019/0336544 | A1 | 11/2019 | Falb et al. | 424/93.4 |
| 2020/0023053 | A1 | 1/2020 | Bermudes | 424/200.1 |
| 2020/0055904 | A1 | 2/2020 | Erhardt et al. | 424/258.1 |
| 2020/0149053 | A1 | 5/2020 | Fisher et al. | 424/93.2 |
| 2020/0155597 | A1 | 5/2020 | Crane et al. | 424/130.1 |
| 2020/0157549 | A1 | 5/2020 | Diamond et al. | 424/258.1 |

FOREIGN PATENT DOCUMENTS

| | | |
|---|---|---|
| CA | 2591565 | 6/2006 |
| CN | 103468626 B | 5/2016 |

(56) References Cited

FOREIGN PATENT DOCUMENTS

| | | |
|---|---|---|
| EP | 1 655 370 | 5/2006 |
| EP | 2 085 466 | 8/2009 |
| EP | 2270136 | 1/2011 |
| EP | 2 238 238 | 11/2014 |
| EP | 2941258 B1 | 9/2019 |
| JP | 2002-500001 | 1/2002 |
| WO | WO 1998/048026 | 10/1998 |
| WO | WO 1999/013053 | 3/1999 |
| WO | WO 1999/025387 | 5/1999 |
| WO | WO 2001/025399 | 4/2001 |
| WO | WO 2003/096812 | 11/2003 |
| WO | WO-2004076644 A2 * | 9/2004 |
| WO | WO 2005/116233 | 12/2005 |
| WO | WO 2006/048344 | 5/2006 |
| WO | WO 2006/066048 | 6/2006 |
| WO | WO 2007/084992 | 7/2007 |
| WO | WO 2007/130604 | 11/2007 |
| WO | WO 2008/039408 | 4/2008 |
| WO | WO 2008/091375 | 7/2008 |
| WO | WO 2009/006450 | 1/2009 |
| WO | WO 2009/095436 | 8/2009 |
| WO | WO 2010/057009 | 5/2010 |
| WO | WO 2011/100489 | 8/2011 |
| WO | WO 2012/149364 | 11/2012 |
| WO | WO 2013/163893 | 11/2013 |
| WO | WO 2014/005683 | 1/2014 |
| WO | WO 2014/107365 | 7/2014 |
| WO | WO 2014/189996 | 11/2014 |
| WO | WO 2015/002969 | 1/2015 |
| WO | WO 2015/032165 | 3/2015 |
| WO | WO 2015/108595 | 7/2015 |
| WO | WO 2015/134722 | 9/2015 |
| WO | WO 2015/142875 | 9/2015 |
| WO | WO 2015/191861 | 12/2015 |
| WO | WO 2016/025582 | 2/2016 |
| WO | WO 2016/164636 | 10/2016 |
| WO | WO 2017/005773 | 1/2017 |
| WO | WO 2017/044487 | 3/2017 |
| WO | WO 2017/123675 | 7/2017 |
| WO | WO 2017/123676 | 7/2017 |
| WO | WO 2017/210649 | 12/2017 |
| WO | WO 2018/011289 | 1/2018 |
| WO | WO 2018/045058 | 3/2018 |
| WO | WO 2018/106754 | 6/2018 |
| WO | WO 2018/129404 | 7/2018 |
| WO | WO 2018/197621 | 11/2018 |
| WO | WO 2019/014391 | 1/2019 |
| WO | WO 2019/183117 | 9/2019 |

OTHER PUBLICATIONS

Letter/Written Disclosure of the Supplemental Information Disclosure Statement for the above-referenced application, filed herewith on Dec. 4, 2018, 2 pages.

Chorobik et al., "*Salmonella* and cancer: from pathogens to therapeutics," Acta Biochimica Polonica 60(3):285-297 (2013).

Hossain et al., "Leukemia cell-targeted STAT3 silencing and TLR9 triggering generate systemic antitumor immunity," Blood 123(1):15-25 (2014).

Kang et al., "Preventative and therapeutic effects of auxotrophic *Edwardsiella tarda* mutant harboring CpG 1668 motif-enriched plasmids against scuticociliatosis in olive flounder (*Paralichthys olivaceus*)," Experimental Parasitology 144:34-38 (2014).

Methner et al., "*Salmonella* Enteritidis with double deletion in *phoP fliC*—A potential live *Salmonella* vaccine candidate with novel characteristics for use in chickens," Vaccine 29:3248-3253 (2011).

Shi et al., "Combined prokaryotic-eukaryotic delivery and expression of therapeutic factors through a primed autocatalytic positive-feedback loop," Journal of Controlled Release 222:130-140 (2016).

Wheeler et al., "*TREX1* Knockdown Induces an Interferon Response to HIV that Delays Viral Infection in Humanized Mice," Cell Reports 15:1715-1727 (2016).

Invitation to Pay Additional Fees and Partial International Search, dated Oct. 17, 2018, in connection with International Patent Application No. PCT/US2018/041713, 25 pages.

Response to Invitation to Pay Additional Fees, submitted Nov. 15, 2018, in connection with International Patent Application No. PCT/US2018/041713, 13 pages.

Letter/Written Disclosure of the Supplemental Information Disclosure Statement for the above-referenced application, filed herewith on Dec. 4, 2019, 2 pages.

Dreher et al., "Genetic background of attenuated *Salmonella typhimurium* has profound influence on infection and cytokine patterns in human dendritic cells," J. Leukoc. Biol. 69:583-589 (2001).

Edwards et al., "DNA Damage Repair Genes Controlling Human Papillomavirus (HPV) Episome Levels under Conditions of Stability and Extreme Instability," PLoS One 8(10):e75406 (2013), 16 pages.

Goodman et al., "Tumor Mutational Burden as an Independent Predictor of Response to Immunotherapy in Diverse Cancers," Mol. Cancer Ther. 16(11):2598-2608 (2017).

Haque, S. and Morris, J.C., "Transforming growth factor-β: A therapeutic target for cancer," Human Vaccines & Immunotherapeutics 13(8):1741-1750 (2017).

Machine-generated English language translation of Chinese Patent No. CN 103468626 B, 35 pages.

Prati et al., "Three Prime Repair Exonuclease 1 (TREX1) expression correlates with cervical cancer cells growth in vitro and disease progression in vivo," Scientific Reports 9:351 (2019), 14 pages.

Torres et al., "Bacteria in cancer therapy: beyond immunostimulation," J. Cancer Metastasis Treat 4:4 (2018), 25 pages.

Wang et al., "New technologies in developing recombinant attenuated *Salmonella* vaccine vectors," Microbial Pathogenesis 58:17-28 (2013).

Zhang et al., "shRNA-armed conditionally replicative adenoviruses: a promising approach for cancer therapy," Oncotarget 7(20):29824-29834 (2016).

Actym Therapeutics, Inc., "The next frontier in immuno-oncology," BioPharma Dealmakers, B22, Mar. 2019, 1 page.

Glickman et al., Actym Therapeutics Poster Presentation, entitled "STACT: A Novel Therapeutic Platform that Delivers Immunomodulatory Payloads to Tumor-Resident Myeloid Cells After IV Dosing and Demonstrates Potent Anti-Tumor Efficacy in Preclinical Studies." Poster # P482. Presented at the Society for Immunotherapy of Cancer (SITC) Annual Meeting, in National Harbor, Maryland, on Nov. 9, 2019, 1 page.

Response, filed May 13, 2019, to International Search Report and Written Opinion, dated Jan. 3, 2019, in connection with corresponding International Patent Application No. PCT/US2018/041713, 55 pages.

Invitation to Restrict or Pay Additional Examination Fees, dated Jun. 7, 2019, in connection with corresponding International Patent Application No. PCT/US2018/041713, 9 pages.

Response, filed Jul. 5, 2019, to Invitation to Restrict or Pay Additional Examination Fees, dated Jun. 7, 2019, in connection with corresponding International Patent Application No. PCT/US2018/041713, 4 pages.

Written Opinion of the International Preliminary Examining Authority, dated Aug. 6, 2019, in connection with corresponding International Patent Application No. PCT/US2018/041713, 13 pages.

Replacement Claim Sets, filed Sep. 6, 2019, and Response, filed Sep. 5, 2019, to the Written Opinion of the International Preliminary Examining Authority, dated Aug. 6, 2019, in connection with corresponding International Patent Application No. PCT/US2018/041713, 61 pages.

International Preliminary Report on Patentability (Chapter II of the PCT), dated Oct. 14, 2019, in connection with corresponding International Patent Application No. PCT/US2018/041713, 17 pages.

Invitation to Pay Additional Fees and Partial International Search, dated Nov. 22, 2019, in connection with International Patent Application No. PCT/US2019/048659, 20 pages.

Invitation to Pay Additional Fees and Partial International Search, dated Oct. 18, 2019, in connection with International Patent Application No. PCT/US2019/041489, 22 pages.

(56) References Cited

OTHER PUBLICATIONS

Response, filed Nov. 15, 2019, to Invitation to Pay Additional Fees and Partial International Search, dated Oct. 18, 2019, in connection with International Patent Application No. PCT/US2019/041489, 17 pages.

Letter/Written Disclosure of the Supplemental Information Disclosure Statement for the above-referenced application, filed herewith on Jan. 15, 2019, 2 pages.

Broadway et al., "Rescuing chemotaxis of the anticancer agent *Salmonella enterica* serovar Typhimurium VNP20009," Journal of Biotechnology 211:117-120 (2015).

Faulds-Pain et al., "Flagellin Redundancy in *Caulobacter crescentus* and its Implications for Flagellar Filament Assembly," Journal of Bacteriology 193(11):2695-2707 (2011).

Liu et al., "Outer membrane vesicles from flagellin-deficient *Salmonella enterica* serovar Typhimurium induce cross-reactive immunity and provide cross-protection against heterologous *Salmonella* challenge," Scientific Reports 6:34776 (2016).

Zheng et al., "Targeted Cancer Therapy Using Engineered *Salmonella typhimurium*," Chonnam Med. J. 52: 173-184 (2016).

International Search Report and Written Opinion, dated Jan. 3, 2019, in connection with International Patent Application No. PCT/US2018/041713, 34 pages.

Letter/Written Disclosure of the Supplemental Information Disclosure Statement for the above-referenced application, filed herewith on Feb. 13, 2019, 2 pages.

Letter/Written Disclosure of the Supplemental Information Disclosure Statement for the above-referenced application, filed herewith on Apr. 8, 2019, 2 pages.

Glickman et al., Actym Therapeutics Poster Presentation, entitled "STACT-TREX1: A Novel Tumor-Targeting Systemically-Delivered STING Pathway Agonist Demonstrates Robust AntiTumor Efficacy in Multiple Murine Cancer Models," Abstract # P235. Presented at the Society for Immunotherapy of Cancer (SITC) Annual Meeting, in Washington, D.C., on Nov. 9, 2018, 1 page.

Makarova et al., Actym Therapeutics Poster Presentation, entitled "STACT-TREX1: A Systemically-Administered STING Pathway Agonist Targets Tumor-Resident Myeloid Cells and Induces Adaptive Anti-Tumor Immunity in Multiple Preclinical Models," Abstract # 5016. Presented at the American Association for Cancer Research (AACR) Annual Meeting, in Atlanta, Ga., on Apr. 3, 2019, 1 page.

Rae et al., Actym Therapeutics Poster Presentation, entitled "Stact: A novel Tumor-Targeting, Systemically-Administered Delivery Platform Capable of Targeting Intractable Pathways and Precise Immuno-Modulation of the Tumor Microenvironment," Abstract # 4782. Presented at the American Association for Cancer Research (AACR) Annual Meeting, in Atlanta, Ga., on Apr. 3, 2019, 1 page.

Letter/Written Disclosure of the Information Disclosure Statement for the above-referenced application, filed herewith on Aug. 24, 2018, 2 pages.

Ablasser et al., "Cell intrinsic immunity spreads to bystander cells via the intercellular transfer of cGAMP," Nature 503(7477):530-534 (2013).

Ablasser et al., "TREX1 Deficiency Triggers Cell-Autonomous Immunity in a cGAS-Dependent Manner," J. Immunol. 192:5993-5997 (2014).

Agbor, T. A. and McCormick, B. A., "*Salmonella* Effectors: Important players modulating host cell function during infection," Cell Microbiol. 13(12):1858-1869 (2011).

Ahn et al., "Intrinsic Self-DNA Triggers Inflammatory Disease Dependent on STING," J. Immunol. 193(9):4634-4642 (2014).

Ahn et al., "Extrinsic Phagocyte-Dependent STING Signaling Dictates the Immunogenicity of Dying Cells," Cancer Cell 33(5):862-873 (2018).

Akira et al., "Toll-like receptors: critical proteins linking innate and acquired immunity," Nat Immunol. 2(8):675-80 (2001).

Aleksic et al., "Different affinity windows for virus and cancer-specific T-cell receptors-implications for therapeutic strategies," Eur J Immunol 42(12):3174-3179 (2012).

Alshangiti et al., "Antiangiogenic therapies in non-small-cell lung cancer," Curr. Oncol. 25(Suppl 1):S45-S58 (2018).

Anassi, E. and Ndefo, U. A., "Sipuleucel-T (Provenge) Injection The First Immunotherapy Agent (Vaccine) For Hormone-Refractory Prostate Cancer," P&T 36(4):197-202 (2011).

Angelakopoulos, H. and Hohmann, E. L., "Pilot Study of *phoP/phoQ*-Deleted *Salmonella enterica* Serovar Typhimurium Expressing *Helicobacter pylori* Urease in Adult Volunteers," Infection and Immunity 68(4):2135-2141 (2000).

Ansel, H.C., "Introduction to Pharmaceutical Dosage Forms," Fourth Edition, 1985, p. 126.

Antonioli et al., "Immunity, inflammation and cancer: a leading role for adenosine," Nat. Rev. Cancer 13(12):842-857 (2013).

Anwar et al., "Modulation of Biofilm-Formation in *Salmonella enterica* Serovar Typhimurium by the Periplasmic DsbA/DsbB Oxidoreductase System Requires the GGDEF-EAL Domain Protein STM3615," PLoS One 9(8):e106095 (2014).

Arpaia et al., "TLR signaling is required for virulence of an intracellular pathogen," Cell 144(5):675-688 (2011).

Auyeung et al., "Beyond secondary structure: primary-sequence determinants license pri-miRNA hairpins for processing," Cell 152(4):844-858 (2013).

Avogardi et al., "Cancer Immunotherapy Based on Killing of *Salmonella*-Infected Tumor Cells," Cancer Res 65(9): 3920-3927 (2005).

Baban et al., "Bacteria as vectors for gene therapy of cancer," Bioengineered Bugs 1(6): 385-394 (2010).

Baguley, B.C., "Antivascular therapy of cancer: DMXAA," Lancet Oncol. 4(3):141-148 (2003).

Barber, G. N., "Cytoplasmic DNA innate immune pathways," Immunol. Rev. 243(1):99-108 (2011).

Barber, G.N., "STING: infection, inflammation and cancer," Nat. Rev. Immunol. 15(12):760-770 (2015).

Bastin et al., "Capitalizing on Cancer Specific Replication: Oncolytic Viruses as a Versatile Platform for the Enhancement of Cancer Immunotherapy Strategies," Biomedicines 4(3), 21 (2016).

Bermudes et al., "Tumour-Selective *Salmonella*-Based Cancer Therapy," Biotechnology and Genetic Engineering Reviews 18(1): 219-233 (2001).

Bermudes et al., "Tumor-Targeted *Salmonella* Highly Selective Delivery Vehicles," Cancer Gene Therapy: Past Achievements and Future Challenges, ed. Habib, Kluwer Academic/Plenum Publishers, New York, Chp. 6, pp. 57-63 (2000).

Bermudes et al., "Live bacteria as anticancer agents and tumor-selective protein delivery vectors," Curr Opin Drug Discov Devel 5(2):194-199 (2002).

Bian et al., "Cd47-Sirpα interaction and IL-10 constrain inflammation-induced macrophage phagocytosis of healthy self-cells," Proc. Natl. Acad. Sci. USA 113(37):E5434-E5443 (2016).

Binder et al., "Antigen-Specific Bacterial Vaccine Combined with Anti-PD-L1 Rescues Dysfunctional Endogenous T Cells to Reject Long-Established Cancer," Cancer Immunol Res 1(2):123-133 (2013).

Blache et al., "Systemic Delivery of *Salmonella typhimurium* Transformed with IDO shRNA Enhances Intratumoral Vector Colonization and Suppresses Tumor Growth," Cancer Res 72(24):6447-6456 (2012).

Boden et al., "Enhanced gene silencing of HIV-1 specific siRNA using microRNA designed hairpins," Nucleic Acids Research 32(3):1154-1158 (2004).

Broadway et al., "Complete genome sequence of *Salmonella enterica* serovar Typhimurium VNP20009, a strain engineered for tumor targeting," Journal of Biotechnology 192: 177-178 (2014).

Broz, P. and Monack, D. M., "Molecular Mechanisms of Inflammasome Activation during Microbial Infections," Immunol. Rev. 243(1):174-190 (2011).

Bucarey et al., "The *Salmonella enterica* Serovar Typhi *tsx* Gene, Encoding a Nucleoside-Specific Porin, Is Essential for Prototrophic Growth in the Absence of Nucleosides," Infection and Immunity 73(10):6210-6219 (2005).

Buchbinder, E. and Hodi, F.S., "Cytotoxic T lymphocyte antigen-4 and immune checkpoint blockade," J. Clin. Invest. 125(9):3377-3383 (2015).

(56) References Cited

OTHER PUBLICATIONS

Burdette et al., "STING is a direct innate immune sensor of cyclic-di-GMP," Nature 478(7370):515-518(2011).
Camacho et al., "Engineering *Salmonella* as intracellular factory for effective killing of tumour cells," Sci Rep 6(30591): 1-12 (2016).
Carroll, VA. and Ashcroft, M., "Targeting the molecular basis for tumor hypoxia," Expert Rev Mol Med 7(6):1-16 (2005).
Caskey et al., "Synthetic double-stranded RNA induces innate immune responses similar to a live viral vaccine in humans," J. Exp. Med. 208(12):2357-66 (2011).
Chang et al., "Creating an miR30-Based shRNA Vector," Cold Spring Harb Protoc doi:10.1101/pdb.prot075853 pp. 631-635 (2013).
Chen, L. and Han, X., "Anti-PD-1/PD-L1 therapy of human cancer: past, present and future." J. Clin. Invest. 125(9):3384-3391 (2015).
Chi et al., "Anti-tumor Activity of Toll-Like Receptor 7 Agonists," Frontiers in Pharmacology 8:304 1-10 (2017).
Chiocca, E.A. and Rabkin, S.D., "Oncolytic Viruses and Their Application to Cancer Immunotherapy," Cancer Immunol Res. 2(4):295-300 (2014).
Chiu et al., "RNA polymerase III detects cytosolic DNA and induces type-I interferons through the RIG-I pathway," Cell 138(3):576-591 (2009).
Chung et al., "Polycistronic RNA polymerase II expression vectors for RNA interference based on BIC/miR-155," Nucleic Acids Res 34(7):e53 (2006).
Civril et al., "Structural mechanism of cytosolic DNA sensing by cGAS," Nature 498(7454):332-337 (2013).
Clairmont et al., "Biodistribution and Genetic Stability of the Novel Antitumor Agent VNP20009, a Genetically Modified Strain of *Salmonella typhimurium*," Journal of Infectious Diseases 181: 1996-2002 (2000).
Clevers H. and Nusse R., "Wnt/β-Catenin Signaling and Disease," Cell 149:1192-1205 (2012).
Corrales et al., "Direct activation of STING in the tumor microenvironment leads to potent and systemic tumor regression and immunity," Cell Rep 11(7):1018-1030 (2015).
Crull et al., "Biofilm formation by *Salmonella enterica* serovar Typhimurium colonizing solid tumours," Cellular Microbiology 13(8):1223-1233 (2011).
Dang et al., "Combination bacteriolytic therapy for the treatment of experimental tumors," Proc. Natl. Acad. Sci. USA 98(26):15155-15160 (2001).
Datsenko, K. A. and Wanner, B. L., "One-step inactivation of chromosomal genes in *Escherichia coli* K-12 using PCR products," PNAS 97(12):6640-6645 (2000).
Dean et al., "Sequence requirements for plasmid nuclear import," Exp Cell Res.253(2):713-722 (1999).
Del Solar et al., "Replication and Control of Circular Bacterial Plasmids," Microbiology and Molecular Biology Reviews 62(2):434-464 (1998).
Deng et al., "A New VISTA on combination therapy for negative checkpoint regulator blockade," Journal for ImmunoTherapy of Cancer 4:86 (2016).
Diamond et al., "Type I interferon is selectively required by dendritic cells for immune rejection of tumors," J. Exp. Med. 208(10):1989-2003 (2011).
Diner et al., "The innate immune DNA sensor cGAS produces a non-canonical cyclic-di-nucleotide that activates human STING," Cell Rep. 3(5):1355-1361 (2013).
Di Domenico et al., "Biofilm Producing *Salmonella* Typhi: Chronic Colonization and Development of Gallbladder Cancer," Int. J. Mol. Sci. 18:1887 (2017).
Dong et al., "DNA Mismatch Repair Gene Polymorphisms Affect Survival in Pancreatic Cancer," The Oncologist 16:61-70 (2011).
Drees et al., "Vasculature Disruption Enhances Bacterial Targeting of Autochthonous Tumors," Journal of Cancer 6(9): 843-848 (2015).
Drees et al., "Attenuated *Salmonella enterica* Typhimurium Reduces Tumor Burden in an Autochthonous Breast Cancer Model," Anti-cancer Research 35:843-850 (2015).
Durfee et al., "The complete genome sequence of *Escherichia coli* DH10B: insights into the biology of a laboratory workhorse," J. Bacteriol. 190(7):2597-2606 (2008).
Esebanmen, G.E. and Langridge, W.H.R., "The role of TGF-beta signaling in dendritic cell tolerance," Immunol. Res. 65(5):987-994 (2017).
Felgner et al., "aroA-Deficient *Salmonella enterica* Serovar Typhimurium Is More Than a Metabolically Attenuated Mutant," mbio 7(5):e01220-16 (2016).
Feigner et al., "Optimizing *Salmonella enterica* serovar Typhimurium for bacteria-mediated tumor therapy," Gut Microbes 7(2): 171-177 (2016).
Feigner et al., "Engineered *Salmonella enterica* serovar Typhimurium overcomes limitations of anti-bacterial immunity in bacteria-mediated tumor therapy," Oncoimmunology 7(2):e1382791 (2018).
Feigner et al., "Tumor-targeting bacteria-based cancer therapies for increased specificity and improved outcome," Microbial Biotechnology 10(5):1074-1078 (2017).
Fellmann et al., "An optimized microRNA backbone for effective single-copy RNAi," Cell Rep. 5(6):1704-1713 (2013).
Fink, S.L. and Cookson, B.T., "Pyroptosis and host cell death responses during *Salmonella* infection," Cellular Microbiology 9(11):2562-2570 (2007).
Frahm et al., "Efficiency of Conditionally Attenuated *Salmonella enterica* Serovar Typhimurium in Bacterium-Mediated Tumor Therapy," mBio 6(2):e00254-15 (2015).
Fuertes et al., "Host type I IFN signals are required for antitumor CD8+ T cell responses through CD8α+ dendritic cells," J. Exp. Med. 208(10):2005-2016 (2011).
Fujita et al., "The Clinical Relevance of the miR-197/CKS1B/STAT3-mediated PD-L1 Network in Chemoresistant Non-small-cell Lung Cancer," Mol Ther 23(4):717-727 (2015).
Gajewski et al., "Molecular profiling to identify relevant immune resistance mechanisms in the tumor microenvironment," Curr. Opin. Immunol. 23(2):286-292 (2011).
Galan, J. E. and Wolf-Watz, H., "Protein delivery into eukaryotic cells by type III secretion machines," Nature Reviews 444:567-573 (2006).
Galan et al., "Cloning and characterization of the *asd* gene of *Salmonella typhimurium*: use in stable maintenance of recombinant plasmids in *Salmonella* vaccine strains," Gene 94(1):29-35 (1990).
Gao et al., "Overexpression of PD-L1 Significantly Associates with Tumor Aggressiveness and Postoperative Recurrence in Human Hepatocellular Carcinoma," Clin Cancer Res 15(3): 971-979 (2009).
Gao et al., "Integrative Analysis of Complex Cancer Genomics and Clinical Profiles Using the cBioPortal," Sci Signal 6(269):pl1 (2013).
Gao et al., "VISTA is an inhibitory immune checkpoint that is increased after ipilimumab therapy in patients with prostate cancer," Nat. Med. 23(5):551-555 (2017).
Gardlik et al., "Gene therapy for cancer: bacteria-mediated anti-angiogenesis therapy," Gene Therapy 18: 425-431 (2011).
Gray et al., "Cutting Edge: cGAS Is Required for Lethal Autoimmune Disease in the Trex1-Deficient Mouse Model of Aicardi-Goutieres Syndrome," J. Immunol. 195 (2015).
Grenga et al., "PD-L1 andMHC-I expression in 19 human tumor cell lines and modulation by interferon-gamma treatment," J. ImmunoTherapy of Cancer 2(Suppl 3):P102 (2014).
Groisman et al., "*Salmonella typhimurium phoP* virulence gene is a transcriptional regulator," Proc. Natl. Acad. Sci. USA 86:7077-7081 (1989).
Guo et al., "Targeting tumor gene by shRNA-expressing *Salmonella*-mediated RNAi," Gene Therapy 18: 95-105 (2011).
Hagar et al., "WildCARDs: Inflammatory caspases directly detect LPS," Cell Research 25:149-150 (2015).
Hasan et al., "Trex1 regulates lysosomal biogenesis and interferon-independent activation of antiviral genes," Nature Immunology 14(1):61-71 (2013).
Hasan, M. and Yan, N., "Safeguard against DNA sensing: the role of TREX1 in HIV-1 infection and autoimmune diseases," Front. Microbiol. 5:193 (2014).

(56) References Cited

OTHER PUBLICATIONS

Heimann, D.M. and Rosenberg S.A., "Continuous Intravenous Administration of Live Genetically Modified *Salmonella typhimurium* in Patients With Metastatic Melanoma," J Immunother. 26(2):179-180 (2003).
Hervas-Stubbs et al., "Conventional but not plasmacytoid dendritic cells foster the systemic virus-induced type I IFN response needed for efficient CD8 T cell priming," J. Immunol. 193(3):1151-1161 (2014).
Hodi et al., "Improved Survival with Ipilimumab in Patients with Metastatic Melanoma," N. Engl. J. Med. 363(8):711-723 (2010).
Hu et al., "Differential outcome of TRIF-mediated signaling in TLR4 and TLR3 induced DC maturation," Proc. Natl. Acad. Sci. USA 112(45):13994-13999 (2015).
Huang et al., "Targeting CD47: the achievements and concerns of current studies on cancer immunotherapy," J. Thorac. Dis. 9(2):E168-E174 (2017).
Husseiny, M.I. and Hensel, M., "Rapid method for the construction of *Salmonella enterica* Serovar Typhimurium vaccine carrier strains," Infect. Immun. 73(3):1598-1605 (2005).
Irandoust et al., "Engagement of SIRPα Inhibits Growth and Induces Programmed Cell Death in Acute Myeloid Leukemia Cells," PLoS One 8(1):e52143 (2013).
Ireton, R. C. and Gale, M. Jr., "RIG-I Like Receptors in Antiviral Immunity and Therapeutic Applications," Viruses 3:906-919 (2011).
Iwasaki, A. and Medzhitov, R., "Regulation of adaptive immunity by the innate immune system," Science 327(5963):291-295 (2010).
Jackson et al., "Driving CAR T-cells forward," Nat Rev Clin Oncol 13(6):370-383 (2016).
Kahn, M., "Can we safely target the WNT pathway?" Nat Rev Drug Discov. 13(7):513-532 (2014).
Kakarla, S. and Gottschalk, S., "CAR T cells for solid tumors: armed and ready to go?" Cancer J 20(2):151-155 (2014).
Kasinkas, R.W. and Forbes, N.S., "*Salmonella typhimurium* lacking ribose chemoreceptors localize in tumor quiescence and induce apoptosis," Cancer Res. 67(7):3201-3209 (2007).
Kawaguchi et al., "High-efficacy targeting of colon-cancer liver metastasis with *Salmonella typhimurium* A1-R via intra-portal-vein injection in orthotopic nude-mouse models," Oncotarget 8(12): 19065-19073 (2017).
Kim et al., "Inhibition of vascular endothelial growth factor-induced angiogenesis suppresses tumour growth in vivo," Nature 362(6423):841-844 (1993).
Kimura et al., "Selective Localization and Growth of *Bifidobacterium bifidum* in Mouse Tumors following Intravenous Administration," Cancer Res. 40:2061-2068 (1980).
Kocijancic et al., "Local application of bacteria improves safety of *Salmonella*-mediated tumor therapy and retains advantages of systemic infection," Oncotarget 8(30):49988-50001 (2017).
Kong et al., "Turning self-destructing *Salmonella* into a universal DNA vaccine delivery platform," PNAS 109(47):19414-19419 (2012).
Kong et al., "Palmitoylation State Impacts Induction of Innate and Acquired Immunity by the *Salmonella enterica* Serovar Typhimurium *msbB* Mutant," Infection and Immunity 79(12):5027-5038 (2011).
Koopman et al., "Inhibition of *Salmonella enterica* Biofilm Formation Using Small-Molecule Adenosine Mimetics," Antimicrobial Agents and Chemotherapy 59(1):76-84 (2015).
Kzhyshkowska et al., "Stabilin-1, a homeostatic scavenger receptor with multiple functions," J Cell Mol Med. 10(3):635-649 (2006).
Lan et al., "Dnase2a deficiency uncovers lysosomal clearance of damaged nuclear DNA via autophagy," Cell Rep 9(1):180-192 (2014).
Larocca, C. and Schlom, J., "Viral Vector-based Therapeutic Cancer Vaccines," Cancer J. 17(5):359-371 (2011).
Le et al., "A Live-attenuated Listeria Vaccine (ANZ-100) and a Live-attenuated Listeria Vaccine Expressing Mesothelin (CRS-207) for Advanced Cancers: Phase 1 Studies of Safety and Immune Induction," Clin Cancer Res. 18(3):858-868 (2012).
Le et al., "Safety and Survival With GVAX Pancreas Prime and *Listeria Monocytogenes*-Expressing Mesothelin (CRS-207) Boost Vaccines for Metastatic Pancreatic Cancer," J. Clin. Oncol. 33(12):1325-1333 (2015).
Lee et al., "B7-H1 (Programmed Cell Death Ligand 1) Is Required for the Development of Multifunctional Th1 Cells and Immunity to Primary, but Not Secondary, *Salmonella* Infection," J Immunol 185: 2442-2449 (2010).
Lee et al., "Comparative Evaluation of the Acute Toxic Effects in Monkeys, Pigs and Mice of a Genetically Engineered *Salmonella* Strain (VNP20009) Being Developed as an Antitumor Agent," Int J Toxicol 19:19-25 (2000).
Lee et al., "MHC class-I-restricted CD8 T cells play a protective role during primary *Salmonella* infection," Immunol. Lett. 148(2):138-143 (2012).
Lee et al., "The *C. elegans* heterochronic gene *lin-4* encodes small RNAs with antisense complementarity to *lin-14*," Cell 75(5):843-854 (1993).
LeMercier et al., "VISTA regulates the development of protective anti-tumor immunity," Cancer Res. 74(7):1933-1944 (2014).
Leschner et al., "Tumor Invasion of *Salmonella enterica* Serovar Typhimurium Is Accompanied by Strong Hemorrhage Promoted by TNF-α," PLoS One 4(8):e6692 (2009).
Li et al., "Increased Susceptibility to *Salmonella* Infection in Signal Regulatory Protein α-Deficient Mice," J. Immunol. 189(5):2537-2544 (2012).
Li, Y. and Kowdley, K.V., "MicroRNAs in Common Human Diseases," Genomics Proteomics Bioinformatics 10:246-253 (2012).
Lightfield et al., "Critical role of Naip5 in inflammasome activation by a conserved C-terminal domain of flagellin," Nat Immunol. 9(10):1171-1178 (2008).
Lindahl et al., "Biochemical properties of mammalian TREX1 and its association with DNA replication and inherited inflammatory disease," Biochem Soc Trans. 37(Pt 3):535-538 (2009).
Liu et al., "Blockage of autophagy pathway enhances *Salmonella* tumor-targeting," Oncotarget 7(16): 22873-22882 (2016).
Liu et al., "NF-kB signaling in inflammation," Signal Transduction and Targeted Therapy 2:e17023 (2017).
Liu et al., "Inhibition of HIV-1 by multiple siRNAs expressed from a single microRNA polycistron," Nucleic Acids Res. 36(9):2811-2824 (2008).
Liu et al., "Immune-checkpoint proteins VISTA and PD-1 nonredundantly regulate murine T-cell responses," Proc. Natl. Acad. Sci. USA 112(21):6682-6687 (2015).
Liu et al., "Pre-Clinical Development of a Humanized Anti-CD47 Antibody with Anti-Cancer Therapeutic Potential," PLoS One 10(9):e0137345 (2015).
Liu et al., "CD47 Blockade Triggers T cell-mediated Destruction of Immunogenic Tumors," Nat. Med. 21(10):1209-1215 (2015).
Lo et al., "T cell responses to Gram-negative intracellular bacterial pathogens: a role for CD8+ T cells in immunity to *Salmonella* infection and the involvement of MHC class Ib molecules," J. Immunol. 162(9):5398-5406 (1999).
Loeffler et al., "Attenuated *Salmonella* engineered to produce human cytokine LIGHT inhibit tumor growth," PNAS 104(31): 12879-12883 (2007).
Loeffler et al., "IL-18-producing *Salmonella* inhibit tumor growth," Cancer Gene Ther. 15(12):787-794 (2008).
Loeffler et al., "Inhibition of Tumor Growth Using *Salmonella* Expressing Fas Ligand," J Natl Cancer Inst 100:1113-1116 (2008).
Low et al., "Construction of VNP20009: A Novel, Genetically Stable Antibiotic-Sensitive Strain of Tumor-Targeting *Salmonella* for Parenteral Administration in Humans," Meth. In Mol. Med., vol. 90, Suicide Gene Therapy: Methods and Reviews (Chp 3), pp. 47-59 (2003).
Low et al., "Lipid A mutant *Salmonella* with suppressed virulence and TNFα induction retain tumor-targeting in vivo," Nature Biotechnology 17:37-41 (1999).
Lundberg et al., "Growth phase-regulated induction of *Salmonella*-induced macrophage apoptosis correlates with transient expression of SPI-1 genes," J. Bacteriol. 181(11):3433-3437 (1999).

(56) References Cited

OTHER PUBLICATIONS

Luo et al., "Antitumor Effect of VNP20009, an Attenuated *Salmonella*, in Murine Tumor Models," Oncology Research 12: 501-508 (2002).
Mackenzie et al., "Ribonuclease H2 mutations induce as cGAS/STING-dependent innate immune response," EMBO J. 35(8):831-844 (2016).
Mahoney et al., "Combination cancer immunotherapy and new immunomodulatory targets," Nat. Rev. DrugDiscov. 14(8):561-584 (2015).
Makinen et al., "Stable RNA interference: comparison of U6 and H1 promoters in endothelial cells and in mouse brain," J Gene Med 8:433-441 (2006).
Manuel et al.,"*Salmonella*-Based Therapy Targeting Indoleamine 2,3-Dioxygenase Coupled with Enzymatic Depletion of Tumor Hyaluronan Induces Complete Regression of Aggressive Pancreatic Tumors," Cancer Immunol Res 3(9): 1096-1107 (2015).
Manuel et al., "Enhancement of Cancer Vaccine Therapy by Systemic Delivery of a Tumor-Targeting *Salmonella*-Based STAT3 shRNA Suppresses the Growth of Established Melanoma Tumors," Cancer Res. 71(12): 4183-4191 (2011).
Manuel, E.R. and Diamond D. J., "A road less traveled paved by IDO silencing," Oncolmmunology 2(3): e23322 (2013).
Maroun et al., "Designing and building oncolytic viruses," Future Virol. 12(4):193-213 (2017).
Mazur, D.J. and Perrino, F.W., "Excision of 3' Termini by the Trex1 and TREX2 3' → 5' Exonucleases," J Biol Chem 276(20):17022-17029 (2001).
McBride et al., "Artificial miRNAs mitigate shRNA-mediated toxicity in the brain: Implications for the therapeutic development of RNAi," Proc. Natl. Acad. Sci. USA 105(15):5868-5873 (2008).
McCracken et al., "Molecular Pathways: Activating T Cells After Cancer Cell Phagocytosis from Blockade of CD47 "Don't Eat Me" Signals," Clin. Cancer Res. 21(16):3597-3601 (2015).
McKelvey et al., "Cell-specific expression of TLR9 isoforms in inflammation," J Autoimmun. 36(1):76-86 (2011).
Miller et al., "A two-component regulatory system (*phoP phoQ*) controls *Salmonella typhimurium* virulence," Proc. Natl. Acad. Sci. USA 86:5054-5058 (1989).
Moore et al., "Short Hairpin RNA (shRNA): Design, Delivery and Assessment of Gene Knockdown," Methods Mol Biol 629:141-158 (2010).
Morita et al., "Gene-Targeted Mice Lacking the Trex1 (Dnase III) 3'→5' DNA Exonuclease Develop Inflammatory Myocarditis," Mol. Cell. Biol. 24(15):6719-6727 (2004).
Murakami et al., "Tumor-targeting *Salmonella typhimurium* A1-R regresses an osteosarcoma in a patient-derived xenograft model resistant to a molecular-targeting drug," Oncotarget 8(5): 8035-8042 (2017).
Murata et al., "The CD47-SIRPα signalling system: its physiological roles and therapeutic application," J. Biochem. 155(6):335-344 (2014).
Nemunaitis et al., "Pilot trial of genetically modified, attenuated *Salmonella* expressing the *E. coli* cytosine deaminase gene in refractory cancer patients," Cancer Gene Therapy 10: 737-744 (2003).
Nie et al., "Regulation of U6 Promoter Activity by Transcriptional Interference in Viral Vector-Based RNAi," Genomics Proteomics Bioinformatics 8(3):170-179 (2010).
Ohlson et al., "Structure and function of SifA indicate that interactions with SKIP, SseJ, and RhoA family GTPases induce endosomal tubulation," Cell Host Microbe 4(5):434-446 (2008).
O'Rourke et al., "A single dose of peripherally infused EGFRvIII-directed CAR T cells mediates antigen loss and induces adaptive resistance in patients with recurrent glioblastoma," Sci Transl Med 9(399):eaaa0984 (2017).
Osterberg et al., "Decrease of VEGF-A in myeloid cells attenuates glioma progression and prolongs survival in an experimental glioma model," Neuro-Oncology 18(7):939-949 (2016).
Owen et al., "*Salmonella* Suppresses the TRIF-Dependent Type I Interferon Response in Macrophages," mBIO 7(1):e02051-15 (2016).
Palani et al., "Monocyte Stabilin-1 Suppresses the Activation of Th1 Lymphocytes," J Immunol. 196(1):115-123 (2016).
Pandey et al., "Microbial Sensing by Toll-Like Receptors and Intracellular Nucleic Acid Sensors," Cold Spring Harb Perspect Biol 7:a016246 (2015).
Park et al., "Analysis of virulence and growth of a purine auxotrophic mutant of *Xanthomonas oryzae* pathovar oryzae," FEMS Microbio. Lett. 276(1):55-59 (2007).
Pasquinelli et al., "Conservation of the sequence and temporal expression of let-7 heterochronic regulatory RNA," Nature 408(6808):86-89 (2000).
Patyar et al., "Bacteria in cancer therapy: a novel experimental strategy," J Biomed Sci 17:21 (2010).
Pawelek et al., "Bacteria as tumour-targeting vectors," Lancet Oncol 4: 548-556 (2003).
Pawelek et al., "Tumor-targeted *Salmonella* as a Novel Anticancer Vector," Cancer Research 57:4537-4544 (1997).
Pebernard, S. and Iggo, R. D., "Determinants of interferon-stimulated gene induction by RNAi vectors," Differentiation 72(2-3):103-111 (2004).
Pereira-Lopes et al., "The exonuclease Trex1 restrains macrophage proinflammatory activation," J. Immunol. 191:6128-6135 (2013).
Peschke et al., "Loss of Trex1 in Dendritic Cells Is Sufficient To Trigger Systemic Autoimmunity," J. Immunol. 197(6):2157-2166 (2016).
Phan et al., "Cancer regression and autoimmunity induced by cytotoxic T lymphocyte-associated antigen 4 blockage inpatients with metastatic melanoma," PNAS 100(14):8372-8377 (2003).
Pulliero et al., "Inhibition of neuroblastoma cell growth by TREX1-mutated human lymphocytes," Oncology Reports 27:1689-1694 (2012).
Rabe, B., "Aicardi-Goutieres syndrome: clues from the Rnase H2 knock-out mouse," J Mol Med (Berl) 91(11):1235-1240 (2013).
Raetz, C.R.H. and Whitfield, C., "Lipopolysaccharide endotoxins," Annu Rev Biochem 71:635-700 (2002).
Rantakari et al., "Stabilin-1 expression defines a subset of macrophages that mediate tissue homeostasis and prevent fibrosis in chronic liver injury," Proc. Natl. Acad. Sci. USA 113(33):9298-9303 (2016).
Ribas, A., "Releasing the Brakes on Cancer Immunotherapy," N. Engl. J. Med. 373(16):1490-1492 (2015).
Rosenberg et al., "Antitumor Effects in Mice of the Intravenous Injection of Attenuated *Salmonella typhimurium*," Journal of Immunotherapy 25(3): 218-225 (2002).
Rosenberg et al., "Cancer immunotherapy: moving beyond current vaccines," Nat Med 10(9):909-915 (2004).
Ruegg et al., "Evidence for the involvement of endothelial cell integrin αVβ3 in the disruption of the tumor vasculature induced by TNF and IFN-γ," Nature Med. 4(4):408-414 (1998).
Ruella, M. and Maus, M.V., "Catch me if you can: Leukemia Escape after CD19-Directed T Cell Immunotherapies," Comput Struct Biotechnol J 14:357-362 (2016).
Sadelain, M., "CAR therapy: the CD 19 paradigm," J. Clin. Invest. 125(9):3392-3400 (2015).
Schadendorf et al., "Pooled Analysis of Long-Term Survival Data From Phase II and Phase III Trials of Ipilimumab in Unresectable or Metastatic Melanoma," J. Clin. Oncol. 33(17):1889-1894 (2015).
Scheiermann, J. and Klinman, D.M., "Clinical evaluation of CpG oligonucleotides as adjuvants for vaccines targeting infectious diseases and cancer," Vaccine 32(48):6377-6389 (2014).
Sharma et al., "Novel cancer immunotherapy agents with survival benefit: recent successes and next steps," Nat Rev Cancer 11(11):805-812 (2011).
Sharma et al., "Primary, Adaptive, and Acquired Resistance to Cancer Immunotherapy," Cell 168:707-723 (2017).
Sorenson et al., "Safety and immunogenicity of *Salmonella typhimurium* expressing C-terminal truncated human IL-2 in a murine model," Biologies: Targets & Therapy 4: 61-73 (2010).
Spranger et al., "Melanoma-intrinsic β-catenin signalling prevents anti-tumour immunity," Nature 523(7559):231-235 (2015).
Stagg, J. and Smyth, M.J., "Extracellular adenosine triphosphate and adenosine in cancer," Oncogene 29:5346-5358 (2010).

(56) References Cited

OTHER PUBLICATIONS

Starks et al., "*Listeria monocytogenes* as a Vaccine Vector: Virulence Attenuation or Existing Antivector Immunity Does Not Diminish Therapeutic Efficacy," J. Immunol. 173:420-427 (2004).
Stetson et al., "Trex1 prevents cell-intrinsic initiation of autoimmunity," Cell 134(4):587-598 (2008).
Stritzker et al., "Enterobacterial tumor colonization in mice depends on bacterial metabolism and macrophages but is independent of chemotaxis and motility," Int J. Med Microbiol 300:449-456 (2010).
Sun et al., "Cyclic GMP-AMP Synthase is a Cytosolic DNA Sensor that Activates the Type-I Interferon Pathway," Science 339(6121):768-791 (2013).
Swift, L.H. and Golsteyn, R.M., "Genotoxic Anti-Cancer Agents and Their Relationship to DNA Damage, Mitosis, and Checkpoint Adaptation in Proliferating Cancer Cells," Int. J. Mol. Sci. 15(3):3404-3431 (2014).
Tai et al., "Targeting the WNT Signaling Pathway in Cancer Therapeutics," The Oncologist 20:1189-1198 (2015).
Tome et al., "Primer Dosing of *S. typhimuium* A1-R Potentiates Tumor-Targeting and Efficacy in Immunocompetent Mice," Anticancer Research 33: 97-102 (2013).
Toley, B. J. and Forbes, N. S., "Motility is Critical for Effective Distribution and Accumulation of Bacteria in Tumor Tissue," Integr Biol (Camb) 4(2):165-176 (2012).
Tomicic et al., "Human three prime exonuclease TREX1 is induced by genotoxic stress and involved in protection of glioma and melanoma cells to anticancer drugs," Biochimica et Biophysica Acta 1833:1832-1843 (2013).
Topalian et al., "Safety, Activity, and Immune Correlates of Anti-PD-1 Antibody in Cancer," N Engl J Med 366(26):2443-2454 (2012).
Toso et al., "Phase I Study of the Intravenous Administration of Attenuated *Salmonella typhimurium* to Patients With Metastatic Melanoma," Journal of Clinical Oncology 20(1): 142-152 (2002).
Travis, M.A. and Sheppard, D., "TGF-β activation and function in immunity," Annu. Rev. Immunol. 32:51-82 (2014).
Tukel et al., "CsgA is a pathogen-associated molecular pattern of *Salmonella enterica* serotype Typhimurium that is recognized by Toll-like receptor 2," Mol Microbiol. 58(1):289-304 (2005).
Tyle, P., "Iontophoretic Devices for Drug Delivery," Pharmaceutical Research 3(6):318-326 (1986).
Vanpouille-Box et al., "DNA exonuclease Trex1 regulates radiotherapy-induced tumor immunogenicity," Nat. Comm. 8:15618 (2017).
Vaupel, P. and Mayer, A., "Hypoxia-Driven Adenosine Accumulation: A Crucial Microenvironmental Factor Promoting Tumor Progression," in: Oxygen Transport to Tissue XXXVII, Advances in Experimental Medicine and Biology 876, C. E. Elwell et al. (eds.), Springer Science + Business Media, New York, Chp 22, pp. 177-183 (2016).
Wang et al., "TREX1 acts in degrading damaged DNA from drug-treated tumor cells," DNA Repair (Amst) 8(10):1179-1189 (2009).
Wang, R.F. and Kushner, S.R., "Construction of versatile low-copy-number vectors for cloning, sequencing and gene expression in *Escherichia coli*" Gene 100:195-199 (1991).
Wang et al., "VISTA, a novel mouse Ig superfamily ligand that negatively regulates T cell responses," J. Exp. Med. 208(3):577-592 (2011).
Wang et al., "IL-10 Contributes to the Suppressive Function of Tumor Associated Myeloid Cells and Enhances Myeloid Cell Accumulation in Tumors," Scand. J. Immunol. 75(3):273-281 (2012).
Watanabe et al., "Quantitative evaluation of first, second, and third generation hairpin systems reveals the limit of mammalian vector-based RNAi," RNA Biology 13(1):25-33 (2016).
Weiskopf et al., "CD47-blocking immunotherapies stimulate macrophage-mediated destruction of small-cell lung cancer," J. Clin. Invest. 126(7):2610-2620 (2016).
Wilson et al., "MicroRNA regulation of endothelial TREX1 reprograms the tumor microenvironment," Nat Comm. 7:13597 (2016).
Wu et al., "Cyclic-GMP-AMP Is An Endogenous Second Messenger in Innate Immune Signaling by Cytosolic DNA," Science 339(6121):826-830 (2013).
Xia et al., "An enhanced U6 promoter for synthesis of short hairpin RNA," Nucleic Acids Res 31(17):e100 (2003).
Xie et al., "MiR-140 Expression Regulates Cell Proliferation and Targets PD-L1 in NSCLC," Cell Physiol Biochem 46(2):654-663 (2018).
Xu et al., "Effective Cancer Vaccine Platform Based on Attenuated *Salmonella* and Type III Secretion System," Cancer Res 74(21): 6260-6270 (2014).
Yan et al., "The cytosolic exonuclease TREX1 inhibits the innate immune response to HIV-1," Nat. Immunol. 11(11):1005-1013 (2010).
Yanagita et al., "Anti-SIRPα antibodies as a potential new tool for cancer immunotherapy," JCI Insight 2(1):e89140 (2017).
Yang et al., "Trex1 Exonuclease Degrades ssDNA to Prevent Chronic Checkpoint Activation and Autoimmune Disease," Cell 131:873-886 (2007).
Yee, C., "Adoptive T Cell Therapy for Cancer: Boutique Therapy or Treatment Modality?" Clin Cancer Res 19(17): 4550-4552 (2013).
Yee et al., "MicroRNA-155 induced via TNF-α and IFN-γ suppresses expression of programmed death ligand-1 (PD-L1) in human primary cells," J. Biol. Chem. 292(50):20683-20693 (2017).
Yoon et al., "Application of genetically engineered *Salmonella typhimurium* for interferon-gama-induced therapy against melanoma," European Journal of Cancer 70: 48-61 (2017).
Yoon et al., "Suppression of Inflammation by Recombinant *Salmonella typhimurium* Harboring CCL22 MicroRNA," DNA and Cell Biology 31(3):289-296 (2012).
Yu et al., "Explicit hypoxia targeting with tumor suppression by creating an "obligate" anaerobic *Salmonella typhimurium* strain," Scientific Reports 2, 436 (2012).
Zakikhany et al., "Unphosphorylated CsgD controls biofilm formation in *Salmonella enterica* serovar Typhimurium," Molecular Microbiology 77(3):771-786 (2010).
Zeng et al., "Flagellin is the Major Proinflammatory Determinant of Enteropathogenic *Salmonella*," J. Immunol. 171:3668-3674 (2003).
Zhang et al., "Intratumoral Delivery and Suppression of Prostate Tumor Growth by Attenuated *Salmonella enterica* serovar *typhimurium* Carrying Plasmid-Based Small Interfering RNAs," Cancer Res 67(12): 5859-5864 (2007).
Zhao et al., "Efficacy against lung metastasis with a tumor-targeting mutant of *Salmonella typhimurium* in immunocompetent mice," Cell Cycle 11(1): 187-193 (2012).
Zhao et al., "Targeted Therapy with a *Salmonella typhimurium* Leucine-Arginine Auxotroph Cures Orthotopic Human Breast Tumors in Nude Mice," Cancer Res 66(15): 7647-7652 (2006).
Zhao et al., "Tumor-targeting bacterial therapy with amino acid auxotrophs of GFP-expressing *Salmonella typhimurium*," PNAS 102(3):755-760 (2005).
Zheng et al., "Two-step enhanced cancer immunotherapy with engineered *Salmonella typhimurium* secreting heterologous flagelin," Sci. Transl. Med. 9:eaak9537 (2017).
Zitvogel et al., "Type I interferons in anticancer immunity" Nature Reviews Immunology 15:405-414 (2015).
Zu, C. and Wang, J., "Tumor-colonizing bacteria: A potential tumor targeting therapy," CritRev Microbiol 40(3):225-235 (2014).
Letter/Written Disclosure of the Supplemental Information Disclosure Statement for the above-referenced application, filed herewith on Feb. 4, 2020, 4 pages.
International Search Report and Written Opinion, dated Jan. 16, 2020, in connection with International Patent Application No. PCT/US2019/041489, 30 pages.
Olsen et al., "The role of flagella and chemotaxis genes in host pathogen interaction of the host adapted *Salmonella enterica* serovar Dublin compared to the broad host range serovar *S. typhimurium*," *BMC Microbiology* 13:67 (2013), 11 pages.
Schmitt et al., "Absence of All Components of the Flagellar Export and Synthesis Machinery Differentially Alters Virulence of *Salmonella enterica* Serovar Typhimurium in Models of Typhoid Fever, Survival in Macrophages, Tissue Culture Invasiveness, and Calf Enterocolitis," *Infection and Immunity* 69(9):5619-5625 (2001).

(56) References Cited

OTHER PUBLICATIONS

Letter/Written Disclosure of the Supplemental Information Disclosure Statement for the above-referenced application, filed herewith on Apr. 10, 2020, 2 pages.
Fisher C., "Recent Insights into the Control of Human Papillomavirus (HPV) Genome Stability, Loss, and Degradation," *J. Clin. Med.* 4(2):204-230 (2015).
Mazurek et al., "Assessment of the total cfDNA and HPV16/18 detection in plasma samples of head and neck squamous cell carcinoma patients," *Oral Oncol.* 54:36-41 (2016).
Prati, B., "Expressao de genes de vias de reparo de dano ao DNA em celulas infectadas por papilomavirus humano (HPV)." M.Sc. Thesis, Aug. 14, 2014, pp. 1-82, Sao Paulo, Brazil. Retrieved on Jan. 14, 2020, from: <URL:teses.usp.br/teses/disponiveis/42/42132/tde-12082014-175455/publico/BrunaPrati_Mestrado.pdf, 83 pages [In Portuguese with English Abstract].
Prati, B., "Expressao de genes de vias de reparo de dano ao DNA em celulas infectadas por papilomavirus humano (HPV)." M.Sc. Thesis, Aug. 14, 2014, pp. 1-82, Sao Paulo, Brazil. Retrieved on Jan. 14, 2020, from: <URL:teses.usp.br/teses/disponiveis/42/42132/tde-12082014-175455/publico/BrunaPrati_Mestrado.pdf, 83 pages [Machine-generated English language translation].
Qin et al., "Cervical Cancer Neoantigen Landscape and Immune Activity is Associated with Human Papillomavirus Master Regulators," *Front. Immunol.* 8:689 (2017), 8 pages.
Seiwert et al., "Integrative and Comparative Genomic Analysis of HPV-Positive and HPV-Negative Head and Neck Squamous Cell Carcinomas," *Clin. Cancer Res.* 21(3):632-641 (2015).
Christopher D. Thanos, Ph.D., Actym Therapeutics Presentation, entitled "A Novel Systemically Delivered STING Pathway Agonist Therapy Demonstrates Robust Anti-Tumor Efficacy in Multiple Murine Cancer Models." Presented on Apr. 12, 2019, at the 15th Annual PEGS Conference in Boston, MA, 35 pages.
Response, filed Dec. 20, 2019, to Invitation to Pay Additional Fees and Partial International Search, mailed Nov. 22, 2019, in connection with International Patent Application No. PCT/US2019/048659, 11 pages.
International Search Report and Written Opinion, dated Mar. 13, 2020, in connection with International Patent Application No. PCT/US2019/048659, 28 pages.
U.S. Appl. No. 16/824,500, filed Mar. 19, 2020.
Letter/Written Disclosure of the Supplemental Information Disclosure Statement for the above-referenced application, filed herewith on Aug. 12, 2020, 2 pages.
Ittig et al., "A bacterial type III secretion-based protein delivery tool for broad applications in cell biology," J. Cell Biol. 211(4):913-931 (2015).
PCT Demand for International Preliminary Examination (Chapter 11) (Demand under Article 31 of the PCT), filed Jun. 29, 2020, in response to the International Search Report and Written Opinion, dated Mar. 13, 2020, in connection with International Patent Application No. PCT/US2019/048659, 7 pages.
Invitation to Submit Amendments (PCT Rule 60.1 (g)), dated Jul. 15, 2020, in connection with International Patent Application No. PCT/US2019/048659, 1 page.
Demand for International Preliminary Examination (Chapter II) and Response under Article 34(2)(b) PCT, filed May 11, 2020, in response to the International Search Report and Written Opinion, dated Jan. 16, 2020, in connection with International Patent Application No. PCT/US2019/041489, 54 pages.
Written Opinion of the International Preliminary Examining Authority, dated May 27. 2020, in connection with International Patent Application No. PCT/US2019/041489, 11 pages.
Response, filed Jun. 29, 2020. to the Written Opinion of the International Preliminary Examining Authority, dated May 27, 2020, in connection with International Patent Application No. PCT/US2019/041489, 63 pages.
Letter/Written Disclosure of the Supplemental Information Disclosure Statement for the above-referenced application, filed herewith on Feb. 19, 2021, 4 pages.
Examiner's Report, dated Jan. 21, 2021, issued in connection with corresponding Canadian Patent Application No. 3,069,523, 5 pages.
International Preliminary Report on Patentability (Chapter II of the PCT), dated Jan. 28, 2021, in connection with International Patent Application No. PCT/US2019/041489, 12 pages.
Letter/Written Disclosure of the Supplemental Information Disclosure Statement for the above-referenced application, filed herewith on Nov. 24, 2020, 2 pages.
Actym Therapeutics Press Release, entitled "Actym Therapeutics Raises $34 Million Series A. Financing will fund Actym's cancer immunotherapv pipeline into clinical development." Published Apr. 27, 2020 [online]; retrieved on Nov. 23, 2020, from: <URL:pinewswire.com/news-releases/actym-therapeutics-raises-34-million-series-a-301047161.html, 3 pages.
International Preliminary Report on Patentability (Chapter II of the PCT), dated Oct. 21, 2020, in connection with International Patent Application No. PCT/US2019/0414S9, 13 pages.
U.S. Appl. No. 16/554,478, filed Aug. 28, 2019, 2020/0071702, Mar. 5, 2020.
U.S. Appl. No. 16/520,155, filed Jul. 23, 2019, 2020/0215123, Jul. 9, 2020.
U.S. Appl. No. 17/037,455, filed Sep. 29, 2020.
U.S. Appl. No. 16/824,500, filed Mar. 19, 2020, 2020/0270613, Aug. 27, 2020.
Letter/Written Disclosure of the Supplemental Information Disclosure Statement for the above-referenced application, filed herewith on Apr. 7, 2021, 2 pages.
Tominaga, A. and Kutsukake, K., "Expressed and cryptic flagellin genes in the H44 and H55 type strains of *Escherichia coli," Genes Genet. Syst.* 82:1-8 (2007).
Actym Therapeutics Press Release, entitled " Actym Therapeutics Announces Expansion of Scientific Advisory Board." Published on Jan. 13, 2021 [online]; retrieved on Apr. 3, 2021, from: <URL:prnewswire.com/news-releases/actym-therapeutics-announces-expansion-of-scientific-advisory-board-301207134.html, 3 pages.
Communication under Rule 164(2)(a) EPC, dated Jan. 29, 2021, issued in connection with corresponding European Patent Application No. 18 752 908.6, 5 pages.
Office Action, dated Mar. 16, 2021, in connection with corresponding Japanese Patent Application No. 2020-523685 [English Summary of Office Action; English translation of Office Action; and original document as issued in Japanese], 10 pages.
Response, filed Dec. 31, 2020, to the International Preliminary Report on Patentability (Chapter II of the PCT), dated Oct. 21, 2020, in connection with International Patent Application No. PCT/US2019/041489, 28 pages.
Letter/Written Disclosure of the Supplemental Information Disclosure Statement for the above-referenced application, filed herewith on Jul. 16, 2021, 3 pages.
Communication Pursuant to Rule 164(2)(b) and Article 94(3) EPC (Examination Report), dated Jun. 10, 2021, issued in connection with corresponding European Patent Application No. 18 752 908.6, 13 pages.
Chen et al., "Proteomic Screening of Anaerobically Regulated Promoters from *Salmonella* and Its Antitumor Applications," *Mol. Cell. Proteomics* 10(6):M111.009399 (2011), 11 pages.
Gao et al., "The Roles of CD73 in Cancer," *Biomed. Res. Int.* 2014:460654 (2014), 9 pages.
Koszalka et al., "CD73 on B16F10 melanoma cells in CD73-deficient mice promotes tumor growth, angiogenesis, neovascularization, macrophage infiltration and metastasis," *Int. J. Biochem. Cell Biol.* 69:1-10 (2015).
Terp et al., "Anti-Human CD73 Monoclonal Antibody Inhibits Metastasis Formation in Human Breast Cancer by Inducing Clustering and Internalization of CD73 Expressed on the Surface of Cancer Cells," *J. Immunol.* 191(8):4165-4173 (2013).
Young et al., "Targeting Adenosine in BRAF-Mutant Melanoma Reduces Tumor Growth and Metastasis," *Cancer Res.* 77(17):4684-4696 (2017).

(56) References Cited

OTHER PUBLICATIONS

Zhang et al., "Chloroquine enhanced the anticancer capacity of VNP 20009 by inhibiting autophagy," *Scientific Reports* 6(1):29774 (2016), 10 pages.

* cited by examiner

ENGINEERED IMMUNOSTIMULATORY BACTERIAL STRAINS AND USES THEREOF

RELATED APPLICATIONS

Benefit of priority is claimed to U.S. Provisional Application Ser. No. 62/531,327, filed Jul. 11, 2017, to Christopher D. Thanos and Laura Hix Glickman, and entitled "ENGINEERED IMMUNOSTIMULATORY BACTERIAL STRAINS AND USES THEREOF." Benefit of priority also is claimed to U.S. Provisional Application Ser. No. 62/648,380, filed Mar. 26, 2018, to Christopher D. Thanos, Laura Hix Glickman, and Justin Skoble, entitled "ENGINEERED IMMUNOSTIMULATORY BACTERIAL STRAINS AND USES THEREOF."

This application is related to International Patent Application No. PCT/US2018/041713, filed the same day herewith, entitled "ENGINEERED IMMUNOSTIMULATORY BACTERIAL STRAINS AND USES THEREOF," which claims priority to U.S. Provisional Application Ser. Nos. 62/531,327 and 62/648,380.

Where permitted, the subject matter of each of these applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Jul. 11, 2018, is 410 kilobytes in size, and is titled 1701SEQ001.txt. A substitute Sequence Listing is filed electronically herewith, the contents of which are incorporated by reference in their entirety. The electronic file was created on Jul. 25, 2018, is 411 kilobytes in size, and is titled 1701SEQ002.txt.

BACKGROUND

The field of cancer immunotherapy has made great strides, as evidenced by clinical successes of anti-CTLA4, anti-PD-1 and anti-PD-L1 immune checkpoint antibodies (see, e.g., Buchbinder et al. (2015) *J. Clin. Invest.* 125: 3377-3383; Hodi et al. (2015) *J. Clin. Invest.* 125:3392-4000; and Chen et al. (2015) *J. Clin. Invest.* 125:3384-3391). Tumors have evolved a profoundly immunosuppressive environment. They initiate multiple mechanisms to evade immune surveillance, reprogram anti-tumor immune cells to suppress immunity, and continually mutate resistance to the latest cancer therapies (see, e.g., Mahoney et al. (2015) *Nat. Rev. Drug Discov.* 14(8):561-584). Designing immunotherapies that overcome immune tolerance and escape, while limiting the autoimmune-related toxicities of current immunotherapies, challenges the field of immuno-oncology. Hence additional and innovative immunotherapies and other therapies are needed.

SUMMARY

Provided are bacteria modified to be immunostimulatory for anti-cancer therapy. Immunostimulatory bacteria, as provided herein, provide a multi-faceted approach to anti-tumor therapy. As provided herein, bacteria, such as species of *Salmonella*, can be fine-tuned to have potent anti-tumor activity. Bacteria provide a platform in which there are numerous avenues for eliciting anti-tumor immunostimulatory activity. The bacteria contain plasmids that encode anti-cancer therapeutics, such as RNA, including microRNA, shRNA, and siRNA, that are designed to suppress, inhibit, disrupt or otherwise silence immune checkpoint genes and products, and other targets that play a role in pathways that are immunosuppressive and pathways that are immunostimulatory and improve an anti-tumor response, such as Stimulator of Interferon Genes (STING) and cGAS. Bacteria by their nature stimulate the immune system; bacterial infection induces immune and inflammatory pathways and responses, some of which are desirable for anti-tumor treatment, and others are undesirable. Modification of the bacteria by deleting or modifying genes and products that result in undesirable inflammatory response, and genes that induce desirable immunostimulatory anti-tumor responses can improve the anti-tumor activity of the bacteria. Bacteria also accumulate in tumor cells and tissues, and by replicating therein can lyse cells. Bacteria migrate from the sites of administration and can accumulate other tumors and tumor cells to provide an abscopal effect. Herein, all of these properties of bacteria are exploited to produce demonstrably immunostimulatory bacteria with a plurality anti-tumor activities and properties that can act synergistically.

Provided are compositions, uses thereof and methods that modulate immune responses for treatment of diseases, including for treatment of cancer. The compositions contain immunostimulatory bacteria provided herein. Methods of treatment and uses of the bacteria for treatment also are provided. The subjects for treatment include humans and other primates, pets, such as dogs and cats, and other animals, such as horses.

Provided are pharmaceutical compositions containing the immunostimulatory bacteria, and methods and uses thereof for treatment of diseases and disorders, particularly proliferative disorders, such as tumors, including solid tumors.

Also provided are methods of inhibiting the growth or reducing the volume of a solid tumor by administering the immunostimulatory bacteria or pharmaceutical compositions or using the compositions for treatment. For example, provided are methods of administering or using a composition that contains, for a single dosage, an effective amount of an attenuated *Salmonella* sp. to a subject, such a human patient, having a solid tumor cancer.

It is understood that all of the RNAis and modifications of the bacteria and the plasmids described can be combined in any desired combination. So reference to immunostimulatory bacteria refers to bacteria that include RNAi against at least one target and that can have any or all of the modifications described herein.

Provided are immunostimulatory bacteria that contain sequence of nucleotides encoding RNA (RNAi) that inhibits, suppresses or disrupts expression of an immune checkpoint or other target whose inhibition, suppression or disruption increase the anti-tumor immune response in a subject; the RNA is encoded on a plasmid in the bacterium; and the immunostimulatory bacterium is aspartate-semialdehyde dehydrogenase$^-$ (asd$^-$).

For purposes herein RNAi includes all forms of double stranded RNA that can be used to silence expression of targeted nucleic acids. RNAi includes, shRNA, siRNA and micro RNA. Any of these forms can be interchanged in the embodiments disclosed and described herein. In general, the RNAi is encoded on a plasmid in the bacterium. The plasmids can include other heterologous nucleic acid that encodes products of interest that modulate or add activities or products to the bacterium, or other such products that can modulate the immune system of a subject to be treated with the bacterium. Bacterial genes also can be added deleted or added or disrupted. These genes can encode products for growth and replication of the bacteria, or products that also modulate the immune response of the host to the bacterium.

Also provided are immunostimulatory bacteria that contain a sequence of nucleotides encoding RNA (RNAi) that inhibits, suppresses or disrupts expression of three prime repair exonuclease 1 (TREX1), and is auxotrophic for adenosine. Also provided are immunostimulatory bacterium that contain a sequence of nucleotides encoding RNA that inhibits, suppresses or disrupts expression of VISTA (the gene encoding V-domain Ig suppressor of T cell activation), and is auxotrophic for adenosine. Also provided are immunostimulatory bacteria that comprise a sequence of nucleotides encoding RNA that inhibits, suppresses, disrupts expression of programmed death-ligand 1 (PD-L1).

Among these immunostimulatory bacteria are those of *Salmonella* species. These include *Salmonella* that contain nucleic acid that encodes an RNA that inhibits or suppresses, disrupts or silences expression of three prime repair exonuclease 1 (TREX1) and/or VISTA.

Also provided are immunostimulatory bacteria that contain a sequence of nucleotides encoding RNA that inhibits, suppresses or disrupts expression of three prime repair exonuclease 1 (TREX1) a, and a sequence of nucleotides encoding RNA that inhibits, suppresses or disrupts expression of PD-L1.

Also provided are immunostimulatory bacteria that contain a sequence of nucleotides encoding RNA that inhibits, suppresses or disrupts expression of VISTA, and a sequence of nucleotides encoding RNA that inhibits, suppresses or disrupts expression of PD-L1.

Provided are immunostimulatory bacteria, such as *S. typhimurium*, carrying plasmids encoding RNAi, such as miRNA or shRNA, mediated gene disruption of one or more of TREX1, VISTSA and PD-L1 and a other such targets known to those of skill in the art and/or enumerated or exemplified herein. Bacterial species that carry such plasmids, include, but are not limited to, for example, strains of *Salmonella, Shigella, Listeria, E. coli*, and *Bifidobacteriae*. For example, species include *Shigella sonnei, Shigella flexneri, Shigella disenteriae, Listeria monocytogenes, Salmonella typhi, Salmonella typhimurium, Salmonella galinarum*, and *Salmonella enteritidis*.

Species include, for example, strains of *Salmonella, Shigella, E. coli, Bifidobacteriae, Rikettsia, Vibrio, Listeria, Klebsiella, Bordetella, Neisseria, Aeromonas, Francisella, Cholera, Corynebacterium, Citrobacter, Chlamydia, Hemophilus, Brucella, Mycobacterium, Mycoplasma, Legionella, Rhodococcus, Pseudomonas, Heliobacter, Bacillus*, and *Erysipelothrix*, or an attenuated strain thereof or modified strain thereof of any of the preceding list of bacterial strains.

Other suitable bacterial species include *Rikettsia, Klebsiella, Bordetella, Neisseria, Aeromonas, Franciesella, Corynebacterium, Citrobacter, Chlamydia, Hemophilus, Brucella, Mycobacterium, Mycoplasma Legionella, Rhodococcus, Pseudomonas, Heliobacter, Vibrio, Bacillus*, and *Erysipelothrix*. For example, *Rickettsia Rikettsiae, Riketsia prowaseckii, Rickettsia tsutsugamuchi, Rickettsia mooseri, Rickettsia sibirica, Bordetella bronchiseptica, Neisseria meningitidis, Neisseria gonorrhoeae, Aeromonas eucrenophila, Aeromonas salminocida, Franciesella tularensis, Corynebacterium pseudotuberculosis, Citrobacter freundii, Chlamydia pneumoniae, Hemophilus sornnus, Brucella abortus, Mycobacterium intracellulare, Legionella pneumophila, Rhodococcus equi, Pseudomonas aeruginosa, Heliobacter mustelae, Vibrio cholerae, Bacillus subtilis, Erysipelothrix rhusiopathiae, Yersinia enterocolitica, Rochalimaea quitana*, and *Agrobacterium tumerfacium.*

*Salmonella* is exemplified herein, and particularly *Salmonella typhimurium* strain, such as the strain designated or strain YS1646 (ATCC #202165) or VNP20009. Other strains include, RE88, SL7207, χ8429, χ8431, and χ8468. Exemplary of modified *Salmonella* strains provided herein are immunostimulatory bacterium strains AST-104, AST-105, AST-106, AST-108, AST-109, AST-112, AST-113, AST-115, AST-117, AST-118, AST-119, AST-120, AST-121, AST-122, and AST-123. Sequences thereof and descriptions are provided in the detailed description, examples and sequence listing. The immunostimulatory bacteria can be derived from attenuated strains of bacteria or they become attenuated by virtue of the modifications described herein, such as deletion of asd, whereby replication is limited in vivo.

The immunostimulatory bacteria provided herein encode inhibitors of various genes and/or expression of genes and/or gene products that contribute to reduced anti-tumoral immune responses and/or products that stimulate the immune system, and thereby are immunostimulatory. As described herein, inhibition of TREX1 is immunostimulatory, as is inhibition of PD-L1. Adenosine auxotrophy also is immunostimulatory. Provided are inhibitory RNA (RNAi), such as shRNA or microRNA or siRNA, targeted for disruption or inhibition of expression of TREX1, PD-L1, VISTA (the gene encoding V-domain Ig suppressor of T cell activation), TGF-beta, and CTNNB1 (the gene that encodes β-catenin) among others, combinations thereof and combinations thereof with any shRNAs that inhibit or disrupt expression of other immune suppressive genes whose expression is activated, or enhanced by tumors or the tumor microenvironment (TME). Expression of these RNA exploits two independent immunostimulatory pathways, and leads to enhanced tumor colonization in a single therapy. The effects of this combination are enhanced by the strains provided herein that are auxotrophic for adenosine, which provides preferential accumulation in or recruitment into adenosine-rich immunosuppressive tumor microenvironments. Reducing adenosine in such TMEs further enhances the immunostimulatory effects. Such combinations of traits in any of the bacterial strains known or that can be engineered for therapeutic administration provide similar immunostimulatory effects.

Among the targets is TGF-beta, which has three isoforms: 1, 2 and 3. Among the targets is TGF-beta, particularly isoform 1, and not isoforms 2 and 3. Toxicities are associated with isoforms 2 and 3. For example, cardiac valve toxicity is associated with inhibition of isoform 2. Isoform 1 is present in most cancers (see, e.g., TCGA database). It is advantageous to inhibit only isoform 1. RNAi can be advantageously employed for this purpose, since it can be designed to very specifically recognize a target. For TGF-beta, specific inhibition of isoform 1 can effected by targeting a sequence unique to isoform 1 (see, e.g., the RNA against TGF-beta isoform 1 in Example 2) that is not present in isoform 2 or 3, or to select a sequence to target isoforms land 3, and not 2. Also provided are immunostimulatory bacteria in which the plasmid encodes an shRNA or microRNA that specifically inhibits, suppresses or disrupts expression of TGF-beta isoform 1 but not TGF-beta isoform2 or TGF-beta isoform 3; or the plasmid encodes an shRNA or microRNA that specifically inhibits, suppresses or disrupts expression of TGF-beta isoforms 1 and 3, but not isoform 2.

Also, RNAi, such a miRNA or shRNA-mediated gene disruption of PD-L1 provided by immunostimulatory bacteria provided herein also improves colonization. It has been shown that knockout of PD-L1 enhances *S. typhimurium* infection. For example, an at least 10-fold higher bacterial load in PD-L1 knockout mice than in wild-type mice has been observed, indicating that PD-L1 is protective against *S. typhimurium* infection (see, e.g., Lee et al. (2010) *Immunol.* 185:2442-2449).

Engineered immunostimulatory bacteria, such as the *S. typhimurium* immunostimulatory bacteria, provided herein contain multiple synergistic modalities to induce immune re-activation of cold tumors to promote tumor antigen-specific immune responses, while inhibiting immune checkpoint pathways that the tumor utilizes to subvert and evade durable anti-tumor immunity. Included in embodiments is adenosine auxotrophy and enhanced vascular disruption. This improvement in tumor targeting through adenosine auxotrophy and enhanced vascular disruption increases potency, while localizing the inflammation to limit systemic cytokine exposure and the autoimmune toxicities observed with other immunotherapy modalities.

Provided are immunostimulatory bacteria that are auxotrophic for adenosine and/or target the TREX1 gene, such as encoding a double-stranded RNA, such as an shRNA or miRNA that inhibits expression thereof, and optionally encodes additional RNAs, such as miRNA or shRNA, that target and inhibit expression of other checkpoint inhibitors. Among these bacteria are immunostimulatory bacteria that are auxotrophic for adenosine. Methods of treatment and uses for treatment of tumors, including solid tumors and hematologic malignancies are provided. Among the methods and uses are those in which the immunostimulatory bacteria are auxotrophic for adenosine and the uses and treatments treat tumors that are cd73+ and/or cd73/cd39+.

The RNAs are expressed under the control of promoters that are recognized by the eukaryotic host cell transcription machinery, such as RNA polymerase II (RNAPII) and RNA polymerase III (RNAPIII) promoters. RNAP III promoters generally are constitutively expressed in a eukaryotic host; RNAP II promoters can be regulated. The RNAs, such as miRNA and shRNA, are provided on plasmids stably expressed by the bacteria. Exemplary of such bacteria are *Salmonella* strains, generally attenuated strains, either attenuated by passage or other methods or by virtue of modifications described herein, such as adenosine auxotrophy. Exemplary of the bacteria are *Salmonella* strains. Exemplary of *Salmonella* strains are modified *S. typhimurium* strains that contain an asd mutation for antibiotic-free selection. These strains also can contain the asd mutation.

The promoters can be selected for the environment of the tumor cell, such as a promoter expressed in a tumor microenvironment (TME), such as a promoter expressed in hypoxic conditions, or in conditions where the pH is less than 7.

Provided are strains of bacteria that contain miRNA or shRNA against the TREX1 or VISTA gene. The TREX1 or VISTA gene can be under control of an RNAPIII promoter, such as the H1 promoter. TREX1 knockdown induces vascular disruption, which increases colonization, and also decreases immune suppression. The strains provided herein can include miRNA or shRNA that inhibits expression of other checkpoint inhibitors, including, but not limited to PD-L1. Strains that include a plurality of RNAs, such as miRNA or shRNAs, generally include different promoters, for each RNA. For example, the bacterium can include a genetically modified *S. typhimurium* strain that contains miRNA or shRNA under control of the U6 promoter against the PD-L1 gene and also contains miRNA or shRNA against TREX1 under control of the H1 promoter. Also provided are genetically modified *S. typhimurium* strains that contain miRNA or shRNA against the SIRP-α gene under control of the H1 promoter. The exemplary bacteria, such as *S. typhimurium* strains, can contain miRNA or shRNA against the β-catenin gene under control of an RNAPIII promoter, such as the H1 promoter and/or miRNA or shRNA against the VISTA gene under control of an RNAPIII promoter, such as the H1 promoter. Various combinations of adenosine auxotrophy, miRNA or shRNA against TREX1, and/or optionally against other immune checkpoint targets, such as RNA that inhibits, suppresses or disrupts PD-L1 or one or both of TREX1 and PD-1 or VISTA, can be included in the modified immunostimulatory bacteria.

Provided are immunostimulatory bacteria that are cGAS agonists. Exemplary of such bacteria is *S. typhimurium* that is one or both of a cGAS agonist and Stimulator of Interferon Genes (STING) agonist. These can be administered, for example, in uses and methods, such as radiotherapy and chemotherapy, in which cytosolic DNA is produced or accumulates. STING activates innate immunity in response to sensing nucleic acids in the cytosol. Downstream signaling is activated through binding of cyclic dinucleotides (CDNs), which are synthesized by bacteria or by host enzyme cGAS in response to binding to cytosolic dsDNA. Bacterial and host-produced CDNs have distinct phosphate bridge structures, which differentiates their capacity to activate STING. CDNs are synthesized by bacteria or by host enzyme cGAS in response to binding cytosolic dsDNA. IFN-β is the signature cytokine of activated STING.

The plasmids in any of the bacteria described and enumerated above and herein contain plasmids that encode the RNAi and other heterologous nucleic acid. Plasmids can be present in many copies or fewer. This can be controlled by selection of elements, such as the origin of replication. Low and high and medium copy number plasmids and origins of replication are well known to those of skill in the art and can be selected. In embodiments of the immunostimulatory bacteria here, the plasmid can be present in low to medium copy number, such as about 150 or 150 and few copies, to low copy number which is less than about 25 or about 20 or 25 copies. Exemplary origins are those derived from pBR322, p15A, pSC101, pMB1, colE1, colE2, pPS10, R6K, R1, PK2, and pUC.

As discussed, the plasmids can include RNAi that the RNA inhibits, suppresses or disrupts expression of an immune checkpoint or other target and additionally or products. Among these are sequence of nucleic acid encoding listeriolysin O (LLO) protein lacking the signal sequence (cytoLLO), a CpG motif, a DNA nuclear targeting sequence (DTS), a deletion of the gene encoding a flagellin subunit(s), and a retinoic acid-inducible gene-I (RIG-1) binding element.

The immunostimulatory bacteria provided herein can be aspartate-semialdehyde dehydrogenase$^-$ (asd), which permits growth in DAP supplemented medium, but limits replication in vivo when administered to subjects for treatment. Such bacteria will be self-limiting, which can be advantageous for treatment. The bacterium can be asd$^-$ by virtue of disruption or deletion of all or a portion of the endogenous gene encoding aspartate-semialdehyde dehydrogenase (asd), whereby the endogenous asd is not expressed. In other embodiments, the gene encoding asd can be included on the plasmid for expression in vivo.

Any of the immunostimulatory bacteria provided herein can include contain acid, generally on the plasmid, that includes a CpG motif or a CpG island), wherein the motif is recognized by toll-like receptor-9 (TLR9). Nucleic acid encoding CpG motifs or islands are plentiful in prokaryotes, and, thus, the CpG motif can be included in or part of a bacterial gene that is encoded in the plasmid. The bacterial gene that encodes asd contains immunostimulatory CpGs.

The immunostimulatory bacterium provided herein can be auxotrophic for adenosine or adenosine and adenine. Any of the bacterium herein can be rendered autotrophic for adenosine, which advantageously can increase the anti-tumor activity, since adenosine accumulates in many tumors, and is immunosuppressive.

The immunostimulatory bacterium provided herein can be flagellin deficient, where the wild-type bacterium comprises flagella. They can be rendered flagellin deficient by disrupting or deleting all or a part of the gene or genes that encode flagella. For example, provided are immunostimulatory bacterium that have deletions in the genes encoding one or both of flagellin subunits fliC and fljB, whereby the bacterium is flagella deficient.

The immunostimulatory bacteria provided herein can include nucleic acid encoding cytoLLO, which is listeriolysin O (LLO) protein lacking the periplasmic secretion signal sequence so that it accumulates in the cytoplasm. This mutation is advantageously combined with $asd^-$ bacteria. LLO is a cholesterol-dependent pore forming hemolysin from *Listeria monocytogenes* that mediates phagosomal escape of bacteria. When the autolytic strain is introduced into tumor bearing hosts, such as humans, the bacteria are taken up by phagocytic immune cells and enter the vacuole. In this environment, the lack of DAP prevents bacterial replication, and result in autolysis of the bacteria in the vacuole. Lysis then releases the plasmid and the accumulated LLO forms pores in the cholesterol-containing vacuole membrane and allows for delivery of the plasmid into the cytosol of the host cell.

The immunostimulatory bacteria can include DNA nuclear targeting sequence (DTS), such as an SV40 DTS, encoded on the plasmid.

The immunostimulatory bacteria can have a deletion or modification in the gene encoding endonuclease A (endA), whereby endA activity is inhibited or eliminated. Exemplary of these are immunostimulatory bacteria that contain one or more of a CpG motif, an asd gene selectable marker for plasmid maintenance and a DNA nuclear targeting sequence.

The immunostimulatory bacteria can contain nucleic acid on the plasmid encoding two or more different RNA molecules that inhibit, suppress or disrupt expression of an immune checkpoint or an RNA molecule encodes an inhibitor of a metabolite that is immunosuppressive or in an immunosuppressive pathway.

The nucleic acid encoding the RNAi, such as shRNA or miRNA or siRNA can include a transcriptional terminator following the RNA-encoding nucleic acid.

In all embodiments, the RNAi encoded on the plasmid in the immunostimulatory bacteria can be short hairpin RNA (shRNA) or micro-RNA (miRNA).

The immunostimulatory bacteria contain RNAi that inhibits, suppresses or disrupts expression or silences expression of immune checkpoints and other targets whose inhibition, disrupting or silencing is immunostimulatory. These targets include, but are not limited to, one or more of three prime repair exonuclease 1 (TREX1), PD-1, PD-L1 (B7-H1), VEGF, TGF-beta isoform 1, Beta-catenin, CTLA-4, PD-L2, PD-1, PD-2, IDO1, IDO2, SIRPα, CD47, VISTA (B7-H5), LIGHT, HVEM, CD28, LAG3, TIM3, TIGIT, Galectin-9, CEACAM1, CD155, CD112, CD226, CD244 (2B4), B7-H2, B7-H3, CD137, ICOS, GITR, B7-H4, B7-H6, CD137, CD27, CD40/CD40L, CD48, CD70, CD80, CD86, CD137 (4-1BB), CD200, CD272 (BTLA), CD160, CD39, CD73, A2a receptor, A2b receptor, HHLA2, ILT-2, ILT-4, gp49B, PIR-B, HLA-G, ILT-2/4, OX40/OX-40L, BTLA, ICOS, KIR, GITR, TIM1, TIM4 and STAT3, Stabilin-1 (CLEVER-1), DNASE II and RNASE H2. For example, any of the immunostimulatory bacteria can contain RNA that inhibits, suppresses or disrupts expression of one or a combination of TREX1, PD-L1, VISTA, TGF-beta, such as TGF-beta isoform 1 or isoform 1 and 3, beta-catenin, SIRP-alpha, VEGF, RNase H2, DNase II, and CLEVER-1/Stabilin-1.

Immunostimulatory bacteria where the plasmid comprises a sequence of nucleotides that encodes RNA that inhibits, suppresses or disrupts expression of at least two targets; and each RNA is expressed from a different promoter, are provided. Exemplary of these are where the targets for inhibition, suppression or disruption combinations are at least two that are selected from among TREX1 and PD-L1, TREX1 and PD-1, TREX1 and VISTA, TREX1 and SIRP-alpha, PD-L1 and TGF-beta isoform 1, PD-L1 and beta-catenin, PD-L1 and VISTA, TGF-beta isoform 1 and VISTA, SIRP-alpha and VISTA and TREX1 and RNASE H2.

Other combinations of RNAi, include RNAi that inhibits, suppresses or disrupts expression of one or a combination of TREX1, PD-L1, VISTA, TGF-beta isoform 1, beta-catenin, SIRP-alpha, VEGF, RNase H2, DNase II, and CLEVER-1/Stabilin-1. Other combinations include those where the target for inhibition, suppression or disruption is a combination of at least two that are selected from among TREX1 and PD-L1, TREX1 and PD-1, TREX1 and VISTA, TREX1 and SIRP-alpha, PD-L1 and TGF-beta isoform 1, PD-L1 and beta-catenin, PD-L1 and VISTA, TGF-beta isoform 1 and VISTA, SIRP-alpha and VISTA and TREX1 and RNASE H2, VISTA and RNASE H2, and VISTA and DNASE H2, or TREX1 and SIRPα, or TREX1 and VISTA, or TREX1 and VEGF or PD-L1 and β-catenin, or PD-L1 and TGF-beta isoform 1, or PD-L1 and VEGF or TREX and PD-1.

The immunostimulatory bacterium can also include nucleic acid encoding RNA that inhibits, suppresses or disrupts expression of another different immune checkpoint or target to be inhibited, suppressed or disrupted, selected from among any of CTLA-4, PD-L1 (B7-H1), PD-L2, PD-1, PD-2, IDOL IDO2, SIRPα, CD47, VISTA (B7-H5), VEGF, TGF-beta, LIGHT, HVEM, CD28, LAG3, TIM3, TIGIT, Galectin-9, CEACAM1, CD155, CD112, CD226, CD244 (2B4), B7-H2, B7-H3, CD137, ICOS, GITR, B7-H4, B7-H6, CD137, CD27, CD40/CD40L, CD48, CD70, CD80, CD86, CD137 (4-1BB), CD200, CD272 (BTLA), CD160, CD39, CD73, A2a receptor, A2b receptor, HHLA2, ILT-2, ILT-4, gp49B, PIR-B, HLA-G, ILT-2/4, OX40/OX-40L, BTLA, ICOS, KIR, GITR, TIM1, TIM4, STAT3, CLEVER-1, DNASE II and RNASE-H2. Exemplary thereof are among human PD-L1 (SEQ ID NO:31), human Beta-catenin (SEQ ID NO:32), human SIRPα (SEQ ID NO:33), human TREX1 (SEQ ID NO:34), human VISTA (SEQ ID NO:35), human TGF-beta isoform 1 (SEQ ID NO:193), and human VEGF (SEQ ID NO:194). RNA can target or contain a sequence in the immune checkpoint nucleic acid set forth in any of SEQ ID NOs.: 1-30, 36-40, and 195-217.

The plasmids in any of the immunostimulatory bacteria also can encode a sequence of nucleotides that is an agonist of retinoic acid-inducible gene I (RIG-I) or a RIG-I binding element.

The immunostimulatory bacteria can include one or more of deletions in genes, such as one or more of purI⁻ (purM⁻), msbB⁻, purD⁻, flagellin⁻ (fliC⁻/fljB⁻), pagP⁻, adrA⁻, CsgD⁻ and hilA⁻. The immunostimulatory bacteria can be msbB⁻. For example, the immunostimulatory bacteria can contain a purI deletion, an msbB deletion, an asd gene deletion, and adrA deletion, and optionally a CsgD deletion. Exemplary of bacterial gene deletions are any of the following:

one or more of a mutation in a gene that alters the biosynthesis of lipopolysaccharide selected from among one or more of rfaL, rfaG, rfaH, rfaD, rfaP, rFb, rfa, msbB, htrB, firA, pagL, pagP, lpxR, arnT, eptA, and lpxT; and/or one or more of a mutation that introduces a suicide gene and is selected from one or more of sacB, nuk, hok, gef, kil or phlA; and/or one or more of a mutation that introduces a bacterial lysis gene and is selected from one or both of hly and cly; and/or a mutation in one or more virulence factor(s) selected from among as IsyA, pag, prg, iscA, virG, plc and act; and/or one or more mutations that modify the stress response selected from among recA, htrA, htpR, hsp and groEL; and/or a mutation in min that disrupts the cell cycle; and/or one or more mutations that disrupt or inactivate regulatory functions selected from among cya, crp, phoP/phoQ, and ompR.

As described, the RNAi includes shRNA and miRNA. Exemplary of an miRNA backbone into which the RNA that encodes the target or complement thereof is inserted is one based on miR-16-2 (SEQ ID NO:248), or the miRNA backbone of SEQ ID NO:249. The immunostimulatory bacteria can include miR-103 (SEQ ID NO:252), where mature miR-103 comprises the sequence: 5'-AGCAG-CAUUGUACAGGGCUAUGA-3.'

The RNAi can be expression under control of an RNA polymerase III or RNA polymerase II promoter. Generally shRNA is expressed under control of an RNAP III promoter; and miRNA is expressed under control of an RNAP II promoter. Many RNAP III and II promoters are known and available to those of skill in the art. RNAP III promoters include, for example, U3, H1, U6, 7SK and 7SL; and RNAP II promoters include viral promoters, a cytomegalovirus SV40 promoter, and adenovirus promoters. Many viral promoters, particularly later promoters are strong constitutive promoters.

The immunostimulatory bacterium can be a strain of *Salmonella, Shigella, E. coli, Bifidobacteriae*, Rikettsia, *Vibrio, Listeria, Klebsiella, Bordetella, Neisseria, Aeromonas, Francisella, Cholera, Corynebacterium, Citrobacter, Chlamydia, Hemophilus, Brucella, Mycobacterium, Mycoplasma, Legionella, Rhodococcus, Pseudomonas, Heliobacter, Bacillus*, and *Erysipelothrix*, or an attenuated strain thereof or modified strain thereof of any of the preceding list of bacterial strains.

Exemplary of the immunostimulatory bacteria are those where the plasmid contains one or more of sequence of nucleic acid encoding listeriolysin O (LLO) protein lacking the signal sequence (cytoLLO), a CpG motif, a DNA nuclear targeting sequence (DTS), a deletion of the gene encoding a flagellin subunit(s), and a retinoic acid-inducible gene-I (RIG-1) binding element.

Where the plasmid contains two or more encoding RNA that inhibits, suppresses or disrupts expression, each is separated by at least about 75 nucleotides, or at least 75 nucleotides, up to about or at least 100, 150, 200, 250, 300, 350, 400, 450, 500, 550, 600, 700, 800, 900, 1000, 1100, 1200, 1300, 1400, 1500 nucleotides (or base pairs), up to about 1600 or 1600 nucleotides (or base pairs), or between 75-1500 or 1600 nucleotides (or base pairs).

Other exemplary immunostimulatory bacteria include those that are auxotrophic for adenosine, and comprise: a deletion in the gene(s) encoding the flagella, a deletion in endA; contain a plasmid that encodes CytoLLO, contain a nuclear localization sequence, an asd plasmid complementation system, and encodes RNA that inhibits, suppresses or disrupts expression of an immune checkpoint or other target whose inhibition, suppression or disruption increases the anti-tumor immune response in a subject.

Such immunostimulatory bacteria include strains of *Salmonella*, such as a *Salmonella typhimurium* strain, such as for example, an attenuated *Salmonella typhimurium* strain selected from among strains designated as AST100, VNP20009, or strain YS1646 (ATCC #202165), RE88, SL7207, χ8429, χ8431, and χ8468.

The immunostimulatory bacterium can contain a plasmid encoding an shRNA encoded by the sequence of nucleotides set forth in any SEQ ID NOs: 36-40 and 75-78, or an miRNA encoded by the sequence of nucleotides set forth in any of SEQ ID NOs: 214-217.

Any of the immunostimulatory bacteria are those that, when grown, are harvested at stationary phase. Methods of producing the immunostimulatory bacteria include those that are cultured by standard methods, and harvested at stationary phase.

Compositions containing the immunostimulatory bacteria are provided. Such compositions contain the bacteria and a pharmaceutically acceptable excipient or vehicle. A single dose is therapeutically effective for treating a disease or disorder in which immune stimulation effects treatment. Exemplary of such stimulation is an immune response, that includes, but is not limited to, one or both of a specific immune response and non-specific immune response, both specific and non-specific response, innate response, primary immune response, adaptive immunity, secondary immune response, memory immune response, immune cell activation, immune cell proliferation, immune cell differentiation, and cytokine expression.

Pharmaceutical composition containing any of the immunostimulatory bacteria are provided. As are uses there for treatment of cancers, and methods of treatment of cancer. Methods and uses include treating a subject who has cancer, comprising administering an immunostimulatory bacterium or the pharmaceutical composition to a subject, such as a human. A method of treating a subject who has cancer, comprising administering an immunostimulatory bacterium. The Methods and uses include combination therapy in which a second anti-cancer agent or treatment is administered. The second anti-cancer agent is a chemotherapeutic agent that results in cytosolic DNA or radiotherapy, or an anti-immune checkpoint inhibitor, such as an anti-PD-1, or anti-PD-L1 or anti-CTLA4 antibody, or CAR-T cells or other therapeutic cells, such as stem cells, TIL cells and modified cells for cancer therapy.

As described herein, the immunostimulatory bacteria, such as the *Salmonella* strains, that encode RNAi, such as miRNA and shRNA, against TREX1 are complementary to therapies that are genotoxic or target or harm DNA to result in cytosolic DNA.

Administration can be by any suitable route, such as parenteral, and include additional agents that can facilitate or enhance delivery. Administrating can be oral or rectal or by aerosol into the lung or intratumoral, intravenously, intramuscularly, or subcutaneously.

Cancers include solid tumors and hematologic malignancies, such as, but not limited to, cancer of the breast, heart, lung, small intestine, colon, spleen, kidney, bladder, uterus, head and neck, ovary, prostate, brain, pancreas, skin, bone, liver, bone marrow, blood, thymus, uterus, testicles, cervix or liver.

The immunostimulatory bacteria can be formulated into compositions for administration, such as suspensions. They can be dried and stored as powders. Combinations of the immunostimulatory bacteria with others of the anti-cancer agents also are provided.

Also provided are shRNA and miRNA, such the nucleic acid molecule comprising the sequence of nucleic acids set forth in any of SEQ ID NOs.: 36-40 and 75-78. Plasmids containing such DNA also are provided. The immunostimulatory bacteria, such as *Salmonella* containing the plasmids are provided.

Combination therapies for treatment of cancers and malignancies are provided. The immunostimulatory bacteria can be administered before, or concurrently with other cancer therapies, including radiotherapy, chemotherapies, particularly genotoxic chemotherapies that result in cytosolic DNA, and immunotherapies, such as anti-checkpoint inhibitor antibodies, including anti-PD-L1, anti CTLA4, and other such immunotherapies.

Also provided are methods of treatment and uses for treating a subject who has a tumor that is $cd73^+$. The immunostimulatory bacteria for such treatment is auxotrophic for adenosine; and the subject has been or is identified as having a tumor that is $cd73^+$ by testing a tumor biopsy or other body tissue or fluid sample.

Methods of increasing colonization of an immunostimulatory bacterium in a subject are provided. These methods include administering the immunostimulatory bacterium to the subject; and inhibiting or suppressing expression of TREX1 and/or the activity of the encoded product of TREX1 in the subject.

The terms and expressions that are employed are used as terms of description and not of limitation, and there is no intention that in the use of such terms and expressions to excluding any equivalents of the features shown and described or portions thereof, but it is recognized that various modifications are contemplated.

BRIEF DESCRIPTION OF THE DRAWINGS

FIG. 2A depicts the results of qPCR analysis to determine the level of mRNA knockdown. FIG. 2B depicts the Western blot analysis of human PD-L1 shRNAs. Western blotting and densitometry were used to measure the level of PD-L1 protein expression.

FIG. 3A depicts results of qPCR analysis, used to determine the level of mRNA knockdown. FIG. 3B depicts results of Western blot analysis of the human TREX1 shRNAs. Western blotting and densitometry were used to measure the level of PD-L1 protein expression.

FIG. 4A depicts results of qPCR, used to determine the level of mRNA knockdown. FIG. 4B depicts the results of Western blot analysis of the human beta-catenin shRNAs. Western blotting and densitometry were used to measure the level of beta-catenin protein expression.

FIG. 5A depicts results of qPCR, used to determine the level of mRNA knockdown. FIG. 5B depicts the results of Western blot analysis of human SIRP-alpha shRNAs. Western blotting and densitometry were used to measure the level of SIRP-alpha protein expression.

FIG. 8A depicts results of qPCR, used to determine the level of mRNA knockdown. FIG. 8B depicts the results of Western blot analysis of human VISTA shRNAs. Western blotting and densitometry were used to measure the level of VISTA protein expression.

FIG. 9A depicts results of qPCR, used to determine the level of PD-L1 mRNA knockdown. FIG. 9B depicts results of qPCR, used to determine the level of TREX1 mRNA knockdown.

FIG. 10A depicts results of qPCR, used to determine the level of PD-L1 mRNA knockdown. FIG. 10B depicts results of qPCR, used to determine the level of SIRP-alpha mRNA knockdown.

FIG. 11A depicts results of qPCR, used to determine the level of PD-L1 mRNA knockdown. FIG. 11B depicts results of qPCR, used to determine the level of beta-catenin mRNA knockdown.

FIG. 12A depicts results of qPCR, used to determine the level of PD-L1 mRNA knockdown. FIG. 12B depicts results of qPCR, used to determine the level of VISTA mRNA knockdown.

FIG. 13A depicts results of qPCR, used to determine the level of PD-L1 mRNA knockdown. FIG. 13B depicts results of qPCR, used to determine the level of TREX1 mRNA knockdown.

FIG. 14A depicts results of qPCR, used to determine the level of PD-L1 mRNA knockdown. FIG. 14B depicts results of qPCR, used to determine the level of SIRP-alpha mRNA knockdown.

FIG. 15A depicts results of qPCR, used to determine the level of PDL1 mRNA knockdown. FIG. 15B depicts results of qPCR, used to determine the level of beta-catenin mRNA knockdown.

FIG. 16A depicts results of qPCR, used to determine the level of TREX1 mRNA knockdown. FIG. 16B depicts results of qPCR, used to determine the level of SIRP-alpha mRNA knockdown.

FIG. 17A depicts results of qPCR, used to determine the level of PD-L1 mRNA knockdown. FIG. 17B depicts results of qPCR, used to determine the level of beta-catenin mRNA knockdown.

FIG. 18A depicts results of qPCR, used to determine the level of TREX1 mRNA knockdown. FIG. 18B depicts results of qPCR, used to determine the level of VISTA mRNA knockdown.

FIG. 19A depicts results of qPCR, used to determine the level of PD-L1 mRNA knockdown. FIG. 19B depicts results of Western blot analysis; Western blotting and densitometry were used to measure the level of PD-L1 protein expression.

FIG. 21A depicts results of qPCR, used to determine the level of mouse TREX1 mRNA knockdown. FIG. 21B depicts results of Western blot analysis; Western blotting and densitometry were used to measure the level of mouse TREX1 protein expression.

FIG. 22A depicts results of qPCR, used to determine the level of mouse PD-L1 mRNA knockdown. FIG. 22B depicts results of Western blot analysis; Western blotting and densitometry were used to measure the level of mouse PD-L1 protein expression.

FIG. 24A depicts levels of pro-inflammatory cytokines. FIG. 24B depicts levels of immuno-suppressive cytokines. *$p<0.05$, **$p<0.01$, student's t-test.

Tumor volume was calculated using the modified ellipsoid formula ½(length×width). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. **p<0.01, student's t-test.

Figure 41:
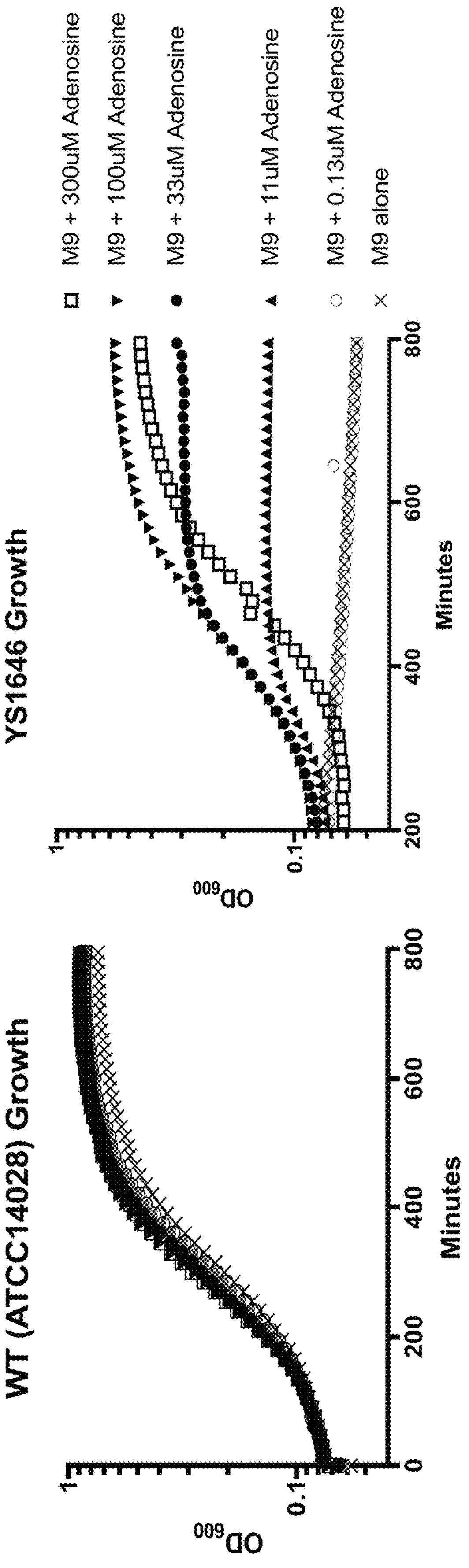

FIG. 41 depicts that strain YS1646 requires tumor microenvironment levels of adenosine for growth. Growth of strains YS1646 (purI−/msbB−) and the wild-type parental strain ATCC14028 at 37° C. in LB broth are shown, as measured by $OD_{600}$ using a Spectramax 96 well plate reader (Molecular devices).

Figure 42:
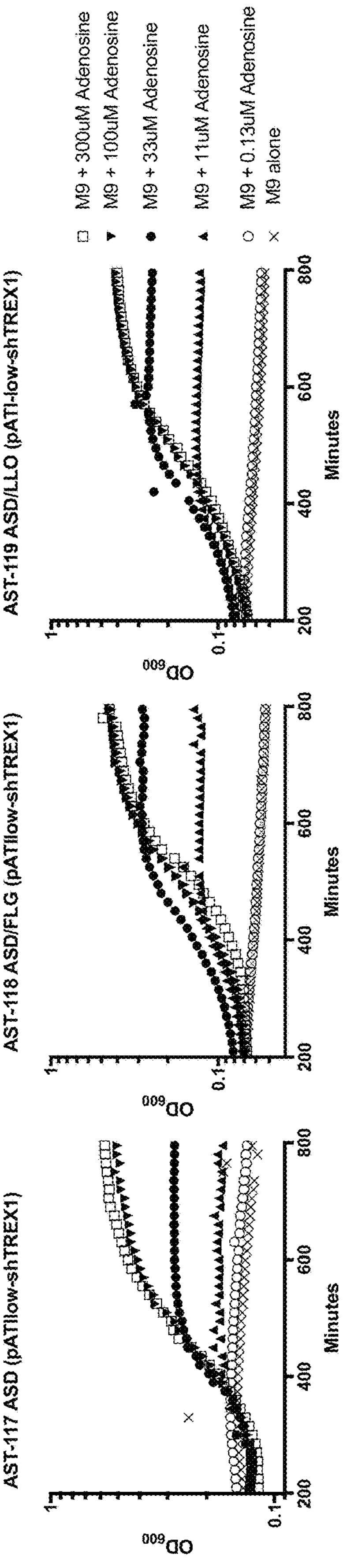

FIG. 42 depicts that ASD, FLG, and CytoLLO engineered strains require high adenosine for growth. The growth of strains AST-117 (YS1646 Δasd containing a low copy shTREX-1 plasmid), AST-118 (YS1646 Δasd/filC/fljB containing a low copy shTREX-1 plasmid), and AST-119 (YS1646 Δasd:LLO containing a low copy shTREX-1 plasmid) at 37° C. in LB broth are shown, as measured by $OD_{600}$ using a Spectramax 96 well plate reader (Molecular devices).

Figure 43:
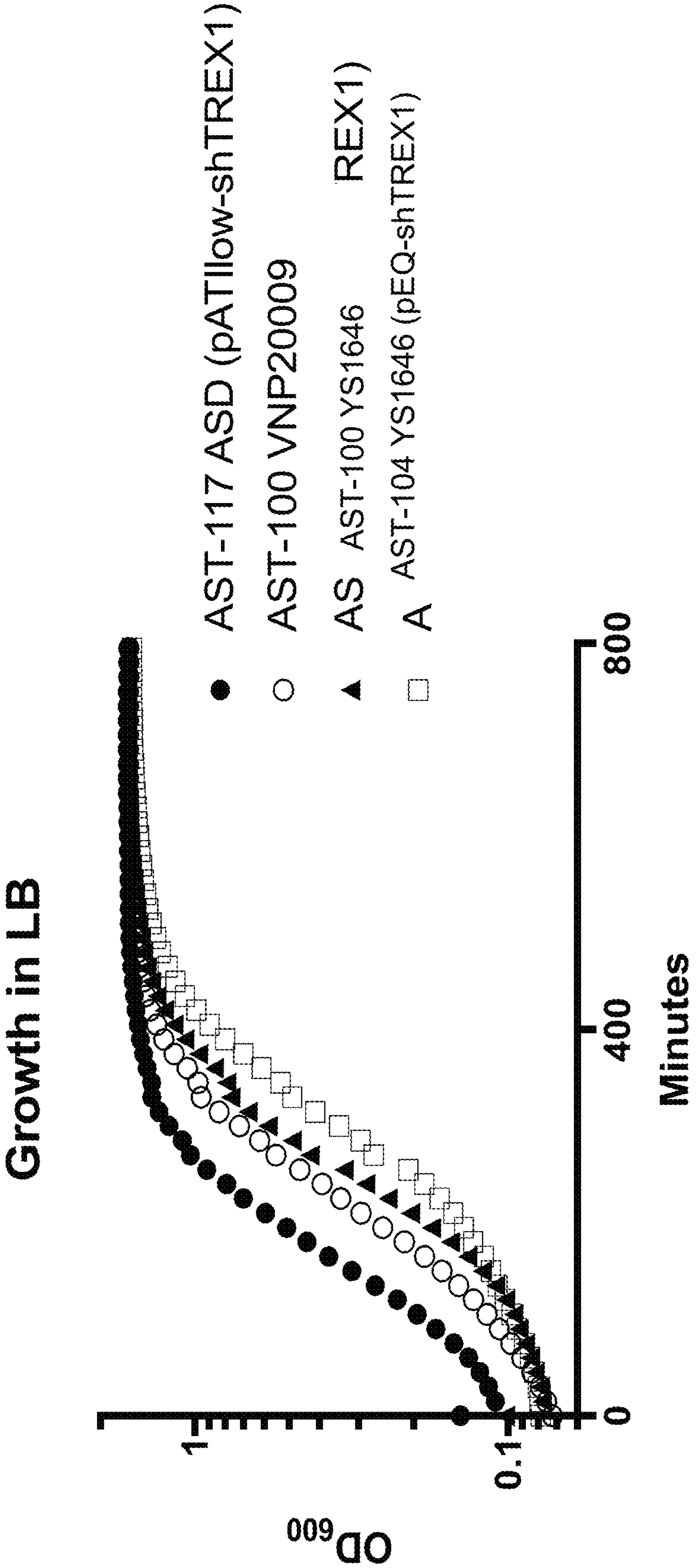

FIG. 43 depicts that a strain with a low copy origin of replication asd-encoding plasmid has superior growth kinetics than a strain with a high copy origin of replication asd-encoding plasmid. The growth of strains YS1646, AST-117 (YS1646 Δasd containing a low copy shTREX-1 plasmid with a functional asd gene), AST-104 (YS1646 containing a low copy pEQ shTREX-1 plasmid without an asd gene), and AST-110 (YS1646 Δasd containing a high copy pATI-shTREX-1 plasmid with a functional asd gene) at 37° C. in LB broth are shown, as measured by $OD_{600}$ using a Spectramax 96 well plate reader (Molecular devices).

Figure 44:
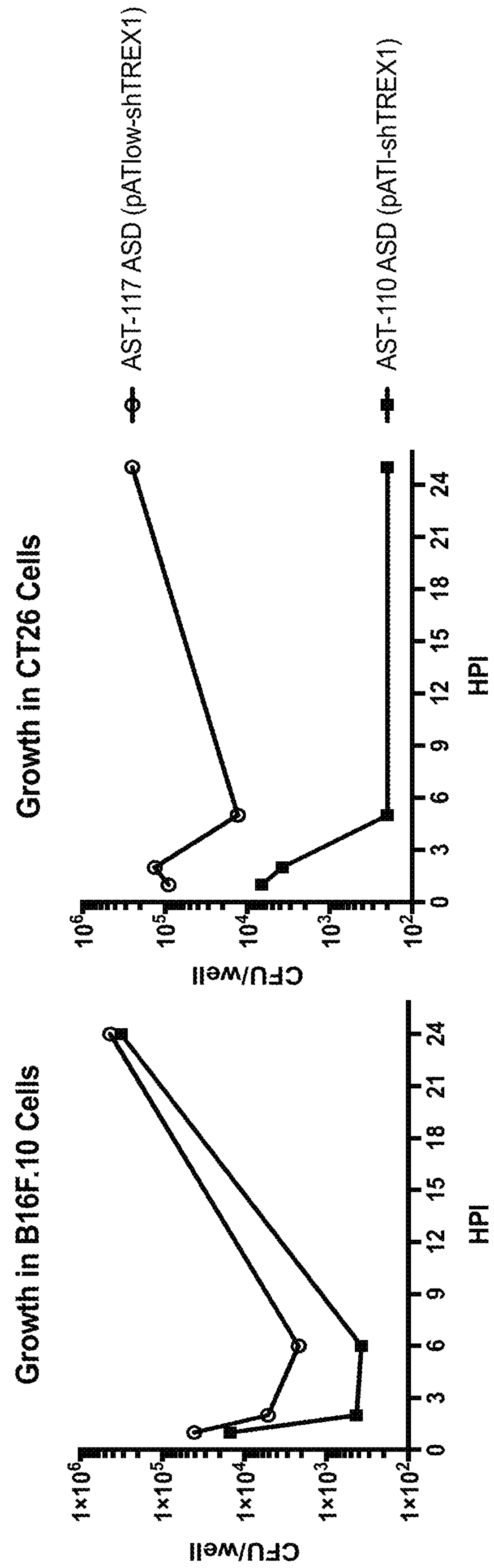

FIG. 44 depicts that a strain with a low copy asd plasmid is more fit than a strain with a high copy asd plasmid in mouse tumor cells. The intracellular growth of strains AST-117 (YS1646 Δasd containing a low copy shTREX-1 plasmid with a functional asd gene) and AST-110 (YS1646 Δasd containing a high copy pATI-shTREX-1 plasmid with a functional asd gene) are shown in B16F.10 mouse melanoma cells and CT26 mouse colon carcinoma cells. $5\times10^5$ cells in a 24 well dish were infected with the *S. typhimurium* strains at a MOI of 5. After 30 minutes of infection, media was replaced with media containing gentamycin to kill extracellular bacteria. At indicated time points, cell monolayers were lysed by osmotic shock the cell lysates were diluted and plated on LB agar to enumerate CFU.

Figure 45:
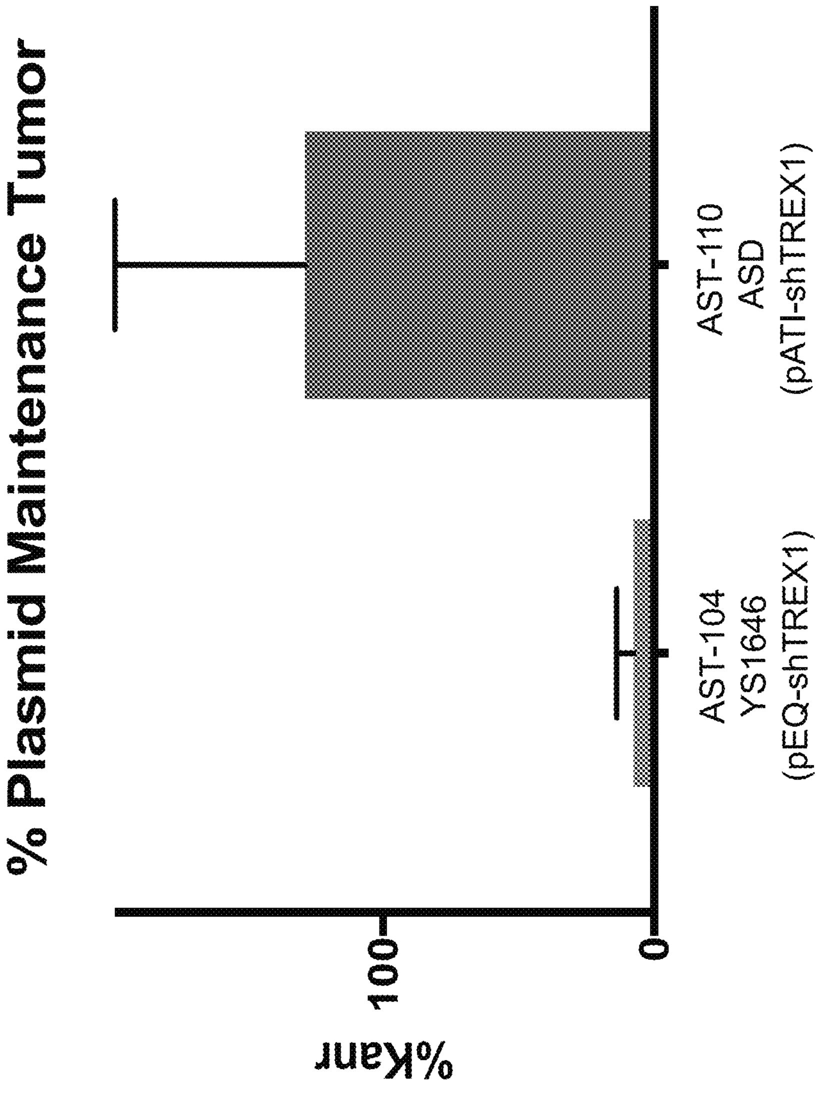

FIG. 45 depicts that in vivo, asd gene complementation systems result in retention of plasmids in *S. typhimurium*-infected tumors. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI shTREX1 plasmid (AST-110) or the YS1646 containing a pEQ shTREX-1 plasmid without an asd gene (AST-104). At 35 days post tumor implantation (12 days after the last dose of engineered *Salmonella* therapy), three mice per group were sacrificed, and tumors were homogenized using a GentleMACs homogenizer (Miltenyi Biotec) and plated on LB agar plates or LB agar plates with 50 ug/mL of Kanamycin. The figure depicts the percentage of Kanamycin resistant CFU in tumor tissue homogenates, ±SD.

Figure 46:
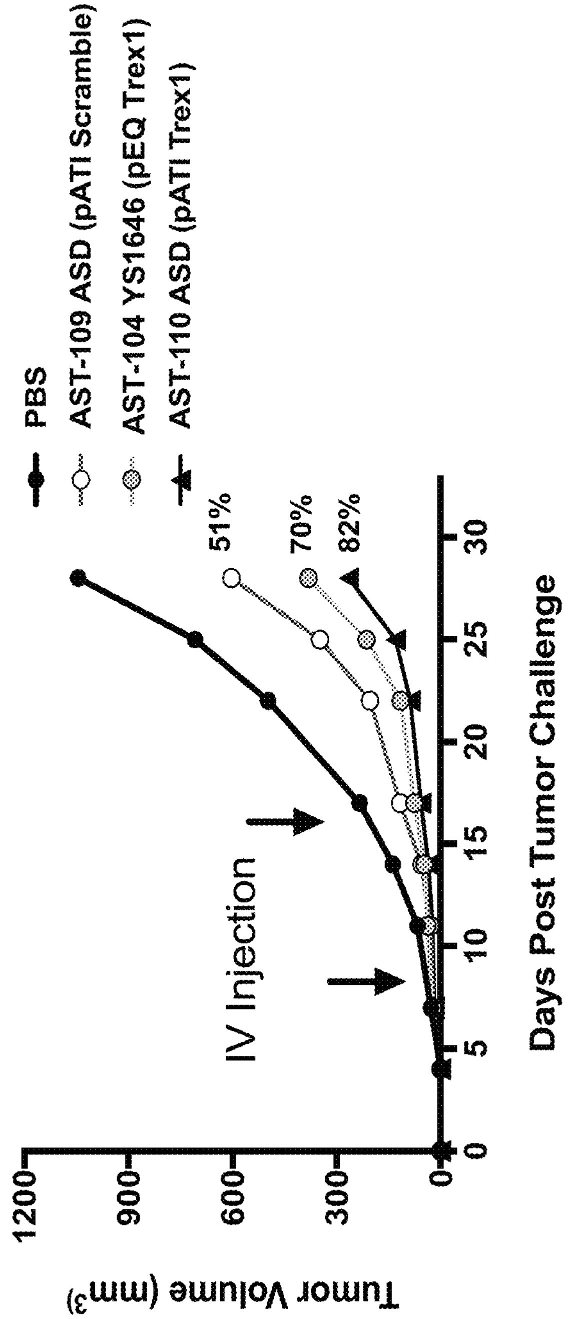

FIG. 46 depicts that the therapeutic efficacy of a strain containing a plasmid with asd gene complementation system and shTREX1 (AST-110) is improved. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid (AST-110) or the asd knockout strain containing the pATI-scramble plasmid (AST-109), or the YS1646 strain containing a pEQ-shTREX-1 plasmid without an asd gene (AST-104), or PBS control, on the days indicated by the arrows. Tumor measurements were performed using electronic calipers (Fowler, Newton, Mass.). Tumor volume was calculated using the modified ellipsoid formula ½(length×width). Mice were euthanized when tumor size reaches >20% of body weight or became necrotic, as per IACUC regulations. TGI was calculated as 1-(mean test tumor volume/mean control tumor volume)×100. The figure depicts the mean tumor growth of each group, ±SEM.

Figure 47:
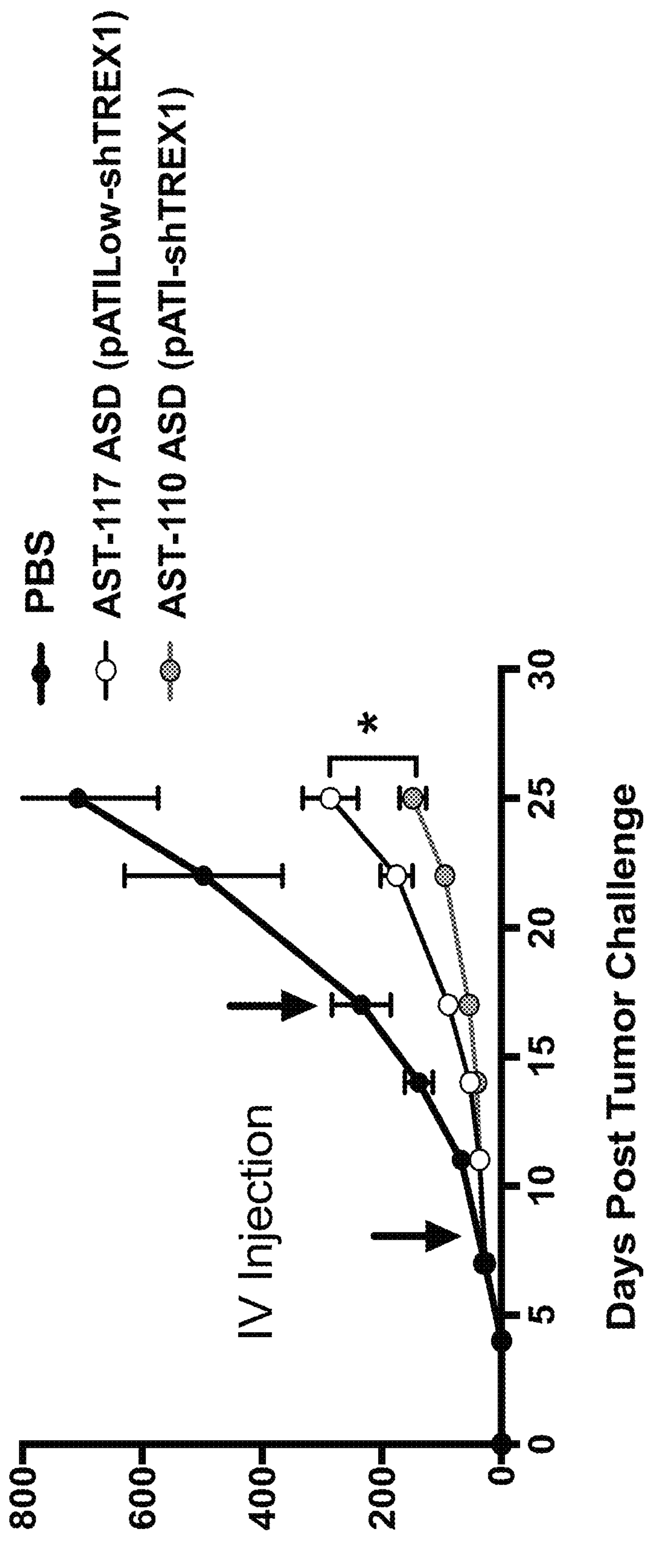

FIG. 47 depicts that a strain containing a low copy shTREX1 plasmid (AST-117) has superior anti-tumor properties compared to a strain containing a high copy plasmid (AST-110). BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid with a high copy number origin of replication (AST-110) or the asd knockout strain containing the pATI-shTREX1 plasmid with a low copy number origin of replication (AST-117), or PBS control, on the days indicated by the arrows. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. *p<0.05, student's t-test.

Figure 48B:
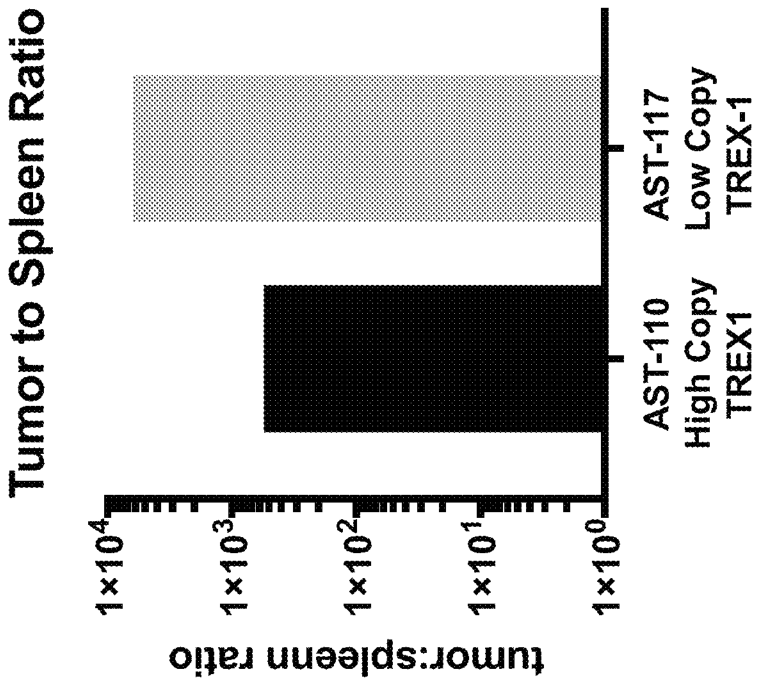
Figure 48A:
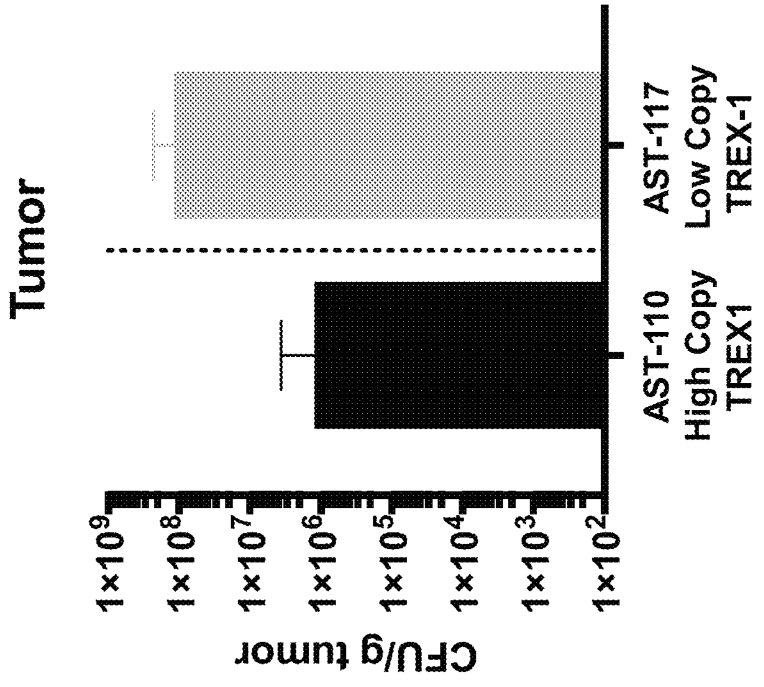

FIGS. 48A and 48B depict that the AST-117 low copy plasmid strain colonizes tumors better and has a higher tumor to spleen colonization ratio than the AST-110 high copy plasmid strain. BALB/c mice (6-8 wk old) were implanted with a single CT26 ($2\times10^5$ cells) subcutaneous flank tumor (n=9 per group). Mice with established tumors were IV injected with $5\times10^6$ CFU of the asd knockout strain containing the pATI-shTREX1 plasmid with a high copy number origin of replication (AST-110) or the asd knockout strain containing the pATI-shTREX1 plasmid with a low copy number origin of replication (AST-117). At 35 days post tumor implantation (12 days after the last dose of engineered *Salmonella* therapy), 3 mice per group were sacrificed, and tumors were homogenized using a GentleMACs homogenizer (Miltenyi Biotec) and plated on LB plates to enumerate the number of CFU per gram of tumor tissue. FIG. 48A depicts the mean CFU per gram of tumor tissue, ±SD. FIG. 48B depicts the tumor to spleen colonization ratios.

Figure 49B:
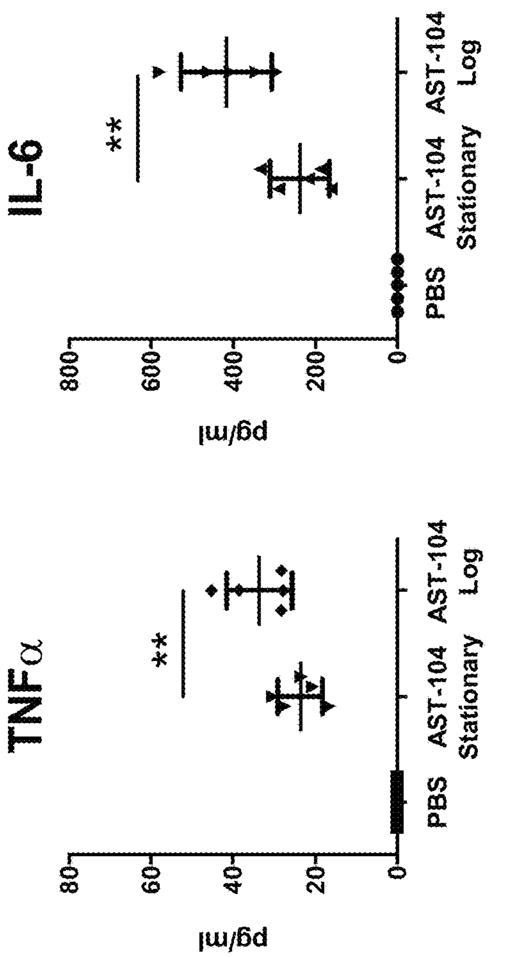
Figure 49A:
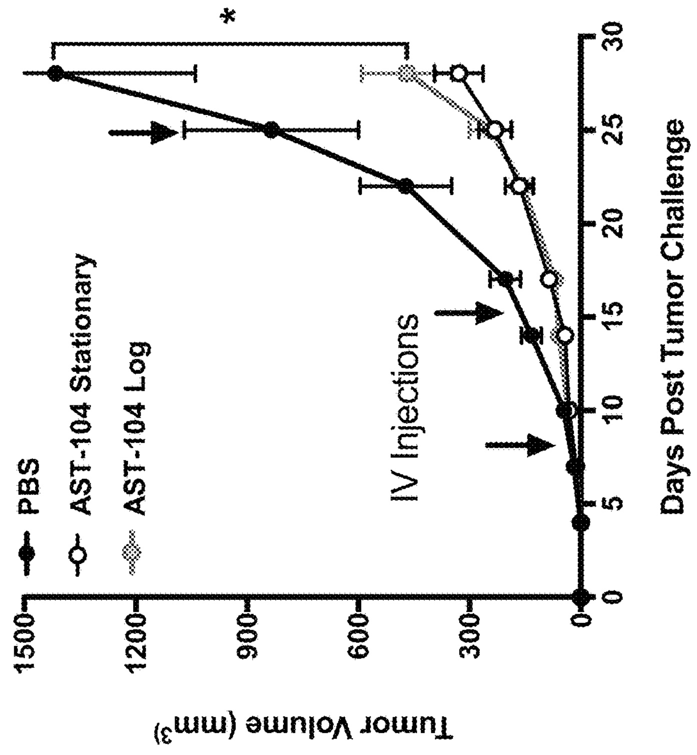

FIGS. 49A and 49B depict that a strain grown to stationary phase is equivalently potent, and less inflammatory than the same strain grown to log phase. BALB/c mice (6-8 wk old) were implanted with a single CT26 ($2\times10^5$ cells) subcutaneous flank tumor (n=9 per group). Mice with established tumors were IV injected with $5\times10^6$ CFU of the YS1646 strain containing a pEQ-shTREX-1 plasmid (AST-104) harvested at log phase or stationary phase, or PBS control, on the days indicated by the arrows. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1-(mean test tumor volume/mean control tumor volume)×100. FIG. 49A depicts the mean tumor growth of each group, ±SEM. *p<0.05, student's t-test. FIG. 49B depicts the levels of TNF-alpha and IL-6. Mice were bled 6 hrs following the first dose and systemic serum cytokines tested by Luminex (Luminex Corp) and mouse cytometric bead array (FACS Fortessa, FCAP software, all BD Biosciences). **p<0.01, student's t-test.

Figure 50:
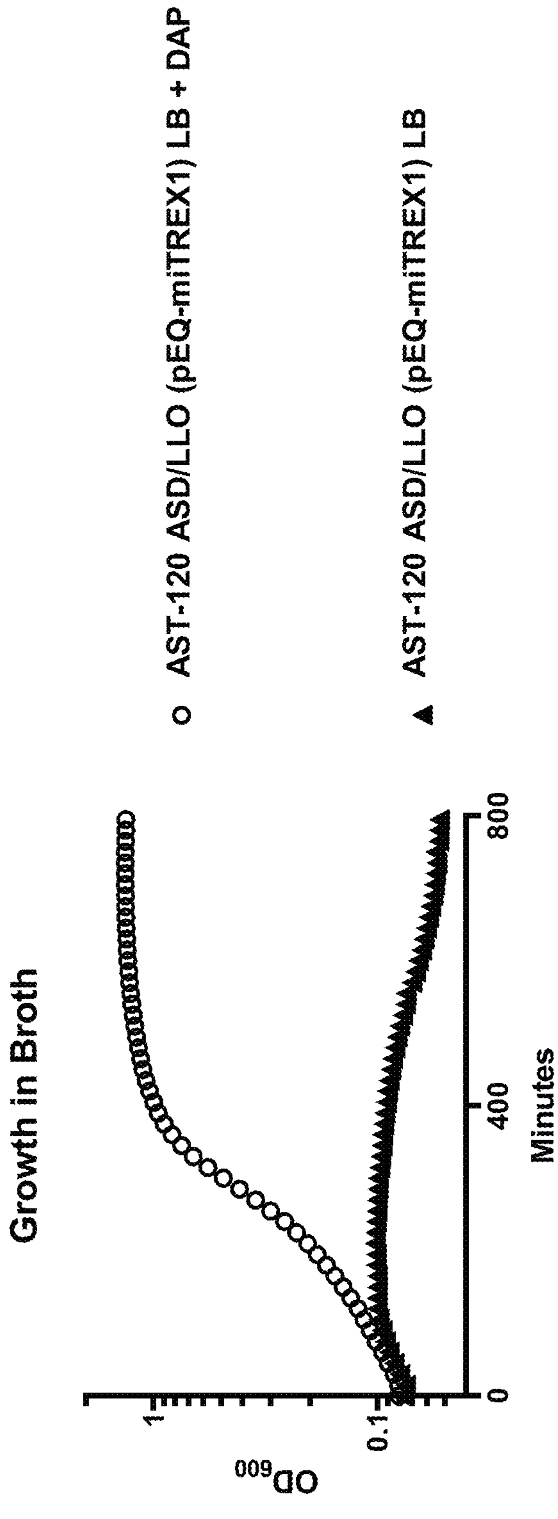

FIG. 50 depicts that autolytic strain (AST-120) cannot grow in the absence of DAP. The figure depicts the growth of Δasd:cytoLLO strain containing a pEQU6-shTREX1 plasmid that does not contain an asd gene (AST-120) over time in LB broth alone, or in LB broth supplemented with 50 μg/mL DAP, as measured by $OD_{600}$ using a Spectramax 96 well plate reader (Molecular devices).

Figure 51:
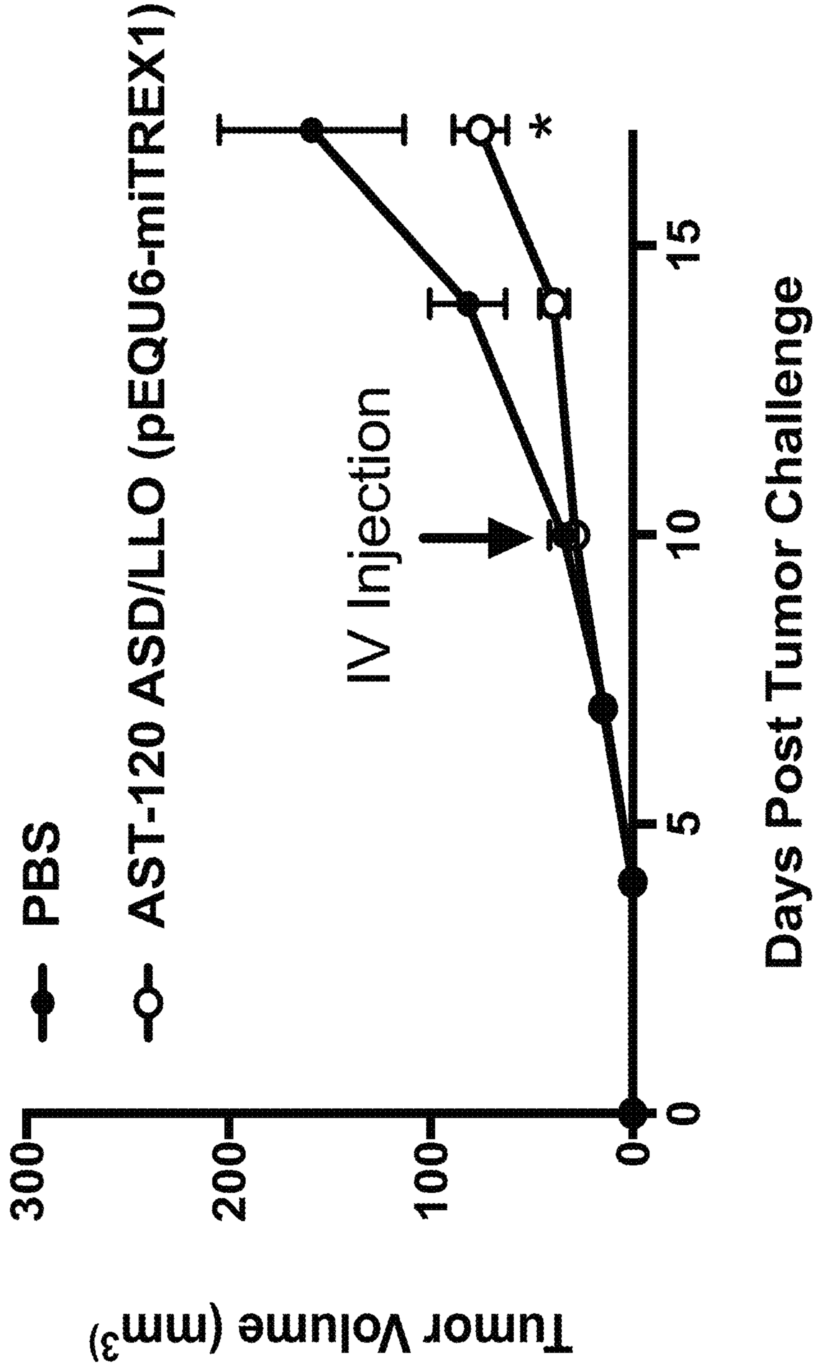

FIG. 51 depicts the anti-tumor activity of the autolytic strain (AST-120). BALB/c mice (6-8 wk old) were implanted with a single CT26 ($2\times10^5$ cells) subcutaneous flank tumor (n=9 per group). Mice with established tumors were IV injected with $5\times10^6$ CFU of the of Δasd:cytoLLO strain containing a pEQU6-shTREX1 plasmid that does not contain an asd gene (AST-120), or PBS control, on the days indicated by the arrows. Tumor measurements were performed using electronic calipers (Fowler, Newton, Mass.). Tumor volume was calculated using the modified ellipsoid formula ½(length×width). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. *p<0.05, student's t-test.

Figure 52:
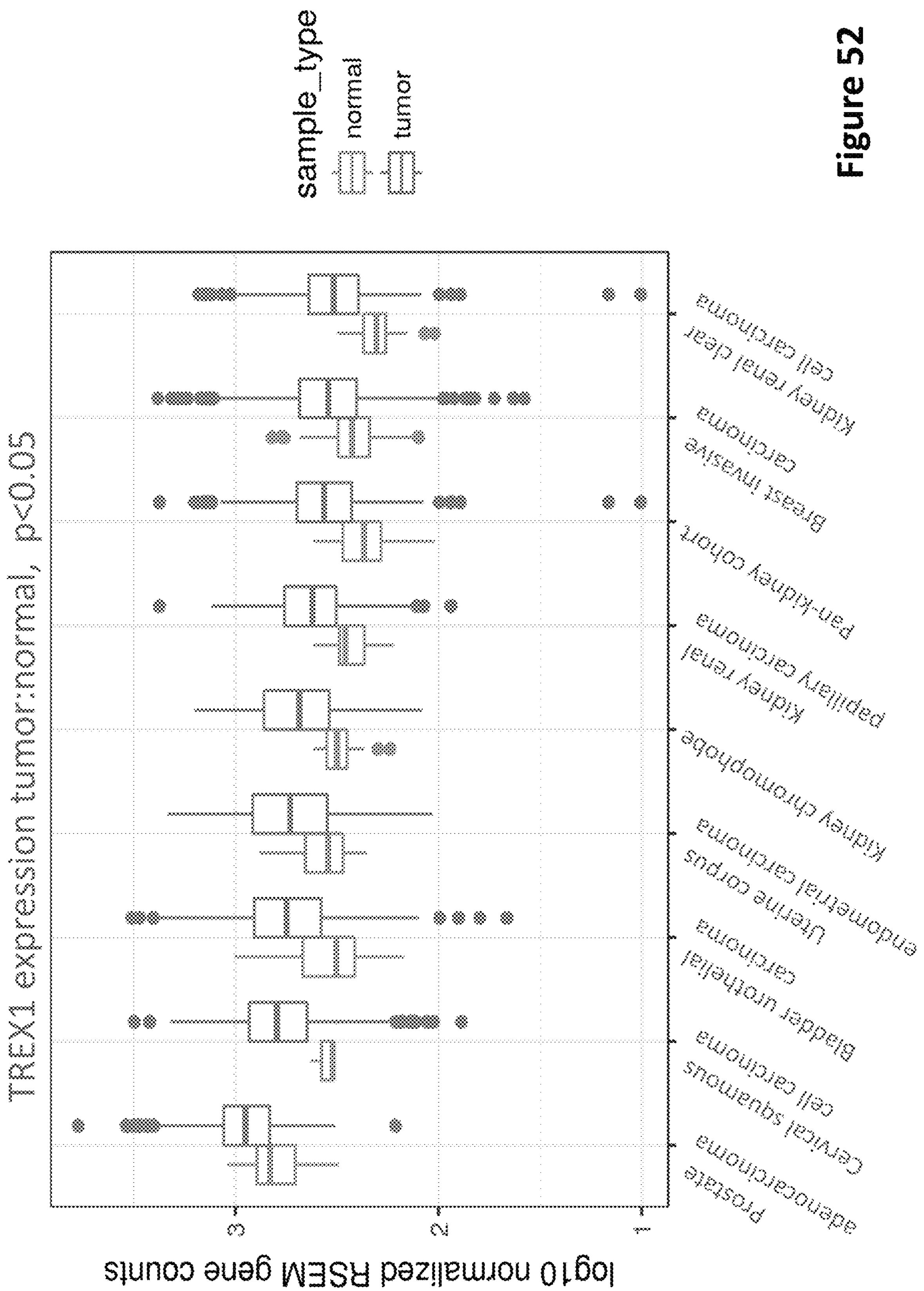

FIG. 52 depicts that TREX1 expression is increased in several human tumor types. Analysis of the relative gene expression of the TREX1 gene using the TCGA database was performed from a broad array of tumor types. Tumor types with a significant upregulation of TREX1 compared to normal tissue are displayed: prostate, breast, cervical, uterine and bladder (p values: BRCA—7.7e-16; PRAD—9.4e-12; UCEC—2.5e-05; BLCA—3.7e-03; CESC—7.7e-03) and multiple forms of kidney cancer (p values: KIPAN—8.9e-39; KIRC—9.6e-35; KIRP—5.8e-14; KICH—4.9e-08).

Figure 53:
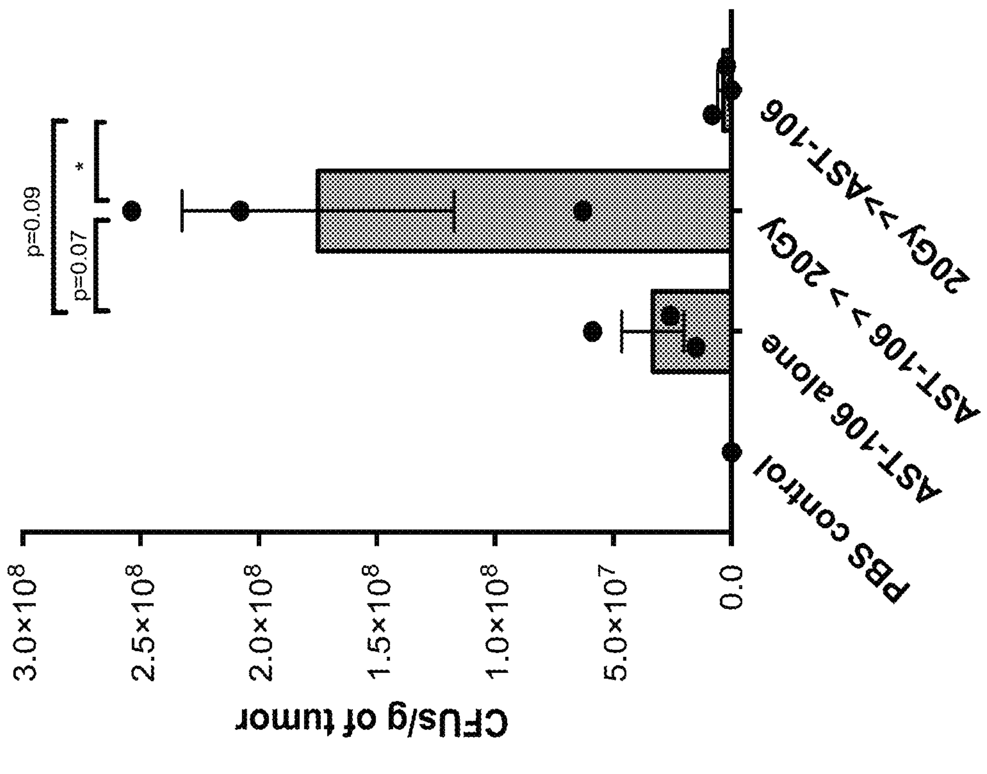

FIG. 53 depicts that radiotherapy after administration of *S. typhimurium* strain AST-106 increases tumor colonization. BALB/c mice (6-8 wk old) were inoculated subcutaneously in the right flank with $1\times10^5$ mouse TSA breast carcinoma cells. Mice bearing established tumors were administered the following: IV injection of $5\times10^6$ CFUs of AST-106 (YS1646 transformed with pEQU6-miTREX1) followed 4 hours later with 0 Gy (3 mice), or $5\times10^6$ CFUs of AST-106 followed 4 hours later with 20 Gy (3 mice); 20 Gy irradiation followed 4 hours later with $5\times10^6$ CFUs of AST-106 (3 mice), or PBS IV followed by 0 Gy radiation (1 mouse). Focal radiotherapy was administered using a small animal radiation research platform (SARRP) device (XStrahl Life Sciences). Mice were sacrificed 24 hours later, and tumors were harvested and weighed. Tumors were homogenized in 10 mL sterile PBS using M tubes in a GentleMacs device (Miltenyi Biotec), then 10-fold serial dilutions were performed and plated on LB agar plates containing kanamycin. The following day, colony forming units (CFU) were counted and CFU per gram of tumor tissue was calculated. *p<0.05, student's t-test.

DETAILED DESCRIPTION

OUTLINE

A. DEFINITIONS
B. OVERVIEW OF THE IMMUNOSTIMULATORY BACTERIA
C. CANCER IMMUNOTHERAPEUTICS
  1. Immunotherapies
  2. Adoptive Immunotherapies
  3. Cancer Vaccines and Oncolytic Viruses
D. BACTERIAL CANCER IMMUNOTHERAPY
  1. Bacterial therapies
  2. Comparison of the Immune Responses to Bacteria and Viruses
  3. *Salmonella* Therapy
    a. Tumor-tropic Bacteria.
    b. *Salmonella enterica* serovar *typhimurium*
    c. Bacterial Attenuation
      i. msbB⁻ Mutants
      ii. purI⁻ Mutants
      iii. Combinations of Attenuating Mutations
      iv. VNP20009 and Other Attenuated *S. typhimurium* strains
      v. Attenuated *S. typhimurium* Engineered To Deliver Macromolecules
  4. Enhancements of Immunostimulatory Bacteria to Increase Therapeutic Index
    a. asd Gene Deletion
    b. Adenosine Auxotrophy
    c. Flagellin Deficient Strains
    d. *Salmonella* Engineered to Escape the *Salmonella* Containing Vacuole (SCV)
    e. Deletions in *Salmonella* Genes Required for Biofilm Formation
    f. Deletions in Genes in the LPS Biosynthetic Pathway
    g. Deletions of SPI-1 Genes
    h. Endonuclease (endA) Mutations To Increase Plasmid Delivery
    i. RIG-I Inhibition
    j. DNase II Inhibition
    k. RNase H2 Inhibition
    l. Stabilin-1/CLEVER-1 Inhibition
    m. Bacterial Culture Conditions
E. CONSTRUCTING EXEMPLARY PLASMIDS
  1. Interfering RNAs (RNAi)
    a. shRNA
    b. micro-RNA
  2. Origin of Replication and Plasmid Copy Number
  3. CpG Motifs and CpG Islands
  4. Plasmid Maintenance/Selection Components
  5. DNA Nuclear Targeting Sequences
F. TUMOR TARGETING IMMUNOSTIMULATORY BACTERIA CONTAIN RNAI AGAINST EXEMPLARY IMMUNE TARGET GENES TO STIMULATE ANTI-TUMOR IMMUNITY
  1. TREX1
  2. PD-L1
  3. VISTA
  4. SIRPα
  5. β-catenin
  6. TGF-β
  7. VEGF
  8. Additional Exemplary Checkpoint Targets
G. COMBINATIONS OF RNAI shRNAS TO MULTIPLE IMMUNE TARGETS WITHIN A SINGLE THERAPEUTIC MODALITY AND COMBINATION THERAPY
  1. TREX1 and Other Targets
  2. TREX1 and Radiotherapy
  3. TREX1 and Immunogenic Chemotherapy
  4. Combination Therapy with Anti-Checkpoint Antibodies
H. PHARMACEUTICAL PRODUCTION, COMPOSITIONS, AND FORMULATIONS
  1. Manufacturing
    a. Cell Bank Manufacturing
    b. Drug Substance Manufacturing
    c. Drug Product Manufacturing
  2. Compositions
  3. Formulations
    a. Liquids, Injectables, Emulsions
    b. Dried Thermostable Formulations -continued

| OUTLINE | |
|---|---|
| | 4. Compositions for Other Routes of Administration |
| | 5. Dosages and Administration |
| | 6. Packaging and Articles of Manufacture |
| I. | METHODS OF TREATMENT AND USES |
| | 1. Cancers and Tumors |
| | 2. Administration |
| | 3. Monitoring |
| J. | EXAMPLES |

A. Definitions

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, therapeutic bacteria are bacteria that effect therapy, such as cancer or anti-tumor therapy, when administered to a subject, such as a human.

As used herein, immunostimulatory bacteria are therapeutic bacteria that, when introduced into a subject, accumulate in immunoprivileged tissues and cells, such as tumors, and replicate and/or express products that are immunostimulatory or that result in immunostimulation. The immunostimulatory bacteria are attenuated in the host by virtue of reduced toxicity or pathogenicity and/or by virtue of encoded products that reduce toxicity or pathogenicity, as the immunostimulatory bacteria cannot replicate and/or express products, except primarily in immunoprivileged environments. Immunostimulatory bacteria provided herein are modified to encode a product or products or exhibit a trait or property that renders them immunostimulatory. Such products, properties and traits include, at least one of an shRNA that targets, disrupts or inhibits a checkpoint gene or gene encoding such inhibitor or a metabolite that is immunosuppressive or an immunosuppressive pathway. These include encoding an siRNA, such an shRNA, that targets or inhibits TREX1 expression, a modification that renders the bacterium auxotrophic for adenosine, and/or an inhibitor or disruptor of an immune checkpoint gene or product thereof, such as an shRNA that disrupts or inhibits PD-L1.

As used herein, the strain designations VNP20009 (see, e.g., International PCT application Publication No. WO 99/13053, see, also U.S. Pat. No. 6,863,894) and YS1646 and 41.2.9 are used interchangeably and each refer to the strain deposited with the American Type Culture Collection and assigned Accession No. 202165. VNP20009 is a modified attenuated strain of *Salmonella typhimurium*, which contains deletions in msbB and purI, and was generated from wild type strain ATCC 14028.

As used herein, the strain designations YS1456 and 8.7 are used interchangeably and each refer to the strain deposited with the American Type Culture Collection and assigned Accession No. 202164 (see, U.S. Pat. No. 6,863,894).

As used herein, an origin of replication is a sequence of DNA at which replication is initiated on a chromosome, plasmid or virus. For small DNA, including bacterial plasmids and small viruses, a single origin is sufficient.

The origin of replication determines the vector copy number, which depends upon the selected origin of replication. For example, if the expression vector is derived from the low-copy-number plasmid pBR322, it is between about 25-50 copies/cell, and if derived from the high-copy-number plasmid pUC, it can be 150-200 copies/cell.

As used herein, medium copy number of a plasmid in cells is about or is 150 or less than 150, low copy number is 15-30, such as 20 or less than 20. Low to medium copy number is less than 150. High copy number is greater than 150 copies/cell.

As used herein, a CpG motif is a pattern of bases that include an unmethylated central CpG ("p" refers to the phosphodiester link between consecutive C and G nucleotides) surrounded by at least one base flanking (on the 3' and the 5' side of) the central CpG. A CpG oligodeoxynucleotide is an oligodeoxynucleotide that is at least about ten nucleotides in length and includes an unmethylated CpG. At least the C of the 5' CG 3' is unmethylated.

As used herein, a RIG-I binding sequence refers to a 5'triphosphate (5'ppp) structure directly, or that which is synthesized by RNA pol III from a poly(dA-dT) sequence, which by virtue of interaction with RIG-I can activate type I IFN via the RIG-I pathway. The RNA includes at least four A ribonucleotides (A-A-A-A); it can contain 4, 5, 6, 7, 8, 9, 10 or more. The RIG-I binding sequence is introduced into a plasmid in the bacterium for transcription into the polyA.

As used herein, a "modification" is in reference to modification of a sequence of amino acids of a polypeptide or a sequence of nucleotides in a nucleic acid molecule and includes deletions, insertions, and replacements of amino acids or nucleotides, respectively. Methods of modifying a polypeptide are routine to those of skill in the art, such as by using recombinant DNA methodologies.

As used herein, a modification to a bacterial genome or to a plasmid or gene includes deletions, replacements and insertions of nucleic acid.

As used herein, RNA interference (RNAi) is a biological process in which RNA molecules inhibit gene expression or translation, by neutralizing targeted mRNA molecules to inhibit translation and thereby expression of a targeted gene.

As used herein, RNA molecules that act via RNAi are referred to as inhibitory by virtue of their silencing of expression of a targeted gene. Silencing expression means that expression of the targeted gene is reduced or suppressed or inhibited.

As used herein, gene silencing via RNAi is said to inhibit, suppress, disrupt or silence expression of a targeted gene. A targeted gene contains sequences of nucleotides that correspond to the sequences in the inhibitory RNA, whereby the inhibitory RNA silences expression of mRNA.

As used herein, inhibiting, suppressing, disrupting or silencing a targeted gene refer to processes that alter expression, such as translation, of the targeted gene, whereby activity or expression of the product encoded by the targeted gene is reduced. Reduction, includes a complete knock-out or a partial knockout, whereby with reference to the immunostimulatory bacterium provided herein and administration herein, treatment is affected.

As used herein, small interfering RNA (siRNA) are small pieces of double-stranded (ds) RNA, usually about 21 nucleotides long, with 3' overhangs (2 nucleotides) at each end that can be used to "interfere" with the translation of proteins by binding to and promoting the degradation of messenger RNA (mRNA) at specific sequences. In doing so, siRNA prevent the production of specific proteins based on the nucleotide sequences of their corresponding mRNA. The process is called RNA interference (RNAi), and also is referred to as siRNA silencing or siRNA knockdown.

As used herein, short-hairpin RNA or small-hairpin RNA (shRNA) is an artificial RNA molecule with a tight hairpin turn that can be used to silence target gene expression via RNA interference (RNAi). Expression of shRNA in cells is typically accomplished by delivery of plasmids or through viral or bacterial vectors. As used herein, a tumor microenvironment (TME) is the cellular environment in which the tumor exists, including surrounding blood vessels, immune cells, fibroblasts, bone marrow-derived inflammatory cells, lymphocytes, signaling molecules and the extracellular matrix (ECM). Conditions that exist include, but are not limited to, increased vascularization, hypoxia, low pH, increased lactate concentration, increased pyruvate concentration, increased interstitial fluid pressure and altered metabolites or metabolism, such as higher levels of adenosine, indicative of a tumor.

As used herein, human type I interferons (IFNs) are a subgroup of interferon proteins that regulate the activity of the immune system. All type I IFNs bind to a specific cell surface receptor complex, as the IFN-α receptor. Type I interferons include IFN-α and IFN-β, among others. IFN-β proteins are produced by fibroblasts, and have antiviral activity that is involved mainly in innate immune response. Two types of IFN-β are IFN-β1 (IFNB1) and IFN-β3 (IFNB3).

As used herein, recitation that a nucleic acid or encoded RNA targets a gene means that it inhibits or suppresses or silences expression of the gene by any mechanism. Generally, such nucleic acid includes at least a portion complementary to the targeted gene, where the portion is sufficient to form a hybrid with the complementary portion.

As used herein, "deletion," when referring to a nucleic acid or polypeptide sequence, refers to the deletion of one or more nucleotides or amino acids compared to a sequence, such as a target polynucleotide or polypeptide or a native or wild-type sequence.

As used herein, "insertion" when referring to a nucleic acid or amino acid sequence, describes the inclusion of one or more additional nucleotides or amino acids, within a target, native, wild-type or other related sequence. Thus, a nucleic acid molecule that contains one or more insertions compared to a wild-type sequence, contains one or more additional nucleotides within the linear length of the sequence.

As used herein, "additions," to nucleic acid and amino acid sequences describe addition of nucleotides or amino acids onto either termini compared to another sequence.

As used herein, "substitution" or "replacement" refers to the replacing of one or more nucleotides or amino acids in a native, target, wild-type or other nucleic acid or polypeptide sequence with an alternative nucleotide or amino acid, without changing the length (as described in numbers of residues) of the molecule. Thus, one or more substitutions in a molecule does not change the number of amino acid residues or nucleotides of the molecule. Amino acid replacements compared to a particular polypeptide can be expressed in terms of the number of the amino acid residue along the length of the polypeptide sequence.

As used herein, "at a position corresponding to" or recitation that nucleotides or amino acid positions "correspond to" nucleotides or amino acid positions in a disclosed sequence, such as set forth in the Sequence Listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g., *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073).

As used herein, alignment of a sequence refers to the use of homology to align two or more sequences of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence. Related or variant polypeptides or nucleic acid molecules can be aligned by any method known to those of skill in the art. Such methods typically maximize matches, and include methods, such as using manual alignments and by using the numerous alignment programs available (e.g., BLASTP) and others known to those of skill in the art. By aligning the sequences of polypeptides or nucleic acids, one skilled in the art can identify analogous portions or positions, using conserved and identical amino acid residues as guides. Further, one skilled in the art also can employ conserved amino acid or nucleotide residues as guides to find corresponding amino acid or nucleotide residues between and among human and non-human sequences. Corresponding positions also can be based on structural alignments, for example by using computer simulated alignments of protein structure. In other instances, corresponding regions can be identified. One skilled in the art also can employ conserved amino acid residues as guides to find corresponding amino acid residues between and among human and non-human sequences.

As used herein, a "property" of a polypeptide, such as an antibody, refers to any property exhibited by a polypeptide, including, but not limited to, binding specificity, structural configuration or conformation, protein stability, resistance to proteolysis, conformational stability, thermal tolerance, and tolerance to pH conditions. Changes in properties can alter an "activity" of the polypeptide. For example, a change in the binding specificity of the antibody polypeptide can alter the ability to bind an antigen, and/or various binding activities, such as affinity or avidity, or in vivo activities of the polypeptide.

As used herein, an "activity" or a "functional activity" of a polypeptide, such as an antibody, refers to any activity exhibited by the polypeptide. Such activities can be empirically determined. Exemplary activities include, but are not limited to, ability to interact with a biomolecule, for example, through antigen-binding, DNA binding, ligand binding, or dimerization, enzymatic activity, for example, kinase activity or proteolytic activity. For an antibody (including antibody fragments), activities include, but are not limited to, the ability to specifically bind a particular antigen, affinity of antigen-binding (e.g., high or low affinity), avidity of antigen-binding (e.g., high or low avidity), on-rate, off-rate, effector functions, such as the ability to promote antigen neutralization or clearance, virus neutralization, and in vivo activities, such as the ability to prevent infection or invasion of a pathogen, or to promote clearance, or to penetrate a particular tissue or fluid or cell in the body. Activity can be assessed in vitro or in vivo using recognized assays, such as ELISA, flow cytometry, surface plasmon resonance or equivalent assays to measure on- or off-rate, immunohistochemistry and immunofluorescence histology and microscopy, cell-based assays, flow cytometry and binding assays (e.g., panning assays).

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs.

As used herein, "antibody" refers to immunoglobulins and immunoglobulin fragments, whether natural or partially or wholly synthetically, such as recombinantly produced, including any fragment thereof containing at least a portion of the variable heavy chain and light region of the immunoglobulin molecule that is sufficient to form an antigen binding site and, when assembled, to specifically bind an antigen. Hence, an antibody includes any protein having a binding domain that is homologous or substantially homologous to an immunoglobulin antigen-binding domain (antibody combining site). For example, an antibody refers to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g., heavy chains include, but are not limited to, VH chains, VH-CH1 chains and VH-CH1-CH2-CH3 chains), and each light chain can be a full-length light chain or a portion thereof sufficient to form an antigen binding site (e.g., light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region.

For purposes herein, the term antibody includes full-length antibodies and portions thereof including antibody fragments, such as anti-EGFR antibody fragments. Antibody fragments, include, but are not limited to, Fab fragments, Fab' fragments, $F(ab)_2$ fragments, Fv fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibody also includes synthetic antibodies, recombinantly produced antibodies, multispecific antibodies (e.g., bispecific antibodies), human antibodies, non-human antibodies, humanized antibodies, chimeric antibodies, and intrabodies. Antibodies provided herein include members of any immunoglobulin class (e.g., IgG, IgM, IgD, IgE, IgA and IgY), any subclass (e.g., IgG1, IgG2, IgG3, IgG4, IgA1 and IgA2) or sub-subclass (e.g., IgG2a and IgG2b).

As used herein, "nucleic acid" refers to at least two linked nucleotides or nucleotide derivatives, including a deoxyribonucleic acid (DNA) and a ribonucleic acid (RNA), joined together, typically by phosphodiester linkages. Also included in the term "nucleic acid" are analogs of nucleic acids such as peptide nucleic acid (PNA), phosphorothioate DNA, and other such analogs and derivatives or combinations thereof. Nucleic acids also include DNA and RNA derivatives containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term also includes, as equivalents, derivatives, variants and analogs of either RNA or DNA made from nucleotide analogs, single (sense or antisense) and double-stranded nucleic acids. Deoxyribonucleotides include deoxyadenosine, deoxycytidine, deoxyguanosine and deoxythymidine. For RNA, the uracil base is uridine.

As used herein, an isolated nucleic acid molecule is one which is separated from other nucleic acid molecules which are present in the natural source of the nucleic acid molecule. An "isolated" nucleic acid molecule, such as a cDNA molecule, can be substantially free of other cellular material, or culture medium when produced by recombinant techniques, or substantially free of chemical precursors or other chemicals when chemically synthesized. Exemplary isolated nucleic acid molecules provided herein include isolated nucleic acid molecules encoding an antibody or antigen-binding fragments provided.

As used herein, "operably linked" with reference to nucleic acid sequences, regions, elements or domains means that the nucleic acid regions are functionally related to each other. For example, nucleic acid encoding a leader peptide can be operably linked to nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, "polypeptide" refers to two or more amino acids covalently joined. The terms "polypeptide" and "protein" are used interchangeably herein. As used herein, a "peptide" refers to a polypeptide that is from 2 to about or 40 amino acids in length.

As used herein, an "amino acid" is an organic compound containing an amino group and a carboxylic acid group. A polypeptide contains two or more amino acids. For purposes herein, amino acids contained in the antibodies provided include the twenty naturally-occurring amino acids (see Table below), non-natural amino acids, and amino acid analogs (e.g., amino acids wherein the α-carbon has a side chain). As used herein, the amino acids, which occur in the various amino acid sequences of polypeptides appearing herein, are identified according to their well-known, three-letter or one-letter abbreviations (see Table below). The nucleotides, which occur in the various nucleic acid molecules and fragments, are designated with the standard single-letter designations used routinely in the art.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.,* 243:3557-59 (1968) and adopted at 37 C.F.R. §§ 1.821-1.822, abbreviations for amino acid residues are shown in the following Table:

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glutamic Acid and/or Glutamine |
| W | Trp | Tryptophan |
| R | Arg | Arginine |
| D | Asp | Aspartic acid |
| N | Asn | Asparagine |
| B | Asx | Aspartic Acid and/or Asparagine |
| C | Cys | Cysteine |
| X | Xaa | Unknown or other |

All sequences of amino acid residues represented herein by a formula have a left to right orientation in the conventional direction of amino-terminus to carboxyl-terminus. The phrase "amino acid residue" is defined to include the amino acids listed in the above Table of Correspondence, modified, non-natural and unusual amino acids. A dash at the beginning or end of an amino acid residue sequence indicates a peptide bond to a further sequence of one or more amino acid residues or to an amino-terminal group such as $NH_2$ or to a carboxyl-terminal group such as COOH.

In a peptide or protein, suitable conservative substitutions of amino acids are known to those of skill in the art and generally can be made without altering a biological activity of a resulting molecule. Those of skill in the art recognize that, in general, single amino acid substitutions in non-essential regions of a polypeptide do not substantially alter biological activity (see, e.g., Watson et al., *Molecular Biology of the Gene,* 4th Edition, 1987, The Benjamin/Cummings Pub. Co., p. 224).

Such substitutions can be made in accordance with the exemplary substitutions set forth in the following Table:

Exemplary conservative amino acid substitutions

| Original residue | Exemplary Conservative substitution(s) |
|---|---|
| Ala (A) | Gly; Ser |
| Arg(R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative or non-conservative substitutions.

As used herein, "naturally occurring amino acids" refer to the 20 L-amino acids that occur in polypeptides.

As used herein, the term "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally occurring amino acids and include, but are not limited to, the D-stereoisomers of amino acids. Exemplary non-natural amino acids are known to those of skill in the art, and include, but are not limited to, 2-Aminoadipic acid (Aad), 3-Aminoadipic acid (bAad), β-alanine/β-Amino-propionic acid (Bala), 2-Aminobutyric acid (Abu), 4-Aminobutyric acid/piperidinic acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethyl asparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Aile), N-Methylglycine, sarcosine (MeGly), N-Methylisoleucine (MeIle), 6-N-Methyllysine (MeLys), N-Methylvaline (MeVal), Norvaline (Nva), Norleucine (Nle), and Ornithine (Orn).

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, production by recombinant means by using recombinant DNA methods means the use of the well-known methods of molecular biology for expressing proteins encoded by cloned DNA.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used to receive, maintain, reproduce and/or amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins, can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide, such as a modified anti-EGFR antibody. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well-known to those of skill in the art. A vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well-known to those of skill in the art and include those that are replicable in eukaryotic cells and/or prokaryotic cells and those that remain episomal or those which integrate into the host cell genome.

As used herein, "primary sequence" refers to the sequence of amino acid residues in a polypeptide or the sequence of nucleotides in a nucleic acid molecule. As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. When using gap penalties, sequence identity can be determined with no penalty for end gaps (e.g., terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. (1970) *J. Mol. Biol.* 48: 443). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2: 482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier. Default parameters for the GAP program can include: (1) a unary comparison matrix (containing a value of 1 for identities and 0 for non-identities) and the weighted comparison matrix of Gribskov et al. (1986) *Nucl. Acids Res.* 14: 6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (*Adv. Appl. Math.* (1991) 12:337-357)); and program from Xiaoqui Huang available at deepc2.psi.iastate.edu/aat/align/align.html. Typically, the full-length sequence of each of the compared polypeptides or nucleotides is aligned across the full-length of each sequence in a global alignment. Local alignment also can be used when the sequences being compared are substantially the same length.

Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differ from those of the reference polypeptide. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software.

As used herein, "disease or disorder" refers to a pathological condition in an organism resulting from cause or condition including, but not limited to, infections, acquired conditions, genetic conditions, and characterized by identifiable symptoms.

As used herein, "treating" a subject with a disease or condition means that the subject's symptoms are partially or totally alleviated, or remain static following treatment.

As used herein, treatment refers to any effects that ameliorate symptoms of a disease or disorder. Treatment encompasses prophylaxis, therapy and/or cure.

Treatment also encompasses any pharmaceutical use of any immunostimulatory bacterium or composition provided herein.

As used herein, prophylaxis refers to prevention of a potential disease and/or a prevention of worsening of symptoms or progression of a disease.

As used herein, "prevention" or prophylaxis, and grammatically equivalent forms thereof, refers to methods in which the risk or probability of developing a disease or condition is reduced.

As used herein, a "pharmaceutically effective agent" includes any therapeutic agent or bioactive agents, including, but not limited to, for example, anesthetics, vasoconstrictors, dispersing agents, and conventional therapeutic drugs, including small molecule drugs and therapeutic proteins.

As used herein, a "therapeutic effect" means an effect resulting from treatment of a subject that alters, typically improves or ameliorates, the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect following administration to a subject. Hence, it is the quantity necessary for preventing, curing, ameliorating, arresting or partially arresting a symptom of a disease or disorder.

As used herein, "therapeutic efficacy" refers to the ability of an agent, compound, material, or composition containing a compound to produce a therapeutic effect in a subject to whom the agent, compound, material, or composition containing a compound has been administered.

As used herein, a "prophylactically effective amount" or a "prophylactically effective dose" refers to the quantity of an agent, compound, material, or composition containing a compound that when administered to a subject, will have the intended prophylactic effect, e.g., preventing or delaying the onset, or reoccurrence, of disease or symptoms, reducing the likelihood of the onset, or reoccurrence, of disease or symptoms, or reducing the incidence of viral infection. The full prophylactic effect does not necessarily occur by administration of one dose, and can occur only after administration of a series of doses. Thus, a prophylactically effective amount can be administered in one or more administrations.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, an "anti-cancer agent" refers to any agent that is destructive or toxic to malignant cells and tissues. For example, anti-cancer agents include agents that kill cancer cells or otherwise inhibit or impair the growth of tumors or cancer cells. Exemplary anti-cancer agents are chemotherapeutic agents.

As used herein "therapeutic activity" refers to the in vivo activity of a therapeutic polypeptide. Generally, the therapeutic activity is the activity that is associated with treatment of a disease or condition.

As used herein, the term "subject" refers to an animal, including a mammal, such as a human being.

As used herein, a patient refers to a human subject.

As used herein, animal includes any animal, such as, but not limited to, primates including humans, gorillas and monkeys; rodents, such as mice and rats; fowl, such as chickens; ruminants, such as goats, cows, deer, sheep; pigs and other animals. Non-human animals exclude humans as the contemplated animal. The polypeptides provided herein are from any source, animal, plant, prokaryotic and fungal. Most polypeptides are of animal origin, including mammalian origin.

As used herein, a "composition" refers to any mixture. It can be a solution, suspension, liquid, powder, paste, aqueous, non-aqueous or any combination thereof.

As used herein, a "combination" refers to any association between or among two or more items. The combination can be two or more separate items, such as two compositions or two collections, a mixture thereof, such as a single mixture of the two or more items, or any variation thereof. The elements of a combination are generally functionally associated or related.

As used herein, combination therapy refers to administration of two or more different therapeutics. The different therapeutic agents can be provided and administered separately, sequentially, intermittently, or can be provided in a single composition.

As used herein, a kit is a packaged combination that optionally includes other elements, such as additional reagents and instructions for use of the combination or elements thereof, for a purpose including, but not limited to, activation, administration, diagnosis, and assessment of a biological activity or property.

As used herein, a "unit dose form" refers to physically discrete units suitable for human and animal subjects and packaged individually as is known in the art.

As used herein, a "single dosage formulation" refers to a formulation for direct administration.

As used herein, a multi-dose formulation refers to a formulation that contains multiple doses of a therapeutic agent and that can be directly administered to provide several single doses of the therapeutic agent. The doses can be administered over the course of minutes, hours, weeks, days or months. Multi-dose formulations can allow dose adjustment, dose-pooling and/or dose-splitting. Because multi-dose formulations are used over time, they generally contain one or more preservatives to prevent microbial growth.

As used herein, an "article of manufacture" is a product that is made and sold. As used throughout this application, the term is intended to encompass any of the compositions provided herein contained in articles of packaging.

As used herein, a "fluid" refers to any composition that can flow. Fluids thus encompass compositions that are in the form of semi-solids, pastes, solutions, aqueous mixtures, gels, lotions, creams and other such compositions.

As used herein, an isolated or purified polypeptide or protein (e.g., an isolated antibody or antigen-binding fragment thereof) or biologically-active portion thereof (e.g., an isolated antigen-binding fragment) is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification does not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound. As used herein, a "cellular extract" or "lysate" refers to a preparation or fraction which is made from a lysed or disrupted cell.

As used herein, a "control" refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a polypeptide, comprising "an immunoglobulin domain" includes polypeptides with one or a plurality of immunoglobulin domains.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 amino acids" means "about 5 amino acids" and also "5 amino acids."

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* (1972) 11(9): 1726-1732).

For clarity of disclosure, and not by way of limitation, the detailed description is divided into the subsections that follow.

B. Overview of the Immunostimulatory Bacteria

Provided are modified bacteria, called immunostimulatory bacteria herein that accumulate and/or replicate in tumors and encode inhibitory RNAs, such as designed shRNAs and designed micro RNAs, that target genes whose inhibition, suppression or silencing effects tumor therapy, upon expression of the RNAs in the treated subject. Strains of bacteria for modification are any suitable for therapeutic use. The modified immunostimulatory bacteria provided herein are for use and for methods for treating cancer. The bacteria are modified for such uses and methods.

The immunostimulatory bacteria provided herein are modified by deletion or modification of bacterial genes to attenuate their inflammatory responses, and are modified to enhance anti-tumor immune responses in hosts treated with the bacteria. For example, the plasmids encoding RNAi that inhibit checkpoint genes in the host are included in the bacteria, and the bacteria can be auxotrophic for adenosine. Attenuation of the inflammatory response to the bacteria can be affected by deletion of the msbB gene, which decreases TNF-alpha in the host, and/or knocking out flagellin genes. The bacteria are modified to stimulate host anti-tumor activity, for example, by adding plasmids encoding RNAi that target host immune checkpoints, and by adding nucleic acid with CpGs.

Bacterial strains can be attenuated strains or strains that are attenuated by standard methods or that by virtue of the modifications provided herein are attenuated in that their ability to colonize is limited primarily to immunoprivileged tissues and organs, particularly immune and tumor cells, including solid tumors. Bacteria include, but are not limited to, for example, strains of *Salmonella, Shigella, Listeria, E. coli*, and *Bifidobacteriae*. For example, species include *Shigella sonnei, Shigella flexneri, Shigella disenteriae, Listeria monocytogenes, Salmonella typhi, Salmonella typhimurium, Salmonella galinarum*, and *Salmonella enteritidis*. Other suitable bacterial species include *Rikettsia, Klebsiella, Bordetella, Neisseria, Aeromonas, Francisella, Corynebacterium, Citrobacter, Chlamydia, Hemophilus, Brucella, Mycobacterium, Mycoplasma Legionella, Rhodococcus, Pseudomonas, Heliobacter, Vibrio, Bacillus*, and *Erysipelothrix*. For example, *Rickettsia* Rikettsiae, *Riketsia prow aseckii, Rickettsia tsutsugamuchi, Rickettsia mooseri, Rickettsia sibirica, Bordetella bronchiseptica, Neisseria meningitidis, Neisseria gonorrhoeae, Aeromonas eucrenophila, Aeromonas salminocida, Francisella tularensis, Corynebacterium pseudotuberculosis, Citrobacter freundii, Chlamydia pneumoniae, Hemophilus sornnus, Brucella abortus, Mycobacterium intracellulare, Legionella pneumophila, Rhodococcus equi, Pseudomonas aeruginosa, Heliobacter mustelae, Vibrio cholerae, Bacillus subtilis, Erysipelothrix rhusiopathiae, Yersinia enterocolitica, Rochalimaea quitana*, and *Agrobacterium tumerfacium.*

The bacteria accumulate by virtue of one or more properties, including, diffusion, migration and chemotaxis to immunoprivileged tissues or organs or environments, environments that provide nutrients or other molecules for which they are auxotrophic and/or environments that contain replicating cells that provide environments for entry and replication of bacteria. The immunostimulatory bacteria provided herein and species that effect such therapy include species of *Salmonella, Listeria*, and *E. coli*. The bacteria contain plasmids that encode one or more short hairpin (sh) RNA construct(s), or other RNAi modalities, whose expression inhibits or disrupts expression of targeted genes. The shRNA constructs are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression. In some embodiments, the plasmids encode a plurality of RNAi molecules, such as shRNAs or microRNAs, that inhibit two or more checkpoint genes, such as shRNAs for inhibiting PD-L1, VISTA, SIRPα, CTNNB1, TGF-beta, and/or VEGF and any others known to those of skill in the art. Where a plurality of shRNAs are encoded, expression of each is under control of different promoters.

Among the bacteria provided herein, are bacteria that are modified so that they are auxotrophic for adenosine. This can be achieved by modification or deletion of genes involved in purine synthesis, metabolism, or transport. For example, disruption of the tsx gene in *Salmonella* species, such as *Salmonella typhi*, results in adenosine auxotrophy. Adenosine is immunosuppressive and accumulates to high concentrations in tumors; auxotrophy for adenosine improves the anti-tumor activity of the bacteria because the bacteria selectively replicate in tissues rich in adenosine.

Also provided are bacteria that are modified so that they have a defective asd gene. These bacteria for use in vivo are modified to include carrying a functional asd gene on the introduced plasmid; this maintains selection for plasmid so that an antibiotic-based plasmid maintenance/selection system is not needed. Also provided is the use of asd defective strains that do not contain a functional asd gene on a plasmid and are thus engineered to be autolytic in the host.

Also provided are bacteria that are modified so that they are incapable of producing flagella. This can be achieved by modifying the bacteria by means of deleting the genes that encode the flagellin subunits. The modified bacteria lacking flagellin are less inflammatory and therefore better tolerated and induce a more potent anti-tumor response.

Also provided are bacteria that are modified to produce listeriolysin O, which improves plasmid delivery in phagocytic cells.

Also provided are bacteria modified to carry a low copy, CpG-containing plasmid. The plasmid further can include other modifications, and RNAi.

The bacteria also can be modified to grow in a manner such that the bacteria, if a *Salmonella* species, expresses less of the toxic SPI-1 (*Salmonella* pathogenicity island-1) genes. In *Salmonella*, genes responsible for virulence, invasion, survival, and extra intestinal spread are located in *Salmonella* pathogenicity islands (SPIs).

The bacteria include plasmids that encode RNAi, such as shRNA or microRNA, that inhibits checkpoints, such as PD-L1 or TREX1 only, or TREX1 and one or more of a second immune checkpoint. The bacteria can be further modified for other desirable traits, including for selection of plasmid maintenance, particularly for selection without antibiotics, for preparation of the strains. The immunostimulatory bacteria optionally can encode therapeutic polypeptides, including anti-tumor therapeutic polypeptides and agents.

Exemplary of the immunostimulatory bacteria provided herein are species of *Salmonella*. Exemplary of bacteria for modification as described herein are engineered strains of *Salmonella typhimurium*, such as strain YS1646 (ATCC Catalog #202165; see, also International PCT application No Publication No. WO 99/13053, also referred to as VNP20009) that is engineered with plasmids to complement an asd gene knockout and antibiotic-free plasmid maintenance.

Modified immunostimulatory bacterial strains that are rendered auxotrophic for adenosine are provided herein as are pharmaceutical compositions containing such strains formulated for administration to a subject, such as a human, for use in methods of treating tumors and cancers.

The engineered immunostimulatory bacteria provided herein contain multiple synergistic modalities to induce immune re-activation of cold tumors and to promote tumor antigen-specific immune responses, while inhibiting immune checkpoint pathways that the tumor utilizes to subvert and evade durable anti-tumor immunity. Improved tumor targeting through adenosine auxotrophy and enhanced vascular disruption have improved potency, while localizing the inflammation to limit systemic cytokine exposure and the autoimmune toxicities observed with other immunotherapy modalities. Exemplary of the bacteria so-modified are *S. typhimurium* strains, including such modifications of the strain YS1646, particularly asd$^-$ strains.

For example, as provided herein, are immunostimulatory bacteria that provide for shRNA-mediated gene disruption of PD-L1. It has been shown in mice that gene disruption of PD-L1 can improve tumor colonization. It has been shown, for example, that *S. typhimurium* infection in PD-L1 knockout mice, results in a 10-fold higher bacterial load than in wild-type mice. (see, Lee et al. (2010) *Immunol.* 185:2442-2449). Hence, PD-L1 is protective against *S. typhimurium* infection. Provided herein are immunostimulatory bacteria, such as *S. typhimurium*, carrying plasmids capable of RNAi-mediated gene knockdown of TREX1, PD-L1, or of PD-L1 and TREX1. Such bacteria provide anti-tumor effects due to the combination of two independent pathways that lead to enhanced and sustained anti-tumor immune responses in a single therapy.

C. Cancer Immunotherapeutics

The immunosuppressive milieu found within the tumor microenvironment (TME) is a driver of tumor initiation and progression. Cancers emerge after the immune system fails to control and contain tumors. Multiple tumor-specific mechanisms create tumor environments wherein the immune system is forced to tolerate tumors and their cells instead of eliminating them. The goal of cancer immunotherapy is to rescue the immune system's natural ability to eliminate tumors. Acute inflammation associated with microbial infection has been observationally linked with the spontaneous elimination of tumors for centuries.

1. Immunotherapies

Several clinical cancer immunotherapies have sought to perturb the balance of immune suppression towards anti-tumor immunity. Strategies to stimulate immunity through directly administering cytokines such as IL-2 and IFN-$\alpha$ have seen modest clinical responses in a minority of patients, while inducing serious systemic inflammation-related toxicities (Sharma et al. (2011) *Nat Rev Cancer* 11:805-812). The immune system has evolved several checks and balances to limit autoimmunity, such as upregulation of programmed cell death protein 1 (PD-1) on T cells and its binding to its cognate ligand, programmed death-ligand 1 (PD-L1), which is expressed on both antigen presenting cells (APCs) and tumor cells. The binding of PD-L1 to PD-1 interferes with CD8$^+$ T cell signaling pathways, impairing the proliferation and effector function of CD8$^+$ T cells, and inducing T cell tolerance. PD-1 and PD-L1 are two examples of numerous inhibitory "immune checkpoints," which function by downregulating immune responses. Other inhibitory immune checkpoints include cytotoxic T-lymphocyte-associated protein 4 (CTLA-4), signal regulatory protein a (SIRP$\alpha$), V-domain Ig suppressor of T cell activation (VISTA), programmed death-ligand 2 (PD-L2), indoleamine 2,3-dioxygenase (IDO) 1 and 2, lymphocyte-activation gene 3 (LAG3), Galectin-9, T cell immunoreceptor with Ig and ITIM domains (TIGIT), T cell immunoglobulin and mucin-domain containing-3 (TIM-3, also known as hepatitis A virus cellular receptor 2 (HAVCR2)), herpesvirus entry mediator (HVEM), CD39, CD73, B7-H3 (also known as CD276), B7-H4, CD47, CD48, CD80 (B7-1), CD86 (B7-2), CD155, CD160, CD244 (2B4), B- and T-lymphocyte attenuator (BTLA, or CD272) and carcinoembryonic antigen-related cell adhesion molecule 1 (CEACAM1, or CD66a).

Antibodies designed to block immune checkpoints, such as anti-PD-1 (for example, pembrolizumab, nivolumab) and anti-PD-L1 (for example, atezolizumab, avelumab, durvalumab), have had durable success in preventing T cell anergy and breaking immune tolerance. Only a fraction of treated patients demonstrate clinical benefit, and those that do often present with autoimmune-related toxicities (see, e.g., Ribas (2015) *N Engl J Med* 373:1490-1492; Topalian et al. (2012) *N Engl J Med* 366:3443-3447). This is further evidence for the need for therapies, provided herein, that are more effective and less toxic.

Another checkpoint blockade strategy inhibits the induction of CTLA-4 on T cells, which binds to and inhibits co-stimulatory receptors on APCs, such as CD80 or CD86, out-competing the co-stimulatory cluster differentiation 28 (CD28), which binds the same receptors, but with a lower affinity. This blocks the stimulatory signal from CD28, while the inhibitory signal from CTLA-4 is transmitted, preventing T cell activation (see, Phan et al. (2003) *Proc. Natl. Acad. Sci. U.S.A.* 100:8372-8377). Anti-CTLA-4 therapy (for example, ipilimumab) have clinical success and durability in some patients, whilst exhibiting an even greater incidence of severe immune-related adverse events (see, e.g., Hodi et al. (2010) *N Engl J Med* 363:711-723; Schadendorf et al. (2015) *J. Clin. Oncol.* 33:1889-1894). It also has been shown that tumors develop resistance to anti-immune checkpoint antibodies, highlighting the need for more durable anticancer therapies, and provided herein.

2. Adoptive Immunotherapies

In seeking to reactivate a cold tumor to become more immunogenic, a class of immunotherapies known as adoptive cell therapy (ACT) encompasses a variety of strategies to harness immune cells and reprogram them to have anti-tumor activity (Hinrichs et al. (2011) *Immunol. Rev.* 240: 40-51). Dendritic cell-based therapies introduce genetically engineered dendritic cells (DCs) with more immune-stimulatory properties. These therapies have not been successful because they fail to break immune tolerance to cancer (see, e.g., Rosenberg et al. (2004) *Nat. Med.* 12:1279). A method using whole irradiated tumor cells containing endogenous tumor antigens and granulocyte macrophage colony-stimulating factor (GM-CSF) to stimulate DC recruitment, known as GVAX, similarly failed in the clinic due to the lack of ability to break tumor tolerance (Copier et al. (2010) *Curr. Opin. Mol. Ther.* 12:647-653). A separate autologous cell-based therapy, Sipuleucel-T (Provenge), was FDA approved in 2010 for castration-resistant prostate cancer. It utilizes APCs retrieved from the patient and re-armed to express prostatic acid phosphatase (PAP) antigen to stimulate a T cell response, then re-introduced following lymphablation. Unfortunately, its broader adoption has been limited by low observed objective response rates and high costs, and its use is limited to only the early stages of prostate cancer (Anassi et al. (2011) P T. 36(4):197-202). Similarly, autologous T cell therapies (ATCs) harvest a patient's own T cells and reactivate them ex vivo to overcome tumor tolerance, then reintroduce them to the patient following lymphablation. ATCs have had limited clinical success, and only in melanoma, while generating serious safety and feasibility issues that limit their utility (Yee et al. (2013) *Clin. Cancer Res.* 19:1-3).

Chimeric antigen receptor T cell (CAR-T) therapies are T cells harvested from patients that have been re-engineered to express a fusion protein between the T cell receptor and an antibody Ig variable extracellular domain. This confers upon them the antigen-recognition properties of antibodies with the cytolytic properties of activated T cells (Sadelain (2015) *Clin. Invest.* 125:3392-400). Success has been limited to B cell and hematopoietic malignancies, at the cost of deadly immune-related adverse events (Jackson et al. (2016) *Nat. Rev. Clin. Oncol.* 13:370-383). Tumors can also mutate to escape recognition by a target antigen, including CD19 (Ruella et al., (2016) *Comput Struct Biotechnol J.* 14: 357-362) and EGFRvIII (O'Rourke et al. (2017) *Sci Transl Med.* July 19; 9:399), thereby fostering immune escape. In addition, while CAR-T therapies are approved and are approved in the context of hematological malignancies, they face a significant hurdle for feasibility to treat solid tumors: overcoming the highly immunosuppressive nature of the solid tumor microenvironment. A number of additional modifications to existing CAR-T therapies will be required to potentially provide feasibility against solid tumors (Kakarla, et al. (2014) *Cancer J.* March-April; 20(2): 151-155). When the safety of CAR-Ts is significantly improved and their efficacy expanded to solid tumors, the feasibility and costs associated with these labor-intensive therapies will continue to limit their broader adoption.

3. Cancer Vaccines and Oncolytic Viruses

Cold tumors lack T cell and dendritic cell (DC) infiltration, and are non-T-cell-inflamed (Sharma et al. (2017) *Cell* 9; 168(4):707-723). In seeking to reactivate a cold tumor to become more immunogenic, another class of immunotherapies harness microorganisms that can accumulate in tumors, either naturally or by virtue of engineering. These include viruses designed to stimulate the immune system to express tumor antigens, thereby activating and reprogramming the immune system to reject the tumor. Virally-based cancer vaccines have largely failed clinically for a number of factors, including pre-existing or acquired immunity to the viral vector itself, as well as a lack of sufficient immunogenicity to the expressed tumor antigens (Larocca et al. (2011) *Cancer J.* 17(5):359-371). Lack of proper adjuvant activation of APCs has also hampered other non-viral vector cancer vaccines, such as DNA vaccines. Oncolytic viruses, in contrast, seek to preferentially replicate in dividing tumor cells over healthy tissue, whereupon subsequent tumor cell lysis leads to immunogenic tumor cell death and further viral dissemination. The oncolytic virus Talimogene laherparepvec (T-VEC), which uses a modified herpes simplex virus in combination with the DC-recruiting cytokine GM-CSF, is FDA approved for metastatic melanoma (Bastin et al. (2016) *Biomedicines* 4(3):21). While demonstrating clinical benefit in some melanoma patients, and with fewer immune toxicities than with other immunotherapies, the intratumoral route of administration and manufacturing conditions have been limiting, as well as its lack of distal tumor efficacy and broader application to other tumor types. Other OV-based vaccines, such as those utilizing paramyxovirus, reovirus and picornavirus, among others, have met with similar limitations in inducing systemic anti-tumor immunity (Chiocca et al. (2014) *Cancer Immunol. Res.* 2(4):295-300). Systemic administration of oncolytic viruses presents unique challenges. Upon IV administration, the virus is rapidly diluted, thus requiring high titers that can lead to hepatotoxicity. Further, if pre-existing immunity exists, the virus is rapidly neutralized in the blood, and acquired immunity then restricts repeat dosing (Maroun et al. (2017) *Future Virol.* 12(4):193-213).

Of the limitations of virally-based vaccine vectors and oncolytic viruses, the greatest limitations can be the virus itself. Viral antigens have strikingly higher affinities to human T cell receptors (TCR) compared to tumor antigens (Aleksic et al. (2012) *Eur J Immunol.* 42(12):3174-3179). Tumor antigens, presented alongside of viral vector antigens by MHC-1 on the surface of even highly activated APCs, will be outcompeted for binding to TCRs, resulting in very poor antigen-specific anti-tumor immunity. A tumor-targeting immunostimulatory vector, as provided herein, that does not itself provide high affinity T cell epitopes can circumvent these limitations.

D. Bacterial Cancer Immunotherapy

1. Bacterial Therapies

The recognition that bacteria have anticancer activity goes back to the 1800s, when several physicians observed regression of tumors in patients infected with *Streptococcus pyogenes*. William Coley began the first study utilizing bacteria for the treatment of end stage cancers, and developed a vaccine composed of *S. pyogenes* and *Serratia marcescnes*, which was successfully used to treat a variety of cancers, including sarcomas, carcinomas, lymphomas and melanomas. Since then, a number of bacteria, including species of *Clostridium, Mycobacterium, Bifidobacterium, Listeria*, such as, *L. monocytogenes*, and *Escherichia* species, have been studied as sources of anti-cancer vaccines (see, e.g., Published International PCT application WO 1999/013053; Published International PCT application WO/2001/025399; Bermudes (2002); Patyar et al. (2010) *Journal of Biomedical Science* 17:21; Pawelek et al. (2003) *Lancet Oncol.* 4:548-556).

Bacteria can infect animal and human cells, and some possess the innate ability to deliver DNA into the cytosol of cells, and these are candidate vectors for gene therapy. Bacteria also are suitable for therapy because they can be administered orally, they propagate readily in vitro and in vivo, and they can be stored and transported in a lyophilized state. Bacterial genetics are readily manipulated, and the complete genomes for many strains have been fully characterized (Felgner et al. (2016) mbio 7(5):e01220-16). As a result, bacteria have been used to deliver and express a wide variety of genes, including those that encode cytokines, angiogenesis inhibitors, toxins and prodrug-converting enzymes. *Salmonella*, for example, has been used to express immune-stimulating molecules like IL-18 (Loeffler et al. (2008) *Cancer Gene Ther.* 15(12):787-794), LIGHT (Loeffler et al. (2007) *PNAS* 104(31):12879-12883), and Fas ligand (Loeffler et al. (2008) *J. Natl. Cancer Inst.* 100:1113-1116) in tumors. Bacterial vectors also are cheaper and easier to produce than viral vectors, and bacterial delivery is favorable over viral delivery because it can be quickly eliminated by antibiotics if necessary, rendering it a safer alternative.

To be used, however, the strains themselves must not be pathogenic or are not pathogenic after modification for use as a therapeutic. For example, in the treatment of cancer, the therapeutic bacterial strains must be attenuated or rendered sufficiently non-toxic so as to not cause systemic disease and/or septic shock, but still maintain some level of infectivity to effectively colonize tumors. Genetically modified bacteria have been described that are to be used as antitumor agents to elicit direct tumoricidal effects and/or to deliver tumoricidal molecules (Clairmont, et al. (2000) *J. Infect. Dis.* 181:1996-2002; Bermudes, D. et al. (2002) *Curr. Opin. Drug Discov. Devel.* 5:194-199; Zhao, M. et al. (2005) *Proc. Natl. Acad. Sci. USA* 102:755-760; Zhao, M. et al. (2006) Cancer Res. 66:7647-7652). Among these are bioengineered strains of *Salmonella enterica* serovar *Typhimurium* (*S. typhimurium*). These bacteria accumulate preferentially >1,000-fold greater in tumors than in normal tissues and disperse homogeneously in tumor tissues (Pawelek, J. et al. (1997) *Cancer Res.* 57:4537-4544; Low, K. B. et al. (1999) *Nat. Biotechnol.* 17:37-41). Preferential replication allows the bacteria to produce and deliver a variety of anticancer therapeutic agents at high concentrations directly within the tumor, while minimizing toxicity to normal tissues. These attenuated bacteria are safe in mice, pigs, and monkeys when administered i.v. (Zhao, M. et al. (2005) *Proc Natl Acad Sci USA* 102:755-760; Zhao, M. et al. (2006) *Cancer Res* 66:7647-7652; Tjuvajev J. et al. (2001) J. *Control Release* 74:313-315; Zheng, L. et al. (2000) *Oncol. Res.* 12:127-135), and certain live attenuated *Salmonella* strains have been shown to be well tolerated after oral administration in human clinical trials (Chatfield, S. N. et al. (1992) *Biotechnology* 10:888-892; DiPetrillo, M. D. et al. (1999) *Vaccine* 18:449-459; Hohmann, E. L. et al. (1996) *J. Infect. Dis.* 173:1408-1414; Sirard, J. C. et al. (1999) *Immunol. Rev.* 171:5-26). The *S. typhimurium* phoP/phoQ operon is a typical bacterial two-component regulatory system composed of a membrane-associated sensor kinase (PhoQ) and a cytoplasmic transcriptional regulator (PhoP: Miller, S. I. et al. (1989) *Proc Natl Acad Sci USA* 86:5054-5058; Groisman, E. A. et al. (1989) *Proc Natl Acad Sci USA* 86: 7077-7081). PhoP/phoQ is required for virulence, and its deletion results in poor survival of this bacterium in macrophages and a marked attenuation in mice and humans (Miller, S. I. et al. (1989) *Proc Natl Acad Sci USA* 86:5054-5058; Groisman, E. A. et al. (1989) *Proc Natl Acad Sci USA* 86: 7077-7081; Galan, J. E. and Curtiss, R. III. (1989) *Microb Pathog* 6:433-443; Fields, P. I. et al. (1986) *Proc Natl Acad Sci USA* 83:189-193). PhoP/phoQ deletion strains have been employed as effective vaccine delivery vehicles (Galan, J. E. and Curtiss, R. III. (1989) *Microb Pathog* 6:433-443; Fields, P. I. et al. (1986) *Proc Natl Acad Sci USA* 83:189-193; Angelakopoulos, H. and Hohmann, E. L. (2000) *Infect Immun* 68:213-241). Attenuated *Salmonella* have been used for targeted delivery of tumoricidal proteins (Bermudes, D. et al. (2002) *Curr Opin Drug Discov Devel* 5:194-199; Tjuvajev J. et al. (2001) *J Control Release* 74:313-315).

Bacterially-based cancer therapies have demonstrated limited clinical benefit. A variety of bacterial species, including *Clostridium novyi* (Dang et al. (2001) *Proc. Natl. Acad. Sci. U.S.A.* 98(26):15155-15160; U.S. Patent Publications Nos. 2017/0020931, 2015/0147315; U.S. Pat. Nos. 7,344, 710; 3,936,354), *Mycobacterium bovis* (U.S. Patent Publications Nos. 2015/0224151; US 2015/0071873), *Bifidobacterium bifidum* (Kimura et al. (1980) *Cancer Res.* 40:2061-2068), *Lactobacillus casei* (Yasutake et al. (1984) *Med Microbiol Immunol.* 173(3):113-125), *Listeria monocytogenes* (Le et al. (2012) *Clin. Cancer Res.* 18(3):858-868; Starks et al. (2004) *J. Immunol.* 173:420-427; U.S. Patent Publication No. 2006/0051380) and *Escherichia coli* (U.S. Pat. No. 9,320,787) have been studied as possible agents for anticancer therapy.

The *Bacillus* Calmette-Guerin (BCG) strain, for example, is approved for the treatment of bladder cancer in humans, and is more effective than intravesical chemotherapy, often being used as a first-line treatment (Gardlik et al. (2011) *Gene therapy* 18:425-431). Another approach utilizes *Listeria monocytogenes*, a live attenuated intracellular bacterium capable of inducing potent $CD8^+$ T cell priming to expressed tumor antigens in mice (Le et al. (2012) *Clin. Cancer Res.* 18(3):858-868). In a clinical trial of the *Listeria*-based vaccine incorporating the tumor antigen mesothelin, together with an allogeneic pancreatic cancer-based GVAX vaccine in a prime-boost approach, a median survival of 6.1 months was noted in patients with advanced pancreatic cancer, versus a median survival of 3.9 months for patients treated with the GVAX vaccine alone (Le et al. (2015) *J. Clin. Oncol.* 33(12):1325-1333). These results were not replicated in a larger phase 2b study, possibly pointing to the difficulties in attempting to induce immunity to a low affinity self-antigen such as mesothelin.

Bacterial strains can be modified as described and exemplified herein to express inhibitory RNA (RNAi), such as shRNAs and microRNAs, that inhibit or disrupt TREX1 and/or PD-L1 and optionally one or more additional immune checkpoint genes. The strains can be attenuated by standard methods and/or by deletion or modification of genes, and by alteration or introduction of genes that render the bacteria able to grow in vivo primarily in immunoprivileged environments, such as the TME, in tumor cells and solid tumors. Strains for modification as described herein can be selected from among, for example, *Shigella, Listeria, E. coli, Bifidobacteriae* and *Salmonella*. For example, *Shigella sonnei, Shigella flexneri, Shigella disenteriae, Listeria monocytogenes, Salmonella typhi, Salmonella typhimurium, Salmonella galinarum*, and *Salmonella enteritidis*. Other suitable bacterial species include Rikettsia, *Klebsiella, Bordetella, Neisseria, Aeromonas, Franciesella, Corynebacterium, Citrobacter, Chlamydia, Hemophilus, Brucella, Mycobacterium, Mycoplasma Legionella, Rhodococcus, Pseudomonas, Heliobacter, Vibrio, Bacillus*, and *Erysipelothrix*. For example, *Rickettsia* Rikettsiae, *Riketsia prow aseckii, Rickettsia tsutsugamuchi, Rickettsia mooseri, Rickettsia sibirica, Bordetella bronchiseptica, Neisseria meningitidis, Neisseria gonorrhoeae, Aeromonas eucrenophila, Aeromonas salminocida, Franciesella tularensis, Corynebacterium pseudotuberculosis, Citrobacter freundii, Chlamydia pneumoniae, Hemophilus sornnus, Brucella abortus, Mycobacterium intracellulare, Legionella pneumophila, Rhodococcus equi, Pseudomonas aeruginosa, Heliobacter mustelae, Vibrio cholerae, Bacillus subtilis, Erysipelothrix rhusiopathiae, Yersinia enterocolitica, Rochalimaea quitana*, and *Agrobacterium tumerfacium*. Any known therapeutic, including immunostimulatory, bacteria can be modified as described herein.

2. Comparison of the Immune Responses to Bacteria and Viruses

Bacteria, like viruses, have the advantage of being naturally immunostimulatory. Bacteria and viruses are known to contain conserved structures known as Pathogen-Associated Molecular Patterns (PAMPs), which are sensed by host cell Pattern Recognition Receptors (PRRs). Recognition of PAMPs by PRRs triggers downstream signaling cascades that result in the induction of cytokines and chemokines, and initiation of immune responses that lead to pathogen clearance (Iwasaki and Medzhitov (2010) *Science* 327(5963): 291-295). The manner in which the innate immune system is engaged by PAMPs, and from what type of infectious agent, determines the appropriate adaptive immune response to combat the invading pathogen.

A class of PRRs known as Toll Like Receptors (TLRs) recognize PAMPs derived from bacterial and viral origins, and are located in various compartments within the cell.

TLRs bind a range of ligands, including lipopolysaccharide (TLR4), lipoproteins (TLR2), flagellin (TLR5), unmethylated CpG motifs in DNA (TLR9), double-stranded RNA (TLR3), and single-stranded RNA (TLR7 and TLR8) (Akira et al. (2001) *Nat. Immunol.* 2(8):675-680; Kawai and Akira (2005) *Curr. Opin. Immunol.* 17(4):338-344). Host surveillance of *S. typhimurium* for example, is largely mediated through TLR2, TLR4 and TLR5 (Arpaia et al. (2011) *Cell* 144(5):675-688). These TLRs signal through MyD88 and TRIF adaptor molecules to mediate induction of NF-kB dependent pro-inflammatory cytokines such as TNF-α, IL-6 and IFN-γ (Pandey et. al. (2015) *Cold Spring Harb Perspect Biol* 7(1):a016246).

Another category of PRRs are the nod-like receptor (NLR) family. These receptors reside in the cytosol of host cells and recognize intracellular PAMPS. For example, *S. Typhimurium* flagellin was shown to activate the NLRC4/NAIP5 inflammasome pathway, resulting in the cleavage of caspase-1 and induction of the pro-inflammatory cytokines IL-1β and IL-18, leading to pyroptotic cell death of infected macrophages (Fink et al. (2007) *Cell Microbiol.* 9(11):2562-2570).

While engagement of TLR2, TLR4, TLR5 and the inflammasome induces pro-inflammatory cytokines that mediate bacterial clearance, they activate a predominantly NF-κB-driven signaling cascade that leads to recruitment and activation of neutrophils, macrophages and $CD4^+$ T cells, but not the DCs and $CD8^+$ T cells that are required for anti-tumor immunity (Lui et al. (2017) *Signal Transduct Target Ther.* 2:17023). In order to activate $CD8^+$ T cell-mediated anti-tumor immunity, IRF3/IRF7-dependent type I interferon signaling is critical for DC activation and cross-presentation of tumor antigens to promote $CD8^+$ T cell priming (Diamond et al. (2011) *J. Exp. Med.* 208(10):1989-2003; Fuertes et al. (2011) *J. Exp. Med.* 208(10):2005-2016). Type I interferons (IFN-α, IFN-β) are the signature cytokines induced by two distinct TLR-dependent and TLR-independent signaling pathways. The TLR-dependent pathway for inducing IFN-β occurs following endocytosis of pathogens, whereby TLR3, 7, 8 and 9 detect pathogen-derived DNA and RNA elements within the endosomes. TLRs 7 and 8 recognize viral nucleosides and nucleotides, and synthetic agonists of these, such as resiquimod and imiquimod have been clinically validated (Chi et al. (2017) *Frontiers in Pharmacology* 8:304). Synthetic dsRNA, such as polyinosinic:polycytidylic acid (poly (I:C) and poly ICLC, an analog that is formulated with poly L lysine to resist RNase digestion, is an agonist for TLR3 and MDA5 pathways and a powerful inducer of IFN-β (Caskey et al. (2011) *J. Exp. Med.* 208(12):2357-66). TLR9 detection of endosomal CpG motifs present in viral and bacterial DNA can also induce IFN-β via IRF3. Additionally, TLR4 has been shown to induce IFN-β via MyD88-independent TRIF activation of IRF3 (Owen et al. (2016) mBio.7:1 e02051-15). It subsequently was shown that TLR4 activation of DCs was independent of type I IFN, so the ability of TLR4 to activate DCs via type I IFN is not likely biologically relevant (Hu et al. (2015) *Proc. Natl. Acad. Sci. U.S.A.* 112:45). Further, TLR4 signaling has not been shown to directly recruit or activate $CD8^+$ T cells.

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1) adaptor protein-mediated phosphorylation of the IRF-3 transcription factor, leading to induction of IFN-β (Ireton and Gale (2011) *Viruses* 3(6):906-919). Synthetic RIG-I-binding elements have also been discovered unintentionally in common lentiviral shRNA vectors, in the form of an AA dinucleotide sequence at the U6 promoter transcription start site. Its subsequent deletion in the plasmid prevented confounding off-target type I IFN activation (Pebernard et al. (2004) *Differentiation.* 72:103-111).

The second type of TLR-independent type I interferon induction pathway is mediated through Stimulator of Interferon Genes (STING), a cytosolic ER-resident adaptor protein that is now recognized as the central mediator for sensing cytosolic dsDNA from infectious pathogens or aberrant host cell damage (Barber (2011) *Immunol. Rev* 243(1):99-108). STING signaling activates the TANK binding kinase (TBK1)/IRF3 axis and the NF-kB signaling axis, resulting in the induction of IFN-β and other pro-inflammatory cytokines and chemokines that strongly activate innate and adaptive immunity (Burdette et al. (2011) *Nature* 478(7370):515-518). Sensing of cytosolic dsDNA through STING requires cyclic GMP-AMP synthase (cGAS), a host cell nucleotidyl transferase that directly binds dsDNA, and in response, synthesizes a cyclic dinucleotide (CDN) second messenger, cyclic GMP-AMP (cGAMP), which binds and activates STING (Sun et al. (2013) *Science* 339(6121):786-791; Wu et al. (2013) *Science* 339(6121):826-830). CDNs derived from bacteria such as c-di-AMP produced from intracellular *Listeria monocytogenes* can also directly bind murine STING, but only 3 of the 5 human STING alleles. Unlike the CDNs produced by bacteria, in which the two purine nucleosides are joined by a phosphate bridge with 3'-3' linkages, the internucleotide phosphate bridge in the cGAMP synthesized by mammalian cGAS is joined by a non-canonical 2'-3' linkage. These 2'-3' molecules bind to STING with 300-fold better affinity than bacterial 3'-3' CDNs, and thus are more potent physiological ligands of human STING (see, e.g., Civril et al. (2013) *Nature* 498(7454):332-337; Diner et al. (2013) *Cell Rep.* 3(5):1355-1361; Gao et al. (2013) *Sci. Signal* 6(269):p 11; Ablasser et al. (2013) *Nature* 503(7477):530-534).

The cGAS/STING signaling pathway in humans may have evolved over time to preferentially respond to viral pathogens over bacterial pathogens, and this can explain why bacterial vaccines harboring host tumor antigens have made for poor $CD8^+$ T cell priming vectors in humans. TLR-independent activation of $CD8^+$ T cells by STING-dependent type I IFN signaling from conventional DCs is the primary mechanism by which viruses are detected, with TLR-dependent type I IFN production by plasmacytoid DCs operating only when the STING pathway has been virally-inactivated (Hervas-Stubbs et al. (2014) *J Immunol.* 193:1151-1161). Further, for bacteria such as *S. typhimurium*, while capable of inducing IFN-β via TLR4, $CD8^+$ T cells are neither induced nor required for clearance or protective immunity (Lee et al. (2012) *Immunol Lett.* 148(2): 138-143). The lack of physiologically relevant $CD8^+$ T epitopes for many strains of bacteria, including *S. typhimurium*, has impeded both bacterial vaccine development and protective immunity to subsequent infections, even from the same genetic strains (Lo et al. (1999) *J Immunol.* 162:5398-5406). Thus, bacterially-based cancer immunotherapies are biologically limited in their ability to induce type I IFN to recruit and activate $CD8^+$ T cells, necessary to promote tumor antigen cross-presentation and durable anti-tumor immunity. Hence, engineering a bacterial immunotherapy provided herein to induce viral-like TLR-independent type I IFN signaling, rather than TLR-dependent bacterial immune signaling, will preferentially induce $CD8^+$ T cell mediated anti-tumor immunity.

STING activates innate immunity in response to sensing nucleic acids in the cytosol. Downstream signaling is activated through binding of CDNs, which are synthesized by bacteria or by the host enzyme cGAS in response to binding to cytosolic dsDNA. Bacterial and host-produced CDNs have distinct phosphate bridge structures, which differentiates their capacity to activate STING. \IFN-β is the signature cytokine of activated STING, and virally-induce type I IFN, rather than bacterially-induced IFN, is required for effective $CD8^+$ T cell mediated anti-tumor immunity. Immunostimulatory bacteria provided herein include those that are STING agonists.

3. *Salmonella* Therapy

*Salmonella* is exemplary of a bacterial genus that can be used as a cancer therapeutic. The *Salmonella* exemplified herein is an attenuated species or one that by virtue of the modifications for use as a cancer therapeutic has reduced toxicity.

a. Tumor-Tropic Bacteria

A number of bacterial species have demonstrated preferential replication within solid tumors when injected from a distal site. These include, but are not limited to, species of *Salmonella, Bifodobacterium, Clostridium*, and *Escherichia*. The natural tumor-homing properties of the bacteria combined with the host's innate immune response to the bacterial infection is thought to mediate the anti-tumor response. This tumor tissue tropism has been shown to reduce the size of tumors to varying degrees. One contributing factor to the tumor tropism of these bacterial species is the ability to replicate in anoxic or hypoxic environments. A number of these naturally tumor-tropic bacteria have been further engineered to increase the potency of the antitumor response (reviewed in Zu et al. (2014) *Crit Rev Microbiol.* 40(3):225-235; and Felgner et al. (2017) *Microbial Biotechnology* 10(5):1074-1078).

b. *Salmonella enterica* Serovar *Typhimurium*

*Salmonella enterica* serovar *typhimurium* (*S. typhimurium*) is exemplary of a bacterial species for use as an anti-cancer therapeutic. One approach to using bacteria to stimulate host immunity to cancer has been through the Gram-negative facultative anaerobe *S. typhimurium*, which preferentially accumulates in hypoxic and necrotic areas in the body, including tumor microenvironments. *S. typhimurium* accumulates in these environments due to the availability of nutrients from tissue necrosis, the leaky tumor vasculature and their increased likelihood to survive in the immune system-evading tumor microenvironment (Baban et al. (2010) *Bioengineered Bugs* 1(6):385-294). *S. typhimurium* is able to grow under both aerobic and anaerobic conditions; therefore it is able to colonize small tumors that are less hypoxic and large tumors that are more hypoxic.

*S. typhimurium* is a Gram-negative, facultative pathogen that is transmitted via the fecal-oral route. It causes localized gastrointestinal infections, but also enters the bloodstream and lymphatic system after oral ingestion, infecting systemic tissues such as the liver, spleen and lungs. Systemic administration of wild-type *S. typhimurium* overstimulates TNF-α induction, leading to a cytokine cascade and septic shock, which, if left untreated, can be fatal. As a result, pathogenic bacterial strains, such as *S. typhimurium*, must be attenuated to prevent systemic infection, without completely suppressing their ability to effectively colonize tumor tissues. Attenuation is often achieved by mutating a cellular structure that can elicit an immune response, such as the bacterial outer membrane or limiting its ability to replicate in the absence of supplemental nutrients.

*S. typhimurium* is an intracellular pathogen that is rapidly taken up by myeloid cells such as macrophages or it can induce its own uptake in non-phagocytic cells such as epithelial cells. Once inside cells, it can replicate within a *salmonella* containing vacuole (SCV) and can also escape into the cytosol of some epithelial cells. Many of the molecular determinants of *S. typhimurium* pathogenicity have been identified and the genes are clustered in *salmonella* pathogenicity islands (SPI). The two best characterized pathogenicity islands are SPI-1 which is responsible for mediating bacterial invasion of non-phagocytic cells, and SPI-2 which is required for replication within the SCV (Agbor and McCormick (2011) *Cell Microbiol.* 13(12): 1858-1869). Both of these pathogenicity islands encode macromolecular structures called type three secretion systems (T3SS) that can translocate effector proteins across the host membrane (Galan and Wolf-Watz (2006) *Nature* 444: 567-573).

c. Bacterial Attenuation

Therapeutic bacteria for administration as a cancer treatment should be attenuated. Various methods for attenuation of bacterial pathogens are known in the art. Auxotrophic mutations, for example, render bacteria incapable of synthesizing an essential nutrient, and deletions/mutations in genes such as aro, pur, gua, thy, nad and asd (U.S. Patent Publication No. 2012/0009153) are widely used. Nutrients produced by the biosynthesis pathways involving these genes are often unavailable in host cells, and as such, bacterial survival is challenging. For example, attenuation of *Salmonella* and other species can be achieved by deletion of the aroA gene, which is part of the shikimate pathway, connecting glycolysis to aromatic amino acid biosynthesis (Felgner et al. (2016) *MBio* 7(5):e01220-16). Deletion of aroA therefore results in bacterial auxotrophy for aromatic amino acids and subsequent attenuation (U.S. Patent Publication Nos. 2003/0170276, 2003/0175297, 2012/0009153, 2016/0369282, International Patent Publication Nos. WO 2015/032165, and WO 2016/025582). Similarly, other enzymes involved in the biosynthesis pathway for aromatic amino acids, including aroC and aroD have been deleted to achieve attenuation (U.S. Patent Publication No. 2016/0369282; International Patent Publication No. WO 2016/025582). For example, *S. typhimurium* strain SL7207 is an aromatic amino acid auxotroph ($aroA^-$ mutant); strains A1 and A1-R are leucine-arginine auxotrophs. VNP20009 is a purine auxotroph ($purI^-$ mutant). As shown herein, it is also auxotrophic for the immunosuppressive nucleoside adenosine.

Mutations that attenuate bacteria also include, but are not limited to, mutations in genes that alter the biosynthesis of lipopolysaccharide, such as rfaL, rfaG, rfaH, rfaD, rfaP, rFb, rfa, msbB, htrB, firA, pagL, pagP, lpxR, arnT, eptA, and lpxT; mutations that introduce a suicide gene such as sacB, nuk, hok, gef, kil or phlA; mutations that introduce a bacterial lysis gene such as hly and cly; mutations in virulence factors such as IsyA, pag, prg, iscA, virG, plc and act; mutations that modify the stress response such as recA, htrA, htpR, hsp and groEL; mutations that disrupt the cell cycle such as min; and mutations that disrupt or inactivate regulatory functions, such as cya, crp, phoP/phoQ, and ompR (U.S. Patent Publication Nos. 2012/0009153, 2003/0170276, 2007/0298012; U.S. Pat. No. 6,190,657; WO 2015/032165; Felgner et al. (2016) *Gut microbes* 7(2):171-177; Broadway et al. (2014) *J. Biotechnology* 192:177-178;

Frahm et al. (2015) *mBio* 6(2):e00254-15; Kong et al. (2011) *Infection and Immunity* 79(12):5027-5038; Kong et al. (2012) *PNAS* 109(47):19414-19419). Ideally the genetic attenuations comprise gene deletions rather than point mutations to prevent spontaneous compensatory mutations that might result in reversion to a virulent phenotype.

i. msbB⁻ Mutants

The enzyme lipid A biosynthesis myristoyltransferase, encoded by the msbB gene in *S. typhimurium*, catalyzes the addition of a terminal myristyl group to the lipid A domain of lipopolysaccharide (LPS) (Low et al. (1999) *Nat. Biotechnol.* 17(1):37-41). Deletion of msbB thus alters the acyl composition of the lipid A domain of LPS, the major component of the outer membranes of Gram-negative bacteria. This modification significantly reduces the ability of the LPS to induce septic shock, attenuating the bacterial strain and reducing the potentially harmful production of TNFα, thus lowering systemic toxicity. *S. typhimurium* msbB mutants maintain their ability to preferentially colonize tumors over other tissues in mice and retain anti-tumor activity, thus increasing the therapeutic index of *Salmonella* based immunotherapeutics (U.S. Patent Publication Nos. 2003/0170276, 2003/0109026, 2004/0229338, 2005/0225088, 2007/0298012).

For example, deletion of msbB in the *S. typhimurium* strain VNP20009 results in production of a predominantly penta-acylated LPS, which is less toxic than native hexa-acylated LPS and allows for systemic delivery without the induction of toxic shock (Lee et al. (2000) *International Journal of Toxicology* 19:19-25). Other LPS mutations can be introduced into the bacterial strains provided herein, including the *Salmonella* strains, that dramatically reduce virulence, and thereby provide for lower toxicity, and permit administration of higher doses.

ii. pur⁻ Mutants

Immunostimulatory bacteria can be attenuated by rendering them auxotrophic for one or more essential nutrients, such as purines (for example, adenine), nucleosides (for example, adenosine) or amino acids (for example, arginine and leucine), are employed. In particular, in embodiments of the immunostimulatory bacteria provided herein, such as *S. typhimurium*, the bacteria are rendered auxotrophic for adenosine, which preferentially accumulates in tumor microenvironments. Hence, strains of immunostimulatory bacteria described herein are attenuated because they require adenosine for growth, and they preferentially colonize TMEs, which, as discussed below, have an abundance of adenosine.

Phosphoribosylaminoimidazole synthetase, an enzyme encoded by the purI gene (synonymous with the purM gene), is involved in the biosynthesis pathway of purines. Disruption of the purI gene thus renders the bacteria auxotrophic for purines. In addition to being attenuated, purI⁻ mutants are enriched in the tumor environment and have significant anti-tumor activity (Pawelek et al. (1997) *Cancer Research* 57:4537-4544). It was previously described that this colonization results from the high concentration of purines present in the interstitial fluid of tumors as a result of their rapid cellular turnover. Since the purI⁻ bacteria are unable to synthesize purines, they require an external source of adenine, and it was thought that this would lead to their restricted growth in the purine-enriched tumor microenvironment (Rosenberg et al. (2002) *J. Immunotherapy* 25(3):218-225). While the VNP20009 strain was initially reported to contain a deletion of the purI gene (Low et al. (2003) *Methods in Molecular Medicine* Vol. 90, *Suicide Gene Therapy:* 47-59), subsequent analysis of the entire genome of VNP20009 demonstrated that the purI gene is not deleted, but is disrupted by a chromosomal inversion (Broadway et al. (2014) *Journal of Biotechnology* 192:177-178). The entire gene is contained within two parts of the VNP20009 chromosome that is flanked by insertion sequences (one of which has an active transposase).

It is shown herein, that, purI mutant *S. typhimurium* strains are auxotrophic for the nucleoside adenosine, which is highly enriched in tumor microenvironments. Hence, when using VNP20009, it is not necessary to introduce any further modification to achieve adenosine auxotrophy. For other strains and bacteria, the purI gene can be disrupted as it has been in VNP20009, or it can contain a deletion of all or a portion of the purI gene to prevent reversion to a wild-type gene.

iii. Combinations of Attenuating Mutations

A bacterium with multiple genetic attenuations by means of gene deletions on disparate regions of the chromosome is desirable for bacterial immunotherapies because the attenuation can be increased, while decreasing the possibility of reversion to a virulent phenotype by acquisition of genes by homologous recombination with a wild-type genetic material. Restoration of virulence by homologous recombination would require two separate recombination events to occur within the same organism. Ideally the combinations of attenuating mutations selected for use in an immunotherapeutic agent increases the tolerability without decreasing the potency, thereby increasing the therapeutic index. For example, disruption of the msbB and purI genes in *S. typhimurium* strain VNP20009, has been used for tumor-targeting and growth suppression, and elicits low toxicity in animal models (Clairmont et al. (2000) *J. Infect. Dis.* 181:1996-2002; Bermudes et al. (2000) *Cancer Gene Therapy: Past Achievements and Future Challenges*, edited by Habib Kluwer Academic/Plenum Publishers, New York, pp. 57-63; Low et al. (2003) *Methods in Molecular Medicine*, Vol. 90, *Suicide Gene Therapy:* 47-59; Lee et al. (2000) *International Journal of Toxicology* 19:19-25; Rosenberg et al. (2002) *J. Immunotherapy* 25(3):218-225; Broadway et al. (2014) *J. Biotechnology* 192:177-178; Loeffler et al. (2007) *Proc. Natl. Acad. Sci. U.S.A.* 104(31): 12879-12883; Luo et al. (2002) *Oncology Research* 12:501-508). When VNP20009 (msbB⁻/purI⁻) was administered to mice bearing syngeneic or human xenograft tumors, the bacteria accumulated preferentially within the extracellular components of tumors at ratios exceeding 300-1000 to 1, reduced TNFα induction, and demonstrated tumor regression and prolonged survival compared to control mice (Clairmont et al. (2000) *J. Infect. Dis.* 181:1996-2002). Results from the Phase 1 clinical trial in humans, however, revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which are required to manifest any anti-tumor activity, were not possible due to toxicity.

Thus, further improvements are needed. The immunostimulatory bacteria provided herein address this problem.

iv. VNP20009 and Other Attenuated *S. typhimurium* Strains

Exemplary of a therapeutic bacterium that can be modified as described herein is the strain designated as VNP20009 (ATCC #202165, YS1646). The clinical candidate, VNP20009 (ATCC #202165, YS1646), was at least 50,000-fold attenuated for safety by deletion of both the msbB and purI genes (Clairmont et al. (2000) *J. Infect. Dis.* 181:1996-2002; Low et al. (2003) *Methods in Molecular*

*Medicine*, Vol. 90, *Suicide Gene Therapy:* 47-59; Lee et al. (2000) *International Journal of Toxicology* 19:19-25). Similar strains of *salmonella* that are attenuated also are contemplated. As described above, deletion of msbB alters the composition of the lipid A domain of lipopolysaccharide, the major component of Gram-negative bacterial outer membranes (Low et al. (1999) *Nat. Biotechnol.* 17(1):37-41). This prevents lipopolysaccharide-induced septic shock, attenuating the bacterial strain and lowering systemic toxicity, while reducing the potentially harmful production of TNFα (Dinarello, C. A. (1997) *Chest* 112(6 Suppl):3215-3295; Low et al. (1999) *Nat. Biotechnol.* 17(1):37-41). Deletion of the purI gene renders the bacteria auxotrophic for purines, which further attenuates the bacteria and enriches it in the tumor micro environment (Pawelek et al. (1997) *Cancer Res.* 57:4537-4544) (Broadway et al. (2014) *J. Biotechnology* 192:177-178).

The accumulation of VNP20009 in tumors results from a combination of factors including: the inherent invasiveness of the parental strain, ATCC14028, its ability to replicate in hypoxic environments, and its requirement for high concentration of purines that are present in the interstitial fluid of tumors. Herein we will demonstrate that VNP20009 is also auxotrophic for the nucleoside adenosine, which can accumulate to pathologically high levels in the tumor microenvironment and contribute to an immunosuppressive tumor microenvironment (Peter Vaupel and Arnulf Mayer Oxygen Transport to Tissue XXXVII, Advances in Experimental Medicine and Biology 876 chapter 22, pp. 177-183). When VNP20009 was administered into mice bearing syngeneic or human xenograft tumors, the bacteria accumulated preferentially within the extracellular components of tumors at ratios exceeding 300-1000 to 1 and demonstrated tumor growth inhibition as well as prolonged survival compared to control mice (Clairmont et al. (2000) 1 Infect. Dis. 181: 1996-2002). Results from the Phase 1 clinical trial revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which would be required to affect any anti-tumor activity, were not possible due to toxicity that correlated with high levels of pro-inflammatory cytokines.

Other strains of *S. typhimurium* can be used for tumor-targeted delivery and therapy, such as, for example, leucine-arginine auxtroph A-1 (Zhao et al. (2005) *PNAS* 102(3):755-760; Yu et al. (2012) *Scientific Reports* 2:436; U.S. Pat. No. 8,822,194; U.S. Patent Publication No. 2014/0178341) and its derivative AR-1 (Yu et al. (2012) *Scientific Reports* 2:436; Kawagushi et al. (2017) *Oncotarget* 8(12):19065-19073; Zhao et al. (2006) *Cancer Res.* 66(15):7647-7652; Zhao et al. (2012) *Cell Cycle* 11(1):187-193; Tome et al. (2013) *Anticancer Research* 33:97-102; Murakami et al. (2017) *Oncotarget* 8(5):8035-8042; Liu et al. (2016) *Oncotarget* 7(16):22873-22882; Binder et al. (2013) *Cancer Immunol Res.* 1(2):123-133); aroA$^-$ mutant *S. typhimurium* strain SL7207 (Guo et al. (2011) *Gene therapy* 18:95-105; U.S. Patent Publication Nos. 2012/0009153, 2016/0369282 and 2016/0184456) and its obligate anaerobe derivative YB1 (WO 2015/032165; Yu et al. (2012) *Scientific Reports* 2:436; Leschner et al. (2009) *PLoS ONE* 4(8): e6692; Yu et al. (2012) *Scientific Reports* 2:436); aroA$^-$/aroD$^-$ mutant *S. typhimurium* strain BRD509, a derivative of the SL1344 (WT) strain (Yoon et al. (2017) *European J. of Cancer* 70:48-61); asd$^-$/cya$^-$/crp$^-$ mutant *S. typhimurium* strain χ4550 (Sorenson et al. (2010) *Biology: Targets & Therapy* 4:61-73) and phoP$^-$/phoQ$^-$*S. typhimurium* strain LH430 (WO 2008/091375).

Although VNP20009 failed to show a clinical benefit in a study involving patients with advanced melanoma, a maximum tolerated dose (MTD) was established and the treatment was safely administered to advanced cancer patients. Hence, this strain, as well as other similarly engineered bacterial strains, can be used as tumor-targeting, therapeutic delivery vehicles. Modifications provided herein provide a strategy to increase efficacy, by increasing the anti-tumor efficiency and/or the safety and tolerability of the therapeutic agent.

v. Attenuated *S. typhimurium* Engineered to Deliver Macromolecules

The bacterial strains are engineered to deliver therapeutic molecules. The strains herein deliver RNAi targeted and inhibitory to immune checkpoints, and also to other such targets.

While the use of VNP20009 in clinical trials of metastatic melanoma resulted in no significant changes in metastatic burden, it did demonstrate some evidence of tumor colonization. VNP20009 and other *S. typhimurium* strains have been used as vectors to deliver a wide variety of genes, such as those encoding cytokines, anti-angiogenic factors, inhibitory enzymes and cytotoxic polypeptides (U.S. Patent Publication No. 2007/0298012). For example, the delivery of cytokine-encoding LIGHT using VNP20009 inhibited growth of primary tumors as well as pulmonary metastases of carcinoma cell lines in immunocompetent mice, with no significant toxicity observed (Loeffler et al. (2007) *Proc. Natl. Acad. Sci. U.S.A.* 104(31):12879-12883). In another study, VNP20009, expressing an *E. coli* cytosine deaminase gene was administered to patients who also received the prodrug 5-fluorocytosine (5-FC) orally. Two out of three patients showed intratumoral bacterial colonization for at least 15 days after initial injection, and the expressed cytosine deaminase converted the 5-FC to the anticancer drug 5-FU. No side effects from the *Salmonella* were observed, and direct IV administration of 5-FU resulted in lower tumor concentrations of the drug than with bacterial delivery of the cytosine deaminase gene (Nemunaitis et al. (2003) *Cancer Gene Therapy* 10:737-744).

In other examples, attenuated *Salmonella* expressing herpes simplex virus thymidine kinase (HSV TK) demonstrated a 2.5-fold reduction in B16 melanoma tumor size via ganciclovir-mediated tumor growth suppression (Pawelek, J. et al. (1997) *Cancer Res* 57:4537-4544), and the C-terminal p53 peptide (Cp53) was delivered using *S. typhimurium* and inducibly-expressed in MCF7 breast cancer cells, resulting in a decrease in tumor cell population (Camacho et al. (2016) *Scientific Reports* 6:30591). *S. typhimurium* has also been utilized in the tumor-targeted expression of IFN-γ (Yoon et al. (2017) *European J. of Cancer* 70:48-61); SIINF antigen (Binder et al. (2013) *Cancer Immunol Res.* 1(2): 123-133); *Vibrio vulnificus* flagellin B (Zheng et al. (2017) *Sci. Transl. Med.* 9, 9537); and truncated IL-2 (Sorenson et al. (2010) *Biology: Targets & Therapy* 4:61-73), for example.

*S. typhimurium* has also been modified to deliver the tumor-associated antigen (TAA) survivin (SVN) to APCs to prime adaptive immunity (U.S. Patent Publication No. 2014/0186401; Xu et al. (2014) *Cancer Res.* 74(21):6260-6270). SVN is an inhibitor of apoptosis protein (IAP) which prolongs cell survival and provides cell cycle control, and is overexpressed in all solid tumors and poorly expressed in normal tissues. This technology utilizes *Salmonella* Pathogenicity Island 2 (SPI-2) and its type III secretion system (T3SS) to deliver the TAAs into the cytosol of APCs, which then are activated to induce TAA-specific CD8+ T cells and anti-tumor immunity (Xu et al. (2014) *Cancer Res.* 74(21): 6260-6270). Similar to the *Listeria*-based TAA vaccines, this approach has shown promise in mouse models, but has yet to demonstrate effective tumor antigen-specific T cell priming in humans.

In addition to gene delivery, *S. typhimurium* also has been used for the delivery of small interfering RNAs (siRNAs) and short hairpin RNAs (shRNAs) for cancer therapy. For example, attenuated *S. typhimurium* have been modified to express certain shRNAs, such as those that target Stat 3 and IDO1 (PCT/US2007/074272, and U.S. Pat. No. 9,453,227). VNP20009 transformed with an shRNA plasmid against the immunosuppressive gene indolamine deoxygenase (IDO), successfully silenced IDO expression in a murine melanoma model, resulting in tumor cell death and significant tumor infiltration by neutrophils (Blache et al. (2012) *Cancer Res.* 72(24):6447-6456). Combining this vector with the co-administration of PEGPH20 (an enzyme that depletes extracellular hyaluronan), showed positive results in the treatment of pancreatic ductal adenocarcinoma tumors (Manuel et al. (2015) *Cancer Immunol. Res.* 3(9):1096-1107; U.S. Patent Publication No. 2016/0184456). In another study, an *S. typhimurium* strain attenuated by a phoP/phoQ deletion and expressing a signal transducer and activator of transcription 3 (STAT3)-specific shRNA, was found to inhibit tumor growth and reduce the number of metastatic organs, extending the life of C57BL6 mice (Zhang et al. (2007) *Cancer Res.* 67(12):5859-5864). In another example, *S. typhimurium* strain SL7207 has been used for the delivery of shRNA targeting CTNNB1, the gene that encodes β-catenin (Guo et al. (2011) *Gene therapy* 18:95-105; U.S. Patent Publication Nos. 2009/0123426, 2016/0369282), while *S. typhimurium* strain VNP20009 has been utilized in the delivery of shRNA targeting the STAT3 (Manuel et al. (2011) *Cancer Res.* 71(12):4183-4191; U.S. Patent Publication Nos. 2009/0208534, 2014/0186401, 2016/0184456; WO 2008/091375; WO 2012/149364). siRNAs targeting the autophagy genes Atg5 and Beclin1 have been delivered to tumor cells using *S. typhimurium* strains A1-R and VNP20009 (Liu et al. (2016) *Oncotarget* 7(16):22873-22882). Improvement of such strains is needed so that they more effectively stimulate the immune response, and have other advantageous properties, such as the immunostimulatory bacteria provided herein.

Any of the bacteria described above can be modified as described herein, such as by adding additional shRNA or micro encoding nucleic acids to target other checkpoints, such as TREX1. The bacteria can be modified as described herein to have reduced inflammatory effects, and, thus to be less toxic. As a result, for example, higher dosages can be administered. Any of these strains of *Salmonella*, as well as other species of bacteria, known to those of skill in the art and/or listed above and herein, can be modified as described herein, such as by introducing adenosine auxotrophy and/or shRNA for inhibiting TREX1 expression and other modifications as described herein. Exemplary are the *S. typhimurium* species described herein. It is shown herein that the *S. typhimurium* strain VNP20009 is auxotrophic for adenosine.

4. Enhancements of Immunostimulatory Bacteria to Increase Therapeutic Index

Provided herein are enhancements to immunostimulatory bacteria that reduce toxicity and improve the anti-tumor activity. Exemplary of such enhancements are the following. They are described with respect to *Salmonella*, particularly *S. typhimurium*; it is understood that the skilled person can affect similar enhancements in other bacterial species and other *salmonella* strains.

a. asd Gene Deletion

The asd gene in bacteria encodes an aspartate-semialdehyde dehydrogenase, asd− mutants of *S. typhimurium* have an obligate requirement for diaminopimelic acid (DAP) which is required for cell wall synthesis and will undergo lysis in environments deprived of DAP. This DAP auxotrophy can be used for plasmid selection and maintenance of plasmid stability in vivo without the use of antibiotics when the asd gene is complemented in trans on a plasmid. Non-antibiotic-based plasmid selection systems are advantageous and allow for 1) use of administered antibiotics as rapid clearance mechanism in the event of adverse symptoms, and 2) for antibiotic-free scale up of production, where such use is commonly avoided. The asd gene complementation system provides for such selection (Galan et al. (1990) *Gene* 28:29-35). The use of the asd gene complementation system to maintain plasmids in the tumor microenvironment are expected to increase the potency of *S. typhimurium* engineered to deliver plasmids encoding genes or interfering RNAs.

An alternative use for an asd mutant of *S. typhimurium* is to exploit the DAP auxotrophy to produce an autolytic (or suicidal) strain for delivery of macromolecules to infected cells without the ability to persistently colonize host tumors. Deletion of the asd gene makes the bacteria auxotrophic for DAP when grown in vitro or in vivo. An example described herein, provides an asd deletion strain that is auxotrophic for DAP and contains a plasmid suitable for delivery of RNAi, such as shRNA or mi-RNA, that does not contain an asd complementing gene, resulting in a strain that is defective for replication in vivo. This strain is propagated in vitro in the presence of DAP and grows normally, and then is administered as an immunotherapeutic agent to a mammalian host where DAP is not present. The suicidal strain is able to invade host cells but is not be able to replicate due to the absence of DAP in mammalian tissues, lysing automatically and delivering its cytosolic contents (e.g., plasmids or proteins). In examples provided herein, an asd gene deleted strain of VNP20009 was further modified to express an LLO protein lacking its endogenous periplasmic secretion signal sequence, causing it to accumulate in the cytoplasm of the *Salmonella*. LLO is a cholesterol-dependent pore forming hemolysin from *Listeria monocytogenes* that mediates phagosomal escape of bacteria. When the autolytic strain is introduced into tumor bearing mice, the bacteria are taken up by phagocytic immune cells and enter the *Salmonella* containing vacuole (SCV). In this environment, the lack of DAP will prevent bacterial replication, and result in autolysis of the bacteria in the SCV. Lysis of the suicidal strain will then allow for release of the plasmid and the accumulated LLO that will form pores in the cholesterol-containing SVC membrane, and allow for delivery of the plasmid into the cytosol of the host cell.

b. Adenosine Auxotrophy

Metabolites derived from the tryptophan and ATP/adenosine pathways are major drivers in forming an immunosuppressive environment within the tumor. Adenosine, which exists in the free form inside and outside of cells, is an effector of immune function. Adenosine decreases T-cell receptor induced activation of NF-κB, and inhibits IL-2, IL-4, and IFN-γ. Adenosine decreases T-cell cytotoxicity, increases T-cell anergy, and increases T-cell differentiation to Foxp3+ or Lag-3+ regulatory (T-reg) T-cells. On NK cells, adenosine decreases IFN-γ production, and suppresses NK cell cytotoxicity. Adenosine blocks neutrophil adhesion and extravasation, decreases phagocytosis, and attenuates levels of superoxide and nitric oxide. Adenosine also decreases the expression of TNF-α, IL-12, and MIP-1α on macrophages, attenuates MHC Class II expression, and increases levels of IL-10 and IL-6. Adenosine immunomodulation activity occurs after its release into the extracellular space of the tumor and activation of adenosine receptors (ADRs) on the surface of target immune cells, cancer cells or endothelial cells. The high adenosine levels in the tumor microenvironment results in local immunosuppression, which limits the capacity of the immune system to eliminate cancer cells.

Extracellular adenosine is produced by the sequential activities of membrane associated ectoenzymes, CD39 and CD73, which are expressed on tumor stromal cells, together producing adenosine by phosphohydrolysis of ATP or ADP produced from dead or dying cells. CD39 converts extracellular ATP (or ADP) to 5'AMP, which is converted to adenosine by 5'AMP. Expression of CD39 and CD73 on endothelial cells is increased under the hypoxic conditions of the tumor microenvironment, thereby increasing levels of adenosine. Tumor hypoxia can result from inadequate blood supply and disorganized tumor vasculature, impairing delivery of oxygen (Carroll and Ashcroft (2005) *Expert. Rev. Mol. Med.* 7(6):1-16). Hypoxia, which occurs in the tumor microenvironment, also inhibits adenylate kinase (AK), which converts adenosine to AMP, leading to very high extracellular adenosine concentrations. The extracellular concentration of adenosine in the hypoxic tumor microenvironment has been measured at 10-100 μM, which is up to about 100-1000 fold higher than the typical extracellular adenosine concentration of approximately 0.1 μM (Vaupel et al. (2016) *Adv Exp Med Biol.* 876:177-183; Antonioli et al. (2013) *Nat. Rev. Can.* 13:842-857). Since hypoxic regions in tumors are distal from microvessels, the local concentration of adenosine in some regions of the tumor can be higher than others.

To direct effects to inhibit the immune system, adenosine also can control cancer cell growth and dissemination by effects on cancer cell proliferation, apoptosis and angiogenesis. For example, adenosine can promote angiogenesis, primarily through the stimulation of $A_{2A}$ and $A_{2B}$ receptors. Stimulation of the receptors on endothelial cells can regulate the expression of intercellular adhesion molecule 1 (ICAM-1) and E-selectin on endothelial cells, maintain vascular integrity, and promote vessel growth (Antonioli et al. (2013 *Nat. Rev. Can.* 13:842-857). Activation of one or more of $A_{2A}$, $A_{2B}$ or $A_3$ on various cells by adenosine can stimulate the production of the pro-angiogenic factors, such as vascular endothelial growth factor (VEGF), interleukin-8 (IL-8) or angiopoietin 2 (Antonioli et al. (2013) *Nat. Rev. Can.* 13:842-857).

Adenosine also can directly regulate tumor cell proliferation, apoptosis and metastasis through interaction with receptors on cancer cells. For example, studies have shown that the activation of $A_1$ and $A_{2A}$ receptors promote tumor cell proliferation in some breast cancer cell lines, and activation of $A_{2B}$ receptors have cancer growth-promoting properties in colon carcinoma cells (Antonioli et al. (2013) *Nat. Rev. Can.* 13:842-857). Adenosine also can trigger apoptosis of cancer cells, and various studies have correlated this activity to activation of the extrinsic apoptotic pathway through $A_3$ or the intrinsic apoptotic pathway through $A_{2A}$ and $A_{2B}$ (Antonioli et al. (2013)). Adenosine can promote tumor cell migration and metastasis, by increasing cell motility, adhesion to the extracellular matrix, and expression of cell attachment proteins and receptors to promote cell movement and motility.

The extracellular release of adenosine triphosphate (ATP) occurs from stimulated immune cells and damaged, dying or stressed cells. The NLR family pyrin domain-containing 3 (NLRP3) inflammasome, when stimulated by this extracellular release of ATP, activates caspase-1 and results in the secretion of the cytokines IL-1β and IL-18, which in turn activate innate and adaptive immune responses (Stagg and Smyth (2010) *Oncogene* 29:5346-5358). ATP is catabolized into adenosine by the enzymes CD39 and CD73. Activated adenosine acts as a highly immunosuppressive metabolite via a negative-feedback mechanism and has a pleiotropic effect against multiple immune cell types in the hypoxic tumor microenvironment (Stagg and Smyth (2010) *Oncogene* 29:5346-5358). Adenosine receptors $A_{2A}$ and $A_{2B}$ are expressed on a variety of immune cells and are stimulated by adenosine to promote cAMP-mediated signaling changes, resulting in immunosuppressive phenotypes of T-cells, B-cells, NK cells, dendritic cells, mast cells, macrophages, neutrophils, and NKT cells. As a result of this, adenosine levels can accumulate to over one hundred times their normal concentration in pathological tissues, such as solid tumors, which have been shown to overexpress ecto-nucleotidases, such as CD73. Adenosine has also been shown to promote tumor angiogenesis and development. An engineered bacterium that is auxotrophic for adenosine would thus exhibit enhanced tumor-targeting and colonization.

Immunostimulatory bacteria, such as *Salmonella typhi*, can be made auxotrophic for adenosine by deletion of the tsx gene (Bucarey et al. (2005) *Infection and Immunity* 73(10): 6210-6219) or by deletion of purD (Husseiny (2005) *Infection and Immunity* 73(3):1598-1605). In the gram negative bacteria *Xanthomonas oryzae*, a purD gene knockout was shown to be auxotrophic for adenosine (Park et al. (2007) *FEMS Microbiol Lett* 276:55-59). As exemplified herein, *S. typhimurium* strain VNP20009, is auxotrophic for adenosine due to its purI deletion, hence, further modification to render it auxotrophic for adenosine is not required. Hence, embodiments of the immunostimulatory bacterial strains, as provided herein, are auxotrophic for adenosine. Such auxotrophic bacteria selectively replicate in the tumor microenvironment, further increasing accumulation and replication of the administered bacteria in tumors and decreasing the levels of adenosine in and around tumors, thereby reducing or eliminating the immunosuppression caused by accumulation of adenosine. Exemplary of such bacteria, provided herein is a modified strain of *S. typhimurium* containing purI−/msbB− mutations to provide adenosine auxotrophy.

c. Flagellin Deficient Strains

Flagella are organelles on the surface of bacteria that are composed of a long filament attached via a hook to a rotary motor that can rotate in a clockwise or counterclockwise manner to provide a means for locomotion. Flagella in *S. typhimurium* are important for chemotaxis and for establishing an infection via the oral route, due to the ability to mediate motility across the mucous layer in the gastrointestinal tract. While flagella have been demonstrated to be required for chemotaxis to and colonization of tumor cylindroids in vitro (Kasinskas and Forbes (2007) *Cancer Res.* 67(7):3201-3209), and motility has been shown to be important for tumor penetration (Toley and Forbes (2012) *Integr Biol* (*Camb*). 4(2):165-176), flagella are not required for tumor colonization in animals when the bacteria are administered intravenously (Stritzker et al. (2010) *International*

*Journal of Medical Microbiology* 300:449-456). Each flagellar filament is composed of tens of thousands of flagellin subunits. The *S. typhimurium* chromosome contains two genes, fliC and fljB, that encode antigenically distinct flagellin monomers. Mutants defective for both fliC and fljB are nonmotile and avirulent when administered via the oral route of infection, but maintain virulence when administered parenterally.

Flagellin is a major pro-inflammatory determinant of *Salmonella* (Zeng et al. (2003) *J Immunol* 171:3668-3674), and is directly recognized by TLR5 on the surface of cells, and by NLCR4 in the cytosol (Lightfield et al. (2008) *Nat Immunol.* 9(10):1171-1178). Both pathways lead to pro-inflammatory responses resulting in the secretion of cytokines, including IL-1β, IL-18, TNF-α and IL-6. Attempts have been made to make *Salmonella*-based cancer immunotherapy more potent by increasing the pro-inflammatory response to flagellin by engineering the bacteria to secrete *Vibrio* vulnificus flagellin B, which induces greater inflammation than flagellin encoded by fliC and fljB (Zheng et al. (2017) *Sci. Transl. Med.* 9(376):eaak9537).

Herein, *Salmonella* bacteria, *S. typhimurium*, are engineered to lack both flagellin subunits fliC and fljB, to reduce pro-inflammatory signaling. For example, as shown herein, a *Salmonella* strain lacking msbB, which results in reduced TNF-alpha induction, is combined with fliC and fljB knockouts. This results in a *Salmonella* strain that has a combined reduction in TNF-alpha induction and reduction in TLR5 recognition. These modifications can be combined with msbB−, fliC− and fljB−, and transformed with an immunostimulatory plasmid, optionally containing CpGs, and also inhibitory RNAi molecule(s), such as shRNA or miRNA, targeting an immune checkpoint, such as TREX1, PD-L1, VISTA, SIRP-alpha, TGF-beta, beta-catenin, VEGF, and combinations thereof. The resulting bacteria have reduced pro-inflammatory signaling, but robust anti-tumor activity.

For example, as provided herein, a fliC and fljB double mutant was constructed in the asd deleted strain of *S. typhimurium* VNP20009. VNP20009, which is attenuated for virulence by disruption of purI/purM, was also engineered to contain an msbB deletion that results in production of a lipid A subunit that is less toxigenic than wild-type lipid A. This results in reduced TNF-α production in the mouse model after intravenous administration, compared to strains with wild-type lipid A. The resulting strain is exemplary of strains that are attenuated for bacterial inflammation by modification of lipid A to reduce TLR2/4 signaling, and deletion of the flagellin subunits to reduce TLR5 recognition and inflammasome induction. Deletion of the flagellin subunits combined with modification of the LPS allows for greater tolerability in the host, and directs the immunostimulatory response towards delivery of RNA interference against desired targets in the TME which elicit an anti-tumor response and promote an adaptive immune response to the tumor.

d. *Salmonella* Engineered to Escape the *Salmonella* Containing Vacuole (SCV)

*Salmonella*, such as *S. typhimurium*, are intracellular pathogens that replicate primarily in a membrane bound compartment called a *Salmonella* containing vacuole (SCV). In some epithelial cell lines and at a low frequency, *S. typhimurium* have been shown to escape into the cytosol where they can replicate. *Salmonella* engineered to escape the SCV with higher efficiency will be more efficient at delivering macromolecules, such as plasmids, as the lipid bilayer of the SCV is a potential barrier. Provided herein are *Salmonella* and methods that have enhanced frequency of SCV escape. This is achieved by deletion of genes required for *Salmonella* induced filament (SIF) formation. These mutants have an increased frequency of SCV escape and can replicate in the cytosol.

For example, enhanced plasmid delivery using a sifA mutant of *S. typhimurium* has been demonstrated. The sifA gene encodes SPI-2, T3SS-2 secreted effector protein that mimics or activates a RhoA family of host GTPases (Ohlson et al. (2008) *Cell Host & Microbe* 4:434-446). Other genes encoding secreted effectors involved in SIF formation can be targeted. These include, for example, sseJ, sseL, sopD2, pipB2, sseF, sseG, spvB, and steA. Enhancing the escape of *S. typhimurium* by prevention of SIF formation releases live bacteria into the cytosol, where they can replicate.

Another method to enhance *S. typhimurium* escape from the SCV and increase the delivery of macromolecules such as plasmids, is the expression of a heterologous hemolysin that results in pore formation in, or rupture of, the SCV membrane. One such hemolysin is the Listeriolysin O protein (LLO) from *Listeria monocytogenes*, which is encoded by the hlyA gene. LLO is a cholesterol-dependent pore-forming cytolysin that is secreted from *L. monocytogenes* and is primarily responsible for phagosomal escape and entry into the cytosol of host cells. Secretion of LLO from *S. typhimurium* can result in bacterial escape and lead to replication in the cytosol. To prevent intact *S. typhimurium* from escaping the SCV and replicating in the cytosol, the nucleotides encoding the signal sequence can be removed from the gene. In this manner, the active LLO is contained within the cytoplasm of the *S. typhimurium* and LLO is only released when the bacteria undergo lysis. As provided herein, VNP20009 engineered to express cytoLLO to enhance delivery of plasmids for expression of interfering RNAs to targets, such as TREX1, can increase the therapeutic potency of the immunostimulatory bacteria.

e. Deletions in *Salmonella* Genes Required for Biofilm Formation

Bacteria and fungi are capable of forming multicellular structures called biofilms. Bacterial biofilms are encased within a mixture of secreted and cell wall-associated polysaccharides, glycoproteins, and glycolipids, as well as extracellular DNA, known collectively as extracellular polymeric substances. These extracellular polymeric substances protect the bacteria from multiple insults, such as cleaning agents, antibiotics, and antimicrobial peptides. Bacterial biofilms allow for colonization of surfaces, and are a cause of significant infection of prosthetics, such as injection ports and catheters. Biofilms can also form in tissues during the course of an infection, which leads to increases in the duration of bacterial persistence and shedding, and limits the effectiveness of antibiotic therapies. Chronic persistence of bacteria in biofilms is associated with increased tumorigenesis, for example in *S. typhi* infection of the gall bladder (Di Domenico et al. (2017) *Int. J. Mol. Sci.* 18:1887).

*S. typhimurium* biofilm formation is regulated by CsgD. CsgD activates the csgBAC operon, which results in increased production of the curli fimbrial subunits CsgA and CsgB (Zakikhani et al. (2010) *Molecular Microbiology* 77(3):771-786). CsgA is recognized as a PAMP by TLR2 and induces production of IL-8 from human macrophages (Tukel et al. (2005) *Molecular Microbiology* 58(1):289-304). Further, CsgD indirectly increases cellulose production by activating the adrA gene that encodes for di-guanylate cyclase. The small molecule cyclic di-guanosine monophosphate (c-di-GMP) generated by AdrA is a ubiquitous secondary messenger found in almost all bacterial species. The AdrA-mediated increase in c-di-GMP enhances expression of the cellulose synthetase gene bcsA, which in turn increases cellulose production via stimulation of the bcsABZC and bcsEFG operons. Reduction in the capability of immunostimulatory bacteria such as *S. typhimurium* to form biofilms can be achieved through deletion of genes involved in biofilm formation such as, for example, csgD, csgA csgB, adrA, bcsA, bcsB, bcsZ, bcsZ, bcsE, bcsF, bcsG, dsbA or dsbB (Anwar et al. (2014) *Plos One* 9(8):e106095).

*S. typhimurium* can form biofilms in solid tumors as protection against phagocytosis by host immune cells. *Salmonella* mutants that cannot form biofilms are taken up more rapidly by host phagocytic cells and are cleared from infected tumors (Crull et al. (2011) *Cellular Microbiology* 13(8):1223-1233). This increase in intracellular localization within phagocytic cells can reduce the persistence of extracellular bacteria, and enhance the effectiveness of plasmid delivery and gene knockdown by RNA interference as described herein. Immunostimulatory bacteria engineered to reduce biofilm formation, will increase clearance rate from tumors/tissues and therefore increase the tolerability of the therapy, and will prevent colonization of prosthetics in patients, thereby increasing the therapeutic benefit of these strains. Adenosine mimetics can inhibit *S. typhimurium* biofilm formation, indicating that the high adenosine concentration in the tumor microenvironment can contribute to tumor-associated biofilm formation (Koopman et al. (2015) *Antimicrob Agents Chemother* 59:76-84). As provided herein, live attenuated strains of bacteria, such as *S. typhimurium*, that contain a purI disruption (and therefore, colonize adenosine-rich tumors), and are also prevented from forming biofilms, by deletion of one or more genes required for biofilm formation, are engineered to deliver plasmids encoding interfering RNA to stimulate a robust anti-tumor immune response.

The adrA gene encodes a di-guanylate cyclase that produces c-di-GMP, which is required for *S. typhimurium* biofilm formation. c-di-GMP binds to and is an agonist for the host cytosolic protein STING. As described above, STING agonists are pursued as anti-cancer treatments, vaccine adjuvants, and bacteria engineered to secrete cyclic di-nucleotides for use in immunotherapies (Libanova 2012, Synlogic 2018 AACR poster). Immunostimulatory bacteria that are reduced in c-di-GMP production via the deletion of adrA appears to be counterintuitive, but bacterial mutants, such as *S. typhimurium* mutants that are unable to form biofilms (including an adrA mutant), have demonstrated reduced therapeutic potential in mouse tumor models (Crull et al. (2011) *Cellular Microbiology* 13(8):1223-1233). Further, several human alleles of STING are refractory to binding bacterially-produced 3'3' CDNs (Corrales et al. (2015) *Cell Reports* 11:1022-1023).

As described herein, bacterial strains, such as *S. typhimurium* strains, that are engineered to be adenosine auxotrophic, and are reduced in their ability to induce pro-inflammatory cytokines by modification of the LPS and/or deletion of flagellin, and/or deletion of genes required for biofilm formation, and further modified to deliver interfering RNAs, promote robust anti-tumor immune responses.

f. Deletions in Genes in the LPS Biosynthetic Pathway

The LPS of Gram negative bacteria is the major component of the outer leaflet of the bacterial membrane. It is composed of three major parts, lipid A, a non-repeating core oligosaccharide, and the O antigen (or O polysaccharide). O antigen is the outermost portion on LPS and serves as a protective layer against bacterial permeability, however, the sugar composition of O antigen varies widely between strains. The lipid A and core oligosaccharide vary less, and are more typically conserved within strains of the same species. Lipid A is the portion of LPS that contains endotoxin activity. It is typically a disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. Typically, LPS in the blood is recognized as a significant pathogen associated molecular pattern (PAMP) and induces a profound pro-inflammatory response. LPS is the ligand for a membrane-bound receptor complex comprising CD14, MD2 and TLR4. TLR4 is a transmembrane protein that can signal through the MyD88 and TRIF pathways to stimulate the NFκB pathway and result in the production of pro-inflammatory cytokines such as TNF-α and IL-1β, the result of which can be endotoxic shock, which can be fatal. LPS in the cytosol of mammalian cells can bind directly to the CARD domains of caspases 4, 5, and 11, leading to autoactivation and pyroptotic cell death (Hagar et al. (2015) *Cell Research* 25:149-150). The composition of lipid A and the toxigeniciy of lipid A variants is well documented. For example, a monophosphorylated lipid A is much less inflammatory than lipid A with multiple phosphate groups. The number and length of the of acyl chains on lipid A can also have a profound impact on the degree of toxicity. Canonical lipid A from *E. coli* has six acyl chains, and this hexa-acylation is potently toxic. *S. typhimurium* lipid A is similar to that of *E. coli*; it is a glucosamine disaccharide that carries four primary and two secondary hydroxyacyl chains (Raetz and Whitfield (2002) *Annu Rev Biochem.* 71:635-700). As described above, msbB mutants of *S. typhimurium* cannot undergo the terminal myristoylation of its LPS and produces predominantly penta-acylated LPS that is significantly less toxic than hexa-acylated lipid A. The modification of lipid A with palmitate is catalyzed by palmitoyl transferase (PagP). Transcription of the pagP gene is under control of the PhoP/PhoQ system which is activated by low concentrations of magnesium, e.g., inside the SCV. Thus, the acyl content of *S. typhimurium* is variable, and with wild type bacteria it can be hexa- or penta-acylated. The ability of *S. typhimurium* to palmitate its lipid A increases resistance to antimicrobial peptides that are secreted into phagolysozomes.

In wild type *S. typhimurium*, expression of pagP results in a lipid A that is hepta-acylated. In an msbB mutant (in which the terminal acyl chain of the lipid A cannot be added), the induction of pagP results in a hexa-acylated LPS (Kong et al. (2011) *Infection and Immunity* 79(12):5027-5038). Hexa-acylated LPS has been shown to be the most pro-inflammatory. While other groups have sought to exploit this pro-inflammatory signal, for example, by deletion of pagP to allow only hexa-acylated LPS to be produced (Felgner et al. (2016) *Gut Microbes* 7(2):171-177; (Felgner et al. (2018) *Oncoimmunology* 7(2): e1382791), this can lead to poor tolerability, due to the TNF-α-mediated pro-inflammatory nature of the LPS and paradoxically less adaptive immunity (Kocijancic et al. (2017) *Oncotarget* 8(30):49988-50001). Provided herein, is a live attenuated strain of *S. typhimurium* that can only produce penta-acylated LPS, that contains a deletion of the msbB gene (that prevents the terminal myristoylation of lipid A, as described above), and is further modified by deletion of pagP (preventing palmitoylation). A strain modified to produce penta-acylated LPS will allow for lower levels of pro-inflammatory cytokines, increased sensitivity to antimicrobial peptides, enhanced tolerability, and increased anti-tumor immunity when further modified to express interfering RNAs against immune checkpoints such as TREX1.

g. Deletions of SPI-1 Genes

As described above, in *Salmonella* species, such as *S. typhimurium*, pathogenesis involves a cluster of genes referred to as *salmonella* pathogenicity islands (SPIs). SPI-1 mediates invasion of epithelial cells. SPI-1 encodes a type 3 secretion system (T3SS) that is responsible for translocation of effector proteins into the cytosol of host cells that can cause actin rearrangements that lead to uptake of *Salmonella*. The SPI-1 T3SS is essential for crossing the gut epithelial layer, but is dispensable for infection when bacteria are injected parenterally. The injection of some proteins and the needle complex itself can also induce inflammasome activation and pyroptosis of phagocytic cells. This pro-inflammatory cell death can limit the initiation of a robust adaptive immune response by directly inducing the death of antigen-presenting cells (APCs), as well as modifying the cytokine milieu to prevent the generation of memory T-cells. SPI-1 genes comprise a number of operons including: sitABCD, sprB, avrA, hilC, orgABC, prgKIIH, hilD, hilA iagB, sptP, sicC, iacP, sipADCB, sicA, spaOPQRS, invFGEABCH, and invH.

As exemplified herein, a live attenuated strain of *S. typhimurium* that contains a purI deletion, an msbB deletion, an asd gene deletion and is engineered to deliver plasmids encoding interfering RNA, is further modified to delete SPI-1 genes. For example, deletion of a regulatory gene (e.g., hilA or invF) required for expression of the SPI-1-associated type 3 secretion system (T3SS-1), a T3SS-1 structural gene (e.g., invG or prgH), or a T3SS-1 effector gene (e.g., sipA or avrA). This secretion system is responsible for injecting effector proteins into the cytosol of non-phagocytic host cells such as epithelial cells that cause the uptake of the bacteria. In this example, the additional deletion of the hilA gene from a therapeutic *Salmonella typhimurium* strain that is administered either intravenously or intratumorally focuses the *S. typhimurium* infection towards phagocytic cells that do not require the SPI-1 T3SS for uptake, and prolongs the longevity of these phagocytic cells. The hilA mutation also reduces the quantity of pro-inflammatory cytokines, increasing the tolerability of the therapy, as well as the quality of the adaptive immune response.

h. Endonuclease (endA) Mutations to Increase Plasmid Delivery

The endA gene (for example, SEQ ID NO:250) encodes an endonuclease (for example, SEQ ID NO:251) that mediates degradation of double stranded DNA in the periplasm of Gram negative bacteria. Most common strains of laboratory *E. coli* are endA−, as a mutation in the endA gene allows for higher yields of plasmid DNA. This gene is conserved among species. To facilitate intact plasmid DNA delivery, the endA gene of the engineered immunostimulatory bacteria is deleted or mutated to prevent its endonuclease activity. Exemplary of such mutations is an E208K amino acid substitution (Durfee, et al. (2008) *J. Bacteriol.* 190(7):2597-2606) or a corresponding mutation in the species of interest. endA, including E208, which is conserved among bacterial species, including *Salmonella*. Thus, the E208K mutation can be used to eliminate endonuclease activity in other species, including *Salmonella* species. Those of skill in the art can introduce other mutations or deletions to eliminate endA activity. Effecting this mutation or deleting or disrupting the gene to eliminate activity of the endA in the immunostimulatory bacteria herein, such as in *Salmonella*, increases efficiency of intact plasmid DNA delivery, thereby increasing expression of the RNAs, such as the shRNA and/or miRNA, targeting any or two or more of the immune checkpoints, encoded in the plasmid, thereby increasing RNAi-mediated knockdown of checkpoint genes and enhancing anti-tumor efficacy.

i. RIG-I Inhibition

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1) adaptor protein-mediated phosphorylation of the IRF-3 transcription factor, leading to induction of type I IFN (Ireton and Gale (2011) *Viruses* 3(6):906-919). RIG-I recognizes dsRNA and ssRNA bearing 5'-triphosphates. This moiety can directly bind RIG-I, or be synthesized from a poly(dA-dT) template by the poly DNA-dependent RNA polymerase III (Pol III) (Chiu, Y. H. et al. (2009) *Cell* 138(3):576-91). A poly(dA-dT) template containing two AA dinucleotide sequences occurs at the U6 promoter transcription start site in a common lentiviral shRNA cloning vector. Its subsequent deletion in the plasmid prevents type I IFN activation (Pebernard et al. (2004) *Differentiation.* 72:103-111). A RIG-I binding sequence can be included in the plasmids provided herein; inclusion can increase immunostimulation that increases anti-tumoral activity of the immunostimulatory bacteria herein.

j. DNase II Inhibition

Another nuclease responsible for degrading foreign and self DNA is DNase II, an endonuclease, which resides in the endosomal compartment and degrades DNA following apoptosis. Lack of DNase II (Dnase2a in mice) results in the accumulation of endosomal DNA that escapes to the cytosol and activates cGAS/STING signaling (Lan Y Y et al. (2014) *Cell Rep.* 9(1):180-192). Similar to TREX1, DNase II-deficiency in humans presents with autoimmune type I interferonopathies. In cancer, dying tumor cells that are engulfed by tumor-resident macrophages prevent cGAS/STING activation and potential autoimmunity through DNase II digestion of DNA within the endosomal compartment (Ahn et al. (2018) *Cancer Cell* 33:862-873). Hence, embodiments of the immunostimulatory bacterial strains, as provided herein, encode RNAi, such as shRNA or miRNA that inhibit, suppress or disrupt expression of DNase II, which can inhibit DNase II in the tumor microenvironment, thereby provoking accumulation of endocytosed apoptotic tumor DNA in the cytosol, where it can act as a potent cGAS/STING agonist.

k. RNase 112 Inhibition

While TREX1 and DNase II function to clear aberrant DNA accumulation, RNase H2 functions similarly to eliminate pathogenic accumulation of RNA:DNA hybrids in the cytosol. Similar to TREX1, deficiencies in RNase H2 also contribute to the autoimmune phenotype of Aicardi-Goutières syndrome (Rabe, B. (2013)*J Mol Med.* 91:1235-1240). Specifically, loss of RNase H2 and subsequent accumulation of RNA:DNA hybrids or genome-embedded ribonucleotide substrates has been shown to activate cGAS/STING signaling. (MacKenzie et al. (2016) *EMBO J.* April15; 35(8):831-44). Hence, embodiments of the immunostimulatory bacterial strains, as provided herein, encode RNAi, such as shRNA or miRNA that inhibit, suppress or disrupt expression of RNAse H2, to thereby inhibit RNase H2, resulting in tumor-derived RNA:DNA hybrids and derivatives thereof, which activate cGAS/STING signaling and anti-tumor immunity.

l. Stabilin-1/CLEVER-1 Inhibition

Another molecule expressed primarily on monocytes and involved in regulating immunity is stabilin-1 (gene name STAB1, also known as CLEVER-1, FEEL-1). Stabilin-1 is a type I transmembrane protein that is upregulated on endothelial cells and macrophages following inflammation, and in particular, on tumor-associated macrophages (Kzhyshkowska et al. (2006) *J. Cell. Mol. Med.* 10(3):635-649). Upon inflammatory activation, stabilin-1 acts as a scavenger and aids in wound healing and apoptotic body clearance, and can prevent tissue injury, such as liver fibrosis (Rantakari et al. (2016) *PNAS* 113(33):9298-9303). Upregulation of stabilin-1 directly inhibits antigen-specific T cell responses, and knockdown by siRNA in monocytes was shown to enhance their pro-inflammatory function (Palani, S. et al. (2016) *J Immunol.* 196:115-123). Hence, embodiments of the immunostimulatory bacterial strains, as provided herein, encode RNAi, such as shRNA or miRNA that inhibit, suppress or disrupt expression of Stabilin-1/CLEVER-1 in the tumor microenvironment, thereby enhancing the pro-inflammatory functions of tumor-resident macrophages.

m. Bacterial Culture Conditions

Culture conditions for bacteria can influence their gene expression. It has been documented that *S. typhimurium* can induce rapid pro-inflammatory caspase-dependent cell death of macrophages, but not epithelial cells, within 30 to 60 min of infection by a mechanism involving the SPI-1 and its associated T3SS-1 (Lundberg et. al (1999) *Journal of Bacteriology* 181(11):3433-3437). It is now known that this cell death is mediated by activation of the inflammasome that subsequently activates caspase-1, which promotes the maturation and release of IL-1β and IL-18 and initiates a novel form of cell death called pyroptosis (Broz and Monack (2011) *Immunol Rev.* 243(1):174-190). This pyroptotic activity can be induced by using log phase bacteria, whereas stationary phase bacteria do not induce this rapid cell death in macrophages. The SPI-1 genes are induced during log phase growth. Thus, by harvesting *S. typhimurium* to be used therapeutically at stationary phase, rapid pyroptosis of macrophages can be prevented. Macrophages are important mediators of the innate immune system and they can act to secrete cytokines that are critical for establishing appropriate anti-tumor responses. In addition, limiting pro-inflammatory cytokines such as IL-1β and IL-18 secretion will improve the tolerability of administered *S. typhimurium* therapy. As provided herein, immunostimulatory *S. typhimurium* harvested at stationary phase will be used to induce anti-tumor responses.

E. Constructing Exemplary Plasmids

The immunostimulatory bacteria provided herein are modified. They include modifications to the bacterial genome and bacterial gene expression, and also, to include plasmids that encode products that are expressed in the bacteria by including a bacterial promoter, or in the host by including an appropriate eukaryotic promoter and other regulatory regions as appropriate.

To introduce the plasmids, the bacteria are transformed using standard methods, such as electroporation with purified DNA plasmids constructed with routine molecular biology tools (DNA synthesis, PCR amplification, DNA restriction enzyme digestion and ligation of compatible cohesive end fragments with ligase).

As discussed below, the plasmids encode one or more short hairpin (sh) RNA construct(s), or other inhibitory RNA modalities, whose expression inhibits or disrupts expression of targeted genes. The RNAi, such as shRNA or microRNA constructs, are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression. In some embodiments the plasmids encode a plurality of shRNAs that target to inhibit two or more checkpoint genes, such as shRNAs for inhibiting PD-L1, VISTA, SIRPα, CTNNB1, TGF-beta, and/or VEGF and any others known to those of skill in the art. Where a plurality of RNAi's, such as shRNAs, are encoded, expression of each is under control of different promoters.

As provided herein, bacterial strains, such as strains of *Salmonella*, including *S. typhimurium*, are modified or identified to be auxotrophic for adenosine in the tumor microenvironment, and to carry plasmids containing genes encoding shRNAs or microRNAs capable of knocking down gene expression of TREX1, PD-L1, VISTA, SIRP-alpha, beta-catenin, TGF-beta and VEGF. *S. typhimurium* is capable of infecting multiple cell types, including both tumor cells and macrophages. For cells infected with *S. typhimurium*, the plasmid is released and capable of being transcribed by RNA polymerases. shRNAs generated are then processed and capable of interfering with target mRNA gene expression.

1. Interfering RNAs (RNAi)

The plasmids herein encode the RNAi nucleic acids targeting the checkpoints and other targets of interest, as described above. RNAi includes shRNA, siRNA, and microRNA. RNA interference (RNAi) allows for the sequence-selective suppression of gene expression in eukaryotic cells using small interfering RNAs (siRNAs), which are short, synthetic, dsRNA molecules with a sequence homologous to the target gene. RNAi technology provides a powerful tool for the depletion of disease-related transcripts.

a. shRNA

The siRNAs, which are typically about 19-29 base pairs long, function by degrading specific host mRNA sequences, precluding translation into their respective protein products, effectively silencing the expression of the target gene. Short hairpin RNAs (shRNAs), containing a tight hairpin loop, are widely used in RNAi. shRNAs contain of two complementary RNA sequences, each 19-29 bps long, linked by a loop spacer of 4-15 nucleotides. The RNA sequence that is complementary to the target gene sequence (and is thus identical to the mRNA sequence), is known as the “sense” strand, while the strand which is complementary to the mRNA (and identical to the target gene sequence) is known as the “antisense” or “guide” strand. shRNA transcripts are processed by an RNase III enzyme known as Dicer into siRNA duplexes. The product is then loaded into the RNA-induced silencing complex (RISC) with Argonaute (Ago) proteins and other RNA-binding proteins. RISC then localizes the antisense, or “guide” strand to its complimentary mRNA sequence, which is subsequently cleaved by Ago (U.S. Pat. No. 9,624,494). The use of shRNA is preferred over siRNA, because it is more cost effective, high intracellular concentrations of siRNA are associated with off-target effects, and because the concentration of siRNA becomes diluted upon cell division. The use of shRNA, on the other hand, results in stable, long-term gene knockdown, without the need for multiple rounds of transfection (Moore et al. (2010) *Methods Mol. Bio.* 629:141-158).

Targets of interest for RNAi, such as micro-RNA and siRNA/shRNA-mediated silencing include, but are not limited to, developmental genes such as cytokines and their receptors, cyclin kinase inhibitors, neurotransmitters and their receptors, growth/differentiation factors and their receptors; oncogenes such as BCL2, ERBA, ERBB, JUN, KRAS, MYB, MYC; tumor suppressor genes such as BRCA1, BRCA2, MCC, p53; and enzymes such as ACC synthases and oxidases, ATPases, alcohol dehydrogenases, amylases, catalases, DNA polymerases, RNA polymerases, kinases, lactases and lipases (U.S. Pat. Nos. 7,732,417, 8,829,254, 8,383,599, 8,426,675, 9,624,494; U.S. Patent Publication No. 2012/0009153). Of particular interest are immune checkpoint targets, such as PD-1, PD-2, PD-L1, PD-L2, CTLA-4, IDO 1 and 2, CTNNB1 (β-catenin), SIRPα, VISTA, RNASE H2, DNase II, CLEVER-1/Stabilin-1, LIGHT, HVEM, LAG3, TIM3, TIGIT, Galectin-9, KIR, GITR, TIM1, TIM4, CEACAM1, CD27, CD40/CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, ILT-2, ILT-4, gp49B, PIR-B, HLA-G, ILT-2/4 and OX40/OX-40L. Other targets include MDR1, Arginase1, iNOs, IL-10, TGF-β, pGE2, STAT3, VEGF, KSP, HER2, Ras, EZH2, NIPP1, PP1, TAK1 and PLK1 (U.S. Patent Publication Nos. 2008/091375, 2009/0208534, 2014/0186401, 2016/0184456, 2016/0369282; International Patent Publication Nos. WO 2012/149364, WO 2015/002969, WO 2015/032165, WO 2016/025582).

Bacteria are attractive vectors for the tumor-targeted delivery of siRNAs and shRNAs. *Salmonella*, for example, can be used for the delivery of shRNA plasmids against genetic targets such as IDO (Blache et al. (2012) *Cancer Res.* 72(24):6447-6456; Manuel et al. (2015) *Cancer Immunol. Res.* 3(9):1096-1107; U.S. Patent Publication Nos. 2014/0186401, 2016/0184456; International Patent Publication Nos. WO 2012/149364, WO 2015/002969); STAT3 (Manuel et al. (2011) *Cancer Res.* 71(12):4183-4191; Zhang et al. (2007) *Cancer Res.* 67(12):5859-5864; U.S. Patent Publication Nos. 2014/0186401, 2016/0184456; International Patent Publication Nos. WO 2008/091375, WO 2012/149364, WO 2015/002969, WO 2015/032165); β-catenin (Guo et al. (2011) *Gene therapy* 18:95-105; International Patent Publication No. WO 2015/032165) and CTLA-4 (U.S. Patent Publication Nos. 2014/0186401, 2016/0184456; International Patent Publication Nos. WO 2012/149364, WO 2015/002969).

Expressed RNAi, such as shRNAs, mediate long-term, stable knockdown of their target transcripts for as long as the shRNAs are transcribed. RNA Pol II and III promoters are used to drive expression of shRNA constructs, depending on the type of expression required. Consistent with their normal cellular roles in producing abundant, endogenous small RNAs, Pol III promoters (such as U6 or H1) drive high levels of constitutive shRNA expression, and their transcription initiation points and termination signals (4-6 thymidines) are well defined. Pol II promoter-driven shRNAs can be expressed tissue-specifically and are transcribed as longer precursors that mimic pri-miRNAs and have cap and polyA signals that must be processed. Such artificial miRNAs/shRNAs are efficiently incorporated into RISC, contributing to a more potent inhibition of target-gene expression; this allows lower levels of shRNA expression and might prevent saturation of components in the RNAi pathway. An additional advantage of Pol II promoters is that a single transcript can simultaneously express several miRNA and mimic shRNAs. This multiplexing strategy can be used to simultaneously knock down the expression of two or more therapeutic targets, or to target several sites in a single gene product (see, e.g., U.S. Publication No. 2009/0208534).

b. MicroRNA

MicroRNAs (miRNAs) are short, non-coding single-stranded RNA molecules that are about or are 20-24 nucleotides long. Naturally-occurring miRNAs are involved in the post-transcriptional regulation of gene expression; miRNAs do not encode genes. miRNAs have been shown to regulate cell proliferation and survival, as well as cellular differentiation. miRNAs inhibit translation or promote RNA degradation by binding to target mRNAs that share sequence complementarity. They affect the stability and translation of mRNAs; miRNAs inhibit translation, and/or promote RNA degradation, by binding to target mRNAs that share sequence complementarity. miRNAs, which occur in eukaryotes, are transcribed by RNA Pol II into capped and polyadenylated hairpin-containing primary transcripts, known as primary miRNAs, or pri-miRNAs. These pri-miRNAs are cleaved by the enzyme Drosha ribonuclease III and its cofactor Pasha/DGCR8 into ~70 nucleotide long precursor miRNA hairpins, known as precursor miRNAs, or pre-miRNAs, which are then transported from the nucleus into the cytoplasm, and cleaved by Dicer ribonuclease III into the miRNA:miRNA*duplex, with sense and antisense strand products that are approximately 22 nucleotides long. The mature miRNA is incorporated into the RNA-induced silencing complex (RISC), which recognizes and binds target mRNAs, usually at the 3'-untranslated region (UTR), through imperfect base pairing with the miRNA, resulting in the inhibition of translation, or destabilization/degradation of the target mRNA (see, e.g., Auyeung et al. (2013) *Cell* 152(4):844-85).

As described herein, regulating gene expression by RNA interference (RNAi), often uses short hairpin RNAs (shRNAs) to inhibit, disrupt or other interfere with expression of targeted genes. While advantageously used, and used herein, in some instances, shRNAs can be poor substrates for small RNA biogenesis factors, they can be processed into a heterogeneous mix of small RNAs, and their precursor transcripts can accumulate in cells, resulting in the induction of sequence-independent, non-specific effects and leading to in vivo toxicity. miRNAs are contemplated for use herein. miRNA-like scaffolds, or artificial miRNAs (amiRNAs) can be used to reduce sequence-independent non-specific effects (Watanabe et al. (2016) *RNA Biology* 13(1):25-33; Fellmann et al. (2013) *Cell Reports* 5:1704-1713). In addition to improved safety profiles, amiRNAs are more readily transcribed by Pol II than shRNAs, allowing for regulated and cell-specific expression. Artificial miRNAs (amiRNAs), in comparison to shRNAs, can effectively, and in some cases, more potently, silence gene expression without generating large amounts of inhibitory RNAs (McBride et al. (2008) *Proc. Natl. Acad. Sci. U.S.A.* 105(15):5868-5873). This effect was determined to be due to the more effective processing of siRNA from pre-miRNA precursors than from shRNA transcripts (Boden et al. (2004) *Nucl Acid Res* 32(3):1154-1158).

miRNAs have been shown to regulate several cellular processes, including cell proliferation and survival, intracellular signaling, cellular metabolism, and cellular differentiation. In 1993, the first miRNA was identified in *C. elegans*

(Lee et al. (1993) *Cell* 75:843-854), and later, mammalian miRNAs were identified (Pasquinelli et al. (2000) *Nature.* 408(6808):86-89). More than 17,000 miRNAs in 142 species have been identified, with more than 1900 miRNAs identified in humans, many of which have been associated with a variety of diseases, including cancer (e.g., miR-15 and miR-16 in B-CLL, miR-125b, miR-145, miR-21, miR-155 and miR-210 in breast cancer, miR-155 and let-7a in lung cancer, miR-145 in gastric cancer, miR-29b in liver cancer); viral infections (e.g., miR-122 and miR-155 in HCV infection, mir-28, miR-125b, miR-150, miR-223 and miR-382 in HIV-1 infection, miR-21 and miR-223 in influenza virus infection); immune-related diseases (e.g., miR-145, miR-34a, miR-155 and miR-326 in multiple sclerosis, miR-146a in systemic lupus erythematosus, miR-144, miR-146a, miR-150, miR-182, miR-103 and miR-107 in type II diabetes, miR-200a, miR-200b, miR-429, miR-122, miR-451 and miR-27 in nonalcoholic fatty liver disease, miR-29c, miR-34a, miR-155 and miR-200b in non-alcoholic steatohepatitis); and neurodegenerative diseases (e.g., miR-30b, miR-30c, miR-26a, miR-133b, miR-184* and let-7 in Parkinson's disease, miR-29b-1, miR-29a and miR-9 in Alzheimer's disease) (Li and Kowdley (2012) *Genomics Proteomics Bioinformatics* 10:246-253).

Studies have shown that specific endogenous miRNAs are up-regulated or down-regulated in certain cancers. For example, miR-140 is down-regulated in non-small cell lung cancer (NSCLC) and its overexpression was found to suppress PD-L1 (Xie et al. (2018) *Cell Physiol. Biochem.* 46:654-663); miR-197 is downregulated in platinum-based chemotherapy resistant NSCLC, resulting in chemoresistance, tumorigenicity and metastasis (Fujita et al. (2015) *Mol Ther* 23(4):717-727); and several miRNAs have been found to be down-regulated in cancer cells to allow PD-L1 expression, including miR-200, miR-34a and miR-138 (Yee et al. (2017) *J. Biol. Chem.* 292(50):20683-20693). Several miRNAs also are upregulated, for example miR-21, miR-17 and miR-221 in lung cancer (Xie et al. (2018 *Cell Physiol. Biochem.* 46:654-663).

MicroRNA-103 (miR-103) was identified as the most upregulated microRNA in endothelial cells as a result of genotoxic stress and DNA damage following radiation. It was found that miR-103 led to the downregulation of the TREX1, TREX2 and FANCF genes, and the decrease in TREX1 expression was identified as the major mechanism by which miR-103 mediates cell death and suppresses angiogenesis (Wilson et al. (2016) *Nature Communications* 7:13597). Since the loss of TREX1 results in the accumulation of ds and ssDNA, defective DNA repair, and release of cytokines, Wilson et al. examined whether miR-103 regulates the expression of cytokines. Results showed that miR-103 expression significantly upregulated the pro-inflammatory chemokines IP-10, RANTES, MIG, and the cytokines IL-15, IL-12 and IFN-γ, and this upregulation was due to a miR-103 mediated decrease in TREX1 levels. Studies also revealed a significant increase in costimulatory receptors CD40 and CD160, and a decrease in the numbers of PD-L1$^+$ macrophages and neutrophils in the 4T1 tumors. miR-103 regulation of TREX1 is therefore a potent modulator of the immune TME. Other miRNAs that target TREX1 include miR-107 (U.S. Pat. No. 9,242,000), miR-27a and miR-148b (U.S. Pat. No. 8,580,757). miRNA-103 can be used in the plasmids herein to inhibit TREX1.

Artificial miRNAs (amiRNAs) can be delivered to cells and used to silence target genes by creating a microRNA-based siRNA or shRNA vector (shRNAmir). The miR-30a backbone is often used in mammals, and approximately 200-300 bases of the primary miRNA transcript are included in the vector, with the miRNA hairpin placed at the center of the fragment, and the natural miRNA stem sequence being replaced with the siRNA/shRNA-encoding sequence of interest. Viral promoters, such as CMV, MSCV and TLR promoters; cellular promoters, such as EIF-1a; inducible chimeric promoters, such as tet-CMV; and tissue-specific promoters, can be used (Chang et al. (2013) *Cold Spring Harb Protoc; doi:*10.1101/pdb.prot075853). Other miRNAs that can be used include mir-16-2 (Watanabe et al. (2016) *RNA Biology* 13(1):25-33), miR-155 (Chung et al. (2006) *Nuc Acids Res* 34:e53), miR17-92 (Liu et al. (2008) *Nuc Acids Res* 36(9):2811-2824), miR-15a, miR-16, miR-19b, miR-20, miR-23a, miR-27b, miR-29a, miR-30b, miR-30c, miR-104, miR-132s, miR-181, miR-191, miR-223 (U.S. Pat. No. 8,426,675), and Let-7 miRNA (WO 2009/006450; WO 2015/032165).

shRNAmirs are limited by the low effectiveness of computationally-predicted shRNA sequences, particularly when expressed under low or single copy conditions. Third generation artificial miRNAs, such as miR-E (based on miR-30a) and miR-3G (based on miR-16-2) have been developed, and were found to exhibit stronger gene silencing in both Pol II- and Pol III-based expression vectors in comparison to shRNAmirs, due to the enhanced processing and accumulation of precisely-defined guide RNAs. miR-E, which was developed by the discovery of the conserved CNNC motif that enhances the processing of miRNA within the stem 3p flanking sequences, is different from endogenous miR-30a in three aspects: the stem of miR-E has no bulge and has the intended guide on the opposite strand; two conserved base pairs flanking the loop were mutated from CU/GG to UA/UA; and XhoI/EcoRI restriction sites were introduced into the flanking regions for shRNA cloning (Fellmann et al. (2013) *Cell Reports* 5:1704-1713). miR-E was found to be more potent than miR-30a, but symmetric processing of both the 3p and 5p strands of miR-30a does not favor guide strand delivery over passenger strand delivery, which is not optimal. Additionally, cloning into miR-E using oligos longer than 100 nt is costly and time consuming (Watanabe et al. (2016) *RNA Biology* 13(1):25-33).

Figure 1:
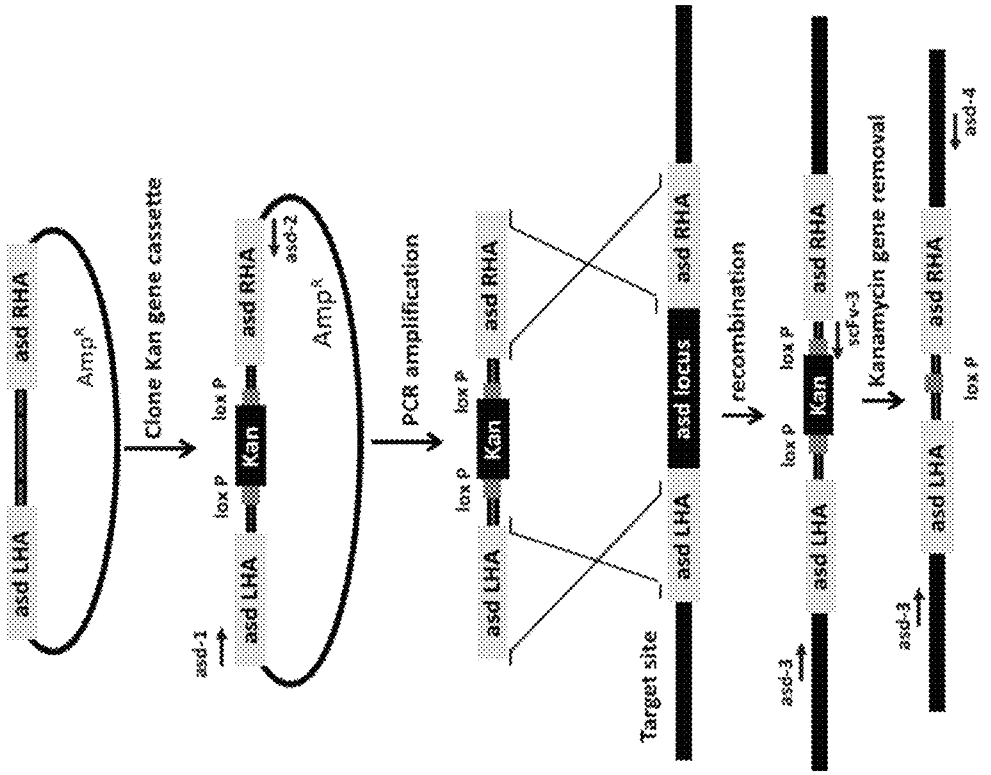
FIG. 1 depicts a schematic of the process used to delete the asd gene from strain YS1646. The asd gene from *S. typhimurium* strain YS1646 was deleted using lambda-derived Red recombination system as described in Datsenko and Wanner (*Proc Natl Acad Sci USA* 97:6640-6645 (2000)).

The amiRNA designated miR-16-2 (see, e.g., (Watanabe et al. (2016) *RNA Biology* 13(1):25-33, see FIG. 1) is a third generation (3G) amiRNA scaffold alternative; it is expressed in several tissues, is naturally asymmetric (the mature strand is derived exclusively from the 5p or 3p arm of the stem), and its stem and loop segments are small and rigid, simplifying vector cloning. miR-3G is generated by cloning the ~175 bp fragment containing the native miR-16-2 stem and loop, and the flanking 35 bps on either side of the stem, into the vector. miR-3G includes further modification of miR-16-2 by introducing cloning sites, such as MluI and EcoRI, into the 5p and 3p arm-flanking sequences, respectively, and fully base-pairing the guide (antisense) and passenger (sense) strand stem, with the exception of a mismatch at position 1 relative to the guide strand. The restriction sites allow for the generation of new targeting constructs via 88-mer duplexed DNA oligonucleotides without compromising the predicted secondary structure of the miR-16-2 hairpin and flanking elements. Additionally, one of the two CNNC motifs and the GHG motif (small RNA processing enhancers) are modified in the 3p flanking sequence of miR-16-2. siRNAs targeting the gene(s) of interest are then exchanged with the first 21 nucleotides of the mature 5p guide and 3p passenger sequences. Studies determined that miR-E and miR-3G were equally potent. miR-3G provides an attractive RNAi system, due to the smaller size of its expression cassette (~175 nts vs. ~375 for miR-E), and the simplified and cost effective single step cloning method for its production As with shRNAs, bacteria can be used as vectors for the in vivo delivery of micro-RNAs. For example, it was shown that attenuated *S. typhimurium* can be used as a vector for the oral delivery of plasmids expressing miRNA against CCL22 in mice with inflammation. Down-regulation of CCL22 gene expression by this method was successful both in vitro and in vivo in mouse models of atopic dermatitis (Yoon et al. (2012) *DNA and Cell Biology* 31(3):289-296). For purposes herein a miRNA 16-2 can be used to produce miRNAs to be used in place of the shRNA. The sequences for the shRNA can be used for design of miRNAs.

DNA encoding RNAi for disrupting and/or inhibiting and/or targeting any of selected target genes, such as any immune checkpoint described herein or known to the skilled artisan, is inserted into a microRNA backbone, such as the microRNA backbone set forth in SEQ ID NO:249, and below. Any suitable microRNA backbone known to the skilled artisan can be used; generally such backbones are based on a naturally-occurring microRNA and are modified for expression of the RNAi. Exemplary of such backbones is one based on miR-16-2 (SEQ ID NO:248). The sequence of the modified microRNA backbone is:

5'-CCGGATC AACGCCCTAG GTTTATGTTT GGATGAACTG ACATACGCGT ATCCGTC NNNNNNNNNNNNNNNNNNNNN GTAG TGAAATATAT ATTAAAC NNNNNNNNNNNNNNNNNNNNN TACGGTAACGCG GAATTCGCAA CTATTTTATC AATTTTTTGC GTCGAC-3' (SEQ ID NO:249), where the N's represent complementary, generally 18-26, such as 19-24, 19-22, 19-20, base pair long anti-sense and sense nucleotide sequences that target the gene to be silenced, and are inserted before and after the microRNA loop. RNAs, such as ARI-205 (SEQ ID NO:214) and ARI-206 (SEQ ID NO:215) are exemplary constructs based on the microRNA backbone of SEQ ID NO:249, that encode 21 and 22 base pair homology sequences, respectively. ARI-207 (SEQ ID NO:216) and ARI-208 (SEQ ID NO:217) are exemplary constructs based on the microRNA backbone of SEQ ID NO:249, that encode 19 base pair homology sequences. Another example, is the construct designated ARI-201, which is microRNA construct ARI-205, wherein the N's are replaced with a sequence of nucleotides targeting mouse PD-L1. The construct designated ARI-202 represents microRNA construct ARI-206, where the N's are replaced with sequences targeting mouse PD-L1. The skilled person readily can construct microRNAs for inclusion in plasmids as described and exemplified herein using the miR-16-2 backbone, or other suitable backbones known to the skilled artisan.

2. Origin of Replication and Plasmid Copy Number

Plasmids are autonomously-replicating extra-chromosomal circular double stranded DNA molecules that are maintained within bacteria by means of a replication origin. Copy number influences the plasmid stability. High copy number generally results in greater stability of the plasmid when the random partitioning occurs at cell division. A high number of plasmids generally decreases the growth rate, thus possibly allowing for cells with few plasmids to dominate the culture, since they grow faster. The origin of replication also determines the plasmid's compatibility: its ability to replicate in conjunction with another plasmid within the same bacterial cell. Plasmids that utilize the same replication system cannot co-exist in the same bacterial cell. They are said to belong to the same compatibility group. The introduction of a new origin, in the form of a second plasmid from the same compatibility group, mimics the result of replication of the resident plasmid. Thus, any further replication is prevented until after the two plasmids have been segregated to different cells to create the correct pre-replication copy number.

| Origin of Replication | Copy Number | SEQ ID NO. |
|---|---|---|
| pMB1 | 15-20 | 254 |
| p15A | 10-12 | 255 |
| pSC101 | ~5 | 256 |
| pBR322 | 15-20 | 243 |
| ColE1 | 15-20 | 257 |
| pPS10 | 15-20 | 258 |
| RK2 | ~5 | 259 |
| R6K (alpha origin) | 15-20 | 260 |
| R6K (beta origin) | 15-20 | 261 |
| R6K (gamma origin) | 15-20 | 262 |
| P1 (oriR) | Low | 263 |
| R1 | Low | 264 |
| pWSK | Low | 265 |
| ColE2 | 10-15 | 266 |
| pUC (pMB1) | 500-700 | 267 |
| F1 | 300-500 | 268 |

Numerous bacterial origins of replication are known to those of skill in the art. The origin can be selected to achieve a desired copy number. Origins of replication contain sequences that are recognized as initiation sites of plasmid replication via DNA dependent DNA polymerases (Solar et al. (1998) *Microbiology And Molecular Biology Reviews* 62(2):434-464). Different origins of replication provide for varying plasmid copy levels within each cell and can range from 1 to hundreds of copies per cell. Commonly used bacterial plasmid origins of replication include, but are not limited to, pMB1 derived origins, which have very high copy derivatives, ColE1 origins, p15A, pSC101, pBR322, and others, which have low copy numbers. Such origins are well known to those of skill in the art. The pUC19 origin results in copy number of 500-700 copies per cell. The pBR322 origin has a known copy number of 15-20. These origins only vary by a single base pair. The ColE1 origin copy number is 15-20, and derivatives such as pBluescript have copy numbers ranging from 300-500. The p15A origin that is in pACYC184, for example, results in a copy number of approximately 10. The pSC101 origins confer a copy number of approximately 5. Other low copy number vectors from which origins can be obtained, include, for example, pWSK29, pWKS30, pWKS129 and pWKS130 (see, Wang et al. (1991) *Gene* 100:195-199). Medium to low copy number is less than 150, or less than 100. Low copy number is less than 20, 25, or 30. Those of skill in the art can identify plasmids with low or high copy number. For example, to determine experimentally if the copy number is high or low is to perform a miniprep. A high-copy plasmid should yield between 3-5 μg DNA per 1 ml LB culture; a low-copy plasmid will yield between 0.2-1 μg DNA per ml of LB culture.

Sequences of bacterial plasmids, including identification of and sequence of the origin of replication, are well known (see, e.g., snapgene.com/resources/plasmid_files/basic_cloning_vectors/pBR322/).

High copy plasmids are selected for heterologous expression of proteins in vitro because the gene dosage is increased relative to chromosomal genes and higher specific yields of protein, and for therapeutic bacteria, higher therapeutic dosages of encoded therapeutics. It is shown, herein, however, that for delivery of plasmids encoding RNA interference (RNAi), such as by *S. typhimurium*, as described herein, while it would appear that a high copy plasmid would be ideally suited, therapeutically, a lower copy number is more effective.

The requirement for bacteria to maintain the high copy plasmids can be a problem if the expressed molecule is toxic to the organism. The metabolic requirements for maintaining these plasmids can come at a cost of replicative fitness in vivo. Optimal plasmid copy number for delivery of interfering RNAs can depend on the mechanism of attenuation of the strain engineered to deliver the plasmid. If needed, the skilled person, in view of the disclosure herein, can select an appropriate copy number for a particular immunostimulatory species and strain of bacteria. It is shown herein, that low copy number can be advantageous.

3. CpG Motifs and CpG Islands

Unmethylated cytidine-phosphate-guanosine (CpG) motifs are prevalent in bacterial, but not vertebrate, genomic DNA. Pathogenic DNA and synthetic oligodeoxynucleotides (ODN) containing CpG motifs activate host defense mechanisms, leading to innate and acquired immune responses. The unmethylated CpG motifs contain a central unmethylated CG dinucleotide plus flanking regions. In humans, four distinct classes of CpG ODN have been identified based on differences in structure and the nature of the immune response they induce. K-type ODNs (also referred to as B-type) contain from 1 to 5 CpG motifs typically on a phosphorothioate backbone. D-type ODNs (also referred to as A-type) have a mixed phosphodiester/phosphorothioate backbone and have a single CpG motif, flanked by palindromic sequences that enables the formation of a stem-loop structure, as well as poly G motifs at the 3' and 5' ends. C-type ODNs have a phosphorothioate backbone and contain multiple palindromic CpG motifs that can form stem loop structures or dimers. P-Class CpG ODN have a phosphorothioate backbone and contain multiple CpG motifs with double palindromes that can form hairpins at their GC-rich 3' ends (Scheiermann and Klinman (2014) *Vaccine* 32(48):6377-6389). For purposes herein, the CpGs are encoded in the plasmid DNA; they can be introduced as a motif, or in a gene.

Toll-like receptors (TLRs) are key receptors for sensing pathogen-associated molecular patterns (PAMPs) and activating innate immunity against pathogens (Akira et al. (2001) *Nat Immunol*. August; 2(8)). TLR9 recognizes hypomethylated CpG motifs in DNA of prokaryotes that do not occur naturally in mammalian DNA (McKelvey et al. (2011) *J Autoimmunity* 36:76). Recognition of CpG motifs upon phagocytosis of pathogens into endosomes in immune cell subsets induces IRF7-dependent type I interferon signaling and activates innate and adaptive immunity.

Immunostimulatory bacteria, such as *Salmonella* species, such as *S. typhimurium*, strains carrying plasmids containing CpG islands, are provided herein. These bacteria can activate TLR9 and induce type I IFN-mediated innate and adaptive immunity. As exemplified herein, bacterial plasmids that contain hypomethylated CpG islands can elicit innate and adaptive anti-tumor immune responses that, in combination with RNAi encoded in the plasmid, such as RNAi that targets immune checkpoints, such as the shRNA or miRNA that targets TREX1, and hence, TREX1-mediated STING pathway activation, can have synergistic or enhanced anti-tumor activity. For example, the asd gene (SEQ ID NO:48) encodes a high frequency of hypomethylated CpG islands. CpG motifs can be included in combination with any of the RNAi described or apparent from the description herein in the immunostimulatory bacteria, and thereby enhance or improve anti-tumor immune responses in a treated subject.

Immunostimulatory CpGs can be included in the plasmids, by including nucleic acid, typically from a bacterial gene, that encodes a gene product, and also by adding nucleic acid that encodes CpG motifs. The plasmids herein can include CpG motifs. Exemplary CpG motifs are known (see, e.g., U.S. Pat. Nos. 8,232,259, 8,426,375 and 8,241,844). These include, for example, synthetic immunostimulatory oligonucleotides, between 10 and 100, 10 and 20, 10 and 30, 10 and 40, 10 and 50, 10 and 75, base pairs long, with the general formula:

$(CpG)_n$, where n is the number of repeats.

Generally, at least one or two repeats are used; non-CG bases can be interspersed. Those of skill in the art are very familiar with the general use of CpG motifs for inducing an immune response by modulating TLRs, particularly TLR9.

4. Plasmid Maintenance/Selection Components

The maintenance of plasmids in laboratory settings is usually ensured by inclusion of an antibiotic resistance gene on the plasmid and use of antibiotics in growth media. As described above the use of an asd deletion mutant complimented with a functional asd gene on the plasmid allows for plasmid selection in vitro without the use of antibiotics and allows for plasmid selection in vivo. The asd gene complementation system provides for such selection (Galan et al. (1990) *Gene* 28:29-35). The use of the asd gene complementation system to maintain plasmids in the tumor microenvironment are expected to increase the potency of *S. typhimurium* engineered to deliver plasmids encoding genes or interfering RNAs.

RNA Polymerase Promoters

Plasmids provided herein are designed to encode interfering RNAs targeting immunological checkpoints as described above. The RNA expression cassette contains a promoter for transcription in human cells such as an H1 promoter or a U6 promoter, or a CMV promoter. U6 and H1 are RNA polymerase III (RNAP III) promoters, which are for production and processing of small RNAs. The CMV promoter is recognized by RNA polymerase II, and is more amenable for expression of long RNA stretches than is RNAP III. The promoter precedes the interfering RN, such as an shRNA, siRNA or miRNA, as described above.

In eukaryotic cells, DNA is transcribed by three types of RNA polymerases; RNA Pol I, II and III. RNA Pol I transcribes only ribosomal RNA (rRNA) genes, RNA Pol II transcribes DNA into mRNA and small nuclear RNAs (snRNAs), and RNA Pol III transcribes DNA into ribosomal 5S rRNA (type I), transfer RNA (tRNA) (type II) and other small RNAs such as U6 snRNAs (type III). shRNAs are typically transcribed in vivo under the control of eukaryotic type III RNA Pol III promoters, such as the human U6 promoter, which transcribes the U6 snRNA component of the spliceosome, and the H1 human promoter, which transcribes the RNA component of RNase P. U6 and H1 promoters are more suitable than other Pol III or Pol II promoters because they are structurally simple, with a well-defined transcription start-site, and naturally drive the transcription of small RNAs. U6 and H1 promoters do not carry the sequences necessary for transcribing anything downstream from the transcription start site (Makinen et al. (2006) *J. Gene Med.* 8:433-441). They are thus the most straightforward promoters for use in shRNA expression.

The use of other promoters such as type II pol III tRNA promoters, while successful in expressing shRNAs, results in longer dsRNA transcripts, which can induce an interferon response. RNA pol II promoters, such as the human cytomegalovirus (CMV) promoter also may be used (U.S. Pat. Nos. 8,202,846; 8,383,599), but are more often utilized for expression of long RNA stretches. Studies have shown that the addition of the enhancer from the CMV promoter near the U6 promoter can increase its activity, increasing shRNA synthesis and improving gene silencing (Xia et al. (2003) *Nucleic Acids Res.* 31(17):e100; Nie et al. (2010) *Genomics Proteomics Bioinformatics* 8(3):170-179). RNA pol II promoters are typically avoided in shRNA transcription due to the generation of cytoplasmic DNA, which leads to a pro-inflammatory interferon response. In this case, a cytoplasmic DNA mediated interferon response in *S. typhimurium*-infected tumor cells has anti-tumor benefit, especially in the context of TREX1 inhibition as provided herein. Prokaryotic promoters, including T7, pBAD and pepT promoters can be utilized when transcription occurs in a bacterial cell (Guo et al. (2011) *Gene therapy* 18:95-105; U.S. Patent Publication Nos. 2012/0009153, 2016/0369282; International Patent Publication Nos. WO 2015/032165, WO 2016/025582).

RNA pol III promoters generally are used for constitutive shRNA expression. For inducible expression, RNA pol II promoters are used. Examples include the pBAD promoter, which is inducible by L-arabinose; tetracycline-inducible promoters such as TRE-tight, IPT, TRE-CMV, Tet-ON and Tet-OFF; retroviral LTR; IPTG-inducible promoters such as Lad, Lac-O responsive promoters; LoxP-stop-LoxP system promoters (U.S. Pat. No. 8,426,675; International Patent Publication No. WO 2016/025582); and pepT, which is a hypoxia-induced promoter. (Yu et al. (2012) *Scientific Reports* 2:436). These promoters are well known. Exemplary of these promoters are human U6 (SEQ ID NO:73) and human H1 (SEQ ID NO:74).

The inclusion of a DTS on a plasmid to increase nuclear transport and expression has been demonstrated by (Dean, D. A. et al. (1999) *Exp. Cell Res.* 253(2):713-722), and has been used to increase gene expression from plasmids delivered by *S. typhimurium* (Kong et al. (2012) *PNAS* 109(47): 19414-19419).

Rho-independent or class I transcriptional terminators such as the T1 terminator of the rrnB gene of *E. coli* contain sequences of DNA that form secondary structures that cause dissociation of the transcription elongation complex. Transcriptional terminators shall be included in the plasmid in order to prevent expression of interfering RNAs by the *S. typhimurium* transcriptional machinery. This ensures that expression of the encoded interfering RNA, such as shRNA, micro-RNA and siRNA, is confined to the host cell transcriptional machinery.

Plasmids used for transformation of *Salmonella*, such as *S. typhimurium*, as a cancer therapy described herein, contain all or some of the following attributes: 1) a CpG island, 2) a bacterial origin of replication, 3) an asd gene selectable marker for plasmid maintenance, 4) one or more human interfering RNA expression cassettes, 5) DNA nuclear targeting sequence, and 6) transcriptional terminators.

F. Tumor Targeting Immunostimulatory Bacteria Contain RNAi Against Exemplary Immune Target Genes to Stimulate Anti-Tumor Immunity RNAi against any immune target can be encoded in the plasmids. These include, but are not limited to, any discussed in the disclosure herein, and any known to those of skill in the art. The following discussion describes exemplary targets. The plasmids can contain any RNAi against such targets, including, but not limited to, shRNA, siRNA and microRNA.

| SEQ ID NO. | Name | | Sequence |
|---|---|---|---|
| 73 | human U6 RNA | | aa ggtcgggcag gaagagggcc |
| | pol III | 721 | tatttcccat gattccttca tatttgcata tacgatacaa ggctgttaga gagataatta |
| | promoter | 781 | gaattaattt gactgtaaac acaaagatat tagtacaaaa tacgtgacgt agaaagtaat |
| | | 841 | aatttcttgg gtagtttgca gttttaaaat tatgttttaa aatggactat catatgctta |
| | | 901 | ccgtaacttg aaagtatttc gatttcttgg ctttatatat cttgtggaaa ggacgaaact |
| | | 961 | ag |
| 74 | human H1 RNA | | atatttgca tgtcgctatg |
| | pol III | 721 | tgttctggga aatcaccata aacgtgaaat gtctttggat ttgggaatct tataagttct |
| | promoter | 781 | gtatgagacc actccctagg |

Tissue specific promoters include TRP2 promoter for melanoma cells and melanocytes; MMTV promoter or WAP promoter for breast and breast cancer cells, Villin promoter or FABP promoter for intestinal cells, RIP promoter for pancreatic beta cells, Keratin promoter for keratinocytes, Probasin promoter for prostatic epithelium, Nestin promoter or GFAP promoter for CNS cells/cancers, Tyrosine Hydroxylase S100 promoter or neurofilament promoter for neurons, Clara cell secretory protein promoter for lung cancer, and Alpha myosin promoter in cardiac cells (U.S. Pat. No. 8,426,675).

5. DNA Nuclear Targeting Sequences

DNA nuclear targeting sequences (DTS)s such as the SV40 DTS mediate the translocation of DNA sequences through the nuclear pore complex. The mechanism of this transport is reported to be depending on the binding of DNA binding proteins that contain nuclear localization sequences.

1. TREX1

In certain embodiments provided herein, the immunostimulatory bacteria encode inhibitory RNA, such as shRNA, that inhibit or disrupt or suppress TREX1 expression. The enzyme product encoded by TREX1, located upstream from cGAS, is a mediator of the type I interferon pathway. TREX1 encodes the major 3' DNA exonuclease in mammalian cells (also called DNase III). Human TREX1 proteins are as catalytically efficient as bacterial exonucleases (Mazur and Perrino (2001) *J. Biol. Chem.* 276:17022-17029). Immunostimulatory bacterium that inhibit TREX1 expression by processes other than RNA silencing also are contemplated herein.

For the immunostimulatory bacteria provided herein, such as those that express shRNA against TREX1, loss of TREX1 activity and subsequent activation of cGAS/STING-induced vascular disruption enhances tumor colonization of *S. typh-*

*imurium*. The TREX1 gene encodes a protein that is 314 amino acids long (Mazur et al. (2001) *J. Biol. Chem* 276: 17022-17029), exists as a homodimer, and lacks endonuclease activity. TREX1 is among several proteins involved in the repair of DNA that is damaged by exogenous genotoxic stress, including UV irradiation and DNA-damaging compounds. TREX1 can function as an editing exonuclease for DNA pol β by excising mispaired nucleotides from the 3' end (Mazur et al. (2001) *J. Biol. Chem* 276:17022-17029). ssDNA is degraded 3-4 times more efficiently than dsDNA (Lindahl et al. (2009) *Biochem Soc Trans* 37 (Pt 3), 535-538). Mutations in residues D18 and D200, frequently associated with autoimmune diseases, disable TREX1 enzyme from degrading dsDNA and reduces its ability to degrade ssDNA. TREX1 enzyme translocates from the endoplasmic reticulum to the nucleus following DNA damage, indicating its involvement in the replication of damaged DNA. Promoter activation and upregulation of TREX1 has been observed as a result of UVC exposure in mouse fibroblasts, and TREX1 null mouse cells have demonstrated hypersensitivity to UVC light (Tomicic et al. (2013) *Bioch. Biophys. Acta* 1833:1834-1844).

Mutations resulting in loss of TREX1 have been identified in patients with the inherited rare disease, Aicardi-Goutieres syndrome (AGS), which has phenotypic overlap with the autoimmune diseases systemic lupus erythematosus (SLE) and chilblain lupus (Aicardi and Goutieres, *Neuropediatrics* (2000)). Mutations in TREX1 also are associated with retinal vasculopathy with cerebral leukodystrophy. TREX1-mediated autoimmune diseases are associated with the cell's inability to prevent autoimmunity via the degradation of ssDNA and dsDNA that accumulates in the cytoplasm. TREX1 null mice suffer from inflammatory myocarditis, resulting in circulatory failure, which is caused by chronic cytokine production (Morita et al., *Mol Cell Biol* (2004); Yang et al., *Cell* (2007); Tomicic et al., *Bioch. Biophys. Acta* (2013)). Hence, TREX1 deficiency induces innate immunity following the cytoplasmic accumulation of DNA, resulting in an inflammatory response (Wang et al. (2009) *DNA Repair* (*Amst*)8: 1179-1189). The source of the DNA that accumulates in the cytosol of TREX1-deficient cells was found to be in part derived from endogenous retroelements that escape from the damaged nucleus, as TREX1 is known to metabolize reverse-transcribed (RT) DNA (Stetson et al., *Cell* (2008)). In HIV infection, HIV RT DNA accumulates in the cytosol of infected T cells and macrophages, and would normally trigger cGAS/STING activation of antiviral immunity. TREX1 digests this viral DNA and permits HIV immune escape (Yan et al., *Nat. Immunol.* (2010)). Thus, TREX1 acts as a negative regulator of STING, and can be exploited to evade detection by several retroviruses, such as murine leukemia virus (MLV), simian immunodeficiency virus (SIV), and many others (Hasan et al. (2014) *Front. Microbiol.* 4:393).

Like STING, TREX1 is expressed in most mammalian cell types, with the key producers of cytokines in TREX1 null mice originating from macrophages and dendritic cells (Ahn et al., *J. Immunol.* (2014)). Data indicate that TREX1 is responsible for degrading self-DNA that can leak from a damaged nucleus into the cytosol, where it would otherwise bind and activate cGAS and lead to autoimmunity (Barber, *Nat. Rev. Immunol.* (2015)). In support of this, TREX1 null mice and TREX1-deficient cells that also lack cGAS are completely protected from type I interferon activation and lethal autoimmunity (Ablasser et al., *J. Immunol.* (2014); Gray et al., *J. Immunol.* (2015)). In a negative feedback loop, type I interferon and type II IFNγ can also induce TREX1, and TREX1 thus serves to limit aberrant autoimmune activation (Tomicic et al. (2013) *Bioch. Biophys. Acta* 1833: 1834-1844).

Lymphocytes derived from an Aicardi-Goutieres syndrome patient, containing mutated TREX1, were found to inhibit angiogenesis and the growth of neuroblastoma cells, the effect being enhanced by the presence of IFN-α (Pulliero et al. (2012) *Oncology Reports* 27:1689-1694). The use of microRNA-103 also has been shown to inhibit the expression of TREX1, disrupting DNA repair and angiogenesis, and resulting in decreased tumor growth in vivo (see, U.S. Patent Publication No. 2014/0127284, Cheresh et al.).

TREX1 is a negative regulator of macrophage activation and pro-inflammatory function. TREX1 null macrophages were found to exhibit increased TNF-α and IFN-α production, higher levels of CD86, and increased antigen presentation to T cells, as well as impaired apoptotic T cell clearance (Pereira-Lopes et al. (2013) *J. Immunol.* 191: 6128-6135). The inability to adequately digest apoptotic DNA in TREX1 null macrophages generates high amounts of aberrant cytosolic DNA, which binds to cGAS and activates the STING pathway to produce higher levels of type I interferon (Ahn et al. (2014) *J. Immunol.* 193:4634-4642). Not all cell types are sensitive to the immunostimulatory effects of Trex1 knockdown, however. In a study of individual cell types, dendritic cells, macrophages, fibroblasts and keratinocytes were found to produce type I IFN upon Trex1 knockdown, while B cells, cardiomyocytes, neurons and astrocytes did not (Peschke et al. (2016) *J. Immunol.* 197:2157-2166). Thus, inhibiting the function of TREX1 in phagocytic cells that have engulfed *S. typhimurium* would enhance their pro-inflammatory activity, while driving an accumulation of cytosolic DNA from phagocytosed tumor cells that can then activate the cGAS/STING pathway. The use of microRNA-103 has inhibits the expression of TREX1, disrupting DNA repair and angiogenesis, and resulting in decreased tumor growth in vivo (see, U.S. Publication No. 2014/0127284, Cheresh et al.).

Studies have found that the expression of cGAS and/or STING is inhibited in over a third of colorectal cancers, while STING expression is lost in many primary and metastatic melanomas and $HPV^+$ cancers. STING signaling remains intact in all tumor-resident APCs that continuously sampling the antigenic milieu of the TME, including Batf3-lineage CD103/$CD8\alpha^+$ DCs that cross-present tumor antigens to $CD8^+$ T cells, and these APCs will also readily phagocytose *S. typhimurium* or be activated by type I IFN from neighboring macrophages that have phagocytosed *S. typhimurium* containing TREX1 gene knockdown.

Inactivation of TREX1 enhances an immune response by enabling cytosolic accumulation of dsDNA to bind to the enzyme cyclic GMP-AMP (cGAMP) synthase (cGAS), a cytosolic DNA sensor that triggers the production of type I interferons and other cytokines through activation of the STING signaling pathway (Sun et al. (2013) *Science* 339 (6121):786-791; Wu et al. (2013) *Science* 339(6121):826-830). Activation of the STING pathway has been shown to induce potent innate and adaptive antitumor immunity (Corrales et al. (2015) *Cell Reports* 11:1018-1030).

Hence, embodiments of the immunostimulatory bacterial strains, as provided herein, are administered to inhibit TREX1 in tumor-resident APCs and induce cGAS/STING activation, thereby activating these DCs to cross-present host tumor antigens to $CD8^+$ T cells and induce local and systemic tumor regression and durable anti-tumor immunity (Corrales et al. (2015) *Cell Reports* 11:1018-1030; Zitvogel et al. (2015) *Nat. Rev. Mol. Cell. Biol.* 16:393-405).

The clinical activity of VNP20009 was largely disappointing in part due to its poor ability to colonize human tumors, a phenomenon that was not observed in mouse models (Nemunaitis et al., *Cancer Gene Ther*. (2003); Toso et al., *J. Clin. Oncol*. (2002); Heimann et al., *J. Immunother*. (2003)). It was later revealed that the reason for the discrepancy between human and mouse tumor colonization was that orthotopically transplanted syngeneic mouse tumors are much more vascularized than human tumors. In order to more closely model the lack of human tumor vascularization in mice, autochthonous tumor models were treated with VNP20009 and found to only enable tumor colonization with pre-treatment of a vascular disrupting agent (Drees et al., *J of Cancer* (2015); Drees et al., *Anticancer Res*. (2015)). Vascular disrupting agents such as 5,6-Dimethylxanthenone-4-acetic acid (DMXAA) have been shown to mediate tumor collapse in mice (but not humans) by directly binding STING and inducing type I interferon signaling (Baguley, *Lancet Oncol*. (2003); Corrales and Glickman et al., *Cell Reports* (2015)). STING signaling induces TNF-α and IFN-γ production, cytokines which have been shown to directly promote vascular disruption by downregulating αVβ3 integrin adhesion receptors on endothelial cells (Rüegg et al., *Nat Medicine* (1998)). Production of innate pro-inflammatory cytokines such as TNF-α, IL-12p40 and IFN-γ that are induced upon STING activation are critical for activating anti-tumor immunity (Burdette et al. (2011) *Nature* 478(7370):515-518).

Thus, the immunostimulatory bacteria provided herein express shRNA against TREX1, and loss of TREX1 and subsequent activation of cGAS/STING-induced vascular disruption enhance tumor colonization of *S. typhimurium.*

2. PD-L1

Programmed cell death protein 1 (PD-1) is an immune-inhibitory receptor that is involved in the negative regulation of immune responses. Its cognate ligand, programmed death-ligand 1 (PD-L1), is expressed on APCs, and upon binding to PD-1 on T cells, leads to loss of $CD8^+$ T cell effector function, inducing T cell tolerance. The expression of PD-L1 is often associated with tumor aggressiveness and reduced survival in certain human cancers (Gao et al. (2009) *Clin. Cancer Res.* 15(3):971-979).

Antibodies designed to block immune checkpoints, such as anti-PD-1 (for example, pembrolizumab, nivolumab) and anti-PD-L1 (for example, atezolizumab, avelumab, durvalumab) antibodies have had durable success in preventing T cell anergy and breaking immune tolerance. Only a fraction of treated patients exhibit clinical benefit, and those that do often present with autoimmune-related toxicities (Ribas (2015) *N. Engl. J. Med.* 373(16):1490-1492; Topalian et al. (2012) *N. Engl. Med.* 366(26):2443-54). Besides acquiring toxicity, PD-1/PD-L1 therapy often leads to resistance, and the concomitant use of anti-CTLA-4 antibodies (for example, ipilimumab) has shown limited success in clinical trials with significantly additive toxicity. To limit the toxicity and enhance the potency of PD-L1 blockade, an immunostimulatory bacteria with an shRNA to PD-L1, as provided herein, will synergize with TLR activation of immune cells to both activate and potentiate anti-tumor immunity.

3. VISTA

Other non-redundant checkpoints in immune activation can synergize with PD-1/PD-L1 and CTLA-4, such as V-domain immunoglobulin (Ig) suppressor of T cell activation (VISTA). VISTA is expressed primarily on APCs, particularly on tumor-infiltrating myeloid cells and myeloid-derived suppressor cells (MDSC), and to a lesser extent on regulatory T cells (CD4+Foxp3+Tregs) (Wang et al. (2011) *J. Exp. Med.* 208(3):577-592). Similar to PD-L1, VISTA upregulation directly suppresses T cell proliferation and cytotoxic function (Liu et al. (2015) *PNAS* 112(21):6682-6687). Monoclonal antibody targeting of VISTA was shown to remodel the tumor microenvironment in mice, increasing APC activation and enhancing anti-tumor immunity (Le-Mercier et al. (2014) *Cancer Res.* 74(7):1933-1944). Clinically, VISTA expression was shown to be upregulated on tumor-resident macrophages following treatment with anti-CTLA-4 therapy in prostate cancer, demonstrating compensatory regulation of immune checkpoints (Gao et al. (2017) *Nat. Med.* 23(5):551-555). The majority of VISTA expression is purported to be located in the intracellular compartment of myeloid cells, rather than on the surface, which may limit the effectiveness of the monoclonal antibody approach (Deng et al. (2016) *J. Immunother. Cancer* 4:86). The ability to inhibit VISTA from within the APC using a tumor-targeting bacteria containing shRNA to VISTA, as provided herein, will more efficiently and completely inhibit the T cell-suppressing function of VISTA, leading to activation of T cell-mediated anti-tumor immunity and tumor regression.

4. SIRPα

One mechanism by which tumor cells evade removal is to prevent their phagocytosis by innate immune cells. Phagocytosis is inhibited by surface expression of CD47, which is widely expressed on hematopoietic and non-hematopoietic cells (Liu et al. (2015) *PLoS ONE* 10(9):e0137345). Upon CD47 binding its receptor, signal regulatory protein alpha (SIRPα), an inhibitory signal for phagocytosis, is initiated. SIRPα is abundantly expressed on phagocytic cells, including macrophages, granulocytes and DCs. As such, the protein-protein interaction between CD47 and SIRPα represents another class of immune checkpoints unique to APCs, and tumor-resident macrophages in particular. The effectiveness of CD47 in preventing phagocytosis is evidenced by the fact that it is often upregulated in a wide variety of tumors, which allow them to avoid being phagocytosed by APCs in the tumor microenvironment (Liu et al. (2015) *Nat. Med.* 21(10):1209-1215). Several methods to block the CD47/SIRPα interaction have been examined, including the development of anti-CD47 or anti-SIRPα antibodies or antibody fragments, the use of small peptides that bind either protein, or the knockdown of CD47 expression (U.S. Patent Publication Nos. 2013/0142786, 2014/0242095; International Patent Publication No. WO 2015/191861; McCracken et al. (2015) *Clin. Cancer Res.* 21(16):3597-3601). To this end, several monoclonal antibodies that directly target SIRPα are in clinical development, either alone or in combination with tumor-targeting antibodies (e.g. Rituximab, Daratumumab, Alemtuzumab, Cetuximab) that can enhance phagocytosis of antibody-opsonized tumor cells, in a process known as antibody-dependent cellular phagocytosis (ADCP) (McCracken et al. (2015) *Clin. Cancer Res.* 21(16):3597-3601; Yanagita et al. (2017) *JCI Insight* 2(1):e89140).

The CD47/SIRPα interaction also serves to preserve the longevity of red blood cells by preventing their phagocytic elimination (Murata et al. (2014) *J. Biochem.* 155(6):335-344). Thus, systemically administered therapies such as anti-CD47 antibodies that broadly disrupt this interaction have resulted in anemia toxicities (Huang et al. (2106) *J Thorac Dis.* 126:2610-20). Systemic SIRPα-based therapies also risk adverse events, such as organ damage by creating systemic hyperphagocytic self-eating macrophages. Using a tumor-targeting immunostimulatory bacteria containing an shRNA to SIRPα, such as provided herein, will localize the CD47/SIRPα disruption to the tumor microenvironment and eliminate these adverse events. Further, inhibition of SIRPα in the context of bacterial activation of TLR-mediated pro-inflammatory signaling pathways will potently activate these macrophages to become hyperphagocytic towards neighboring tumor cells (Bian et al. (2016) *PNAS.* 113(37): E5434-E5443).

5. β-Catenin

Immune checkpoint pathways exemplify the multiple layers of regulation that exist to prevent immune hyper-activation and autoimmunity, and the difficulties in subverting these pathways to promote anti-tumor immunity. One mechanism by which tumors have evolved to be refractory to checkpoint therapies is through their lack of T cell and dendritic cell (DC) infiltration, described as non-T-cell-inflamed, or "cold tumors" (Sharma et al. (2017) *Cell* 9; 168(4):707-723). Several tumor-intrinsic mechanisms have been identified that lead to the exclusion of anti-tumor T cells and resistance to immunotherapy. In melanoma, in particular, molecular profiling of checkpoint therapy-refractory tumors revealed a signature of elevated β-catenin and its downstream target genes, correlating with a lack of tumor-infiltrating lymphocytes (Gajewski et al. (2011) *Curr. Opin. Immunol.* 23(2):286-292).

CTNNB1 is an oncogene that encodes β-catenin, and can induce the expression of the genes c-Myc and cyclin D1, resulting in tumor proliferation. Mutations in CTNNB1 are associated with certain cancers. Gene silencing of CTNNB1/β-catenin using *S. typhimurium* shRNA vectors can be used in the treatment of cancer (Guo et al. (2011) *Gene therapy* 18:95-105; U.S. Patent Publication Nos. 2012/0009153, 2016/0369282; International Patent Publication No. WO 2015/032165). For example, shRNA silencing of CTNNB1, using *S. typhimurium* strain SL7207 as a delivery vector, reduced tumor proliferation and growth in SW480 xenograft mice, when compared to control cells, and reduced expression of c-Myc and cyclin D1 (Guo et al. (2011) *Gene therapy* 18:95-105). Silencing of CTNNB1 for the treatment of hepatoblastoma also can be achieved using miRNA, with or without antibody therapeutics against the immune checkpoints PD-land PD-L1 (International Patent Publication No. WO 2017/005773). The use of siRNA or shRNA targeting CTNNB1, delivered via alternative vectors, such as liposomes, for the treatment of CTNNB1-related cancers, including adenocarcinomas and squamous cell carcinomas, also can be affected (U.S. Patent Publication Nos. 2009/0111762, 2012/0294929).

Elevated β-catenin signaling directly inhibits the chemokine CCL4 from recruiting Batf3-lineage CD103/CD8$\alpha^+$ DCs, thereby preventing them from priming tumor antigen-specific CD8$^+$ T cells (Spranger et al. (2015) *Nature* 523 (7559):231-235). β-catenin is the major downstream mediator of the WNT signaling pathway, a key embryonic developmental pathway that is also critical for adult tissue regeneration, homeostasis and hematopoiesis (Clevers et al. (2012) *Cell* 149(6):1192-1205). Excessive WNT/β-catenin signaling has been implicated in a variety of cancers (Tai et al. (2015) *Oncologist* 20(10):1189-1198). Accordingly, several strategies to target WNT/β-catenin signaling have been pursued, but success has been hampered by a lack of specificity to the tumor microenvironment, resulting in off-target toxicities to intestinal stem cells, bone turnover and hematopoiesis (Kahn (2014) *Nat. Rev. Drug Dis.* 13(7): 513-532). The immunostimulatory bacteria provided herein overcome these problems.

For example, an advantage of using an immunostimulatory bacteria with shRNA to β-catenin as provided herein, is enhancing chemokine-mediated infiltration of T cell-priming DCs and the conversion of a cold tumor to a T-cell-inflamed tumor microenvironment, without the systemic toxicities of existing therapeutic modalities. Further, bacterial activation of TLR innate immune signaling pathways synergize with β-catenin inhibition to further promote immune activation and anti-tumor immunity.

6. TGF-β

Transforming growth factor beta (TGF-β) is a pleiotropic cytokine with numerous roles in embryogenesis, wound healing, angiogenesis and immune regulation. It exists in three isoforms in mammalian cells, TGF-β1, TGF-β2 and, TGF-β3; TGF-β1 is the most predominant in immune cells (Esebanmen et al. (2017) *Immunol Res.* 65:987-994). TGF-β's role as an immunosuppressant is arguably its most dominant function. Its activation from a latent form in the tumor microenvironment, in particular, has profound immunosuppressive effects on DCs and their ability to tolerize antigen-specific T cells. TGF-β can also directly convert Th1 CD4$^+$ T cells to immunosuppressive Tregs, furthering promoting tumor tolerance (Travis et al. (2014) *Annu Rev Immunol.* 32: 51-82). Based on its tumor-specific immunosuppressive functions, and irrespective of its known cancer cell growth and metastasis-promoting properties, inhibition of TGF-β is a cancer therapy target. High TGF-β signaling has been demonstrated in several human tumor types, including CRC, HCC, PDAC and NSCLC (Colak et al. (2017) *Trends in Cancer* 3:1). Systemic inhibition of TGF-β can lead to unacceptable autoimmune toxicities, and its inhibition should be localized to the tumor microenvironment. As such, a tumor-targeting immunostimulatory bacteria with RNAi, such as shRNA, to TGF-β, provided herein, or an shRNA to TGF-βRII, breaks tumor immune tolerance and stimulates anti-tumor immunity.

7. VEGF

Angiogenesis, or the development of new blood vessels, is an essential step for any tumor microenvironment to become established. Vascular endothelial growth factor (VEGF) is the critical mitogen for endothelial proliferation and angiogenesis, and inhibition of VEGF in the tumor microenvironment markedly decreases tumor vascularity, thereby starving the tumor of its blood supply (Kim et al. (1993) *Nature* 362(6423):841-4). This early research led to the development of the monoclonal antibody inhibitor of VEGF, bevacizumab (Avastin; Genentech), which in combination with chemotherapy, has become the standard of care for metastatic CRC. Systemic administration of bevacizumab also demonstrated significant toxicities, including multiple fatalities in a Phase II trial of NSCLC, largely due to hemorrhaging. As such, several next generation anti-angiogenics have been evaluated, such as the anti-VEGF receptor 2 antibody ramucirumab (Cyramza, Imclone) and the anti-angiogenic tyrosine kinase inhibitor axitinib (Inlyta, Pfizer), yet none have been able to overcome systemic toxicity or markedly improve progression-free survival (Alshangiti et al. (2018) *Curr Oncol.* 25(Suppl 1):545-558). While the anti-tumor activity of anti-VEGF therapy has shown some promise, systemic toxicity is clearly limiting. As such, a therapy that targets only the tumor microenvironment, such as an immunostimulatory tumor-targeting bacteria with shRNA to VEGF, provided herein, delivers local anti-angiogenic therapy while preventing systemic toxicity. This therapeutic modality has the additional advantage of being taken up into myeloid cells, which predominantly produce VEGF in the tumor microenvironment, where it will have maximum impact on tumor progression (Osterberg et al. (2016) *Neuro-Oncology.* 18(7):939-949).

8. Additional Exemplary Checkpoint Targets

Exemplary checkpoint targets for which RNAi, such as micro-RNA and shRNA, can be prepared or are exemplified herein include, but are not limited to:

| Checkpoint target |
| --- |
| CTLA-4 |
| PD-L1 (B7-H1) |
| PD-L2 |
| PD-1, PD-2 |
| IDO1 |
| IDO2 |
| SIRP alpha (CD47) |
| VISTA (B7-H5) |
| LIGHT |
| HVEM |
| CD28 |
| LAG3, TIM3, TIGIT |
| Galectin-9 |
| CEACAM1, CD155, CD112, CD226, CD244 (2B4), B7-H2, B7-H3, CD137, ICOS, GITR, B7-H4. B7-H6 CD137, CD27, CD40/CD40L, CD48, CD70, CD80, CD86, CD137(4-1BB), CD200, CD272 (BTLA), CD160 A2a receptor, A2b receptor, HHLA2, ILT-2, ILT-4, gp49B, PIR-B OX40/OX-40L, BTLA, ICOS, HLA-G, ILT-2/4 KIR, GITR, TIM1, TIM4 |

Other exemplary targets, include but are not limited to:

| Target |
| --- |
| CTNNB1 (beta-catenin) |
| STAT3 |
| BCL-2 |
| MDR1 |
| Arginase 1 |
| iNOS |
| TGF-β |
| IL-10 |
| pGE2 |
| VEGF |
| KSP |
| HER2 |
| KRAS |
| TAK1 |
| PLK1 |
| K-Ras (Ras) |
| Stablin-1/CLEVER-1 |
| RNase H2 |
| DNase II |

G. Combinations of RNAi shRNAs to Multiple Immune Targets within a Single Therapeutic Modality and Combination Therapy Combinations of RNAi, such as shRNAs or microRNAs, that inhibit different targets in one bacterium, are contemplated. Combinations of such targets can be selected to act synergistically. RNAi that targets any two immune checkpoints can be combined, and introduced into the immunostimulatory bacterial hosts modified as described herein, or into therapeutic bacterial hosts of others.

1. TREX1 and Other Targets

In order to mitigate the induction of compensatory immune checkpoint pathways that can be upregulated upon STING activation and enhance anti-tumor immunity, the modified immunostimulatory bacteria provided herein contain short hairpin (sh)-RNA sequences against TREX1 in combination with shRNA to other immune targets, including but not limited to PD-L1, VISTA and SIRPα. Knockdown of TREX1 and SIRPα in tumor-resident phagocytic cells enables blockade of "don't eat me" interactions with CD47 on tumor cells, as well as further enhances the susceptibility of the tumor microenvironment to *S. typhimurium* infection (Li et al., *J Immunol* (2012)), and is provided herein. The combination of enhanced phagocytosis enabled by SIRPα inhibition and simultaneous knockdown of TREX1, facilitates greater cytosolic delivery and stabilization of tumor DNA that can more potently activate cGAS/STING signaling. Notably, the anti-tumor effects of CD47/SIRPα blockade were shown to require intact STING signaling, demonstrating the potential synergy of combining TREX1-mediated STING activation with SIRPα inhibition (Liu et al., *Nat. Med.* (2015)). Knockdown of TREX1 in combination with shRNA to PD-L1, provided herein, enhances the pathogenesis and immune-stimulatory properties of the modified *S. typhimurium* (Lee et al., *J. Immunol.* (2010)), thereby igniting a more inflamed and immunogenic tumor microenvironment. shRNA targets against β-catenin and TGF-β also lead to a more T cell inflamed tumor microenvironment and synergize well with shRNA to PD-L1, and are provided herein. Combining immune activation with local checkpoint blockade within the macrophage/myeloid compartment in particular, such as through combined shRNAs to TREX1 and VISTA, provided herein, potentiates the immune response by enhancing both tumor neoantigen presentation by *S. typhimurium*-infected APCs and enhanced activation of tumor-specific T cells.

2. TREX1 and Radiotherapy

The success of anticancer radiotherapy depends on the induction of type I interferon-dependent innate and adaptive immunity. TREX1 has been shown to attenuate anti-tumor immunity following high levels of Gy radiation by degrading the cytosolic DNA that is produced in the damaged cancer cells, thus inhibiting the type I interferon pathway mediated by cGAS and STING (Vanpouille-Box et al. (2017) *Nature Communications* 8:15618). Thus, the overexpression of TREX1, or the knockout of cGAS/STING, which prevents activation of the IFN-I pathway, attenuates the abscopal tumor response upon irradiation. In order to activate STING-mediated Batf3-DC priming of $CD8^+$ T cells and achieve maximal abscopal anti-tumor immunity, a lower dose of radiation was required that would not induce TREX1 (Vanpouille-Box et al. (2017) *Nature Communications* 8:15618). The downregulation of TREX1 has been shown to restore the sensitivity of tumor cells towards ionizing radiation. For example, high dose irradiation induced TREX1 expression and prevented cytoplasmic accumulation of dsDNA, thereby inhibiting abscopal tumor regression (Vanpouille-Box et al. (2017) *Nature Communications* 8:15618). The immunostimulatory strains provided herein that block or inhibit TREX1 expression can reduce or eliminate or blunt the expression of TREX1 upon high dose radiation treatment, significantly extending the therapeutic window.

While radiotherapy (RT) has an abscopal effect at lower doses, the lower doses are not necessarily effective. At higher doses, however, the abscopal effect is no longer observed. This is a known problem with RT. Radiotherapy has been shown to promote the upregulation of TREX1 that degrades cytosolic dsDNA, precluding IFN-secretion secondary to cGAS/STING signaling (see, Vanpouille-Box et al. (2017) *Nat. Commun.* 8:15618). Hence, the immunostimulatory bacterium provided herein can be administered with RT to prevent upregulation of TREX1. Administration of an immunostimulatory bacterium, provided herein, that encodes shRNA or other product that inhibits TREX1 abrogates this response, thereby improving and complementing RT. Hence, provided herein are combination therapies in which the immunostimulatory bacteria that encode shRNA or other product that inhibit or reduce expression of TREX1 are administered with RT, either before, in conjunction with, or after, or intermittently with RT. The combination therapy of the immunostimulatory bacteria and RT therapy also can include other anti-cancer therapies, such as administration of a checkpoint inhibitor, and/or inclusion of shRNA against other checkpoints, such as PD-L1, as described herein.

3. TREX1 and Immunogenic Chemotherapy

Induction of TREX1 was observed following DNA-damaging UV irradiation of mouse and human fibroblasts, as well as treatment of glioma and malignant melanoma cells with the DNA alkylating agents nimustine, carmustine and fotemustine, and the topoisomerase I inhibitor topotecan. These tumor cells were re-sensitized to these anti-cancer therapeutics following siRNA knockdown of TREX1 (Tomicic et al. (2013) *Biochimica et Biophysica Acta* 1833:1832-1843). TREX1 was only induced by damage agents that induce AP-1 efficiently, while agents that are weak inducers of Fos/Jun/AP-1, such as the methylating agent temozolomide and the topoisomerase II inhibitor etoposide, did not induce TREX1.

A separate study found that dsDNA accumulates and activates type I IFN upon treatment with chemotherapies that stall DNA replication in the S phase, such as cisplatin, irinotecan, doxorubicin and etoposide, but not agents that act in M phase, such as vinorelnine and paclitaxel (Wilkinson R. presented at ESMO TAT Conference 2018). S phase agents likely lead to the release of damaged DNA fragments that accumulate in the cytosol and upregulate TREX1. These chemotherapeutic agents, which include those that cause DNA strand breaks, such as nucleotide analogs, alkylating agents, platinum drugs, and intercalating agents (see, e.g., Swift et al. (2014) *Int. J. Mol. Sci* 15:3403-3431), can induce TREX1 at levels sufficient to degrade the DNA, thereby precluding activation of the type-I interferon (IFN-I) pathway mediated via cyclic GMP-AMP (cGAMP) synthase (cGAS) and its downstream adaptor stimulator of interferon genes (STING). Treatment with the immunostimulatory bacteria provided herein can be combined with chemotherapeutic agents, and further with other checkpoint inhibitors. Hence, the immunostimulatory bacteria provided herein can advantageously be used in combination therapy with a variety of anti-cancer agents and treatments.

4. Combination Therapy with Anti-Checkpoint Antibodies

Therapy with the immunostimulatory bacteria provided herein can be combined with any other anti-cancer therapy, including checkpoint inhibitor therapies and, as discussed above, other cancer treatments and chemotherapy.

H. Pharmaceutical Production, Compositions, and Formulations

Provided herein are methods for manufacturing, pharmaceutical compositions and formulations containing any of the immunostimulatory bacteria provided herein and pharmaceutically acceptable excipients or additives. The pharmaceutical compositions can be used in treatment of diseases, such as hyperproliferative diseases or condition, such as a tumor or cancer. The immunostimulatory bacteria can be administered in a single agent therapy, or can be administered in a combination therapy with a further agent or treatment. The compositions can be formulated for single dosage administration or for multiple dosage administration. The agents can be formulated for direct administration. The compositions can be provided as a liquid or dried formulation.

1. Manufacturing a. Cell Bank Manufacturing

As the active ingredient of the immunotherapeutic described herein is composed of engineered self-replicating bacteria, the selected composition will be expanded into a series of cell banks that will be maintained for long-term storage and as the starting material for manufacturing of drug substance. Cell banks are produced under current good manufacturing practices (cGMP) in an appropriate manufacturing facility per the Code of Federal Regulations (CFR) 21 part 211 or other relevant regulatory authority. As the active agent of the immunotherapeutic is a live bacterium, the products described herein are, by definition, non-sterile and cannot be terminally sterilized. Care must be taken to ensure that aseptic procedures are used throughout the manufacturing process to prevent contamination. As such, all raw materials and solutions must be sterilized prior to use in the manufacturing process.

A master cell bank (MCB) is produced by sequential serial single colony isolation of the selected bacterial strain to ensure no contaminants are present in the starting material. A sterile culture vessel containing sterile media (can be complex media e.g., LB or MSBB or defined media e.g., M9 supplemented with appropriate nutrients) is inoculated with a single well-isolated bacterial colony and the bacteria are allowed to replicate e.g., by incubation at 37° C. with shaking. The bacteria are then prepared for cryopreservation by suspension in a solution containing a cryoprotective agent or agents.

Examples of cryoprotective agents include: proteins such as human or bovine serum albumin, gelatin, immunoglobulins; carbohydrates including monosaccharides (galactose, D-mannose, sorbose, etc.) and their non-reducing derivatives (e.g., methylglucoside), disaccharides (trehalose, sucrose, etc.), cyclodextrins, and polysaccharides (raffinose, maltodextrins, dextrans, etc.); amino-acids (glutamate, glycine, alanine, arginine or histidine, tryptophan, tyrosine, leucine, phenylalanine, etc.); methylamines such as betaine; polyols such as trihydric or higher sugar alcohols, e.g., glycerin, erythritol, glycerol, arabitol, xylitol, sorbitol, and mannitol; propylene glycol; polyethylene glycol; surfactants e.g., pluronic; or organo-sulfur compounds such as dimethyl sulfoxide (DMSO), and combinations thereof. Cryopreservation solutions may include one or more cryoprotective agents in a solution that may also contain salts (e.g., sodium chloride, potassium chloride, magnesium sulfate, and or buffering agents such as sodium phosphate, tris(hydroxymethyl)aminomethane (TRIS), 4-(2-hydroxyethyl)-1-piperazineethanesulfonic acid (HEPES), and other such buffering agents known to those of skill.

Suspension of the bacteria in cryopropreservation solution can be achieved either by addition of a concentrated cryoprotective agent or agents to the culture material to achieve a final concentration that preserves viability of the bacteria during the freezing and thawing process (e.g. 0.5% to 20% final concentration of glycerol), or by harvesting the bacteria (e.g., by centrifugation) and suspending in a cryopreservative solution containing the appropriate final concentration of cryoprotective agent(s). The suspension of bacteria in cryopreservation solution is then filled into appropriate sterile vials (plastic or glass) with a container closure system that is capable of maintaining closure integrity under frozen conditions (e.g., butyl stoppers and crimp seals). The vials of master cell bank are then frozen (either slowly by means of a controlled rate freezer, or quickly by means of placing directly into a freezer). The MCB is then stored frozen at a temperature that preserves long-term viability (e.g., at or below −60° C.). Thawed master cell bank material is thoroughly characterized to ensure identity, purity, and activity per regulatory the appropriate authorities.

Working cell banks (WCBs) are produced much the same way as the master cell bank, but the starting material is derived from the MCB. MCB material can be directly transferred into a fermentation vessel containing sterile media and expanded as above. The bacteria are then suspended in a cryopreservation solution, filled into containers, sealed, and frozen at or below −20° C. Multiple WCBs can be produced from MCB material, and WCB material can be used to make additional cell banks (e.g., a manufacturer's working cell bank MWCB). WCBs are stored frozen and characterized to ensure identity, purity, and activity. WCB material is typically the starting material used in production of the drug substance of biologics such as engineered bacteria.

b. Drug Substance Manufacturing

Drug substance is manufactured using aseptic processes under cGMP as described above. Working cell bank material is typically used as starting material for manufacturing of drug substance under cGMP, however other cell banks can be used (e.g., MCB or MWCB). Aseptic processing is used for production of all cell therapies including bacterial cell-based therapies. The bacteria from the cell bank are expanded by fermentation, this can be achieved by production of a pre-culture (e.g., in a shake flask) or by direct inoculation of a fermenter. Fermentation is accomplished in a sterile bioreactor or flask that can be single-use disposable or re-usable. Bacteria are harvested by concentration (e.g., by centrifugation, continuous centrifugation, or tangential flow filtration). Concentrated bacteria are purified from media components and bacterial metabolites by exchange of the media with buffer (e.g., by diafiltration). The bulk drug product is formulated and preserved as an intermediate (e.g., by freezing or drying) or is processed directly into a drug product. Drug substance is tested for identity, strength, purity, potency, and quality.

c. Drug Product Manufacturing

Drug product is defined as the final formulation of the active substance contained in its final container. Drug product is manufactured using aseptic processes under cGMP. Drug product is produced from drug substance. Drug substance is thawed or reconstituted if necessary, then formulated at the appropriate target strength. Because the active component of the drug product is live, engineered bacteria, the strength is determined by the number of CFU contained within the suspension. The bulk product is diluted in a final formulation appropriate for storage and use as described below. Containers are filled, and sealed with a container closure system and the drug product is labeled. The drug product is stored at an appropriate temperature to preserve stability and is tested for identity, strength, purity, potency, and quality and released for human use if it meets specified acceptance criteria.

2. Compositions

Pharmaceutically acceptable compositions are prepared in view of approvals for a regulatory agency or other agency prepared in accordance with generally recognized pharmacopeia for use in animals and in humans. The compositions can be prepared as solutions, suspensions, powders, or sustained release formulations. Typically, the compounds are formulated into pharmaceutical compositions using techniques and procedures well known in the art (see e.g., Ansel *Introduction to Pharmaceutical Dosage Forms*, Fourth Edition, 1985, 126). The formulation should suit the mode of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. Compositions also can be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease and the particular composition which is used. Pharmaceutical compositions can be formulated in dosage forms appropriate for each route of administration. In particular, the compositions can be formulated into any suitable pharmaceutical preparations for systemic, local intraperitoneal, oral or direct administration. For example, the compositions can be formulated for administration subcutaneously, intramuscularly, intratumorally, intravenously or intradermally. Administration methods can be employed to decrease the exposure of the active agent to degradative processes, such as immunological intervention via antigenic and immunogenic responses. Examples of such methods include local administration at the site of treatment or continuous infusion.

The immunostimulatory bacteria can be formulated into suitable pharmaceutical preparations such as solutions, suspensions, tablets, dispersible tablets, pills, capsules, powders, sustained release formulations or elixirs, for oral administrations well as transdermal patch preparation and dry powder inhalers. Typically, the compounds are formulated into pharmaceutical compositions using techniques and procedures well known in the art (see e.g., Ansel *Introduction to Pharmaceutical Dosage Forms*, Fourth Edition, 1985, 126). Generally, the mode of formulation is a function of the route of administration. The compositions can be formulated in dried (lyophilized or other forms of vitrification) or liquid form. Where the compositions are provided in dried form they can be reconstituted just prior to use by addition of an appropriate buffer, for example, a sterile saline solution.

3. Formulations a. Liquids, Injectables, Emulsions

The formulation generally is made to suit the route of administration. Parenteral administration, generally characterized by injection or infusion, either subcutaneously, intramuscularly, intratumorally, intravenously or intradermally is contemplated herein. Preparations of bacteria for parenteral administration include suspensions ready for injection (direct administration) or frozen suspension that are thawed prior to use, dry soluble products, such as lyophilized powders, ready to be combined with a resuspension solution just prior to use, and emulsions. Dried thermostable formulations such as lyophilized formulations can be used for storage of unit doses for later use.

The pharmaceutical preparation can be in a frozen liquid form, for example a suspension. If provided in frozen liquid form, the drug product can be provided as a concentrated preparation to be thawed and diluted to a therapeutically effective concentration before use.

The pharmaceutical preparations also can be provided in a dosage form that does not require thawing or dilution for use. Such liquid preparations can be prepared by conventional means with pharmaceutically acceptable additives, as appropriate, such as suspending agents (e.g., sorbitol, cellulose derivatives or hydrogenated edible fats); emulsifying agents (e.g., lecithin or acacia); non-aqueous vehicles (e.g., almond oil, oily esters, or fractionated vegetable oils); and preservatives suitable for use with microbial therapeutics. The pharmaceutical preparations can be presented in dried form, such as lyophilized or spray-dried, for reconstitution with water or other sterile suitable vehicle before use.

Suitable excipients are, for example, water, saline, dextrose, or glycerol. The solutions can be either aqueous or nonaqueous. If administered intravenously, suitable carriers include physiological saline or phosphate buffered saline (PBS), and other buffered solutions used for intravenous hydration. For intratumoral administration solutions containing thickening agents such as glucose, polyethylene glycol, and polypropylene glycol, oil emulsions and mixtures thereof may be appropriate to maintain localization if the injectant.

Pharmaceutical compositions can include carriers or other excipients. For example, pharmaceutical compositions provided herein can contain any one or more of a diluents(s), adjuvant(s), antiadherent(s), binder(s), coating(s), filler(s), flavor(s), color(s), lubricant(s), glidant(s), preservative(s), detergent(s), or sorbent(s) and a combination thereof or vehicle with which a modified therapeutic bacteria is administered. For example, pharmaceutically acceptable carriers or excipients used in parenteral preparations include aqueous vehicles, nonaqueous vehicles, isotonic agents, buffers, antioxidants, local anesthetics, suspending and dispersing agents, emulsifying agents, sequestering or chelating agents and other pharmaceutically acceptable substances. Formulations, including liquid preparations, can be prepared by conventional means with pharmaceutically acceptable additives or excipients.

Pharmaceutical compositions can include carriers such as a diluent, adjuvant, excipient, or vehicle with which the composition are administered. Examples of suitable pharmaceutical carriers are described in "Remington's Pharmaceutical Sciences" by E. W. Martin. Such compositions will contain a therapeutically effective amount of the compound or agent, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. For example, suitable excipients are, for example, water, saline, dextrose, glycerol or ethanol. A composition, if desired, also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include, for example, polysorbates, such Polysorbate 80 (TWEEN 80). Sequestering or chelating agents of metal ions, such as EDTA, can be included. Pharmaceutical carriers also include polyethylene glycol and propylene glycol for water miscible vehicles and sodium hydroxide, hydrochloric acid, citric acid or lactic acid for pH adjustment. Non-anti-microbial preservatives can be included.

The pharmaceutical compositions also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

b. Dried Thermostable Formulations

The bacteria can be dried. Dried thermostable formulations, such as lyophilized or spray dried powders and vitrified glass can be reconstituted for administration as solutions, emulsions and other mixtures. The dried thermostable formulation can be prepared from any of the liquid formulations, such as the suspensions, described above. The pharmaceutical preparations can be presented in lyophilized or vitrified form for reconstitution with water or other suitable vehicle before use.

The thermostable formulation is prepared for administration by reconstituting the dried compound with a sterile solution. The solution can contain an excipient which improves the stability or other pharmacological attribute of the active substance or reconstituted solution, prepared from the powder. The thermostable formulation is prepared by dissolving an excipient, such as dextrose, sorbitol, fructose, corn syrup, xylitol, glycerin, glucose, sucrose or other suitable agent, in a suitable buffer, such as citrate, sodium or potassium phosphate or other such buffer known to those of skill in the art. Then, the drug substance is added to the resulting mixture, and stirred until it mixed. The resulting mixture is apportioned into vials for drying. Each vial will contain a single dosage containing $1\times10^5$-$1\times10^{11}$ CFU per vial. After drying, the product vial is sealed with a container closure system that prevents moisture or contaminants from entering the sealed vial. The dried product can be stored under appropriate conditions, such as at −20° C., 4° C., or room temperature. Reconstitution of this dried formulation with water or a buffer solution provides a formulation for use in parenteral administration. The precise amount depends upon the indication treated and selected compound. Such amount can be empirically determined.

4. Compositions for Other Routes of Administration

Depending upon the condition treated, other routes of administration in addition to parenteral, such as topical application, transdermal patches, oral and rectal administration are also contemplated herein. The suspensions and powders described above can be administered orally or can be reconstituted for oral administration. Pharmaceutical dosage forms for rectal administration are rectal suppositories, capsules and tablets and gel capsules for systemic effect. Rectal suppositories include solid bodies for insertion into the rectum which melt or soften at body temperature releasing one or more pharmacologically or therapeutically active ingredients. Pharmaceutically acceptable substances in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration are manufactured using the same pharmaceutically acceptable substance and by the same methods as for formulations for oral administration. Formulations suitable for rectal administration can be provided as unit dose suppositories. These can be prepared by admixing the drug substance with one or more conventional solid carriers, for example, cocoa butter, and then shaping the resulting mixture.

For oral administration, pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well-known in the art.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

Topical mixtures are prepared as described for the local and systemic administration. The resulting mixtures can be solutions, suspensions, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compositions can be formulated as aerosols for topical application, such as by inhalation (see, e.g., U.S. Pat. Nos. 4,044,126; 4,414,209 and 4,364,923, which describe aerosols for delivery of a steroid useful for treatment of lung diseases). These formulations, for administration to the respiratory tract, can be in the form of an aerosol or solution for a nebulizer, or as a microfine powder for insufflation, alone or in combination with an inert carrier such as lactose. In such a case, the particles of the formulation will typically have diameters of less than 50 microns, or less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered.

Formulations suitable for transdermal administration are provided. They can be provided in any suitable format, such as discrete patches adapted to remain in intimate contact with the epidermis of the recipient for a prolonged period of time. Such patches contain the active compound in an optionally buffered aqueous solution of, for example, 0.1 to 0.2 M concentration with respect to the active compound. Formulations suitable for transdermal administration also can be delivered by iontophoresis (see, e.g., Tyle, P, (1986) *Pharmaceutical Research* 3(6):318-326) and typically take the form of an optionally buffered aqueous solution of the active compound.

Pharmaceutical compositions also can be administered by controlled release formulations and/or delivery devices (see e.g., in U.S. Pat. Nos. 3,536,809; 3,598,123; 3,630,200; 3,845,770; 3,916,899; 4,008,719; 4,769,027; 5,059,595; 5,073,543; 5,120,548; 5,591,767; 5,639,476; 5,674,533 and 5,733,566).

5. Dosages and Administration

The compositions can be formulated as pharmaceutical compositions for single dosage or multiple dosage administration. The immunostimulatory bacteria can be included in an amount sufficient to exert a therapeutically useful effect in the absence of undesirable side effects on the patient treated. For example, the concentration of the pharmaceutically active compound is adjusted so that an injection provides an effective amount to produce the desired pharmacological effect. The therapeutically effective concentration can be determined empirically by testing the immunostimulatory bacteria in known in vitro and in vivo systems such as by using the assays described herein or known in the art. For example, standard clinical techniques can be employed. In vitro assays and animal models can be employed to help identify optimal dosage ranges. The precise dose, which can be determined empirically, can depend on the age, weight, body surface area, and condition of the patient or animal, the particular immunostimulatory bacteria administered, the route of administration, the type of disease to be treated and the seriousness of the disease.

Hence, it is understood that the precise dosage and duration of treatment is a function of the disease being treated and can be determined empirically using known testing protocols or by extrapolation from in vivo or in vitro test data. Concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of compositions and combinations containing them. The compositions can be administered hourly, daily, weekly, monthly, yearly or once. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects).

The immunostimulatory bacteria are included in the composition in an amount sufficient to exert a therapeutically useful effect. For example, the amount is one that achieves a therapeutic effect in the treatment of a hyperproliferative disease or condition, such as cancer.

Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Unit dosage forms, include, but are not limited to, tablets, capsules, pills, powders, granules, parenteral suspensions, and oral solutions or suspensions, and oil water emulsions containing suitable quantities of the compounds or pharmaceutically acceptable derivatives thereof. Unit dose forms can be contained in vials, ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical composition can be formulated in dosage forms appropriate for each route of administration.

The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

As indicated, compositions provided herein can be formulated for any route known to those of skill in the art including, but not limited to, subcutaneous, intramuscular, intravenous, intradermal, intralesional, intraperitoneal injection, epidural, vaginal, rectal, local, otic, transdermal administration or any route of administration. Formulations suited for such routes are known to one of skill in the art. Compositions also can be administered with other biologically active agents, either sequentially, intermittently or in the same composition.

Pharmaceutical compositions can be administered by controlled release formulations and/or delivery devices (see, e.g., in U.S. Pat. Nos. 3,536,809; 3,598,123; 3,630,200; 3,845,770; 3,847,770; 3,916,899; 4,008,719; 4,687,660; 4,769,027; 5,059,595; 5,073,543; 5,120,548; 5,354,556; 5,591,767; 5,639,476; 5,674,533 and 5,733,566). Various delivery systems are known and can be used to administer selected compositions, are contemplated for use herein, and such particles can be easily made.

6. Packaging and Articles of Manufacture

Also provided are articles of manufacture containing packaging materials, any pharmaceutical composition provided herein, and a label that indicates that the compositions are to be used for treatment of diseases or conditions as described herein. For example, the label can indicate that the treatment is for a tumor or cancer.

Combinations of immunostimulatory bacteria described herein and another therapeutic agent also can be packaged in an article of manufacture. In one example, the article of manufacture contains a pharmaceutical composition containing the immunostimulatory bacteria composition and no further agent or treatment. In other examples, the article of manufacture another further therapeutic agent, such as a different anti-cancer agent. In this example, the agents can be provided together or separately, for packaging as articles of manufacture.

The articles of manufacture provided herein contain packaging materials. Packaging materials for use in packaging pharmaceutical products are well known to those of skill in the art. See, for example, U.S. Pat. Nos. 5,323,907, 5,052,558 and 5,033,252, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. Exemplary of articles of manufacture are containers including single chamber and dual chamber containers. The containers include, but are not limited to, tubes, bottles and syringes. The containers can further include a needle for intravenous administration.

The choice of package depends on the agents, and whether such compositions will be packaged together or separately. In general, the packaging is non-reactive with the compositions contained therein. In other examples, some of the components can be packaged as a mixture. In other examples, all components are packaged separately. Thus, for example, the components can be packaged as separate compositions that, upon mixing just prior to administration, can be directly administered together. Alternatively, the components can be packaged as separate compositions for administration separately.

Selected compositions including articles of manufacture thereof also can be provided as kits. Kits can include a pharmaceutical composition described herein and an item for administration provided as an article of manufacture. The compositions can be contained in the item for administration or can be provided separately to be added later. The kit can, optionally, include instructions for application including dosages, dosing regimens and instructions for modes of administration. Kits also can include a pharmaceutical composition described herein and an item for diagnosis.

I. Methods of Treatment and Uses

The methods provided herein include methods of administering or using the immunostimulatory bacteria, for treating subjects having a disease or condition whose symptoms can be ameliorated or lessened by administration of such bacteria, such as cancer. In particular examples, the disease or condition is a tumor or a cancer. Additionally, methods of combination therapies with one or more additional agents for treatment, such as an anticancer agent or an anti-hyaluronan agent, also are provided. The bacteria can be administered by any suitable route, including, but not limited to, parenteral, systemic, topical and local, such as intra-tumoral, intravenous, rectal, oral, intramuscular, mucosal and other routes. Formulations suitable for each are provided. The skilled person can establish suitable regimens and doses and select routes.

1. Cancers and Tumors

The immunostimulatory bacteria, combinations, uses and methods provided herein are applicable to treating all types of tumors, including cancers, particularly solid tumors including lung cancer, bladder, non-small cell lung cancer, gastric cancers, head and neck cancers, ovarian cancer, liver cancer, pancreatic cancer, kidney cancer, breast cancer, colorectal cancer, and prostate cancer. The methods also can be used for hematological cancers.

Tumors and cancers subject to treatment by the uses methods provided herein include, but are not limited to, those that originate in the immune system, skeletal system, muscles and heart, breast, pancreas, gastrointestinal tract, central and peripheral nervous system, renal system, reproductive system, respiratory system, skin, connective tissue systems, including joints, fatty tissues, and circulatory system, including blood vessel walls. Examples of tumors that can be treated with the immunostimulatory bacteria provided herein include carcinomas, gliomas, sarcomas (including liposarcoma), adenocarcinomas, adenosarcomas, and adenomas. Such tumors can occur in virtually all parts of the body, including, for example, breast, heart, lung, small intestine, colon, spleen, kidney, bladder, head and neck, ovary, prostate, brain, pancreas, skin, bone, bone marrow, blood, thymus, uterus, testicles, cervix or liver.

Tumors of the skeletal system include, for example, sarcomas and blastomas such as osteosarcoma, chondrosarcoma, and chondroblastoma. Muscle and heat tumors include tumors of both skeletal and smooth muscles, e.g., leiomyomas (benign tumors of smooth muscle), leiomyosarcomas, rhabdomyomas (benign tumors of skeletal muscle), rhabdomyosarcomas, cardiac sarcoma. Tumors of the gastrointestinal tract include e.g., tumors of the mouth, esophagus, stomach, small intestine, colon and colorectal tumors, as well as tumors of gastrointestinal secretory organs such as salivary glands, liver, pancreas, and the biliary tract. Tumors of the central nervous system include tumors of the brain, retina, and spinal cord, and can also originate in associated connective tissue, bone, blood vessels or nervous tissue. Treatment of tumors of the peripheral nervous system are also contemplated. Tumors of the peripheral nervous system include malignant peripheral nerve sheath tumors. Tumors of the renal system include those of the kidneys, e.g., renal cell carcinoma, as well as tumors of the ureters and bladder. Tumors of the reproductive system include tumors of the cervix, uterus, ovary, prostate, testes and related secretory glands. Tumors of the immune system include both blood based and solid tumors, including lymphomas, e.g., both Hodgkin's and non-Hodgkin's. Tumors of the respiratory system include tumors of the nasal passages, bronchi and lungs. Tumors of the breast include, e.g., both lobular and ductal carcinoma.

Other examples of tumors that can be treated by the immunostimulatory bacteria and methods provided herein include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma (such as glioblastoma multiforme) and leiomyosarcoma. Examples of other cancer that can be treated as provided herein include but are not limited to lymphoma, blastoma, neuroendocrine tumors, mesothelioma, schwannoma, meningioma, melanoma, and leukemia or lymphoid malignancies. Examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (e.g., nasopharyngeal cancer, salivary gland carcinoma, and esophageal cancer), lung (e.g., small-cell lung cancer, non-small cell lung cancer, adenocarcinoma of the lung and squamous carcinoma of the lung), digestive system (e.g., gastric or stomach cancer including gastrointestinal cancer, cancer of the bile duct or biliary tract, colon cancer, rectal cancer, colorectal cancer, and anal carcinoma), reproductive system (e.g., testicular, penile, or prostate cancer, uterine, vaginal, vulval, cervical, ovarian, and endometrial cancer), skin (e.g., melanoma, basal cell carcinoma, squamous cell cancer, actinic keratosis, cutaneous melanoma), liver (e.g., liver cancer, hepatic carcinoma, hepatocellular cancer, and hepatoma), bone (e.g., osteoclastoma, and osteolytic bone cancers) additional tissues and organs (e.g., pancreatic cancer, bladder cancer, kidney or renal cancer, thyroid cancer, breast cancer, cancer of the peritoneum, and Kaposi's sarcoma), tumors of the vascular system (e.g., angiosarcoma and hemangiopericytoma), Wilms' tumor, retinoblastoma, osteosarcoma and Ewing's sarcoma.

2. Administration

In practicing the uses and methods herein, immunostimulatory bacteria provided herein can be administered to a subject, including a subject having a tumor or having neoplastic cells, or a subject to be immunized. One or more steps can be performed prior to, simultaneously with or after administration of the immunostimulatory bacteria to the subject including, but not limited to, diagnosing the subject with a condition appropriate for administering immunostimulatory bacteria, determining the immunocompetence of the subject, immunizing the subject, treating the subject with a chemotherapeutic agent, treating the subject with radiation, or surgically treating the subject.

For embodiments that include administering immunostimulatory bacteria to a tumor-bearing subject for therapeutic purposes, the subject typically has previously been diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject.

Some embodiments of therapeutic methods for administering immunostimulatory bacteria to a subject can include a step of determination of the size of the primary tumor or the stage of the neoplastic disease, and if the size of the primary tumor is equal to or above a threshold volume, or if the stage of the neoplastic disease is at or above a threshold stage, an immunostimulatory bacterium is administered to the subject. In a similar embodiment, if the size of the primary tumor is below a threshold volume, or if the stage of the neoplastic disease is at or below a threshold stage, the immunostimulatory bacterium is not yet administered to the subject; such methods can include monitoring the subject until the tumor size or neoplastic disease stage reaches a threshold amount, and then administering the immunostimulatory bacterium to the subject. Threshold sizes can vary according to several factors, including rate of growth of the tumor, ability of the immunostimulatory bacterium to infect a tumor, and immunocompetence of the subject. Generally the threshold size will be a size sufficient for an immunostimulatory bacterium to accumulate and replicate in or near the tumor without being completely removed by the host's immune system, and will typically also be a size sufficient to sustain a bacterial infection for a time long enough for the host to mount an immune response against the tumor cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

Any mode of administration of a microorganism to a subject can be used, provided the mode of administration permits the immunostimulatory bacteria to enter a tumor or metastasis. Modes of administration can include, but are not limited to, intravenous, intraperitoneal, subcutaneous, intramuscular, topical, intratumoral, multipuncture, inhalation, intranasal, oral, intracavity (e.g., administering to the bladder via a catheter, administering to the gut by suppository or enema), aural, rectal, and ocular administration.

One skilled in the art can select any mode of administration compatible with the subject and the bacteria, and that also is likely to result in the bacteria reaching tumors and/or metastases. The route of administration can be selected by one skilled in the art according to any of a variety of factors, including the nature of the disease, the kind of tumor, and the particular bacteria contained in the pharmaceutical composition. Administration to the target site can be performed, for example, by ballistic delivery, as a colloidal dispersion system, or systemic administration can be performed by injection into an artery.

The dosage regimen can be any of a variety of methods and amounts, and can be determined by one skilled in the art according to known clinical factors. A single dose can be therapeutically effective for treating a disease or disorder in which immune stimulation effects treatment. Exemplary of such stimulation is an immune response, that include, but not limited to, one or both of a specific immune response and non-specific immune response, both specific and non-specific response, innate response, primary immune response, adaptive immunity, secondary immune response, memory immune response, immune cell activation, immune cell proliferation, immune cell differentiation, and cytokine expression.

As is known in the medical arts, dosages for a subject can depend on many factors, including the subject's species, size, body surface area, age, sex, immunocompetence, and general health, the particular bacteria to be administered, duration and route of administration, the kind and stage of the disease, for example, tumor size, and other compounds such as drugs being administered concurrently. In addition to the above factors, such levels can be affected by the infectivity of the bacteria and the nature of the bacteria, as can be determined by one skilled in the art. In the present methods, appropriate minimum dosage levels of bacteria can be levels sufficient for the bacteria to survive, grow and replicate in a tumor or metastasis. Exemplary minimum levels for administering a bacterium to a 65 kg human can include at least about $5\times10^6$ colony forming units (CFU), at least about $1\times10^7$ CFU, at least about $5\times10^7$ CFU, at least about $1\times10^8$ CFU, or at least about $1\times10^9$ CFU. In the present methods, appropriate maximum dosage levels of bacteria can be levels that are not toxic to the host, levels that do not cause splenomegaly of 3× or more, levels that do not result in colonies or plaques in normal tissues or organs after about 1 day or after about 3 days or after about 7 days. Exemplary maximum levels for administering a bacterium to a 65 kg human can include no more than about $5\times10^{11}$ CFU, no more than about $1\times10^{11}$ CFU, no more than about $5\times10^{10}$ CFU, no more than about $1\times10^{10}$ CFU, or no more than about $1\times10^9$ CFU.

The methods and uses provided herein can include a single administration of immunostimulatory bacteria to a subject or multiple administrations of immunostimulatory bacteria to a subject or others of a variety of regimens, including combination therapies with other anti-tumor therapeutics and/or treatments. These include, cellular therapies, such as administration of modified immune cells, CAR-T therapy, CRISPR therapy, checkpoint inhibitors, such as antibodies, and chemotherapeutic compounds, such as nucleoside analogs, surgery and radiotherapy.

In some embodiments, a single administration is sufficient to establish immunostimulatory bacteria in a tumor, where the bacteria can colonize and can cause or enhance an anti-tumor response in the subject. In other embodiments, the immunostimulatory bacteria provided for use in the methods herein can be administered on different occasions, separated in time typically by at least one day. Separate administrations can increase the likelihood of delivering a bacterium to a tumor or metastasis, where a previous administration may have been ineffective in delivering the bacterium to a tumor or metastasis. In embodiments, separate administrations can increase the locations on a tumor or metastasis where bacterial colonization/proliferation can occur or can otherwise increase the titer of bacteria accumulated in the tumor, which can increase eliciting or enhancing a host's anti-tumor immune response.

When separate administrations are performed, each administration can be a dosage amount that is the same or different relative to other administration dosage amounts. In one embodiment, all administration dosage amounts are the same. In other embodiments, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art readily can determine the number of administrations to perform, or the desirability of performing one or more additional administrations, according to methods known in the art for monitoring therapeutic methods and other monitoring methods provided herein. Accordingly, the methods provided herein include methods of providing to the subject one or more administrations of a immunostimulatory bacteria, where the number of administrations can be determined by monitoring the subject, and, based on the results of the monitoring, determining whether or not to provide one or more additional administrations. Deciding whether or not to provide one or more additional administrations can be based on a variety of monitoring results, including, but not limited to, indication of tumor growth or inhibition of tumor growth, appearance of new metastases or inhibition of metastasis, the subject's anti-bacterial antibody titer, the subject's anti-tumor antibody titer, the overall health of the subject and the weight of the subject.

The time period between administrations can be any of a variety of time periods. The time period between administrations can be a function of any of a variety of factors, including monitoring steps, as described in relation to the number of administrations, the time period for a subject to mount an immune response, the time period for a subject to clear bacteria from normal tissue, or the time period for bacterial colonization/proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for bacterial colonization/proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month.

The methods uses herein also can be performed by administering compositions, such as suspensions and other formulations, containing the immunostimulatory bacteria provided herein Such compositions contain the bacteria and a pharmaceutically acceptable excipient or vehicle, as provided herein or known to those of skill in the art.

As discussed above, the uses and methods provided herein also can include administering one or more therapeutic compounds, such as anti-tumor compounds or other cancer therapeutics, to a subject in addition to administering immunostimulatory bacteria to the subject. The therapeutic compounds can act independently, or in conjunction with the immunostimulatory bacteria, for tumor therapeutic effects. Therapeutic compounds that can act independently include any of a variety of known chemotherapeutic compounds that can inhibit tumor growth, inhibit metastasis growth and/or formation, decrease the size of a tumor or metastasis, eliminate a tumor or metastasis, without reducing the ability of the immunostimulatory bacteria to accumulate in a tumor, replicate in the tumor, and cause or enhance an anti-tumor immune response in the subject. Examples of such chemotherapeutic agents include, but are not limited to, alkylating agents such as thiotepa and cyclosphosphamide; alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodepa, carboquone, meturedepa, and uredepa; ethylenimines and methylmelamines including altretamine, triethylenemelamine, triethylenephosphoramide, triethylenethiophosphoramide and trimethylol melamine; folic acid replenisher such as folinic acid; nitrogen mustards such as chlorambucil, chlornaphazine, *chlorophosphamide*, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, such as paclitaxel and docetaxel and albuminated forms thereof (i.e., nab-paclitaxel and nab-docetaxel), topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatrexate; defosfamide; demecolcine; diaziquone; difluoromethylornithine (DMFO); eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; Navelbine; Novantrone; teniposide; daunomycin; aminopterin; Xeloda; ibandronate; CPT-11; retinoic acid; esperamycins; capecitabine; and topoisomerase inhibitors such as irinotecan. Pharmaceutically acceptable salts, acids or derivatives of any of the above can also be used.

Therapeutic compounds that act in conjunction with the immunostimulatory bacteria include, for example, compounds that increase the immune response eliciting properties of the bacteria, e.g., by increasing expression of the RNAi, such as shRNA and miRNA, that inhibit, suppress or disrupt expression of the checkpoint genes, such as PD-L1, or TREX1 or other checkpoint genes, or compounds that can further augment bacterial colonization/proliferation. For example, a gene expression-altering compound can induce or increase transcription of a gene in a bacterium, such as an exogenous gene, e.g., encoding shRNA that inhibit, suppress or disrupt expression of one or more checkpoint genes, thereby provoking an immune response. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, shRNA, siRNA, and ribozymes. In other embodiments, therapeutic compounds that can act in conjunction with the immunostimulatory bacteria to increase the colonization/proliferation or immune response eliciting properties of the bacteria are compounds that can interact with a bacteria-expressed gene product, and such interaction can result in an increased killing of tumor cells or an increased anti-tumor immune response in the subject. A therapeutic compound that can interact with a bacteria-expressed gene product can include, for example a prodrug or other compound that has little or no toxicity or other biological activity in its subject-administered form, but after interaction with a bacteria-expressed gene product, the compound can develop a property that results in tumor cell death, including but not limited to, cytotoxicity, ability to induce apoptosis, or ability to trigger an immune response. A variety of prodrug-like substances are known in the art, including ganciclovir, 5-fluorouracil, 6-methylpurine deoxyriboside, cephalosporin-doxorubicin, 4-[(2-chloroethyl)(2-mesuloxyethyl)amino]benzoyl-L-glutamic acid, acetominophen, indole-3-acetic acid, CB1954, 7-ethyl-10-[4-(1-piperidino)-1-piperidino]carbonyloxycampotothecin, bis-(2-chloroethyl)amino-4-hydroxyphenylaminomethanone 28, 1-chloromethyl-5-hydroxy-1,2-dihyro-3H-benz[e]indole, epirubicin-glucoronide, 5'-deoxy5-fluorouridine, cytosine arabinoside, and linamarin.

3. Monitoring

The methods provided herein can further include one or more steps of monitoring the subject, monitoring the tumor, and/or monitoring the immunostimulatory bacteria administered to the subject. Any of a variety of monitoring steps can be included in the methods provided herein, including, but not limited to, monitoring tumor size, monitoring the presence and/or size of metastases, monitoring the subject's lymph nodes, monitoring the subject's weight or other health indicators including blood or urine markers, monitoring anti-bacterial antibody titer, monitoring bacterial expression of a detectable gene product, and directly monitoring bacterial titer in a tumor, tissue or organ of a subject.

The purpose of the monitoring can be simply for assessing the health state of the subject or the progress of therapeutic treatment of the subject, or can be for determining whether or not further administration of the same or a different immunostimulatory bacterium is warranted, or for determining when or whether or not to administer a compound to the subject where the compound can act to increase the efficacy of the therapeutic method, or the compound can act to decrease the pathogenicity of the bacteria administered to the subject.

In some embodiments, the methods provided herein can include monitoring one or more bacterially expressed genes. Bacteria, such as those provided herein or otherwise known in the art, can express one or more detectable gene products, including but not limited to, detectable proteins.

As provided herein, measurement of a detectable gene product expressed in a bacterium can provide an accurate determination of the level of bacteria present in the subject. As further provided herein, measurement of the location of the detectable gene product, for example, by imaging methods including tomographic methods, can determine the localization of the bacteria in the subject. Accordingly, the methods provided herein that include monitoring a detectable bacterial gene product can be used to determine the presence or absence of the bacteria in one or more organs or tissues of a subject, and/or the presence or absence of the bacteria in a tumor or metastases of a subject. Further, the methods provided herein that include monitoring a detectable bacterial gene product can be used to determine the titer of bacteria present in one or more organs, tissues, tumors or metastases. Methods that include monitoring the localization and/or titer of bacteria in a subject can be used for determining the pathogenicity of bacteria since bacterial infection, and particularly the level of infection, of normal tissues and organs can indicate the pathogenicity of the bacteria. The methods that include monitoring the localization and/or titer of immunostimulatory bacteria in a subject can be performed at multiple time points and, accordingly, can determine the rate of bacterial replication in a subject, including the rate of bacterial replication in one or more organs or tissues of a subject; accordingly, methods that include monitoring a bacterial gene product can be used for determining the replication competence of the bacteria. The methods provided herein also can be used to quantitate the amount of immunostimulatory bacteria present in a variety of organs or tissues, and tumors or metastases, and can thereby indicate the degree of preferential accumulation of the bacteria in a subject; accordingly, the bacterial gene product monitoring can be used in methods of determining the ability of the bacteria to accumulate in tumor or metastases in preference to normal tissues or organs. Since the immunostimulatory bacteria used in the methods provided herein can accumulate in an entire tumor or can accumulate at multiple sites in a tumor, and can also accumulate in metastases, the methods provided herein for monitoring a bacterial gene product can be used to determine the size of a tumor or the number of metastases are present in a subject. Monitoring such presence of bacterial gene product in tumor or metastasis over a range of time can be used to assess changes in the tumor or metastases, including growth or shrinking of a tumor, or development of new metastases or disappearance of metastases, and also can be used to determine the rate of growth or shrinking of a tumor, or development of new metastases or disappearance of metastases, or the change in the rate of growth or shrinking of a tumor, or development of new metastases or disappearance of metastases. Accordingly, monitoring a bacterial gene product can be used for monitoring a neoplastic disease in a subject, or for determining the efficacy of treatment of a neoplastic disease, by determining rate of growth or shrinking of a tumor, or development of new metastases or disappearance of metastases, or the change in the rate of growth or shrinking of a tumor, or development of new metastases or disappearance of metastases.

Any of a variety of detectable proteins can be detected by monitoring, exemplary of which are any of a variety of fluorescence proteins (e.g., green fluorescence proteins), any of a variety of luciferases, transferring or other iron binding proteins; or receptors, binding proteins, and antibodies, where a compound that specifically binds the receptor, binding protein or antibody can be a detectable agent or can be labeled with a detectable substance (e.g., a radionuclide or imaging agent).

Tumor and/or metastasis size can be monitored by any of a variety of methods known in the art, including external assessment methods or tomographic or magnetic imaging methods. In addition to the methods known in the art, methods provided herein, for example, monitoring bacterial gene expression, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

The methods provided herein also can include monitoring the antibody titer in a subject, including antibodies produced in response to administration of immunostimulatory bacteria to a subject. The bacteria administered in the methods provided herein can elicit an immune response to endogenous bacterial antigens. The bacteria administered in the methods provided herein also can elicit an immune response to exogenous genes expressed by the bacteria. The bacteria administered in the methods provided herein also can elicit an immune response to tumor antigens. Monitoring antibody titer against bacterial antigens, bacterially expressed exogenous gene products, or tumor antigens can be used to monitor the toxicity of the bacteria, monitoring the efficacy of treatment methods, or monitoring the level of gene product or antibodies for production and/or harvesting.

Monitoring antibody titer can be used to monitor the toxicity of the bacteria. Antibody titer against a bacteria can vary over the time period after administration of the bacteria to the subject, where at some particular time points, a low anti-(bacterial antigen) antibody titer can indicate a higher toxicity, while at other time points a high anti-(bacterial antigen) antibody titer can indicate a higher toxicity. The bacteria used in the methods provided herein can be immunogenic, and can, therefore, elicit an immune response soon after administering the bacteria to the subject. Generally, immunostimulatory bacteria against which the immune system of a subject can mount a strong immune response can be bacteria that have low toxicity when the subject's immune system can remove the bacteria from all normal organs or tissues. Thus, in some embodiments, a high antibody titer against bacterial antigens soon after administering the bacteria to a subject can indicate low toxicity of the bacteria.

In other embodiments, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis.

In other embodiments, monitoring antibody titer can be used for monitoring the level of gene product or antibodies for production and/or harvesting. As provided herein, methods can be used for producing proteins, RNA molecules or other compounds, particularly RNA molecules such as shRNA, by expressing an exogenous gene in a microorganism that has accumulated in a tumor. Monitoring antibody titer against the protein, RNA molecule or other compound can indicate the level of production of the protein, RNA molecule or other compound by the tumor-accumulated microorganism, and also can directly indicate the level of antibodies specific for such a protein, RNA molecule or other compound.

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject an immunostimulatory bacterium, as provided herein. Monitoring the health of a subject can be used to determine the pathogenicity of an immunostimulatory bacterium administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, c-reactive protein concentration.

The methods provided herein can include monitoring a therapy, where therapeutic decisions can be based on the results of the monitoring. Therapeutic methods provided herein can include administering to a subject immunostimulatory bacteria, where the bacteria can preferentially accumulate in a tumor and/or metastasis, and where the bacteria can cause or enhance an anti-tumor immune response. Such therapeutic methods can include a variety of steps including multiple administrations of a particular immunostimulatory bacterium, administration of a second immunostimulatory bacterium, or administration of a therapeutic compound. Determination of the amount, timing or type of immunostimulatory bacteria or compound to administer to the subject can be based on one or more results from monitoring the subject. For example, the antibody titer in a subject can be used to determine whether or not it is desirable to administer an immunostimulatory bacterium and, optionally, a compound, the quantity of bacteria and/or compound to administer, and the type of bacteria and/or compound to administer, where, for example, a low antibody titer can indicate the desirability of administering an additional immunostimulatory bacterium, a different immunostimulatory bacterium, and/or a therapeutic compound such as a compound that induces bacterial gene expression or a therapeutic compound that is effective independent of the immunostimulatory bacteria.

In another example, the overall health state of a subject can be used to determine whether or not it is desirable to administer an immunostimulatory bacterium and, optionally, a compound, the quantity of bacterium or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. In another example, monitoring a detectable bacterially expressed gene product can be used to determine whether it is desirable to administer an immunostimulatory bacterium and, optionally, a compound, the quantity of bacterium and/or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. Such monitoring methods can be used to determine whether or not the therapeutic method is effective, whether or not the therapeutic method is pathogenic to the subject, whether or not the bacteria have accumulated in a tumor or metastasis, and whether or not the bacteria have accumulated in normal tissues or organs. Based on such determinations, the desirability and form of further therapeutic methods can be derived.

In another example, monitoring can determine whether or not immunostimulatory bacteria have accumulated in a tumor or metastasis of a subject. Upon such a determination, a decision can be made to further administer additional bacteria, a different immunostimulatory bacterium and, optionally, a compound to the subject.

J. Examples

The following examples are included for illustrative purposes only and are not intended to limit the scope of the invention.

Summary of Exemplary Engineered Immunostimulatory Bacterial Strains and Nomenclature:

| Strain # | Plasmid | Strain Background | RNAi Targets | Alternate name |
|---|---|---|---|---|
| AST-100 | None | YS1646 | none | VNP 20009 |
| AST-101 | None | YS1646-ASD | none | ASD (asd gene knockout) |
| AST-102 | pEQU6 | YS1646 | none | YS1646 (pEQU6 - plasmid) |
| AST-103 | pEQU6 | YS1646 | Scrambled (shRNA) | YS1646 (pEQU6-shSCR) |
| AST-104 | pEQU6 | YS1646 | muTREX1 (shRNA) ARI-108 | YS1646 (pEQU6-shTREX1) |
| AST-105 | pEQU6 | YS1646 | muPD-L1 (shRNA) ARI-115 | YS1646 (pEQU6-shPDL1) |
| AST-106 | pEQU6 | YS1646 | muTREX1 (microRNA) ARI-203 | YS1646 (pEQU6-miTREX1) |
| AST-107 | pATI-U6 | YS1646-ASD | Scrambled (shRNA) | ASD (pATI-shSCR) |
| AST-108 | pATI-U6 | YS1646-ASD | muTREX1 (shRNA) ARI-108 | ASD (pATI-shTREX1) |
| AST-109 | pATIKAN-U6 | YS1646-ASD | Scrambled (shRNA) | ASD (pATIKan-shSCR) |

-continued

| Strain # | Plasmid | Strain Background | RNAi Targets | Alternate name |
|---|---|---|---|---|
| AST-110 | pATIKAN-U6 | YS1646-ASD | muTREX1 (shRNA) ARI-108 | ASD (pATIKan-shTREX1) |
| AST-111 | None | YS1646-ASD-fljb-fliC | None | ASD/FLG (asd and flagellin knockout) |
| AST-112 | pATI-U6 | YS1646-ASD-fljb-fliC | muTREX1 (shRNA) ARI-108 | ASD/FLG (pATI-shTREX1) |
| AST-113 | pATI-U6 | YS1646-ASD-fljb-fliC | muTREX1 (shRNA) ARI-108 | ASD/FLG (pATI-U6 Kan shTREX1) |
| AST-114 | None | YS1646-ASD-LLO | None | ASD/LLO (asd knockout/cytoLLO knock-in) |
| AST-115 | pATI-U6 | YS1646-ASD-LLO | muTREX1 (shRNA) ARI-108 | ASD/LLO (pATIKan-shTREX1) |
| AST-116 | pATIKanpBRori-U6 | YS1646-ASD | Scrambled | ASD (pATIKanLow-shSCR) |
| AST-117 | pATIKanpBRori-U6 | YS1646-ASD | muTREX1 (shRNA) ARI-108 | ASD (pATIKanLow-shTREX1) |
| AST-118 | pATIKanpBRori-U6 | YS1646-ASD-fljb-fliC | muTREX1 (shRNA) ARI-108 | ASD/FLG (pATIKanLow-shTREX1) |
| AST-119 | pATIKanpBRori-U6 | YS1646-ASD-pMTL-LLO | muTREX1 (shRNA) ARI-108 | ASD/LLO (pATIKanLow-shTREX1) |
| AST-120 | pEQU6 | YS1646-ASD-pMTL-LLO | muTREX1 (microRNA) ARI-203 | ASD/LLO (pEQU6-miTREX1) Suicidal |
| AST-121 | pEQU6 | YS1646 | muVISTA ARI-157 | YS1646 (pEQU6-shVISTA) |
| AST-122 | pEQU6 | YS1646 | muTGF-beta ARI-149 | YS1646 (pEQU6-TGF-beta) |
| AST-123 | pEQU6 | YS1645 | muBeta-Catenin ARI-166 | YS1646 (pEQU6-Beta-Catenin) |

Example 1

*Salmonella* asd Gene Knockout Strain Engineering Strain AST-101 was prepared. it is an attenuated *Salmonella typhimurium* derived from YS1646 (which can be purchased from ATCC, Catalog #202165) that has been engineered to be asd$^-$ (an asd gene knockout). In this example, the *Salmonella typhimurium* strain YS1646 asd$^-$ gene deletion was engineered using modifications of the method of Datsenko and Wanner (*Proc Natl Acad Sci USA* 97:6640-6645 (2000)) as outlined in FIG. 1, and described below.

Introduction of the Lambda Red Helper Plasmid into YS1646

The YS1646 strain was prepared to be electrocompetent as described previously (Sambrook J., (1998), *Molecular Cloning, A Laboratory Manual, 2nd edn. Cold Spring Harbor, N.Y.: Cold Spring Harbor Laboratory*) by growing a culture in LB and concentrating 100-fold and washing three times with ice-cold 10% glycerol. The electrocompetent strain was electroporated with the Lambda red helper plasmid pKD46 (SEQ ID NO:218) using a 0.2 cm gap cuvette at the following settings: 2.5 kV, 186 ohms, 50 μF. Transformants carrying pKD46 were grown in 5 mL SOC medium with ampicillin and 1 mM L-arabinose at 30° C. and selected on LB agar plates containing ampicillin. A YS1646 clone containing the lambda red helper plasmid pKD46 then was made electrocompetent, as described above for YS1646.

Construction of asd Gene Knockout Cassette

The asd gene from the genome of YS1646 (Broadway et al. (2014) *J. Biotechnology* 192:177-178) was used for designing the asd gene knockout cassette. A plasmid containing 204 and 203 bp of homology to the left hand and right hand regions, respectively, of the asd gene, was transformed into DH5-alpha competent cells. A kanamycin gene cassette flanked by lox P sites was cloned into this plasmid. The asd gene knockout cassette then was PCR amplified using primers asd-1 and asd-2 (Table 1) and gel purified.

Execution of asd Gene Deletion

The YS1646 strain carrying plasmid pKD46 was electroporated with the gel-purified linear asd gene knock-out cassette. Electroporated cells were recovered in SOC medium and plated onto LB Agar plates supplemented with Kanamycin (20 μg/mL) and diaminopimelic acid (DAP, 50 μg/ml). During this step, lambda red recombinase induces homologous recombination of the chromosomal asd gene with the kan cassette (due to the presence of homologous flanking sequences upstream and downstream of the chromosomal asd gene), and knockout of the chromosomal copy of the asd gene occurs. The presence of the disrupted asd gene in the selected kanamycin resistant clones was confirmed by PCR amplification with primers from the YS1646 genome flanking the sites of disruption (primer asd-3) and from the multi-cloning site (primer scFv-3) (Table 1). Colonies were also replica plated onto LB plates with and without supplemental DAP to demonstrate DAP auxotrophy. All clones with the asd gene deletion were unable to grow in the absence of supplemental DAP, demonstrating DAP auxotrophy.

TABLE 1

Primer information

| Primer name | Primer sequence | SEQ ID NO. |
|---|---|---|
| asd-1 | ccttcctaacgcaaattccctg | 219 |
| asd-2 | ccaatgctctgcttaactcctg | 220 |
| asd-3 | gcctcgccatgtttcagtacg | 221 |
| asd-4 | ggtctggtgcattccgagtac | 222 |
| scFv-3 | cataatctgggtccttggtctgc | 223 |

Kanamycin Gene Cassette Removal

The kan selectable marker was removed by using the Cre/loxP site-specific recombination system. The YS1646 asd$^-$ gene Kan$^R$ mutant was transformed with pJW168 (a temperature sensitive plasmid expressing the cre recombinase, SEQ ID NO:224). Amp$^R$ colonies were selected at 30° C.; pJW168 was subsequently eliminated by growth at 42° C. A selected clone (AST-101) then was tested for loss of kan by replica plating on LB agar plates with and without kanamycin, and confirmed by PCR verification using primers from YS1646 genome flanking the sites of disruption (primer asd-3 and asd-4, for primer sequence, see Table 1).

Characterization of the asd Deletion Mutant Strain AST-101

The asd mutant AST-101 was unable to grow on LB agar plates at 37° C., but was able to grow on LB plates containing 50 μg/mL diaminopimelic acid (DAP). The asd mutant growth rate was evaluated in LB liquid media and it was unable to grow in liquid LB but was able to grow in LB supplemented with 50 μg/mL DAP, as determined by measuring absorbance at 600 nM.

Sequence Confirmation of the AST-101 asd Locus Sequence after asd Gene Deletion

The AST-101 asd gene deletion strain was verified by DNA sequencing using primer asd-3 and asd-4. Sequencing of the region flanking the asd locus was performed and the sequence confirmed that the asd gene was deleted from the YS1646 chromosome.

Example 2

Design and Characterization of Exemplary shRNAs

In order to generate recombinant *Salmonella typhimurium* transformed with plasmids encoding shRNAs against desired target genes, a set of 6 shRNAs were designed against each of human PD-L1, SIRP-alpha, beta-catenin, VISTA, TREX1, and VEGF. A total of 9 shRNAs were designed against human TGF-beta isoform 1. The shRNAs were subcloned into the pEQU6 vector (SEQ ID NO:41), for a total of 45 shRNAs.

Proteins Targeted by shRNA

| SEQ ID NO. | Protein |
|---|---|
| 31 | Human PD-L1 |
| 32 | Human CTNNB1 |
| 33 | Human SIRP-alpha |
| 34 | Human TREX1 |
| 35 | Human VISTA |
| 193 | Human TGF-beta, isoform 1 |
| 194 | Human VEGF |

The target sequences in each gene are as follows:

| SEQ ID NO. | Target | Target Sequence | Reference |
|---|---|---|---|
| 1 | Human PD-L1 | gtagagtatggtagcaata | ARI-122 |
| 2 | Human PD-L1 | gccgactacaagcgaatta | ARI-123 |
| 3 | Human PD-L1 | gacaagcagtgaccatcaa | ARI-124 |
| 4 | Human PD-L1 | gaatcaacacaacaactaa | ARI-125 |

-continued

| SEQ ID NO. | Target | Target Sequence | Reference |
|---|---|---|---|
| 5 | Human PD-L1 | gcacatcctccaaatgaaa | ARI-126 |
| 6 | Human PD-L1 | gtagcactgacattcatct | ARI-127 |
| 7 | Human CTNNB1 | gacagactgccttcaaatt | ARI-168 |
| 8 | Human CTNNB1 | gcagctggaattctttcta | ARI-169 |
| 9 | Human CTNNB1 | gactaccagttgtggttaa | ARI-170 |
| 10 | Human CTNNB1 | ggacacagcagcaatttgt | ARI-171 |
| 11 | Human CTNNB1 | ggatgttcacaaccgaatt | ARI-172 |
| 12 | Human CTNNB1 | gccacaagattacaagaaa | ARI-173 |
| 13 | Human SIRP-alpha | gccaggtgaggaagttcta | ARI-174 |
| 14 | Human SIRP-alpha | gagctggctcctggtgaat | ARI-175 |
| 15 | Human SIRP-alpha | gctgagaacactggatcta | ARI-176 |
| 16 | Human SIRP-alpha | gaagaatgccagagaaata | ARI-177 |
| 17 | Human SIRP-alpha | ggacacaaatgatatcaca | ARI-178 |
| 18 | Human SIRP-alpha | ggagtatgccagcattcag | ARI-179 |
| 19 | Human TREX1 | gcagcgcatgggcgtcaat | ARI-109 |
| 20 | Human TREX1 | ggcccaaggaagagctata | ARI-110 |
| 21 | Human TREX1 | gcaccatcaggcccatgta | ARI-111 |
| 22 | Human TREX1 | gccacaaccaggaacacta | ARI-112 |
| 23 | Human TREX1 | gcaggggtaccaaggatct | ARI-113 |
| 24 | Human TREX1 | gccacactgtatggactat | ARI-114 |
| 25 | Human VISTA | gatgtgaccttctacaaga | ARI-195 |
| 26 | Human VISTA | gaccaccatggcaacttct | ARI-196 |
| 27 | Human VISTA | ggtgcagacaggcaaagat | ARI-197 |
| 28 | Human VISTA | gtgcctgcatcgtaggaat | ARI-198 |
| 29 | Human VISTA | gcaacattcaagggattga | ARI-199 |
| 30 | Human VISTA | gtccctgactctccaaact | ARI-200 |
| 195 | Human TGF-beta isoform 1 | gaaacccacaacgaaatct | ARI-180 |
| 196 | Human TGF-beta isoform 1 | gtacacacagcatatatat | ARI-181 |
| 197 | Human TGF-beta isoform 1 | ctgctgaggctcaagttaa | ARI-182 |
| 198 | Human TGF-beta isoform 1 | gtggagctgtaccagaaat | ARI-183 |
| 199 | Human TGF-beta isoform 1 | gactcgccagagtggttat | ARI-184 |
| 200 | Human TGF-beta isoform 1 | gagccgtggaggggaaatt | ARI-185 |
| 201 | Human TGF-beta isoform 1 | cctgtgacagcagggataa | ARI-186 |
| 202 | Human TGF-beta isoform 1 | gccctggacaccaactatt | ARI-187 |
| 203 | Human TGF-beta isoform 1 | ccctgtacaaccagcataa | ARI-188 |
| 204 | Human VEGF | gagatcgagtacatcttca | ARI-189 |
| 205 | Human VEGF | gcagattatgcggatcaaa | ARI-190 |
| 206 | Human VEGF | gatagagcaagacaagaaa | ARI-191 |

| SEQ ID NO. | Target | Target Sequence | Reference |
|---|---|---|---|
| 207 | Human VEGF | ggagaaagcatttgtttgt | ARI-192 |
| 208 | Human VEGF | gatccgcagacgtgtaaat | ARI-193 |
| 209 | Human VEGF | gcgaggcagcttgagttaa | ARI-194 |

To generate each shRNA, a pair of designed oligonucleotides was synthesized to form a cassette encoding the shRNA. The oligonucleotides were allowed to anneal to each other to form the cassette and ligated to linearized pEQU6 vector that was predigested with the restriction enzymes Spe1 and Xho1. The linked DNA fragments were transformed into E. coli cells and the positive clones were selected with restriction enzyme digestion. The shRNA sequences were purified and sequenced. Six sequences for RNA interference were selected from different cDNA-coding regions and analyzed by a BLAST search to ensure that they did not have significant sequence homology with other genes. The six exemplary shRNA encoding sequences are as follows:

| SEQ ID NO. | Target Protein | shRNA-encoding Sequence |
|---|---|---|
| 36 | Human PD-L1 | gtagagta tggtagcaat atctagagta ttgctaccat actctac |
| 37 | Human CTNNB1 | g acagactgcc ttcaaatttc tagagaattt gaaggcagtc tgtc |
| 38 | Human SIRP-alpha | g ccaggtgagg aagttctatc tagagtagaa cttcctcacc tggc |
| 39 | Human TREX1 | g cagcgcatgg gcgtcaattc tagagattga cgcccatgcg ctgc |
| 40 | Human VISTA | g accaccatgg caacttcttc tagagagaag ttgccatggt ggtc |

The sequences of the resulting vectors, designated pEQU6-shPDL1-shRNA, pEQU6-shPDL1-H1-shCTNNB1, pEQU6-shPDL1-H1-shSIRP-alpha, pEQU6-shPDL1-H1-shTREX1, and pEQU6-shPDL1-H1-shVISTA, are set forth in SEQ ID NOs: 43-47. Each shRNA then is individually screened to identify the best shRNA against each target protein. The plasmid used for screening contains a bacterial origin of replication, a kanamycin resistance marker, and a human U6 promoter sequence, followed by the individual shRNA, which then is followed by a terminator poly-T sequence. The vector can employ an H1 promoter instead of a U6 promoter. U6 and H1 are RNA polymerase III promoters, which generally are used for production and processing of small RNAs (see, Sequence Listing). Each shRNA was designed to hybridize with a 19 nucleotide overlap to the target sequence, and contains a 7 nucleotide loop-spacer, followed by the reverse complement of the initial target sequence. The shRNA designs are not limited to these nucleotide lengths. Complementary shRNA sequences range from 19-29 nucleotides (the "sense" sequence derived from the target gene), followed by a loop spacer of 4-15 nucleotides, and then completed with a 19-29 nucleotide sequence, which is the "antisense" sequence of the primary target sequence.

A second vector was used to achieve knockdown of gene expression for separate targets. This vector uses a second promoter, H1, which is separated by a length of at least 75 nucleotides, which can be from about 60-100, from the U6 promoter, in order to achieve effective gene knockdown by both target shRNAs. As an example, one particular vector carries shRNA sequences to PD-L1 and SIRP-alpha, with the anti-PD-L1 shRNA under the U6 promoter, followed by an anti-SIRP-alpha shRNA under an H1 promoter. Multiple targeting shRNAs can be added to a plasmid by utilizing additional promoters, such as U6 or H1 promoters from orthologous species.

In order to identify the top performing shRNAs against each target, individual shRNAs subcloned into pEQU6 were tested for their ability to knockdown gene expression. First, HEK293 cells are co-transfected with both the pEQU6 plasmid (encoding a distinct shRNA sequence) and a cDNA expression plasmid (expressing target protein cDNA under a CMV promoter). For example, the pEQU6 plasmid encoding shRNA to PD-L1, clone 1, is co-transfected with a PD-L1 cDNA expressing plasmid. shRNA-mediated knockdown of gene expression is measured by Western blot and qPCR. Commercially available cDNAs are available from GE/Dharmacon or Origene, and are subcloned into a CMV expression vector that results in a fused HA tag to the C-terminus of the target protein. This allows for uniform measurement of gene knockdown using an anti-HA antibody-HRP fusion. The cDNA molecules correspond to portions of the cDNA encoding genes.

In addition to shRNAs targeting human genes, shRNAs for use for testing in in vivo models are provided. shRNAs are generated that target orthologous murine genes, in order to test in syngeneic murine transplant and autochthonous murine tumor models. Murine targeting shRNA sequences (SIGMA) are subcloned into the pEQU6 vector described above and characterized for gene knockdown propensity by Western blot and qPCR. Furthermore, a combination of shRNAs against PD-L1 and TREX1 were subcloned into pEQU6-H1 (SEQ ID NO:42), with the shRNA against PD-L1 under the U6 promoter and the shRNA against TREX1 under the H1 promoter. For use in the mouse models the following shRNA-encoding sequences were designed:

| SEQ ID NO. | Target (mouse) | shRNA encoding sequence (SIGMA) | Reference |
|---|---|---|---|
| 75 | muPD-L1 | ccggccgaaatgatacacaattcgactcg agtcgaattgtgtatcatttcggtttttg | ARI-115 |
| 76 | muSIRP-alpha | ccggccacaactggaatgtcttcatctcg agatgaagacattccagttgtggttttt | ARI-138 |
| 77 | muTREX1-clone1 | ccggacaaccaacctaaggccacatctc gagatgtggccttaggttggttgttttt tg | ARI-101 |
| 78 | muTREX1-clone2 | ccggcctagatggtaccttctgtgtctcg agacacagaaggtaccatctaggtttttg | ARI-102 |

For screening individual shRNA performance against each target, the positive control for Western blot corresponds to beta-tubulin expression, and the negative control for both Western blot and qPCR screening corresponds to a scrambled shRNA that lacks homology to any mammalian sequences. Each shRNA is individually tested by western blot. For qPCR gene expression, knockdown is quantified as % gene knockdown, and triplicate testing with error bars is generated.

Western blot screening was performed as follows. First, the co-transfection experiment was setup with the target gene expression plasmid (pCMV-cDNA-HA) and each of 6 designed shRNA vectors, as individual reactions, using Lipofectamine 2000 (Invitrogen). The chart below describes the component of each reaction. 48 hours after transfection, cells were lysed in SDS-PAGE buffer and subjected to 4-20% SDS-PAGE gel electrophoresis and Western blot analyses. The Western blot was carried out using the anti-HA-antibody purchased from Santa Cruz Biotechnology at a 1:1000 dilution. The membranes were detected by ECL reagents. For each 6-well:

| | 293 cells | cDNA | shRNA 1 | shRNA 2 | shRNA 3 | shRNA 4 | shRNA 5 | shRNA 6 |
|---|---|---|---|---|---|---|---|---|
| DNA | | 1.0 μg | 1.0 μg | 1.0 μg | 1.0 μg | 1.0 μg | 1.0 μg | 1.0 μg |
| pEQ-shRNA | | | 2.0 μg | 2.0 μg | 2.0 μg | 2.0 μg | 2.0 μg | 2.0 μg |
| pEQ-scramble-shRNA | 3.0 μg | 2.0 μg | | | | | | |
| Total DNA | 3.0 μg | 3.0 μg | 3.0 μg | 3.0 μg | 3.0 μg | 3.0 μg | 3.0 μg | 3.0 μg |

The gene silencing assessment by qPCR was performed as follows. First, the co-transfection experiment was setup with the target gene expression plasmid pCMV-cDNA-HA and 6 shRNA vectors using Lipofectamine 2000 (Invitrogen). The chart below describes the component of each reaction. The cDNA to shRNA ratio is 1:6. 48 hours after transfection, RNA was extracted using the RNeasy Plus kit (Qiagen). cDNA was synthesized from mRNA using oligo $(dT)_{20}$ primer, SuperScript™ IV reverse transcriptase (ThermoFisher) and 100 ng of total RNA. The real time PCR assay was performed with PowerUP™ SYBR™ master mix (ThermoFisher) on an Applied Biosystems StepOne™ Real-Time PCR System against cDNA-HA and GAPDH (endogenous control) targets. For each 6-well:

| | 293 cells | cDNA | shRNA 1 | shRNA 2 | shRNA 3 | shRNA 4 | shRNA 5 | shRNA 6 |
|---|---|---|---|---|---|---|---|---|
| cDNA | | 0.2 μg | 0.2 μg | 0.2 μg | 0.2 μg | 0.2 μg | 0.2 μg | 0.2 μg |
| pEQ-shRNA | | | 1.2 μg | 1.2 μg | 1.2 μg | 1.2 μg | 1.2 μg | 1.2 μg |
| pEQ-plasmid control | 1.2 μg | 1.2 μg | | | | | | |
| Total DNA | 1.2 μg | 2.2 μg | 2.2 μg | 2.2 μg | 2.2 μg | 2.2 μg | 2.2 μg | 2.2 μg |

Figure 2B:
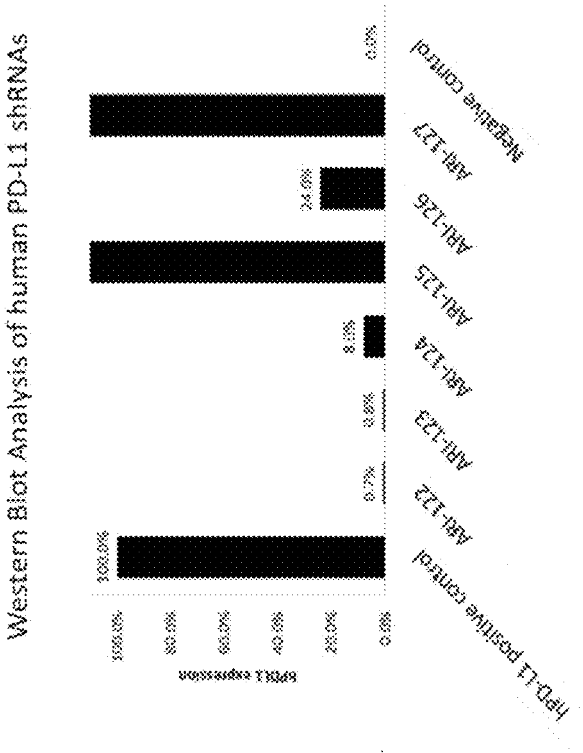
FIGS. 2A and 2B depict the results of human PD-L1 shRNA screening using qPCR and Western blot. HEK 293 cells were co-transfected with a PD-L1 cDNA expression plasmid and various pEQU6 plasmids encoding distinct shRNAs targeting PDL1.
Figure 2A:
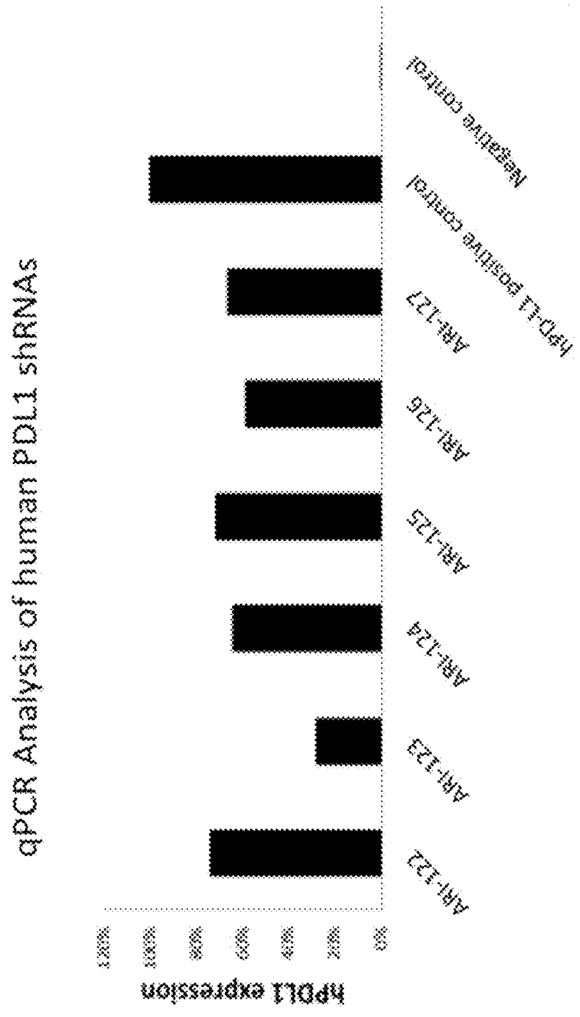

The shRNA-mediated gene knockdown with these shRNAs were functionally characterized. See, *Methods Mol Biol.* (2010) 629:141-158 for a description of the methods used. Using the human PD-L1 gene as a reference, a set of 6 shRNAs were designed with a 19 base pair complementary region to the PD-L1 gene (SEQ ID NO: 31), and cloned into the pEQU6 screening vector (SEQ ID NO:41) behind the U6 promoter, utilizing the cloning strategy that is described above. Each shRNA construct was screened for disruption of human PD-L1 gene expression by using the qPCR and western blot protocols described above. As shown in FIG. 2A, several shRNAs were effective at knocking down PD-L1 gene expression. ARI-123 (SEQ ID NO:2) resulted in the highest potency, with approximately 75% knockdown of human PD-L1 gene expression. This was confirmed by western blot (FIG. 2B), where ARI-123 demonstrated >99% knockdown of PD-L1 gene expression. In addition, ARI-122 (SEQ ID NO:1) showed >99% knockdown of PD-L1 gene expression by Western blot.

Figure 3B:
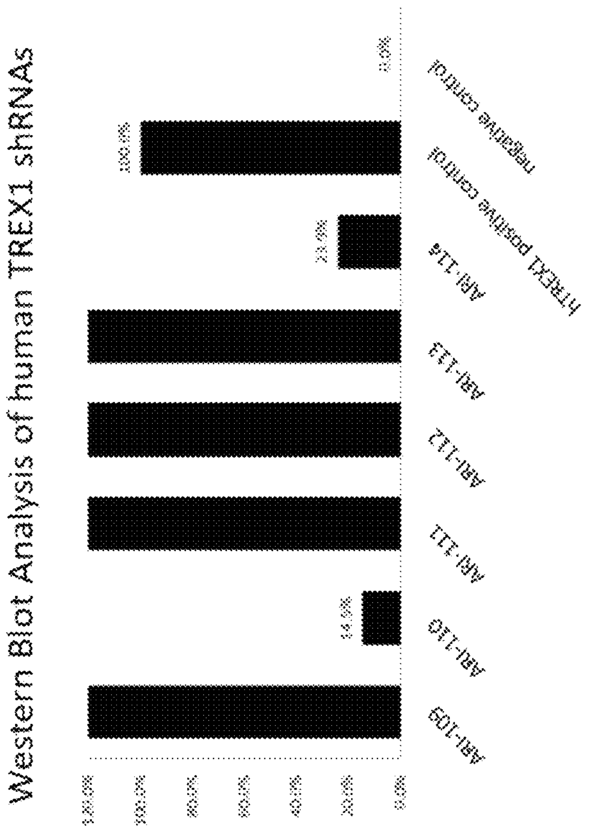
FIGS. 3A and 3B depict the results of human TREX1 shRNA screening using qPCR and Western blot. HEK 293 cells were co-transfected with a TREX1 cDNA expression plasmid and various pEQU6 plasmids encoding distinct shRNAs targeting TREX1.
Figure 3A:
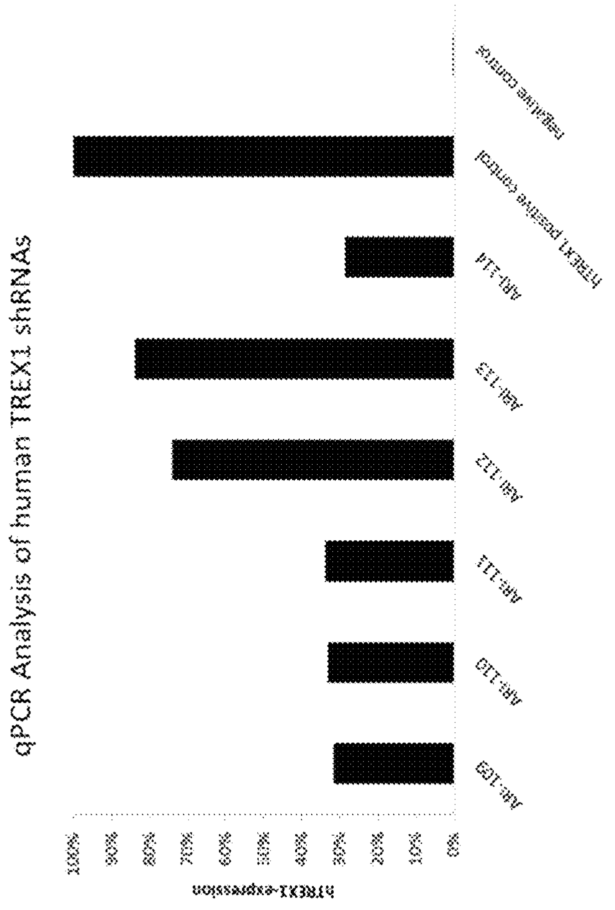

A set of 6 shRNAs with 19 bp complementary regions were designed to disrupt the expression of the human TREX1 gene (SEQ ID NO:34), and cloned into the pEQU6 screening vector (SEQ ID NO:41) behind the U6 promoter in the manner described above. As shown in FIG. 3A, ARI-109 (SEQ ID NO:19), ARI-110 (SEQ ID NO:20), ARI-111 (SEQ ID NO:21) and ARI-114 (SEQ ID NO:24) all showed approximately 70% knockdown of TREX1 gene expression by qPCR. Western blot analysis was used to confirm the gene disruption findings identified by qPCR (FIG. 3B). Both ARI-110 (SEQ ID NO:20) and ARI-114 (SEQ ID NO:24) showed a high degree of gene knockdown, 85.5% and 76.1%, respectively.

Figure 4B:
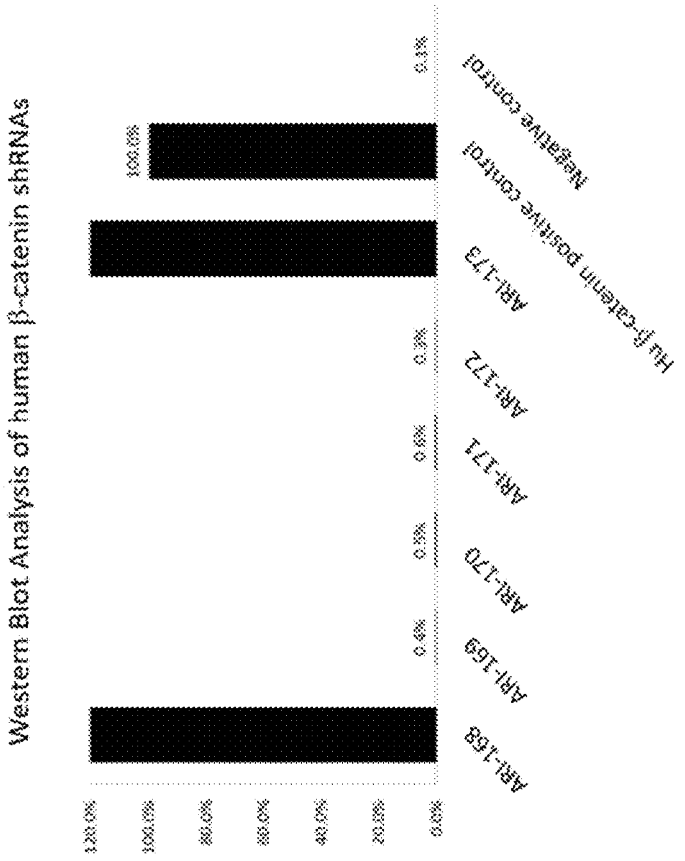
FIGS. 4A and 4B depict the results of human beta-catenin shRNA screening using qPCR and Western blot. HEK 293 cells were co-transfected with a beta-catenin cDNA expression plasmid and various pEQU6 plasmids encoding distinct shRNAs targeting beta-catenin.
Figure 4A:
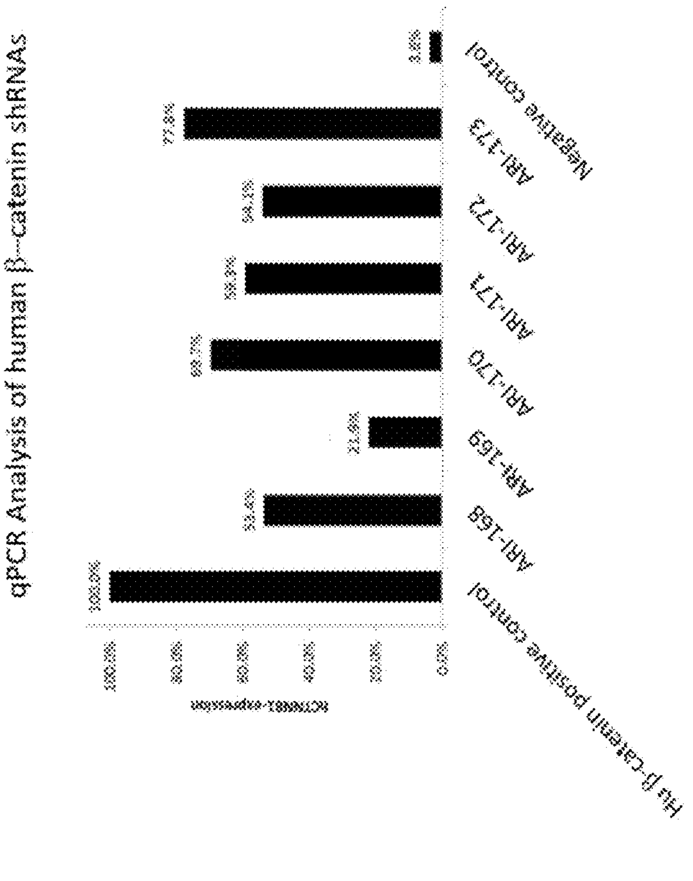

Using the human beta-catenin gene (SEQ ID NO:32) as a reference, a set of 6 shRNAs were designed with a 19 base complementary region to the beta-catenin gene and cloned into the pEQU6 screening vector (SEQ ID NO:41) behind the U6 promoter as described above. Each shRNA construct was screened for disruption of human beta-catenin gene expression by both qPCR and Western blot. As shown in FIG. 4A, several shRNAs were effective at knocking down beta-catenin gene expression. ARI-169 (SEQ ID NO:8) demonstrated >75% knockdown of human beta-catenin gene expression. In the Western blot analysis (FIG. 4B) ARI-169 (SEQ ID NO:8), ARI-170 (SEQ ID NO:9), ARI-171 (SEQ ID NO:10), and ARI-172 (SEQ ID NO:11), each showed >99% knockdown of beta-catenin gene expression.

Figure 5A:
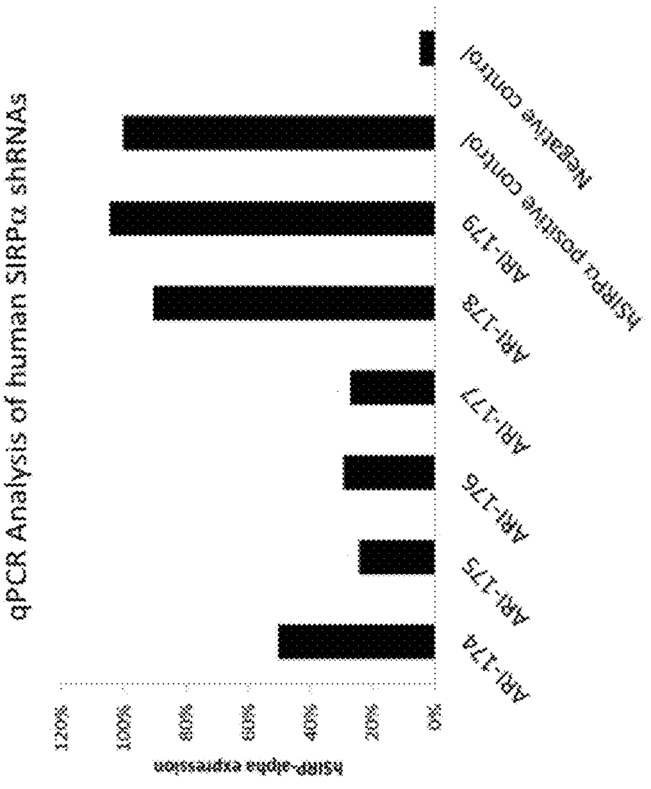
FIGS. 5A and 5B depict the results of human SIRP-alpha shRNA screening using qPCR and Western blot. HEK 293 cells were co-transfected with a SIRP-alpha cDNA expression plasmid and various pEQU6 plasmids encoding distinct shRNAs targeting SIRP-alpha.
Figure 5B:
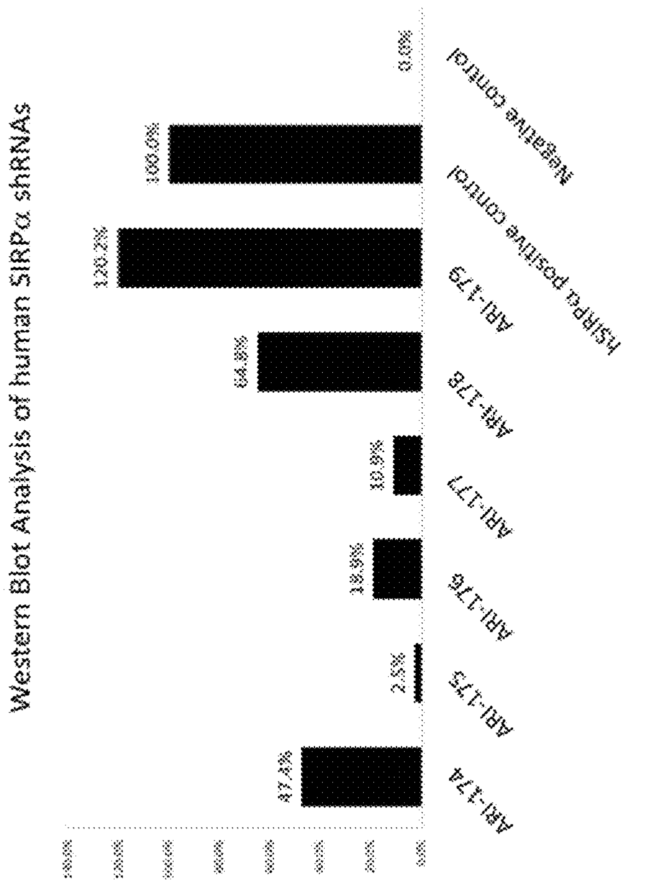

The human SIRP-alpha gene (SEQ ID NO:33) was also screened for shRNAs that disrupt gene expression. A set of 6 shRNAs with 19 bp complementary regions were designed and cloned into the pEQU6 screening vector (SEQ ID NO:41) behind the U6 promoter as described above. As shown in FIG. 5A, several shRNA constructs were able to significantly knockdown SIRP-alpha gene expression. ARI-175 (SEQ ID NO:14), ARI-176 (SEQ ID NO:15), and ARI-177 (SEQ ID NO:16) all showed approximately greater than 70% knockdown of SIRP-alpha gene expression by qPCR. In the Western blot analysis (FIG. 5B), a high degree of knockdown was observed for several constructs: ARI-175 (>95% knockdown), ARI-176 (>80% knockdown), and ARI-177 (approximately 90% knockdown), which was consistent with the findings by these three constructs when screened by qPCR.

Figure 6:
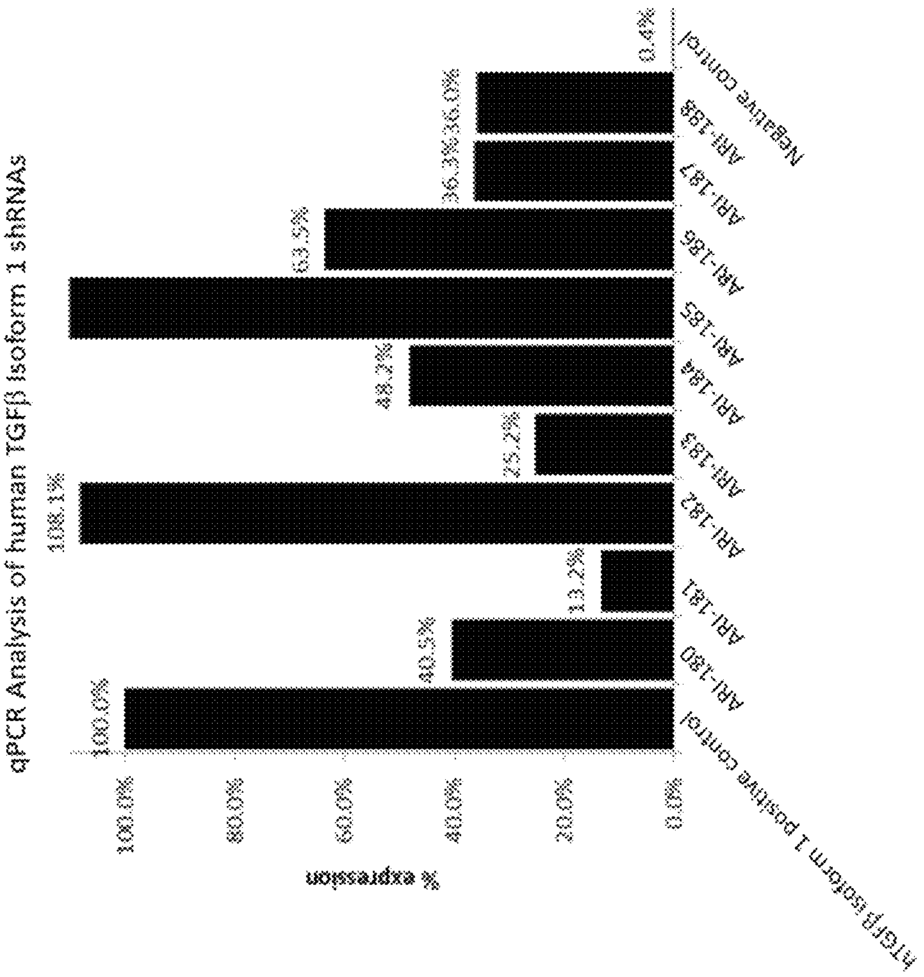
FIG. 6 depicts the results of human TGF-beta isoform 1 shRNA screening using qPCR. HEK 293 cells were co-transfected with a TGF-beta isoform 1 cDNA expression plasmid and various pEQU6 plasmids encoding distinct shRNAs targeting TGF-beta. qPCR was used to determine the level of mRNA knockdown.

Using the human TGF-beta isoform 1 gene (SEQ ID NO:193) as a reference, a set of nine shRNAs were designed and cloned into the pEQU6 screening vector (SEQ ID NO:41) behind the U6 promoter as described above. Each shRNA construct was screened for disruption of human TGF-beta isoform 1 gene expression by qPCR. As shown in FIG. 6, several shRNAs were effective at knocking down TGF-beta gene expression. ARI-181 (SEQ ID NO:196) was the most potent shRNA, with approximately >85% knockdown of human TGF-beta gene expression. This was followed by ARI-183 (SEQ ID NO:198), which showed approximately 75% knockdown of TGF-beta gene expression.

Figure 7:
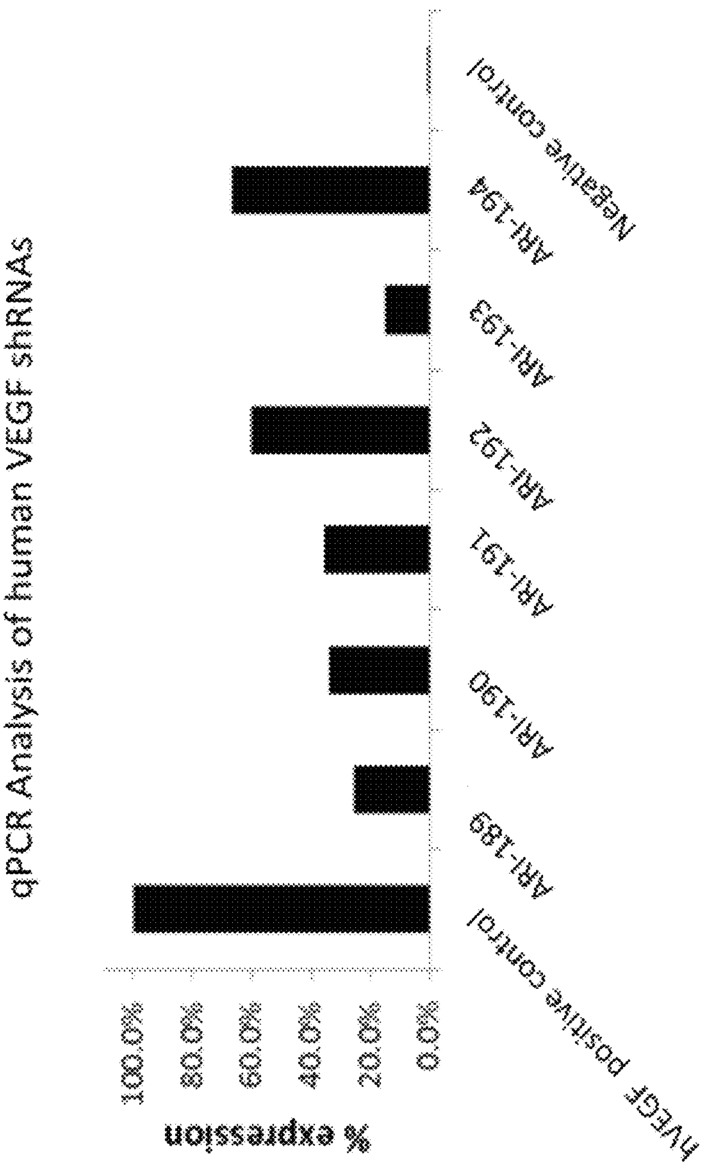
FIG. 7 depicts the results of human VEGF shRNA screening using qPCR. HEK 293 cells were co-transfected with a VEGF cDNA expression plasmid and various pEQU6 plasmids encoding distinct shRNAs targeting VEGF. qPCR was used to determine the level of mRNA knockdown.

A set of 6 shRNAs with 19 bp complementary regions were designed to disrupt the expression of human VEGF (SEQ ID NO:194), and cloned into the pEQU6 screening vector (SEQ ID NO:41) behind the U6 promoter as described above. As shown in FIG. 7, several shRNA constructs possessed a high degree of knockdown efficiency against VEGF gene expression, when assessed by qPCR. ARI-189 (SEQ ID NO:204), ARI-190 (SEQ ID NO:205), and ARI-191 (SEQ ID NO:206) all showed approximately equal to, or greater than, 70% knockdown of VEGF gene expression by qPCR. In addition, ARI-193 (SEQ ID NO:208) showed greater than 80% knockdown of VEGF gene expression. Western blot analysis was used to confirm the gene disruption findings identified by qPCR, with ARI-189 (SEQ ID NO:204), ARI-190 (SEQ ID NO:205), ARI-191 (SEQ ID NO:206), ARI-193 (SEQ ID NO:208) all showing very faint VEGF Western blot bands as individual lanes on a gel when compared to a positive control, a VEGF lane that lacked a cognate shRNA to VEGF in the transfection reaction. Therefore, the findings from the Western blot analysis confirmed the findings from the qPCR reaction.

Figure 8B:
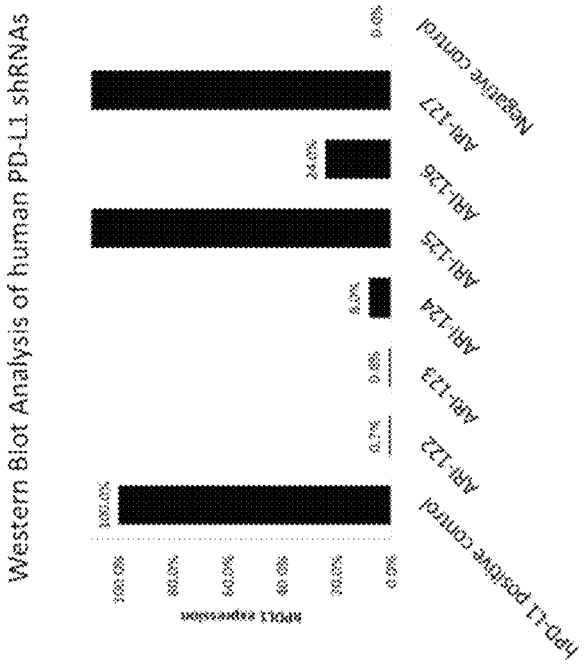
FIGS. 8A and 8B depict the results of human VISTA shRNA screening using qPCR and Western blot. HEK 293 cells were co-transfected with a VISTA cDNA expression plasmid and various pEQU6 plasmids encoding distinct shRNAs targeting VISTA.
Figure 8A:
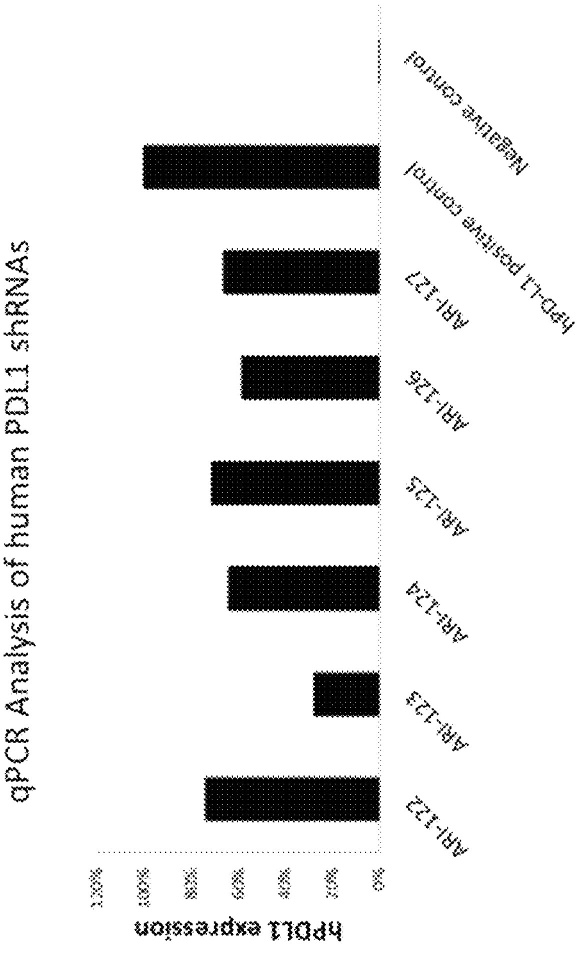

Using the human VISTA gene as a reference (SEQ ID NO:35), a set of six shRNAs were designed and cloned into the pEQU6 screening vector (SEQ ID NO:41) behind the U6 promoter as described above. Each shRNA construct was screened for disruption of VISTA gene expression in a qPCR knockdown experiment. As shown in FIG. 8A, several shRNAs were effective at knocking down human VISTA gene expression. ARI-195 (SEQ ID NO:25) and ARI-196 (SEQ ID NO:26) were the most potent shRNAs, with approximately 80% and 65% knockdown of human VISTA gene expression, respectively. These results were confirmed by Western blot analysis, which demonstrated nearly complete knockdown (approximately 99%) for ARI-195 and ARI-196 (FIG. 8B).

Combination RNAi

Figure 9B:
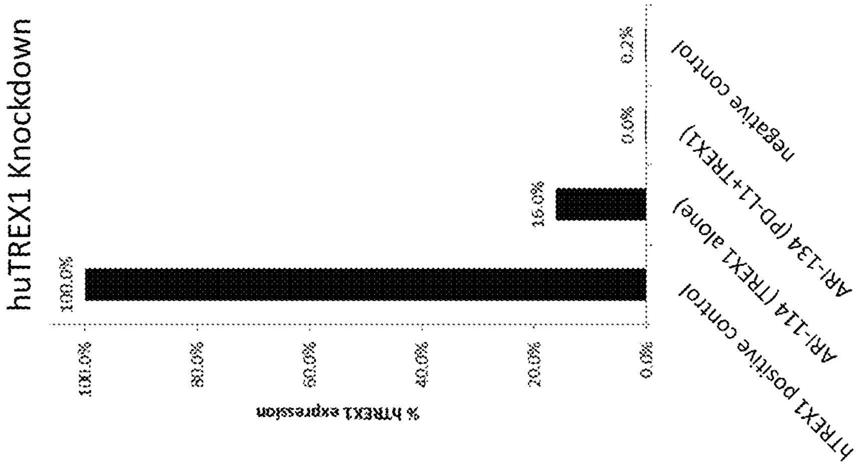
FIGS. 9A and 9B depict the results of qPCR assessment of combination gene knockdown with HuPD-L1+HuTREX1 RNAi's. HEK 293 cells were co-transfected with a TREX1 cDNA expression plasmid, a PD-L1 cDNA expression plasmid, and pEQU6-H1 plasmid encoding ARI-134 shRNAs targeting PD-L1 and TREX1, or pEQU6 plasmid encoding ARI-123 shRNA targeting PD-L1 alone, or pEQU6 plasmid encoding ARI-114 shRNA targeting TREX1.
Figure 9A:
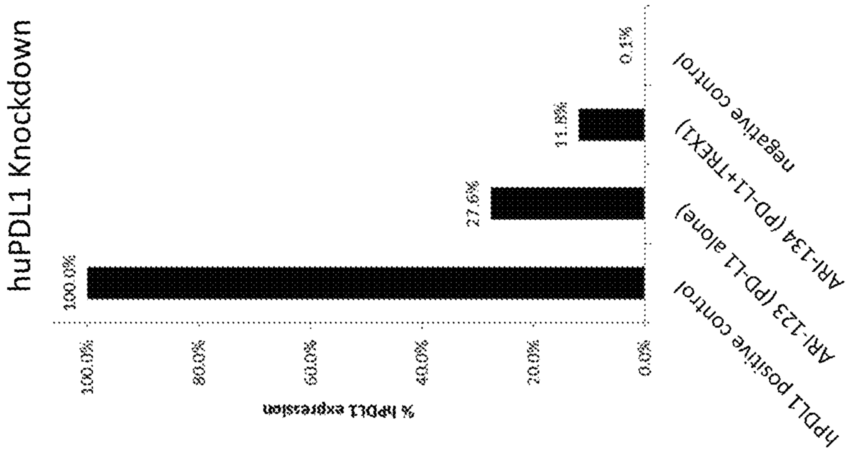

Combined RNAi knockdown of two separate gene targets by separate shRNAs expressed from the same plasmid was tested using an engineered plasmid carrying both a U6 and H1 promoter (SEQ ID NO:42). Individual shRNAs each targeting PD-L1 (ARI-123, SEQ ID NO:2) and TREX1 (ARI-114, SEQ ID NO:24) were subcloned to generate the combination RNAi ARI-134 (SEQ ID NO:210). ARI-134 then was tested for the ability to simultaneously express two separate shRNAs in situ, that can each individually knockdown expression of their respective targets (PD-L1 and TREX1). As a control, knockdown of human PD-L1 expression in HEK293 cells by ARI-134 was compared to ARI-123 (the single RNAi targeting solely PD-L1 (SEQ ID NO:2)), and knockdown of human TREX1 in HEK 293 cells by ARI-134 was compared to ARI-114 (a single RNAi solely targeting TREX1 (SEQ ID NO:24)). Whereas the ARI-123 knockdown had 27.6% of wild type human PD-L1 gene expression, knockdown of human PD-L1 by ARI-134 (the combination vector) was improved with 11.8% of wild type human PD-L1 gene expression (FIG. 9A). Likewise, whereas human TREX1 knockdown with ARI-114 had 16% of wild type TREX1 expression, the knockdown of human TREX1 with ARI-134 was 100% (FIG. 9B). When knockdown against PD-L1 and TREX1 by ARI-134 was analyzed by Western blot, there was no detectable expression of either human PD-L1 or human TREX1 versus their respective positive controls (individual human PD-L1 and human TREX1 expression reactions lacking any RNAi). Therefore, the combination RNAi ARI-134 is able to knockdown expression of PD-L1 and TREX1.

Figure 10B:
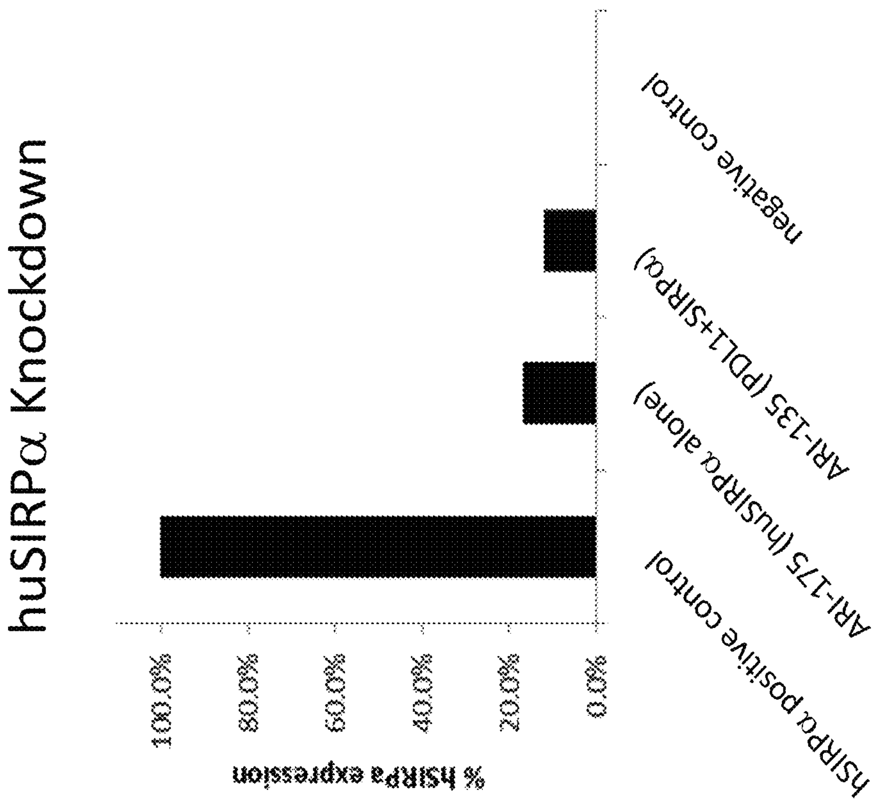
FIGS. 10A and 10B depict the results of qPCR assessment of combination gene knockdown with HuPD-L1+HuSIRP-alpha RNAi's. HEK 293 cells were co-transfected with a PD-L1 cDNA expression plasmid, a SIRP-alpha cDNA expression plasmid, and pEQU6-H1 plasmid encoding ARI-135 containing shRNAs targeting PD-L1 and SIRP-alpha, or pEQU6 plasmid encoding ARI-123 shRNA targeting PD-L1 alone, or pEQU6 plasmid encoding ARI-175 shRNA targeting SIRPalpha.
Figure 10A:
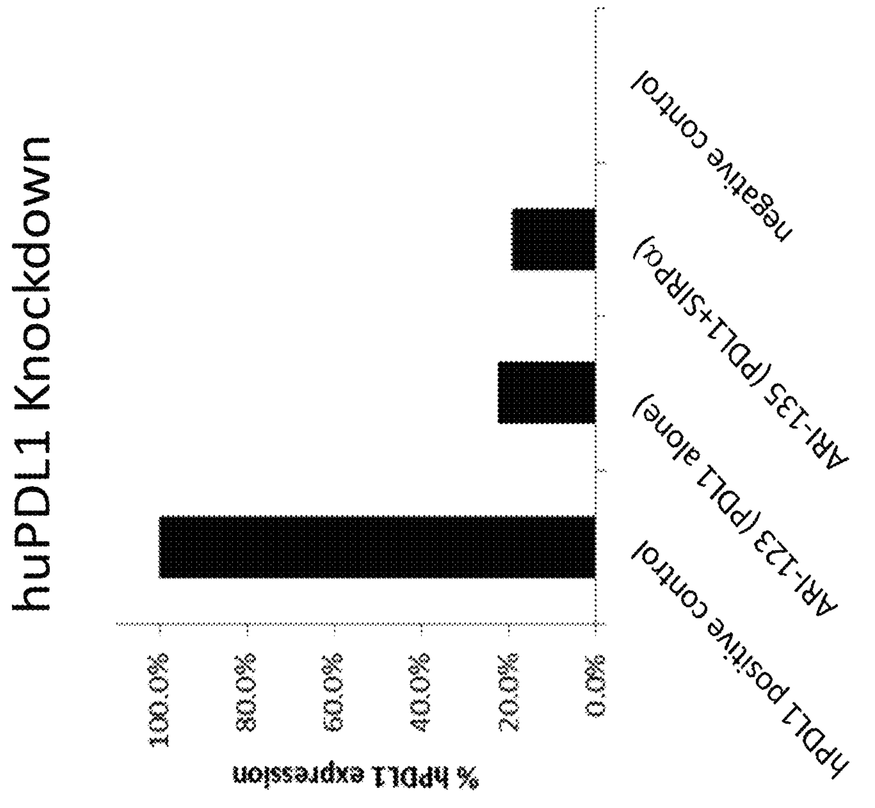

Similarly, the individual RNAis, each targeting PD-L1 (ARI-123, SEQ ID NO:2) and SIRP-alpha (ARI-175, SEQ ID NO:14) described above, were subcloned into an engineered plasmid carrying both a U6 and H1 promoter (SEQ ID NO:42) to generate the combination RNAi, ARI-135 (SEQ ID NO:211). ARI-135 was tested for the ability to simultaneously express two separate shRNAs in situ that can each individually knockdown expression of PD-L1 and SIRP-alpha. As a control, knockdown of human PD-L1 expression in HEK293 cells by ARI-135 was compared to ARI-123 (a single RNAi solely targeting PD-L1 alone (SEQ ID NO:2), described above). Likewise, knockdown of human SIRP-alpha in HEK 293 cells by ARI-135 was compared to ARI-175 (a single RNAi targeting SIRP-alpha alone (SEQ ID NO:14), described above). Knockdown of PD-L1 by both ARI-123 and ARI-135 resulted in approximately 20% of wild type human PD-L1 gene expression (FIG. 10A). Likewise, knockdown of SIRP-alpha with both ARI-175 and ARI-135 resulted in <20% wild type SIRP-alpha expression (FIG. 10B). When knockdown against both PD-L1 and SIRP-alpha by ARI-135 was analyzed by Western blot, there was no detectable expression of either human PD-L1 or human SIRP-alpha versus their respective positive controls (human PD-L1 and human SIRP-alpha expression reactions lacking any RNAi). Therefore, the combination RNAi ARI-135 is able to knockdown expression of PD-L1 and SIRP-alpha.

Figure 11B:
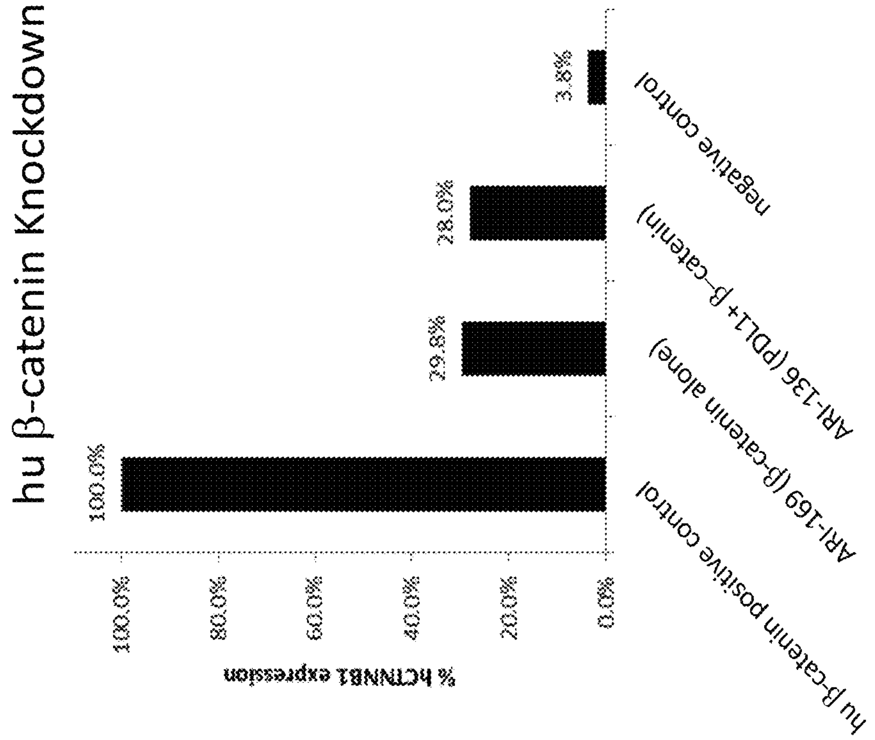
FIGS. 11A and 11B depict the results of qPCR assessment of combination gene knockdown with HuPD-L1+Hu beta-catenin RNAi's. HEK 293 cells were co-transfected with a PD-L1 cDNA expression plasmid, a beta-catenin cDNA expression plasmid, and pEQU6-H1 plasmid encoding ARI-136 containing shRNAs targeting PD-L1 and beta-catenin, or pEQU6 plasmid encoding ARI-123 shRNA targeting PD-L1 alone, or pEQU6 plasmid encoding ARI-169 shRNA targeting beta-catenin.
Figure 11A:
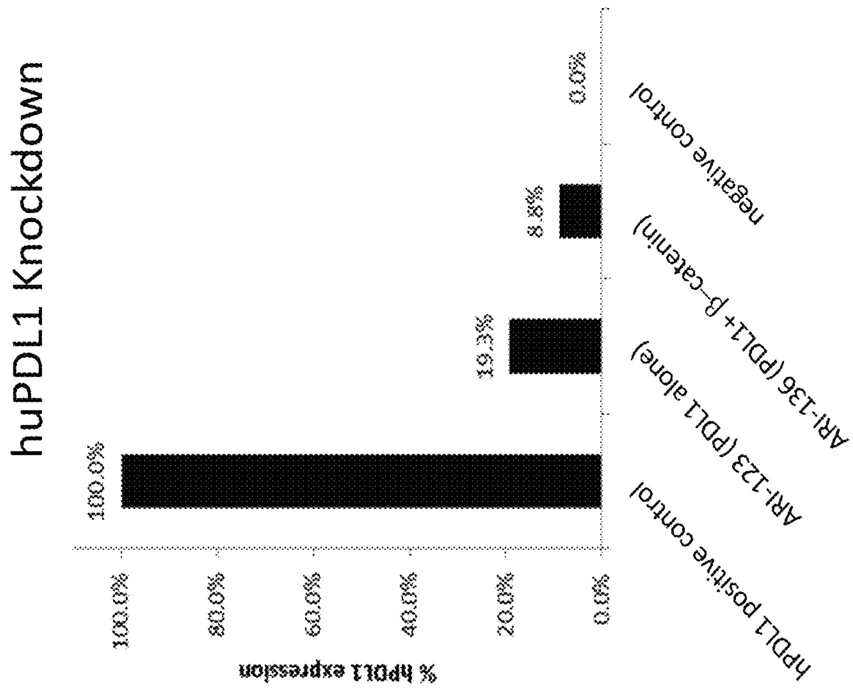

Next, the individual RNAi's, each targeting PD-L1 (ARI-123, SEQ ID NO:2) and beta-catenin (ARI-169, SEQ ID NO:8) described above, were subcloned into the engineered combination RNAi plasmid carrying the U6 and H1 promoter (SEQ ID NO:42) to generate the combination RNAi ARI-136 (SEQ ID NO:212). ARI-136 then was tested for the ability to simultaneously express two separate RNAi's in situ that can each individually knockdown expression of PD-L1 and beta-catenin. As a control, knockdown of human PD-L1 expression in HEK293 cells by ARI-136 was compared to ARI-123 (the single RNAi targeting PD-L1 alone (SEQ ID NO:2), described above). Likewise, knockdown of human beta-catenin in HEK 293 cells by ARI-136 was compared to ARI-169 (the single RNAi targeting beta-catenin alone (SEQ ID NO:8), described above). Knockdown of PD-L1 by ARI-123 resulted in approximately 20% of wild type human PD-L1 gene expression (FIG. 11A). Knockdown of PD-L1 by ARI-136 resulted in approximately 10% of wild type human PD-L1 gene expression, which is approximately two-fold better than ARI-123 (FIG. 11A). Knockdown of beta-catenin with ARI-136 and ARI-169 resulted in approximately 30% of wild type beta-catenin expression (FIG. 11B). When knockdown against PD-L1 and beta-catenin by ARI-136 was analyzed by Western blot, there was no detectable expression of either human PD-L1 or human beta-catenin versus their respective positive controls (human PD-L1 and human beta-catenin expression reactions lacking any RNAi). Therefore, the combination RNAi ARI-136 is able to knockdown expression of PD-L1 and beta-catenin.

Figure 12A:
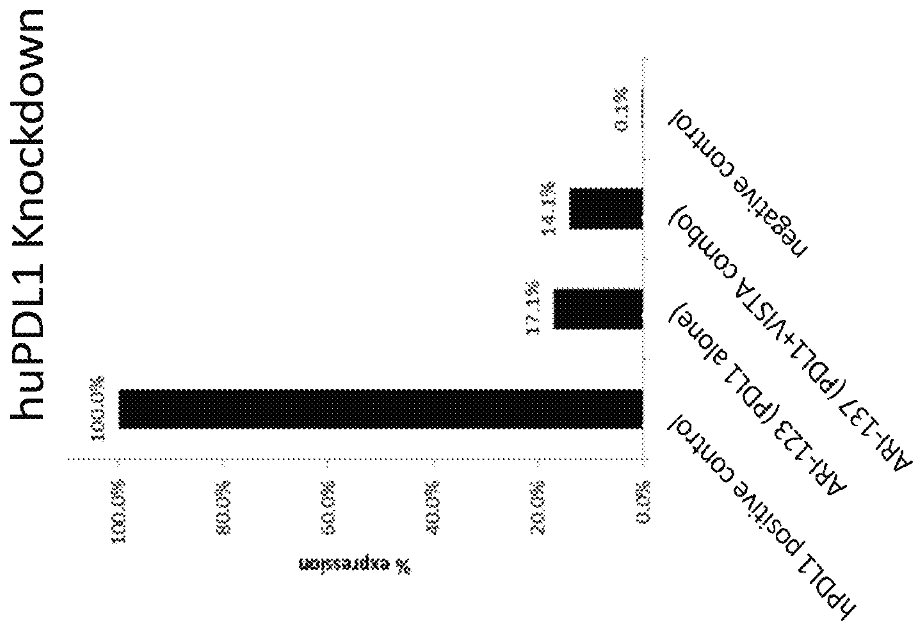
FIGS. 12A and 12B depict the results of qPCR assessment of combination gene knockdown with HuPD-L1+HuVISTA RNAi's. HEK 293 cells were co-transfected with a PD-L1 cDNA expression plasmid, a VISTA cDNA expression plasmid, and pEQU6-H1 plasmid encoding ARI-137 (SEQ ID NO:213) containing shRNAs targeting PD-L1 and VISTA, or pEQU6 plasmid encoding ARI-123 (SEQ ID NO:2) shRNA targeting PD-L1 alone, or pEQU6 plasmid encoding ARI-195 (SEQ ID NO:25) shRNA targeting VISTA.
Figure 12B:
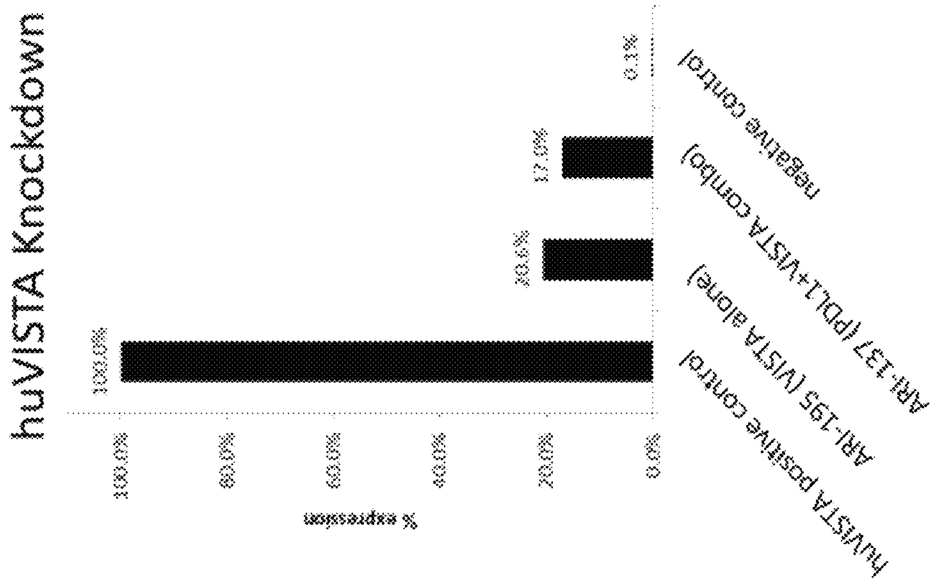

The individual RNAi's, each targeting PD-L1 (ARI-123, SEQ ID NO:2) and VISTA (ARI-195, SEQ ID NO:25) described above, were subcloned into an engineered plasmid carrying both a U6 and H1 promoter (SEQ ID NO:42) to generate the combination RNAi, ARI-137 (SEQ ID NO:213). ARI-137 was tested for the ability to simultaneously express two separate shRNAs in situ that can each individually knockdown expression of PD-L1 and VISTA. As a control, knockdown of human PD-L1 expression in HEK293 cells by ARI-137 was compared to ARI-123 (a single RNAi solely targeting PD-L1 alone (SEQ ID NO:2), described above). Likewise, knockdown of human VISTA in HEK 293 cells by ARI-137 was compared to ARI-195 (a single RNAi targeting VISTA alone, described above, SEQ ID NO:25). Knockdown of PD-L1 by both ARI-123 and ARI-137 resulted in approximately 20% of wild type human PD-L1 gene expression (FIG. 12A). Likewise, knockdown of VISTA with both ARI-195 and ARI-137 resulted in less than, or approximately equal to, 20% wild type VISTA expression (FIG. 12B). When knockdown against PD-L1 and VISTA by ARI-137 was analyzed by Western blot, there was no detectable expression of either human PD-L1 or human VISTA versus their respective positive controls (human PD-L1 and human VISTA expression reactions lacking any RNAi). Therefore, the combination RNAi ARI-137 is able to knockdown expression of PD-L1 and VISTA.

Figure 13A:
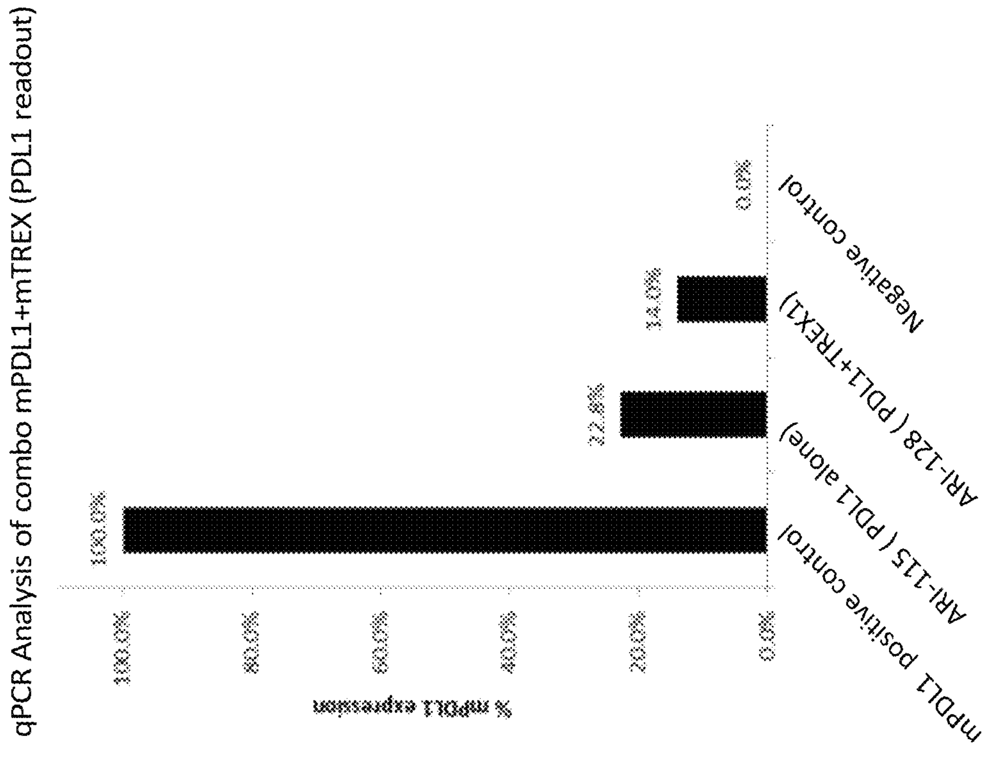
FIGS. 13A and 13B depict the results of qPCR assessment of combination gene knockdown with mouse TREX1+ mouse PD-L1 RNAi's. HEK 293 cells were co-transfected with a mouse TREX1 cDNA expression plasmid, a mouse PD-L1 cDNA expression plasmid, and pEQU6-H1 plasmid encoding containing shRNA (designated ARI-128) targeting mouse TREX1 and mouse PD-L1, or pEQU6 plasmid encoding shRNA (designated ARI-115 targeting mouse PD-L1 alone, or pEQU6 plasmid encoding shRNA (designated ARI-108) targeting mouse TREX1.
Figure 13B:
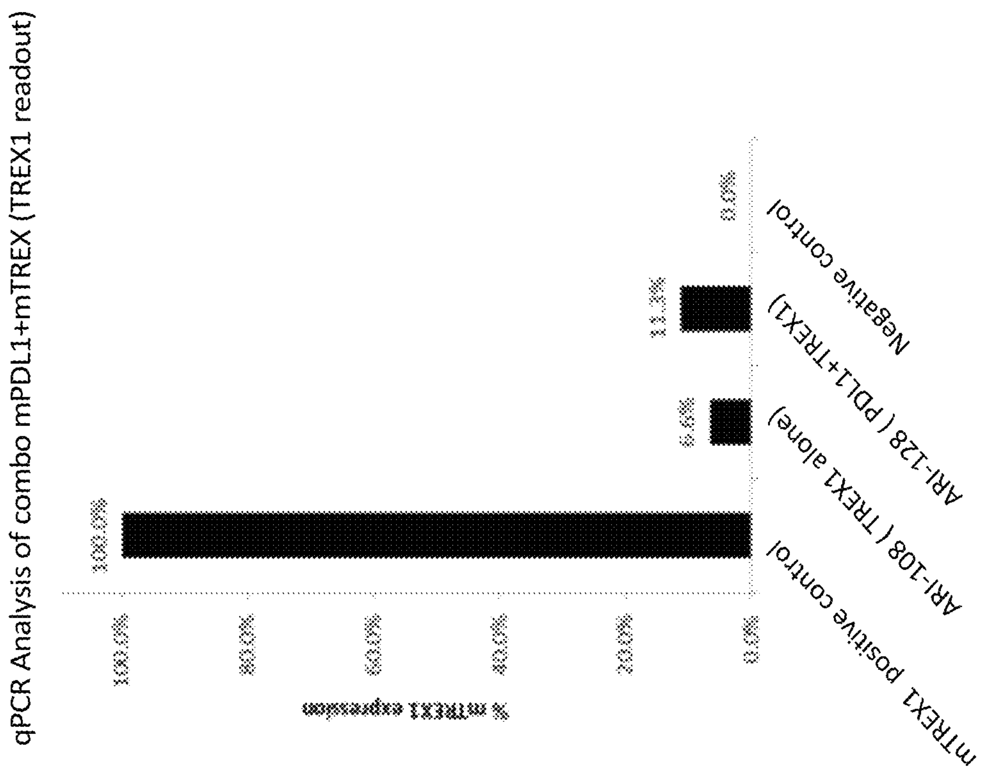

In addition to human targets, combined RNAi knockdown of two mouse gene targets by separate shRNAs expressed from the same plasmid was tested using the engineered plasmid carrying both a U6 and H1 promoter (SEQ ID NO:42). Individual shRNAs each targeting mouse PD-L1 (ARI-115, SEQ ID NO:75) and mouse TREX1 (ARI-108) were subcloned to generate the combination RNAi ARI-128. ARI-128 then was tested for the ability to simultaneously express two separate shRNAs in situ that can each individually knockdown expression of their respective targets (mouse PD-L1 and mouse TREX1). As a control, knockdown of mouse PD-L1 expression in HEK293 cells by ARI-128 was compared to ARI-115 (the single RNAi targeting solely targeting PD-L1 (SEQ ID NO:75)), and knockdown of mouse TREX1 in HEK 293 cells by ARI-128 was compared to ARI-108 (a single RNAi solely targeting TREX1). Whereas the ARI-115 knockdown had 22.8% of wild type mouse PD-L1 gene expression, knockdown of mouse PD-L1 by ARI-128 (the combination vector) was improved, allowing only 14.0% of wild type mouse TREX1 gene expression (FIG. 13A). Knockdown of mouse TREX1 with either ARI-108 or ARI-128 was very efficient (6.6% and 11.3%, respectively, of wild-type mouse TREX1 expression) (FIG. 13B). When knockdown against both mouse PD-L1 and mouse TREX1 by ARI-128 was analyzed by Western blot, there was no detectable expression of either mouse PD-L1 or mouse TREX1 versus their respective positive controls (individual mouse PD-L1 and mouse TREX1 expression reactions lacking any RNAi).

Figure 14B:
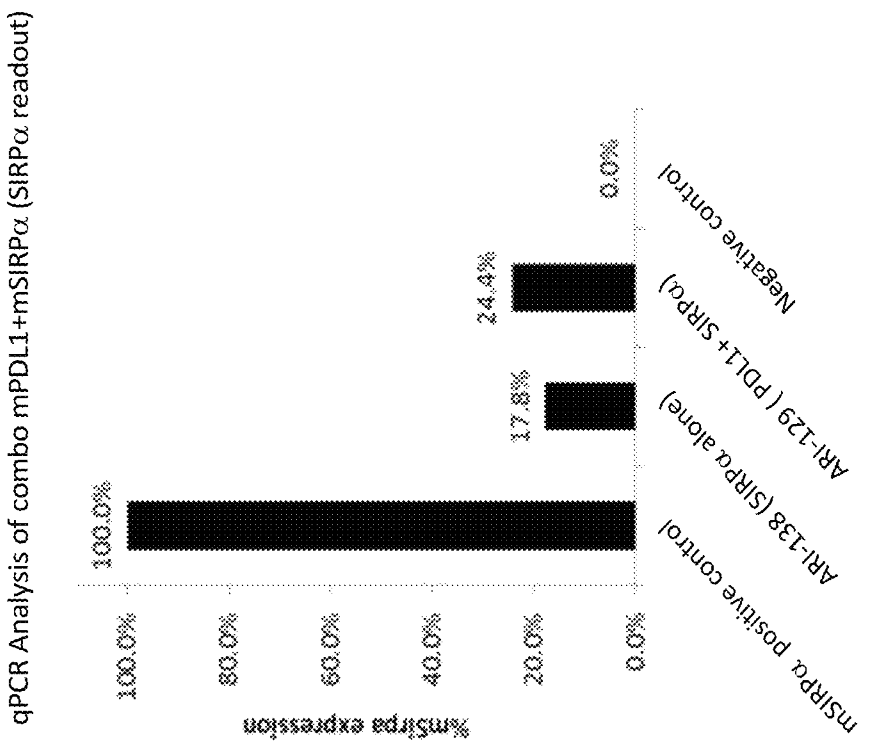
FIGS. 14A and 14B depict the results of qPCR assessment of combination gene knockdown with mouse PD-L1+mouse SIRP-alpha RNAi's. HEK 293 cells were co-transfected with a mouse PD-L1 cDNA expression plasmid, a mouse SIRP-alpha cDNA expression plasmid, and pEQU6-H1 plasmid encoding shRNA (designated ARI-129) targeting mouse PD-L1 and SIRP-alpha, or pEQU6 plasmid encoding shRNA (designated ARI-115) targeting PD-L1 alone, or pEQU6 plasmid encoding shRNA (designated ARI-138) targeting SIRP-alpha.
Figure 14A:
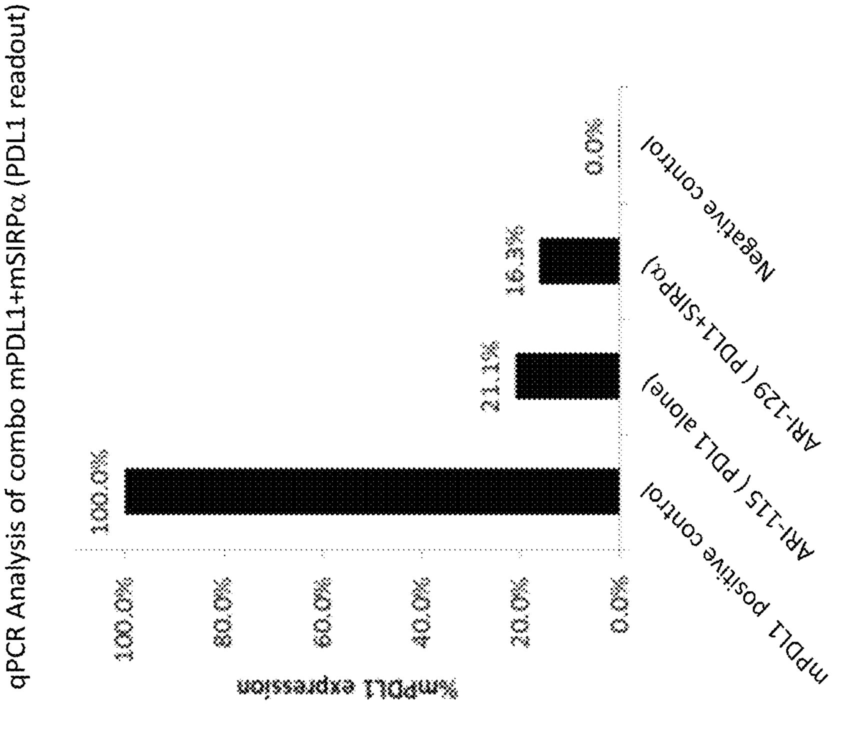

A combination RNAi was generated for targeting mouse PD-L1 and mouse SIRP-alpha using the engineered plasmid carrying both a U6 and H1 promoter (SEQ ID NO:42). Individual shRNAs each targeting mouse PD-L1 (ARI-115, SEQ ID NO:75) and mouse SIRP-alpha (ARI-138, SEQ ID NO:76) were subcloned to generate the combination RNAi ARI-129. ARI-129 then was tested for the ability to simultaneously express two separate shRNAs in situ that can each individually knockdown expression of their respective targets (mouse PD-L1 and mouse SIRP-alpha). As a control, knockdown of mouse PD-L1 expression in HEK293 cells by ARI-129 was compared to ARI-115 (the single RNAi targeting solely targeting PD-L1), and knockdown of mouse SIRP-alpha in HEK 293 cells by ARI-129 was compared to ARI-138 (a single RNAi solely targeting SIRP-alpha). ARI-115 and ARI-129 had knockdown of approximately 20% or less of wild type mouse PD-L1 gene expression (FIG. 14A). Knockdown of mouse SIRP-alpha with either ARI-138 or ARI-129 was approximately 25% or less of wild-type mouse SIRP-alpha expression (FIG. 14B). When knockdown against both mouse PD-L1 and mouse SIRP-alpha by ARI-129 was analyzed by Western blot, there was no detectable expression of either mouse PD-L1 or mouse SIRP-alpha versus their respective positive controls (individual mouse PD-L1 and mouse SIRP-alpha expression reactions lacking any RNAi).

Figure 15B:
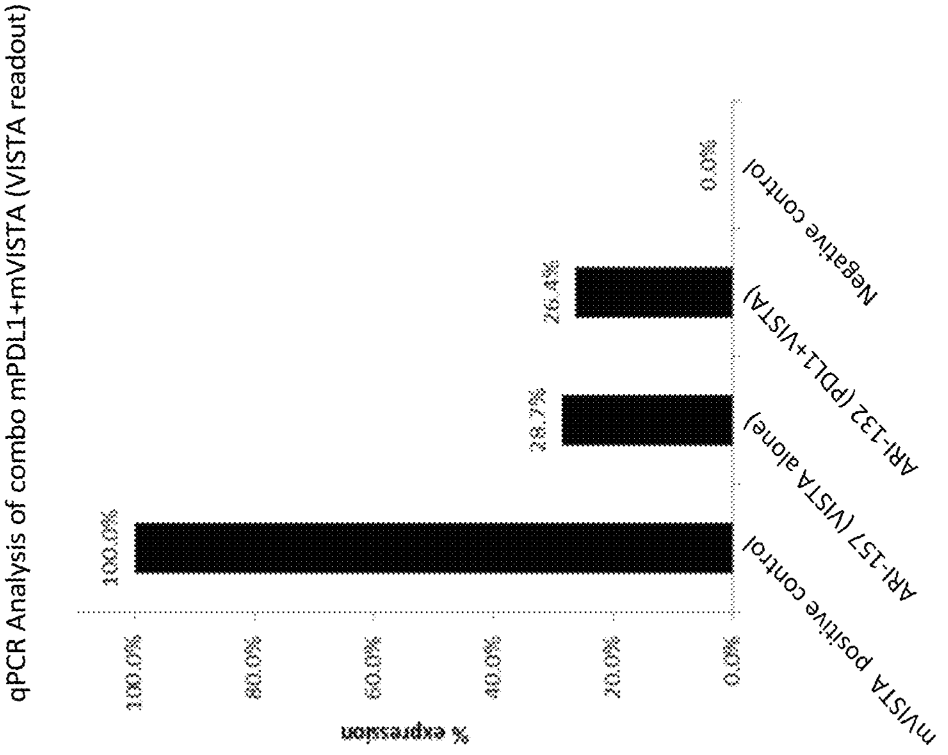
FIGS. 15A and 15B depict the results of qPCR assessment of combination gene knockdown with mouse PD-L1+mouse VISTA RNAi's. HEK 293 cells were co-transfected with a mouse PD-L1 cDNA expression plasmid, a mouse VISTA cDNA expression plasmid, and pEQU6-H1 plasmid encoding containing shRNA (designated ARI-132) targeting PD-L1 and VISTA, or pEQU6 plasmid encoding shRNA (designated ARI-115) targeting PD-L1 alone, or pEQU6 plasmid encoding shRNA (designated ARI-157) targeting VISTA.
Figure 15A:
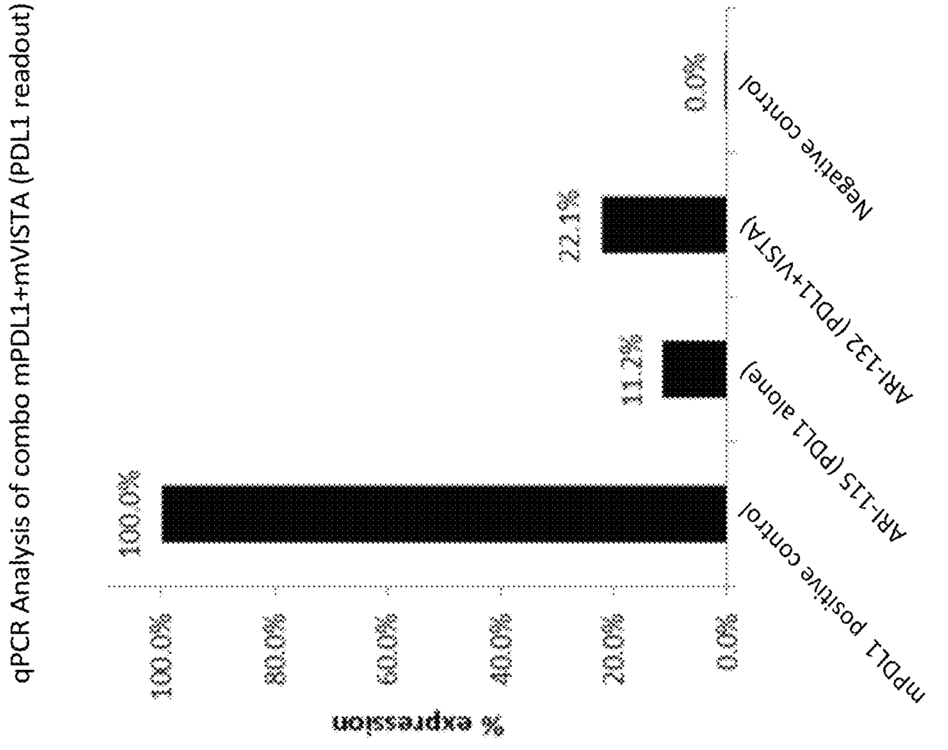

Next, a combination RNAi was generated for targeting mouse PD-L1 and mouse VISTA using the engineered plasmid carrying both a U6 and H1 promoter (SEQ ID NO:42). Individual shRNAs each targeting mouse PD-L1 (ARI-115, SEQ ID NO:75) and mouse VISTA (ARI-157) were subcloned to generate the combination RNAi ARI-132. ARI-132 then was tested for the ability to simultaneously express two separate shRNAs in situ that can each individually knockdown expression of their respective targets (mouse PD-L1 and mouse VISTA). As a control, knockdown of mouse PD-L1 expression in HEK293 cells by ARI-132 was compared to ARI-115 (the single RNAi targeting solely targeting PD-L1), and knockdown of mouse VISTA in HEK 293 cells by ARI-132 was compared to ARI-157 (a single RNAi solely targeting VISTA). Both ARI-115 and ARI-132 had knockdown of approximately 20% or less of wild type mouse PD-L1 gene expression (FIG. 15A). Knockdown of mouse VISTA with either ARI-157 or ARI-132 was approximately 30% or less of wild-type mouse VISTA expression (FIG. 15B). When knockdown against both mouse PD-L1 and mouse VISTA by ARI-132 was analyzed by Western blot, there was no detectable expression of either mouse PD-L1 or mouse VISTA versus their respective positive controls (individual mouse PD-L1 and mouse VISTA expression reactions lacking any RNAi).

Figure 16B:
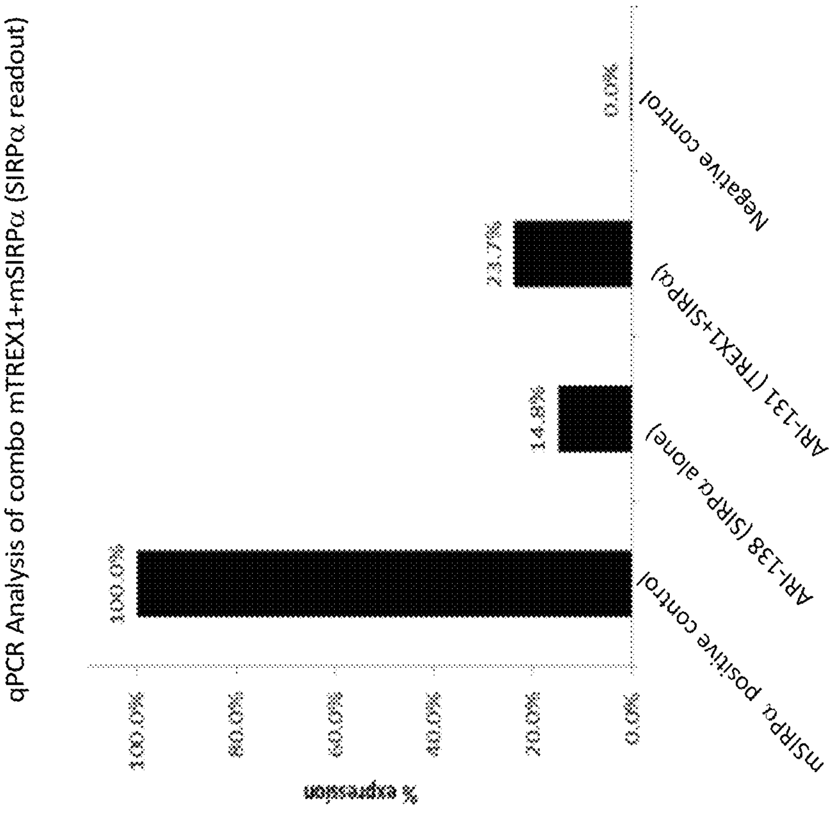
FIGS. 16A and 16B depict the results of qPCR assessment of combination gene knockdown with mouse TREX1+ mouse SIRP-alpha RNAi's. HEK 293 cells were co-transfected with a mouse TREX1 cDNA expression plasmid, a mouse VISTA cDNA expression plasmid, and pEQU6-H1 plasmid encoding containing shRNA (designated ARI-131) targeting PD-L1 and VISTA, or pEQU6 plasmid encoding shRNA (designated ARI-108) targeting TREX1 alone, or pEQU6 plasmid encoding shRNA (designated ARI-138) targeting SIRP-alpha.
Figure 16A:
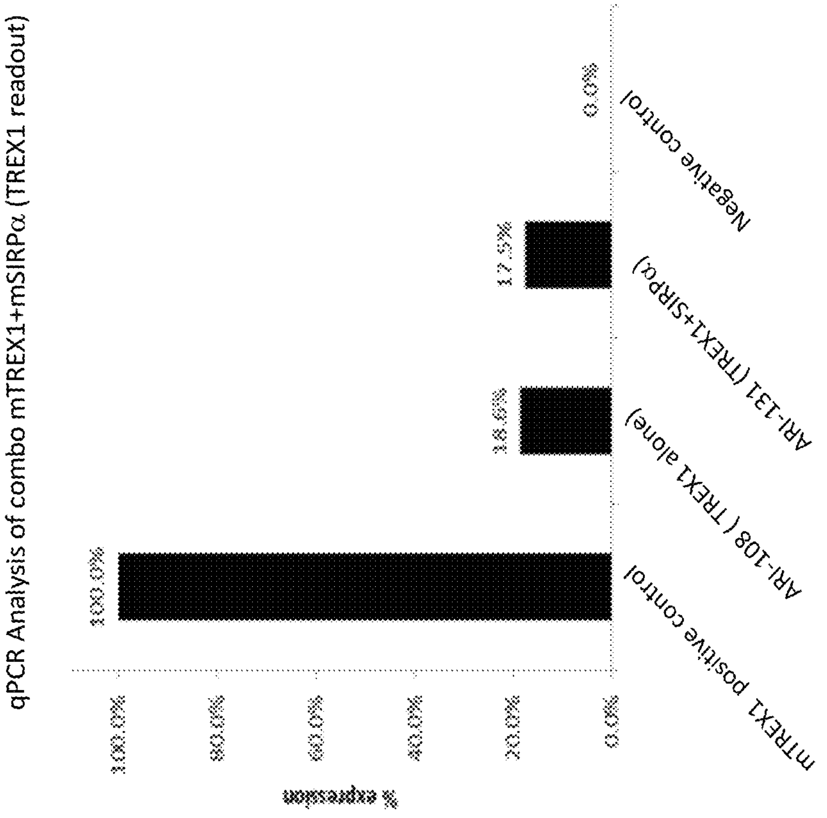

A combination of RNAi was generated for targeting mouse TREX1 and mouse SIRP-alpha using the engineered plasmid carrying a U6 and H1 promoter (SEQ ID NO:42). Individual shRNAs, one targeting mouse TREX1 (ARI-108) and the other targeting mouse SIRP-alpha (ARI-138, SEQ ID NO:76), were subcloned to generate the combination RNAi designated ARI-131. ARI-131 was tested for the ability to simultaneously express two separate shRNAs in situ that can each individually knockdown expression of the respective targets (mouse TREX1 and mouse SIRP-alpha). As a control, knockdown of mouse TREX1 expression in HEK293 cells by ARI-131 was compared to ARI-108 (the single RNAi targeting solely targeting TREX1), and knockdown of mouse SIRP-alpha in HEK 293 cells by ARI-131 was compared to ARI-138 (a single RNAi solely targeting SIRP-alpha). ARI-108 and ARI-131 had knockdown of approximately 20% or less of wild type mouse TREX1 gene expression (FIG. 16A). Knockdown of mouse SIRP-alpha with either ARI-138 or ARI-131 was approximately 25% or less than wild-type mouse SIRP-alpha expression (FIG. 16B).

Figure 17A:
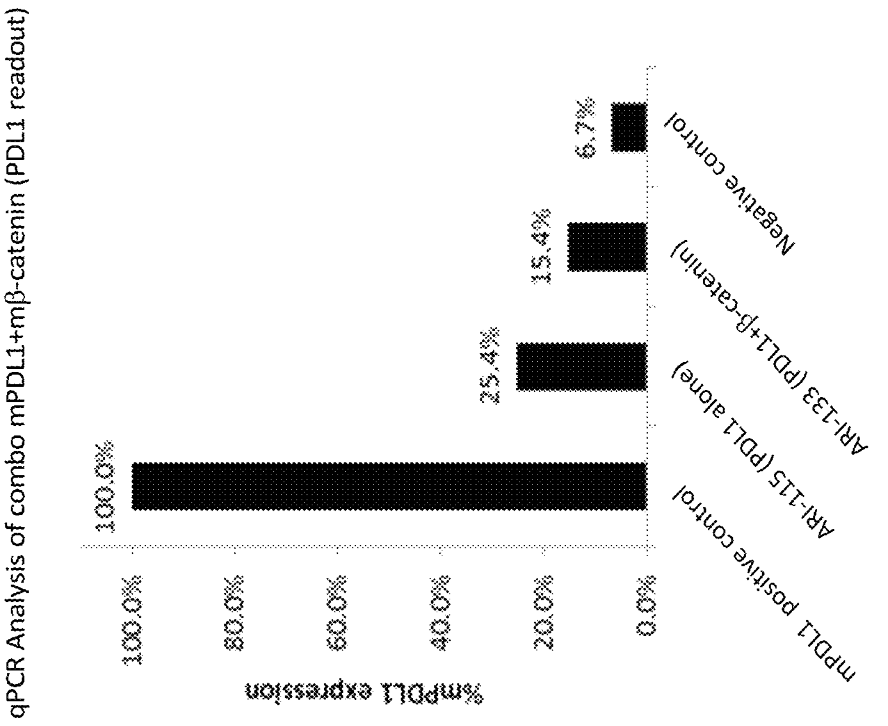
FIGS. 17A and 17B depict the results of qPCR assessment of combination gene knockdown with mouse PD-L1+mouse beta-catenin RNAi's. HEK 293 cells were co-transfected with a mouse PD-L1 cDNA expression plasmid, a mouse beta-catenin cDNA expression plasmid, and pEQU6-H1 plasmid encoding containing shRNA (designated ARI-133) targeting PD-L1 and VISTA, or pEQU6 plasmid encoding shRNA (designated ARI-115) targeting PD-L1 alone, or pEQU6 plasmid encoding shRNA (designated ARI-166) targeting beta catenin.
Figure 17B:
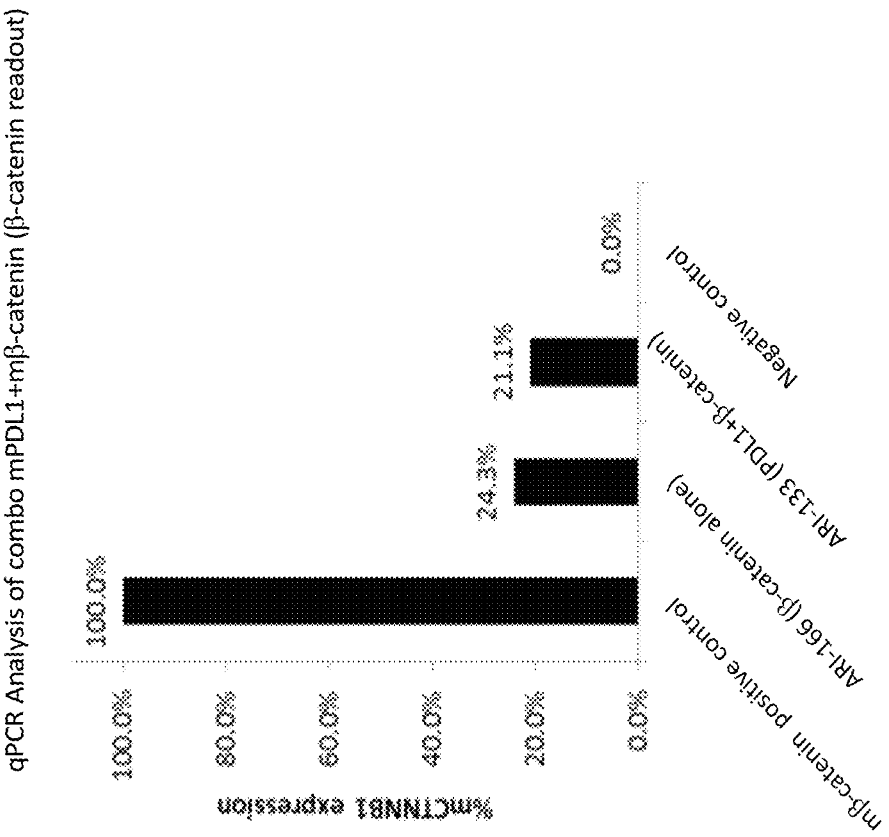

A combination RNAi was generated that targets mouse PD-L1 and mouse beta-catenin using the engineered plasmid carrying a U6 and H1 promoter (SEQ ID NO:42). Individual shRNAs each targeting mouse PD-L1 (ARI-115, SEQ ID NO:75) and mouse beta-catenin (ARI-166) were subcloned to generate the combination RNAi ARI-133. ARI-133 then was tested for the ability to simultaneously express two separate shRNAs in situ that can each individually knockdown expression of their respective targets (mouse PD-L1 and mouse beta-catenin). As a control, knockdown of mouse PD-L1 expression in HEK293 cells by ARI-133 was compared to ARI-115 (the single RNAi targeting solely targeting PD-L1), and knockdown of mouse beta-catenin in HEK 293 cells by ARI-133 was compared to ARI-166 (a single RNAi solely targeting beta-catenin). ARI-115 and ARI-133 had knockdown of approximately 25% or less of wild type mouse PD-L1 gene expression (FIG. 17A). Knockdown of mouse beta-catenin with either ARI-166 or ARI-133 was approximately 25% or less of wild-type mouse beta-catenin expression (FIG. 17B). When knockdown against mouse PD-L1 and mouse beta-catenin by ARI-133 was analyzed by Western blot, there was no detectable expression of either mouse PD-L1 or mouse beta-catenin versus their respective positive controls (individual mouse PD-L1 and mouse beta-catenin expression reactions lacking any RNAi).

Figure 18B:
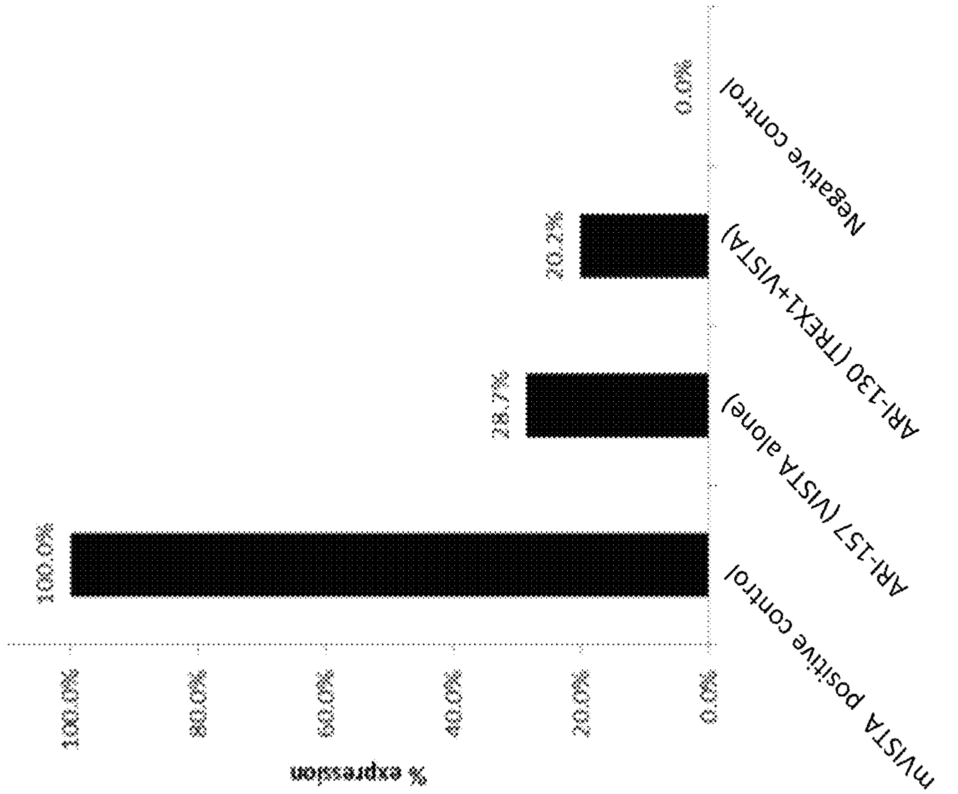
FIGS. 18A and 18B depict the results of qPCR assessment of combination gene knockdown with mouse TREX1+ mouse VISTA RNAi's. HEK 293 cells were co-transfected with a mouse TREX1 cDNA expression plasmid, a mouse VISTA cDNA expression plasmid, and pEQU6-H1 plasmid encoding shRNA (designated ARI-130) targeting PD-L1 and VISTA, or pEQU6 plasmid encoding shRNA (designated ARI-108) targeting TREX1 alone, or pEQU6 plasmid encoding shRNA (designated ARI-157) targeting VISTA.
Figure 18A:
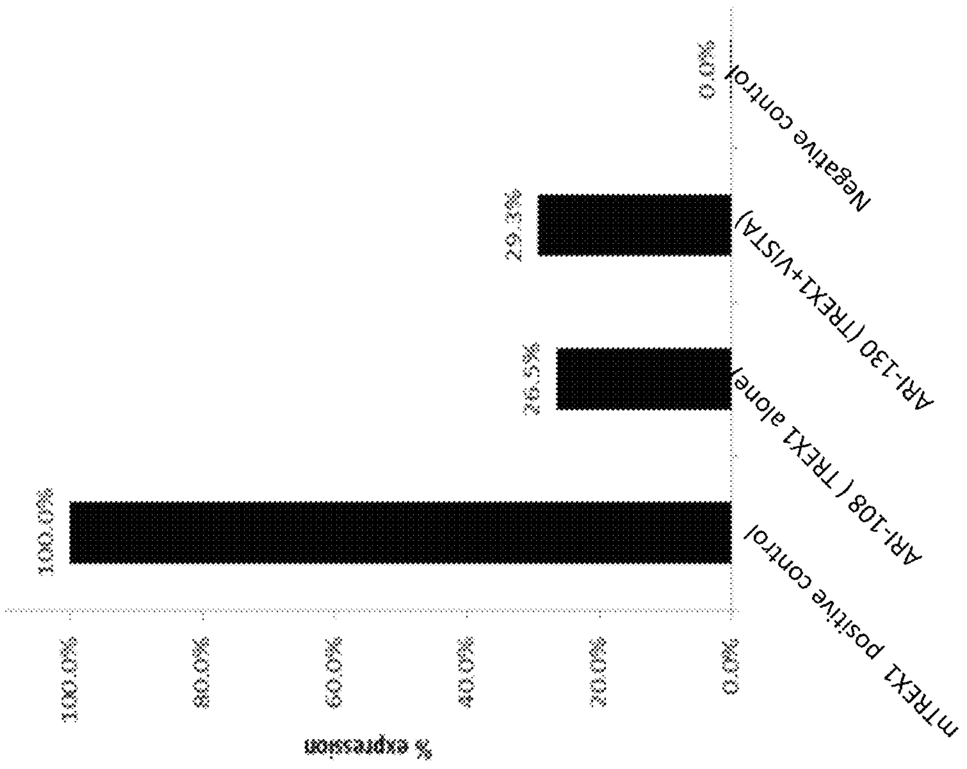

Next, a combination RNAi was generated for targeting mouse TREX1 and mouse VISTA using the engineered plasmid carrying both a U6 and H1 promoter (SEQ ID NO:42). Individual shRNAs each targeting mouse TREX1 (ARI-108) and mouse VISTA (ARI-157) were subcloned to generate the combination RNAi ARI-130. ARI-130 then was tested for the ability to simultaneously express two separate shRNAs in situ that can each individually knockdown expression of their respective targets (mouse TREX1 and mouse VISTA). As a control, knockdown of mouse TREX1 expression in HEK293 cells by ARI-130 was compared to ARI-108 (a RNAi targeting solely targeting TREX1), and knockdown of mouse VISTA in HEK 293 cells by ARI-130 was compared to ARI-157 (a single RNAi solely targeting VISTA). Both ARI-108 and ARI-130 had knockdown of approximately 30% or less of wild type mouse TREX1 gene expression (FIG. 18A). Knockdown of mouse VISTA with either ARI-157 or ARI-130 was approximately 30% or less of wild-type mouse VISTA expression (FIG. 18B). When knockdown against both mouse TREX1 and mouse VISTA by ARI-130 was analyzed by Western blot, there was no detectable expression of either mouse TREX1 or mouse VISTA versus their respective positive controls (individual mouse TREX1 and mouse VISTA expression reactions lacking any RNAi).

Micro RNA (mi-RNA)

Figure 19B:
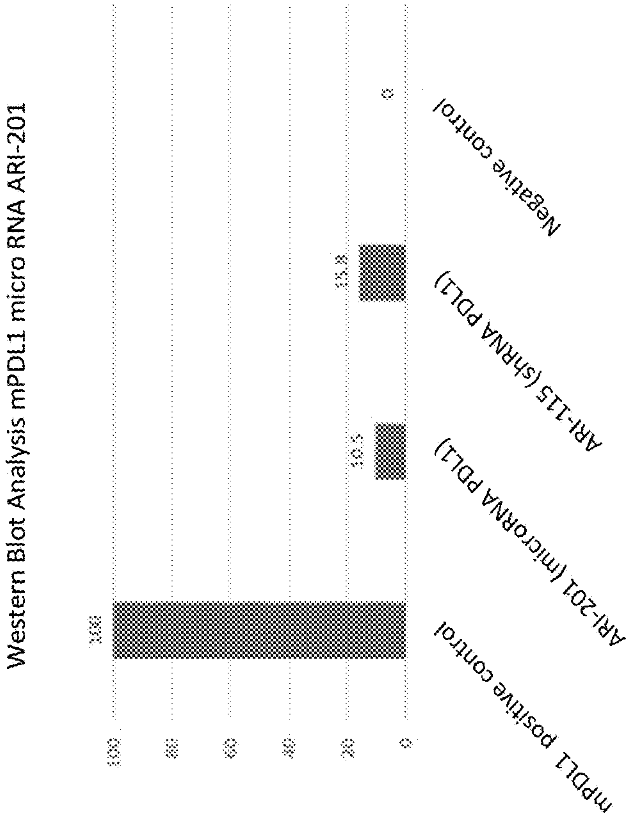
FIGS. 19A and 19B depict a comparison of micro-RNA and shRNA-mediated knockdown of mouse PD-L1. HEK 293 cells were co-transfected with a mouse PD-L1 cDNA expression plasmid and either pEQU6 plasmids encoding micro-RNA (ARI-201) or shRNA (designated AR-115) targeting PD-L1.
Figure 19A:
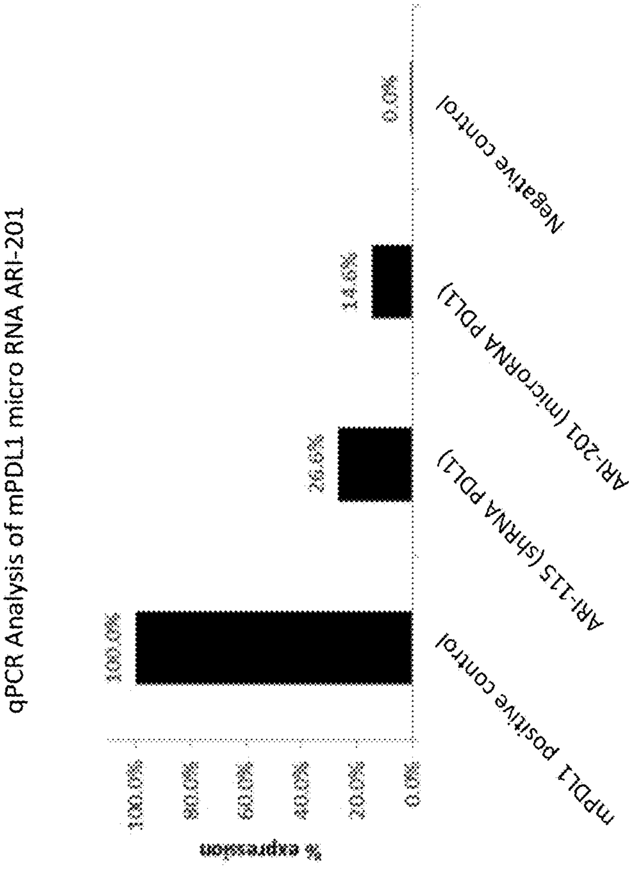

A microRNA construct, ARI-205 (SEQ ID NO:214), was used to generate a mouse PD-L1 targeting microRNA, ARI-201, by inserting RNAi targeting mouse PD-L1 into the microRNA backbone of SEQ ID NO:249, and compared to the PD-L1 targeting shRNA construct ARI-115 (SEQ ID NO:75) by qPCR and Western blot analysis, as described above. Whereas ARI-115 knockdown was 26.6% of wild-type PD-L1 expression, knockdown by ARI-201 was improved, with 14.6% of PD-L1 expression (FIG. 19A). By Western blot, ARI-115 was able to knockdown PD-L1 to 15.8% of wild type PD-L1 expression, and knockdown by ARI-201 was improved, with 10.5% of PD-L1 expression (FIG. 19B).

Figure 20:
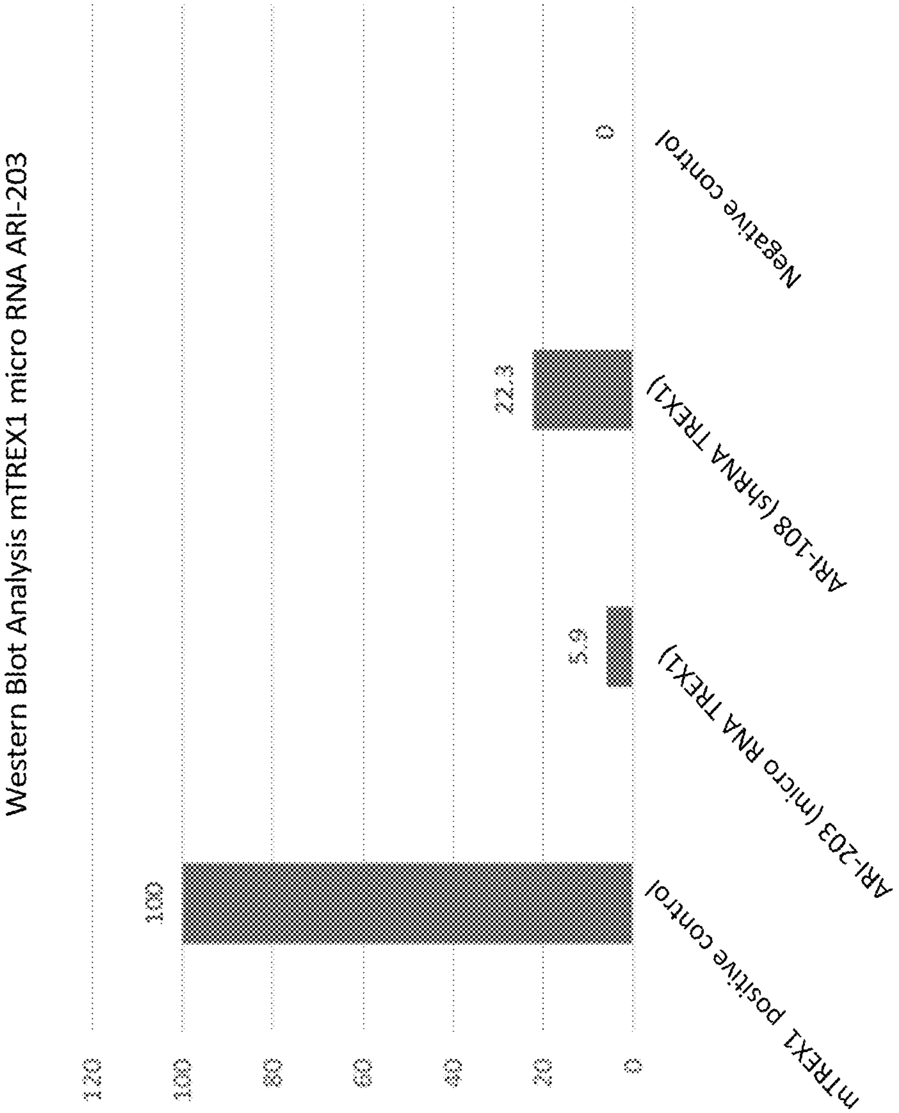
FIG. 20 depicts a comparison of micro-RNA and shRNA-mediated knockdown of mouse TREX1. HEK 293 cells were co-transfected with a mouse TREX1 cDNA expression plasmid and pEQU6 plasmids encoding micro-RNA (designated ARI-203) or shRNA (designated ARI-108) targeting TREX1. Western blot was used to determine the level of mRNA knockdown.

A microRNA was generated against mouse TREX1, ARI-203, based on the microRNA construct described above, ARI-205 (SEQ ID NO:214), using oligonucleotide synthesis, overlapping PCR and restriction digest cloning, and tested by qPCR. Whereas ARI-108, a shRNA that targets mouse TREX1, had a gene knockdown efficiency of 22.3% versus wild-type TREX1, ARI-203 possessed a knockdown efficiency of 5.9% (FIG. 20). Therefore, the microRNA was approximately three to four-fold improved in its knockdown efficiency of mouse TREX1, when compared to the shRNA.

Figure 21A:
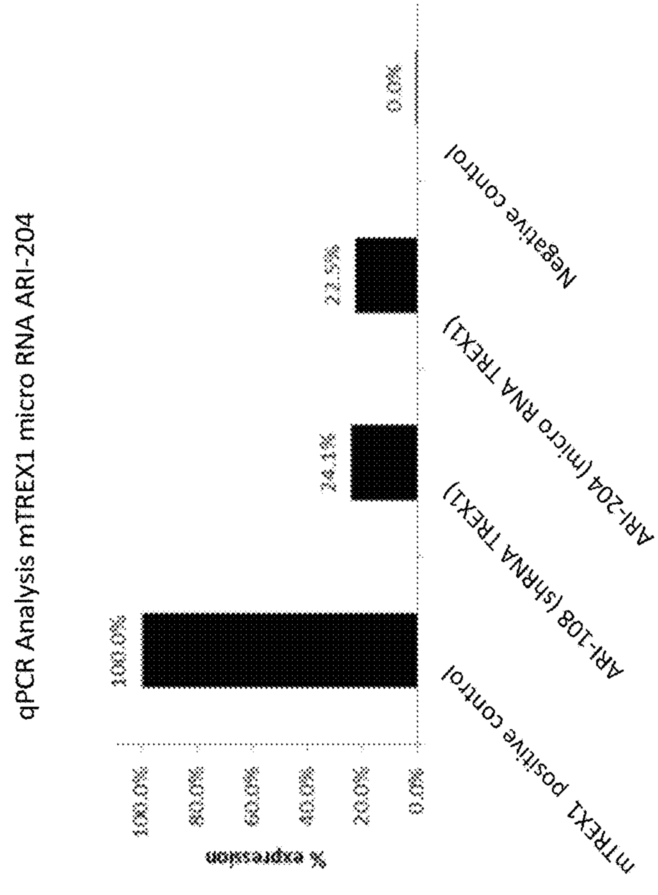
FIGS. 21A and 21B depict the results of TREX1 knockdown with RNA Pol II expression of micro-RNA. HEK 293 cells were co-transfected with a mouse TREX1 cDNA expression plasmid and pEQU6 plasmid shRNA targeting mouse TREX1 (designated ARI-108) or a pEQ plasmid encoding a CMV promoter and micro-RNA targeting mouse TREX1 (designated ARI-204).
Figure 21B:
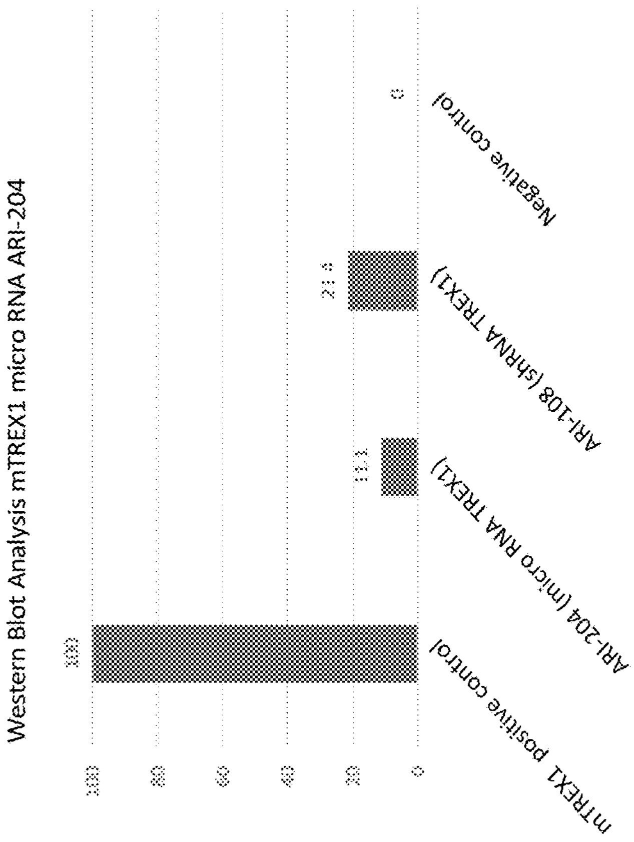

A large microRNA construct, ARI-206 (SEQ ID NO:215), requiring expression under an RNA polymerase II promoter, was constructed for testing knockdown of target genes and testing by qPCR and Western blot analysis. A mouse TREX1 targeting version of this microRNA, ARI-204, was tested against ARI-108, the mouse TREX1 targeting shRNA described above. ARI-204 and ARI-108 were able to efficiently knock down expression of mouse TREX1 (22.5% and 24.1% of wild type mouse TREX1 expression, respectively, FIG. 21A). The activity of ARI-204 mouse TREX1 targeting microRNA was slightly improved over the ARI-108 mouse TREX1 targeting shRNA, when assessed for knockdown of mouse TREX1 gene expression by Western blot (11.1% for ARI-204, versus 21.4% for ARI-108, FIG. 21B).

Figure 22B:
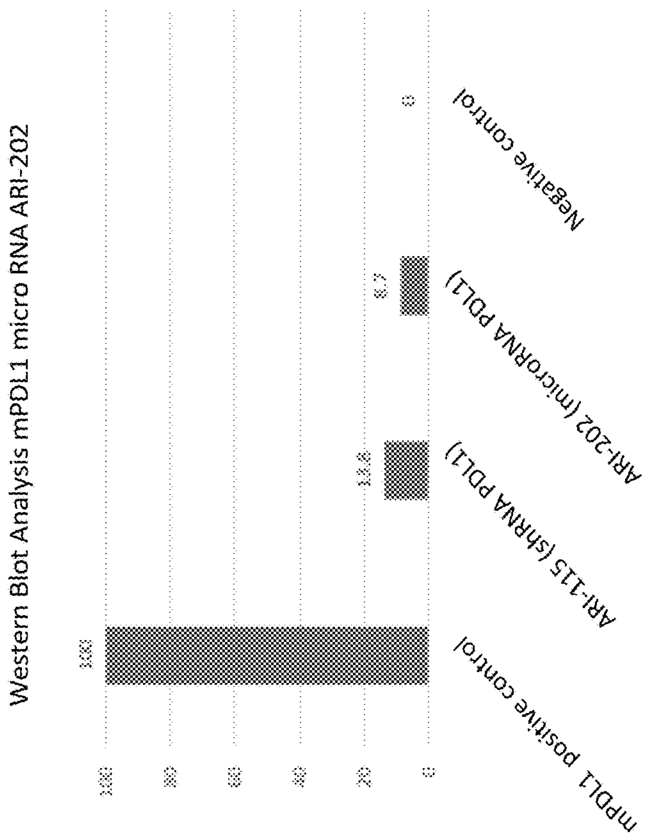
FIGS. 22A and 22B depict the results of PD-L1 knockdown with RNA Pol II expression of micro-RNA. HEK 293 cells were co-transfected with a mouse PD-L1 cDNA expression plasmid and pEQU6 plasmid shRNA targeting mouse PD-L1 (designated ARI-115) or a pEQ plasmid encoding a CMV promoter and micro-RNA targeting mouse TREX1 (designated ARI-202).
Figure 22A:
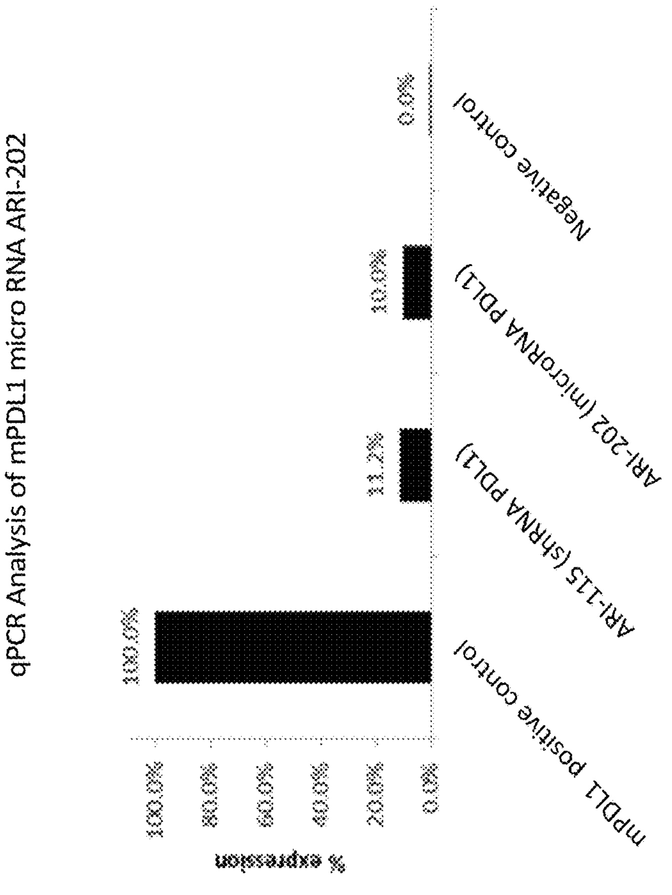

A mouse PD-L1 targeting version of microRNA construct ARI-206, ARI-202, was tested against ARI-115, the mouse PD-L1 targeting shRNA described above. ARI-202 and ARI-115 were able to efficiently knock down expression of mouse PD-L1 (10.0 and 11.2% of wild type mouse PD-L1 expression, respectively, FIG. 22A). The ARI-202 mouse PD-L1 targeting microRNA was slightly improved over the ARI-115 mouse PD-L1 targeting shRNA, when assessed for knockdown of mouse PD-L1 gene expression by Western blot (8.7% for ARI-202, versus 13.8% for ARI-115, FIG. 22B).

The shRNA gene knockdown can be directly measured in tumor cell lines that are known to overexpress the target gene. For example, the following are known tumor cell lines with high PD-L1 expression: PC-3 (prostate), MDA-MB-231 (breast), and ASPC-1 (pancreatic) (Grenga et al. (2014) *J. ImmunoTherapy of Cancer* 2(Suppl 3):P102). Cells can be stimulated with IFN-gamma to see induction of PD-L1 expression. The U937 tumor cell line overexpresses SIRP-alpha (Irandoust et al. (2013) *PLoS ONE* 8(1):e52143. Simultaneous knockdown of gene expression against PD-L1 and SIRP-alpha can be performed in U937 cells induced with IFN-gamma.

The microRNA constructs above, ARI-205 (SEQ ID NO:214) and ARI-206 (SEQ ID NO:215) encode 21 and 22 base pair homology sequences, respectively. Alternatively, microRNA constructs can be used that encode 19 base pair homology sequences, for example, ARI-207 (SEQ ID NO: 216) and ARI-208 (SEQ ID NO:217). The individual microRNAs against target genes can be generated by gene synthesis, PCR amplification with primers containing restriction sites and subcloning into the expression vector with matched restriction enzyme generated overhangs.

Example 3

Modified *Salmonella typhimurium* Targets Demonstrate Robust Tumor Growth Inhibition in Multiple Syngeneic Murine Tumor Models

TREX1

Delivery of an shRNA to TREX1, following tumor microenvironment uptake of systemically administered attenuated *Salmonella*, results in activation of STING-mediated anti-tumor immunity and tumor growth inhibition. To assess the ability of AST-104 (strain YS1646 transformed with pEQU6-shTREX1) to induce tumor growth inhibition in a murine colon carcinoma model, 6-8 week-old female BALB/c mice (8 mice per group) were inoculated subcutaneously (SC) in the right flank with CT26 murine colon carcinoma ($2\times10^5$ cells in 100 μL PBS). Mice bearing established flank tumors were intravenously (IV) injected twice, four days apart, with $1\times10^7$ CFUs of AST-104, or AST-102 (strain YS1646 transformed with pEQU6 plasmid control), and compared to PBS control. Six hours following the first IV dose, mice were bled, and plasma was collected and assessed for pro-inflammatory cytokines, using the Mouse Inflammation Cytometric Bead Array kit and analyzed by FACS (BD Biosciences).

Figure 23:
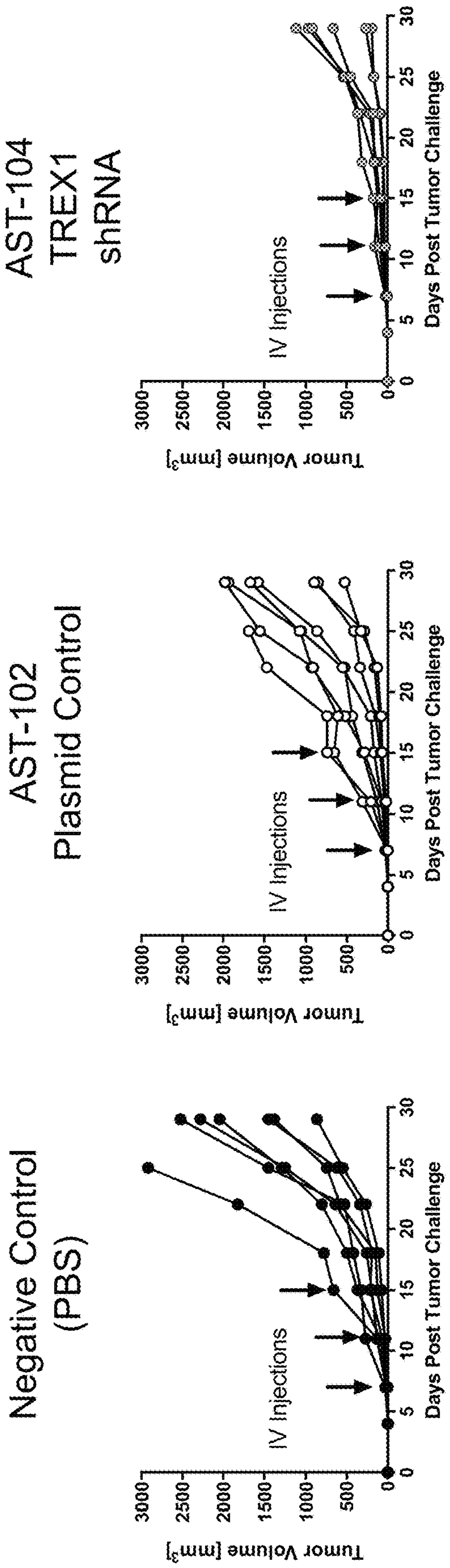
FIG. 23 depicts the efficacy of systemically administered strain AST-104 in a CT26 colon tumor model. BALB/c mice were implanted with a single CT26 ($2\times10^5$ cells) subcutaneous flank tumor (n=8 per group). Mice with established tumors were IV injected with $1\times10^7$ CFU of YS1646 strains containing either plasmid control (stain AST-102) or the Trex1 shRNA plasmid (of strain AST-104), or PBS control, on the days indicated by the arrows. Spaghetti plots depict tumor growth, each line representing an individual mouse. Tumor measurements were performed using electronic calipers (Fowler, Newton, Mass.). Tumor volume was calculated using the modified ellipsoid formula ½(length× width$^2$). Mice were euthanized when tumor size reached >20% of body weight or became necrotic, as per IACUC regulations. % Tumor Growth Inhibition (TGI) was calculated as 1-(mean test tumor volume/mean control tumor volume)×100. *$p<0.05$ vs. plasmid control, student's t-test.

As shown in FIG. 23, the control strain, AST-102 demonstrated modest tumor control, compared to PBS (18% tumor growth inhibition (TGI), p=ns at day 25). However, the shTREX1-containing strain, AST-104, demonstrated significant tumor growth inhibition compared to PBS (66% TGI, p=0.01 at day 25, calculated over the average of 8 animals per group), and significant tumor control compared to AST-102 (p=0.02 at day 28). The percent tumor growth inhibition (TGI) is calculated as 1-(mean test tumor volume/mean control tumor volume)×100.

Activation of Pro-Inflammatory Cytokines

TREX1

Figures 24A, 24B:
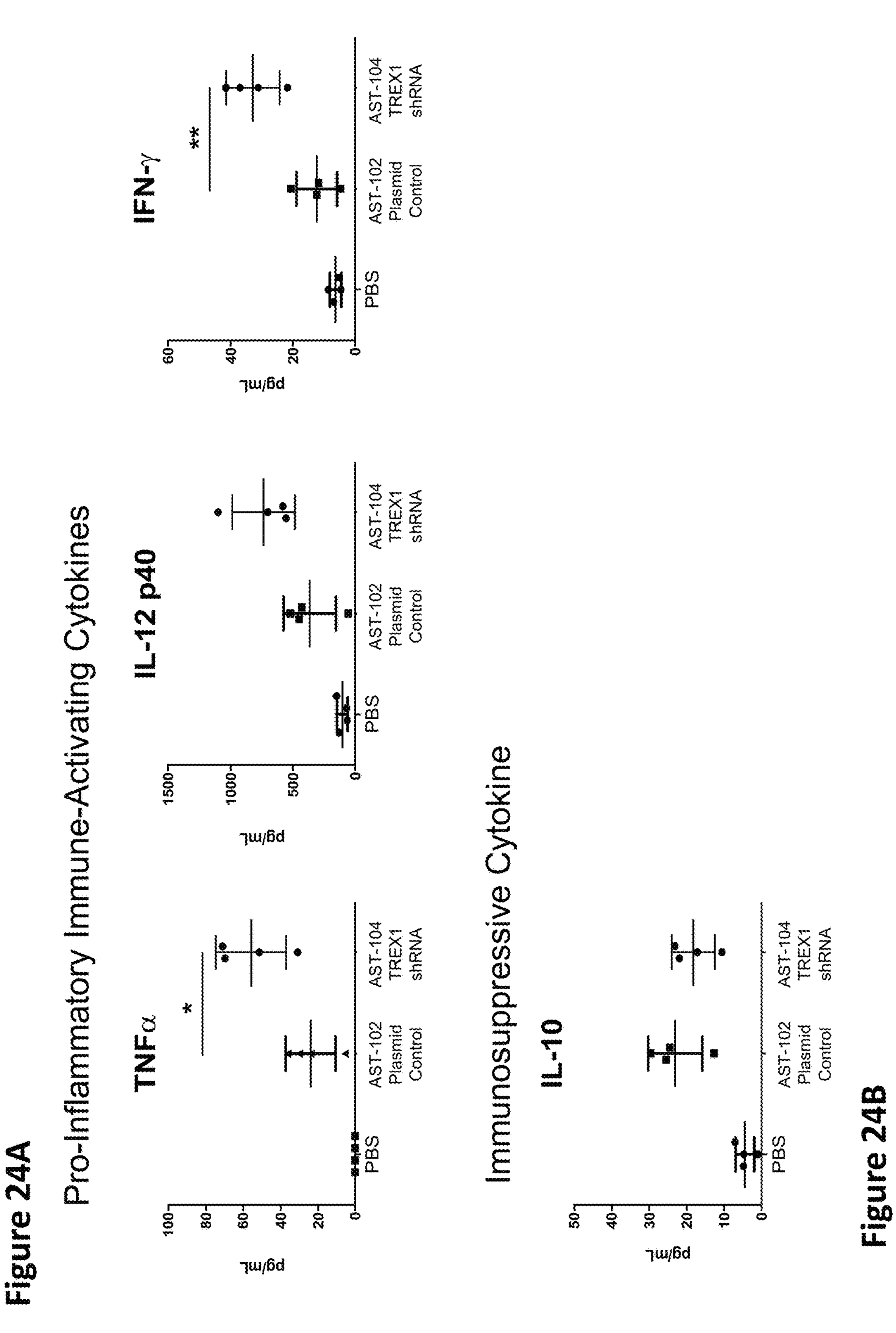
FIGS. 24A and 24B depict the correlation of strain AST-104 mediated cytokine changes with STING signature. BALB/c were implanted with a single CT26 ($2\times10^5$ cells) subcutaneous flank tumor (n=8 per group). Mice with established tumors were IV injected with $5\times10^6$ CFU of YS1646 strains containing either plasmid control (strain AST-102) or the TREX1 shRNA plasmid (AST-104), or PBS control. Mice were bled 6 hrs following the first dose and systemic serum cytokines tested on a Luminex 200 device (Luminex Corporation) and mouse cytometric bead array (BD bead array, FACS Fortessa, FCAP software, BD Biosciences).

The level of systemic serum cytokines at 6 hours post IV injection were assessed. The immune-activating cytokines TNF-alpha, IL-12, and interferon-gamma, elicited by AST-104 (containing an shTREX1 plasmid that includes the asd complementation in the plasmid; asd contains CpG elements) were significantly higher, compared to the AST-102 plasmid control (also containing CpG from the asd) and PBS groups (FIG. 24A). IL-10, a cytokine known to suppress immunity (see, e.g., Wang et al. (2012) *Scand J Immunol.* 3:273-281), trended lower in the shTREX1 group compared to the plasmid control (FIG. 24B). These data demonstrate that inhibiting TREX1 activates known STING pathway-induced cytokines that promote anti-tumor immunity and potent tumor growth inhibition in a murine model of colon carcinoma.

To assess the ability of AST-104 (containing an shTREX1 plasmid with CpG elements) to induce tumor growth inhibition in a separate aggressive murine colon carcinoma model, as well as a checkpoint therapy-resistant melanoma model, 6-8 week-old female C57BL/6 mice (10 mice per group) were inoculated SC in the right flank with MC38 colon carcinoma cells or B16.F10 melanoma cells (5 and $2\times10^5$ cells, respectively, in 100 μL PBS). Mice bearing established flank tumors were IV injected twice, four days apart, with $5\times10^6$ CFUs of AST-104, or AST-102, and compared to PBS control.

Figure 25:
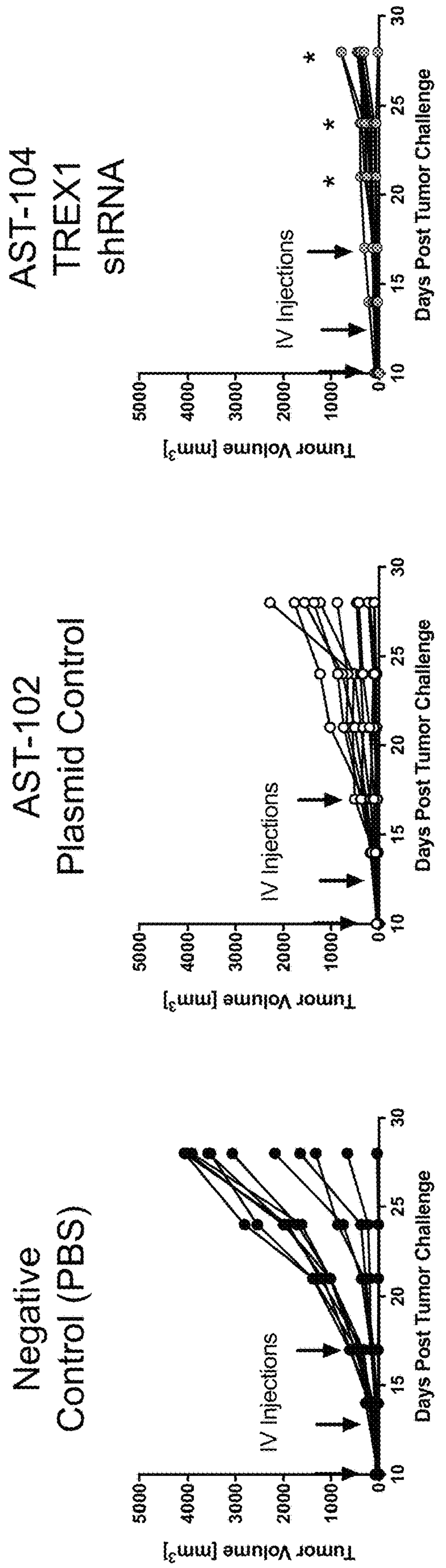
FIG. 25 depicts the efficacy of systemically administered strain AST-104 in a MC38 colon tumor model. C57B1/6 mice (6-8 wk old) were implanted with a single MC38 ($2\times10^5$ cells) subcutaneous flank tumor (n=10 per group). Mice with established tumors were IV injected with $5\times10^6$ CFU of YS1646 strains containing either plasmid control (strain AST-102) or the TREX1 shRNA plasmid (strain AST-104), or PBS control, on the days indicated by the arrows. Spaghetti plots depict tumor growth, each line representing an individual mouse. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1-(mean test tumor volume/mean control tumor volume)× 100. *$p<0.05$ vs. plasmid control, student's t-test.
Figure 26:
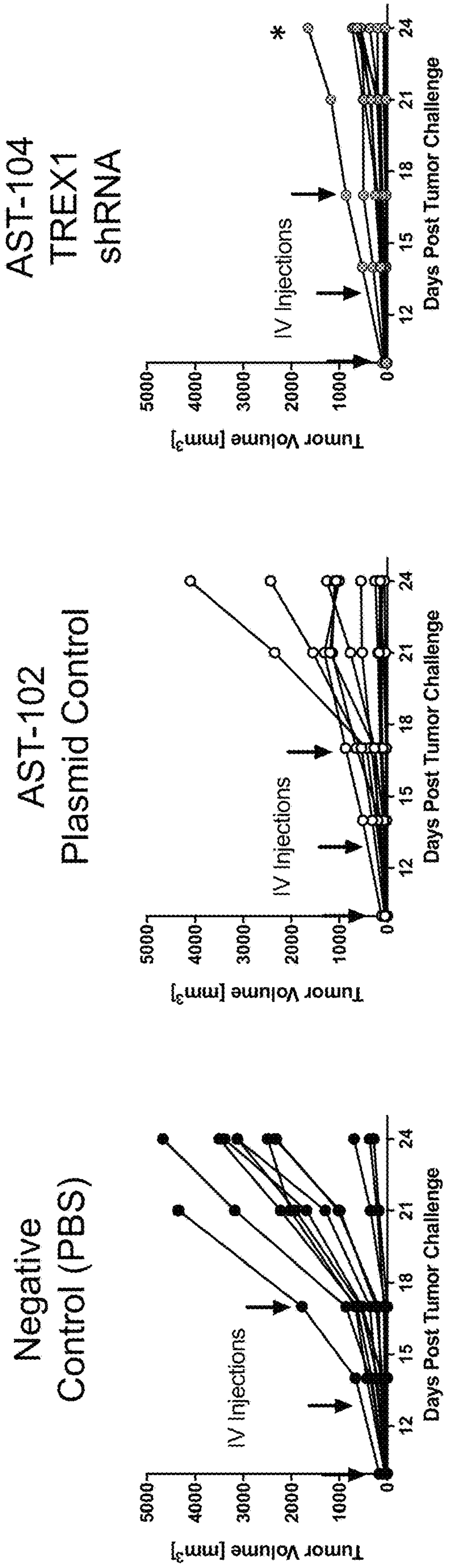
FIG. 26 depicts the efficacy of AST-104 in a checkpoint-resistant B16.F10 melanoma model. C57B1/6 mice (6-8 wk old) were implanted with a single B16.F10 ($5\times10^5$ cells) subcutaneous flank tumor (n=10 per group). Mice with established tumors were IV injected with $5\times10^6$ CFU of YS1646 strains containing either plasmid control (AST-102) or the TREX1 shRNA plasmid (AST-104), or PBS control, on the days indicated by the arrows. Spaghetti plots depict tumor growth, each line representing an individual mouse. Tumor measurements were performed using electronic calipers (Fowler, Newton, Mass.). Tumor volume was calculated using the modified ellipsoid formula ½(length× width$^2$). Mice were euthanized when tumor size reached >20% of body weight or became necrotic, as per IACUC regulations. TGI was calculated as 1-(mean test tumor volume/mean control tumor volume)×100. * $p<0.05$ vs. plasmid control, student's t-test.

As shown in FIG. 25, strain AST-104, containing shRNA to TREX1, induced potent tumor growth inhibition of MC38 tumors (85% TGI, p<0.0001, day 28), and significant tumor growth inhibition compared to the plasmid control (p=0.049, day 28). Similarly, as shown in FIG. 26, AST-104 induced highly significant tumor growth inhibition in B16.F10 melanoma compared to PBS (83% TGI, p=0.0012, day 24), and greater tumor growth inhibition compared to plasmid control strain AST-102, which had significant efficacy in this model compared to PBS (p=0.019, day 24). These results also show that plasmids containing CpG elements, in combination with shTREX1-mediated STING activation demonstrate synergy and efficacy, and have the benefit of systemic, instead of intratumoral, administration.

In summary, in multiple aggressive murine tumor models, the addition of a plasmid encoding shRNA against TREX1 in the YS1646 strain significantly enhanced anti-tumor responses compared to the YS1646 strain containing a control plasmid. These data demonstrate the potency of activating the STING pathway through systemic administration of an immunostimulatory tumor-targeting bacteria.

PD-L1

The immune system has evolved several checks and balances to limit autoimmunity. Programmed cell death protein 1 (PD-1) and programmed death-ligand 1 (PD-L1) are two examples of numerous inhibitory "immune checkpoints," which function by downregulating immune responses. The binding of PD-L1 to PD-1 interferes with $CD8^+$ T cell signaling pathways, impairing the proliferation and effector function of $CD8^+$ T cells, and inducing T cell tolerance (Topalian et al. (2012) *N Engl J Med* 366:3443-3447).

Tumor colonization of a modified *Salmonella typhimurium* strain delivering shRNA to knockdown the PD-L1 gene disrupts its binding to PD-1, and its inhibition of $CD8^+$ T cell function. PD-L1/PD-1 checkpoint inhibition synergizes well with the immunostimulatory *S. typhimurium* containing CpG plasmid DNA, all in one therapeutic modality. To demonstrate the in vivo efficacy of the YS1646 strain containing a plasmid encoding shRNA to PD-L1 (AST-105), this strain, in comparison to the AST-102 strain (containing a control plasmid that also contains CpG motifs) in a murine colon carcinoma model was evaluated. For this experiment, 6-8 week-old female BALB/c mice (10 mice per group) were inoculated SC in the right flank with CT26 murine colon carcinoma ($2\times10^5$ cells in 100 μL PBS). Mice bearing established flank tumors were IV injected twice, four days apart, with $5\times10^6$ CFUs of AST-105, AST-102, or IV administration of anti-PD-L1 antibody (4 mg/kg, BioXCell clone 10F.9G2). Six hours following the first IV dose, mice were bled, and plasma was collected and assessed for pro-inflammatory cytokines using the Mouse Inflammation Cytometric Bead Array kit and analyzed by FACS (BD Biosciences).

Figure 27:
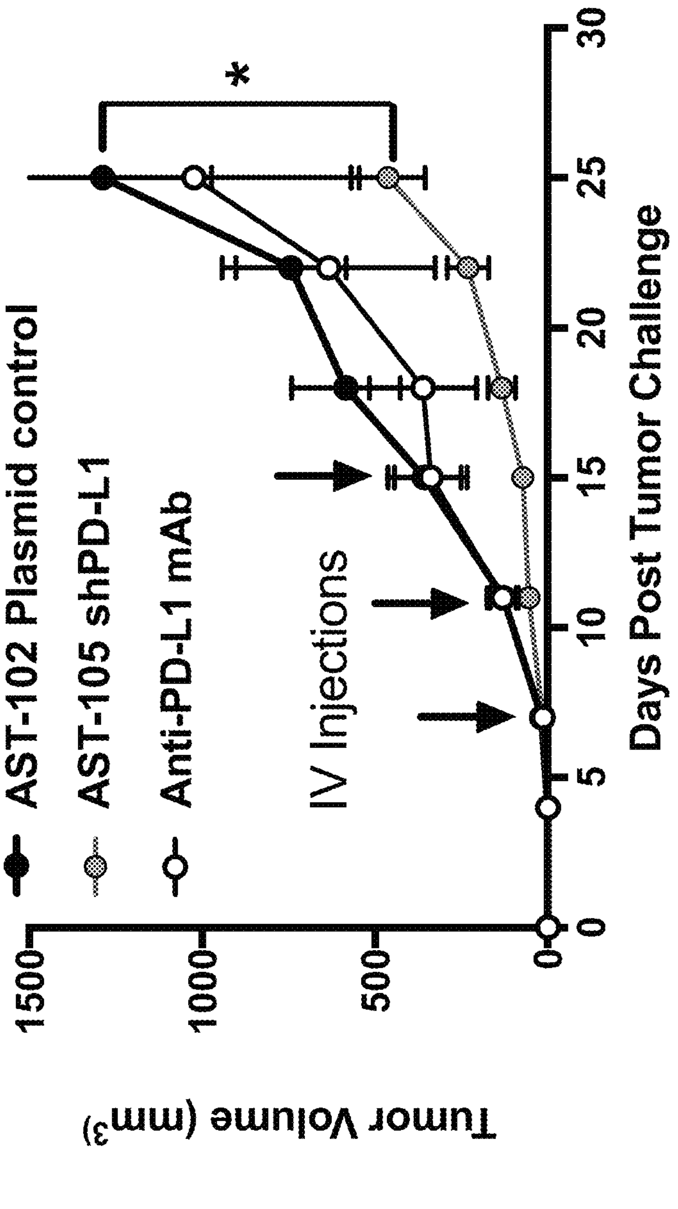
FIG. 27 depicts the efficacy of systemically administered AST-105 (shPD-L1) in a CT26 tumor model. BALB/c (6-8 wk old) were implanted with a single CT26 ($2\times10^5$ cells) subcutaneous flank tumor (n=8 per group). Mice with established tumors were IV injected with $5\times10^6$ CFU of YS1646 strains containing either plasmid control (AST-102) or the PD-L1 shRNA plasmid (AST-105), or PBS control, on the days indicated by the arrows. A separate group was administered 100 μg anti-PD-L1 antibody (clone 10F.9G2 clone, BioXCell) by IP injection weekly, beginning with the first IV injection. Spaghetti plots depicting tumor growth, each line representing an individual mouse. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1−(mean test tumor volume/mean control tumor volume)× 100. *$p<0.05$ vs. plasmid control, student's t-test.

As shown in FIG. 27, treatment with strain AST-105 demonstrated statistically significant tumor control compared to treatment with the plasmid-containing control strain AST-102 (69% TGI, p=0.05, day 25). Tumor growth inhibition was also greater for treatment with AST-105 (expressing shPD-L1) than from systemic administration of an anti-PD-L1 antibody (68% TGI vs. anti-PD-L1).

Figure 28:
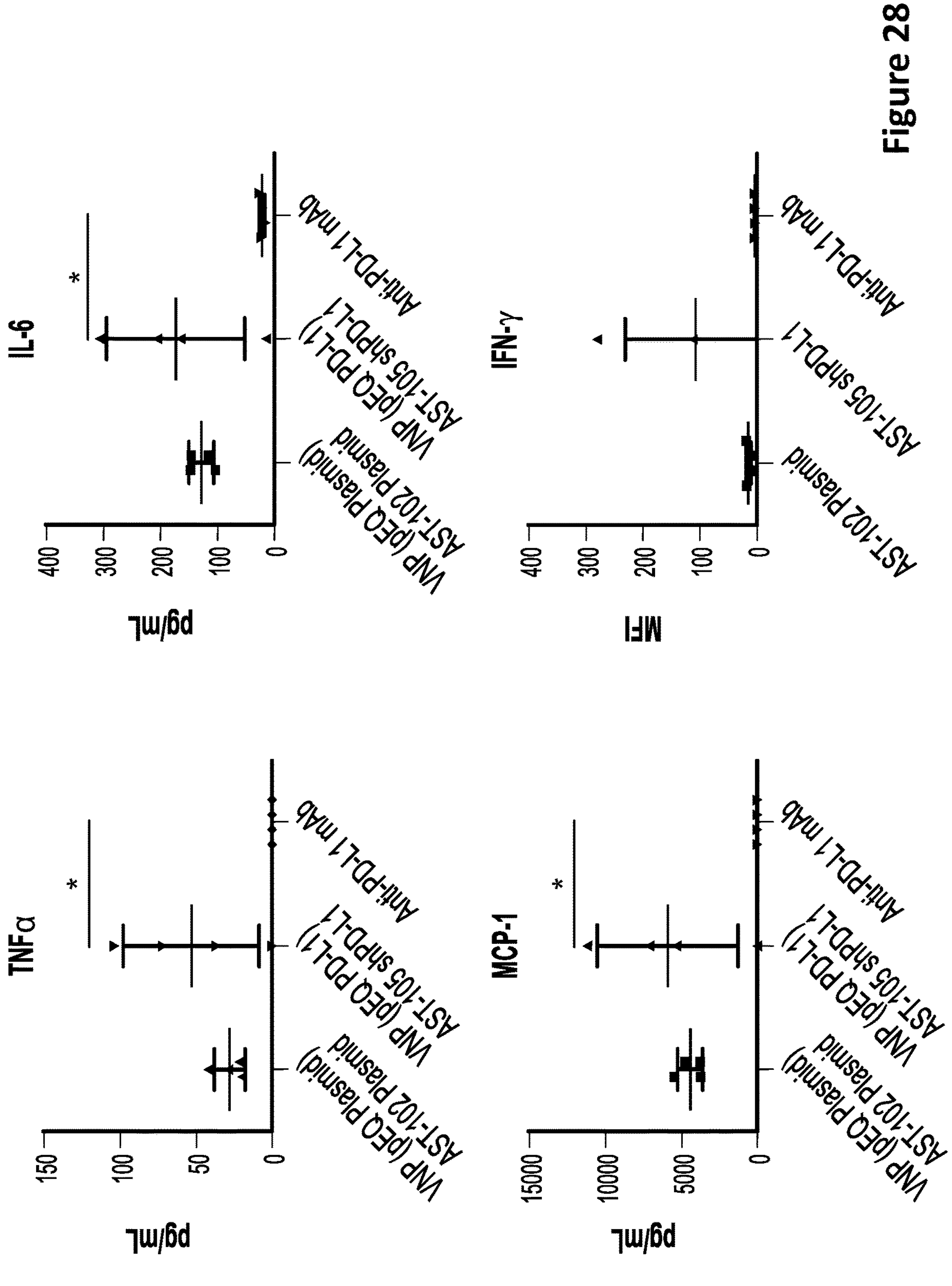
FIG. 28 depicts results showing that AST-105 induces significant cytokine responses observed over PD-L1 mAb. BALB/c mice (6-8 wk old) were implanted with a single CT26 ($2\times10^5$ cells) subcutaneous flank tumor (n=8 per group). Mice with established tumors were IV injected with $5\times10^6$ CFU of YS1646 strains containing either plasmid control (AST-102) or the PD-L1 shRNA plasmid (AST-105), or PBS control, on the days indicated by the arrows. A separate group was administered 100 μg anti-PD-L1 antibody IP (clone 10F.9G2 clone, BioXCell) weekly, beginning with the first IV injection. Mice were bled 6 hrs following the first dose and systemic serum cytokines tested by Luminex (BD bead array and Luminex 200) and mouse cytometric bead array (FACS Fortessa, FCAP software, all BD Biosciences). *$p<0.05$, **$p<0.01$, student's t-test.

Comparing the production of innate pro-inflammatory cytokines at 6 hours post IV injection, the cytokines elicited by strain AST-105 were significantly higher compared to the anti-PD-L1 antibody (p<0.05, FIG. 28), and much higher than those from AST-102. These data demonstrate that inhibiting PD-L1 within the tumor microenvironment, compared to systemic administration of anti-PD-L1 antibody, uniquely activates potent pro-inflammatory cytokines that induce anti-tumor immunity and promote tumor growth inhibition in a murine model of colon carcinoma.

Example 4

Intratumoral Administration of Modified *S. typhimurium* shTREX1 Provides Distal Tumor Colonization and Complete Anti-Tumor Responses in a Dual Flank Murine Colon Carcinoma Model A hallmark of inducing adaptive immunity to a tumor is the ability to induce regression of a distal, untreated tumor. To assess the ability of the YS1646 strain containing the pEQU6 shRNA plasmids to induce primary and distal tumor growth inhibition in a dual flank murine colon carcinoma model, 6-8 week-old female BALB/c mice (10 mice per group) were inoculated SC in the right and left flanks with CT26 murine colon carcinoma ($2\times10^5$ cells in 100 μL PBS). Mice bearing established flank tumors were intratumorally (IT) injected twice, four days apart, into the right flank tumor with $5\times10^6$ CFUs of AST-104, (pEQU6 shTREX1 in YS1646), AST-105 (pEQU6 shPD-L1 in YS1646) or AST-102 (plasmid control in YS1646), and compared to PBS control.

Figure 29:
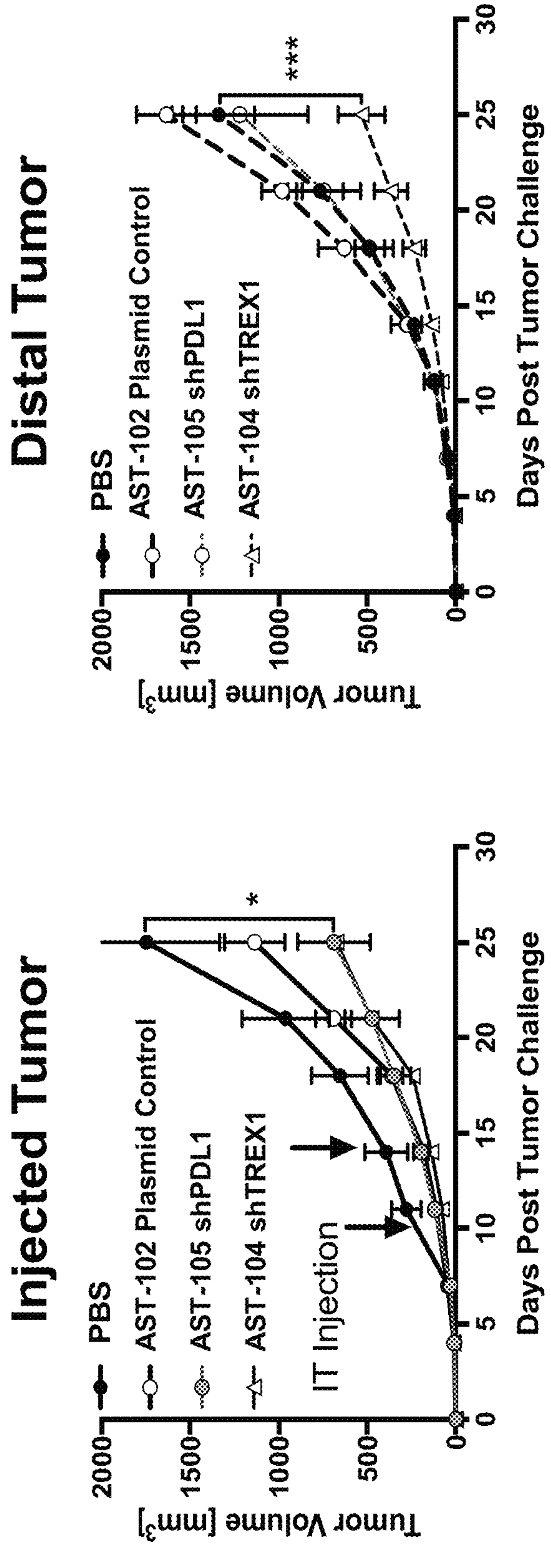
FIG. 29 depicts the effects of intratumoral administration of strains AST-104 and AST-105 in dual flank colon tumors on tumor volume. BALB/c mice (6-8 wk old) were implanted with dual CT26 ($2\times10^5$ cells) subcutaneous flank tumors on the right and left flanks (n=10 per group). Mice with established tumors were IT injected into the right flank with $5\times10^6$ CFU of YS1646 strains containing either plasmid control (AST-102) or the strain containing Trex1 shRNA plasmid (AST-104), or PD-L1 shRNA plasmid (AST-105), or PBS control, on the days indicated by the arrows. Tumor measurements were performed using electronic calipers (Fowler, Newton, Mass.). Tumor volume was calculated using the modified ellipsoid formula ½(length× width$^2$). Mice were euthanized when tumor size reaches >20% of body weight or became necrotic, as per IACUC regulations. % Tumor Growth Inhibition (TGI) is calculated as 1-(mean test tumor volume/mean control tumor volume)× 100. The plots depict mean tumor growth of each group in the injected (left graph) and distal (right graph) groups, ±SEM. *$p<0.05$, ***$p<0.001$, student's t-test.
Figure 30:
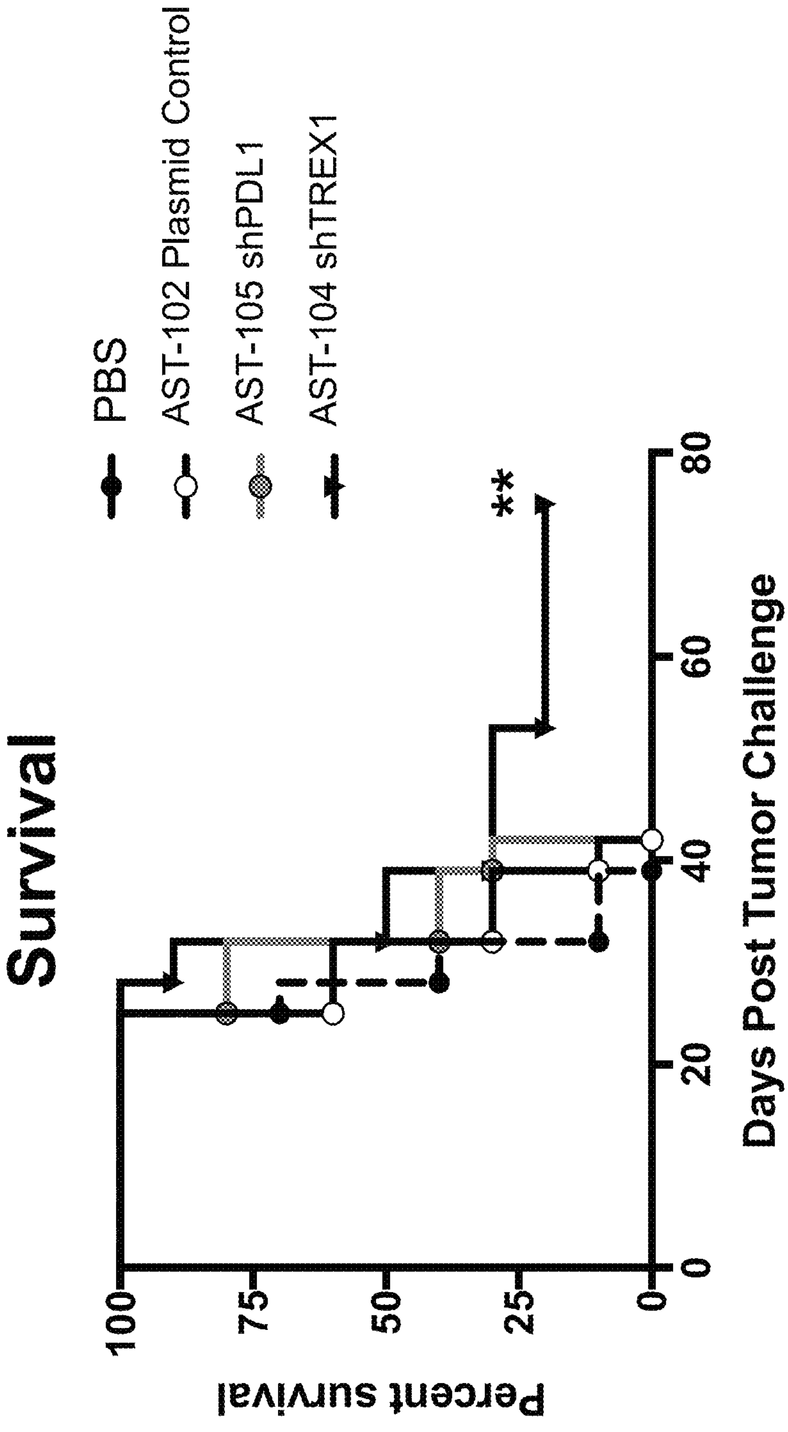
FIG. 30 depicts the curative effects of intratumoral AST-104 administration in dual flank colon tumors in mice. BALB/c mice (6-8 wk old) were implanted with dual CT26 ($2\times10^5$ cells) subcutaneous flank tumors on the right and left flanks (n=10 per group). Mice with established tumors were IT injected into the right flank with $5\times10^6$ CFU of YS1646 strains containing either plasmid control (AST-102) or the Trex1 shRNA plasmid (AST-104), or the shPD-L1 plasmid (AST-105), or PBS control on days 10 and 14 after tumor implantation. Mice were euthanized when tumor size reached >20% of body weight or became necrotic, as per IACUC regulations. The figure depicts the overall survival of the mice, **p<0.01, log-rank (Mantel-Cox) test.

As shown in FIG. 29, IT injection of AST-104 and AST-105 induced significant tumor growth inhibition in the injected tumor, compared to the PBS control (AST-105—60.5% TGI, p=0.03; AST-104—61.4% TGI, p=0.03 day 25). Unlike AST-105, only AST-104 induced significant growth inhibition of the distal, untreated tumor compared to PBS (60% TGI, p<0.0001, day 25), and significant distal tumor growth inhibition compared to AST-102 containing the plasmid control (p=0.004, day 25). The AST-104 strain also demonstrated significant tumor regression and increased survival compared to PBS control (p=0.0076, Log-rank (Mantel-Cox) test) with 2/10 complete remissions (FIG. 30).

Figure 31:
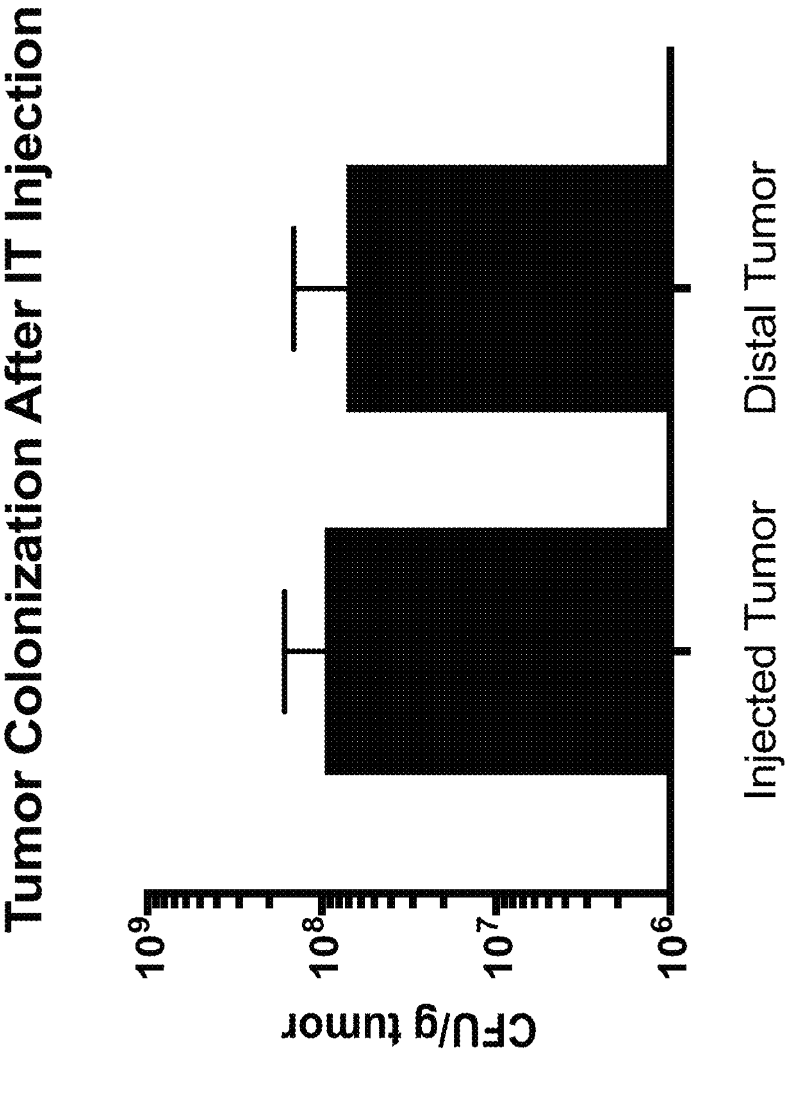
FIG. 31 depicts the levels of tumor colonization in injected and distal tumors after IT administration of AST-104. BALB/c mice (6-8 wk old) were implanted with dual CT26 ($2\times10^5$ cells) subcutaneous flank tumors on the right and left flanks (n=10 per group). Mice with established tumors were IT injected into the right flank with $5\times10^6$ CFU of the YS1646 strain containing a Trex1 shRNA plasmid (AST-104). At 35 days post tumor implantation (12 days after the last dose of AST-104), three mice were sacrificed, and injected and distal tumors were homogenized (GentleMACs, Miltenyi Biotec) and plated on LB plates to enumerate the number of colony forming units (CFU) per gram of tumor tissue. The figure depicts the mean CFU per gram of tissue, ±SD.

To determine whether the bacteria colonize injected, as well as distal tumors, tumor-bearing mice treated with AST-104 were sacrificed and tumors were collected. Injected and distal tumors were transferred to M tubes and were homogenized in PBS using a gentleMACS Dissociator (Miltenyi Biotec). Tumor homogenates were serially diluted and plated on LB agar plates and incubated at 37° C. for colony forming unit (CFU) determination. As shown in FIG. 31, the distal tumor was colonized to the same extent as the injected tumor, indicating that the engineered *Salmonella* strains dosed with an intratumoral route of administration are able to transit and colonize distal lesions. These data demonstrate the potency of administering an immunostimulatory bacteria IT with the ability to systemically colonize distal tumor lesions preferentially over other organs, and the potency of activating the STING Type I Interferon pathway, leading to systemic tumor regression and complete remissions.

Example 5

Modified *S. typhimurium* Strains with Plasmids Containing Cpg Elements Demonstrate Enhanced Anti-Tumor Activity Compared to YS1646 Parental Strain Toll-like receptors (TLRs) are key receptors for sensing pathogen-associated molecular patterns (PAMPs) and activating innate immunity against pathogens (Akira et al. (2001) *Nat Immunol*. August; 2(8)). Of these, TLR9 is responsible for recognizing hypomethylated CpG motifs in pathogenic DNA which do not occur naturally in mammalian DNA (McKelvey et al. (2011) *J Autoimmunity* 36:76). Recognition of CpG motifs upon phagocytosis of pathogens into endosomes in immune cell subsets induces IFR7-dependent type I interferon signaling and activates innate and adaptive immunity. It is shown herein, that the *S. typhimurium* strain YS1646 carrying modified *Salmonella typhimurium* plasmids containing CpG motifs (YS1646 pEQU6 Scramble) similarly activate TLR9 and induce type I IFN-mediated innate and adaptive immunity, as compared to the YS1646 strain without a plasmid.

The CpG motifs in the engineered plasmids used here are shown in Table 2. The pEQU6 shSCR (non-cognate shRNA) plasmid in strain AST-103 possesses 362 CpG motifs, indicating that *Salmonella*-based plasmid delivery can be immuno-stimulatory and have an anti-tumor effect, when compared to the same *Salmonella* lacking transformation with this plasmid. To assess the ability of CpG-containing plasmids within YS1646 to induce tumor growth inhibition in a murine colon carcinoma model, 6-8 week-old female BALB/c mice (9 mice per group) were inoculated SC in the right flank with CT26 ($2\times10^5$ cells in 100 μL PBS). Mice bearing established flank tumors were IV injected weekly with three doses of $5\times10^6$ CFUs of YS1646 (AST-100) or YS1646 containing an shRNA scrambled plasmid with CpG motifs (AST-103), and compared to PBS control.

TABLE 2

CpG motifs in the engineered plasmids

| Sequence name | Number of CpG Motifs | SEQ ID NO. |
|---|---|---|
| pBR322 Origin | 80 | 243 |
| pEQU6 (shSCR) | 362 | 244 |
| Asd Gene ORF | 234 | 242 |
| pATI-2.0 | 538 | 245 |

Figure 32:
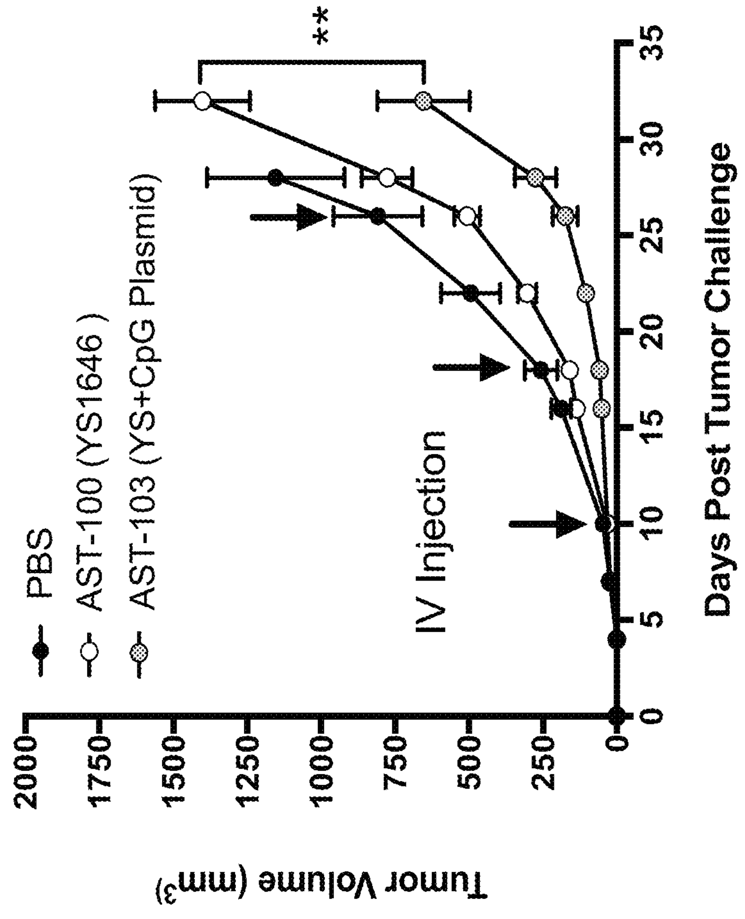
FIG. 32 depicts that CpG scrambled plasmid has immunostimulatory anti-tumor properties. BALB/c mice (6-8 wk old) were implanted with a single CT26 ($2\times10^5$ cells) subcutaneous flank tumor (n=9 per group). Mice with established tumors were IV injected with $5\times10^6$ CFU of the YS1646 strain (AST-100), or the YS1646 stain containing the scrambled shRNA control plasmid (AST-103), or PBS control, on the days indicated by the arrows. Tumor measurements were performed using electronic calipers (Fowler, Newton, Mass.). Tumor volume was calculated using the modified ellipsoid formula ½ (length×width). Mice were euthanized when tumor size reached >20% of body weight or became necrotic, as per IACUC regulations. TGI is calculated as 1-(mean test tumor volume/mean control tumor volume)×100. The figure depicts mean tumor growth of each group, ±SEM. **p<0.01, student's t-test.

As shown in FIG. 32, the YS1646 (AST-100) strain demonstrated modest tumor control (32% TGI, p=ns, day 28) as compared to PBS. The AST-103 strain, that varies from YS1646 only by the addition of the CpG-containing plasmid encoding a non-cognate scrambled shRNA, demonstrated highly significant tumor growth inhibition compared to YS1646 alone, untransformed and therefore lacking a plasmid (p=0.004, day 32).

The asd gene possesses 234 CpG motifs (Table 2), indicating that a plasmid containing it can have immunostimulatory properties. As shown in FIG. 46, AST-109 (YS1646-ASD with scrambled shRNA) had 51% tumor growth inhibition vs PBS alone, indicative of a strong immuno-stimulatory effect.

These data demonstrate the potent immunostimulatory properties of plasmid DNA containing TLR9-activating CpG motifs within a tumor-targeting attenuated strain of *S. typhimurium*.

Example 6

The Modified *Salmonella typhimurium* Strains Containing MicroRNA Inhibition Demonstrate Enhanced Anti-Tumor Activity Compared to shRNA Superior TREX1 gene knockdown was achieved in vitro with microRNA ARI-203 (see Example 2, FIG. 20). The microRNA strain AST-106 was generated by transforming YS1646 with ARI-203, pEQU6 plasmid encoding a microRNA (miRNA) against TREX1. AST-106 was compared to the shRNA strain, AST-104 (YS1646 transformed with pEQU6 shTREX1). In vivo potency in a murine colon carcinoma model was tested. For this experiment, 6-8 week-old female BALB/c mice (10 mice per group) were inoculated SC in the right flank with CT26 ($2\times10^5$ cells in 100 μL PBS). Mice bearing established flank tumors were IV injected weekly on day 8, day 15 and day 23 with $5\times10^6$ CFUs of AST-104 or AST-106 and compared to PBS control.

Figure 33:
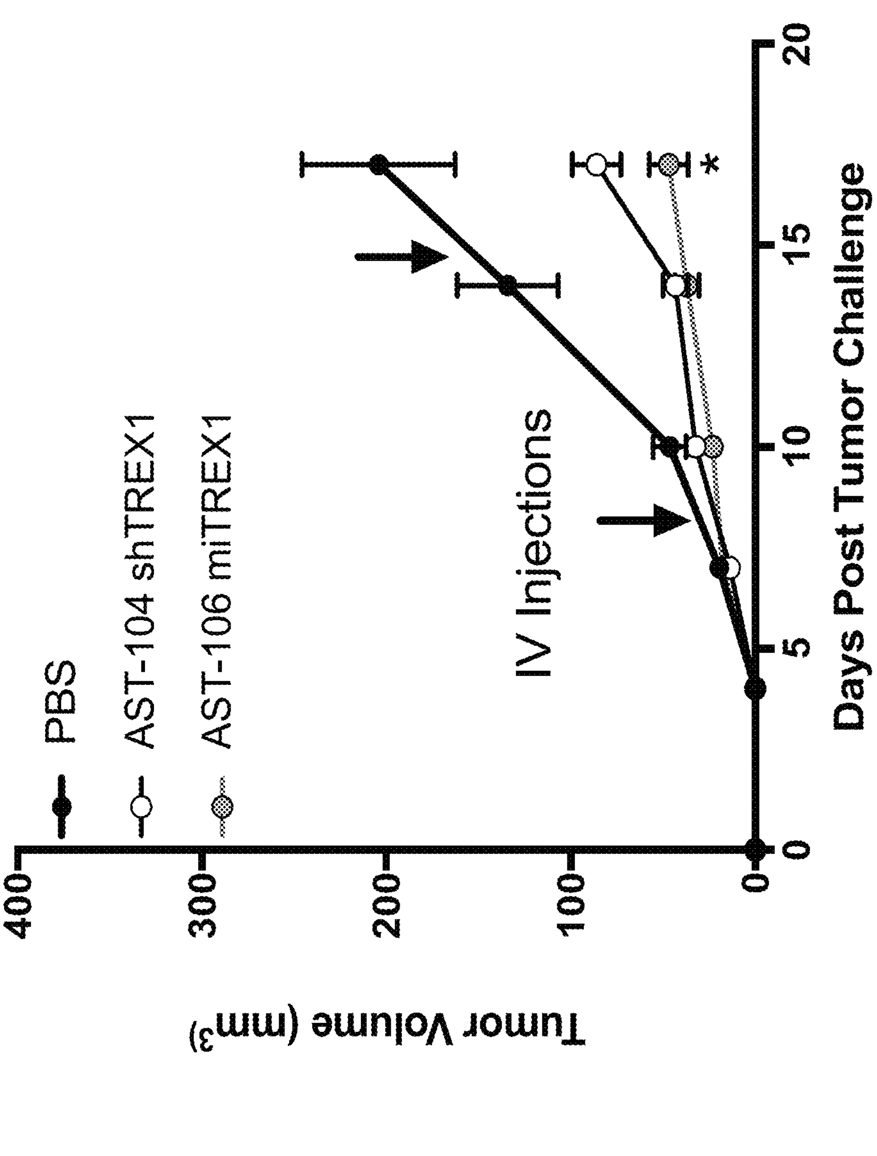
FIG. 33 depicts the efficacy of AST-106 (microRNA TREX1) vs. AST-104 (shRNA TREX1). BALB/c mice (6-8 wk old) were implanted with a single CT26 ($2\times10^5$ cells) subcutaneous flank tumor (n=9 per group). Mice with established tumors were IV injected with $5\times10^6$ CFU of the YS1646 containing the Trex1 shRNA plasmid (AST-104) or the YS1646 stain containing a TREX1 microRNA plasmid (AST-106), or PBS control, on the days indicated by the arrows. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. *p<0.05, student's t-test.

As shown in FIG. 33, both versions of the TREX1 knockdown strains demonstrated significant tumor growth inhibition compared to PBS control (AST-104 58% TGI, p=0.014; AST-106 77% TGI, p=0.003, day 17), with the AST-106 miTREX1 exhibiting the most potent tumor control after the second dose, which was significantly better than the shTREX1 strain AST-104 (p=0.036, day 17). These data demonstrate that the microRNA based inhibitory RNAs can deliver more potent gene knockdown in vivo and outperform the shRNA-based inhibitory RNAs in a tumor growth inhibition model.

Example 7

Vector Synthesis

Complementation of asd Deletion by asd Expression from Plasmids

A plasmid (pATIU6) was chemically synthesized and assembled (SEQ ID NO:225). The plasmid contained the following features: a high copy (pUC19) origin or replication, a U6 promoter for driving expression of a short hairpin, an ampicillin resistance gene flanked by HindIII restriction sites for subsequent removal, and the asd gene containing 85 base pairs of sequence upstream of the start codon (SEQ ID NO:246). Into this vector, shRNAs targeting murine TREX1 or a scrambled, non-cognate shRNA sequence were introduced by restriction digestion with Spe1 and XhoI and ligation and cloning into *E. coli* DH5-alpha. The resulting plasmids, designated pATI-shTREX1 and pATI-shSCR, respectively, were amplified in *E. coli* and purified for transformation into the asd knockout strain AST-101 by electroporation and clonal selection on LB amp plates to produce stains AST-108, and AST-107, respectively. asd− mutants complemented with pATIU6-derived plasmids were able to grow on LB agar and liquid media in the absence of DAP.

In a subsequent iteration, the ampicillin resistance gene (AmpR) from pATI-shTREX1 was replaced with a kanamycin resistance gene. This was accomplished by digestion of pATI-shTREX1 plasmid with HindIII followed by gel purification to remove the AmpR gene. PCR amplification of the kanamycin resistance (KanR) gene using primers APR-001 and APR-002 (SEQ ID NO:226 and SEQ ID NO:227), digestion with HindIII and ligation into the gel purified, digested pATIU6 plasmid.

In subsequent iterations, a single point mutation was introduced into the pATIKan plasmid at the pUC19 origin of replication using the Q5® Site-Directed Mutagenesis Kit (New England Biolabs) and the primers APR-003 (SEQ ID NO:228) and APR-004 (SEQ ID NO:229) to change the nucleotide T at position 148 to a C. This mutation makes the origin of replication homologous to the pBR322 origin of replication in order to reduce the plasmid copy number.

| Primer ID | Description | Sequence | SEQ ID NO |
|---|---|---|---|
| APR-001 | Kan primerF | AAAAAAGCTTGCAGCTCTGGCCCGTG | 226 |
| APR-002 | Kan PrimerR | AAAAAAGCTTTTAGAAAAACTCATCGAGCATCAAATGA | 227 |
| APR-003 | pATI ori T148CF | ACACTAGAAGgACAGTATTTGGTATCTG | 228 |
| APR-004 | pATI ori T148CR | AGCCGTAGTTAGGCCACC | 229 |

pATI2.0

A plasmid was designed and synthesized that contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, the asd gene, an rrnG terminator, and a kanamycin resistance gene flanked by HindIII sites for curing and a multicloning site (SEQ ID NO:247). In addition, a plasmid was designed and synthesized for expression of two separate shRNA or microRNAs. This plasmid contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, an H1 promoter for driving the expression of a 2nd shRNA or microRNA, a 450 bp randomly generated stuffer sequence placed between the H1 and U6 promoters, the asd gene, an rrnG terminator, and a kanamycin resistance gene flanked by HindIII sites for curing and a multicloning site (SEQ ID NO:245).

Example 8

*S. typhimurium* Flagellin Knockout Strain Engineering by Deletion of the Flic and Fljb Genes In the example herein, *S. typhimurium* strains were engineered to lack both flagellin subunits fliC and fljB to reduce pro-inflammatory signaling. Deletions of fliC and fljB were sequentially engineered into the chromosome of the asd gene deleted strain of YS1646 (AST-101).

Deletion of fliC

Figure 34:
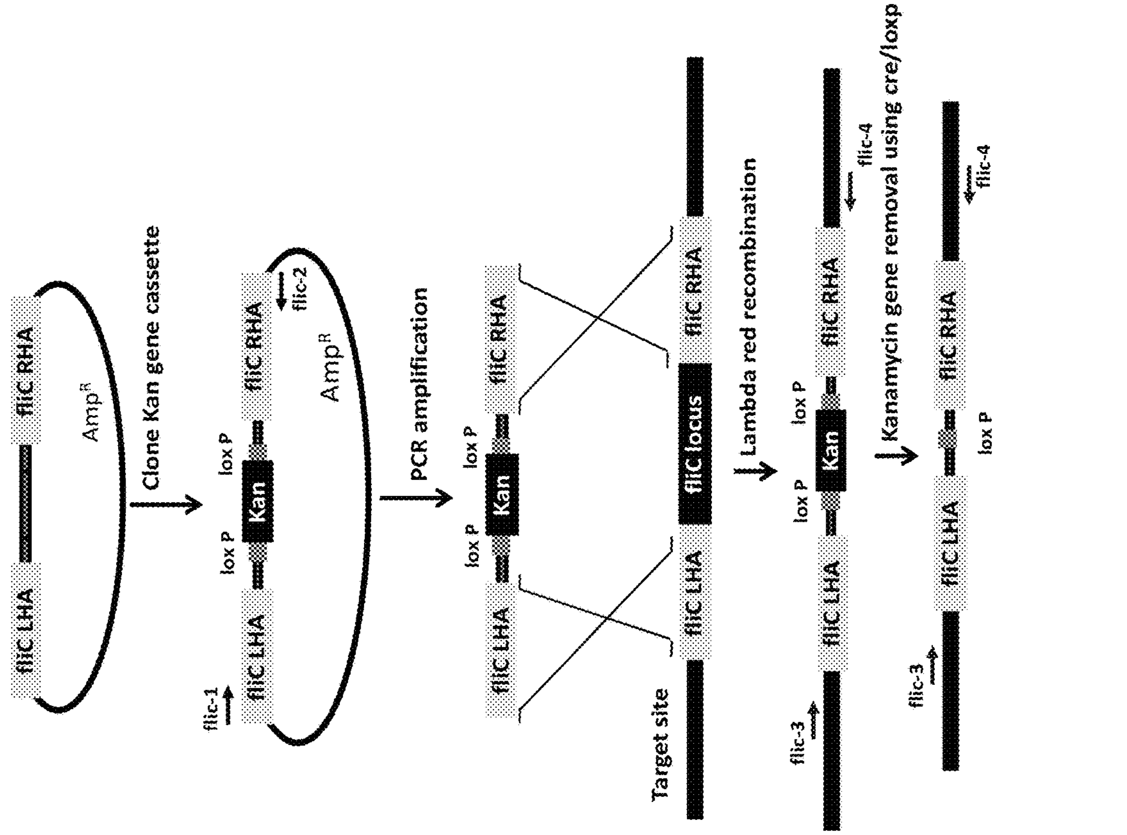
FIG. 34 depicts a schematic of the process used to delete the fliC gene. The flic gene was deleted from the chromosome of *S. typhimurium* strain AST-101 (asd deleted strain of YS1646) using lambda-derived Red recombination system as described in Datsenko and Wanner (*Proc Natl Acad Sci USA* 97:6640-6645 (2000)).

In this example, fliC was deleted from the chromosome of the AST-101 strain using modifications of the method of Datsenko and Wanner (*Proc Natl Acad Sci USA* 97:6640-6645 (2000)) as described in detail in Example 1 and schematically depicted in FIG. 34. Synthetic fliC gene homology arm sequences were ordered that contained 224 and 245 bases of homologous sequence flanking the fliC gene, cloned into a plasmid called pSL0147 (SEQ ID NO:230). A kanamycin gene cassette flanked by cre/lox p sites then was cloned into pSL0147, the fliC gene knockout cassette was then PCR amplified with primer flic-1 (SEQ ID NO:232) and flic-2 (SEQ ID NO:233) and gel purified and introduced into the AST-101 strain carrying the temperature sensitive lambda red recombination plasmid pKD46 by electroporation. Electroporated cells were recovered in SOC+DAP medium and plated onto LB Agar plates supplemented with Kanamycin (20 μg/mL) and diaminopimelic acid (DAP, 50 μg/ml). Colonies were selected and screened for insertion of the knockout fragment by PCR using primers flic-3 (SEQ ID NO:234) and flic-4 (SEQ ID NO:235).

pKD46 then was cured by culturing the selected kanamycin resistant strain at 42° C. and screening for loss of ampicillin resistance. The Kanamycin resistance marker then was cured by electroporation of a temperature sensitive plasmid expressing the Cre recombinase (pJW1680) and $Amp^R$ colonies were selected at 30° C.; pJW168 was subsequently eliminated by growing cultures at 42° C. Selected fliC knockout clones were then tested for loss of kanamycin marker by PCR using primers flanking the sites of disruption (flic-3 and flic-4) and evaluation of the electrophoretic mobility on agarose gels.

Deletion of fljB fljB was then deleted in the asd/fliC deleted YS1646 strain using modifications of the methods described above. Synthetic fljB gene homology arm sequences that contained 249 and 213 bases of the left hand and right hand sequence, respectively, flanking the fliC gene, were synthesized and cloned into a plasmid called pSL0148 (SEQ ID NO:231). A kanamycin gene cassette flanked by cre/loxP sites then was cloned into pSL0148 and the fljB gene knockout cassette then was PCR amplified with primer fljb-1 (SEQ ID NO:236) and fljb-2 (SEQ ID NO:237) and gel purified and introduced into AST-101 carrying the temperature sensitive lambda red recombination plasmid pKD46 by electroporation. The kanamycin resistance gene then was cured by cre-mediated recombination as described above, and the temperature-sensitive plasmids were cured by growth at non-permissive temperature. The fliC and fljB gene knockout sequences were amplified by PCR using primers flic-3 and flic-4 or fljb-3 (SEQ ID NO:238) and fljb-4 (SEQ ID NO:239), and verified by DNA sequencing. This $asd^-/fliC^-/fljB^-$ mutant derivative of YS1646 was designated AST-111.

Primer sequence information

| Primer name | Primer sequence | SEQ ID NO. |
|---|---|---|
| flic-1 | CGTTATCGGCAATCTGGAGGC | 232 |
| flic-2 | CCAGCCCTTACAACAGTGGTC | 233 |
| flic-3 | GTCTGTCAACAACTGGTCTAACGG | 234 |
| flic-4 | AGACGGTCCTCATCCAGATAAGG | 235 |
| fljb-1 | TTCCAGACGACAAGAGTATCGC | 236 |
| fljb-2 | CCTTTAGGTTTATCCGAAGCCAGAATC | 237 |
| fljb-3 | CACCAGGTTTTTCACGCTGC | 238 |
| fljb-4 | ACACGCATTTACGCCTGTCG | 239 |

Figure 35:
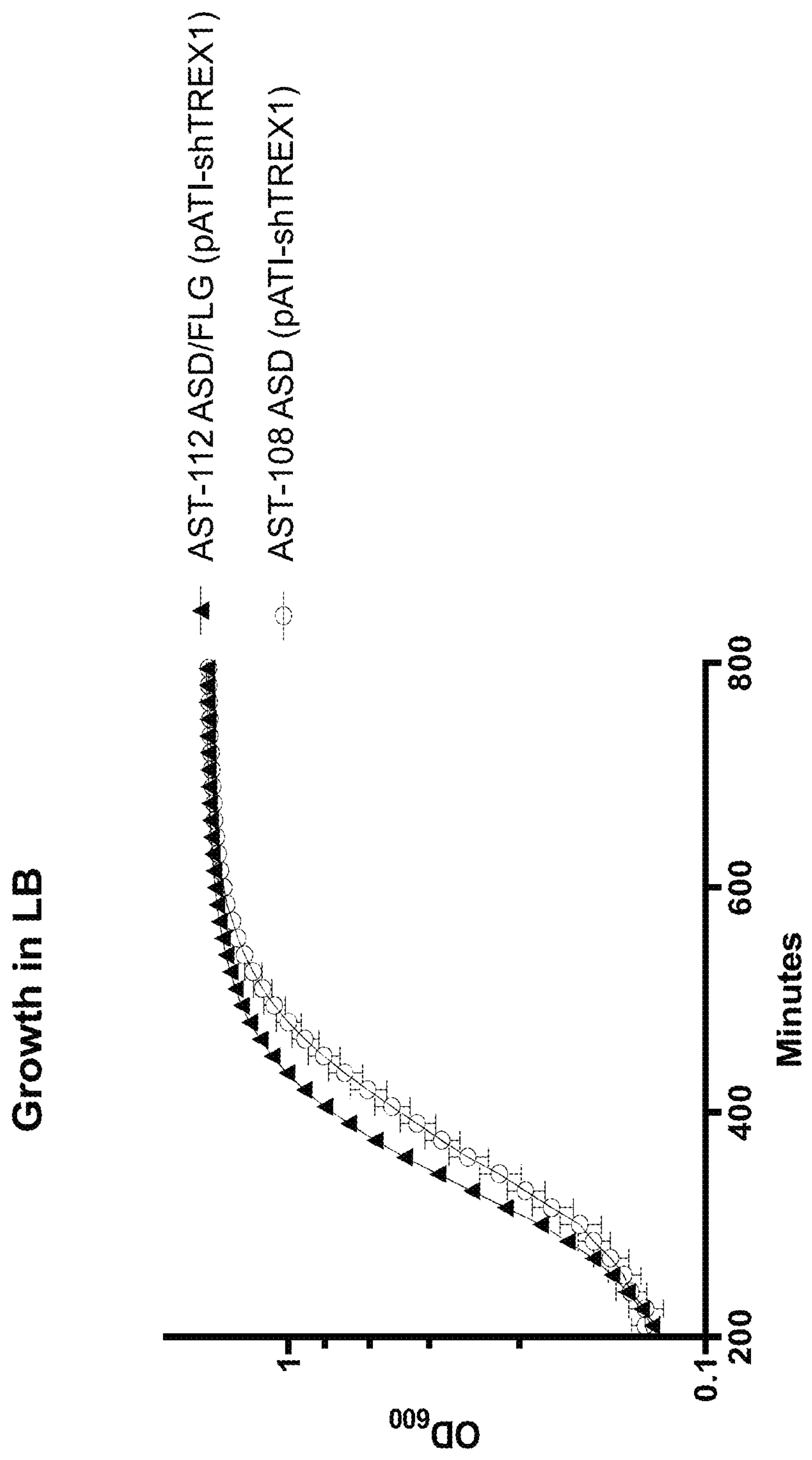
FIG. 35 depicts that the Flagellin deletion strain grows normally in LB. The figure depicts the growth of strains AST-108 ASD (pATI-shTREX1) and AST-112 ASD/FLG (pATI-shTREX1) at 37° C. in LB broth, as measured by $OD_{600}$ using a Spectramax 96 well plate reader (Molecular devices).

In Vitro Characterization of Engineered *S. typhimurium* Flagellin Knockout Strain The YS1646 derived asd mutant strain harboring the deletions of both fliC and fljB, herein referred to as AST-111 or ASD/FLG, was evaluated for swimming motility by spotting 10 microliters of overnight cultures onto swimming plates (LB containing 0.3% agar and 50 mg/mL DAP). While motility was observed for YS1646 and the asd deleted strain AST-101, no motility was evident with the asd/fliC/fljB-deleted strain AST-111. The AST-111 strain then was electroporated with pATIshTREX1 (a plasmid containing an asd gene and an shRNA targeting TREX1), to produce AST-112, and its growth rate in the absence of DAP was assessed. As shown in FIG. 35 ASD/FLG (pATI-shTREX1) strain AST-112 was able to replicate in LB in the absence of supplemental DAP, and grew at a rate comparable to the asd strain containing pATIshTREX1(AST-108). These data demonstrate that the elimination of flagellin does not decrease the fitness of *S. typhimurium* in vitro.

Elimination of flagellin subunits decreases pyroptosis in macrophages. To demonstrate this, $5\times10^5$ mouse RAW-Dual™ macrophage cells (InvivoGen, San Diego, Ca.) were infected with the asd/fliC/fljB deleted strain harboring a low copy shTREX1 plasmid, designated AST-118, or the asd deleted strain harboring the same plasmid (AST-117) at an MOI of approximately 100 in a gentamycin protection assay. After 24 hours of infection, culture supernatants were collected and assessed for lactate dehydrogenase release as a marker of cell death using a Pierce™ LDH Cytotoxicity Assay Kit (Thermo Fisher Scientific, Waltham, Ma.). AST-117 induced 75% maximal LDH release, while AST-118 induced 54% maximal LDH release, demonstrating that the deletion of the flagellin genes reduce the *S. typhimurium*-induced pyroptosis.

ASD/FLG Knockout Strain Containing shTrex1 Plasmid Demonstrates Enhanced Anti-Tumor Activity, Enhanced Interferon Gamma Responses, and Increased Tumor Colonization in Mice Compared to Parental asd Strain.

To assess the impact of the flagellin knockout strains administered in a murine model of colon carcinoma, 6-8 week-old female BALB/c mice (10 mice per group) were inoculated SC in the right flank with CT26 ($2\times10^5$ cells in 100 μL PBS). Mice bearing established flank tumors were IV injected with three weekly doses of $5\times10^6$ CFUs of the ASD/FLG strain containing the pATIKan-shTREX1 plasmid (AST-113) or the ASD strain with the same pATIKan-shTREX1 plasmid (AST-110), and compared to PBS control. Six hours following the first IV dose, mice were bled, and plasma was collected and assessed for pro-inflammatory cytokines using the Mouse Inflammation Cytometric Bead Array kit and analyzed by FACS (BD Biosciences).

Figure 36:
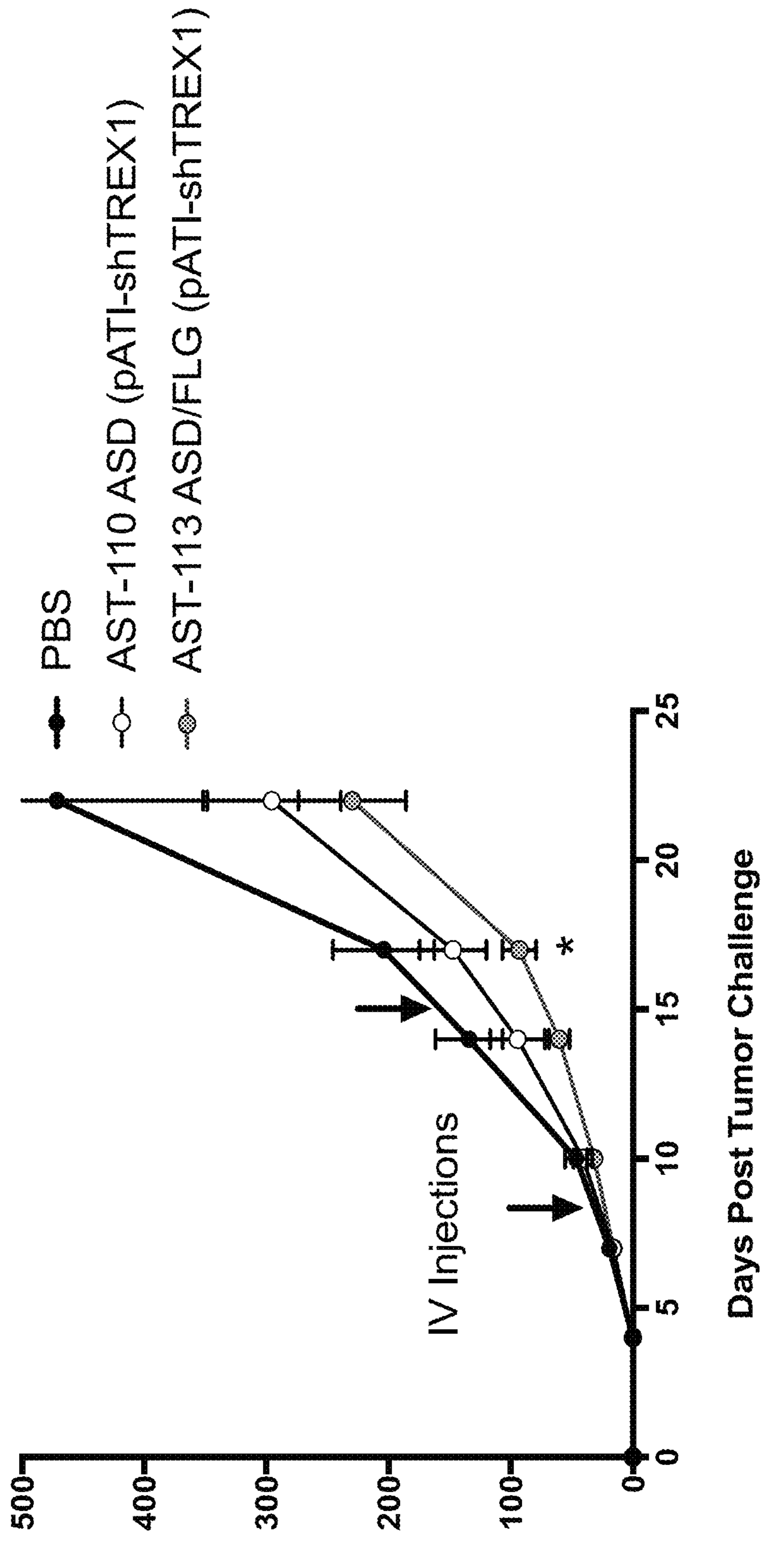
FIG. 36 depicts that Flagellin knockout improves anti-tumor efficacy. BALB/c mice (6-8 wk old) were implanted with a single CT26 ($2\times10^5$ cells) subcutaneous flank tumor (n=9 per group). Mice with established tumors were IV injected with $5\times10^6$ CFU of the asdlfigB/fliC knockout strain containing the pATI shTREX1 plasmid (AST-113), or asd knockout strain containing the pATI shTREX1 plasmid (AST-110), or PBS control, on the days indicated by the arrows. Tumor measurements were performed using electronic calipers (Fowler, Newton, Mass.). Tumor volume was calculated using the modified ellipsoid formula ½(length×width$^2$). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. *p<0.05, student's t-test.

As shown in FIG. 36, The AST-113 strain, incapable of making flagella and containing the pATIshTrex1 plasmid (ASD/FLG pATI-shTREX1), demonstrated enhanced tumor control compared to the parental ASD pATI-shTREX1 strain AST-110, and significant tumor control compared to the PBS control (54% TGI, p=0.02, day 17).

Figure 37:
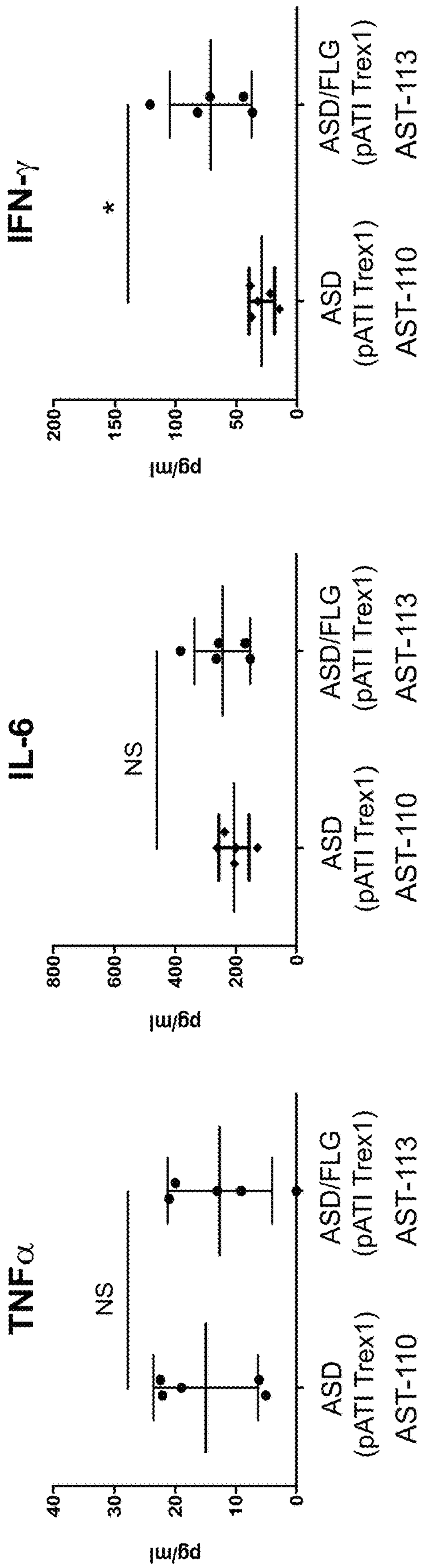
FIG. 37 depicts that Flagellin knockout shows an increased IFN-gamma signature. BALB/c mice (6-8 wk old) were implanted with a single CT26 ($2\times10^5$ cells) subcutaneous flank tumor (n=9 per group). Mice with established tumors were IV injected with $5\times10^6$ CFU of the asdlfigB/fliC knockout strain containing the pATI shTREX1 plasmid (AST-113), or asd knockout strain containing the pATI shTREX1 plasmid (AST-110), or PBS control. Mice were bled 6 hrs following the first dose and systemic serum cytokines tested by Luminex 200 device (Luminex Corporation) and mouse cytometric bead array (BD bead array, FACS Fortessa, FCAP software, all BD Biosciences). *p<0.05, p<0.01, *p<0.001, student's t-test.

Comparing the levels of systemic serum cytokines at 6 hours post IV injection, the cytokines elicited by the AST-113 strain were comparable for TNF-α and IL-6 as compared to the parental AST-110 strain capable of making flagella. The levels of the potent anti-tumor immune cytokine IFN-γ were significantly higher with AST-113 compared to AST-110, indicating that the flagellin deficient strain can provide for superior anti-tumor potency over the parental asd knockout strain (FIG. 37).

Figure 38:
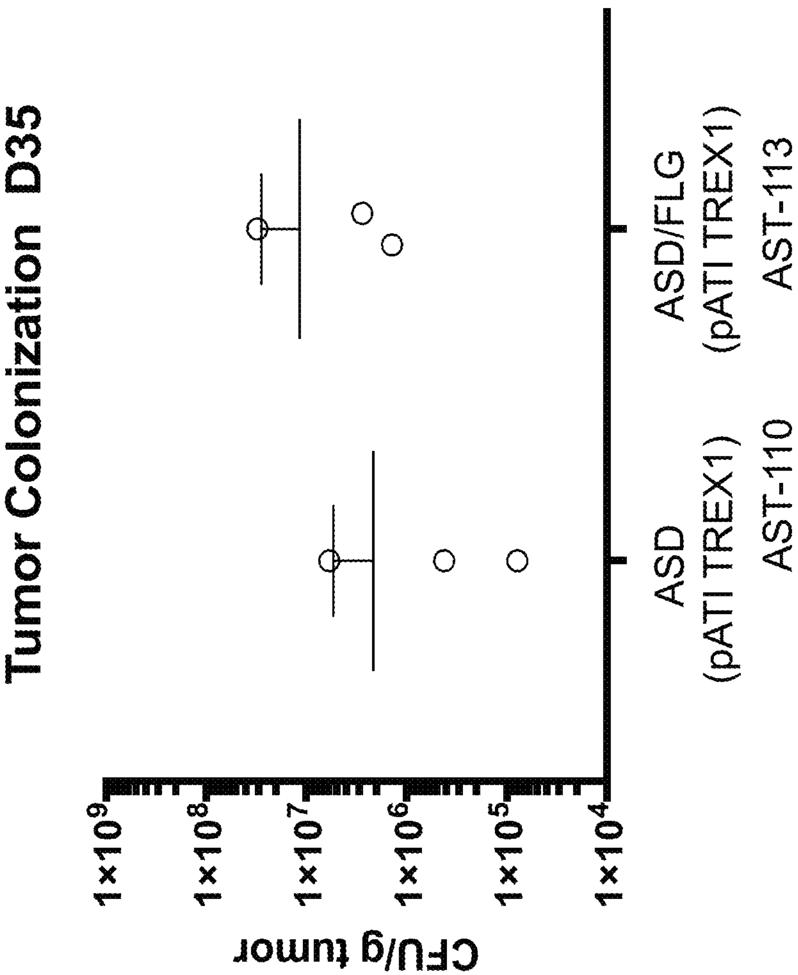
FIG. 38 depicts that Flagellin is not required for tumor colonization. BALB/c mice (6-8 wk old) were implanted with a single CT26 ($2\times10^5$ cells) subcutaneous flank tumor (n=9 per group). Mice with established tumors were IV injected with $5\times10^6$ CFU of the asdlfigB/fliC knockout strain containing the pATI shTREX1 plasmid (AST-113), or asd knockout strain containing the pATI shTREX1 plasmid (AST-110), or PBS control. At 35 days post tumor implantation (12 days after the last dose of engineered *Salmonella* therapy), three mice per group were sacrificed, and tumors were homogenized (GentleMACs, Miltenyi Biotec) and plated on LB plates to enumerate the number of colony forming units per gram of tumor tissue. The figure depicts the mean colony forming units (CFU) per gram of tissue, ±SD.

At 35 days post tumor implantation (12 days after the last dose of engineered *Salmonella* therapy), three mice per group were euthanized, and tumors were homogenized and plated on LB plates to enumerate the number of colony forming units (CFUs) per gram of tumor tissue as described above. As shown in FIG. 38, the AST-113 strain, deleted of fliC and fljB and containing the pATIshTREX1 plasmid, was able to colonize tumors at least as well as the strain that only had the asd gene deletion and contained the same plasmid (AST-110). AST-113 colonized tumors with a mean of $1.2\times10^7$ CFU per gram of tissue compared with a mean of $2.1\times10^6$ cfu/g of tumor for AST-110, indicating that the absence of flagellin can lead to an increased tumor colonization by greater than 5 times that of strains with a functional flagella. Together, these data demonstrate that, contrary to the expectation from the art, not only is the flagella not required for tumor colonization, but its loss can enhance tumor colonization and anti-tumor immunity.

Example 9

*S. typhimurium* Engineered to Express cytoLLO for Enhanced Plasmid Delivery In this example, the asd deleted strain of YS1646 described in Example 1 (AST-101) was further modified to express the listeriolysin O (LLO) protein lacking the signal sequence that accumulates in the cytoplasm of the *Salmonella* strain (referred to herein as cytoLLO). LLO is a cholesterol-dependent pore-forming cytolysin that is secreted from *Listeria monocytogenes* and mediates phagosomal escape of bacteria. A gene encoding LLO, with codons 2-24 deleted, was synthesized with codons optimized for expression in *Salmonella*. The sequence of the open reading frame of cytoLLO is in SEQ ID NO:240. The cytoLLO gene was placed under control of a promoter that induces transcription in *S. typhimurium* (SEQ ID NO: 241, reproduced below). The cytoLLO expression cassette was inserted in single copy into the knockout-out asd locus of the asd deleted strain AST-101 using modifications of the method of Datsenko and Wanner (*Proc Natl Acad Sci USA* (2000) 97:6640-6645), as described in Example 1.

Sequence of Promoter Driving Expression of cytoLLO

```
LLO promoter
                                        SEQ ID NO: 241
attatgtcttgacatgtagtgagtgggctggtataatgcagcaag
```

Figure 39:
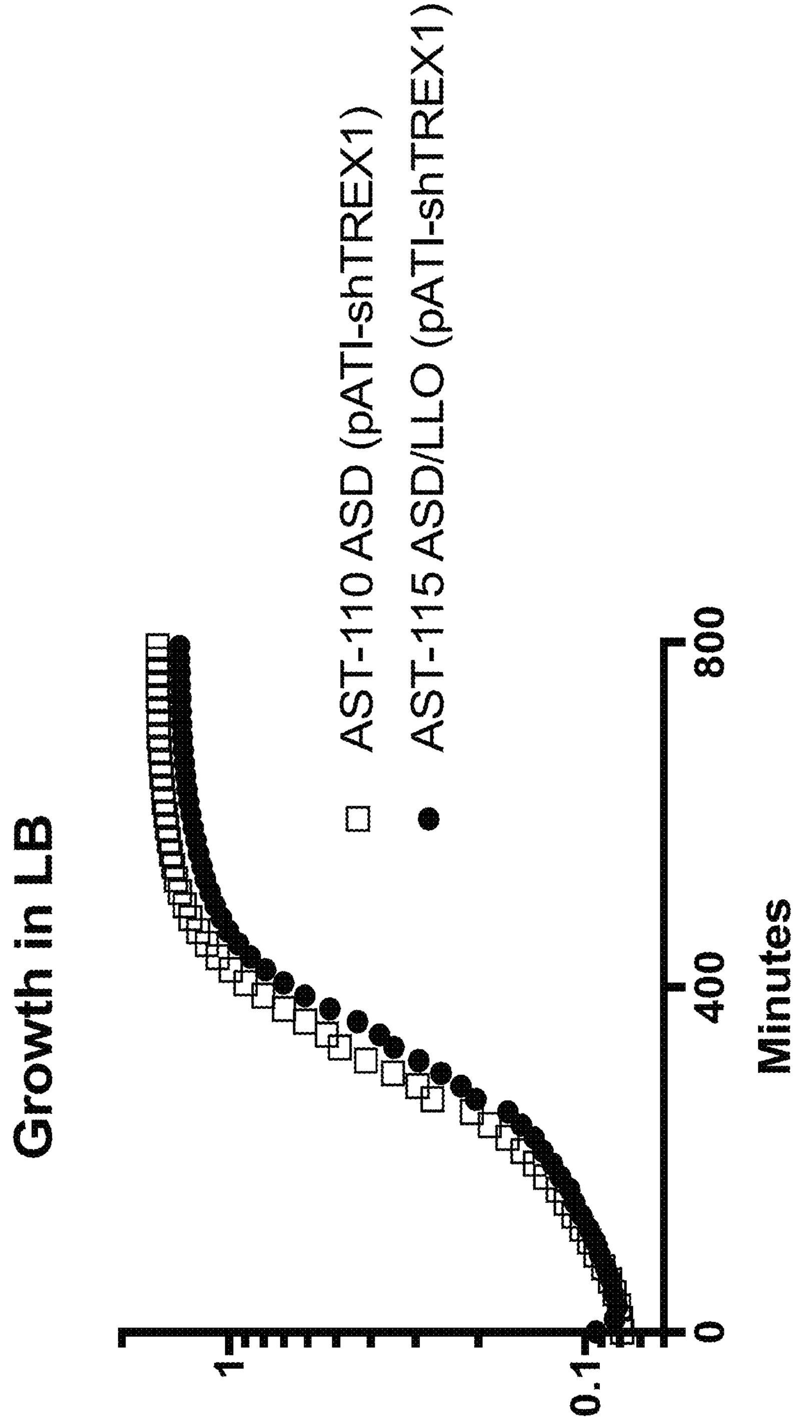
FIG. 39 depicts that a cytoLLO expressing strain grows normally in vitro. The figure depicts the growth of strains AST-110 (YS1646 with asd deletion containing (pATI-shTREX1)) and AST-115 (YS1646 with asd deletion and knock-in of cytoLLO expression cassette containing (pATI-shTREX1)) at 37° C. in LB broth, as measured by $OD_{600}$ using a Spectramax 96 well plate reader (Molecular devices).

The asd deleted strain with the cytoLLO expression cassette inserted at the asd locus (referred to herein as ASD/LLO or AST-114) was further modified by electroporation with a pATI plasmid encoding an asd gene that allows the strain to grow in the absence of exogenous DAP and selects for plasmid maintenance, and also contains a U6 promoter driving expression of shTREX1 as described in Example 7 (referred to herein as ASD/LLO (pATI-shTREX1) or AST-115). As shown in FIG. 39, the ASD/LLO (pATI-shTREX1) strain AST-115 grew at a comparable rate to the asd deleted strain containing the same plasmid (pATI-shTREX1), AST-110, demonstrating that the LLO knock-in does not impact bacterial fitness in vitro.

*S. typhimurium* Engineered to Produce cytoLLO Demonstrate Potent Anti-Tumor Activity To determine whether the cytoLLO gene knock-in provided anti-tumor efficacy, the ASD/LLO (pATI-shTREX1) strain AST-115 was evaluated in a murine model of colon carcinoma. For this study, 6-8 week-old female BALB/c mice (8 mice per group) were inoculated SC in the right flank with CT26 ($2\times10^5$ cells in 100 PBS). Mice bearing established flank tumors were IV injected with a single dose of $5\times10^6$ CFUs of AST-115, and compared to PBS control.

Figure 40:
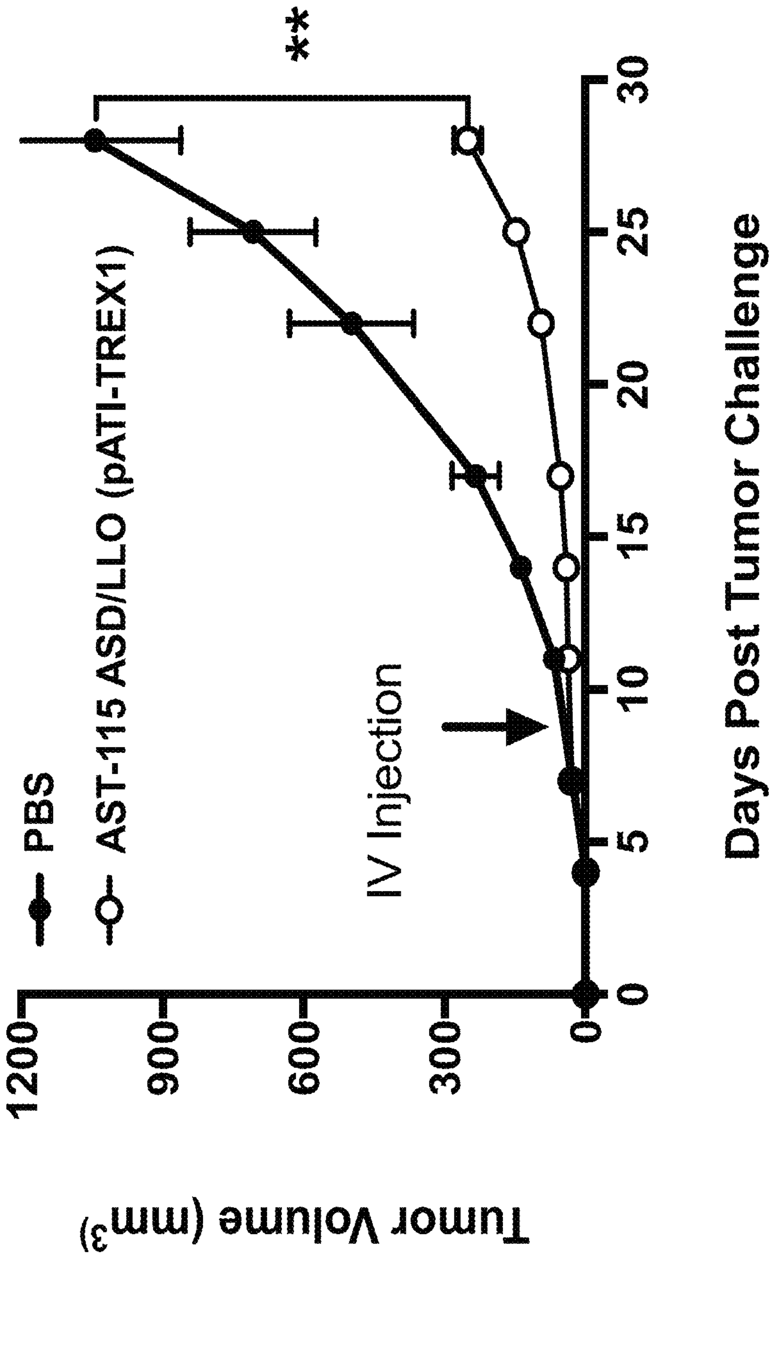
FIG. 40 depicts that AST-115 (ASD knockout+CytoLLO Knock-in strain carrying shTREX1 plasmid) demonstrates potent, single-dose efficacy in a murine CT26 tumor model. BALB/c mice (6-8 wk old) were implanted with a single CT26 ($2\times10^5$ cells) subcutaneous flank tumor (n=9 per group). Mice with established tumors were IV injected with $5\times10^6$ CFU of AST-115 (YS1646 with asd deletion and knock-in of cytoLLO expression cassette at asd locus containing (pATI-shTREX1), or PBS control, on the days indicated by the arrows. Tumor measurements were performed using electronic calipers (Fowler, Newton, Mass.).

As shown in FIG. 40, the addition of the cytoLLO gene into the asd strain ASD/LLO (pATI-shTREX1) demonstrated highly significant tumor control compared to PBS control (76% TGI, p=0.002, day 28), and comparable efficacy after a single dose to previous studies where the TREX1 shRNA plasmid containing strains were given at multiple doses. These data demonstrate the cytoLLO-mediated advantage of delivering more plasmid into the cytosol, resulting in greater gene knockdown, thereby improving the therapeutic efficacy of RNAi against targets such as TREX1.

Example 10

Adenosine Auxotrophic Strains of *S. typhimurium*

Strains provided herein are engineered to be auxotrophic for adenosine. As a result, they are attenuated in vivo because they are unable to replicate in the low adenosine concentrations of normal tissue, therefore colonization occurs primarily in the solid tumor microenvironment where adenosine levels are high. The *Salmonella* strain YS1646 (AST-100) is a derivative of the wild type strain ATCC14028, and was engineered to be auxotrophic for purine due to disruption of the purI gene (Low et al., (2004) *Methods Mol. Med* 90:47-60). Subsequent analysis of the entire genome of YS1646 demonstrated that the purI gene (synonymous with purM) was not in fact deleted, but was instead disrupted by a chromosomal inversion (Broadway et al. (2014) *J. Biotechnol.* 20:177-178), and that the entire gene is still contained within two parts of the YS1646 chromosome that is flanked by insertion sequences (one of which has an active transposase). The presence of the complete genetic sequence of the purI gene disrupted by means of a chromosomal reengagement leaves open the possibility of reversion to a wild type gene. While it has previously been demonstrated that purine auxotrophy of YS1646 was stable after serial passage in vitro, it was not clear what the reversion rate is (Clairmont et al. (2000) *J. Infect. Dis.* 181:1996-2002).

It is shown herein that, when provided with adenosine, YS1646 is able to replicate in minimal medium; whereas the wild-type parental strain ATCC14028 can grow in minimal media that is not supplemented with adenosine. YS1646 was grown overnight in LB medium washed with M9 minimal medium and diluted into M9 minimal media containing no adenosine, or increasing concentrations of adenosine. Growth was measured using a SpectraMax M3 spectrophotometer (Molecular Devices) at 37° C., reading the $OD_{600}$ every 15 minutes.

As shown in FIG. 41, YS1646 was able to replicate when adenosine was provided at concentrations ranging from 11 to 300 micromolar, but was completely unable to replicate in M9 alone or M9 supplemented with 130 nanomolar adenosine. These data demonstrate that purI mutants are able to replicate in concentrations of adenosine that are found in the tumor microenvironment, but not at concentrations found in normal tissues. Engineered adenosine auxotrophic strains exemplified herein include strains wherein all, or portions of the purI open reading frame are deleted from the chromosome to prevent reversion to wild-type. Such gene deletions can be achieved utilizing the lambda red system as described in Example 1.

*Salmonella* strains containing a purI disruption, further engineered to contain an asd gene deletion (ASD) as described in Example 1, or asd gene deletion further engineered to have deletions of fliC and fljB and (ASD/FLG), as described in Example 8, or asd mutants further engineered to express cytoLLO (ASD/cLLO) as described in Example 9 and complemented with a low copy number plasmid (pATIlow) expressing asd as described in Example 7 (Strains AST-117, AST-118, and AST-119, respectively), were also evaluated for growth in M9 minimal media. The data in FIG. 42 show that each strain was able to replicate when adenosine was provided at concentrations ranging from 11 to 300 micromolar, but was completely unable to replicate in M9 alone or M9 supplemented with 130 nanomolar adenosine.

Example 11

Characterization and Use of the asd Gene Complementation System In Vitro Growth of Strains with asd Gene Complementation To assess fitness of the bacterial strains containing plasmids, growth curves were performed in LB liquid media using a Spectramax plate reader at 37° C., reading the $OD_{600}$ every 15 minutes. As Shown in FIG. 43, YS1646 containing a low copy plasmid pEQU6-shTREX1 (AST-104) grew comparably to YS1646 that did not contain a plasmid (AST-100). An asd mutant strain harboring a high copy shTREX1 plasmid with an asd gene that can complement the asd auxotrophy (AST-110) was able to replicate in LB in the absence of DAP, but grew slower than YS1646. An asd deleted strain containing an shTREX-1 expression plasmid with low copy number origin of replication and an asd gene that can complement the asd auxotrophy (pATIlow-shTREX1), strain AST-117, grew at a faster rate than AST-110. These data demonstrate that low copy number plasmids that complement the asd gene auxotrophy are superior to high copy number plasmids, as they allow for more rapid replication rates of *S. typhimurium* in vitro.

Intracellular Growth of asd Complemented Strains

To measure fitness of the asd mutants complemented with asd on high and low copy plasmids, the ability of bacterial strains to replicate intracellularly in mouse tumor cell lines was assessed using a gentamycin protection assay. In this assay, mouse melanoma B16.F10 cells or mouse colon cancer CT26 cells were infected with asd mutant *Salmonella* strains containing plasmids that contain a complementary asd gene and have either a high copy origin of replication, AST-110 (ASD pATI-shTREX1) or a low copy origin of replication, AST-117 (ASD pATI low copy-shTREX1). Cells were infected at a multiplicity of approximately 5 bacteria per cell for 30 minutes, then cells were washed with PBS, and medium containing gentamicin was added to kill extracellular bacteria. Intracellular bacteria are not killed by gentamicin, as it cannot cross the cell membrane. At various time points after infection, cell monolayers were lysed by osmotic shock with water and the cell lysates were diluted and plated on LB agar to enumerate surviving colony forming units (CFU).

As shown in FIG. 44, the asd mutant strain complemented with a high copy plasmid, AST-110, had an initial decline in CFU, but was able to grow in B16.F10 cells but not in CT26 cells, demonstrating that the asd gene complementation system is sufficient to support growth inside mammalian tumor cells. The asd mutant strain containing the low copy plasmid, AST-117, was able to invade and replicate in both cell types, demonstrating that asd gene complementation on a low copy plasmid allows for robust asd mutant growth inside mammalian cells. The strain with low copy plasmid replicated to higher numbers in both tumor cell types compared to the strain with a high copy plasmid. This demonstrates that *Salmonella* strains with low copy plasmids have enhanced fitness over strains with high copy plasmids.

Plasmid Maintenance in Tumors Using asd Complementation System

In this example, CT26 tumor-bearing mice were treated with YS1646 containing a plasmid that expresses an shRNA targeting TREX1 (pEQU6-TREX1), strain AST-104, or an asd deleted strain of YS1646 containing a plasmid with a functional asd gene and an shRNA targeting TREX1 (pATI-shTREX1), strain AST-110. At 12 days after the final *Salmonella* injection, tumors were homogenized, and homogenates were serially diluted and plated on LB agar plates to enumerate the total number of CFUs present, or on LB plates containing kanamycin to enumerate the number of kanamycin resistant colonies.

As shown in FIG. 45, *S. typhimurium* that did not have selective pressure to maintain the shRNA plasmid, AST-104, demonstrated plasmid loss, as the percent kanamycin resistant (KanR) colonies was less than 10%. The strain that used the asd gene complementation system for plasmid maintenance, AST-110, had nearly identical numbers of kanamycin resistant and kanamycin sensitive CFUs. These data demonstrate that the asd gene complementation system is sufficient to maintain the plasmid in the context of the tumor microenvironment in mice.

Enhanced Anti-Tumor Efficacy Using asd Complementation System

The asd complementation system is designed to prevent plasmid loss and potentiate the anti-tumor efficacy of the inhibitory RNA delivery by *S. typhimurium* strains in vivo. To test this, asd deleted strains containing shTREX1 plasmid (AST-110) or scrambled control (AST-109) that contain a functional asd gene cassette were compared to YS1646 containing pEQU6-shTrex1 (AST-104, a plasmid that lacks an asd gene cassette and therefore does not have a mechanism for plasmid maintenance) for anti-tumor efficacy in a murine colon carcinoma model. For this experiment, 6-8 week-old female BALB/c mice (8 mice per group) were inoculated SC in the right flank with CT26 ($2\times10^5$ cells in 100 μL PBS). Mice bearing established flank tumors were IV injected twice, on day 8 and day 18, with $5\times10^6$ CFUs of AST-109 (ASD transformed with pATI-shScramble), AST-110 (ASD transformed with pATI-shTREX1), or AST-104 (YS1646 transformed with pEQU6-shTREX1) and compared to PBS control.

As shown in FIG. 46, the YS1646 strain AST-104 demonstrated tumor control compared to PBS (70% TGI, day 28) despite its demonstrated plasmid loss over time. The asd strain containing the scramble control in a pATI plasmid with the asd gene complementation system (AST-109) demonstrated tumor control compared to PBS (51% TGI, day 25), indicating that maintained delivery of CpG plasmids stimulates an anti-tumor response. The asd strain containing plasmid with the asd gene complementation system and shTREX1 (AST-110) demonstrated the highest tumor growth inhibition compared to PBS (82% TGI, p=0.002, day 25). These data demonstrate that improved potency is achieved by preventing plasmid loss using the asd complementation system and delivery of shTREX1, as compared to YS1646 containing plasmids without gene complementation systems or shTREX1.

*S. typhimurium* Stains with Low Copy Plasmids Demonstrate Superior Anti-Tumor Efficacy and Tumor Colonization Compared to High Copy Plasmids In order to compare the anti-tumor efficacy of the low copy shTREX1 plasmid with the asd complementation system, relative to the high copy shTREX1 plasmid in a murine model of colon carcinoma, 6-8 week-old female BALB/c mice (10 mice per group) were inoculated SC in the right flank with CT26 ($2\times10^5$ cells in 100 μL PBS). Mice bearing established flank tumors were IV injected with two weekly doses of $5\times10^6$ CFUs of AST-117 (ASD (pATI Low-shTREX1)) or AST-110 (ASD (pATI-shTREX1) and were compared to PBS injections as a negative control. As shown in FIG. 47, the strain with the low copy plasmid, AST-117, demonstrated superior anti-tumor efficacy compared to the strain with the high copy plasmid AST-110 (High 59% TGI, Low 79% TGI, p=0.042, day 25).

At the end of this tumor growth inhibition study, 4 mice from each group were euthanized, and tumors and spleens were homogenized as described above to evaluate tumor colonization and tumor to spleen colonization ratios. As shown in FIG. 48A, the strain containing the low copy plasmid, AST-117, colonized tumors at a level greater than 100 times higher than the strain with the high copy plasmid, AST-110. When the ratio of colonies recovered from tumor and spleen were calculated, AST-117 had a greater than 10-fold higher tumor to spleen colonization ratio compared to AST-110 (FIG. 48B), demonstrating that the strain with the low copy plasmid had greater specificity for tumor colonization than the strain with the high copy plasmid. These data demonstrate a previously unknown attribute that *S. typhimurium* engineered to deliver plasmids encoding interfering RNAs have improved tumor colonizing capabilities and anti-tumor efficacy when the plasmids have low copy number origins of replication.

Example 12

*S. typhimurium* Harvested at Log Vs Stationary Phase Production of Log Vs Stationary Injection Stocks It has been demonstrated that the *Salmonella* pathogenicity island-1 (SPI-1) genes of *Salmonella typhimurium* are induced during logarithmic growth (Lundberg et al. (1999) *Journal Of Bacteriology* 181:3433-3437). This pathogenicity island is essential for uptake in non-phagocytic cells, such as epithelial cells, or cells derived from solid tumors. Induction of SPI-1 genes during late log has also been demonstrated to result in rapid pyroptosis (caspase-1-dependent proinflammatory programmed cell death) of macrophages (Fink et al. (2007) *Cell Microbiol.* 9(11): 2562-2570).

To determine the optimal phase of growth for production of *Salmonella typhimurium*-based immunotherapy, strains were produced by growing overnight cultures in LB at 37° C. with agitation. The overnight cultures were diluted into fresh LB in disposable shaker flasks and grown until the $OD_{600}$ reached 1.0 for late-log phase, or until the culture stopped increasing in OD for stationary phase (approximately 2 hours). The cultures were washed in PBS and suspended in a volume of PBS+15% glycerol that result in a stock concentration $OD_{600}$ of 1.0 for cryopreservation to produce injection stocks at approximately $1\times10^9$ CFU/mL. The injection stocks were then stored at −80° C.

Modified *S. typhimurium* Strains Grown to Stationary Phase Demonstrate Equivalent Anti-Tumor Potency with and Superior Tolerability Compared to Strains Grown to Log Phase To determine the impact that the phase of culture at harvest has on in vivo activity, log vs stationary phase cultures of the modified *Salmonella typhimurium* strains were evaluated in a murine model of colon carcinoma. 6-8 week-old female BALB/c mice (10 mice per group) were inoculated SC in the right flank with CT26 ($2\times10^5$ cells in 100 μL PBS). Mice bearing established flank tumors were IV injected with three weekly doses of $5\times10^6$ CFUs of AST-104 (YS1646 transformed with pEQU6-shTREX1) strains harvested at log or stationary phase, and compared to PBS control. Six hours following the first IV dose, mice were bled, and plasma was collected and assessed for pro-inflammatory cytokines using the Mouse Inflammation Cytometric Bead Array kit and analyzed by FACS (BD Biosciences).

As shown in FIG. 49A, the AST-104 log and AST-104 stationary phase injection stocks demonstrated comparable anti-tumor efficacy compared to the PBS control group (log—67% TGI, p=0.04, stationary—77% p=0.01, day 28), with the stationary phase injection stock demonstrating slightly better tumor growth inhibition. Comparing the levels of systemic serum cytokines at 6 hours post IV injection, the inflammatory cytokines elicited by the log phase injection stock were significantly higher for both TNF-α (p=0.007), and IL-6 (p=0.016), compared to the AST-104 stationary phase strain (FIG. 49B). These data demonstrate that growing bacterial therapeutic strains to stationary phase prior to IV administration can significantly reduce inflammatory toxicity and can improve tumor growth inhibition, indicating that the therapeutic index can be improved with material harvested at stationary phase.

Example 13

Engineering of an Autolytic *S. typhimurium* Strain for Delivery of RNAi

As described above, the asd gene in *S. typhimurium* encodes aspartate semialdehyde dehydrogenase. Deletion of this gene renders the bacteria auxotrophic for diaminopimelic acid (DAP) when grown in vitro or in vivo. This example employs an asd deletion strain (described in Example 1) that is auxotrophic for DAP and contains a plasmid suitable for delivery of RNAi that does not contain an asd-complementing gene so that the strain is defective for replication in vivo. This strain is propagated in vitro in the presence of DAP and grows normally, and then is administered as an immunotherapeutic agent to mammalian hosts where DAP is not present, which results in autolysis of the bacteria. Autolytic strains are able to invade host cells, but are not able to replicate due to the absence of DAP in mammalian tissues; this combination of attributes allows for RNAi-mediated gene knockdown and increased safety relative to replicating strains.

In this example, the asd deleted strain of YS1646 (AST-101, described in Example 1) was further modified to express cytoLLO to generate strain AST-114 (described in Example 9), was electroporated to contain a plasmid encoding ARI-203 (a microRNA targeting TREX1, described in Example 2), to make strain AST-120 (ASD/LLO (pEQU6-miTREX1). When this strain is introduced into tumor bearing mice, the bacteria are expected to be taken up by host cells and enter the *Salmonella* containing vacuole (SCV). In this environment, the lack of DAP is expected to prevent replication, and result in lysis of the bacteria in the SCV. Lysis of AST-120 allows for release of the plasmid, and the accumulated cytoLLO that form pores in the cholesterol-containing SVC membrane, resulting in efficient delivery of the plasmid into the cytosol of the host cell.

The ability of the autolytic strain AST-120, to replicate in LB in the presence or absence of DAP was assessed using a SpectraMax M3 spectrophotometer (Molecular Devices) at 37° C., reading the $OD_{600}$ every 15 minutes. As shown in FIG. 50, AST-120 is able to grow robustly in LB supplemented with 50 μg/mL DAP, but cannot replicate in LB alone.

Increased Attenuation of Autolytic *S. typhimurium* in Mice

To determine whether the autolytic strain AST-120, engineered to deliver cytoLLO and a microRNA targeting TREX1, was attenuated for virulence, a median lethal dose ($LD_{50}$) study was performed. Increasing doses of AST-120, ranging from $1\times10^6$ to $5\times10^7$ CFU, were administered IV to C57BL/6 mice (a strain of mouse that is highly sensitive to LPS). After IV administration, AST-120 was well tolerated at all doses with transient weight loss observed after a single dose. A second dose was administered 7 days after the first dose and one mouse out of four, at the highest dose level ($5\times10^7$ CFU), was found moribund and required euthanasia. All other mice administered AST-120 experienced transient weight loss, but recovered. These data indicate that the $LD_{50}$ for the autolytic strain of *S. typhimurim* delivering a micro-RNA targeting TREX1 (AST-120) is greater than $5\times10^7$ CFU. The $LD_{50}$ for the VNP20009 strain is known to be approximately $5\times10^6$ in C57BL/6 mice (Lee et al. (2000) *International Journal of Toxicology* 19:19-25), demonstrating that AST-120 is at least 10-fold attenuated compared to VNP20009.

Antitumor Activity of Autolytic *S. typhimurium*

To determine whether the autolytic strain AST-120, engineered to deliver cytoLLO and a microRNA targeting TREX1, was able to provide an anti-tumor response, 6-8 week-old female BALB/c mice (10 mice per group) were inoculated SC in the right flank with CT26 ($2\times10^5$ cells in 100 μL PBS). Mice bearing established flank tumors were IV injected with a single dose of $5\times10^6$ CFUs of the autolytic strain AST-120 (ASD/LLO (pEQU6-miTREX1) and compared to mice treated with PBS as a control. As shown in FIG. 51, an antitumor response was detected after only a single dose, compared to animals treated with PBS alone (52.4% TGI, p=0.02, day 17). Together, these data demonstrate that *S. typhimurium* engineered to be autolytic by means of DAP auxotrophy and engineered to contain a plasmid for delivery of RNAi targeting TREX1, are exquisitely attenuated and can elicit an anti-tumor response.

Example 14

Exemplary Strains Engineered for Increased Tolerability adrA or csgD Deletion In this example, a live attenuated strain of *Salmonella typhimurium* that contains a purI deletion, an msbB deletion, an asd gene deletion and is engineered to deliver plasmids encoding interfering RNA, is further modified to delete adrA, a gene required for *Salmonella typhimurium* biofilm formation. *Salmonella* that cannot form biofilms are taken up more rapidly by host phagocytic cells and are cleared more rapidly. This increase in intracellular localization enhances the effectiveness of plasmid delivery and gene knockdown by RNA interference. The increased clearance rate from tumors/tissues increases the tolerability of the therapy, and the lack of biofilm formation prevents colonization of prosthetics and gall bladders in patients. In another example, a live attenuated strain of *Salmonella typhimurium* that contains a purI deletion, an msbB deletion, an asd gene deletion and is engineered to deliver plasmids encoding interfering RNA, is further modified to delete csgD. This gene is responsible for activation of adrA, and also induces expression of the curli fimbriae, a TLR2 agonist. Loss of csgD also prevents biofilm formation, with the added benefit of inhibiting TLR2 activation, thereby further reducing the bacterial virulence and enhancing delivery of RNAi.

pagP Deletion

In this example a live attenuated strain of *S. typhimurium* that contains a purI deletion, an msbB deletion, and an asd gene deletion, and is engineered to deliver plasmids encoding interfering RNA, is further modified to delete pagP. The pagP gene is induced during the infectious life cycle of *S. typhimurium* and encodes an enzyme that palmitylates lipid A. In wild type *S. typhimurium*, expression of pagP results in a lipidA that is hepta-acylated. In an msbB− mutant in which the terminal acyl chain of the lipid A cannot be added, the expression of pagP results in a hexa-acylated LPS. Hexa-acylated LPS has been shown to be the most pro-inflammatory. In this example, a strain deleted of pagP and msbB can produce only penta-acylated LPS, allowing for lower pro-inflammatory cytokines, enhanced tolerability, and increased adaptive immunity when the bacteria are engineered to deliver interfering RNAs.

hilA Deletion

In this example a live attenuated strain of *Salmonella typhimurium* that contains a purI deletion, an msbB deletion, an asd gene deletion and is engineered to deliver plasmids encoding interfering RNA, is further modified to delete hilA. hilA is a regulatory gene that is required for expression of the *salmonella* pathogenicity island-1 (SPI-1)-associated type 3 secretion system (T3SS). This secretion system is responsible for injecting effector proteins into the cytosol of non-phagocytic host cells, such as epithelial cells, that cause the uptake of modified *S. typhimurium*. The SPI-1 T3SS has been shown to be essential for crossing the gut epithelial layer, but is dispensable for infection when bacteria are injected parenterally. The injection of some proteins and the needle complex itself can also induce inflammasome activation and pyroptosis of phagocytic cells. This pro-inflammatory cell death can limit the initiation of a robust adaptive immune response by directly inducing the death of antigen-presenting cells (APCs), as well as modifying the cytokine milieu to prevent the generation of memory T-cells. In this example, the additional deletion of the hilA gene from a therapeutic *Salmonella typhimurium* strain that is administered either intravenously or intratumorally focus the *Salmonella typhimurium* infection towards phagocytic cells that do not require the SPI-1 T3SS for uptake, and then prolong the longevity of these phagocytic cells. The hilA mutation reduces the quantity of pro-inflammatory cytokines, increasing the tolerability of the therapy, as well as the quality of the adaptive immune response.

Example 15

TREX1 Expression is Upregulated in Multiple Human Tumor Types

In order to evaluate whether TREX1 is found upregulated in tumor tissue as compared to normal human tissue, an analysis was performed to assess the relative gene expression of the TREX1 gene using the cancer genome atlas (TCGA) database. As shown in FIG. 52, a broad array of tumor types demonstrated significant upregulation of TREX1 compared to normal tissue, including breast, prostate, uterine, bladder and cervical (p values: BRCA: 7.7e-16; PRAD: 9.4e-12; UCEC: 2.5e-05; BLCA: 3.7e-03; CESC: 7.7e-03). In addition, TREX1 was found upregulated in multiple forms of kidney cancer (p values: KIPAN: 8.9e-39; KIRC: 9.6e-35; KIRP: 5.8e-14; KICH: 4.9e-08). These data validate the phenomenon of TREX1 upregulation broadly correlating with tumor progression, and support its targeting as a promising cancer therapeutic strategy, as provided herein.

Example 16

The Modified *Salmonella typhimurium* pEQU6 Strains Containing shRNA to Multiple Immune Targets Demonstrate Potent Anti-Tumor Growth Inhibition To compare the efficacy of a set of shRNA immune targets in a murine colon tumor flank model, 6-8 week-old female BALB/c mice (10 mice per group) were inoculated SC in the right and left flanks with CT26 ($2\times10^5$ cells in 100 μL PBS). Mice bearing established flank tumors were intratumorally (IT) injected twice, four days apart, on days 10 and 14 post tumor implantation into the right flank tumor with $5\times10^6$ CFUs each of YS1646, YS1646 (pEQU6-shVISTA), YS1646 (pEQU6-shBeta-catenin), or YS1646 (pEQU6-shTGF-beta), and compared to PBS control.

IT injection of AST-121 (YS1646 carrying pEQU6-shVISTA) induced significant tumor growth inhibition in the injected and distal tumors compared to the PBS control (injected tumor=75% TGI, p=0.01; distal tumor TGI=57% TGI, p=0.04), including one complete response, demonstrating the in vivo potency of inhibiting this immune checkpoint using this therapeutic modality. AST-122, (YS1646 carrying pEQU6-shTGF-beta) also demonstrated potent tumor inhibition of both the injected and distal lesions (injected tumor=52%; distal TGI=48.4%). AST-123 (YS1646 carrying pEQU6-shBeta-catenin) demonstrated tumor growth inhibition (injected TGI=33.1%, distal TGI=17% TGI), including one complete response. These strains were prepared in stationary phase instead of log-phase. In log-phase, SPI-1 would be expected to be maximally upregulated, which would have enhanced tumor cell targeting and improved the efficacy of targeting beta-catenin.

Example 17

Radiotherapy Enhances Tumor Colonization of Immunostimulatory Bacteria Containing a Plasmid Encoding a microRNA to TREX1 and Enhances Efficacy in Combination with Immune Checkpoint Blockade Radiation therapy has been shown to synergize with *S. typhimurium* to promote tumor growth inhibition. A previous study demonstrated enhanced tumor growth inhibition with the combination of a single IV administration of $5\times10^5$ CFU of *S. typhimurium* (YS1646) followed by 15 Gy radiation by in a murine B16.F10 melanoma flank model (Bermudes et al. (2001) *Biotechnol Genet Eng Rev.* 18:1).

To determine the effect of radiation on bacterial tumor colonization, 6-8 week-old female BALB/c mice were inoculated subcutaneously in the right flank with $1\times10^5$ mouse TSA breast carcinoma cells (in 100 μL PBS). Mice bearing established tumors were administered the following: 1) PBS IV followed by 0 Gy radiation (1 mouse); 2) IV injection of $5\times10^6$ CFUs of AST-106 (YS1646 transformed with pEQU6-miTREX1, ARI-203), followed 4 hours later with 0 Gy (3 mice); 3) $5\times10^6$ CFUs of AST-106, followed 4 hours later with 20 Gy (3 mice); 4) 20 Gy, followed 4 hours later with $5\times10^6$ CFUs of AST-106 (3 mice). Radiotherapy was administered using an XStrahl SARRP as described in Vanpouille-Box et al. (2017) *Nat Commun.* 8:15618. Mice were sacrificed 24 hours later, and tumors were harvested and weighed. Tumors were homogenized in 10 mL sterile PBS (M tubes, GentleMacs, Miltenyi Biotec), then 10-fold serial dilutions were performed and plated on LB (Luria Broth) agar plates containing kanamycin. The following day, colony forming units (CFUs) were counted and CFU per gram of tumor tissue was calculated.

As shown in FIG. 53, administration of 20 Gy of radiation prior to IV administration of AST-106 resulted in fewer CFU/g than administering AST-106 IV alone, with no radiation. Administration of 20 Gy of radiation after administration of AST-106 IV demonstrated significantly enhanced tumor colonization, compared to the opposite regimen ($p<0.05$).

Experiments are performed to determine whether IV administration of *S. typhimurium* containing shTREX1, prior to administering 20 Gy of radiation, would inhibit the activity of TREX1 and potentiate the abscopal activity of the radiation therapy. As discussed in the detailed description, TREX1 has been shown to suppress the abscopal anti-tumor efficacy of radiation, even with the addition of the checkpoint inhibitor anti-CTLA4. The potentiating effects of administration of the *S. typhimurium* containing shTREX1 prior to administration of the radiation therapy is further enhanced in the presence of anti-CTLA4 or anti-PD-1 therapy.

To demonstrate this, administration of the modified *S. typhimurium* shTREX1 is combined with 20 Gy of radiotherapy in the presence or absence of anti-CTLA4 or anti-PD-1 immune checkpoint blockade in a dual flank TSA murine mammary carcinoma model. For these studies, 6-8 week-old female BALB/c mice are inoculated subcutaneously in the right and left flanks with $1\times10^5$ mouse TSA breast carcinoma cells (in 100 μL PBS). Mice bearing established tumors are administered radiotherapy to the right flank tumor on concurrent days using an XStrahl SARRP as described in Vanpouille-Box et al. ((2017) *Nat Commun.* 8:15618), in two doses of 20 Gy, or 3 fractions of 8 Gy on consecutive days. Mice are administered IV injections beginning 4 hours post the initial radiation treatment and repeated 4 and 7 days later with $1\text{-}5\times10^6$ CFUs of the modified *Salmonella typhimurium* shTREX1, or the modified *Salmonella typhimurium* containing a scrambled shRNA control, (modified *Salmonella typhimurium* scr). Some groups of mice are concurrently administered the checkpoint therapy anti-CTLA4 or anti-PD-1 (100 μg) or isotype control IP twice weekly. Mice are bled seven days following the last IV modified *Salmonella typhimurium* injection and PBMCs assessed for the ability to produce IFN-γ in response to the immunodominant $CD8^+$ T cell epitope AH1 [SPSYVYHQF]-specific tetramer by flow cytometry. Separate groups of mice are harvested for spleen, tumor and tumor-draining lymph nodes 48 hours and 7 days post modified *Salmonella typhimurium* IV treatment and assessed for lymphoid and myeloid populations by flow cytometry, and tissue is assessed for CFUs by homogenization and plating on LB agar plates. Remaining mice are assessed for tumor growth in the primary irradiated tumor and the distal (abscopal) tumor by caliper measurements, and mice that demonstrate complete tumor regression are re-challenged with autologous tumors and compared to age-matched, tumor-naïve mice. Separate groups of mice are depleted of $CD4^+$ and/or $CD8^+$ T cells prior to re-challenge, to demonstrate the requirement for adaptive immunity. These data demonstrate that inhibition of Trex1 in the context of high dose radiation therapy enhances the anti-tumor immunity of the combined immunotherapies.

Example 18

The Addition of Anti-PD-1 Antibody to Modified *Salmonella typhimurium* Therapy Containing Plasmid Encoding Anti-TREX1 microRNA Enhances Distal Tumor Regression in a CD8-Dependent Manner in the Dual Flank Murine Colon Carcinoma Model To demonstrate that addition of anti-PD-1 checkpoint therapy can enhance the efficacy of AST-106 (YS1646 carrying a plasmid encoding a microRNA to TREX1), 6-8 week-old female BALB/c mice (10 mice per group) were inoculated subcutaneously (SC) in the right and left flanks with CT26 ($2\times10^5$ cells in 100 PBS) to establish tumors. Mice bearing established flank tumors were intratumorally (IT) injected on days 10 and 14 post tumor implantation into the right flank tumor with $5\times10^6$ CFUs of AST-106 (YS1646 transformed with pEQU6-miTREX1, ARI-203), or AST-103 (YS1646 transformed with pEQU6-scrambled shRNA), and compared to PBS control, either alone or in combination with weekly IP injections of anti-PD-1 (4 mg/kg, clone RMP1-14, BioXCell). To determine whether the primary and distal tumor efficacy was dependent on $CD8\alpha^+$ T cells and DCs, groups were administered anti-CD8α depleting antibody IP on days 5 and 7, prior to IT injection, and then on days 10, 14 and 17 (4 mg/kg, clone 2.43, BioXCell).

IT injection of AST-106, the YS1646 strain containing a plasmid encoding a miTREX1, induced significant tumor growth inhibition in the injected tumor and distal tumors, compared to PBS control (injected TGI: 67.5%, distal TGI: 67.2%; p=0.027). This anti-tumor activity was completely abrogated with depletion of $CD8\alpha^+$ cells (injected TGI: 14.6%, distal TGI: 0%), demonstrating the requirement for cytolytic $CD8^+$ T cells and $CD8\alpha^+$ DCs for AST-106 anti-tumor activity. The administration of anti-PD-1 antibody with AST-106 further enhances the activity of the AST-106, resulting in 2/10 complete remissions. This effect also was completely reversed upon $CD8\alpha^+$ cell depletion. No other groups of mice, other than those treated with the combination of AST-106 miTREX1 with anti-PD1 mAb, resulted in complete dual flank remissions, including the scramble control (AST-103) with anti-PD-1 antibody, or the anti-PD-1 antibody alone. These data demonstrate that engineered *S. typhimurium* containing a plasmid encoding an anti-TREX1 inhibitory microRNA induces a potent, CD8α-dependent adaptive immune response. This activity is synergistic with anti-PD-1 checkpoint therapy.

Example 19

Examples of Additional Therapeutic Bacteria and Combination Therapy

The table below sets forth, in the first column, targets of the RNA; the second column sets forth combinations of targets encoded by RNA in the plasmid; the third column sets forth the types (format) of the encoded RNA in the plasmids; and the fourth column sets forth exemplary additional therapeutic agents that can be used in combination therapy with the immunostimulatory bacteria in the table, or herein. The next column lists modifications to the genome of the bacterial strain, and the last column describes features of plasmids that can be used. Each of the listed elements in the columns can be matched with any other elements/features listed in the table and provided throughout the disclosure herein. The bacterium can be any therapeutic bacterium, particularly any listed throughout the disclosure herein, such as, but not limited to, *Salmonella, Shigella, E. coli, Bifidobacteriae, Rikettsia, Vibrio, Listeria, Klebsiella, Bordetella, Neisseria, Aeromonas, Franciesella, Cholera, Corynebacterium, Citrobacter, Chlamydia, Hemophilus, Brucella, Mycobacterium, Mycoplasma, Legionella, Rhodococcus, Pseudomonas, Heliobacter, Bacillus*, and *Erysipelothrix*. Exemplary of such bacteria are *Salmonella* strains, such as *S. typhimurium*. Among the *Salmonella typhimurium* strains are the well known strains designated VNP20009 (ATCC #202165), RE88, SL7207, χ8429, χ8431, and χ8468.

| Target | RNAi + RNAi Combinations | RNAi format | Therapeutic Combinations | Therapeutic Strains | Plasmid features |
|---|---|---|---|---|---|
| TREX1 | TREX1 + PD-L1 | shRNA | anti-PD-1 mAb | asd knockout | encodes asd gene |
| PD-L1 | TREX1 + VISTA | microRNA | anti-CTLA4 mAb | purI (purM) knockout | low copy origin |
| VISTA | TREX1 + SIRP-alpha | shRNA with RIG-I binding element | anti-VEGF mAb | msbB knockout | medium copy origin |
| TGF-beta | PD-L1 + TGF-beta | micro RNA with RIG-I binding element (polyA) | Radiation Therapy | cytoLLO knock-in | U6 Promoter |
| beta-catenin | PD-L1 + beta-catenin | | Immunogenic chemotherapy: nimustine, carmustine, fotemustine, topotecan, cisplatin, irinotecan, doxorubicin and etoposide | purD knockout | H1 Promoter |
| SIRP-alpha | PD-L1 + VISTA | | | flagellin (fliC/FljB) knockout | CMV Promoter for RNAi expression |
| VEGF | TGF-beta + VISTA | | | pagP knockout | removable Kan Cassette |
| Rnase H2 | SIRP-alpha + VISTA | | | adrA knockout | SV40 DNA nuclear targeting sequence |

-continued

| Target | RNAi + RNAi Combinations | RNAi format | Therapeutic Combinations | Therapeutic Strains | Plasmid features |
|---|---|---|---|---|---|
| Dnase II | TREX1 + Rnase H2 | | | hilA knockout | CpG sequences |
| CLEVER-1/Stabilin-1 | | | | | |

Since modifications will be apparent to those of skill in the art, it is intended that this invention be limited only by the scope of the appended claims.

What is claimed:

1. An immunostimulatory bacterium, comprising a plasmid encoding a therapeutic product, wherein:

the immunostimulatory bacterium is a *Salmonella* species;

the immunostimulatory bacterium is an adenosine auxotroph;

the immunostimulatory bacterium is flagellin$^-$, whereby the bacterium lacks flagella;

the immunostimulatory bacterium includes deletions in one or more genes, whereby the bacterium is one or more of purI$^-$ (purM$^-$), msbB$^-$, purD$^-$, pagP$^-$, adrA$^-$, csgD$^-$, and hilA$^-$; and the plasmid is present in a copy number of less than 150.

2. The immunostimulatory bacterium of claim 1, wherein: the therapeutic product encoded on the plasmid is inhibitory RNA (RNAi); the RNAi inhibits, suppresses or disrupts expression of an immune checkpoint or other target whose inhibition, suppression or disruption increases the antitumor immune response in a subject; the RNAi is encoded on the plasmid in the bacterium; and the immunostimulatory bacterium further includes a deletion in the gene encoding aspartate-semialdehyde dehydrogenase (asd), whereby the bacterium is asd⁻.

3. The immunostimulatory bacterium of claim 1, wherein the copy number of the plasmid is less than 25.

4. The immunostimulatory bacterium of claim 1, wherein the immunostimulatory bacterium is purI⁻.

5. The immunostimulatory bacterium of claim 1 that further includes a deletion or disruption in the gene encoding the enzyme aspartate-semialdehyde dehydrogenase (asd), whereby the genome of the bacterium does not encode functional aspartate-semialdehyde dehydrogenase (asd).

6. The immunostimulatory bacterium of claim 5, wherein the plasmid that encodes the therapeutic product further encodes asd under control of a bacterial promoter for expression in the bacterium.

7. The immunostimulatory bacterium of claim 1 that further comprises a nucleic acid that includes a CpG motif, wherein:

the CpG motif is recognized by toll-like receptor 9 (TLR9); and the nucleic acid comprising the CpG motif is encoded on the plasmid that encodes the therapeutic product.

8. The immunostimulatory bacterium of claim 1, that further comprises a nucleic acid encoding a CpG motif, wherein the nucleic acid encoding the CpG motif is included in or is part of a bacterial gene that is encoded on the plasmid that encodes the therapeutic product.

9. The immunostimulatory bacterium of claim 2 that further comprises a nucleic acid encoding cytoLLO, which is a listeriolysin O (LLO) protein lacking the signal sequence, wherein the nucleic acid encoding cytoLLO is encoded on the plasmid that encodes the therapeutic product.

10. The immunostimulatory bacterium of claim 1 that further comprises a DNA nuclear targeting sequence (DTS) encoded on the plasmid that encodes the therapeutic product.

11. The immunostimulatory bacterium of claim 1 that further has a deletion or modification in the gene encoding endonuclease-1 (endA), whereby endA activity is inhibited or eliminated.

12. The immunostimulatory bacterium of claim 1 that further comprises one or more of a CpG motif, an asd gene selectable marker for plasmid maintenance, and a DNA nuclear targeting sequence, wherein the CpG motif, asd gene selectable marker, and DNA nuclear targeting sequence are encoded on the plasmid that encodes the therapeutic product.

13. The immunostimulatory bacterium of claim 2, wherein the RNAi is a short hairpin RNA (shRNA) or micro-RNA (miRNA).

14. The immunostimulatory bacterium of claim 1, wherein the plasmid that encodes the therapeutic product further encodes a sequence of nucleotides that is an agonist of retinoic acid-inducible gene I (RIG-I).

15. The immunostimulatory bacterium of claim 1 that is msbB⁻.

16. The immunostimulatory bacterium of claim 1 that comprises:

a purI deletion, an msbB deletion, and an adrA deletion or a csgD deletion; and further comprises an asd deletion.

17. The immunostimulatory bacterium of claim 1, wherein the bacterium is a modified strain of:

an attenuated *Salmonella typhimurium* strain selected from among strains designated as AST-100, VNP20009, YS1646 (ATCC #202165), RE88, SL7207, χ8429, χ8431, and χ8468; or a *Salmonella typhimurium* strain that has all of the identifying characteristics of the strain deposited as ATCC #14028.

18. The immunostimulatory bacterium of claim 1, wherein the bacterium is harvested at stationary phase.

19. The immunostimulatory bacterium of claim 5, wherein:

the plasmid that encodes the therapeutic product does not comprise a sequence of nucleotides encoding aspartate-semialdehyde dehydrogenase (asd), whereby the resulting strain is asd⁻, and the resulting strain has limited replication in vivo.

20. A pharmaceutical composition, comprising the immunostimulatory bacterium of claim 1 in a pharmaceutically acceptable vehicle.

21. A method for producing immunostimulatory bacteria, comprising:

culturing the immunostimulatory bacterium of claim 1 under conditions for growth and replication; and harvesting the resulting culture at stationary phase.

22. The immunostimulatory bacterium of claim 1 that is a Stimulator of Interferon Genes (STING) agonist.

23. The immunostimulatory bacterium of claim 1, wherein the *Salmonella* species is *S. typhimurium*.

24. The immunostimulatory bacterium of claim 1 that is a modified strain of a *Salmonella* strain that has all of the identifying characteristics of the strain deposited as ATCC #14028.

25. The immunostimulatory bacterium of claim 1 that comprises deletions in pagP and msbB, whereby the bacterium is pagP⁻/msbB⁻.

26. The immunostimulatory bacterium of claim 25 that is flagellin⁻ (fliC⁻/fljB⁻), whereby the bacterium lacks flagella.

27. An immunostimulatory bacterium, comprising a plasmid encoding a therapeutic product, wherein:

the immunostimulatory bacterium is a *Salmonella* species;

the immunostimulatory bacterium is an adenosine auxotroph;

the immunostimulatory bacterium has a deletion of a gene involved in biofilm formation;

the immunostimulatory bacterium includes deletions in one or more genes, whereby the bacterium is one or more of purI⁻ (purM⁻), msbB⁻, purD⁻, flagellin⁻ (fliC⁻/fljB⁻), pagP⁻, adrA⁻, and hilA⁻; and the plasmid is present in a copy number of less than 150.

28. The immunostimulatory bacterium of claim 1 that is pagP⁻ and is flagellin⁻ (fliC⁻/fljB⁻), whereby the bacterium lacks flagella.

29. The immunostimulatory bacterium of claim 27, wherein:

the bacterium contains a purI deletion, an msbB deletion, and further contains an asd deletion; and the gene involved in biofilm formation is csgD.

30. The immunostimulatory bacterium of claim 16 that further comprises a deletion in the genome whereby the bacterium is flagellin⁻ (fliC⁻/fljB⁻), whereby the bacterium lacks flagella.

31. The immunostimulatory bacterium of claim 1, wherein the copy number of the plasmid is less than 100.

32. The immunostimulatory bacterium of claim 1, wherein the copy number of the plasmid is less than 30.

33. The immunostimulatory bacterium of claim 27, wherein the copy number of the plasmid is less than 25.

34. The immunostimulatory bacterium of claim 1, wherein the copy number of the plasmid is less than 20.

35. The immunostimulatory bacterium of claim 27 that is flagellin$^-$ (fliC$^-$/fljB$^-$), whereby the bacterium lacks flagella.

36. The immunostimulatory bacterium of claim 27, wherein the copy number of the plasmid is less than 30.

37. An immunostimulatory bacterium, comprising a plasmid encoding a therapeutic product, wherein:

the immunostimulatory bacterium is a *Salmonella* species;

the immunostimulatory bacterium is an adenosine auxotroph;

the genome of the immunostimulatory bacterium is modified to delete or disrupt all or part of the genes encoding flagella subunits, whereby the bacterium lacks flagella; and the plasmid is present in a copy number of less than 150.

38. The immunostimulatory bacterium of claim 37 that further is pagP$^-$.

* * * * *

UNITED STATES PATENT AND TRADEMARK OFFICE

CERTIFICATE OF CORRECTION

PATENT NO. : 11,168,326 B2
APPLICATION NO. : 16/033187
DATED : November 9, 2021
INVENTOR(S) : Thanos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this
Thirteenth Day of December, 2022

Katherine Kelly Vidal
*Director of the United States Patent and Trademark Office*

SEQUENCE LISTING

<160> NUMBER OF SEQ ID NOS: 268

<210> SEQ ID NO 1
<211> LENGTH: 19
<212> TYPE: DNA
<213> ORGANISM: Homo sapiens
<220> FEATURE:
<223> OTHER INFORMATION: Human PD-L1 shRNA target 1

<400> SEQUENCE: 1
gtagagtatg gtagcaata 19

<210> SEQ ID NO 2
<211> LENGTH: 19
<212> TYPE: DNA
<213> ORGANISM: Homo sapiens
<220> FEATURE:
<223> OTHER INFORMATION: Human PD-L1 shRNA target 2

<400> SEQUENCE: 2
gccgactaca agcgaatta 19

<210> SEQ ID NO 3
<211> LENGTH: 19
<212> TYPE: DNA
<213> ORGANISM: Homo sapiens
<220> FEATURE:
<223> OTHER INFORMATION: Human PD-L1 shRNA target 3

<400> SEQUENCE: 3
gacaagcagt gaccatcaa 19

<210> SEQ ID NO 4
<211> LENGTH: 19
<212> TYPE: DNA
<213> ORGANISM: Homo sapiens
<220> FEATURE:
<223> OTHER INFORMATION: Human PD-L1 shRNA target 4

<400> SEQUENCE: 4
gaatcaacac aacaactaa 19

<210> SEQ ID NO 5
<211> LENGTH: 19
<212> TYPE: DNA
<213> ORGANISM: Homo sapiens
<220> FEATURE:
<223> OTHER INFORMATION: Human PD-L1 shRNA target 5

<400> SEQUENCE: 5
gcacatcctc caaatgaaa 19

<210> SEQ ID NO 6
<211> LENGTH: 19
<212> TYPE: DNA
<213> ORGANISM: Homo sapiens
<220> FEATURE:
<223> OTHER INFORMATION: Human PD-L1 shRNA target 6

<400> SEQUENCE: 6
gtagcactga cattcatct 19

<210> SEQ ID NO 7
<211> LENGTH: 19
<212> TYPE: DNA
<213> ORGANISM: Homo sapiens
<220> FEATURE:
<223> OTHER INFORMATION: Human CTNNB1 shRNA target 1

<400> SEQUENCE: 7
gacagactgc cttcaaatt 19

<210> SEQ ID NO 8
<211> LENGTH: 19
<212> TYPE: DNA
<213> ORGANISM: Homo sapiens
<220> FEATURE:
<223> OTHER INFORMATION: Human CTNNB1 shRNA target 2

<400> SEQUENCE: 8
gcagctggaa ttctttcta 19

<210> SEQ ID NO 9
<211> LENGTH: 19
<212> TYPE: DNA
<213> ORGANISM: Homo sapiens
<220> FEATURE:
<223> OTHER INFORMATION: Human CTNNB1 shRNA target 3

<400> SEQUENCE: 9
gactaccagt tgtggttaa 19

<210> SEQ ID NO 10
<211> LENGTH: 19
<212> TYPE: DNA
<213> ORGANISM: Homo sapiens
<220> FEATURE:
<223> OTHER INFORMATION: Human CTNNB1 shRNA target 4

<400> SEQUENCE: 10
ggacacagca gcaatttgt 19

<210> SEQ ID NO 11
<211> LENGTH: 19
<212> TYPE: DNA
<213> ORGANISM: Homo sapiens
<220> FEATURE:
<223> OTHER INFORMATION: Human CTNNB1 shRNA target 5

<400> SEQUENCE: 11
ggatgttcac aaccgaatt 19

<210> SEQ ID NO 12
<211> LENGTH: 19
<212> TYPE: DNA
<213> ORGANISM: Homo sapiens
<220> FEATURE:
<223> OTHER INFORMATION: Human CTNNB1 shRNA target 6

<400> SEQUENCE: 12
gccacaagat tacaagaaa 19

<210> SEQ ID NO 13
<211> LENGTH: 19
<212> TYPE: DNA
<213> ORGANISM: Homo sapiens
<220> FEATURE:
<223> OTHER INFORMATION: Human SIRP-alpha shRNA target 1

<400> SEQUENCE: 13
gccaggtgag gaagttcta 19

<210> SEQ ID NO 14
<211> LENGTH: 19
<212> TYPE: DNA
<213> ORGANISM: Homo sapiens
<220> FEATURE:
<223> OTHER INFORMATION: Human SIRP-alpha shRNA target 2

<400> SEQUENCE: 14
gagctggctc ctggtgaat 19

<210> SEQ ID NO 15
<211> LENGTH: 19
<212> TYPE: DNA
<213> ORGANISM: Homo sapiens
<220> FEATURE:
<223> OTHER INFORMATION: Human SIRP-alpha shRNA target 3

<400> SEQUENCE: 15
gctgagaaca ctggatcta 19

<210> SEQ ID NO 16
<211> LENGTH: 19
<212> TYPE: DNA
<213> ORGANISM: Homo sapiens
<220> FEATURE:
<223> OTHER INFORMATION: Human SIRP-alpha shRNA target 4

<400> SEQUENCE: 16
gaagaatgcc agagaaata 19

<210> SEQ ID NO 17
<211> LENGTH: 19
<212> TYPE: DNA
<213> ORGANISM: Homo sapiens
<220> FEATURE:
<223> OTHER INFORMATION: Human SIRP-alpha shRNA target 5

<400> SEQUENCE: 17
ggacacaaat gatatcaca 19

<210> SEQ ID NO 18
<211> LENGTH: 19
<212> TYPE: DNA
<213> ORGANISM: Homo sapiens
<220> FEATURE:
<223> OTHER INFORMATION: Human SIRP-alpha shRNA target 6

<400> SEQUENCE: 18
ggagtatgcc agcattcag 19

<210> SEQ ID NO 19
<211> LENGTH: 19

<212> TYPE: DNA
<213> ORGANISM: Homo sapiens
<220> FEATURE:
<223> OTHER INFORMATION: Human Trex1 shRNA target 1

<400> SEQUENCE: 19
gcagcgcatg ggcgtcaat 19

<210> SEQ ID NO 20
<211> LENGTH: 19
<212> TYPE: DNA
<213> ORGANISM: Homo sapiens
<220> FEATURE:
<223> OTHER INFORMATION: Human Trex1 shRNA target 2

<400> SEQUENCE: 20
ggcccaagga agagctata 19

<210> SEQ ID NO 21
<211> LENGTH: 19
<212> TYPE: DNA
<213> ORGANISM: Homo sapiens
<220> FEATURE:
<223> OTHER INFORMATION: Human Trex1 shRNA target 3

<400> SEQUENCE: 21
gcaccatcag gcccatgta 19

<210> SEQ ID NO 22
<211> LENGTH: 19
<212> TYPE: DNA
<213> ORGANISM: Homo sapiens
<220> FEATURE:
<223> OTHER INFORMATION: Human Trex1 shRNA target 4

<400> SEQUENCE: 22
gccacaacca ggaacacta 19

<210> SEQ ID NO 23
<211> LENGTH: 19
<212> TYPE: DNA
<213> ORGANISM: Homo sapiens
<220> FEATURE:
<223> OTHER INFORMATION: Human Trex1 shRNA target 5

<400> SEQUENCE: 23
gcaggggtac caaggatct 19

<210> SEQ ID NO 24
<211> LENGTH: 19
<212> TYPE: DNA
<213> ORGANISM: Homo sapiens
<220> FEATURE:
<223> OTHER INFORMATION: Human Trex1 shRNA target 6

<400> SEQUENCE: 24
gccacactgt atggactat 19

<210> SEQ ID NO 25
<211> LENGTH: 19
<212> TYPE: DNA
<213> ORGANISM: Homo sapiens
<220> FEATURE:
<223> OTHER INFORMATION: Human VISTA shRNA target 1

<400> SEQUENCE: 25
gatgtgacct tctacaaga 19

<210> SEQ ID NO 26
<211> LENGTH: 19
<212> TYPE: DNA
<213> ORGANISM: Homo sapiens
<220> FEATURE:
<223> OTHER INFORMATION: Human VISTA shRNA target 2

<400> SEQUENCE: 26
gaccaccatg gcaacttct 19

<210> SEQ ID NO 27
<211> LENGTH: 19
<212> TYPE: DNA
<213> ORGANISM: Homo sapiens
<220> FEATURE:
<223> OTHER INFORMATION: Human VISTA shRNA target 3

<400> SEQUENCE: 27
ggtgcagaca ggcaaagat 19

<210> SEQ ID NO 28
<211> LENGTH: 19
<212> TYPE: DNA
<213> ORGANISM: Homo sapiens
<220> FEATURE:
<223> OTHER INFORMATION: Human VISTA shRNA target 4

<400> SEQUENCE: 28
gtgcctgcat cgtaggaat 19

<210> SEQ ID NO 29
<211> LENGTH: 19
<212> TYPE: DNA
<213> ORGANISM: Homo sapiens
<220> FEATURE:
<223> OTHER INFORMATION: Human VISTA shRNA target 5

<400> SEQUENCE: 29
gcaacattca agggattga 19

<210> SEQ ID NO 30
<211> LENGTH: 19
<212> TYPE: DNA
<213> ORGANISM: Homo sapiens
<220> FEATURE:
<223> OTHER INFORMATION: Human VISTA shRNA target 6

<400> SEQUENCE: 30
gtccctgact ctccaaact 19

<210> SEQ ID NO 31
<211> LENGTH: 870
<212> TYPE: DNA
<213> ORGANISM: Homo sapiens
<220> FEATURE:
<223> OTHER INFORMATION: programmed death-ligand 1 (PD-L1), isoform 1

<400> SEQUENCE: 31
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240

```
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg atacacattt ggaggagacg                                     870
```

<210> SEQ ID NO 32
<211> LENGTH: 2343
<212> TYPE: DNA
<213> ORGANISM: Homo sapiens
<220> FEATURE:
<223> OTHER INFORMATION: CTNNB1 (Beta-catenin), isoform 1

<400> SEQUENCE: 32

```
atggctactc aagctgattt gatggagttg gacatggcca tggaaccaga cagaaaagcg     60
gctgttagtc actggcagca acagtcttac ctggactctg gaatccattc tggtgccact    120
accacagctc cttctctgag tggtaaaggc aatcctgagg aagaggatgt ggatacctcc    180
caagtcctgt atgagtggga acagggattt tctcagtcct tcactcaaga acaagtagct    240
gatattgatg gacagtatgc aatgactcga gctcagaggg tacgagctgc tatgttccct    300
gagacattag atgagggcat gcagatccca tctacacagt ttgatgctgc tcatcccact    360
aatgtccagc gtttggctga accatcacag atgctgaaac atgcagttgt aaacttgatt    420
aactatcaag atgatgcaga acttgccaca cgtgcaatcc ctgaactgac aaaactgcta    480
aatgacgagg accaggtggt ggttaataag gctgcagtta tggtccatca gctttctaaa    540
aaggaagctt ccagacacgc tatcatgcgt tctcctcaga tggtgtctgc tattgtacgt    600
accatgcaga atacaaatga tgtagaaaca gctcgttgta ccgctgggac cttgcataac    660
ctttcccatc atcgtgaggg cttactggcc atctttaagt ctggaggcat tcctgccctg    720
gtgaaaatgc ttggttcacc agtggattct gtgttgtttt atgccattac aactctccac    780
aaccttttat tacatcaaga aggagctaaa atggcagtgc gtttagctgg tgggctgcag    840
aaaatggttg ccttgctcaa caaaacaaat gttaaattct tggctattac gacagactgc    900
cttcaaattt tagcttatgg caaccaagaa agcaagctca tcatactggc tagtggtgga    960
ccccaagctt tagtaaatat aatgaggacc tatacttacg aaaaactact gtggaccaca   1020
agcagagtgc tgaaggtgct atctgtctgc tctagtaata agccggctat tgtagaagct   1080
ggtggaatgc aagctttagg acttcacctg acagatccaa gtcaacgtct tgttcagaac   1140
tgtctttgga ctctcaggaa tctttcagat gctgcaacta aacaggaagg gatggaaggt   1200
ctccttggga ctcttgttca gcttctgggt tcagatgata taaatgtggt cacctgtgca   1260
gctggaattc tttctaacct cacttgcaat aattataaga acaagatgat ggtctgccaa   1320
gtgggtggta tagaggctct tgtgcgtact gtccttcggg ctggtgacag ggaagacatc   1380
```

-continued

```
actgagcctg ccatctgtgc tcttcgtcat ctgaccagcc gacaccaaga agcagagatg   1440

gcccagaatg cagttcgcct tcactatgga ctaccagttg tggttaagct cttacaccca   1500

ccatcccact ggcctctgat aaaggctact gttggattga ttcgaaatct tgccctttgt   1560

cccgcaaatc atgcaccttt gcgtgagcag ggtgccattc cacgactagt tcagttgctt   1620

gttcgtgcac atcaggatac ccagcgccgt acgtccatgg gtgggacaca gcagcaattt   1680

gtggaggggg tccgcatgga agaaatagtt gaaggttgta ccggagccct tcacatccta   1740

gctcgggatg ttcacaaccg aattgttatc agaggactaa ataccattcc attgtttgtg   1800

cagctgcttt attctcccat tgaaaacatc caaagagtag ctgcaggggt cctctgtgaa   1860

cttgctcagg acaaggaagc tgcagaagct attgaagctg agggagccac agctcctctg   1920

acagagttac ttcactctag gaatgaaggt gtggcgacat atgcagctgc tgttttgttc   1980

cgaatgtctg aggacaagcc acaagattac aagaaacggc tttcagttga gctgaccagc   2040

tctctcttca gaacagagcc aatggcttgg aatgagactg ctgatcttgg acttgatatt   2100

ggtgcccagg gagaacccct tggatatcgc caggatgatc ctagctatcg ttcttttcac   2160

tctggtggat atggccagga tgccttgggt atggacccca tgatggaaca tgagatgggt   2220

ggccaccacc ctggtgctga ctatccagtt gatgggctgc cagatctggg gcatgcccag   2280

gacctcatgg atgggctgcc tccaggtgac agcaatcagc tggcctggtt tgatactgac   2340

ctg                                                                 2343
```

<210> SEQ ID NO 33
<211> LENGTH: 1512
<212> TYPE: DNA
<213> ORGANISM: Homo sapiens
<220> FEATURE:
<223> OTHER INFORMATION: signal regulatory protein alpha (SIRP-alpha) isoform 1

<400> SEQUENCE: 33

```
atggagcccg ccggcccggc ccccggccgc ctcgggccgc tgctctgcct gctgctcgcc     60

gcgtcctgcg cctggtcagg agtggcgggt gaggaggagc tgcaggtgat tcagcctgac    120

aagtccgtgt tggttgcagc tggagagaca gccactctgc gctgcactgc gacctctctg    180

atccctgtgg ggcccatcca gtggttcaga ggagctggac caggccggga attaatctac    240

aatcaaaaag aaggccactt cccccgggta acaactgttt cagacctcac aaagagaaac    300

aacatggact tttccatccg catcggtaac atcaccccag cagatgccgg cacctactac    360

tgtgtgaagt tccggaaagg gagccccgat gacgtggagt ttaagtctgg agcaggcact    420

gagctgtctg tgcgcgccaa accctctgcc cccgtggtat cgggccctgc ggcgagggcc    480

acacctcagc acacagtgag cttcacctgc gagtcccacg gcttctcacc cagagacatc    540

accctgaaat ggttcaaaaa tgggaatgag ctctcagact tccagaccaa cgtggacccc    600

gtaggagaga gcgtgtccta cagcatccac agcacagcca aggtggtgct gacccgcgag    660

gacgttcact ctcaagtcat ctgcgaggtg gcccacgtca ccttgcaggg ggaccctctt    720

cgtgggactg ccaacttgtc tgagaccatc cgagttccac ccaccttgga ggttactcaa    780

cagcccgtga gggcagagaa ccaggtgaat gtcacctgcc aggtgaggaa gttctacccc    840

cagagactac agctgacctg gttggagaat ggaaacgtgt cccggacaga aacggcctca    900

accgttacag agaacaagga tggtacctac aactggatga gctggctcct ggtgaatgta    960

tctgcccaca gggatgatgt gaagctcacc tgccaggtgg agcatgacgg gcagccagcg   1020
```

gtcagcaaaa gccatgacct gaaggtctca gcccacccga aggagcaggg ctcaaatacc 1080
gccgctgaga acactggatc taatgaacgg aacatctata ttgtggtggg tgtggtgtgc 1140
accttgctgg tggccctact gatggcggcc ctctacctcg tccgaatcag acagaagaaa 1200
gcccagggct ccacttcttc tacaaggttg catgagcccg agaagaatgc cagagaaata 1260
acacaggaca caaatgatat cacatatgca gacctgaacc tgcccaaggg gaagaagcct 1320
gctccccagg ctgcggagcc caacaaccac acggagtatg ccagcattca gaccagcccg 1380
cagcccgcgt cggaggacac cctcacctat gctgacctgg acatggtcca cctcaaccgg 1440
acccccaagc agccggcccc caagcctgag ccgtccttct cagagtacgc cagcgtccag 1500
gtcccgagga ag 1512

<210> SEQ ID NO 34
<211> LENGTH: 1108
<212> TYPE: DNA
<213> ORGANISM: Homo sapiens
<220> FEATURE:
<223> OTHER INFORMATION: TREX1 isoform 1

<400> SEQUENCE: 34
aatgggccct ggagctcgca gacagggcag gattgtgcag ggaaggcctg agatgtgctt 60
ctgcccaccc cctaccccac tccctcccct tcggatctta acactgggca ctcacacacc 120
caccccatgc tcctctccag gctcagcagc aggtacgtac ccaaccatgg gctcgcaggc 180
cctgcccccg gggcccatgc agaccctcat ctttttcgac atggaggcca ctggcttgcc 240
cttctcccag cccaaggtca cggagctgtg cctgctggct gtccacagat gtgccctgga 300
gagccccccc acctctcagg ggccacctcc cacagttcct ccaccaccgc gtgtggtaga 360
caagctctcc ctgtgtgtgg ctccggggaa ggcctgcagc cctgcagcca gcgagatcac 420
aggtctgagc acagctgtgc tggcagcgca tgggcgtcaa tgttttgatg acaacctggc 480
caacctgctc ctagccttcc tgcggcgcca gccacagccc tggtgcctgg tggcacacaa 540
tggtgaccgc tacgacttcc ccctgctcca agcagagctg gctatgctgg gcctcaccag 600
tgctctggat ggtgccttct gtgtggatag catcactgcg ctgaaggccc tggagcgagc 660
aagcagcccc tcagaacacg gcccaaggaa gagctatagc ctaggcagca tctacactcg 720
cctgtatggg cagtcccctc cagactcgca cacggctgag ggtgatgtcc tggccctgct 780
cagcatctgt cagtggagac cacaggccct gctgcggtgg gtggatgctc acgccaggcc 840
tttcggcacc atcaggccca tgtatggggt cacagcctct gctaggacca agccaagacc 900
atctgctgtc acaaccactg cacacctggc cacaaccagg aacactagtc ccagccttgg 960
agagagcagg ggtaccaagg atcttcctcc agtgaaggac cctggagccc tatccaggga 1020
ggggctgctg gccccactgg gtctgctggc catcctgacc ttggcagtag ccacactgta 1080
tggactatcc ctggccacac ctggggag 1108

<210> SEQ ID NO 35
<211> LENGTH: 933
<212> TYPE: DNA
<213> ORGANISM: Homo sapiens
<220> FEATURE:
<223> OTHER INFORMATION: V-domain Ig suppressor of T cell activation
(VISTA)

<400> SEQUENCE: 35
atgggcgtcc ccacggccct ggaggccggc agctggcgct ggggatccct gctcttcgct 60

-continued

```
ctcttcctgg ctgcgtccct aggtccggtg gcagccttca aggtcgccac gccgtattcc    120

ctgtatgtct gtcccgaggg gcagaacgtc accctcacct gcaggctctt gggccctgtg    180

gacaaagggc acgatgtgac cttctacaag acgtggtacc gcagctcgag gggcgaggtg    240

cagacctgct cagagcgccg gcccatccgc aacctcacgt tccaggacct tcacctgcac    300

catggaggcc accaggctgc caacaccagc cacgacctgg ctcagcgcca cgggctggag    360

tcggcctccg accaccatgg caacttctcc atcaccatgc gcaacctgac cctgctggat    420

agcggcctct actgctgcct ggtggtggag atcaggcacc accactcgga gcacagggtc    480

catggtgcca tggagctgca ggtgcagaca ggcaaagatg caccatccaa ctgtgtggtg    540

tacccatcct cctcccagga tagtgaaaac atcacggctg cagccctggc tacgggtgcc    600

tgcatcgtag gaatcctctg cctccccctc atcctgctcc tggtctacaa gcaaaggcag    660

gcagcctcca accgccgtgc ccaggagctg gtgcggatgg acagcaacat tcaagggatt    720

gaaaaccccg gctttgaagc ctcaccacct gcccagggga tacccgaggc caaagtcagg    780

cacccccctgt cctatgtggc ccagcggcag ccttctgagt ctgggcggca tctgctttcg    840

gagcccagca cccccctgtc tcctccaggc cccggagacg tcttcttccc atccctggac    900

cctgtccctg actctccaaa ctttgaggtc atc                                 933
```

<210> SEQ ID NO 36
<211> LENGTH: 45
<212> TYPE: DNA
<213> ORGANISM: Artificial Sequence
<220> FEATURE:
<223> OTHER INFORMATION: shRNA-encoding sequence for huPD-L1

<400> SEQUENCE: 36

```
gtagagtatg gtagcaatat ctagagtatt gctaccatac tctac                     45
```

<210> SEQ ID NO 37
<211> LENGTH: 45
<212> TYPE: DNA
<213> ORGANISM: Artificial Sequence
<220> FEATURE:
<223> OTHER INFORMATION: shRNA-encoding sequence for huCTNNB1

<400> SEQUENCE: 37

```
gacagactgc cttcaaattt ctagagaatt tgaaggcagt ctgtc                     45
```

<210> SEQ ID NO 38
<211> LENGTH: 45
<212> TYPE: DNA
<213> ORGANISM: Artificial Sequence
<220> FEATURE:
<223> OTHER INFORMATION: shRNA-encoding sequence for huSIRPalpha

<400> SEQUENCE: 38

```
gccaggtgag gaagttctat ctagagtaga acttcctcac ctggc                     45
```

<210> SEQ ID NO 39
<211> LENGTH: 45
<212> TYPE: DNA
<213> ORGANISM: Artificial Sequence
<220> FEATURE:
<223> OTHER INFORMATION: shRNA-encoding sequence for huTREX1

<400> SEQUENCE: 39

```
gcagcgcatg ggcgtcaatt ctagagattg acgcccatgc gctgc                     45
```

<210> SEQ ID NO 40
<211> LENGTH: 45
<212> TYPE: DNA
<213> ORGANISM: Artificial Sequence
<220> FEATURE:
<223> OTHER INFORMATION: shRNA-encoding sequence for huVISTA

<400> SEQUENCE: 40
gaccaccatg gcaacttctt ctagagagaa gttgccatgg tggtc 45

<210> SEQ ID NO 41
<211> LENGTH: 3220
<212> TYPE: DNA
<213> ORGANISM: Artificial Sequence
<220> FEATURE:
<223> OTHER INFORMATION: pEQU6 vector

<400> SEQUENCE: 41
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga ctggatccaa ggtcgggcag gaagagggcc 720
tatttcccat gattccttca tatttgcata tacgatacaa ggctgttaga gagataatta 780
gaattaattt gactgtaaac acaaagatat tagtacaaaa tacgtgacgt agaaagtaat 840
aatttcttgg gtagtttgca gttttaaaat tatgttttaa aatggactat catatgctta 900
ccgtaacttg aaagtatttc gatttcttgg ctttatatat cttgtggaaa ggacgaaact 960
agtttttctt cgagtagcta gagaattcat ggtaatagcg atgactaata cgtagatgta 1020
ctgccaagta ggaaagtccc ataaggtcat gtactgggca taatgccagg cgggccattt 1080
accgtcattg acgtcaatag ggggcgtact tggcatatga tacacttgat gtactgccaa 1140
gtgggcagtt taccgtaaat agtccaccca ttgacgtcaa tggaaagtcc ctattggcgt 1200
tactatggga acatacgtca ttattgacgt caatgggcgg gggtcgttgg gcggtcagcc 1260
aggcgggcca tttaccgtaa gttatgtaac gcggaactcc atatatgggc tatgaactaa 1320
tgaccccgta attgattact attaataact agacccagct ttcttgtaca aagttggcat 1380
tataagaaag cattgcttat caatttgttg caacgaacag gtcactatca gtcaaaataa 1440
aatcattatt tgccatccag ctgatatccc ctatagtgag tcgtattaca tggtcatagc 1500
tgtttcctgg cagctctggc ccgtgtctca aaatctctga tgttacattg cacaagataa 1560
aaatatatca tcatgaacaa taaaactgtc tgcttacata aacagtaata caaggggtgt 1620
tatgagccat attcaacggg aaacgtcgag gccgcgatta aattccaaca tggatgctga 1680
tttatatggg tataaatggg ctcgcgataa tgtcgggcaa tcaggtgcga caatctatcg 1740

```
cttgtatggg aagcccgatg cgccagagtt gtttctgaaa catggcaaag gtagcgttgc   1800
caatgatgtt acagatgaga tggtcagact aaactggctg acggaattta tgcctcttcc   1860
gaccatcaag cattttatcc gtactcctga tgatgcatgg ttactcacca ctgcgatccc   1920
cggaaaaaca gcattccagg tattagaaga atatcctgat tcaggtgaaa atattgttga   1980
tgcgctggca gtgttcctgc gccggttgca ttcgattcct gtttgtaatt gtccttttaa   2040
cagcgatcgc gtatttcgtc tcgctcaggc gcaatcacga atgaataacg gtttggttga   2100
tgcgagtgat tttgatgacg agcgtaatgg ctggcctgtt gaacaagtct ggaaagaaat   2160
gcataaactt ttgccattct caccggattc agtcgtcact catggtgatt tctcacttga   2220
taaccttatt tttgacgagg ggaaattaat aggttgtatt gatgttggac gagtcggaat   2280
cgcagaccga taccaggatc ttgccatcct atggaactgc ctcggtgagt tttctccttc   2340
attacagaaa cggctttttc aaaaatatgg tattgataat cctgatatga ataaattgca   2400
gtttcatttg atgctcgatg agtttttcta atcagaattg gttaattggt tgtaacactg   2460
gcagagcatt acgctgactt gacgggacgg cgcaagctca tgaccaaaat cccttaacgt   2520
gagttacgcg tcgttccact gagcgtcaga ccccgtagaa aagatcaaag gatcttcttg   2580
agatcctttt tttctgcgcg taatctgctg cttgcaaaca aaaaaaccac cgctaccagc   2640
ggtggtttgt ttgccggatc aagagctacc aactcttttt ccgaaggtaa ctggcttcag   2700
cagagcgcag ataccaaata ctgtccttct agtgtagccg tagttaggcc accacttcaa   2760
gaactctgta gcaccgccta catacctcgc tctgctaatc ctgttaccag tggctgctgc   2820
cagtggcgat aagtcgtgtc ttaccgggtt ggactcaaga cgatagttac cggataaggc   2880
gcagcggtcg ggctgaacgg ggggttcgtg cacacagccc agcttggagc gaacgaccta   2940
caccgaactg agatacctac agcgtgagca ttgagaaagc gccacgcttc ccgaagggag   3000
aaaggcggac aggtatccgg taagcggcag ggtcggaaca ggagagcgca cgagggagct   3060
tccaggggga aacgcctggt atctttatag tcctgtcggg tttcgccacc tctgacttga   3120
gcgtcgattt ttgtgatgct cgtcaggggg gcggagccta tggaaaaacg ccagcaacgc   3180
ggccttttta cggttcctgg ccttttgctg gccttttgct                         3220
```

<210> SEQ ID NO 42
<211> LENGTH: 3802
<212> TYPE: DNA
<213> ORGANISM: Artificial Sequence
<220> FEATURE:
<223> OTHER INFORMATION: pEQU6-H1 Vector

<400> SEQUENCE: 42

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
```

```
ctgttcgttg caacaaattg atgagcaatg ctttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg tttttgtcga cagatctggc gcgccatagt ggccagcggc    840
cgcaggtaag ccagcccagg cctcgccctc cagctcaagg cgggacaggt gccctagagt    900
agcctgcatc cagggacagg ccccagccgg gtgctgacac gtccacctcc atctcttcct    960
caggtctgcc cgggtggcat ccctgtgacc cctccccagt gcctctcctg gccctggaag   1020
ttgccactcc agtgcccacc agccttgtcc taataaaatt aagttgcatc attttgtctg   1080
actaggtgtc cttctataat attatggggt ggaggggggt ggtatggagc aaggggccca   1140
agttaacttg tttattgcag cttataatgg ttacaaataa agcaatagca tcacaaattt   1200
cacaaataaa gcattttttt cactgcattc tagttgtggt ttgtccaaac tcatcaatgt   1260
atcttatcat gtctggatcc aaggtcgggc aggaagaggg cctatttccc atgattcctt   1320
catatttgca tatacgatac aaggctgtta gagagataat tagaattaat ttgactgtaa   1380
acacaaagat attagtacaa aatacgtgac gtagaaagta ataatttctt gggtagtttg   1440
cagttttaaa attatgtttt aaaatggact atcatatgct taccgtaact tgaaagtatt   1500
tcgatttctt ggctttatat atcttgtgga aaggacgaaa ctagtttttt ctcgagtagc   1560
tagagaattc atggtaatag cgatgactaa tacgtagatg tactgccaag taggaaagtc   1620
ccataaggtc atgtactggg cataatgcca ggcgggccat ttaccgtcat tgacgtcaat   1680
agggggcgta cttggcatat gatacacttg atgtactgcc aagtgggcag tttaccgtaa   1740
atagtccacc cattgacgtc aatggaaagt ccctattggc gttactatgg gaacatacgt   1800
cattattgac gtcaatgggc gggggtcgtt gggcggtcag ccaggcgggc catttaccgt   1860
aagttatgta acgcggaact ccatatatgg gctatgaact aatgaccccg taattgatta   1920
ctattaataa ctagacccag ctttcttgta caaagttggc attataagaa agcattgctt   1980
atcaatttgt tgcaacgaac aggtcactat cagtcaaaat aaaatcatta tttgccatcc   2040
agctgatatc ccctatagtg agtcgtatta catggtcata gctgtttcct ggcagctctg   2100
gcccgtgtct caaaatctct gatgttacat tgcacaagat aaaaatatat catcatgaac   2160
aataaaactg tctgcttaca taaacagtaa tacaaggggt gttatgagcc atattcaacg   2220
ggaaacgtcg aggccgcgat taaattccaa catggatgct gatttatatg ggtataaatg   2280
ggctcgcgat aatgtcgggc aatcaggtgc gacaatctat cgcttgtatg ggaagcccga   2340
tgcgccagag ttgtttctga aacatggcaa aggtagcgtt gccaatgatg ttacagatga   2400
gatggtcaga ctaaactggc tgacggaatt tatgcctctt ccgaccatca agcattttat   2460
ccgtactcct gatgatgcat ggttactcac cactgcgatc cccggaaaaa cagcattcca   2520
ggtattagaa gaatatcctg attcaggtga aaatattgtt gatgcgctgg cagtgttcct   2580
gcgccggttg cattcgattc ctgtttgtaa ttgtcctttt aacagcgatc gcgtatttcg   2640
tctcgctcag gcgcaatcac gaatgaataa cggtttggtt gatgcgagtg attttgatga   2700
cgagcgtaat ggctggcctg ttgaacaagt ctggaaagaa atgcataaac ttttgccatt   2760
ctcaccggat tcagtcgtca ctcatggtga tttctcactt gataacctta tttttgacga   2820
ggggaaatta ataggttgta ttgatgttgg acgagtcgga atcgcagacc gataccagga   2880
tcttgccatc ctatggaact gcctcggtga gttttctcct tcattacaga aacggctttt   2940
```

-continued

```
tcaaaaatat ggtattgata atcctgatat gaataaattg cagtttcatt tgatgctcga   3000

tgagtttttc taatcagaat tggttaattg gttgtaacac tggcagagca ttacgctgac   3060

ttgacgggac ggcgcaagct catgaccaaa atcccttaac gtgagttacg cgtcgttcca   3120

ctgagcgtca gaccccgtag aaaagatcaa aggatcttct tgagatcctt tttttctgcg   3180

cgtaatctgc tgcttgcaaa caaaaaaacc accgctacca gcggtggttt gtttgccgga   3240

tcaagagcta ccaactcttt ttccgaaggt aactggcttc agcagagcgc agataccaaa   3300

tactgtcctt ctagtgtagc cgtagttagg ccaccacttc aagaactctg tagcaccgcc   3360

tacatacctc gctctgctaa tcctgttacc agtggctgct gccagtggcg ataagtcgtg   3420

tcttaccggg ttggactcaa gacgatagtt accggataag gcgcagcggt cgggctgaac   3480

ggggggttcg tgcacacagc ccagcttgga gcgaacgacc tacaccgaac tgagatacct   3540

acagcgtgag cattgagaaa gcgccacgct tcccgaaggg agaaaggcgg acaggtatcc   3600

ggtaagcggc agggtcggaa caggagagcg cacgagggag cttccagggg gaaacgcctg   3660

gtatctttat agtcctgtcg ggtttcgcca cctctgactt gagcgtcgat ttttgtgatg   3720

ctcgtcaggg gggcggagcc tatggaaaaa cgccagcaac gcggcctttt tacggttcct   3780

ggccttttgc tggccttttg ct                                            3802
```

<210> SEQ ID NO 43
<211> LENGTH: 3263
<212> TYPE: DNA
<213> ORGANISM: Artificial Sequence
<220> FEATURE:
<223> OTHER INFORMATION: pEQU6-shPDL1-shRNA Vector

<400> SEQUENCE: 43

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga ctggatccaa ggtcgggcag gaagagggcc    720

tatttcccat gattccttca tatttgcata tacgatacaa ggctgttaga gagataatta    780

gaattaattt gactgtaaac acaaagatat tagtacaaaa tacgtgacgt agaaagtaat    840

aatttcttgg gtagtttgca gttttaaaat tatgttttaa aatggactat catatgctta    900

ccgtaacttg aaagtatttc gatttcttgg ctttatatat cttgtggaaa ggacgaaact    960

aggtagagta tggtagcaat atctagagta ttgctaccat actctacttt tttcgagtag   1020

ctagagaatt catggtaata gcgatgacta atacgtagat gtactgccaa gtaggaaagt   1080

cccataaggt catgtactgg gcataatgcc aggcgggcca tttaccgtca ttgacgtcaa   1140

tagggggcgt acttggcata tgatacactt gatgtactgc caagtgggca gtttaccgta   1200
```

-continued

```
aatagtccac ccattgacgt caatggaaag tccctattgg cgttactatg ggaacatacg   1260
tcattattga cgtcaatggg cgggggtcgt tgggcggtca gccaggcggg ccatttaccg   1320
taagttatgt aacgcggaac tccatatatg ggctatgaac taatgacccc gtaattgatt   1380
actattaata actagaccca gctttcttgt acaaagttgg cattataaga aagcattgct   1440
tatcaatttg ttgcaacgaa caggtcacta tcagtcaaaa taaaatcatt atttgccatc   1500
cagctgatat cccctatagt gagtcgtatt acatggtcat agctgtttcc tggcagctct   1560
ggcccgtgtc tcaaaatctc tgatgttaca ttgcacaaga taaaaatata tcatcatgaa   1620
caataaaact gtctgcttac ataaacagta atacaagggg tgttatgagc catattcaac   1680
gggaaacgtc gaggccgcga ttaaattcca acatggatgc tgatttatat gggtataaat   1740
gggctcgcga taatgtcggg caatcaggtg cgacaatcta tcgcttgtat gggaagcccg   1800
atgcgccaga gttgtttctg aaacatggca aaggtagcgt tgccaatgat gttacagatg   1860
agatggtcag actaaactgg ctgacggaat ttatgcctct tccgaccatc aagcatttta   1920
tccgtactcc tgatgatgca tggttactca ccactgcgat ccccggaaaa acagcattcc   1980
aggtattaga agaatatcct gattcaggtg aaaatattgt tgatgcgctg gcagtgttcc   2040
tgcgccggtt gcattcgatt cctgtttgta attgtccttt taacagcgat cgcgtatttc   2100
gtctcgctca ggcgcaatca cgaatgaata acggtttggt tgatgcgagt gattttgatg   2160
acgagcgtaa tggctggcct gttgaacaag tctggaaaga aatgcataaa cttttgccat   2220
tctcaccgga ttcagtcgtc actcatggtg atttctcact tgataacctt atttttgacg   2280
aggggaaatt aataggttgt attgatgttg gacgagtcgg aatcgcagac cgataccagg   2340
atcttgccat cctatggaac tgcctcggtg agttttctcc ttcattacag aaacggcttt   2400
ttcaaaaata tggtattgat aatcctgata tgaataaatt gcagtttcat ttgatgctcg   2460
atgagttttt ctaatcagaa ttggttaatt ggttgtaaca ctggcagagc attacgctga   2520
cttgacggga cggcgcaagc tcatgaccaa aatcccttaa cgtgagttac gcgtcgttcc   2580
actgagcgtc agaccccgta gaaaagatca aaggatcttc ttgagatcct ttttttctgc   2640
gcgtaatctg ctgcttgcaa acaaaaaaac caccgctacc agcggtggtt tgtttgccgg   2700
atcaagagct accaactctt tttccgaagg taactggctt cagcagagcg cagataccaa   2760
atactgtcct tctagtgtag ccgtagttag gccaccactt caagaactct gtagcaccgc   2820
ctacatacct cgctctgcta atcctgttac cagtggctgc tgccagtggc gataagtcgt   2880
gtcttaccgg gttggactca agacgatagt taccggataa ggcgcagcgg tcgggctgaa   2940
cggggggttc gtgcacacag cccagcttgg agcgaacgac ctacaccgaa ctgagatacc   3000
tacagcgtga gcattgagaa agcgccacgc ttcccgaagg gagaaaggcg gacaggtatc   3060
cggtaagcgg cagggtcgga acaggagagc gcacgaggga gcttccaggg ggaaacgcct   3120
ggtatcttta tagtcctgtc gggtttcgcc acctctgact tgagcgtcga tttttgtgat   3180
gctcgtcagg ggggcggagc ctatggaaaa acgccagcaa cgcggccttt ttacggttcc   3240
tggccttttg ctggcctttt gct                                           3263
```

<210> SEQ ID NO 44
<211> LENGTH: 3888
<212> TYPE: DNA
<213> ORGANISM: Artificial Sequence
<220> FEATURE:
<223> OTHER INFORMATION: pEQU6-shPDL1-H1-shCTNNB1 Vector

<400> SEQUENCE: 44

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg acagactgcc ttcaaatttc tagagaattt gaaggcagtc    840
tgtctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accccctccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct actttttcg agtagctaga gaattcatgg taatagcgat gactaatacg    1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
```

gatgctgatt tatatgggta taaatgggct cgcgataatg tcgggcaatc aggtgcgaca 2400
atctatcgct tgtatgggaa gcccgatgcg ccagagttgt ttctgaaaca tggcaaaggt 2460
agcgttgcca atgatgttac agatgagatg gtcagactaa actggctgac ggaatttatg 2520
cctcttccga ccatcaagca ttttatccgt actcctgatg atgcatggtt actcaccact 2580
gcgatccccg gaaaaacagc attccaggta ttagaagaat atcctgattc aggtgaaaat 2640
attgttgatg cgctggcagt gttcctgcgc cggttgcatt cgattcctgt ttgtaattgt 2700
ccttttaaca gcgatcgcgt atttcgtctc gctcaggcgc aatcacgaat gaataacggt 2760
ttggttgatg cgagtgattt tgatgacgag cgtaatggct ggcctgttga acaagtctgg 2820
aaagaaatgc ataaactttt gccattctca ccggattcag tcgtcactca tggtgatttc 2880
tcacttgata accttatttt tgacgagggg aaattaatag gttgtattga tgttggacga 2940
gtcggaatcg cagaccgata ccaggatctt gccatcctat ggaactgcct cggtgagttt 3000
tctccttcat tacagaaacg gctttttcaa aaatatggta ttgataatcc tgatatgaat 3060
aaattgcagt ttcatttgat gctcgatgag tttttctaat cagaattggt taattggttg 3120
taacactggc agagcattac gctgacttga cgggacggcg caagctcatg accaaaatcc 3180
cttaacgtga gttacgcgtc gttccactga gcgtcagacc ccgtagaaaa gatcaaagga 3240
tcttcttgag atcctttttt tctgcgcgta atctgctgct tgcaaacaaa aaaaccaccg 3300
ctaccagcgg tggtttgttt gccggatcaa gagctaccaa ctctttttcc gaaggtaact 3360
ggcttcagca gagcgcagat accaaatact gtccttctag tgtagccgta gttaggccac 3420
cacttcaaga actctgtagc accgcctaca tacctcgctc tgctaatcct gttaccagtg 3480
gctgctgcca gtggcgataa gtcgtgtctt accgggttgg actcaagacg atagttaccg 3540
gataaggcgc agcggtcggg ctgaacgggg ggttcgtgca cacagcccag cttggagcga 3600
acgacctaca ccgaactgag atacctacag cgtgagcatt gagaaagcgc cacgcttccc 3660
gaagggagaa aggcggacag gtatccggta agcggcaggg tcggaacagg agagcgcacg 3720
agggagcttc cagggggaaa cgcctggtat ctttatagtc ctgtcgggtt tcgccacctc 3780
tgacttgagc gtcgattttt gtgatgctcg tcaggggggc ggagcctatg gaaaaacgcc 3840
agcaacgcgg cctttttacg gttcctggcc ttttgctggc cttttgct 3888

<210> SEQ ID NO 45
<211> LENGTH: 3888
<212> TYPE: DNA
<213> ORGANISM: Artificial Sequence
<220> FEATURE:
<223> OTHER INFORMATION: pEQU6-shPDL1-H1-shSIRPalpha Vector

<400> SEQUENCE: 45
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480

-continued

```
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg ccaggtgagg aagttctatc tagagtagaa cttcctcacc    840
tggctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accccctccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct actttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
```

-continued

```
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct               3888
```

```
<210> SEQ ID NO 46
<211> LENGTH: 3888
<212> TYPE: DNA
<213> ORGANISM: Artificial Sequence
<220> FEATURE:
<223> OTHER INFORMATION: pEQU6-shPDL1-H1-shTREX1

<400> SEQUENCE: 46
```

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg cagcgcatgg gcgtcaattc tagagattga cgcccatgcg    840
ctgctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
```

-continued catccctgtg accccctcccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560
tatatcttgt ggaaaggacg aaactaggta gagtatggta gcaatatcta gagtattgct 1620
accatactct actttttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800
actgccaagt gggcagttta ccgtaaatag tccacccatt gacgtcaatg gaaagtccct 1860
attggcgtta ctatgggaac atacgtcatt attgacgtca atgggcgggg gtcgttgggc 1920
ggtcagccag gcgggccatt taccgtaagt tatgtaacgc ggaactccat atatgggcta 1980
tgaactaatg accccgtaat tgattactat taataactag acccagcttt cttgtacaaa 2040
gttggcatta taagaaagca ttgcttatca atttgttgca acgaacaggt cactatcagt 2100
caaaataaaa tcattatttg ccatccagct gatatcccct atagtgagtc gtattacatg 2160
gtcatagctg tttcctggca gctctggccc gtgtctcaaa atctctgatg ttacattgca 2220
caagataaaa atatatcatc atgaacaata aaactgtctg cttacataaa cagtaataca 2280
aggggtgtta tgagccatat tcaacgggaa acgtcgaggc cgcgattaaa ttccaacatg 2340
gatgctgatt tatatgggta taaatgggct cgcgataatg tcgggcaatc aggtgcgaca 2400
atctatcgct tgtatgggaa gcccgatgcg ccagagttgt ttctgaaaca tggcaaaggt 2460
agcgttgcca atgatgttac agatgagatg gtcagactaa actggctgac ggaatttatg 2520
cctcttccga ccatcaagca ttttatccgt actcctgatg atgcatggtt actcaccact 2580
gcgatccccg gaaaaacagc attccaggta ttagaagaat atcctgattc aggtgaaaat 2640
attgttgatg cgctggcagt gttcctgcgc cggttgcatt cgattcctgt ttgtaattgt 2700
ccttttaaca gcgatcgcgt atttcgtctc gctcaggcgc aatcacgaat gaataacggt 2760
ttggttgatg cgagtgattt tgatgacgag cgtaatggct ggcctgttga acaagtctgg 2820
aaagaaatgc ataaactttt gccattctca ccggattcag tcgtcactca tggtgatttc 2880
tcacttgata accttatttt tgacgagggg aaattaatag gttgtattga tgttggacga 2940
gtcggaatcg cagaccgata ccaggatctt gccatcctat ggaactgcct cggtgagttt 3000
tctccttcat tacagaaacg gctttttcaa aaatatggta ttgataatcc tgatatgaat 3060
aaattgcagt ttcatttgat gctcgatgag tttttctaat cagaattggt taattggttg 3120
taacactggc agagcattac gctgacttga cgggacggcg caagctcatg accaaaatcc 3180
cttaacgtga gttacgcgtc gttccactga gcgtcagacc ccgtagaaaa gatcaaagga 3240
tcttcttgag atcctttttt tctgcgcgta atctgctgct tgcaaacaaa aaaaccaccg 3300
ctaccagcgg tggtttgttt gccggatcaa gagctaccaa ctctttttcc gaaggtaact 3360
ggcttcagca gagcgcagat accaaatact gtccttctag tgtagccgta gttaggccac 3420
cacttcaaga actctgtagc accgcctaca tacctcgctc tgctaatcct gttaccagtg 3480
gctgctgcca gtggcgataa gtcgtgtctt accgggttgg actcaagacg atagttaccg 3540
gataaggcgc agcggtcggg ctgaacgggg ggttcgtgca cacagcccag cttggagcga 3600
acgacctaca ccgaactgag atacctacag cgtgagcatt gagaaagcgc cacgcttccc 3660
gaagggagaa aggcggacag gtatccggta agcggcaggg tcggaacagg agagcgcacg 3720
agggagcttc cagggggaaa cgcctggtat ctttatagtc ctgtcgggtt tcgccacctc 3780
tgacttgagc gtcgattttt gtgatgctcg tcaggggggc ggagcctatg gaaaaacgcc 3840
agcaacgcgg cctttttacg gttcctggcc ttttgctggc cttttgct 3888

<210> SEQ ID NO 47
<211> LENGTH: 3888
<212> TYPE: DNA
<213> ORGANISM: Artificial Sequence
<220> FEATURE:
<223> OTHER INFORMATION: pEQU6-shPDL1-H1-shVISTA

<400> SEQUENCE: 47
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg accaccatgg caacttcttc tagagagaag ttgccatggt 840
ggtctttttt cgacagatct ggcgcgccat agtggccagc ggccgcaggt aagccagccc 900
aggcctcgcc ctccagctca aggcgggaca ggtgccctag agtagcctgc atccagggac 960
aggccccagc cgggtgctga cacgtccacc tccatctctt cctcaggtct gcccgggtgg 1020
catccctgtg accccctccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560

-continued tatatcttgt ggaaaggacg aaactaggta gagtatggta gcaatatcta gagtattgct 1620
accatactct actttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800
actgccaagt gggcagttta ccgtaaatag tccacccatt gacgtcaatg gaaagtccct 1860
attggcgtta ctatgggaac atacgtcatt attgacgtca atgggcgggg gtcgttgggc 1920
ggtcagccag gcgggccatt taccgtaagt tatgtaacgc ggaactccat atatgggcta 1980
tgaactaatg accccgtaat tgattactat taataactag acccagcttt cttgtacaaa 2040
gttggcatta taagaaagca ttgcttatca atttgttgca acgaacaggt cactatcagt 2100
caaaataaaa tcattatttg ccatccagct gatatcccct atagtgagtc gtattacatg 2160
gtcatagctg tttcctggca gctctggccc gtgtctcaaa atctctgatg ttacattgca 2220
caagataaaa atatatcatc atgaacaata aaactgtctg cttacataaa cagtaataca 2280
aggggtgtta tgagccatat tcaacgggaa acgtcgaggc cgcgattaaa ttccaacatg 2340
gatgctgatt tatatgggta taaatgggct cgcgataatg tcgggcaatc aggtgcgaca 2400
atctatcgct tgtatgggaa gcccgatgcg ccagagttgt ttctgaaaca tggcaaaggt 2460
agcgttgcca atgatgttac agatgagatg gtcagactaa actggctgac ggaatttatg 2520
cctcttccga ccatcaagca ttttatccgt actcctgatg atgcatggtt actcaccact 2580
gcgatccccg gaaaaacagc attccaggta ttagaagaat atcctgattc aggtgaaaat 2640
attgttgatg cgctggcagt gttcctgcgc cggttgcatt cgattcctgt ttgtaattgt 2700
ccttttaaca gcgatcgcgt atttcgtctc gctcaggcgc aatcacgaat gaataacggt 2760
ttggttgatg cgagtgattt tgatgacgag cgtaatggct ggcctgttga acaagtctgg 2820
aaagaaatgc ataaactttt gccattctca ccggattcag tcgtcactca tggtgatttc 2880
tcacttgata accttatttt tgacgagggg aaattaatag gttgtattga tgttggacga 2940
gtcggaatcg cagaccgata ccaggatctt gccatcctat ggaactgcct cggtgagttt 3000
tctccttcat tacagaaacg gctttttcaa aaatatggta ttgataatcc tgatatgaat 3060
aaattgcagt ttcatttgat gctcgatgag tttttctaat cagaattggt taattggttg 3120
taacactggc agagcattac gctgacttga cgggacggcg caagctcatg accaaaatcc 3180
cttaacgtga gttacgcgtc gttccactga gcgtcagacc ccgtagaaaa gatcaaagga 3240
tcttcttgag atcctttttt tctgcgcgta atctgctgct tgcaaacaaa aaaaccaccg 3300
ctaccagcgg tggtttgttt gccggatcaa gagctaccaa ctctttttcc gaaggtaact 3360
ggcttcagca gagcgcagat accaaatact gtccttctag tgtagccgta gttaggccac 3420
cacttcaaga actctgtagc accgcctaca tacctcgctc tgctaatcct gttaccagtg 3480
gctgctgcca gtggcgataa gtcgtgtctt accgggttgg actcaagacg atagttaccg 3540
gataaggcgc agcggtcggg ctgaacgggg ggttcgtgca cacagcccag cttggagcga 3600
acgacctaca ccgaactgag atacctacag cgtgagcatt gagaaagcgc cacgcttccc 3660
gaagggagaa aggcggacag gtatccggta agcggcaggg tcggaacagg agagcgcacg 3720
agggagcttc caggggaaa cgcctggtat ctttatagtc ctgtcgggtt tcgccacctc 3780
tgacttgagc gtcgattttt gtgatgctcg tcaggggggc ggagcctatg gaaaaacgcc 3840
agcaacgcgg cctttttacg gttcctggcc ttttgctggc cttttgct 3888

<210> SEQ ID NO 48
<211> LENGTH: 1104
<212> TYPE: DNA
<213> ORGANISM: Salmonella typhimurium
<220> FEATURE:
<223> OTHER INFORMATION: Strain LT2 Aspartate-semialdehyde dehydrogenase (asd)

<400> SEQUENCE: 48
atgaaaaatg ttggttttat cggctggcgc ggaatggtcg gctctgttct catgcaacgc 60
atggtagagg agcgcgattt cgacgctatt cgccctgttt tcttttctac ctcccagttt 120
ggacaggcgg cgcccacctt cggcgacacc tccaccggca cgctacagga cgcttttgat 180
ctggatgcgc taaaagcgct cgatatcatc gtgacctgcc agggcggcga ttataccaac 240
gaaatttatc caaagctgcg cgaaagcgga tggcagggtt actggattga tgcggcttct 300
acgctgcgca tgaaagatga tgccattatt attctcgacc cggtcaacca ggacgtgatt 360
accgacggcc tgaacaatgg cgtgaagacc tttgtgggcg gtaactgtac cgttagcctg 420
atgttgatgt cgctgggcgg tctctttgcc cataatctcg ttgactgggt atccgtcgcg 480
acctatcagg ccgcctccgg cggcggcgcg cgccatatgc gcgagctgtt aacccagatg 540
ggtcagttgt atggccatgt cgccgatgaa ctggcgacgc cgtcttccgc aattcttgat 600
attgaacgca aagttacggc attgacccgc agcggcgagc tgccggttga taactttggc 660
gtaccgctgg cgggaagcct gatcccctgg atcgacaaac agctcgataa cggccagagc 720
cgcgaagagt ggaaaggcca ggcggaaacc aacaagattc tcaatactgc ctctgtgatt 780
ccggttgatg gtttgtgtgt gcgcgtcggc gcgctgcgct gtcacagcca ggcgttcacc 840
atcaagctga aaaaagaggt atccattccg acggtggaag aactgctggc ggcacataat 900
ccgtgggcga aagtggtgcc gaacgatcgt gatatcacta tgcgcgaatt aaccccggcg 960
gcggtgaccg gcacgttgac tacgccggtt ggtcgtctgc gtaagctgaa catggggcca 1020
gagttcttgt cggcgtttac cgtaggcgac cagttgttat ggggcgccgc cgagccgctg 1080
cgtcgaatgc tgcgccagtt ggcg 1104

<210> SEQ ID NO 49
<211> LENGTH: 861
<212> TYPE: DNA
<213> ORGANISM: Salmonella typhimurium
<220> FEATURE:
<223> OTHER INFORMATION: Strain LT2 TSX

<400> SEQUENCE: 49
atgaaaaaaa ctttactcgc agtcagcgca gcgctggcgc tcacctcatc ttttactgct 60
aacgcagcag aaaatgatca gccgcagtat ttgtccgact ggtggcacca gagcgtaaac 120
gtggtaggca gctaccatac ccgtttctcg ccgaaattga acaacgacgt ctatctggaa 180
tatgaagcat ttgccaaaaa agactggttt gatttctacg gctatatcga tattcccaaa 240
acctttgatt ggggtaacgg caacgataaa ggtatctggt ccgacggttc tccgctgttc 300
atggaaatcg aaccgcgttt ctcaattgat aagctgaccg gcgcagacct gagcttcggc 360
ccgtttaaag agtggtattt cgccaacaac tacatctacg atatgggcga taacaaagcc 420
agccgccaga gcacgtggta tatgggtctg ggaccgata tcgacaccgg cctgccgatg 480
ggtctgtcgc tgaacgtgta tgcgaaatat cagtggcaaa actacggcgc gtccaatgaa 540
aacgaatggg acggctaccg tttcaaagtg aaatacttcg tccccatcac cgatctgtgg 600
ggcggtaaac tgagctatat cggctttacc aactttgact ggggatctga tttaggcgac 660
gatccgaacc gtaccagcaa ctccatcgct tccagccata tcctggcgct gaactacgat 720
cactggcact actcggtcgt tgcgcgttac ttccataacg gcggacagtg gcagaatggc 780
gcaaaactga actggggcga cggcgatttc agcgcgaaat ctaccggctg gggcggctac 840
ctggtcgtgg gttacaactt c 861

<210> SEQ ID NO 50
<211> LENGTH: 864
<212> TYPE: DNA
<213> ORGANISM: Homo sapiens
<220> FEATURE:
<223> OTHER INFORMATION: programmed cell death protein 1 (PD-1)

<400> SEQUENCE: 50
atgcagatcc cacaggcgcc ctggccagtc gtctgggcgg tgctacaact gggctggcgg 60
ccaggatggt tcttagactc cccagacagg ccctggaacc cccccacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggcc 240
gccttccccg aggaccgcag ccagcccggc caggactgcc gcttccgtgt cacacaactg 300
cccaacgggc gtgacttcca catgagcgtg gtcagggccc ggcgcaatga cagcggcacc 360
tacctctgtg gggccatctc cctggccccc aaggcgcaga tcaaagagag cctgcgggca 420
gagctcaggg tgacagagag aagggcagaa gtgcccacag cccaccccag cccctcaccc 480
aggccagccg gccagttcca aaccctggtg gttggtgtcg tgggcggcct gctgggcagc 540
ctggtgctgc tagtctgggt cctggccgtc atctgctccc gggccgcacg agggacaata 600
ggagccaggc gcaccggcca gcccctgaag gaggacccct cagccgtgcc tgtgttctct 660
gtggactatg gggagctgga tttccagtgg cgagagaaga ccccggagcc ccccgtgccc 720
tgtgtccctg agcagacgga gtatgccacc attgtctttc ctagcggaat gggcacctca 780
tcccccgccc gcaggggctc agctgacggc cctcggagtg cccagccact gaggcctgag 840
gatggacact gctcttggcc cctc 864

<210> SEQ ID NO 51
<211> LENGTH: 933
<212> TYPE: DNA
<213> ORGANISM: Homo sapiens
<220> FEATURE:
<223> OTHER INFORMATION: programmed cell death protein 2 (PD-2,) isoform
1

<400> SEQUENCE: 51
atggctgccg ccggggccag gcctgtggag ctgggcttcg ccgagtcggc gccggcgtgg 60
cgactgcgca gcgagcagtt ccccagcaag gtgtatgcgc cgctgcctgg ccgcccggac 120
gccttccacc gctgcatctt cctcttctgc tgccgcgagc agccgtgctg tgccggcctg 180
cgagttttta ggaatcaact acccaggaaa aacgattttt actcatatga gccaccttct 240
gagaatcctc ccccagaaac aggagaatca gtgtgtctcc agcttaagtc tggtgctcat 300
ctctgcaggg tttgtggctg tttaggcccc aaaacgtgct ccagatgcca caaagcatat 360
tactgcagca aggagcatca gaccctagac tggagattgg gacataagca ggcttgtgca 420
caaccagatc atctggacca tataattcca gaccacaact tcctttttcc agaatttgaa 480
attgtaatag aaacagaaga tgagattatg cctgaggttg tggaaaagga agattactca 540
gagattatag ggagcatggg tgaagcactt gaggaagaac tggattccat ggcaaaacat 600
gaatccaggg aagataaaat ttttcagaag tttaaaactc agatagccct tgaaccagaa 660
cagattctta gatatggcag aggtattgcc cccatctgga tttctggtga aaatattcct 720
caagaaaagg atattccaga ttgcccctgt ggtgccaaga gaatattgga attccaggtc 780
atgcctcagc tcctaaacta cctgaaggct gacagactgg gcaagagcat tgactggggc 840
atcctggctg tcttcacctg tgctgagagc tgcagcttgg gtactggcta tacagaagaa 900
tttgtgtgga agcaggatgt aacagataca ccg 933

<210> SEQ ID NO 52
<211> LENGTH: 819
<212> TYPE: DNA
<213> ORGANISM: Homo sapiens
<220> FEATURE:
<223> OTHER INFORMATION: programmed death-ligand 2 (PD-L2), isoform 1

<400> SEQUENCE: 52
atgatcttcc tcctgctaat gttgagcctg gaattgcagc ttcaccagat agcagcttta 60
ttcacagtga cagtccctaa ggaactgtac ataatagagc atggcagcaa tgtgaccctg 120
gaatgcaact ttgacactgg aagtcatgtg aaccttggag caataacagc cagtttgcaa 180
aaggtggaaa atgatacatc cccacaccgt gaaagagcca ctttgctgga ggagcagctg 240
cccctaggga aggcctcgtt ccacatacct caagtccaag tgagggacga aggacagtac 300
caatgcataa tcatctatgg ggtcgcctgg gactacaagt acctgactct gaaagtcaaa 360
gcttcctaca ggaaaataaa cactcacatc ctaaaggttc cagaaacaga tgaggtagag 420
ctcacctgcc aggctacagg ttatcctctg gcagaagtat cctggccaaa cgtcagcgtt 480
cctgccaaca ccagccactc caggacccct gaaggcctct accaggtcac cagtgttctg 540
cgcctaaagc caccccctgg cagaaacttc agctgtgtgt tctggaatac tcacgtgagg 600
gaacttactt tggccagcat tgaccttcaa agtcagatgg aacccaggac ccatccaact 660
tggctgcttc acattttcat cccctcctgc atcattgctt tcattttcat agccacagtg 720
atagccctaa gaaaacaact ctgtcaaaag ctgtattctt caaaagacac aacaaaaaga 780
cctgtcacca caacaaagag ggaagtgaac agtgctatc 819

<210> SEQ ID NO 53
<211> LENGTH: 669
<212> TYPE: DNA
<213> ORGANISM: Homo sapiens
<220> FEATURE:
<223> OTHER INFORMATION: cytotoxic T-lymphocyte-associated protein 4
(CTLA-4), isoform 1

<400> SEQUENCE: 53
atggcttgcc ttggatttca gcggcacaag gctcagctga acctggctac caggacctgg 60
ccctgcactc tcctgttttt tcttctcttc atccctgtct tctgcaaagc aatgcacgtg 120
gcccagcctg ctgtggtact ggccagcagc cgaggcatcg ccagctttgt gtgtgagtat 180
gcatctccag gcaaagccac tgaggtccgg gtgacagtgc ttcggcaggc tgacagccag 240
gtgactgaag tctgtgcggc aacctacatg atggggaatg agttgacctt cctagatgat 300
tccatctgca cgggcacctc cagtggaaat caagtgaacc tcactatcca aggactgagg 360
gccatggaca cgggactcta catctgcaag gtggagctca tgtacccacc gccatactac 420
ctgggcatag gcaacggaac ccagatttat gtaattgatc cagaaccgtg cccagattct 480
gacttcctcc tctggatcct tgcagcagtt agttcggggt tgttttttta tagctttctc 540
ctcacagctg tttctttgag caaaatgcta aagaaaagaa gccctcttac aacaggggtc 600
tatgtgaaaa tgcccccaac agagccagaa tgtgaaaagc aatttcagcc ttattttatt 660
cccatcaat 669

<210> SEQ ID NO 54
<211> LENGTH: 969
<212> TYPE: DNA
<213> ORGANISM: Homo sapiens
<220> FEATURE:
<223> OTHER INFORMATION: CD47 transcript variant 1

<400> SEQUENCE: 54
atgtggcccc tggtagcggc gctgttgctg ggctcggcgt gctgcggatc agctcagcta 60
ctatttaata aaacaaaatc tgtagaattc acgttttgta atgacactgt cgtcattcca 120
tgctttgtta ctaatatgga ggcacaaaac actactgaag tatacgtaaa gtggaaattt 180
aaaggaagag atatttacac ctttgatgga gctctaaaca agtccactgt ccccactgac 240
tttagtagtg caaaaattga agtctcacaa ttactaaaag gagatgcctc tttgaagatg 300
gataagagtg atgctgtctc acacacagga aactacactt gtgaagtaac agaattaacc 360
agagaaggtg aaacgatcat cgagctaaaa tatcgtgttg tttcatggtt ttctccaaat 420
gaaaatattc ttattgttat tttcccaatt tttgctatac tcctgttctg ggacagttt 480 ggtattaaaa cacttaaata tagatccggt ggtatggatg agaaaacaat tgctttactt 540
gttgctggac tagtgatcac tgtcattgtc attgttggag ccattctttt cgtcccaggt 600
gaatattcat taaagaatgc tactggcctt ggtttaattg tgacttctac agggatatta 660
atattacttc actactatgt gtttagtaca gcgattggat taacctcctt cgtcattgcc 720
atattggtta ttcaggtgat agcctatatc ctcgctgtgg ttggactgag tctctgtatt 780
gcggcgtgta taccaatgca tggccctctt ctgatttcag gtttgagtat cttagctcta 840
gcacaattac ttggactagt ttatatgaaa tttgtggctt ccaatcagaa gactatacaa 900
cctcctagga aagctgtaga ggaacccctt aatgcattca aagaatcaaa aggaatgatg 960
aatgatgaa 969

<210> SEQ ID NO 55
<211> LENGTH: 1209
<212> TYPE: DNA
<213> ORGANISM: Homo sapiens
<220> FEATURE:
<223> OTHER INFORMATION: indoleamine 2,3-dioxygenase (IDO) 1

<400> SEQUENCE: 55
atggcacacg ctatggaaaa ctcctggaca atcagtaaag agtaccatat tgatgaagaa 60
gtgggctttg ctctgccaaa tccacaggaa aatctacctg atttttataa tgactggatg 120
ttcattgcta aacatctgcc tgatctcata gagtctggcc agcttcgaga aagagttgag 180
aagttaaaca tgctcagcat tgatcatctc acagaccaca agtcacagcg ccttgcacgt 240
ctagttctgg gatgcatcac catggcatat gtgtggggca aaggtcatgg agatgtccgt 300
aaggtcttgc caagaaatat tgctgttcct tactgccaac tctccaagaa actggaactg 360
cctcctattt tggtttatgc agactgtgtc ttggcaaact ggaagaaaaa ggatcctaat 420
aagcccctga cttatgagaa catggacgtt ttgttctcat ttcgtgatgg agactgcagt 480
aaaggattct tcctggtctc tctattggtg gaaatagcag ctgcttctgc aatcaaagta 540

-continued

```
attcctactg tattcaaggc aatgcaaatg caagaacggg acactttgct aaaggcgctg    600

ttggaaatag cttcttgctt ggagaaagcc cttcaagtgt ttcaccaaat ccacgatcat    660

gtgaacccaa aagcattttt cagtgttctt cgcatatatt tgtctggctg gaaaggcaac    720

ccccagctat cagacggtct ggtgtatgaa aggttctggg aagacccaaa ggagtttgca    780

gggggcagtg caggccaaag cagcgtcttt cagtgctttg acgtcctgct gggcatccag    840

cagactgctg gtggaggaca tgctgctcag ttcctccagg acatgagaag atatatgcca    900

ccagctcaca ggaacttcct gtgctcatta gagtcaaatc cctcagtccg tgagtttgtc    960

ctttcaaaag gtgatgctgg cctgcgggaa gcttatgacg cctgtgtgaa agctctggtc   1020

tccctgagga gctaccatct gcaaatcgtg actaagtaca tcctgattcc tgcaagccag   1080

cagccaaagg agaataagac ctctgaagac ccttcaaaac tggaagccaa aggaactgga   1140

ggcactgatt taatgaattt cctgaagact gtaagaagta caactgagaa atcccttttg   1200

aaggaaggt                                                           1209
```

```
<210> SEQ ID NO 56
<211> LENGTH: 1260
<212> TYPE: DNA
<213> ORGANISM: Homo sapiens
<220> FEATURE:
<223> OTHER INFORMATION: indoleamine 2,3-dioxygenase (IDO) 2

<400> SEQUENCE: 56

atgttgcatt ttcattatta tgatacttca aacaaaataa tggagcccca cagaccgaat     60

gtgaagacag cagtgccatt gtctttggaa agctatcaca tatctgaaga gtatggcttt    120

cttcttccag attctctgaa agaacttcca gatcattata ggccttggat ggaaattgcc    180

aacaaacttc ctcaattgat tgatgctcac cagcttcaag ctcatgtgga caagatgccc    240

ctgctgagct gccagttcct gaagggtcac cgggagcagc gcctggccca cctggtcctg    300

agcttcctca ccatgggtta tgtctggcag gaaggagagg cgcagcctgc agaggtcctg    360

ccaaggaatc ttgcccttcc atttgtcgaa gtctccagga acttggggct ccctcctatc    420

ctggtccact cagacttggt gctgacgaac tggaccaaaa aagatccaga cggattcctg    480

gaaattggga acctggagac catcatctca tttcctgggg gagagagcct gcatggtttt    540

atactggtga ctgctttggt agagaaagaa gcagtgcctg ggataaaggc tcttgttcag    600

gccacgaatg ctatcttgca gcccaaccag gaggccctgc tccaagccct gcagcgactg    660

agactgtcta ttcaggacat caccaaaacc ttaggacaga tgcatgatta tgtagatcca    720

gacatatttt atgcaggcat ccggatcttt ctctctggat ggaaagacaa cccagcaatg    780

cctgcagggc tgatgtatga aggagtttcc caagagcccc tgaaatactc cggcgggagt    840

gcagctcaga gcacagtgct tcatgccttt gatgagttct taggcattcg tcatagcaag    900

gaaagtggtg actttctgta cagaatgagg gattacatgc ctccttccca taaggccttc    960

atagaagaca tccactcagc accttccctg agggactaca tcctgtcatc tggacaggac   1020

cacttgctga cagcttataa ccagtgtgtg caggccctgg cagagctgcg gagctatcac   1080

atcaccatgg tcaccaaata cctcatcaca gctgcagcca aggcaaagca tgggaagcca   1140

aaccatctcc cagggcctcc tcaggcttta aaagacaggg gcacaggtgg aaccgcagtt   1200

atgagctttc ttaagagtgt cagggataag accttggagt caatccttca cccacgtggt   1260
```

```
<210> SEQ ID NO 57
<211> LENGTH: 2310
```

-continued

<212> TYPE: DNA
<213> ORGANISM: Homo sapiens
<220> FEATURE:
<223> OTHER INFORMATION: signal transducer and activator of
      transcription 3 (STAT3)

<400> SEQUENCE: 57

```
atggcccaat ggaatcagct acagcagctt gacacacggt acctggagca gctccatcag      60

ctctacagtg acagcttccc aatggagctg cggcagtttc tggccccttg gattgagagt     120

caagattggg catatgcggc cagcaaagaa tcacatgcca ctttggtgtt tcataatctc     180

ctgggagaga ttgaccagca gtatagccgc ttcctgcaag agtcgaatgt tctctatcag     240

cacaatctac gaagaatcaa gcagtttctt cagagcaggt atcttgagaa gccaatggag     300

attgcccgga ttgtggcccg gtgcctgtgg gaagaatcac gccttctaca gactgcagcc     360

actgcggccc agcaaggggg ccaggccaac caccccacag cagccgtggt gacggagaag     420

cagcagatgc tggagcagca ccttcaggat gtccggaaga gagtgcagga tctagaacag     480

aaaatgaaag tggtagagaa tctccaggat gactttgatt tcaactataa aaccctcaag     540

agtcaaggag acatgcaaga tctgaatgga aacaaccagt cagtgaccag gcagaagatg     600

cagcagctgg aacagatgct cactgcgctg gaccagatgc ggagaagcat cgtgagtgag     660

ctggcggggc ttttgtcagc gatggagtac gtgcagaaaa ctctcacgga cgaggagctg     720

gctgactgga agaggcggca acagattgcc tgcattggag gcccgcccaa catctgccta     780

gatcggctag aaaactggat aacgtcatta gcagaatctc aacttcagac ccgtcaacaa     840

attaagaaac tggaggagtt gcagcaaaaa gtttcctaca aaggggaccc cattgtacag     900

caccggccga tgctggagga gagaatcgtg gagctgttta gaaacttaat gaaaagtgcc     960

tttgtggtgg agcggcagcc ctgcatgccc atgcatcctg accggcccct cgtcatcaag    1020

accggcgtcc agttcactac taaagtcagg ttgctggtca aattccctga gttgaattat    1080

cagcttaaaa ttaaagtgtg cattgacaaa gactctgggg acgttgcagc tctcagagga    1140

tcccggaaat ttaacattct gggcacaaac acaaaagtga tgaacatgga agaatccaac    1200

aacggcagcc tctctgcaga attcaaacac ttgaccctga gggagcagag atgtgggaat    1260

gggggccgag ccaattgtga tgcttccctg attgtgactg aggagctgca cctgatcacc    1320

tttgagaccg aggtgtatca ccaaggcctc aagattgacc tagagaccca ctccttgcca    1380

gttgtggtga tctccaacat ctgtcagatg ccaaatgcct gggcgtccat cctgtggtac    1440

aacatgctga ccaacaatcc caagaatgta aactttttta ccaagccccc aattggaacc    1500

tgggatcaag tggccgaggt cctgagctgg cagttctcct ccaccaccaa gcgaggactg    1560

agcatcgagc agctgactac actggcagag aaactcttgg gacctggtgt gaattattca    1620

gggtgtcaga tcacatgggc taaattttgc aaagaaaaca tggctggcaa gggcttctcc    1680

ttctgggtct ggctggacaa tatcattgac cttgtgaaaa agtacatcct ggccctttgg    1740

aacgaagggt acatcatggg ctttatcagt aaggagcggg agcgggccat cttgagcact    1800

aagcctccag gcaccttcct gctaagattc agtgaaagca gcaaagaagg aggcgtcact    1860

ttcacttggg tggagaagga catcagcggt aagacccaga tccagtccgt ggaaccatac    1920

acaaagcagc agctgaacaa catgtcattt gctgaaatca tcatgggcta taagatcatg    1980

gatgctacca atatcctggt gtctccactg gtctatctct atcctgacat tcccaaggag    2040

gaggcattcg gaaagtattg tcggccagag agccaggagc atcctgaagc tgacccaggt    2100

agcgctgccc catacctgaa gaccaagttt atctgtgtga caccaacgac ctgcagcaat    2160
```

accattgacc tgccgatgtc cccccgcact ttagattcat tgatgcagtt tggaaataat 2220
ggtgaaggtg ctgaaccctc agcaggaggg cagtttgagt ccctcacctt tgacatggag 2280
ttgacctcgg agtgcgctac ctcccccatg 2310

<210> SEQ ID NO 58
<211> LENGTH: 1575
<212> TYPE: DNA
<213> ORGANISM: Homo sapiens
<220> FEATURE:
<223> OTHER INFORMATION: lymphocyte-activation gene 3 (LAG3)

<400> SEQUENCE: 58
atgtgggagg ctcagttcct gggcttgctg tttctgcagc cgctttgggt ggctccagtg 60
aagcctctcc agccaggggc tgaggtcccg gtggtgtggg cccaggaggg ggctcctgcc 120
cagctcccct gcagccccac aatccccctc caggatctca gccttctgcg aagagcaggg 180
gtcacttggc agcatcagcc agacagtggc ccgcccgctg ccgcccccgg ccatcccctg 240
gcccccggcc ctcacccggc ggcgccctcc tcctgggggc ccaggccccg ccgctacacg 300
gtgctgagcg tgggtcccgg aggcctgcgc agcgggaggc tgcccctgca gccccgcgtc 360
cagctggatg agcgcggccg gcagcgcggg gacttctcgc tatggctgcg cccagcccgg 420
cgcgcggacg ccggcgagta ccgcgccgcg gtgcacctca gggaccgcgc cctctcctgc 480
cgcctccgtc tgcgcctggg ccaggcctcg atgactgcca gcccccccagg atctctcaga 540 gcctccgact gggtcatttt gaactgctcc ttcagccgcc ctgaccgccc agcctctgtg 600
cattggttcc ggaaccgggg ccagggccga gtccctgtcc gggagtcccc ccatcaccac 660
ttagcggaaa gcttcctctt cctgccccaa gtcagcccca tggactctgg gccctggggc 720
tgcatcctca cctacagaga tggcttcaac gtctccatca tgtataacct cactgttctg 780
ggtctggagc ccccaactcc cttgacagtg tacgctggag caggttccag ggtggggctg 840
ccctgccgcc tgcctgctgg tgtggggacc cggtctttcc tcactgccaa gtggactcct 900
cctgggggag gccctgacct cctggtgact ggagacaatg gcgactttac ccttcgacta 960
gaggatgtga gccaggccca ggctgggacc tacacctgcc atatccatct gcaggaacag 1020
cagctcaatg ccactgtcac attggcaatc atcacagtga ctcccaaatc ctttgggtca 1080
cctggatccc tggggaagct gctttgtgag gtgactccag tatctggaca agaacgcttt 1140
gtgtggagct ctctggacac ccatcccag aggagtttct caggaccttg gctggaggca 1200
caggaggccc agctcctttc ccagccttgg caatgccagc tgtaccaggg ggagaggctt 1260
cttggagcag cagtgtactt cacagagctg tctagcccag gtgcccaacg ctctgggaga 1320
gccccaggtg ccctcccagc aggccacctc ctgctgtttc tcatccttgg tgtcctttct 1380
ctgctccttt tggtgactgg agcctttggc tttcaccttt ggagaagaca gtggcgacca 1440
agacgatttt ctgccttaga gcaagggatt caccctccgc aggctcagag caagatagag 1500
gagctggagc aagaaccgga gccggagccg gagccggaac cggagcccga gcccgagccc 1560
gagccggagc agctc 1575

<210> SEQ ID NO 59
<211> LENGTH: 903
<212> TYPE: DNA
<213> ORGANISM: Homo sapiens
<220> FEATURE:
<223> OTHER INFORMATION: T cell immunoglobulin and mucin-domain
containing-3 (TIM-3)

<400> SEQUENCE: 59

```
atgttttcac atcttccctt tgactgtgtc ctgctgctgc tgctgctact acttacaagg     60
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa ccagccaagg tcacccctgc accgactcgg    420
cagagagact tcactgcagc ctttccaagg atgcttacca ccaggggaca tggcccagca    480
gagacacaga cactggggag cctccctgat ataaatctaa cacaaatatc cacattggcc    540
aatgagttac gggactctag attggccaat gacttacggg actctggagc aaccatcaga    600
ataggcatct acatcggagc agggatctgt gctgggctgg ctctggctct tatcttcggc    660
gctttaattt tcaaatggta ttctcatagc aaagagaaga tacagaattt aagcctcatc    720
tctttggcca acctccctcc ctcaggattg gcaaatgcag tagcagaggg aattcgctca    780
gaagaaaaca tctataccat tgaagagaac gtatatgaag tggaggagcc caatgagtat    840
tattgctatg tcagcagcag gcagcaaccc tcacaacctt tgggttgtcg ctttgcaatg    900
cca                                                                  903
```

<210> SEQ ID NO 60
<211> LENGTH: 732
<212> TYPE: DNA
<213> ORGANISM: Homo sapiens
<220> FEATURE:
<223> OTHER INFORMATION: T cell immunoreceptor with Ig and ITIM domains (TIGIT), isoform 1

<400> SEQUENCE: 60

```
atgcgctggt gtctcctcct gatctgggcc caggggctga ggcaggctcc cctcgcctca     60
ggaatgatga caggcacaat agaaacaacg gggaacattt ctgcagagaa aggtggctct    120
atcatcttac aatgtcacct ctcctccacc acggcacaag tgacccaggt caactgggag    180
cagcaggacc agcttctggc catttgtaat gctgacttgg ggtggcacat ctccccatcc    240
ttcaaggatc gagtggcccc aggtcccggc ctgggcctca ccctccagtc gctgaccgtg    300
aacgatacag gggagtactt ctgcatctat cacacctacc ctgatgggac gtacactggg    360
agaatcttcc tggaggtcct agaaagctca gtggctgagc acggtgccag gttccagatt    420
ccattgcttg gagccatggc cgcgacgctg gtggtcatct gcacagcagt catcgtggtg    480
gtcgcgttga ctagaaagaa gaaagccctc agaatccatt ctgtggaagg tgacctcagg    540
agaaaatcag ctggacagga ggaatggagc cccagtgctc cctcaccccc aggaagctgt    600
gtccaggcag aagctgcacc tgctgggctc tgtggagagc agcggggaga ggactgtgcc    660
gagctgcatg actacttcaa tgtcctgagt tacagaagcc tgggtaactg cagcttcttc    720
acagagactg gt                                                        732
```

<210> SEQ ID NO 61
<211> LENGTH: 1065
<212> TYPE: DNA
<213> ORGANISM: Homo sapiens
<220> FEATURE:
<223> OTHER INFORMATION: GALECTIN-9/LGALS9, isoform 1

<400> SEQUENCE: 61
atggccttca gcggttccca ggctccctac ctgagtccag ctgtcccctt ttctgggact 60
attcaaggag gtctccagga cggacttcag atcactgtca atgggaccgt tctcagctcc 120
agtggaacca ggtttgctgt gaactttcag actggcttca gtggaaatga cattgccttc 180
cacttcaacc ctcggtttga agatggaggg tacgtggtgt gcaacacgag gcagaacgga 240
agctgggggc ccgaggagag gaagacacac atgcctttcc agaaggggat gccctttgac 300
ctctgcttcc tggtgcagag ctcagatttc aaggtgatgg tgaacgggat cctcttcgtg 360
cagtacttcc accgcgtgcc cttccaccgt gtggacacca tctccgtcaa tggctctgtg 420
cagctgtcct acatcagctt ccagaacccc cgcacagtcc ctgttcagcc tgccttctcc 480
acggtgccgt tctcccagcc tgtctgtttc ccacccaggc ccagggggcg cagacaaaaa 540
cctcccggcg tgtggcctgc caacccggct cccattaccc agacagtcat ccacacagtg 600
cagagcgccc ctggacagat gttctctact cccgccatcc cacctatgat gtacccccac 660
cccgcctatc cgatgccttt catcaccacc attctgggag ggctgtaccc atccaagtcc 720
atcctcctgt caggcactgt cctgcccagt gctcagaggt tccacatcaa cctgtgctct 780
gggaaccaca tcgccttcca cctgaacccc cgttttgatg agaatgctgt ggtccgcaac 840
acccagatcg acaactcctg gggtctgag gagcgaagtc tgccccgaaa aatgcccttc 900
gtccgtggcc agagcttctc agtgtggatc ttgtgtgaag ctcactgcct caaggtggcc 960
gtggatggtc agcacctgtt tgaatactac catcgcctga ggaacctgcc caccatcaac 1020
agactggaag tgggggcga catccagctg acccatgtgc agaca 1065

<210> SEQ ID NO 62
<211> LENGTH: 720
<212> TYPE: DNA
<213> ORGANISM: Homo sapiens
<220> FEATURE:
<223> OTHER INFORMATION: LIGHT/TNSF14

<400> SEQUENCE: 62
atggaggaga gtgtcgtacg gccctcagtg tttgtggtgg atggacagac cgacatccca 60
ttcacgaggc tgggacgaag ccaccggaga cagtcgtgca gtgtggcccg ggtgggtctg 120
ggtctcttgc tgttgctgat gggggccggg ctggccgtcc aaggctggtt cctcctgcag 180
ctgcactggc gtctaggaga gatggtcacc cgcctgcctg acggacctgc aggctcctgg 240
gagcagctga tacaagagcg aaggtctcac gaggtcaacc cagcagcgca tctcacaggg 300
gccaactcca gcttgaccgg cagcgggggg ccgctgttat gggagactca gctgggcctg 360
gccttcctga ggggcctcag ctaccacgat ggggcccttg tggtcaccaa agctggctac 420
tactacatct actccaaggt gcagctgggc ggtgtgggct gcccgctggg cctggccagc 480
accatcaccc acggcctcta caagcgcaca ccccgctacc ccgaggagct ggagctgttg 540
gtcagccagc agtcaccctg cggacgggcc accagcagct cccgggtctg gtgggacagc 600
agcttcctgg gtggtgtggt acacctggag gctggggaga aggtggtcgt ccgtgtgctg 660
gatgaacgcc tggttcgact gcgtgatggt acccggtctt acttcggggc tttcatggtg 720

<210> SEQ ID NO 63
<211> LENGTH: 849
<212> TYPE: DNA
<213> ORGANISM: Homo sapiens
<220> FEATURE:

<223> OTHER INFORMATION: HVEM/TNSFR14 (receptor for LIGHT ligand)

<400> SEQUENCE: 63
atggagcctc ctggagactg gggggcctcct ccctggagat ccaccccccaa aaccgacgtc 60 ttgaggctgg tgctgtatct caccttcctg ggagcccccct gctacgcccc agctctgccg 120
tcctgcaagg aggacgagta cccagtgggc tccgagtgct gccccaagtg cagtccaggt 180
tatcgtgtga aggaggcctg cggggagctg acgggcacag tgtgtgaacc ctgccctcca 240
ggcacctaca ttgcccacct caatggccta agcaagtgtc tgcagtgcca aatgtgtgac 300
ccagccatgg gcctgcgcgc gagccggaac tgctccagga cagagaacgc cgtgtgtggc 360
tgcagcccag gccacttctg catcgtccag gacggggacc actgcgccgc gtgccgcgct 420
tacgccacct ccagcccggg ccagagggtg cagaagggag gcaccgagag tcaggacacc 480
ctgtgtcaga actgcccccc ggggaccttc tctcccaatg ggaccctgga ggaatgtcag 540
caccagacca agtgcagctg gctggtgacg aaggccggag ctgggaccag cagctcccac 600
tgggtatggt ggtttctctc agggagcctc gtcatcgtca ttgtttgctc cacagttggc 660
ctaatcatat gtgtgaaaag aagaaagcca aggggtgatg tagtcaaggt gatcgtctcc 720
gtccagcgga aaagacagga ggcagaaggt gaggccacag tcattgaggc cctgcaggcc 780
cctccggacg tcaccacggt ggccgtggag gagacaatac cctcattcac ggggaggagc 840
ccaaaccac 849

<210> SEQ ID NO 64
<211> LENGTH: 660
<212> TYPE: DNA
<213> ORGANISM: Homo sapiens
<220> FEATURE:
<223> OTHER INFORMATION: CD28

<400> SEQUENCE: 64
atgctcaggc tgctcttggc tctcaactta ttcccttcaa ttcaagtaac aggaaacaag 60
attttggtga agcagtcgcc catgcttgta gcgtacgaca atgcggtcaa ccttagctgc 120
aagtattcct acaatctctt ctcaagggag ttccgggcat cccttcacaa aggactggat 180
agtgctgtgg aagtctgtgt tgtatatggg aattactccc agcagcttca ggtttactca 240
aaaacggggt tcaactgtga tgggaaattg ggcaatgaat cagtgacatt ctacctccag 300
aatttgtatg ttaaccaaac agatatttac ttctgcaaaa ttgaagttat gtatcctcct 360
ccttacctag acaatgagaa gagcaatgga accattatcc atgtgaaagg gaaacacctt 420
tgtccaagtc ccctatttcc cggaccttct aagccctttt gggtgctggt ggtggttggt 480
ggagtcctgg cttgctatag cttgctagta acagtggcct ttattatttt ctgggtgagg 540
agtaagagga gcaggctcct gcacagtgac tacatgaaca tgactccccg ccgccccggg 600
cccacccgca agcattacca gccctatgcc ccaccacgcg acttcgcagc ctatcgctcc 660

<210> SEQ ID NO 65
<211> LENGTH: 1578
<212> TYPE: DNA
<213> ORGANISM: Homo sapiens
<220> FEATURE:
<223> OTHER INFORMATION: carcinoembryonic antigen-related cell adhesion
molecule 1 (CEACAM1, or CD66a)

<400> SEQUENCE: 65
atggggcacc tctcagcccc acttcacaga gtgcgtgtac cctggcaggg gcttctgctc 60

-continued

```
acagcctcac ttctaacctt ctggaacccg cccaccactg cccagctcac tactgaatcc    120
atgccattca atgttgcaga ggggaaggag gttcttctcc ttgtccacaa tctgccccag    180
caactttttg gctacagctg gtacaaaggg gaaagagtgg atggcaaccg tcaaattgta    240
ggatatgcaa taggaactca acaagctacc ccagggcccg caaacagcgg tcgagagaca    300
atataccccca atgcatccct gctgatccag aacgtcaccc agaatgacac aggattctac    360
accctacaag tcataaagtc agatcttgtg aatgaagaag caactggaca gttccatgta    420
tacccggagc tgcccaagcc ctccatctcc agcaacaact ccaaccctgt ggaggacaag    480
gatgctgtgg ccttcacctg tgaacctgag actcaggaca caacctacct gtggtggata    540
aacaatcaga gcctcccggt cagtcccagg ctgcagctgt ccaatggcaa caggaccctc    600
actctactca gtgtcacaag gaatgacaca ggaccctatg agtgtgaaat acagaaccca    660
gtgagtgcga accgcagtga cccagtcacc ttgaatgtca cctatggccc ggacaccccc    720
accatttccc cttcagacac ctattaccgt ccaggggcaa acctcagcct ctcctgctat    780
gcagcctcta acccacctgc acagtactcc tggcttatca atggaacatt ccagcaaagc    840
acacaagagc tctttatccc taacatcact gtgaataata gtggatccta tacctgccac    900
gccaataact cagtcactgg ctgcaacagg accacagtca agacgatcat agtcactgag    960
ctaagtccag tagtagcaaa gccccaaatc aaagccagca agaccacagt cacaggagat   1020
aaggactctg tgaacctgac ctgctccaca aatgacactg gaatctccat ccgttggttc   1080
ttcaaaaacc agagtctccc gtcctcggag aggatgaagc tgtcccaggg caacaccacc   1140
ctcagcataa accctgtcaa gagggaggat gctgggacgt attggtgtga ggtcttcaac   1200
ccaatcagta agaaccaaag cgaccccatc atgctgaacg taaactataa tgctctacca   1260
caagaaaatg gcctctcacc tggggccatt gctggcattg tgattggagt agtggccctg   1320
gttgctctga tagcagtagc cctggcatgt tttctgcatt tcgggaagac cggcagggca   1380
agcgaccagc gtgatctcac agagcacaaa ccctcagtct ccaaccacac tcaggaccac   1440
tccaatgacc cacctaacaa gatgaatgaa gttacttatt ctaccctgaa ctttgaagcc   1500
cagcaaccca cacaaccaac ttcagcctcc ccatccctaa cagccacaga aataatttat   1560
tcagaagtaa aaaagcag                                                 1578
```

<210> SEQ ID NO 66
<211> LENGTH: 864
<212> TYPE: DNA
<213> ORGANISM: Homo sapiens
<220> FEATURE:
<223> OTHER INFORMATION: CD80/B7-1

<400> SEQUENCE: 66

```
atgggccaca cacggaggca gggaacatca ccatccaagt gtccatacct caatttcttt     60
cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
```

-continued gaattaaatg ccatcaacac aacagtttcc caagatcctg aaactgagct ctatgctgtt 600
agcagcaaac tggatttcaa tatgacaacc aaccacagct tcatgtgtct catcaagtat 660
ggacatttaa gagtgaatca gaccttcaac tggaatacaa ccaagcaaga gcattttcct 720
gataacctgc tcccatcctg ggccattacc ttaatctcag taaatggaat ttttgtgata 780
tgctgcctga cctactgctt tgccccaaga tgcagagaga gaaggaggaa tgagagattg 840
agaagggaaa gtgtacgccc tgta 864

<210> SEQ ID NO 67
<211> LENGTH: 995
<212> TYPE: DNA
<213> ORGANISM: Homo sapiens
<220> FEATURE:
<223> OTHER INFORMATION: CD86/B7-2

<400> SEQUENCE: 67
cagccaaaat ggatccccag tgcactatgg gactgagtaa cattctcttt gtgatggcct 60
tcctgctctc tggtgctgct cctctgaaga ttcaagctta tttcaatgag actgcagacc 120
tgccatgcca atttgcaaac tctcaaaacc aaagcctgag tgagctagta gtattttggc 180
aggaccagga aaacttggtt ctgaatgagg tatacttagg caaagagaaa tttgacagtg 240
ttcattccaa gtatatgggc cgcacaagtt ttgattcgga cagttggacc ctgagacttc 300
acaatcttca gatcaaggac aagggcttgt atcaatgtat catccatcac aaaaagccca 360
caggaatgat tcgcatccac cagatgaatt ctgaactgtc agtgcttgct aacttcagtc 420
aacctgaaat agtaccaatt tctaatataa cagaaaatgt gtacataaat ttgacctgct 480
catctataca cggttaccca gaacctaaga agatgagtgt tttgctaaga accaagaatt 540
caactatcga gtatgatggt attatgcaga aatctcaaga taatgtcaca gaactgtacg 600
acgtttccat cagcttgtct gtttcattcc ctgatgttac gagcaatatg accatcttct 660
gtattctgga aactgacaag acgcggcttt tatcttcacc tttctctata gagcttgagg 720
accctcagcc tcccccagac cacattcctt ggattacagc tgtacttcca acagttatta 780
tatgtgtgat ggttttctgt ctaattctat ggaaatggaa gaagaagaag cggcctcgca 840
actcttataa atgtggaacc aacacaatgg agagggaaga gagtgaacag accaagaaaa 900
gagaaaaaat ccatatacct gaaagatctg atgaagccca gcgtgttttt aaaagttcga 960
agacatcttc atgcgacaaa agtgatacat gtttt 995

<210> SEQ ID NO 68
<211> LENGTH: 1095
<212> TYPE: DNA
<213> ORGANISM: Homo sapiens
<220> FEATURE:
<223> OTHER INFORMATION: CD244/2B4

<400> SEQUENCE: 68
atgctggggc aagtggtcac cctcatactc ctcctgctcc tcaaggtgta tcagggcaaa 60
ggatgccagg gatcagctga ccatgtggtt agcatctcgg gagtgcctct tcagttacaa 120
ccaaacagca tacagacgaa ggttgacagc attgcatgga agaagttgct gccctcacaa 180
aatggatttc atcacatatt gaagtgggag aatggctctt tgccttccaa tacttccaat 240
gatagattca gttttatagt caagaacttg agtcttctca tcaaggcagc tcagcagcag 300
gacagtggcc tctactgcct ggaggtcacc agtatatctg gaaaagttca gacagccacg 360

-continued ttccaggttt ttgtatttga taaagttgag aaaccccgcc tacaggggca ggggaagatc 420
ctggacagag ggagatgcca agtggctctg tcttgcttgg tctccaggga tggcaatgtg 480
tcctatgctt ggtacagagg gagcaagctg atccagacag cagggaacct cacctacctg 540
gacgaggagg ttgacattaa tggcactcac acatatacct gcaatgtcag caatcctgtt 600
agctgggaaa gccacaccct gaatctcact caggactgtc agaatgccca tcaggaattc 660
agattttggc cgtttttggt gatcatcgtg attctaagcg cactgttcct tggcaccctt 720
gcctgcttct gtgtgtggag gagaaagagg aaggagaagc agtcagagac cagtcccaag 780
gaatttttga caatttacga agatgtcaag gatctgaaaa ccaggagaaa tcacgagcag 840
gagcagactt ttcctggagg ggggagcacc atctactcta tgatccagtc ccagtcttct 900
gctcccacgt cacaagaacc tgcatataca ttatattcat taattcagcc ttccaggaag 960
tctggatcca ggaagaggaa ccacagccct tccttcaata gcactatcta tgaagtgatt 1020
ggaaagagtc aacctaaagc ccagaaccct gctcgattga gccgcaaaga gctggagaac 1080
tttgatgttt attcc 1095

<210> SEQ ID NO 69
<211> LENGTH: 1251
<212> TYPE: DNA
<213> ORGANISM: Homo sapiens
<220> FEATURE:
<223> OTHER INFORMATION: CD155/PVR

<400> SEQUENCE: 69
atggcccgag ccatggccgc cgcgtggccg ctgctgctgg tggcgctact ggtgctgtcc 60
tggccacccc caggaaccgg ggacgtcgtc gtgcaggcgc ccacccaggt gcccggcttc 120
ttgggcgact ccgtgacgct gccctgctac ctacaggtgc ccaacatgga ggtgacgcat 180
gtgtcacagc tgacttgggc gcggcatggt gaatctggca gcatggccgt cttccaccaa 240
acgcagggcc ccagctattc ggagtccaaa cggctggaat tcgtggcagc cagactgggc 300
gcggagctgc ggaatgcctc gctgaggatg ttcgggttgc gcgtagagga tgaaggcaac 360
tacacctgcc tgttcgtcac gttcccgcag ggcagcagga gcgtggatat ctggctccga 420
gtgcttgcca agccccagaa cacagctgag gttcagaagg tccagctcac tggagagcca 480
gtgcccatgg cccgctgcgt ctccacaggg ggtcgcccgc cagcccaaat cacctggcac 540
tcagacctgg gcgggatgcc caatacgagc caggtgccag ggttcctgtc tggcacagtc 600
actgtcacca gcctctggat attggtgccc tcaagccagg tggacggcaa gaatgtgacc 660
tgcaaggtgg agcacgagag ctttgagaag cctcagctgc tgactgtgaa cctcaccgtg 720
tactaccccc cagaggtatc catctctggc tatgataaca actggtacct tggccagaat 780
gaggccaccc tgacctgcga tgctcgcagc aacccagagc ccacaggcta taattggagc 840
acgaccatgg gtcccctgcc acccctttgct gtggcccagg gcgcccagct cctgatccgt 900
cctgtggaca aaccaatcaa cacaactta atctgcaacg tcaccaatgc cctaggagct 960
cgccaggcag aactgaccgt ccaggtcaaa gagggacctc ccagtgagca ctcaggcatg 1020
tcccgtaacg ccatcatctt cctggttctg ggaatcctgg tttttctgat cctgctgggg 1080
atcgggattt atttctattg gtccaaatgt tcccgtgagg tcctttggca ctgtcatctg 1140
tgtccctcga gtacagagca tgccagcgcc tcagctaatg ggcatgtctc ctattcagct 1200
gtgagcagag agaacagctc ttcccaggat ccacagacag agggcacaag g 1251

<210> SEQ ID NO 70
<211> LENGTH: 1614
<212> TYPE: DNA
<213> ORGANISM: Homo sapiens
<220> FEATURE:
<223> OTHER INFORMATION: CD122/nectin-2

<400> SEQUENCE: 70

```
atggcccggg ccgctgccct cctgccgtcg agatcgccgc cgacgccgct gctgtggccg     60

ctgctgctgc tgctgctcct ggaaaccgga gcccaggatg tgcgagttca agtgctaccc    120

gaggtgcgag gccagctcgg gggcaccgtg gagctgccgt gccacctgct gccacctgtt    180

cctggactgt acatctccct ggtgacctgg cagcgcccag atgcacctgc gaaccaccag    240

aatgtggccg ccttccaccc taagatgggt cccagcttcc ccagcccgaa gcctggcagc    300

gagcggctgt ccttcgtctc tgccaagcag agcactgggc aagacacaga ggcagagctc    360

caggacgcca cgctggccct ccacgggctc acggtggagg acgagggcaa ctacacttgc    420

gagtttgcca ccttccccaa ggggtccgtc cgagggatga cctggctcag agtcatagcc    480

aagcccaaga accaagctga ggcccagaag gtcacgttca gccaggaccc tacgacagtg    540

gccctctgca tctccaaaga gggccgccca cctgcccgga tctcctggct ctcatccctg    600

gactgggaag ccaaagagac tcaggtgtca gggaccctgg ccggaactgt cactgtcacc    660

agccgcttca ccttggtgcc ctcgggccga gcagatggtg tcacggtcac ctgcaaagtg    720

gagcatgaga gcttcgagga accagccctg atacctgtga ccctctctgt acgctaccct    780

cctgaagtgt ccatctccgg ctatgatgac aactggtacc tcggccgtac tgatgccacc    840

ctgagctgtg acgtccgcag caacccagag cccacgggct atgactggag cacgacctca    900

ggcaccttcc cgacctccgc agtggcccag ggctcccagc tggtcatcca cgcagtggac    960

agtctgttca ataccacctt cgtctgcaca gtcaccaatg ccgtgggcat gggccgcgct   1020

gagcaggtca tctttgtccg agagaccccc aacacagcag gcgcaggggc cacaggcggc   1080

atcatcgggg gcatcatcgc cgccatcatt gctactgctg tggctgccac gggcatcctt   1140

atctgccggc agcagcggaa ggagcagacg ctgcaggggg cagaggagga cgaagacctg   1200

gagggacctc cctcctacaa gccaccgacc ccaaaagcga agctggaggc acaggagatg   1260

ccctcccagc tcttcactct gggggcctcg gagcacagcc cactcaagac cccctacttt   1320

gatgctggcg cctcatgcac tgagcaggaa atgcctcgat accatgagct gcccaccttg   1380

gaagaacggt caggaccctt gcaccctgga gccacaagcc tggggtcccc catcccggtg   1440

cctccagggc cacctgctgt ggaagacgtt tccctggatc tagaggatga ggagggggag   1500

gaggaggaag agtatctgga caagatcaac cccatctatg atgctctgtc ctatagcagc   1560

ccctctgatt cctaccaggg caaaggcttt gtcatgtccc gggccatgta tgtg          1614
```

<210> SEQ ID NO 71
<211> LENGTH: 1008
<212> TYPE: DNA
<213> ORGANISM: Homo sapiens
<220> FEATURE:
<223> OTHER INFORMATION: CD226 antigen

<400> SEQUENCE: 71

```
atggattatc ctactttact tttggctctt cttcatgtat acagagctct atgtgaagag     60

gtgctttggc atacatcagt tccctttgcc gagaacatgt ctctagaatg tgtgtatcca    120

tcaatgggca tcttaacaca ggtggagtgg ttcaagatcg ggacccagca ggattccata    180
```

-continued

```
gccattttca gccctactca tggcatggtc ataaggaagc cctatgctga gagggtttac    240

tttttgaatt caacgatggc ttccaataac atgactcttt tctttcggaa tgcctctgaa    300

gatgatgttg gctactattc ctgctctctt tacacttacc cacagggaac ttggcagaag    360

gtgatacagg tggttcagtc agatagtttt gaggcagctg tgccatcaaa tagccacatt    420

gtttcggaac ctggaaagaa tgtcacactc acttgtcagc ctcagatgac gtggcctgtg    480

caggcagtga ggtgggaaaa gatccagccc cgtcagatcg acctcttaac ttactgcaac    540

ttggtccatg gcagaaattt cacctccaag ttcccaagac aaatagtgag caactgcagc    600

cacggaaggt ggagcgtcat cgtcatcccc gatgtcacag tctcagactc ggggctttac    660

cgctgctact tgcaggccag cgcaggagaa aacgaaacct tcgtgatgag attgactgta    720

gccgagggta aaaccgataa ccaatatacc ctctttgtgg ctggagggac agttttattg    780

ttgttgtttg ttatctcaat taccaccatc attgtcattt tccttaacag aaggagaagg    840

agagagagaa gagatctatt tacagagtcc tgggatacac agaaggcacc caataactat    900

agaagtccca tctctaccag tcaacctacc aatcaatcca tggatgatac aagagaggat    960

atttatgtca actatccaac cttctctcgc agaccaaaga ctagagtt                1008
```

```
<210> SEQ ID NO 72
<211> LENGTH: 545
<212> TYPE: DNA
<213> ORGANISM: Homo sapiens
<220> FEATURE:
<223> OTHER INFORMATION: CD160 antigen

<400> SEQUENCE: 72

ggatgctgtt ggaacccggc agaggctgct gtgccctggc catcctgctg gcaattgtgg     60

acatccagtc tggtggatgc attaacatca ccagctcagc ttcccaggaa ggaacgcgac    120

taaacttaat ctgtactgta tggcataaga aagaagaggc tgaggggttt gtagtgtttt    180

tgtgcaagga caggtctgga gactgttctc ctgagaccag tttaaaacag ctgagactta    240

aaagggatcc tgggatagat ggtgttggtg aaatatcatc tcagttgatg ttcaccataa    300

gccaagtcac accgttgcac agtgggacct accagtgttg tgccagaagc cagaagtcag    360

gtatccgcct tcagggccat tttttctcca ttctattcac agagacaggg aactacacag    420

tgacgggatt gaaacaaaga caacaccttg agttcagcca taatgaaggc actctcagtt    480

caggcttcct acaagaaaag gtctgggtaa tgctggtcac cagccttgtg gcccttcaag    540

ctttg                                                                545
```

```
<210> SEQ ID NO 73
<211> LENGTH: 264
<212> TYPE: DNA
<213> ORGANISM: Homo sapiens
<220> FEATURE:
<223> OTHER INFORMATION: human U6 RNA Pol III promoter

<400> SEQUENCE: 73

aaggtcgggc aggaagaggg cctatttccc atgattcctt catatttgca tatacgatac     60

aaggctgtta gagagataat tagaattaat ttgactgtaa acacaaagat attagtacaa    120

aatacgtgac gtagaaagta ataatttctt gggtagtttg cagttttaaa attatgtttt    180

aaaatggact atcatatgct taccgtaact tgaaagtatt tcgatttctt ggctttatat    240

atcttgtgga aaggacgaaa ctag                                          264
```

<210> SEQ ID NO 74
<211> LENGTH: 99
<212> TYPE: DNA
<213> ORGANISM: Homo sapiens
<220> FEATURE:
<221> NAME/KEY: promoter
<222> LOCATION: (0)...(0)
<223> OTHER INFORMATION: human H1 RNA Pol III promoter

<400> SEQUENCE: 74
atatttgcat gtcgctatgt gttctgggaa atcaccataa acgtgaaatg tctttggatt 60
tgggaatctt ataagttctg tatgagacca ctccctagg 99

<210> SEQ ID NO 75
<211> LENGTH: 58
<212> TYPE: DNA
<213> ORGANISM: Artificial Sequence
<220> FEATURE:
<223> OTHER INFORMATION: shRNA-encoding sequence targeting muPD-L1

<400> SEQUENCE: 75
ccggccgaaa tgatacacaa ttcgactcga gtcgaattgt gtatcatttc ggtttttg 58

<210> SEQ ID NO 76
<211> LENGTH: 57
<212> TYPE: DNA
<213> ORGANISM: Artificial Sequence
<220> FEATURE:
<223> OTHER INFORMATION: shRNA-encoding sequence targeting muSIRPA

<400> SEQUENCE: 76
ccggccacaa ctggaatgtc ttcatctcga gatgaagaca ttccagttgt ggttttt 57

<210> SEQ ID NO 77
<211> LENGTH: 58
<212> TYPE: DNA
<213> ORGANISM: Artificial Sequence
<220> FEATURE:
<223> OTHER INFORMATION: shRNA-encoding sequence targeting muTREX1,
      clone 1

<400> SEQUENCE: 77
ccggacaacc aacctaaggc cacatctcga gatgtggcct taggttggtt gtttttg 58

<210> SEQ ID NO 78
<211> LENGTH: 58
<212> TYPE: DNA
<213> ORGANISM: Artificial Sequence
<220> FEATURE:
<223> OTHER INFORMATION: shRNA-encoding sequence targeting muTREX1,
      clone 2

<400> SEQUENCE: 78
ccggcctaga tggtaccttc tgtgtctcga gacacagaag gtaccatcta ggtttttg 58

<210> SEQ ID NO 79
<211> LENGTH: 3966
<212> TYPE: DNA
<213> ORGANISM: Artificial Sequence
<220> FEATURE:
<223> OTHER INFORMATION: Vector1-human shTREX1-1_shPDL1-1

<400> SEQUENCE: 79
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120

-continued

```
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggccctt aaaggaacca attcagtcga gaattggtac    600
catatttgca tgtcgctatg tgttctggga aatcaccata aacgtgaaat gtctttggat    660
ttgggaatct tataagttct gtatgagacc actccctagg cagcgcatgg gcgtcaattc    720
tagagattga cgcccatgcg ctgctttttt cgacagatct ggcgcgccat agtggccagc    780
ggccgcaggt aagccagccc aggcctcgcc ctccagctca aggcgggaca ggtgccctag    840
agtagcctgc atccagggac aggccccagc cgggtgctga cacgtccacc tccatctctt    900
cctcaggtct gcccgggtgg catccctgtg acccctcccc agtgcctctc ctggccctgg    960
aagttgccac tccagtgccc accagccttg tcctaataaa attaagttgc atcattttgt   1020
ctgactaggt gtccttctat aatattatgg ggtggagggg ggtggtatgg agcaaggggc   1080
ccaagttaac ttgtttattg cagcttataa tggttacaaa taaagcaata gcatcacaaa   1140
tttcacaaat aaagcatttt tttcactgca ttctagttgt ggtttgtcca aactcatcaa   1200
tgtatcttat catgtctgga tccaaggtcg ggcaggaaga gggcctattt cccatgattc   1260
cttcatattt gcatatacga tacaaggctg ttagagagat aattagaatt aatttgactg   1320
taaacacaaa gatattagta caaaatacgt gacgtagaaa gtaataattt cttgggtagt   1380
ttgcagtttt aaaattatgt tttaaaatgg actatcatat gcttaccgta acttgaaagt   1440
atttcgattt cttggcttta tatatcttgt ggaaaggacg aaactaggta gagtatggta   1500
gcaatatcta gagtattgct accatactct actttttcg agtagctaga gaattcatgg    1560
taatagcgat gactaatacg tagatgtact gccaagtagg aaagtcccat aaggtcatgt   1620
actgggcata atgccaggcg ggccatttac cgtcattgac gtcaataggg ggcgtacttg   1680
gcatatgata cacttgatgt actgccaagt gggcagttta ccgtaaatag tccacccatt   1740
gacgtcaatg gaaagtccct attggcgtta ctatgggaac atacgtcatt attgacgtca   1800
atgggcgggg gtcgttgggc ggtcagccag gcgggccatt taccgtaagt tatgtaacgc   1860
ggaactccat atatgggcta tgaactaatg accccgtaat tgattactat taataactag   1920
ccatccagct gatatcccat ggtcatagct gtttcctggc agctctggcc cgtgtctcaa   1980
aatctctgat gttacattgc acaagataaa aatatatcat catgaacaat aaaactgtct   2040
gcttacataa acagtaatac aaggggtgtt atgaaaaatg ttggttttat cggctggcgc   2100
ggaatggtcg gctctgttct catgcaacgc atggtagagg agcgcgattt cgacgctatt   2160
cgccctgttt tcttttctac ctcccagttt ggacaggcgg cgcccacctt cggcgacacc   2220
tccaccggca cgctacagga cgcttttgat ctggatgcgc taaaagcgct cgatatcatc   2280
gtgacctgcc agggcggcga ttataccaac gaaatttatc caaagctgcg cgaaagcgga   2340
tggcagggtt actggattga tgcggcttct acgctgcgca tgaaagatga tgccattatt   2400
attctcgacc cggtcaacca ggacgtgatt accgacggcc tgaacaatgg cgtgaagacc   2460
tttgtgggcg gtaactgtac cgttagcctg atgttgatgt cgctgggcgg tctctttgcc   2520
```

cataatctcg ttgactgggt atccgtcgcg acctatcagg ccgcctccgg cggcggcgcg 2580
cgccatatgc gcgagctgtt aacccagatg ggtcagttgt atggccatgt cgccgatgaa 2640
ctggcgacgc cgtcttccgc aattcttgat attgaacgca aagttacggc attgacccgc 2700
agcggcgagc tgccggttga taactttggc gtaccgctgg cgggaagcct gatcccctgg 2760
atcgacaaac agctcgataa cggccagagc cgcgaagagt ggaaaggcca ggcggaaacc 2820
aacaagattc tcaatactgc ctctgtgatt ccggttgatg gtttgtgtgt gcgcgtcggc 2880
gcgctgcgct gtcacagcca ggcgttcacc atcaagctga aaaaagaggt atccattccg 2940
acggtggaag aactgctggc ggcacataat ccgtgggcga aagtggtgcc gaacgatcgt 3000
gatatcacta tgcgcgaatt aaccccggcg gcggtgaccg gcacgttgac tacgccggtt 3060
ggtcgtctgc gtaagctgaa catggggcca gagttcttgt cggcgtttac cgtaggcgac 3120
cagttgttat ggggcgccgc cgagccgctg cgtcgaatgc tgcgccagtt ggcgtagtca 3180
gaattggtta attggttgta acactggcag agcattacgc tgacttgacg ggacggcgca 3240
agctcatgac caaaatccct taacgtgagt tacgcgtcgt tccactgagc gtcagacccc 3300
gtagaaaaga tcaaaggatc ttcttgagat cctttttttc tgcgcgtaat ctgctgcttg 3360
caaacaaaaa aaccaccgct accagcggtg gtttgtttgc cggatcaaga gctaccaact 3420
ctttttccga aggtaactgg cttcagcaga gcgcagatac caaatactgt ccttctagtg 3480
tagccgtagt taggccacca cttcaagaac tctgtagcac cgcctacata cctcgctctg 3540
ctaatcctgt taccagtggc tgctgccagt ggcgataagt cgtgtcttac cgggttggac 3600
tcaagacgat agttaccgga taaggcgcag cggtcgggct gaacgggggg ttcgtgcaca 3660
cagcccagct tggagcgaac gacctacacc gaactgagat acctacagcg tgagcattga 3720
gaaagcgcca cgcttcccga agggagaaag gcggacaggt atccggtaag cggcagggtc 3780
ggaacaggag agcgcacgag ggagcttcca gggggaaacg cctggtatct ttatagtcct 3840
gtcgggtttc gccacctctg acttgagcgt cgatttttgt gatgctcgtc aggggggcgg 3900
agcctatgga aaaacgccag caacgcggcc tttttacggt tcctggcctt ttgctggcct 3960
tttgct 3966

<210> SEQ ID NO 80
<211> LENGTH: 3972
<212> TYPE: DNA
<213> ORGANISM: Artificial Sequence
<220> FEATURE:
<223> OTHER INFORMATION: Vector2-mouse shTREX1-1_shPDL1-1

<400> SEQUENCE: 80
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540

-continued

```
aacgacggcc agtcttaagc tcgggccctt aaaggaacca attcagtcga gaattggtac    600
catatttgca tgtcgctatg tgttctggga aatcaccata aacgtgaaat gtctttggat    660
ttgggaatct tataagttct gtatgagacc actccctaga caaccaacct aaggccacat    720
ctcgagatgt ggccttaggt tggttgtttt tttcgacaga tctggcgcgc catagtggcc    780
agcggccgca ggtaagccag cccaggcctc gccctccagc tcaaggcggg acaggtgccc    840
tagagtagcc tgcatccagg gacaggcccc agccgggtgc tgacacgtcc acctccatct    900
cttcctcagg tctgcccggg tggcatccct gtgacccctc cccagtgcct ctcctggccc    960
tggaagttgc cactccagtg cccaccagcc ttgtcctaat aaaattaagt tgcatcattt   1020
tgtctgacta ggtgtccttc tataatatta tggggtggag gggggtggta tggagcaagg   1080
ggcccaagtt aacttgttta ttgcagctta taatggttac aaataaagca atagcatcac   1140
aaatttcaca aataaagcat ttttttcact gcattctagt tgtggtttgt ccaaactcat   1200
caatgtatct tatcatgtct ggatccaagg tcgggcagga agagggccta tttcccatga   1260
ttccttcata tttgcatata cgatacaagg ctgttagaga gataattaga attaatttga   1320
ctgtaaacac aaagatatta gtacaaaata cgtgacgtag aaagtaataa tttcttgggt   1380
agtttgcagt tttaaaatta tgttttaaaa tggactatca tatgcttacc gtaacttgaa   1440
agtatttcga tttcttggct ttatatatct tgtggaaagg acgaaactag ccgaaatgat   1500
acacaattcg actcgagtcg aattgtgtat catttcggtt ttttcgagta gctagagaat   1560
tcatggtaat agcgatgact aatacgtaga tgtactgcca agtaggaaag tcccataagg   1620
tcatgtactg ggcataatgc caggcgggcc atttaccgtc attgacgtca atagggggcg   1680
tacttggcat atgatacact tgatgtactg ccaagtgggc agtttaccgt aaatagtcca   1740
cccattgacg tcaatggaaa gtccctattg gcgttactat gggaacatac gtcattattg   1800
acgtcaatgg gcgggggtcg ttgggcggtc agccaggcgg gccatttacc gtaagttatg   1860
taacgcggaa ctccatatat gggctatgaa ctaatgaccc cgtaattgat tactattaat   1920
aactagccat ccagctgata tcccatggtc atagctgttt cctggcagct ctggcccgtg   1980
tctcaaaatc tctgatgtta cattgcacaa gataaaaata tatcatcatg aacaataaaa   2040
ctgtctgctt acataaacag taatacaagg ggtgttatga aaaatgttgg ttttatcggc   2100
tggcgcggaa tggtcggctc tgttctcatg caacgcatgg tagaggagcg cgatttcgac   2160
gctattcgcc ctgttttctt ttctacctcc cagtttggac aggcggcgcc caccttcggc   2220
gacacctcca ccggcacgct acaggacgct tttgatctgg atgcgctaaa agcgctcgat   2280
atcatcgtga cctgccaggg cggcgattat accaacgaaa tttatccaaa gctgcgcgaa   2340
agcggatggc agggttactg gattgatgcg gcttctacgc tgcgcatgaa agatgatgcc   2400
attattattc tcgacccggt caaccaggac gtgattaccg acggcctgaa caatggcgtg   2460
aagacctttg tgggcggtaa ctgtaccgtt agcctgatgt tgatgtcgct gggcggtctc   2520
tttgcccata atctcgttga ctgggtatcc gtcgcgacct atcaggccgc ctccggcggc   2580
ggcgcgcgcc atatgcgcga gctgttaacc cagatgggtc agttgtatgg ccatgtcgcc   2640
gatgaactgg cgacgccgtc ttccgcaatt cttgatattg aacgcaaagt tacggcattg   2700
acccgcagcg gcgagctgcc ggttgataac tttggcgtac cgctggcggg aagcctgatc   2760
ccctggatcg acaaacagct cgataacggc cagagccgcg aagagtggaa aggccaggcg   2820
gaaaccaaca agattctcaa tactgcctct gtgattccgg ttgatggttt gtgtgtgcgc   2880
gtcggcgcgc tgcgctgtca cagccaggcg ttcaccatca agctgaaaaa agaggtatcc   2940
```

```
attccgacgg tggaagaact gctggcggca cataatccgt gggcgaaagt ggtgccgaac   3000

gatcgtgata tcactatgcg cgaattaacc ccggcggcgg tgaccggcac gttgactacg   3060

ccggttggtc gtctgcgtaa gctgaacatg gggccagagt tcttgtcggc gtttaccgta   3120

ggcgaccagt tgttatgggg cgccgccgag ccgctgcgtc gaatgctgcg ccagttggcg   3180

tagtcagaat tggttaattg gttgtaacac tggcagagca ttacgctgac ttgacgggac   3240

ggcgcaagct catgaccaaa atcccttaac gtgagttacg cgtcgttcca ctgagcgtca   3300

gaccccgtag aaaagatcaa aggatcttct tgagatcctt tttttctgcg cgtaatctgc   3360

tgcttgcaaa caaaaaaacc accgctacca gcggtggttt gtttgccgga tcaagagcta   3420

ccaactcttt ttccgaaggt aactggcttc agcagagcgc agataccaaa tactgtcctt   3480

ctagtgtagc cgtagttagg ccaccacttc aagaactctg tagcaccgcc tacatacctc   3540

gctctgctaa tcctgttacc agtggctgct gccagtggcg ataagtcgtg tcttaccggg   3600

ttggactcaa gacgatagtt accggataag gcgcagcggt cgggctgaac ggggggttcg   3660

tgcacacagc ccagcttgga gcgaacgacc tacaccgaac tgagatacct acagcgtgag   3720

cattgagaaa gcgccacgct tcccgaaggg agaaaggcgg acaggtatcc ggtaagcggc   3780

agggtcggaa caggagagcg cacgagggag cttccagggg gaaacgcctg gtatctttat   3840

agtcctgtcg ggtttcgcca cctctgactt gagcgtcgat ttttgtgatg ctcgtcaggg   3900

gggcggagcc tatggaaaaa cgccagcaac gcggcctttt tacggttcct ggccttttgc   3960

tggccttttg ct                                                       3972
```

<210> SEQ ID NO 81
<211> LENGTH: 1281
<212> TYPE: DNA
<213> ORGANISM: Salmonella typhimurium
<220> FEATURE:
<223> OTHER INFORMATION: aroA

<400> SEQUENCE: 81

```
atggaatccc tgacgttaca acccatcgcg cgggtcgatg gcgccattaa tttacctggc     60

tccaaaagtg tttcaaaccg tgctttgctc ctggcggctt tagcttgtgg taaaaccgct    120

ctgacgaatc tgctggatag cgatgacgtc cgccatatgc tcaatgccct gagcgcgttg    180

gggatcaatt acacccttc tgccgatcgc acccgctgtg atatcacggg taatggcggc    240

gcattacgtg cgccaggcgc tctggaactg tttctcggta atgccggaac cgcgatgcgt    300

ccgttagcgg cagcgctatg tctggggcaa aatgagatag tgttaaccgg cgaaccgcgt    360

atgaaagagc gtccgatagg ccatctggtc gattcgctgc gtcagggcgg ggcgaatatt    420

gattacctgg agcaggaaaa ctatccgccc ctgcgtctgc gcggcggttt taccggcggc    480

gacattgagg ttgatggtag cgtttccagc cagttcctga ccgctctgct gatgacggcg    540

ccgctggccc ctaaagacac aattattcgc gttaaaggcg aactggtatc aaaaccttac    600

atcgatatca cgctaaattt aatgaaaacc tttggcgtgg agatagcgaa ccaccactac    660

caacaatttg tcgtgaaggg aggtcaacag tatcactctc caggtcgcta tctggtcgag    720

ggcgatgcct cgtcagcgtc ctattttctc gccgctgggg cgataaaagg cggcacggta    780

aaagtgaccg gaattggccg caaaagtatg cagggcgata ttcgttttgc cgatgtgctg    840

gagaaaatgg gcgcgaccat tacctggggc gatgatttta ttgcctgcac gcgcggtgaa    900

ttgcacgcca tagatatgga tatgaaccat attccggatg cggcgatgac gattgccacc    960
```

-continued

```
acggcgctgt ttgcgaaagg aaccacgacg ttgcgcaata tttataactg gcgagtgaaa   1020

gaaaccgatc gcctgttcgc gatggcgacc gagctacgta aagtgggcgc tgaagtcgaa   1080

gaagggcacg actatattcg tatcacgccg ccggcgaagc tccaacacgc ggatattggc   1140

acgtacaacg accaccgtat ggcgatgtgc ttctcactgg tcgcactgtc cgatacgcca   1200

gttacgatcc tggaccctaa atgtaccgca aaaacgttcc ctgattattt cgaacaactg   1260

gcgcgaatga gtacgcctgc c                                             1281
```

<210> SEQ ID NO 82
<211> LENGTH: 1094
<212> TYPE: DNA
<213> ORGANISM: Salmonella typhimurium
<220> FEATURE:
<223> OTHER INFORMATION: aroC

<400> SEQUENCE: 82

```
acggagccgt gatggcagga aacacaattg gacaactctt tcgcgtaacc actttcggcg     60

aatcacacgg gctggcgctt gggtgtatcg tcgatggcgt gccgcccggc atcccgttga    120

cggaggccga tctgcaacac gatctcgaca gacgccgccc cggcacctcg cgctatacta    180

cccagcgccg cgaaccggac caggtaaaaa ttctctccgg cgtgtttgat ggcgtgacga    240

ccggcaccag cattggccta ctgattgaaa acaccgatca gcgctcgcag gactacagcg    300

cgattaaaga tgtttttcgt ccgggacacg cggattacac ctatgagcag aaatacggcc    360

tgcgcgatta ccgtggcggt ggacgttctt ccgcgcgtga aaccgcgatg cgcgtagcgg    420

caggggcgat cgccaagaaa tacctggcgg aaaagttcgg catcgaaatc cgcggctgcc    480

tgacccagat gggcgacatt ccgctggaga ttaaagactg gcgtcaggtt gagcttaatc    540

cgttcttttg tcccgatgcg gacaaacttg acgcgctgga cgaactgatg cgcgcgctga    600

aaaaagaggg tgactccatc ggcgcgaaag tgacggtgat ggcgagcggc gtgccggcag    660

ggcttggcga accggtattt gaccgactgg atgcggacat cgcccatgcg ctgatgagca    720

ttaatgcggt gaaaggcgtg gagatcggcg aaggatttaa cgtggtggcg ctgcgcggca    780

gccagaatcg cgatgaaatc acggcgcagg gttttcagag caaccacgct ggcggcatcc    840

tcggtggcat cagtagcggg caacacattg tggcgcatat ggcgctgaaa cctacctcca    900

gcattaccgt gccgggacgt acgatcaacc gggcaggtga agaagtcgaa atgatcacca    960

aagggcgcca cgatccgtgt gtggggattc gcgcagtgcc gatcgcagaa gccatgctgg   1020

cgatcgtgct gatggatcac ctgctgcgcc atcgggcaca gaatgcggat gtaaagacag   1080

agattccacg ctgg                                                     1094
```

<210> SEQ ID NO 83
<211> LENGTH: 767
<212> TYPE: DNA
<213> ORGANISM: Salmonella typhimurium
<220> FEATURE:
<223> OTHER INFORMATION: aroD

<400> SEQUENCE: 83

```
aagggtacca aatgaaaacc gtaactgtaa gagatctcgt ggttggcgaa ggcgcgccaa     60

agatcattgt gtcgctaatg ggaaaaacca ttaccgatgt gaaatcggaa gcactcgcct    120

accgtgaagc ggatttcgat attctggagt ggcgcgttga ccattttgcc aacgtgacaa    180

cggcggaaag cgtacttgag gccgccggcg ccatccggga gattattacc gataaaccct    240

tgctatttac cttccgcagc gcgaaagaag gcggcgaaca ggcgctaacc accggacagt    300
```

-continued

```
atatcgatct gaatcgtgca gcggttgaca gcggtctggt cgatatgatc gatcttgagc    360

tttttaccgg cgacgatgag gtgaaagcca ccgtcggcta tgctcatcaa cacaatgttg    420

cggtgatcat gtctaaccat gattttcata aaacgcccgc agcggaagag attgttcagc    480

gtctgcgtaa aatgcaggaa ctgggcgctg atattccgaa gatcgccgtc atgccacaga    540

ctaaagccga tgtcctgacc ttacttaccg ccactgtaga aatgcaggag cgctatgcgg    600

atcgtccgat tattaccatg tcgatgtcga aaaccggggt aatatctcgt cttgccggcg    660

aagtgttcgg ttctgcggca acgtttggcg cggtgaaaaa agcatctgcg ccgggacaaa    720

tatcggtagc cgatctgcgt accgtattaa ctatattgca ccaggcg                  767
```

```
<210> SEQ ID NO 84
<211> LENGTH: 684
<212> TYPE: DNA
<213> ORGANISM: Salmonella typhimurium
<220> FEATURE:
<223> OTHER INFORMATION: PhoP

<400> SEQUENCE: 84

aagggagaag agatgatgcg cgtactggtt gtagaggata atgcattatt acgccaccac     60

ctgaaggttc agctccagga ttcaggtcac caggtcgatg ccgcagaaga tgccagggaa    120

gctgattact accttaatga acaccttccg gatatcgcta ttgtcgattt aggtctgccg    180

gatgaagacg gcctttcctt aatacgccgc tggcgcagca gtgatgtttc actgccggtt    240

ctggtgttaa ccgcgcgcga aggctggcag gataaagtcg aggttctcag ctccggggcc    300

gatgactacg tgacgaagcc attccacatc gaagaggtaa tggcgcgtat gcaggcgtta    360

atgcgccgta atagcggtct ggcctcccag gtgatcaaca tcccgccgtt ccaggtggat    420

ctctcacgcc gggaattatc cgtcaatgaa gaggtcatca aactcacggc gttcgaatac    480

accattatgg aaacgcttat ccgtaacaac ggtaaagtgg tcagcaaaga ttcgctgatg    540

cttcagctgt atccggatgc ggaactgcgg gaaagtcata ccattgatgt tctcatgggg    600

cgtctgcgga aaaaaataca ggcccagtat ccgcacgatg tcattaccac cgtacgcgga    660

caaggatatc tttttgaatt gcgc                                            684
```

```
<210> SEQ ID NO 85
<211> LENGTH: 1461
<212> TYPE: DNA
<213> ORGANISM: Salmonella typhimurium
<220> FEATURE:
<223> OTHER INFORMATION: PhoQ

<400> SEQUENCE: 85

atgaataaat ttgctcgcca ttttctgccg ctgtcgctgc gggttcgttt tttgctggcg     60

acagccggcg tcgtgctggt gctttctttg gcatatggca tagtggcgct ggtcggctat    120

agcgtaagtt ttgataaaac cacctttcgt ttgctgcgcg gcgaaagcaa cctgttttat    180

accctcgcca aatgggaaaa taataaaatc agcgttgagc tgcctgaaaa tctggacatg    240

caaagcccga ccatgacgct gatttacgat gaaacgggca aattattatg gacgcagcgc    300

aacattccct ggctgattaa aagcattcaa ccggaatggt taaaaacgaa cggcttccat    360

gaaattgaaa ccaacgtaga cgccaccagc acgctgttga gcgaagacca ttccgcgcag    420

gaaaaactca aagaagtacg tgaagatgac gatgatgccg agatgaccca ctcggtagcg    480

gtaaatattt atcctgccac ggcgcggatg ccgcagttaa ccatcgtggt ggtcgatacc    540
```

-continued

```
attccgatag aactaaaacg ctcctatatg gtgtggagct ggttcgtata cgtgctggcc    600

gccaatttac tgttagtcat tcctttactg tggatcgccg cctggtggag cttacgccct    660

atcgaggcgc tggcgcggga agtccgcgag cttgaagatc atcaccgcga aatgctcaat    720

ccggagacga cgcgtgagct gaccagcctt gtgcgcaacc ttaatcaact gctcaaaagc    780

gagcgtgaac gttataacaa ataccgcacg accctgaccg acctgacgca cagtttaaaa    840

acgccgctcg cggttttgca gagtacgtta cgctctttac gcaacgaaaa gatgagcgtc    900

agcaaagctg aaccggtgat gctggaacag atcagccgga tttcccagca gatcggctat    960

tatctgcatc gcgccagtat gcgcggtagc ggcgtgttgt taagccgcga actgcatccc   1020

gtcgcgccgt tgttagataa cctgatttct gcgctaaata aagtttatca gcgtaaaggg   1080

gtgaatatca gtatggatat ttcaccagaa atcagttttg tcggcgagca aaacgacttt   1140

gtcgaagtga tgggcaacgt actggacaac gcttgtaaat attgtctgga gtttgtcgag   1200

atttcggctc gccagaccga cgatcatttg catattttcg tcgaagatga cggcccaggc   1260

attccccaca gcaaacgttc cctggtgttt gatcgcggtc agcgcgccga taccctacga   1320

ccaggacaag gcgtggggct ggctgtcgcg cgcgagatta cggaacaata cgccgggcag   1380

atcattgcca gcgacagtct gctcggtggc gcccgtatgg aggtcgtttt tggccgacag   1440

catcccacac agaaagagga a                                             1461
```

<210> SEQ ID NO 86
<211> LENGTH: 2731
<212> TYPE: DNA
<213> ORGANISM: Salmonella typhimurium
<220> FEATURE:
<223> OTHER INFORMATION: Adenylate cyclase (cyaA)

<400> SEQUENCE: 86

```
tctttcttta cggtcaatga gcaaggtgtt aaattgatca cgttttagac catttttttcg     60

tcggtattag ataaaaatat gcaggcgaga aagggtaacg gttatttttg acatacggtt    120

tatcccgaat ggcgacggtc aagtactgac ctgcaccatg acgggtagca acatcaggcg    180

atacgtcttg tacctctata ttgagactct gaaacagaga ctggatgcca taaatcaact    240

gcgtgtggat cgcgcgcttg ctgccatggg acccgctttt cagcaggttt acagtcttct    300

gccgacatta ttgcactatc accatccact gatgccgggt taccttgatg gtaacgttcc    360

cagcggtatt tgcttctaca cgcctgatga aacccaacgc cactatctga acgaacttga    420

gctgtaccgc ggtatgacgc cgcaggaccc gccgaagggc gagctgccga ttaccggcgt    480

ttacaccatg ggcagcacct cctcggtcgg gcagagctgc tcgtccgacc tggatatctg    540

ggtgtgccat cagtcctggc tcgacggcga agagcgtcag ttgctgcaac gtaagtgtag    600

cctgctggaa agctgggccg cctcgcttgg cgttgaggtg agcttcttcc tgatcgacga    660

gaaccgtttc cgccataacg aaagcggcag tctgggcggg gaagactgtg gttctacgca    720

gcatatcctg ttgcttgatg agttttatcg taccgctgtg cgcctggccg ggaagcgtat    780

cctgtggagt atggtgccgt gcgacgaaga agagcattac gacgactatg tcatgacgct    840

ctatgcgcag ggcgtattaa cgccaaacga atggctggat ctgggggggct taagctcgct    900

ctccgccgaa gagtactttg gcgccagcct gtggcagcta tacaagagca ttgactcgcc    960

gtacaaagcg gtgctgaaaa cgctgctgct ggaagcctat tcatgggaat atcctaaccc   1020

acgtctgctg gcgaaagata ttaaacaacg tctgcatgac ggtgaaatcg tatcgtttgg   1080

actcgatccc tactgcatga tgctggaacg ggtcactgaa tacctgacgg cgattgaaga   1140
```

-continued

```
tccgacgcgg ctggatttag tccgccgctg cttttacctg aaagtgtgcg agaaattaag   1200
tcgcgagcgt gcctgcgtag gctggcgtcg ggaagtatta agccagttag tcagcgagtg   1260
gggatgggac gacgcgcgtc tgaccatgct cgataatcgc gcaaactgga aaatcgatca   1320
ggtgcgcgaa gcccacaacg aattgctcga cgccatgatg caaagctatc gtaatctgat   1380
tcgctttgcg cggcgcaaca acctcagcgt gagtgccagc ccgcaggata tcggcgtact   1440
gacgcgtaag ctgtacgcgg cttttgaagc gttgccgggt aaagtcacgc tggtgaaccc   1500
gcagatatcg ccggatctgt ccgagccgaa tttaaccttt atccatgtgc cgccgggacg   1560
cgccaaccgt tcaggctggt atctctacaa ccgcgcgccg aacatggatt ccatcatcag   1620
ccatcagccg ctggaatata accgttatct taataagctg gtcgcgtggg cgtggttcaa   1680
cggcctgctg acgtcgcgaa cgcatctgtt tattaagggc aacggtattg tcgacctgcc   1740
taagttacag gagatggtcg ccgatgtttc gcaccatttc ccgctgcgct tgcctgctcc   1800
gacgccgaaa gcgctctaca gcccctgtga aattcgccat ctggcgatta tcgttaacct   1860
cgaatatgac ccgacggcgg cgtttcgcaa taaagtggtc cattttgact tccgtaagct   1920
ggacgttttc agctttggcg aagagcaaaa ctgtctgata ggcagtatcg acttgttata   1980
tcgcaactcg tggaacgaag tgcgtactct gcactttaac ggcgagcagg cgatgatcga   2040
agcgctgaaa acgattctgg ggaaaatgca ccaggatgcc gcgccgccgg atagcgtgga   2100
ggtgttctgc tacagtcagc atcttcgcgg cctgattcgc acccgtgtgc agcaactggt   2160
ctccgaatgt attgagctac gtctttccag cacccgtcag gagaccggtc gcttcaaggc   2220
gctgcgggtt tccgggcaga cgtgggggct attcttcgaa cgcttgaatg tctcggtgca   2280
gaagctggag aacgctatcg aattctacgg cgcgatttcg cataacaagc tgcacgggct   2340
gtcggtacag gtggaaacca accaggtgaa attgccgtca gtggtggatg gcttcgccag   2400
cgaagggatt atccagttct tctttgaaga aacaggcgat gagaaaggct ttaacattta   2460
tattctggat gaaagtaacc gggcggaagt atatcaccac tgcgaaggta gcaaggaaga   2520
actggtgcgc gacgtcagtc gcttctattc gtcatcgcac gatcgcttca cgtatggctc   2580
cagttttatc aactttaacc tgccgcagtt ctaccagata gtgaaaaccg atggccgcgc   2640
gcaggtgatc ccattccgta cgcagcctat caacaccgtg ccgccagcaa accaggatca   2700
tgacgcgccg ctattgcagc agtatttttc g                                  2731
```

<210> SEQ ID NO 87
<211> LENGTH: 826
<212> TYPE: DNA
<213> ORGANISM: Salmonella typhimurium
<220> FEATURE:
<223> OTHER INFORMATION: cAMP-activated global transcriptional regulator (crp)

<400> SEQUENCE: 87

```
aagctatgct aaaacagaca agatgctaca gtaatacatt gacgtactgc atgtatgcag     60
aggacatcac attacaggct acaatctatt ttcgtagccc ccttcccagg tagcgggaag    120
tatatttttg caaccccaga gacagtgccg ttttctggct ctggagacag cttataacag    180
aggataaccg cgcatggtgc ttggcaaacc gcaaacagac ccgactcttg aatggttctt    240
gtctcattgc cacattcata agtacccgtc aaagagcacg ctgattcacc agggtgaaaa    300
agcagaaacg ctgtactaca tcgttaaagg ctccgtggca gtgctgatca aagatgaaga    360
agggaaagaa atgatccttt cttatctgaa tcagggtgat tttattggtg aactgggcct    420
```

```
gtttgaagaa ggccaggaac gcagcgcctg ggtacgtgcg aaaaccgcat gtgaggtcgc    480

tgaaatttcc tacaaaaaat ttcgccaatt aatccaggtc aacccggata ttctgatgcg    540

cctctcttcc cagatggctc gtcgcttaca agtcacctct gaaaaagtag gtaacctcgc    600

cttccttgac gtcaccgggc gtatcgctca gacgctgctg aatctggcga aacagcccga    660

tgccatgacg cacccggatg ggatgcagat caaaatcact cgtcaggaaa tcggccagat    720

cgtcggctgc tcccgcgaaa ccgttggtcg tattttgaaa atgctggaag atcaaaacct    780

gatctccgcg catggcaaga ccatcgtcgt ctacggcacc cgttaa                   826


<210> SEQ ID NO 88
<211> LENGTH: 1566
<212> TYPE: DNA
<213> ORGANISM: Homo sapiens
<220> FEATURE:
<223> OTHER INFORMATION: cyclic GMP-AMP (cGAMP) synthase (cGAS), isoform
      1

<400> SEQUENCE: 88

atgcagcctt ggcacggaaa ggccatgcag agagcttccg aggccggagc cactgccccc     60

aaggcttccg cacggaatgc caggggcgcc ccgatggatc ccaccgagtc tccggctgcc    120

cccgaggccg ccctgcctaa ggcgggaaag ttcggccccg ccaggaagtc gggatcccgg    180

cagaaaaaga gcgccccgga cacccaggag aggccgcccg tccgcgcaac tggggcccgc    240

gccaaaaagg cccctcagcg cgcccaggac acgcagccgt ctgacgccac cagcgcccct    300

ggggcagagg ggctggagcc tcctgcggct cgggagccgg ctctttccag ggctggttct    360

tgccgccaga ggggcgcgcg ctgctccacg aagccaagac ctccgcccgg gccctgggac    420

gtgcccagcc ccggcctgcc ggtctcggcc cccattctcg tacggaggga tgcggcgcct    480

ggggcctcga agctccgggc ggttttggag aagttgaagc tcagccgcga tgatatctcc    540

acggcggcgg ggatggtgaa aggggttgtg gaccacctgc tgctcagact gaagtgcgac    600

tccgcgttca gaggcgtcgg gctgctgaac accgggagct actatgagca cgtgaagatt    660

tctgcaccta atgaatttga tgtcatgttt aaactggaag tccccagaat tcaactagaa    720

gaatattcca acactcgtgc atattacttt gtgaaattta aaagaaatcc gaaagaaaat    780

cctctgagtc agtttttaga aggtgaaata ttatcagctt ctaagatgct gtcaaagttt    840

aggaaaatca ttaaggaaga aattaacgac attaaagata cagatgtcat catgaagagg    900

aaaagaggag ggagccctgc tgtaacactt cttattagtg aaaaaatatc tgtggatata    960

accctggctt tggaatcaaa aagtagctgg cctgctagca cccaagaagg cctgcgcatt   1020

caaaactggc tttcagcaaa agttaggaag caactacgac taaagccatt ttaccttgta   1080

cccaagcatg caaaggaagg aaatggtttc caagaagaaa catggcggct atccttctct   1140

cacatcgaaa aggaaatttt gaacaatcat ggaaaatcta aaacgtgctg tgaaaacaaa   1200

gaagagaaat gttgcaggaa agattgttta aaactaatga aatacctttt agaacagctg   1260

aaagaaaggt ttaaagacaa aaaacatctg gataaattct cttcttatca tgtgaaaact   1320

gccttctttc acgtatgtac ccagaaccct caagacagtc agtgggaccg caaagacctg   1380

ggcctctgct ttgataactg cgtgacatac tttcttcagt gcctcaggac agaaaaactt   1440

gagaattatt ttattcctga attcaatcta ttctctagca acttaattga caaaagaagt   1500

aaagaatttc tgacaaagca aattgaatat gaaagaaaca atgagtttcc agtttttgat   1560

gaattt                                                              1566
```

<210> SEQ ID NO 89
<211> LENGTH: 1137
<212> TYPE: DNA
<213> ORGANISM: Homo sapiens
<220> FEATURE:
<223> OTHER INFORMATION: Stimulator of Interferon Genes (STING)

<400> SEQUENCE: 89
atgccccact ccagcctgca tccatccatc ccgtgtccca ggggtcacgg ggcccagaag 60
gcagccttgg ttctgctgag tgcctgcctg gtgaccettt gggggctagg agagccacca 120
gagcacactc tccggtacct ggtgctccac ctagcctccc tgcagctggg actgctgtta 180
aacggggtct gcagcctggc tgaggagctg cgccacatcc actccaggta ccggggcagc 240
tactggagga ctgtgcgggc ctgcctgggc tgccccctcc gccgtggggc cctgttgctg 300
ctgtccatct atttctacta ctccctccca aatgcggtcg gcccgccctt cacttggatg 360
cttgccctcc tgggcctctc gcaggcactg aacatcctcc tgggcctcaa gggcctggcc 420
ccagctgaga tctctgcagt gtgtgaaaaa gggaatttca acgtggccca tgggctggca 480
tggtcatatt acatcggata tctgcggctg atcctgccag agctccaggc ccggattcga 540
acttacaatc agcattacaa caacctgcta cggggtgcag tgagccagcg gctgtatatt 600
ctcctcccat tggactgtgg ggtgcctgat aacctgagta tggctgaccc caacattcgc 660
ttcctggata aactgcccca gcagaccggt gaccatgctg gcatcaagga tcgggtttac 720
agcaacagca tctatgagct tctggagaac gggcagcggg cgggcacctg tgtcctggag 780
tacgccaccc ccttgcagac tttgtttgcc atgtcacaat acagtcaagc tggctttagc 840
cgggaggata ggcttgagca ggccaaactc ttctgccgga cacttgagga catcctggca 900
gatgcccctg agtctcagaa caactgccgc ctcattgcct accaggaacc tgcagatgac 960
agcagcttct cgctgtccca ggaggttctc cggcacctgc ggcaggagga aaaggaagag 1020
gttactgtgg gcagcttgaa gacctcagcg gtgcccagta cctccacgat gtcccaagag 1080
cctgagctcc tcatcagtgg aatggaaaag cccctccctc tccgcacgga tttctct 1137

<210> SEQ ID NO 90
<211> LENGTH: 972
<212> TYPE: DNA
<213> ORGANISM: Salmonella typhimurium
<220> FEATURE:
<223> OTHER INFORMATION: lipid A biosynthesis myristoyltransferase (msbB)

<400> SEQUENCE: 90
ttatttgatg ggataaagat ctttacgctt atacggctga atctcgcctg gcttgcgggt 60
tttgagcagc ttcaggatcc aggtgtactg ttccggatgc gggccgacaa aaatttcgac 120
ctcttcgttc atccgtctgg cgatagtgtg gtcgtcagcc gtgagcagat cgtccattgg 180
cgggcgaatc tggatagtca ggcgatgcgt tttaccatta tacaccggga aaagcggtat 240
cacgcgtgcg cggcacactt tcatcagccg accaattgca ggcagcgtcg ctttgtatgt 300
cgcaaagaaa tcaacgaatt cactatgctc cgggccgtga tcctggtccg gcaggtagta 360
accccagtag ccctgacgaa cagactgaat aaagggttta atcccgtcat tacgcgcatg 420
caaacgtccg ccgaaacgcc gacgcactgt gttccagata tagtcaaaaa ccggattacc 480
ctgattatga aacatcgccg ccattttttg cccctgagag gccatcagca tggctggaat 540
gtcgacgccc cagccatgcg gtacgagaaa aatgactttt tcgtcgttac gacgcatctc 600

-continued

```
ctcgataatc tccagacctt cccagtcaac acgctgttga atttttttcg gaccgcgcat    660

cgccaactca gccatcatcg ccattgcctg tggcgcggtg gcgaacatct catcgacaat    720

cgcttcgcgc tcagcttcgc tacgctgcgg aaagcacaac gacagattaa ttagcgcccg    780

gcgacgagaa ctcttcccca gccgtccggc aaaacgcccc agcgtcgcca gcaaagggtc    840

gcggaatgat gccggtgtta atgcgatccc cgccattgcc gccgcgccca accaggcgcc    900

ccaatactgt ggatagcgaa aggatttttc gaattcaggg atatactcac tattattttt    960

tttggtttcc at                                                        972
```

<210> SEQ ID NO 91
<211> LENGTH: 1038
<212> TYPE: DNA
<213> ORGANISM: Salmonella typhimurium
<220> FEATURE:
<223> OTHER INFORMATION: Phosphoribosylaminoimidazole synthetase (purI)

<400> SEQUENCE: 91

```
ttattcaata accacacgct gttcggaatc agaggctttg atgataccga ttttccatgc     60

gttttcacct ttctcgttta gcagagcaag cgctttgtcc gcttccggag cggagagcgc    120

aatcaccatg ccgacgccgc agttaaaggt acggtacatt tcatgtcggc tgacattacc    180

ggcggtttgc agccaggtaa agatggcggg ccactgccag gacgactcat taattaccgc    240

ctgggtattc tccggcagaa cgcgcggaat attttcccaa aagcccccgc cggtgaggtg    300

ggcgatagcg tgtacatcga cgttttcaat cagttccaga accgatttta cgtagatacg    360

ggtcggttca agcagatgat cggccagcgg cttcccttcc agcagagtgg tttgtgggtc    420

gcagccgcta acgtcaataa ttttccgcac cagcgaatat ccattcgagt gcgggccgct    480

ggagccgagt gcaatcagca cgtcgccttc ggcaacccgg gagccgtcga tgatttctga    540

tttttcgact acgccgacgc agaaacccgc cacatcgtaa tcttcgccgt gatacatgcc    600

cggcatttcc gccgtctcgc cgccgaccag cgcgcagccg gattgcaggc agccttcggc    660

aataccgttg atcacgctgg cggcggtatc gacatccagt ttacccgtgg catagtaatc    720

gaggaaaaac agcggttccg cgccctgaac gaccagatcg tttacgcaca ttgccaccag    780

atcaataccg atagcgtcgt gacgctttaa gtccatcgcc aggcgaagtt tggtacctac    840

gccgtcagtg ccggaaacca gtaccggttc acgatatttt tgcggcaacg cgcacagcgc    900

accgaaaccg cccagaccgc ccataacctc cgggcggcga gttttcttca ctacgccttt    960

gattcgatca accagagcgt tacccgcatc aatatcgacg ccggcatctt tatagctaag   1020

agaggtctta tcggtcac                                                 1038
```

<210> SEQ ID NO 92
<211> LENGTH: 426
<212> TYPE: DNA
<213> ORGANISM: Homo sapiens
<220> FEATURE:
<223> OTHER INFORMATION: Survivin (SVN)/BIRC5, isoform 1

<400> SEQUENCE: 92

```
atgggtgccc cgacgttgcc ccctgcctgg cagccctttc tcaaggacca ccgcatctct     60

acattcaaga actggccctt cttggagggc tgcgcctgca ccccggagcg gatggccgag    120

gctggcttca tccactgccc cactgagaac gagccagact tggcccagtg tttcttctgc    180

ttcaaggagc tggaaggctg ggagccagat gacgacccca tagaggaaca taaaaagcat    240
```

-continued

```
tcgtccggtt gcgctttcct ttctgtcaag aagcagtttg aagaattaac ccttggtgaa    300

tttttgaaac tggacagaga aagagccaag aacaaaattg caaaggaaac caacaataag    360

aagaaagaat ttgaggaaac tgcggagaaa gtgcgccgtg ccatcgagca gctggctgcc    420

atggat                                                               426
```

<210> SEQ ID NO 93
<211> LENGTH: 285
<212> TYPE: DNA
<213> ORGANISM: E. coli
<220> FEATURE:
<223> OTHER INFORMATION: araBAD promoter (pBAD)

<400> SEQUENCE: 93

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcttacctg acgcttttta tcgcaactct ctactgtttc tccat                    285
```

<210> SEQ ID NO 94
<211> LENGTH: 459
<212> TYPE: DNA
<213> ORGANISM: Homo sapiens
<220> FEATURE:
<223> OTHER INFORMATION: Interleukin 2 (IL-2)

<400> SEQUENCE: 94

```
atgtacagga tgcaactcct gtcttgcatt gcactaagtc ttgcacttgt cacaaacagt     60

gcacctactt caagttctac aaagaaaaca cagctacaac tggagcattt actgctggat    120

ttacagatga ttttgaatgg aattaataat tacaagaatc ccaaactcac caggatgctc    180

acatttaagt tttacatgcc caagaaggcc acagaactga aacatcttca gtgtctagaa    240

gaagaactca aacctctgga ggaagtgcta aatttagctc aaagcaaaaa ctttcactta    300

agacccaggg acttaatcag caatatcaac gtaatagttc tggaactaaa gggatctgaa    360

acaacattca tgtgtgaata tgctgatgag acagcaacca ttgtagaatt tctgaacaga    420

tggattacct tttgtcaaag catcatctca acactgact                           459
```

<210> SEQ ID NO 95
<211> LENGTH: 567
<212> TYPE: DNA
<213> ORGANISM: Homo sapiens
<220> FEATURE:
<223> OTHER INFORMATION: Interferon (IFN) alpha

<400> SEQUENCE: 95

```
atggcctcgc cctttgcttt actgatggtc ctggtggtgc tcagctgcaa gtcaagctgc     60

tctctgggct gtgatctccc tgagacccac agcctggata acaggaggac cttgatgctc    120

ctggcacaaa tgagcagaat ctctccttcc tcctgtctga tggacagaca tgactttgga    180

tttccccagg aggagtttga tggcaaccag ttccagaagg ctccagccat ctctgtcctc    240

catgagctga tccagcagat cttcaacctc tttaccacaa aagattcatc tgctgcttgg    300

gatgaggacc tcctagacaa attctgcacc gaactctacc agcagctgaa tgacttggaa    360

gcctgtgtga tgcaggagga gagggtggga gaaactcccc tgatgaatgc ggactccatc    420

ttggctgtga agaaatactt ccgaagaatc actctctatc tgacagagaa gaaatacagc    480
```

ccttgtgcct gggaggttgt cagagcagaa atcatgagat ccctctcttt atcaacaaac 540
ttgcaagaaa gattaaggag gaaggaa 567

<210> SEQ ID NO 96
<211> LENGTH: 729
<212> TYPE: DNA
<213> ORGANISM: Homo sapiens
<220> FEATURE:
<223> OTHER INFORMATION: CD48, isoform 1

<400> SEQUENCE: 96
atgtgctcca gaggttggga ttcgtgtctg gctctggaat tgctactgct gcctctgtca 60
ctcctggtga ccagcattca aggtcacttg gtacatatga ccgtggtctc cggcagcaac 120
gtgactctga acatctctga gagcctgcct gagaactaca aacaactaac ctggttttat 180
actttcgacc agaagattgt agaatgggat tccagaaaat ctaagtactt tgaatccaaa 240
tttaaaggca gggtcagact tgatcctcag agtggcgcac tgtacatctc taaggtccag 300
aaagaggaca acagcaccta catcatgagg gtgttgaaaa agactgggaa tgagcaagaa 360
tggaagatca agctgcaagt gcttgaccct gtacccaagc ctgtcatcaa aattgagaag 420
atagaagaca tggatgacaa ctgttatctg aaactgtcat gtgtgatacc tggcgagtct 480
gtaaactaca cctggtatgg ggacaaaagg cccttcccaa aggagctcca gaacagtgtg 540
cttgaaacca cccttatgcc acataattac tccaggtgtt atacttgcca agtcagcaat 600
tctgtgagca gcaagaatgg cacggtctgc ctcagtccac cctgtaccct ggcccggtcc 660
tttggagtag aatggattgc aagttggcta gtggtcacgg tgcccaccat tcttggcctg 720
ttacttacc 729

<210> SEQ ID NO 97
<211> LENGTH: 1602
<212> TYPE: DNA
<213> ORGANISM: Homo sapiens
<220> FEATURE:
<223> OTHER INFORMATION: CD276/B7-H3, isoform 1

<400> SEQUENCE: 97
atgctgcgtc ggcggggcag ccctggcatg ggtgtgcatg tgggtgcagc cctgggagca 60
ctgtggttct gcctcacagg agccctggag gtccaggtcc ctgaagaccc agtggtggca 120
ctggtgggca ccgatgccac cctgtgctgc tccttctccc ctgagcctgg cttcagcctg 180
gcacagctca acctcatctg gcagctgaca gataccaaac agctggtgca cagctttgct 240
gagggccagg accagggcag cgcctatgcc aaccgcacgg ccctcttccc ggacctgctg 300
gcacagggca acgcatccct gaggctgcag cgcgtgcgtg tggcggacga gggcagcttc 360
acctgcttcg tgagcatccg ggatttcggc agcgctgccg tcagcctgca ggtggccgct 420
ccctactcga agcccagcat gaccctggag cccaacaagg acctgcggcc aggggacacg 480
gtgaccatca cgtgctccag ctaccagggc taccctgagg ctgaggtgtt ctggcaggat 540
gggcagggtg tgcccctgac tggcaacgtg accacgtcgc agatggccaa cgagcagggc 600
ttgtttgatg tgcacagcat cctgcgggtg gtgctgggtg caaatggcac ctacagctgc 660
ctggtgcgca accccgtgct gcagcaggat gcgcacagct ctgtcaccat cacaccccag 720
agaagcccca caggagccgt ggaggtccag gtccctgagg acccggtggt ggccctagtg 780
ggcaccgatg ccaccctgcg ctgctccttc tcccccgagc ctggcttcag cctggcacag 840

```
ctcaacctca tctggcagct gacagacacc aaacagctgg tgcacagttt caccgaaggc    900

cgggaccagg gcagcgccta tgccaaccgc acggccctct tcccggacct gctggcacaa    960

ggcaatgcat ccctgaggct gcagcgcgtg cgtgtggcgg acgagggcag cttcacctgc   1020

ttcgtgagca tccgggattt cggcagcgct gccgtcagcc tgcaggtggc cgctccctac   1080

tcgaagccca gcatgaccct ggagcccaac aaggacctgc ggccagggga cacggtgacc   1140

atcacgtgct ccagctaccg gggctaccct gaggctgagg tgttctggca ggatgggcag   1200

ggtgtgcccc tgactggcaa cgtgaccacg tcgcagatgg ccaacgagca gggcttgttt   1260

gatgtgcaca gcgtcctgcg ggtggtgctg ggtgcgaatg gcacctacag ctgcctggtg   1320

cgcaaccccg tgctgcagca ggatgcgcac ggctctgtca ccatcacagg gcagcctatg   1380

acattccccc cagaggccct gtgggtgacc gtggggctgt ctgtctgtct cattgcactg   1440

ctggtggccc tggctttcgt gtgctggaga aagatcaaac agagctgtga ggaggagaat   1500

gcaggagctg aggaccagga tggggaggga gaaggctcca agacagccct gcagcctctg   1560

aaacactctg acagcaaaga agatgatgga caagaaatag cc                      1602


<210> SEQ ID NO 98
<211> LENGTH: 846
<212> TYPE: DNA
<213> ORGANISM: Homo sapiens
<220> FEATURE:
<223> OTHER INFORMATION: B7-H4/VTCN1

<400> SEQUENCE: 98

atggcttccc tggggcagat cctcttctgg agcataatta gcatcatcat tattctggct     60

ggagcaattg cactcatcat tggctttggt atttcaggga gacactccat cacagtcact    120

actgtcgcct cagctgggaa cattggggag gatggaatcc tgagctgcac ttttgaacct    180

gacatcaaac tttctgatat cgtgatacaa tggctgaagg aaggtgtttt aggcttggtc    240

catgagttca aagaaggcaa agatgagctg tcggagcagg atgaaatgtt cagaggccgg    300

acagcagtgt ttgctgatca agtgatagtt ggcaatgcct ctttgcggct gaaaaacgtg    360

caactcacag atgctggcac ctacaaatgt tatatcatca cttctaaagg caaggggaat    420

gctaaccttg agtataaaac tggagccttc agcatgccgg aagtgaatgt ggactataat    480

gccagctcag agaccttgcg gtgtgaggct ccccgatggt tcccccagcc cacagtggtc    540

tgggcatccc aagttgacca gggagccaac ttctcggaag tctccaatac cagctttgag    600

ctgaactctg agaatgtgac catgaaggtt gtgtctgtgc tctacaatgt tacgatcaac    660

aacacatact cctgtatgat tgaaaatgac attgccaaag caacagggga tatcaaagtg    720

acagaatcgg agatcaaaag gcggagtcac ctacagctgc taaactcaaa ggcttctctg    780

tgtgtctctt ctttctttgc catcagctgg gcacttctgc ctctcagccc ttacctgatg    840

ctaaaa                                                               846


<210> SEQ ID NO 99
<211> LENGTH: 867
<212> TYPE: DNA
<213> ORGANISM: Homo sapiens
<220> FEATURE:
<223> OTHER INFORMATION: BTLA/CD272, isoform 1

<400> SEQUENCE: 99

atgaagacat tgcctgccat gcttggaact gggaaattat tttgggtctt cttcttaatc     60

ccatatctgg acatctggaa catccatggg aaagaatcat gtgatgtaca gctttatata    120
```

-continued

```
aagagacaat ctgaacactc catcttagca ggagatccct ttgaactaga atgccctgtg    180

aaatactgtg ctaacaggcc tcatgtgact tggtgcaagc tcaatggaac aacatgtgta    240

aaacttgaag atagacaaac aagttggaag gaagagaaga acatttcatt tttcattcta    300

cattttgaac cagtgcttcc taatgacaat gggtcatacc gctgttctgc aaattttcag    360

tctaatctca ttgaaagcca ctcaacaact ctttatgtga cagatgtaaa aagtgcctca    420

gaacgaccct ccaaggacga aatggcaagc agaccctggc tcctgtatag tttacttcct    480

ttggggggat tgcctctact catcactacc tgtttctgcc tgttctgctg cctgagaagg    540

caccaaggaa agcaaaatga actctctgac acagcaggaa gggaaattaa cctggttgat    600

gctcacctta agagtgagca aacagaagca agcaccaggc aaaattccca agtactgcta    660

tcagaaactg gaatttatga taatgaccct gacctttgtt tcaggatgca ggaagggtct    720

gaagtttatt ctaatccatg cctggaagaa aacaaaccag gcattgttta tgcttccctg    780

aaccattctg tcattggacc gaactcaaga ctggcaagaa atgtaaaaga agcaccaaca    840

gaatatgcat ccatatgtgt gaggagt                                         867
```

```
<210> SEQ ID NO 100
<211> LENGTH: 276
<212> TYPE: DNA
<213> ORGANISM: Homo sapiens
<220> FEATURE:
<223> OTHER INFORMATION: Chemokine (C-C motif) ligand 4 (CCL4)

<400> SEQUENCE: 100

atgaagctct gcgtgactgt cctgtctctc ctcatgctag tagctgcctt ctgctctcca     60

gcgctctcag caccaatggg ctcagaccct cccaccgcct gctgcttttc ttacaccgcg    120

aggaagcttc ctcgcaactt tgtggtagat tactatgaga ccagcagcct ctgctcccag    180

ccagctgtgg tattccaaac caaaagaagc aagcaagtct gtgctgatcc cagtgaatcc    240

tgggtccagg agtacgtgta tgacctggaa ctgaac                               276
```

```
<210> SEQ ID NO 101
<211> LENGTH: 3537
<212> TYPE: DNA
<213> ORGANISM: Homo sapiens
<220> FEATURE:
<223> OTHER INFORMATION: CD103/ITGAE

<400> SEQUENCE: 101

atgtggctct tccacactct gctctgcata gccagcctgg ccctgctggc cgctttcaat     60

gtggatgtgg cccggccctg gctcacgccc aagggaggtg cccctttcgt gctcagctcc    120

cttctgcacc aagaccccag caccaaccag acctggctcc tggtcaccag ccccagaacc    180

aagaggacac cagggcccct ccatcgatgt tcccttgtcc aggatgaaat cctttgccat    240

cctgtagagc atgtccccat ccccaagggg aggcaccggg gagtgaccgt tgtccggagc    300

caccacggtg ttttgatatg cattcaagtg ctggtccggc ggcctcacag cctcagctca    360

gaactcacag gcacctgtag cctcctgggc cctgacctcc gtccccaggc tcaggccaac    420

ttcttcgacc ttgaaaatct cctggatcca gatgcacgtg tggacactgg agactgctac    480

agcaacaaag aaggcggtgg agaagacgat gtgaacacag ccaggcagcg ccgggctctg    540

gagaaggagg aggaggaaga caaggaggag gaggaagacg aggaggagga ggaagctggc    600

accgagattg ccatcatcct ggatggctca ggaagcattg atcccccaga ctttcagaga    660
```

-continued

```
gccaaagact tcatctccaa catgatgagg aacttctatg aaaagtgttt tgagtgcaac    720
tttgccttgg tgcagtatgg aggagtgatc cagactgagt ttgaccttcg ggacagccag    780
gatgtgatgg cctccctcgc cagagtccag aacatcactc aagtggggag tgtcaccaag    840
actgcctcag ccatgcaaca cgtcttagac agcatcttca cctcaagcca cggctccagg    900
agaaaggcat ccaaggtcat ggtggtgctc accgatggtg gcatattcga ggaccccctc    960
aaccttacga cagtcatcaa ctcccccaaa atgcagggtg ttgagcgctt tgccattggg   1020
gtgggagaag aatttaagag tgctaggact gcgagggaac tgaacctgat cgcctcagac   1080
ccggatgaga cccatgcttt caaggtgacc aactacatgg cgctggatgg gctgctgagc   1140
aaactgcggt acaacatcat cagcatggaa ggcacggttg gagacgccct tcactaccag   1200
ctggcacaga ttggcttcag tgctcagatc ctggatgagc ggcaggtgct gctcggcgcc   1260
gtcggggcct ttgactggtc cggaggggcg ttgctctacg acacacgcag ccgccggggc   1320
cgcttcctga accagacagc ggcggcggcg gcagacgcgg aggctgcgca gtacagctac   1380
ctgggttacg ctgtggccgt gctgcacaag acctgcagcc tctcctacat cgcgggggct   1440
ccacggtaca aacatcatgg ggccgtgttt gagctccaga aggagggcag agaggccagc   1500
ttcctgccag tgctggaggg agagcagatg ggtcctattt tggctctgga gctgtgccct   1560
gtggacattg acatggatgg aagcacggac ttcttgctgg tggctgctcc attttaccac   1620
gttcatggag aagaaggcag agtctacgtg taccgtctca gcgagcagga tggttctttc   1680
tccttggcac gcatactgag tgggcacccc gggttcacca atgcccgctt tggctttgcc   1740
atggcggcta tgggggatct cagtcaggat aagctcacag atgtggccat cggggccccc   1800
ctggaaggtt ttggggcaga tgatggtgcc agcttcggca gtgtgtatat ctacaatgga   1860
cactgggacg gcctctccgc cagcccctcg cagcggatca gagcctccac ggtggcccca   1920
ggactccagt acttcggcat gtccatggct ggtggctttg atattagtgg cgacggcctt   1980
gccgacatca ccgtgggcac tctgggccag gcggttgtgt tccgctcccg gcctgtggtt   2040
cgcctgaagg tctccatggc cttcaccccc agcgcactgc ccatcggctt caacggcgtc   2100
gtgaatgtcc gtttatgttt tgaaatcagc tctgtaacca cagcctctga gtcaggcctc   2160
cgcgaggcac ttctcaactt cacgctggat gtggatgtgg ggaagcagag gagacggctg   2220
cagtgttcag acgtaagaag ctgtctgggc tgcctgaggg agtggagcag cggatcccag   2280
ctttgtgagg acctcctgct catgcccaca gagggagagc tctgtgagga ggactgcttc   2340
tccaatgcca gtgtcaaagt cagctaccag ctccagaccc ctgagggaca gacggaccat   2400
ccccagccca tcctggaccg ctacactgag ccctttgcca tcttccagct gccctatgag   2460
aaggcctgca agaataagct gttttgtgtc gcagaattac agttggccac caccgtctct   2520
cagcaggagt tggtggtggg tctcacaaag gagctgaccc tgaacattaa cctaactaac   2580
tccgggggaag attcctacat gacaagcatg gccttgaatt accccagaaa cctgcagttg   2640
aagaggatgc aaaagcctcc ctctccaaac attcagtgtg atgaccctca gccggttgct   2700
tctgtcctga tcatgaactg caggattggt caccccgtcc tcaagaggtc atctgctcat   2760
gtttcagtcg tttggcagct agaggagaat gcctttccaa acaggacagc agacatcact   2820
gtgactgtca ccaattccaa tgaaagacgg tctttggcca acgagaccca cacccttcaa   2880
ttcaggcatg gcttcgttgc agttctgtcc aaaccatcca taatgtacgt gaacacaggc   2940
caggggcttt ctcaccacaa agaattcctc ttccatgtac atggggagaa cctctttgga   3000
gcagaatacc agttgcaaat ttgcgtccca accaaattac gaggtctcca ggttgtagca   3060
```

-continued gtgaagaagc tgacgaggac tcaggcctcc acggtgtgca cctggagtca ggagcgcgct 3120
tgtgcgtaca gttcggttca gcatgtggaa gaatggcatt cagtgagctg tgtcatcgct 3180
tcagataaag aaaatgtcac cgtggctgca gagatctcct gggatcactc tgaggagtta 3240
ctaaaagatg taactgaact gcagatcctt ggtgaaatat ctttcaacaa atctctatat 3300
gagggactga atgcagagaa ccacagaact aagatcactg tcgtcttcct gaaagatgag 3360
aagtaccatt ctttgcctat catcattaaa ggcagcgttg gtggacttct ggtgttgatc 3420
gtgattctgg tcatcctgtt caagtgtggc ttttttaaaa gaaaatatca acaactgaac 3480
ttggagagca tcaggaaggc ccagctgaaa tcagagaatc tgctcgaaga agagaat 3537

<210> SEQ ID NO 102
<211> LENGTH: 1671
<212> TYPE: DNA
<213> ORGANISM: Homo sapiens
<220> FEATURE:
<223> OTHER INFORMATION: CD19, isoform 1

<400> SEQUENCE: 102
atgccacctc ctcgcctcct cttcttcctc ctcttcctca cccccatgga agtcaggccc 60
gaggaacctc tagtggtgaa ggtggaagag ggagataacg ctgtgctgca gtgcctcaag 120
gggacctcag atggccccac tcagcagctg acctggtctc gggagtcccc gcttaaaccc 180
ttcttaaaac tcagcctggg gctgccaggc ctgggaatcc acatgaggcc cctggccatc 240
tggcttttca tcttcaacgt ctctcaacag atgggggggct tctacctgtg ccagccgggg 300 ccccccctctg agaaggcctg gcagcctggc tggacagtca atgtggaggg cagcggggag 360
ctgttccggt ggaatgtttc ggacctaggt ggcctgggct gtggcctgaa gaacaggtcc 420
tcagagggcc ccagctcccc ttccgggaag ctcatgagcc ccaagctgta tgtgtgggcc 480
aaagaccgcc ctgagatctg ggagggagag cctccgtgtc tcccaccgag ggacagcctg 540
aaccagagcc tcagccagga cctcaccatg gcccctggct ccacactctg gctgtcctgt 600
ggggtacccc ctgactctgt gtccaggggc cccctctcct ggacccatgt gcaccccaag 660
gggcctaagt cattgctgag cctagagctg aaggacgatc gcccggccag agatatgtgg 720
gtaatggaga cgggtctgtt gttgccccgg gccacagctc aagacgctgg aaagtattat 780
tgtcaccgtg gcaacctgac catgtcattc cacctggaga tcactgctcg gccagtacta 840
tggcactggc tgctgaggac tggtggctgg aaggtctcag ctgtgacttt ggcttatctg 900
atcttctgcc tgtgttccct tgtgggcatt cttcatcttc aaagagccct ggtcctgagg 960
aggaaaagaa agcgaatgac tgaccccacc aggagattct tcaaagtgac gcctccccca 1020
ggaagcgggc cccagaacca gtacgggaac gtgctgtctc tccccacacc cacctcaggc 1080
ctcggacgcg cccagcgttg ggccgcaggc ctgggggggca ctgccccgtc ttatggaaac 1140
ccgagcagcg acgtccaggc ggatggagcc ttggggtccc ggagcccgcc gggagtgggc 1200
ccagaagaag aggaagggga gggctatgag gaacctgaca gtgaggagga ctccgagttc 1260
tatgagaacg actccaacct tgggcaggac cagctctccc aggatggcag cggctacgag 1320
aaccctgagg atgagcccct gggtcctgag gatgaagact ccttctccaa cgctgagtct 1380
tatgagaacg aggatgaaga gctgacccag ccggtcgcca ggacaatgga cttcctgagc 1440
cctcatgggt cagcctggga ccccagccgg gaagcaacct ccctggcagg gtcccagtcc 1500
tatgaggata tgagaggaat cctgtatgca gccccccagc tccgctccat tcggggccag 1560
cctggaccca atcatgagga agatgcagac tcttatgaga acatggataa tcccgatggg 1620
ccagacccag cctggggagg agggggccgc atgggcacct ggagcaccag g 1671

<210> SEQ ID NO 103
<211> LENGTH: 579
<212> TYPE: DNA
<213> ORGANISM: Homo sapiens
<220> FEATURE:
<223> OTHER INFORMATION: Interleukin 18 (IL-18), isoform 1

<400> SEQUENCE: 103
atggctgctg aaccagtaga agacaattgc atcaactttg tggcaatgaa atttattgac 60
aatacgcttt actttatagc tgaagatgat gaaaacctgg aatcagatta ctttggcaag 120
cttgaatcta aattatcagt cataagaaat ttgaatgacc aagttctctt cattgaccaa 180
ggaaatcggc ctctatttga agatatgact gattctgact gtagagataa tgcaccccgg 240
accatattta ttataagtat gtataaagat agccagccta gaggtatggc tgtaactatc 300
tctgtgaagt gtgagaaaat ttcaactctc tcctgtgaga acaaaattat ttcctttaag 360
gaaatgaatc ctcctgataa catcaaggat acaaaaagtg acatcatatt ctttcagaga 420
agtgtcccag gacatgataa taagatgcaa tttgaatctt catcatacga aggatacttt 480
ctagcttgtg aaaaagagag agaccttttt aaactcattt tgaaaaaaga ggatgaattg 540
ggggatagat ctataatgtt cactgttcaa aacgaagac 579

<210> SEQ ID NO 104
<211> LENGTH: 1005
<212> TYPE: DNA
<213> ORGANISM: Homo sapiens
<220> FEATURE:
<223> OTHER INFORMATION: Fas ligand

<400> SEQUENCE: 104
atgctgggca tctggaccct cctacctctg gttcttacgt ctgttgctag attatcgtcc 60
aaaagtgtta atgcccaagt gactgacatc aactccaagg gattggaatt gaggaagact 120
gttactacag ttgagactca gaacttggaa ggcctgcatc atgatggcca attctgccat 180
aagccctgtc ctccaggtga aaggaaagct agggactgca cagtcaatgg ggatgaacca 240
gactgcgtgc cctgccaaga agggaaggag tacacagaca aagcccattt ttcttccaaa 300
tgcagaagat gtagattgtg tgatgaagga catggcttag aagtggaaat aaactgcacc 360
cggacccaga ataccaagtg cagatgtaaa ccaaactttt tttgtaactc tactgtatgt 420
gaacactgtg acccttgcac caaatgtgaa catggaatca tcaaggaatg cacactcacc 480
agcaacacca agtgcaaaga ggaaggatcc agatctaact tggggtggct ttgtcttctt 540
cttttgccaa ttccactaat tgtttgggtg aagagaaagg aagtacagaa aacatgcaga 600
aagcacagaa aggaaaacca aggttctcat gaatctccaa ctttaaatcc tgaaacagtg 660
gcaataaatt tatctgatgt tgacttgagt aaatatatca ccactattgc tggagtcatg 720
acactaagtc aagttaaagg ctttgttcga aagaatggtg tcaatgaagc caaaatagat 780
gagatcaaga atgacaatgt ccaagacaca gcagaacaga aagttcaact gcttcgtaat 840
tggcatcaac ttcatggaaa gaaagaagcg tatgacacat tgattaaaga tctcaaaaaa 900
gccaatcttt gtactcttgc agagaaaatt cagactatca tcctcaagga cattactagt 960
gactcagaaa attcaaactt cagaaatgaa atccaaagct tggtc 1005

<210> SEQ ID NO 105
<211> LENGTH: 1023
<212> TYPE: DNA
<213> ORGANISM: Salmonella typhimurium
<220> FEATURE:
<223> OTHER INFORMATION: firA/SSC

<400> SEQUENCE: 105
atgccttcaa ttcgactggc tgacttagca gaacagttgg atgcagaatt acacggtgat 60
ggcgatatcg tcatcaccgg cgttgcgtcc atgcaatctg caacaacagg ccacattacg 120
tttatggtga atcctaagta ccgtgaacac ttaggtttat gccaggcttc tgcggttgtc 180
atgacgcagg acgatcttcc ttttgctaag agtgcggcgc tggtagttaa aaatccctac 240
ctgacctacg cgcgcatggc gcaaatttta gatactacgc cgcagcccgc gcagaatatc 300
gcgccaagcg ccgtgattga tgcgacggca acgctgggta gcaatgtttc agtcggcgcg 360
aatgcggtga ttgaatctgg cgtacaactg ggcgataacg tggttatcgg cgcaggctgt 420
ttcgtcggaa aaaatagcaa aatcggggcg ggttcacgct tgtgggcgaa cgtaacgatt 480
taccacgaca ttcagatcgg tgagaattgc ctgatccagt ccagtacggt gatcggcgcg 540
gacggttttg gctacgctaa cgatcgtggc aactgggtga agatcccaca actgggccgg 600
gtcattattg gcgatcgtgt cgagatcggc gcttgtacca ccattgaccg tggcgcgttg 660
gatgatactg ttattggcaa tggcgtgatt attgataatc agtgccagat tgcacataac 720
gtcgtgattg gcgacaatac ggcagttgcc ggtggcgtca ttatggcggg tagcctgaag 780
attggccgtt actgcatgat tggcggcgcc agcgtgatca atgggcatat ggaaatatgc 840
gacaaagtca cggtaactgg catgggtatg gtgatgcgtc ccatcacgga accgggcgtc 900
tactcctcag gcattccgct gcaacccaac aaagtatggc gtaaaactgc tgcactggtg 960
atgaacattg atgatatgag caagcgtctc aaagcgattg agcgcaaggt taatcaacaa 1020
gac 1023

<210> SEQ ID NO 106
<211> LENGTH: 918
<212> TYPE: DNA
<213> ORGANISM: E. coli
<220> FEATURE:
<223> OTHER INFORMATION: htrB

<400> SEQUENCE: 106
atgacgaatc tacccaagtt ctccaccgca ctgcttcatc cgcgttattg gttaacctgg 60
ttgggtattg gcgtactttg gttagtcgtg caattgccct acccggttat ctaccgcctc 120
ggttgtggat taggaaaact ggcgttacgt tttatgaaac gacgcgcaaa aattgtgcat 180
cgcaacctgg aactgtgctt cccggaaatg agcgaacaag aacgccgtaa aatggtggtg 240
aagaatttcg aatccgttgg catgggcctg atggaaaccg gcatggcgtg gttctggccg 300
gaccgccgaa tcgcccgctg gacggaagtg atcggcatgg aacacattcg tgacgtgcag 360
gcgcaaaaac gcggcatcct gttagttggc atccattttc tgacactgga gctgggtgcg 420
cggcagtttg gtatgcagga accgggtatt ggcgtttatc gcccgaacga taatccactg 480
attgactggc tacaaacctg ggccgtttg cgctcaaata aatcgatgct cgaccgcaaa 540
gatttaaaag gcatgattaa agccctgaaa aaaggcgaag tggtctggta cgcaccggat 600
catgattacg gcccgcgctc aagcgttttc gtcccgttgt ttgccgttga gcaggctgcg 660
accacgaccg gaacctggat gctggcacgg atgtccggcg catgtctggt gcccttcgtt 720

-continued

```
ccacgccgta agccagatgg caaagggtat caattgatta tgctgccgcc agagtgttct    780

ccgccactgg atgatgccga aactaccgcc gcgtggatga acaaagtggt cgaaaaatgc    840

atcatgatgg caccagagca gtatatgtgg ttacaccgtc gctttaaaac acgcccggaa    900

ggcgttcctt cacgctat                                                  918
```

<210> SEQ ID NO 107
<211> LENGTH: 717
<212> TYPE: DNA
<213> ORGANISM: Salmonella typhimurium
<220> FEATURE:
<223> OTHER INFORMATION: ompR

<400> SEQUENCE: 107

```
atgcaagaga attataagat tctggtggtt gatgacgata tgcgtctgcg ggcgctactg     60

gaacgttatc tgaccgagca gggcttccag gttcgaagcg tcgctaacgc tgagcagatg    120

gatcgtctgc tgacccgtga atctttccat ctcatggtac tggatttaat gctgccaggt    180

gaagatggtc tgtcgatttg tcgtcgcctg cgtagtcaaa gtaatccaat gccgatcatt    240

atggtcacgg cgaagggtga agaggttgac cgtatcgtcg ggctggaaat cggcgccgat    300

gactacattc ctaaaccgtt taacccgcgc gagctgttgg cgcgtattcg gcccgtgtta    360

cgtcgtcagg caaacgaact gcccggcgcg ccgtcgcagg aagaggccgt tatcgcgttc    420

ggtaagttta aactgaacct cggtacgcgc gagatgttcc gtgaagatga accgatgccg    480

ctgaccagcg gggagtttgc ggtactgaaa gcgttagtca gccatccgcg cgagccgctc    540

tctcgcgata agctgatgaa tctggcccgt ggccgcgagt attccgcgat ggaacgctcc    600

atcgacgtcc agatctcccg cctgcgccgt atggtggaag aagatccggc acatccgcgt    660

tatattcaga ccgtctgggg cctgggctac gtctttgtac cggacggttc taaagca       717
```

<210> SEQ ID NO 108
<211> LENGTH: 498
<212> TYPE: DNA
<213> ORGANISM: Homo sapiens
<220> FEATURE:
<223> OTHER INFORMATION: Inteferon (IFN) gamma

<400> SEQUENCE: 108

```
atgaaatata caagttatat cttggctttt cagctctgca tcgttttggg ttctcttggc     60

tgttactgcc aggacccata tgtaaaagaa gcagaaaacc ttaagaaata ttttaatgca    120

ggtcattcag atgtagcgga taatggaact cttttcttag gcattttgaa gaattggaaa    180

gaggagagtg acagaaaaat aatgcagagc caaattgtct ccttttactt caaacttttt    240

aaaaacttta aagatgacca gagcatccaa aagagtgtgg agaccatcaa ggaagacatg    300

aatgtcaagt tttcaatag caacaaaaag aaacgagatg acttcgaaaa gctgactaat    360

tattcggtaa ctgacttgaa tgtccaacgc aaagcaatac atgaactcat ccaagtgatg    420

gctgaactgt cgccagcagc taaaacaggg aagcgaaaaa ggagtcagat gctgtttcga    480

ggtcgaagag catcccag                                                  498
```

<210> SEQ ID NO 109
<211> LENGTH: 699
<212> TYPE: DNA
<213> ORGANISM: Homo sapiens
<220> FEATURE:
<223> OTHER INFORMATION: Tumor necrosis factor (TNF) alpha

<400> SEQUENCE: 109
atgagcactg aaagcatgat ccgggacgtg gagctggccg aggaggcgct ccccaagaag 60 acagggggc cccagggctc caggcggtgc ttgttcctca gcctcttctc cttcctgatc 120
gtggcaggcg ccaccacgct cttctgcctg ctgcactttg gagtgatcgg cccccagagg 180
gaagagttcc ccagggacct ctctctaatc agccctctgg cccaggcagt cagatcatct 240
tctcgaaccc cgagtgacaa gcctgtagcc catgttgtag caaaccctca agctgagggg 300
cagctccagt ggctgaaccg ccgggccaat gccctcctgg ccaatggcgt ggagctgaga 360
gataaccagc tggtggtgcc atcagagggc ctgtacctca tctactccca ggtcctcttc 420
aagggccaag gctgcccctc cacccatgtg ctcctcaccc acaccatcag ccgcatcgcc 480
gtctcctacc agaccaaggt caacctcctc tctgccatca agagcccctg ccagagggag 540
accccagagg gggctgaggc caagccctgg tatgagccca tctatctggg aggggtcttc 600
cagctggaga agggtgaccg actcagcgct gagatcaatc ggcccgacta tctcgacttt 660
gccgagtctg ggcaggtcta ctttgggatc attgccctg 699

<210> SEQ ID NO 110
<211> LENGTH: 825
<212> TYPE: DNA
<213> ORGANISM: Homo sapiens
<220> FEATURE:
<223> OTHER INFORMATION: Atg5 long isoform

<400> SEQUENCE: 110
atgacagatg acaaagatgt gcttcgagat gtgtggtttg gacgaattcc aacttgtttc 60
acgctatatc aggatgagat aactgaaagg gaagcagaac catactattt gcttttgcca 120
agagtaagtt atttgacgtt ggtaactgac aaagtgaaaa agcactttca gaaggttatg 180
agacaagaag acattagtga gatatggttt gaatatgaag gcacaccact gaaatggcat 240
tatccaattg gtttgctatt tgatcttctt gcatcaagtt cagctcttcc ttggaacatc 300
acagtacatt ttaagagttt tccagaaaaa gaccttctgc actgtccatc taaggatgca 360
attgaagctc attttatgtc atgtatgaaa gaagctgatg ctttaaaaca taaaagtcaa 420
gtaatcaatg aaatgcagaa aaaagatcac aagcaactct ggatgggatt gcaaaatgac 480
agatttgacc agttttgggc catcaatcgg aaactcatgg aatatcctgc agaagaaaat 540
ggatttcgtt atatcccctt tagaatatat cagacaacga ctgaaagacc tttcattcag 600
aagctgtttc gtcctgtggc tgcagatgga cagttgcaca cactaggaga tctcctcaaa 660
gaagtttgtc cttctgctat tgatcctgaa gatggggaaa aaaagaatca agtgatgatt 720
catggaattg agccaatgtt ggaaacacct ctgcagtggc tgagtgaaca tctgagctac 780
ccggataatt ttcttcatat tagtatcatc ccacagccaa cagat 825

<210> SEQ ID NO 111
<211> LENGTH: 1350
<212> TYPE: DNA
<213> ORGANISM: Homo sapiens
<220> FEATURE:
<223> OTHER INFORMATION: Beclin1

<400> SEQUENCE: 111
atggaagggt ctaagacgtc caacaacagc accatgcagg tgagcttcgt gtgccagcgc 60
tgcagccagc ccctgaaact ggacacgagt ttcaagatcc tggaccgtgt caccatccag 120
gaactcacag ctccattact taccacagcc caggcgaaac caggagagac ccaggaggaa 180

-continued

```
gagactaact caggagagga gccatttatt gaaactcctc gccaggatgg tgtctctcgc    240
agattcatcc ccccagccag gatgatgtcc acagaaagtg ccaacagctt cactctgatt    300
ggggaggcat ctgatggcgg caccatggag aacctcagcc gaagactgaa ggtcactggg    360
gaccttttg acatcatgtc gggccagaca gatgtggatc acccactctg tgaggaatgc     420
acagatactc ttttagacca gctggacact cagctcaacg tcactgaaaa tgagtgtcag    480
aactacaaac gctgtttgga gatcttagag caaatgaatg aggatgacag tgaacagtta    540
cagatggagc taaaggagct ggcactagag gaggagaggc tgatccagga gctggaagac    600
gtggaaaaga accgcaagat agtggcagaa aatctcgaga aggtccaggc tgaggctgag    660
agactggatc aggaggaagc tcagtatcag agagaataca gtgaatttaa acgacagcag    720
ctggagctgg atgatgagct gaagagtgtt gaaaaccaga tgcgttatgc ccagacgcag    780
ctggataagc tgaagaaaac caacgtcttt aatgcaacct tccacatctg gcacagtgga    840
cagtttggca caatcaataa cttcaggctg ggtcgcctgc ccagtgttcc cgtggaatgg    900
aatgagatta atgctgcttg ggccagact gtgttgctgc tccatgctct ggccaataag     960
atgggtctga aatttcagag ataccgactt gttccttacg gaaaccattc atatctggag   1020
tctctgacag acaaatctaa ggagctgccg ttatactgtt ctggggggtt gcggtttttc   1080
tgggacaaca agtttgacca tgcaatggtg gctttcctgg actgtgtgca gcagttcaaa   1140
gaagaggttg agaaaggcga gacacgtttt tgtcttccct acaggatgga tgtggagaaa   1200
ggcaagattg aagacacagg aggcagtggc ggctcctatt ccatcaaaac ccagtttaac   1260
tctgaggagc agtggacaaa agctctcaag ttcatgctga cgaatcttaa gtggggtctt   1320
gcttgggtgt cctcacaatt ttataacaaa                                    1350
```

```
<210> SEQ ID NO 112
<211> LENGTH: 2352
<212> TYPE: DNA
<213> ORGANISM: Homo sapiens
<220> FEATURE:
<223> OTHER INFORMATION: Toll-like receptor 2 (TLR2)

<400> SEQUENCE: 112

atgccacata ctttgtggat ggtgtgggtc ttgggggtca tcatcagcct ctccaaggaa     60
gaatcctcca atcaggcttc tctgtcttgt gaccgcaatg gtatctgcaa gggcagctca    120
ggatctttaa actccattcc ctcagggctc acagaagctg taaaaagcct tgacctgtcc    180
aacaacagga tcacctacat tagcaacagt gacctacaga ggtgtgtgaa cctccaggct    240
ctggtgctga catccaatgg aattaacaca atagaggaag attctttttc ttccctgggc    300
agtcttgaac atttagactt atcctataat tacttatcta atttatcgtc ttcctggttc    360
aagcccttt cttctttaac attcttaaac ttactgggaa atccttacaa aaccctaggg     420
gaaacatctc tttttctca tctcacaaaa ttgcaaatcc tgagagtggg aaatatggac     480
accttcacta agattcaaag aaaagatttt gctggactta ccttccttga ggaacttgag    540
attgatgctt cagatctaca gagctatgag ccaaaaagtt tgaagtcaat tcagaatgta    600
agtcatctga tccttcatat gaagcagcat attttactgc tggagatttt tgtagatgtt    660
acaagttccg tggaatgttt ggaactgcga gatactgatt tggacacttt ccatttttca    720
gaactatcca ctggtgaaac aaattcattg attaaaaagt ttacatttag aaatgtgaaa    780
atcaccgatg aaagtttgtt tcaggttatg aaactttga atcagatttc tggattgtta     840
gaattagagt ttgatgactg taccettaat ggagttggta attttagagc atctgataat    900
```

-continued

```
gacagagtta tagatccagg taaagtggaa acgttaacaa tccggaggct gcatattcca    960

aggttttact tattttatga tctgagcact ttatattcac ttacagaaag agttaaaaga   1020

atcacagtag aaaacagtaa agtttttctg gttccttgtt tactttcaca acatttaaaa   1080

tcattagaat acttggatct cagtgaaaat ttgatggttg aagaatactt gaaaaattca   1140

gcctgtgagg atgcctggcc ctctctacaa actttaattt taaggcaaaa tcatttggca   1200

tcattggaaa aaaccggaga gactttgctc actctgaaaa acttgactaa cattgatatc   1260

agtaagaata gttttcattc tatgcctgaa acttgtcagt ggccagaaaa gatgaaatat   1320

ttgaacttat ccagcacacg aatacacagt gtaacaggct gcattcccaa gacactggaa   1380

attttagatg ttagcaacaa caatctcaat ttattttctt tgaatttgcc gcaactcaaa   1440

gaactttata tttccagaaa taagttgatg actctaccag atgcctccct cttacccatg   1500

ttactagtat tgaaaatcag taggaatgca ataactacgt tttctaagga gcaacttgac   1560

tcatttcaca cactgaagac tttggaagct ggtggcaata acttcatttg ctcctgtgaa   1620

ttcctctcct tcactcagga gcagcaagca ctggccaaag tcttgattga ttggccagca   1680

aattacctgt gtgactctcc atcccatgtg cgtggccagc aggttcagga tgtccgcctc   1740

tcggtgtcgg aatgtcacag gacagcactg gtgtctggca tgtgctgtgc tctgttcctg   1800

ctgatcctgc tcacgggggt cctgtgccac cgtttccatg gcctgtggta tatgaaaatg   1860

atgtgggcct ggctccaggc caaaaggaag cccaggaaag ctcccagcag gaacatctgc   1920

tatgatgcat ttgtttctta cagtgagcgg gatgcctact gggtggagaa ccttatggtc   1980

caggagctgg agaacttcaa tccccccttc aagttgtgtc ttcataagcg ggacttcatt   2040

cctggcaagt ggatcattga caatatcatt gactccattg aaaagagcca caaaactgtc   2100

tttgtgcttt ctgaaaactt tgtgaagagt gagtggtgca agtatgaact ggacttctcc   2160

catttccgtc tttttgatga gaacaatgat gctgccattc tcattcttct ggagcccatt   2220

gagaaaaaag ccattcccca gcgcttctgc aagctgcgga agataatgaa caccaagacc   2280

tacctggagt ggcccatgga cgaggctcag cgggaaggat tttgggtaaa tctgagagct   2340

gcgataaagt cc                                                       2352
```

<210> SEQ ID NO 113
<211> LENGTH: 2517
<212> TYPE: DNA
<213> ORGANISM: Homo sapiens
<220> FEATURE:
<223> OTHER INFORMATION: TLR4, isoform 1

<400> SEQUENCE: 113

```
atgatgtctg cctcgcgcct ggctgggact ctgatcccag ccatggcctt cctctcctgc     60

gtgagaccag aaagctggga gccctgcgtg gaggtggttc ctaatattac ttatcaatgc    120

atggagctga atttctacaa aatccccgac aacctcccct tctcaaccaa gaacctggac    180

ctgagcttta atcccctgag gcatttaggc agctatagct tcttcagttt cccagaactg    240

caggtgctgg atttatccag gtgtgaaatc cagacaattg aagatggggc atatcagagc    300

ctaagccacc tctctacctt aatattgaca ggaaacccca tccagagttt agccctggga    360

gccttttctg gactatcaag tttacagaag ctggtggctg tggagacaaa tctagcatct    420

ctagagaact tccccattgg acatctcaaa actttgaaag aacttaatgt ggctcacaat    480

cttatccaat ctttcaaatt acctgagtat ttttctaatc tgaccaatct agagcacttg    540
```

```
gacctttcca gcaacaagat tcaaagtatt tattgcacag acttgcgggt tctacatcaa    600
atgcccctac tcaatctctc tttagacctg tccctgaacc ctatgaactt tatccaacca    660
ggtgcattta aagaaattag gcttcataag ctgactttaa gaaataattt tgatagttta    720
aatgtaatga aacttgtat tcaaggtctg gctggtttag aagtccatcg tttggttctg     780
ggagaattta gaaatgaagg aaacttggaa aagtttgaca aatctgctct agagggcctg    840
tgcaatttga ccattgaaga attccgatta gcatacttag actactacct cgatgatatt    900
attgacttat ttaattgttt gacaaatgtt tcttcatttt ccctggtgag tgtgactatt    960
gaaagggtaa aagacttttc ttataatttc ggatggcaac atttagaatt agttaactgt   1020
aaatttggac agtttcccac attgaaactc aaatctctca aaaggcttac tttcacttcc   1080
aacaaaggtg ggaatgcttt ttcagaagtt gatctaccaa gccttgagtt tctagatctc   1140
agtagaaatg gcttgagttt caaaggttgc tgttctcaaa gtgattttgg gacaaccagc   1200
ctaaagtatt tagatctgag cttcaatggt gttattacca tgagttcaaa cttcttgggc   1260
ttagaacaac tagaacatct ggatttccag cattccaatt tgaaacaaat gagtgagttt   1320
tcagtattcc tatcactcag aaacctcatt taccttgaca tttctcatac tcacaccaga   1380
gttgctttca atggcatctt caatggcttg tccagtctcg aagtcttgaa aatggctggc   1440
aattctttcc aggaaaactt ccttccagat atcttcacag agctgagaaa cttgaccttc   1500
ctggacctct ctcagtgtca actggagcag ttgtctccaa cagcatttaa ctcactctcc   1560
agtcttcagg tactaaatat gagccacaac aacttctttt cattggatac gtttccttat   1620
aagtgtctga actccctcca ggttcttgat tacagtctca atcacataat gacttccaaa   1680
aaacaggaac tacagcattt tccaagtagt ctagctttct taaatcttac tcagaatgac   1740
tttgcttgta cttgtgaaca ccagagtttc ctgcaatgga tcaaggacca gaggcagctc   1800
ttggtggaag ttgaacgaat ggaatgtgca acaccttcag ataagcaggg catgcctgtg   1860
ctgagtttga atatcacctg tcagatgaat aagaccatca ttggtgtgtc ggtcctcagt   1920
gtgcttgtag tatctgttgt agcagttctg gtctataagt tctattttca cctgatgctt   1980
cttgctggct gcataaagta tggtagaggt gaaaacatct atgatgcctt tgttatctac   2040
tcaagccagg atgaggactg ggtaaggaat gagctagtaa agaatttaga agaaggggtg   2100
cctccatttc agctctgcct tcactacaga gactttattc ccggtgtggc cattgctgcc   2160
aacatcatcc atgaaggttt ccataaaagc cgaaaggtga ttgttgtggt gtcccagcac   2220
ttcatccaga gccgctggtg tatctttgaa tatgagattg ctcagacctg gcagtttctg   2280
agcagtcgtg ctggtatcat cttcattgtc ctgcagaagg tggagaagac cctgctcagg   2340
cagcaggtgg agctgtaccg ccttctcagc aggaacactt acctggagtg ggaggacagt   2400
gtcctggggc ggcacatctt ctggagacga ctcagaaaag ccctgctgga tggtaaatca   2460
tggaatccag aaggaacagt gggtacagga tgcaattggc aggaagcaac atctatc      2517
```

<210> SEQ ID NO 114
<211> LENGTH: 2574
<212> TYPE: DNA
<213> ORGANISM: Homo sapiens
<220> FEATURE:
<223> OTHER INFORMATION: TLR5

<400> SEQUENCE: 114

```
atgggagacc acctggacct tctcctagga gtggtgctca tggccggtcc tgtgtttgga     60
attccttcct gctcctttga tggccgaata gccttttatc gtttctgcaa cctcacccag    120
```

gtcccccagg tcctcaacac cactgagagg ctcctgctga gcttcaacta tatcaggaca 180
gtcactgctt catccttccc ctttctggaa cagctgcagc tgctggagct cgggagccag 240
tatacccct tgactattga caaggaggcc ttcagaaacc tgcccaacct tagaatcttg 300
gacctgggaa gtagtaagat atacttcttg catccagatg cttttcaggg actgttccat 360
ctgtttgaac ttagactgta tttctgtggt ctctctgatg ctgtattgaa agatggttat 420
ttcagaaatt taaaggcttt aactcgcttg gatctatcca aaaatcagat tcgtagcctt 480
taccttcatc cttcatttgg gaagttgaat tccttaaagt ccatagattt ttcctccaac 540
caaatattcc ttgtatgtga acatgagctc gagcccctac aagggaaaac gctctccttt 600
tttagcctcg cagctaatag cttgtatagc agagtctcag tggactgggg aaaatgtatg 660
aacccattca gaaacatggt gctggagata ctagatgttt ctggaaatgg ctggacagtg 720
gacatcacag gaaactttag caatgccatc agcaaaagcc aggccttctc tttgattctt 780
gcccaccaca tcatgggtgc cgggtttggc ttccataaca tcaaagatcc tgaccagaac 840
acatttgctg gcctggccag aagttcagtg agacacctgg atctttcaca tgggtttgtc 900
ttctccctga actcacgagt ctttgagaca ctcaaggatt tgaaggttct gaaccttgcc 960
tacaacaaga taaataagat tgcagatgaa gcattttacg gacttgacaa cctccaagtt 1020
ctcaatttgt catataacct tctgggggaa ctttacagtt cgaatttcta tggactacct 1080
aaggtagcct acattgattt gcaaaagaat cacattgcaa taattcaaga ccaaacattc 1140
aaattcctgg aaaaattaca gaccttggat ctccgagaca atgctcttac aaccattcat 1200
tttattccaa gcatacccga tatcttcttg agtggcaata aactagtgac tttgccaaag 1260
atcaacctta cagcgaacct catccactta tcagaaaaca ggctagaaaa tctagatatt 1320
ctctactttc tcctacgggt acctcatctc cagattctca ttttaaatca aaatcgcttc 1380
tcctcctgta gtggagatca aacccccttca gagaatccca gcttagaaca gcttttcctt 1440
ggagaaaata tgttgcaact tgcctgggaa actgagctct gttgggatgt ttttgaggga 1500
ctttctcatc ttcaagttct gtatttgaat cataactatc ttaattccct tccaccagga 1560
gtatttagcc atctgactgc attaaggga ctaagcctca actccaacag gctgacagtt 1620
ctttctcaca atgatttacc tgctaattta gagatcctgg acatatccag gaaccagctc 1680
ctagctccta atcctgatgt atttgtatca cttagtgtct tggatataac tcataacaag 1740
ttcatttgtg aatgtgaact tagcactttt atcaattggc ttaatcacac caatgtcact 1800
atagctgggc ctcctgcaga catatattgt gtgtaccctg actcgttctc tggggtttcc 1860
ctcttctctc tttccacgga aggttgtgat gaagaggaag tcttaaagtc cctaaagttc 1920
tcccttttca ttgtatgcac tgtcactctg actctgttcc tcatgaccat cctcacagtc 1980
acaaagttcc ggggcttctg ttttatctgt tataagacag cccagagact ggtgttcaag 2040
gaccatcccc agggcacaga acctgatatg tacaaatatg atgcctattt gtgcttcagc 2100
agcaaagact tcacatgggt gcagaatgct ttgctcaaac acctggacac tcaatacagt 2160
gaccaaaaca gattcaacct gtgctttgaa gaaagagact ttgtcccagg agaaaaccgc 2220
attgccaata tccaggatgc catctggaac agtagaaaga tcgtttgtct tgtgagcaga 2280
cacttcctta gagatggctg gtgccttgaa gccttcagtt atgcccaggg caggtgctta 2340
tctgacctta acagtgctct catcatggtg gtggttgggt ccttgtccca gtaccagttg 2400
atgaaacatc aatccatcag aggctttgta cagaaacagc agtatttgag gtggcctgag 2460

-continued

```
gatctccagg atgttggctg gtttcttcat aaactctctc aacagatact aaagaaagaa   2520

aaagaaaaga agaaagacaa taacattccg ttgcaaactg tagcaaccat ctcc         2574


<210> SEQ ID NO 115
<211> LENGTH: 2712
<212> TYPE: DNA
<213> ORGANISM: Homo sapiens
<220> FEATURE:
<223> OTHER INFORMATION: TLR3, isoform 1

<400> SEQUENCE: 115

atgagacaga ctttgccttg tatctacttt tggggggggcc ttttgccctt tgggatgctg     60

tgtgcatcct ccaccaccaa gtgcactgtt agccatgaag ttgctgactg cagccacctg    120

aagttgactc aggtacccga tgatctaccc acaaacataa cagtgttgaa ccttacccat    180

aatcaactca gaagattacc agccgccaac ttcacaaggt atagccagct aactagcttg    240

gatgtaggat ttaacaccat ctcaaaactg gagccagaat tgtgccagaa acttcccatg    300

ttaaaagttt tgaacctcca gcacaatgag ctatctcaac tttctgataa aacctttgcc    360

ttctgcacga atttgactga actccatctc atgtccaact caatccagaa aattaaaaat    420

aatccctttg tcaagcagaa gaatttaatc acattagatc tgtctcataa tggcttgtca    480

tctacaaaat taggaactca ggttcagctg gaaaatctcc aagagcttct attatcaaac    540

aataaaattc aagcgctaaa aagtgaagaa ctggatatct ttgccaattc atctttaaaa    600

aaattagagt tgtcatcgaa tcaaattaaa gagttttctc cagggtgttt tcacgcaatt    660

ggaagattat ttggcctctt tctgaacaat gtccagctgg gtcccagcct tacagagaag    720

ctatgtttgg aattagcaaa cacaagcatt cggaatctgt ctctgagtaa cagccagctg    780

tccaccacca gcaatacaac tttcttggga ctaaagtgga caaatctcac tatgctcgat    840

ctttcctaca acaacttaaa tgtggttggt aacgattcct ttgcttggct tccacaacta    900

gaatatttct tcctagagta taataatata cagcatttgt tttctcactc tttgcacggg    960

cttttcaatg tgaggtacct gaatttgaaa cggtctttta ctaaacaaag tatttccctt   1020

gcctcactcc ccaagattga tgatttttct tttcagtggc taaaatgttt ggagcacctt   1080

aacatggaag ataatgatat tccaggcata aaaagcaata tgttcacagg attgataaac   1140

ctgaaatact taagtctatc caactccttt acaagtttgc gaactttgac aaatgaaaca   1200

tttgtatcac ttgctcattc tcccttacac atactcaacc taaccaagaa taaaatctca   1260

aaaatagaga gtgatgcttt ctcttggttg ggccacctag aagtacttga cctgggcctt   1320

aatgaaattg ggcaagaact cacaggccag gaatggagag gtctagaaaa tattttcgaa   1380

atctatcttt cctacaacaa gtacctgcag ctgactagga actcctttgc cttggtccca   1440

agccttcaac gactgatgct ccgaagggtg gcccttaaaa atgtggatag ctctccttca   1500

ccattccagc ctcttcgtaa cttgaccatt ctggatctaa gcaacaacaa catagccaac   1560

ataaatgatg acatgttgga gggtcttgag aaactagaaa ttctcgattt gcagcataac   1620

aacttagcac ggctctggaa acacgcaaac cctggtggtc ccatttattt cctaaagggt   1680

ctgtctcacc tccacatcct taacttggag tccaacggct ttgacgagat cccagttgag   1740

gtcttcaagg atttatttga actaaagatc atcgatttag gattgaataa tttaaacaca   1800

cttccagcat ctgtctttaa taatcaggtg tctctaaagt cattgaacct tcagaagaat   1860

ctcataacat ccgttgagaa gaaggttttc gggccagctt tcaggaacct gactgagtta   1920

gatatgcgct ttaatccctt tgattgcacg tgtgaaagta ttgcctggtt tgttaattgg   1980
```

-continued attaacgaga cccataccaa catccctgag ctgtcaagcc actacctttg caacactcca 2040
cctcactatc atgggttccc agtgagactt tttgatacat catcttgcaa agacagtgcc 2100
ccctttgaac tctttttcat gatcaatacc agtatcctgt tgatttttat ctttattgta 2160
cttctcatcc actttgaggg ctggaggata tctttttatt ggaatgtttc agtacatcga 2220
gttcttggtt tcaaagaaat agacagacag acagaacagt ttgaatatgc agcatatata 2280
attcatgcct ataaagataa ggattgggtc tgggaacatt tctcttcaat ggaaaaggaa 2340
gaccaatctc tcaaattttg tctggaagaa agggactttg aggcgggtgt ttttgaacta 2400
gaagcaattg ttaacagcat caaaagaagc agaaaaatta tttttgttat aacacaccat 2460
ctattaaaag acccattatg caaaagattc aaggtacatc atgcagttca acaagctatt 2520
gaacaaaatc tggattccat tatattggtt ttccttgagg agattccaga ttataaactg 2580
aaccatgcac tctgtttgcg aagaggaatg tttaaatctc actgcatctt gaactggcca 2640
gttcagaaag aacggatagg tgcctttcgt cataaattgc aagtagcact tggatccaaa 2700
aactctgtac at 2712

<210> SEQ ID NO 116
<211> LENGTH: 3096
<212> TYPE: DNA
<213> ORGANISM: Homo sapiens
<220> FEATURE:
<223> OTHER INFORMATION: TLR9

<400> SEQUENCE: 116
atgggtttct gccgcagcgc cctgcacccg ctgtctctcc tggtgcaggc catcatgctg 60
gccatgaccc tggccctggg taccttgcct gccttcctac cctgtgagct ccagccccac 120
ggcctggtga actgcaactg gctgttcctg aagtctgtgc cccacttctc catggcagca 180
ccccgtggca atgtcaccag cctttccttg tcctccaacc gcatccacca cctccatgat 240
tctgactttg cccacctgcc cagcctgcgg catctcaacc tcaagtggaa ctgcccgccg 300
gttggcctca gccccatgca cttcccctgc cacatgacca tcgagcccag caccttcttg 360
gctgtgccca ccctggaaga gctaaacctg agctacaaca acatcatgac tgtgcctgcg 420
ctgcccaaat ccctcatatc cctgtccctc agccatacca acatcctgat gctagactct 480
gccagcctcg ccggcctgca tgccctgcgc ttcctattca tggacggcaa ctgttattac 540
aagaacccct gcaggcaggc actggaggtg gccccgggtg ccctccttgg cctgggcaac 600
ctcacccacc tgtcactcaa gtacaacaac ctcactgtgg tgccccgcaa cctgccttcc 660
agcctggagt atctgctgtt gtcctacaac cgcatcgtca aactggcgcc tgaggacctg 720
gccaatctga ccgccctgcg tgtgctcgat gtgggcggaa attgccgccg ctgcgaccac 780
gctcccaacc cctgcatgga gtgccctcgt cacttccccc agctacatcc cgataccttc 840
agccacctga gccgtcttga aggcctggtg ttgaaggaca gttctctctc ctggctgaat 900
gccagttggt tccgtgggct gggaaacctc cgagtgctgg acctgagtga gaacttcctc 960
tacaaatgca tcactaaaac caaggccttc cagggcctaa cacagctgcg caagcttaac 1020
ctgtccttca attaccaaaa gagggtgtcc tttgcccacc tgtctctggc cccttccttc 1080
gggagcctgg tcgccctgaa ggagctggac atgcacggca tcttcttccg ctcactcgat 1140
gagaccacgc tccggccact ggcccgcctg cccatgctcc agactctgcg tctgcagatg 1200
aacttcatca accaggccca gctcggcatc ttcagggcct tccctggcct gcgctacgtg 1260
gacctgtcgg acaaccgcat cagcggagct tcggagctga cagccaccat gggggaggca 1320
gatggagggg agaaggtctg gctgcagcct ggggaccttg ctccggcccc agtggacact 1380
cccagctctg aagacttcag gcccaactgc agcaccctca acttcacctt ggatctgtca 1440
cggaacaacc tggtgaccgt gcagccggag atgtttgccc agctctcgca cctgcagtgc 1500
ctgcgcctga gccacaactg catctcgcag gcagtcaatg gctcccagtt cctgccgctg 1560
accggtctgc aggtgctaga cctgtcccac aataagctgg acctctacca cgagcactca 1620
ttcacggagc taccgcgact ggaggccctg gacctcagct acaacagcca gccctttggc 1680
atgcagggcg tgggccacaa cttcagcttc gtggctcacc tgcgcaccct gcgccacctc 1740
agcctggccc acaacaacat ccacagccaa gtgtcccagc agctctgcag tacgtcgctg 1800
cgggccctgg acttcagcgg caatgcactg ggccatatgt gggccgaggg agacctctat 1860
ctgcacttct tccaaggcct gagcggtttg atctggctgg acttgtccca gaaccgcctg 1920
cacaccctcc tgccccaaac cctgcgcaac ctccccaaga gcctacaggt gctgcgtctc 1980
cgtgacaatt acctggcctt ctttaagtgg tggagcctcc acttcctgcc caaactggaa 2040
gtcctcgacc tggcaggaaa ccagctgaag gccctgacca atggcagcct gcctgctggc 2100
acccggctcc ggaggctgga tgtcagctgc aacagcatca gcttcgtggc ccccggcttc 2160
ttttccaagg ccaaggagct gcgagagctc aaccttagcg ccaacgccct caagacagtg 2220
gaccactcct ggtttgggcc cctggcgagt gccctgcaaa tactagatgt aagcgccaac 2280
cctctgcact gcgcctgtgg ggcggccttt atggacttcc tgctggaggt gcaggctgcc 2340
gtgcccggtc tgcccagccg ggtgaagtgt ggcagtccgg gccagctcca gggcctcagc 2400
atctttgcac aggacctgcg cctctgcctg gatgaggccc tctcctggga ctgtttcgcc 2460
ctctcgctgc tggctgtggc tctgggcctg ggtgtgccca tgctgcatca cctctgtggc 2520
tgggacctct ggtactgctt ccacctgtgc ctggcctggc ttccctggcg ggggcggcaa 2580
agtgggcgag atgaggatgc cctgccctac gatgccttcg tggtcttcga caaaacgcag 2640
agcgcagtgg cagactgggt gtacaacgag cttcgggggc agctggagga gtgccgtggg 2700
cgctgggcac tccgcctgtg cctggaggaa cgcgactggc tgcctggcaa aaccctcttt 2760
gagaacctgt gggcctcggt ctatggcagc cgcaagacgc tgtttgtgct ggcccacacg 2820
gaccgggtca gtggtctctt gcgcgccagc ttcctgctgg cccagcagcg cctgctggag 2880
gaccgcaagg acgtcgtggt gctggtgatc ctgagccctg acggccgccg ctcccgctac 2940
gtgcggctgc gccagcgcct ctgccgccag agtgtcctcc tctggcccca ccagcccagt 3000
ggtcagcgca gcttctgggc ccagctgggc atggccctga ccagggacaa ccaccacttc 3060
tataaccgga acttctgcca gggacccacg gccgaa 3096

<210> SEQ ID NO 117
<211> LENGTH: 3147
<212> TYPE: DNA
<213> ORGANISM: Homo sapiens
<220> FEATURE:
<223> OTHER INFORMATION: TLR7

<400> SEQUENCE: 117
atggtgtttc caatgtggac actgaagaga caaattctta tcctttttaa cataatccta 60
atttccaaac tccttggggc tagatggttt cctaaaactc tgccctgtga tgtcactctg 120
gatgttccaa agaaccatgt gatcgtggac tgcacagaca agcatttgac agaaattcct 180
ggaggtattc ccacgaacac cacgaacctc accctcacca ttaaccacat accagacatc 240

-continued

```
tccccagcgt cctttcacag actggaccat ctggtagaga tcgatttcag atgcaactgt    300
gtacctattc cactggggtc aaaaaacaac atgtgcatca agaggctgca gattaaaccc    360
agaagcttta gtggactcac ttatttaaaa tccctttacc tggatggaaa ccagctacta    420
gagataccgc agggcctccc gcctagctta cagcttctca gccttgaggc caacaacatc    480
ttttccatca gaaaagagaa tctaacagaa ctggccaaca tagaaatact ctacctgggc    540
caaaactgtt attatcgaaa tccttgttat gtttcatatt caatagagaa agatgccttc    600
ctaaacttga caaagttaaa agtgctctcc ctgaaagata acaatgtcac agccgtccct    660
actgttttgc catctacttt aacagaacta tatctctaca acaacatgat tgcaaaaatc    720
caagaagatg attttaataa cctcaaccaa ttacaaattc ttgacctaag tggaaattgc    780
cctcgttgtt ataatgcccc atttccttgt gcgccgtgta aaaataattc tcccctacag    840
atccctgtaa atgcttttga tgcgctgaca gaattaaaag ttttacgtct acacagtaac    900
tctcttcagc atgtgccccc aagatggttt aagaacatca acaaactcca ggaactggat    960
ctgtcccaaa acttcttggc caaagaaatt ggggatgcta aatttctgca ttttctcccc   1020
agcctcatcc aattggatct gtctttcaat tttgaacttc aggtctatcg tgcatctatg   1080
aatctatcac aagcattttc ttcactgaaa agcctgaaaa ttctgcggat cagaggatat   1140
gtctttaaag agttgaaaag ctttaacctc tcgccattac ataatcttca aaatcttgaa   1200
gttcttgatc ttggcactaa ctttataaaa attgctaacc tcagcatgtt taaacaattt   1260
aaaagactga aagtcataga tctttcagtg aataaaatat caccttcagg agattcaagt   1320
gaagttggct tctgctcaaa tgccagaact tctgtagaaa gttatgaacc ccaggtcctg   1380
gaacaattac attatttcag atatgataag tatgcaagga gttgcagatt caaaaacaaa   1440
gaggcttctt tcatgtctgt taatgaaagc tgctacaagt atgggcagac cttggatcta   1500
agtaaaaata gtatattttt tgtcaagtcc tctgattttc agcatctttc tttcctcaaa   1560
tgcctgaatc tgtcaggaaa tctcattagc caaactctta atggcagtga attccaacct   1620
ttagcagagc tgagatattt ggacttctcc aacaaccggc ttgatttact ccattcaaca   1680
gcatttgaag agcttcacaa actggaagtt ctggatataa gcagtaatag ccattatttt   1740
caatcagaag gaattactca tatgctaaac tttaccaaga acctaaaggt tctgcagaaa   1800
ctgatgatga acgacaatga catctcttcc tccaccagca ggaccatgga gagtgagtct   1860
cttagaactc tggaattcag aggaaatcac ttagatgttt tatggagaga aggtgataac   1920
agatacttac aattattcaa gaatctgcta aaattagagg aattagacat ctctaaaaat   1980
tccctaagtt tcttgccttc tggagttttt gatggtatgc ctccaaatct aaagaatctc   2040
tctttggcca aaaatgggct caaatctttc agttggaaga aactccagtg tctaaagaac   2100
ctggaaactt tggacctcag ccacaaccaa ctgaccactg tccctgagag attatccaac   2160
tgttccagaa gcctcaagaa tctgattctt aagaataatc aaatcaggag tctgacgaag   2220
tattttctac aagatgcctt ccagttgcga tatctggatc tcagctcaaa taaaatccag   2280
atgatccaaa agaccagctt cccagaaaat gtcctcaaca atctgaagat gttgcttttg   2340
catcataatc ggtttctgtg cacctgtgat gctgtgtggt ttgtctggtg ggttaaccat   2400
acggaggtga ctattcctta cctggccaca gatgtgactt gtgtggggcc aggagcacac   2460
aagggccaaa gtgtgatctc cctggatctg tacacctgtg agttagatct gactaacctg   2520
attctgttct cactttccat atctgtatct ctctttctca tggtgatgat gacagcaagt   2580
```

cacctctatt tctgggatgt gtggtatatt taccatttct gtaaggccaa gataaagggg 2640
tatcagcgtc taatatcacc agactgttgc tatgatgctt ttattgtgta tgacactaaa 2700
gacccagctg tgaccgagtg ggttttggct gagctggtgg ccaaactgga agacccaaga 2760
gagaaacatt ttaatttatg tctcgaggaa agggactggt taccagggca gccagttctg 2820
gaaaaccttt cccagagcat acagcttagc aaaaagacag tgtttgtgat gacagacaag 2880
tatgcaaaga ctgaaaattt taagatagca ttttacttgt cccatcagag gctcatggat 2940
gaaaaagttg atgtgattat cttgatattt cttgagaagc cctttcagaa gtccaagttc 3000
ctccagctcc ggaaaaggct ctgtgggagt tctgtccttg agtggccaac aaacccgcaa 3060
gctcacccat acttctggca gtgtctaaag aacgccctgg ccacagacaa tcatgtggcc 3120
tatagtcagg tgttcaagga aacggtc 3147

<210> SEQ ID NO 118
<211> LENGTH: 3177
<212> TYPE: DNA
<213> ORGANISM: Homo sapiens
<220> FEATURE:
<223> OTHER INFORMATION: TLR8, isoform 1

<400> SEQUENCE: 118
atgaaggagt catctttgca aaatagctcc tgcagcctgg gaaaggagac taaaaaggaa 60
aacatgttcc ttcagtcgtc aatgctgacc tgcattttcc tgctaatatc tggttcctgt 120
gagttatgcg ccgaagaaaa tttttctaga agctatcctt gtgatgagaa aaagcaaaat 180
gactcagtta ttgcagagtg cagcaatcgt cgactacagg aagttcccca aacggtgggc 240
aaatatgtga cagaactaga cctgtctgat aatttcatca cacacataac gaatgaatca 300
tttcaagggc tgcaaaatct cactaaaata aatctaaacc acaaccccaa tgtacagcac 360
cagaacggaa atcccggtat acaatcaaat ggcttgaata tcacagacgg ggcattcctc 420
aacctaaaaa acctaaggga gttactgctt gaagacaacc agttacccca aataccctct 480
ggtttgccag agtctttgac agaacttagt ctaattcaaa acaatatata caacataact 540
aaagagggca tttcaagact tataaacttg aaaaatctct atttggcctg gaactgctat 600
tttaacaaag tttgcgagaa aactaacata gaagatggag tatttgaaac gctgacaaat 660
ttggagttgc tatcactatc tttcaattct ctttcacacg tgccacccaa actgccaagc 720
tccctacgca aactttttct gagcaacacc cagatcaaat acattagtga agaagatttc 780
aagggattga taaatttaac attactagat ttaagcggga actgtccgag gtgcttcaat 840
gccccatttc catgcgtgcc ttgtgatggt ggtgcttcaa ttaatataga tcgttttgct 900
tttcaaaact tgacccaact tcgataccta aacctctcta gcacttccct caggaagatt 960
aatgctgcct ggtttaaaaa tatgcctcat ctgaaggtgc tggatcttga attcaactat 1020
ttagtgggag aaatagcctc tggggcattt ttaacgatgc tgccccgctt agaaatactt 1080
gacttgtctt ttaactatat aaaggggagt tatccacagc atattaatat ttccagaaac 1140
ttctctaaac ttttgtctct acgggcattg catttaagag gttatgtgtt ccaggaactc 1200
agagaagatg atttccagcc cctgatgcag cttccaaact tatcgactat caacttgggt 1260
attaatttta ttaagcaaat cgatttcaaa cttttccaaa atttctccaa tctggaaatt 1320
atttacttgt cagaaaacag aatatcaccg ttggtaaaag atacccggca gagttatgca 1380
aatagttcct cttttcaacg tcatatccgg aaacgacgct caacagattt tgagtttgac 1440
ccacattcga acttttatca tttcacccgt cctttaataa agccacaatg tgctgcttat 1500

```
ggaaaagcct tagatttaag cctcaacagt attttcttca ttgggccaaa ccaatttgaa   1560
aatcttcctg acattgcctg tttaaatctg tctgcaaata gcaatgctca agtgttaagt   1620
ggaactgaat tttcagccat tcctcatgtc aaatatttgg atttgacaaa caatagacta   1680
gactttgata atgctagtgc tcttactgaa ttgtccgact tggaagttct agatctcagc   1740
tataattcac actatttcag aatagcaggc gtaacacatc atctagaatt tattcaaaat   1800
ttcacaaatc taaaagtttt aaacttgagc cacaacaaca tttatacttt aacagataag   1860
tataacctgg aaagcaagtc cctggtagaa ttagttttca gtggcaatcg ccttgacatt   1920
ttgtggaatg atgatgacaa caggtatatc tccattttca aaggtctcaa gaatctgaca   1980
cgtctggatt tatcccttaa taggctgaag cacatcccaa atgaagcatt ccttaatttg   2040
ccagcgagtc tcactgaact acatataaat gataatatgt taaagttttt taactggaca   2100
ttactccagc agtttcctcg tctcgagttg cttgacttac gtggaaacaa actactcttt   2160
ttaactgata gcctatctga ctttacatct tcccttcgga cactgctgct gagtcataac   2220
aggatttccc acctaccctc tggctttctt tctgaagtca gtagtctgaa gcacctcgat   2280
ttaagttcca atctgctaaa aacaatcaac aaatccgcac ttgaaactaa gaccaccacc   2340
aaattatcta tgttggaact acacggaaac ccctttgaat gcacctgtga cattggagat   2400
ttccgaagat ggatggatga acatctgaat gtcaaaattc ccagactggt agatgtcatt   2460
tgtgccagtc ctggggatca aagagggaag agtattgtga gtctggagct aacaacttgt   2520
gtttcagatg tcactgcagt gatattattt ttcttcacgt tctttatcac caccatggtt   2580
atgttggctg ccctggctca ccatttgttt tactgggatg tttggtttat atataatgtg   2640
tgtttagcta aggtaaaagg ctacaggtct ctttccacat cccaaacttt ctatgatgct   2700
tacatttctt atgacaccaa agatgcctct gttactgact gggtgataaa tgagctgcgc   2760
taccaccttg aagagagccg agacaaaaac gttctccttt gtctagagga gagggattgg   2820
gacccgggat tggccatcat cgacaacctc atgcagagca tcaaccaaag caagaaaaca   2880
gtatttgttt taaccaaaaa atatgcaaaa agctggaact ttaaaacagc tttttacttg   2940
gctttgcaga ggctaatgga tgagaacatg gatgtgatta tatttatcct gctggagcca   3000
gtgttacagc attctcagta tttgaggcta cggcagcgga tctgtaagag ctccatcctc   3060
cagtggcctg acaacccgaa ggcagaaggc ttgttttggc aaactctgag aaatgtggtc   3120
ttgactgaaa atgattcacg gtataacaat atgtatgtcg attccattaa gcaatac      3177
```

<210> SEQ ID NO 119
<211> LENGTH: 636
<212> TYPE: DNA
<213> ORGANISM: Homo sapiens
<220> FEATURE:
<223> OTHER INFORMATION: Interleukin 6 (IL-6)

<400> SEQUENCE: 119

```
atgaactcct tctccacaag cgccttcggt ccagttgcct tctccctggg gctgctcctg     60
gtgttgcctg ctgccttccc tgccccagta cccccaggag aagattccaa agatgtagcc    120
gccccacaca gacagccact cacctcttca gaacgaattg acaaacaaat tcggtacatc    180
ctcgacggca tctcagccct gagaaaggag acatgtaaca agagtaacat gtgtgaaagc    240
agcaaagagg cactggcaga aaacaacctg aaccttccaa agatggctga aaaagatgga    300
tgcttccaat ctggattcaa tgaggagact tgcctggtga aaatcatcac tggtcttttg    360
```

```
gagtttgagg tatacctaga gtacctccag aacagatttg agagtagtga ggaacaagcc    420

agagctgtgc agatgagtac aaaagtcctg atccagttcc tgcagaaaaa ggcaaagaat    480

ctagatgcaa taaccacccc tgacccaacc acaaatgcca gcctgctgac gaagctgcag    540

gcacagaacc agtggctgca ggacatgaca actcatctca ttctgcgcag ctttaaggag    600

ttcctgcagt ccagcctgag ggctcttcgg caaatg                              636
```

<210> SEQ ID NO 120
<211> LENGTH: 951
<212> TYPE: DNA
<213> ORGANISM: Homo sapiens
<220> FEATURE:
<223> OTHER INFORMATION: MyD88, isoform 1

<400> SEQUENCE: 120

```
atgcgacccg accgcgctga ggctccagga ccgcccgcca tggctgcagg aggtcccggc     60

gcggggtctg cggccccggt ctcctccaca tcctcccttc ccctggctgc tctcaacatg    120

cgagtgcggc gccgcctgtc tctgttcttg aacgtgcgga cacaggtggc ggccgactgg    180

accgcgctgg cggaggagat ggactttgag tacttggaga tccggcaact ggagacacaa    240

gcggacccca ctggcaggct gctggacgcc tggcagggac gccctggcgc ctctgtaggc    300

cgactgctcg agctgcttac caagctgggc cgcgacgacg tgctgctgga gctgggaccc    360

agcattgagg aggattgcca aaagtatatc ttgaagcagc agcaggagga ggctgagaag    420

cctttacagg tggccgctgt agacagcagt gtcccacgga cagcagagct ggcgggcatc    480

accacacttg atgacccccct ggggcatatg cctgagcgtt tcgatgcctt catctgctat    540

tgccccagcg acatccagtt tgtgcaggag atgatccggc aactggaaca gacaaactat    600

cgactgaagt tgtgtgtgtc tgaccgcgat gtcctgcctg gcacctgtgt ctggtctatt    660

gctagtgagc tcatcgaaaa gaggttggct agaaggccac ggggtgggtg ccgccggatg    720

gtggtggttg tctctgatga ttacctgcag agcaaggaat gtgacttcca gaccaaattt    780

gcactcagcc tctctccagg tgcccatcag aagcgactga tccccatcaa gtacaaggca    840

atgaagaaag agttccccag catcctgagg ttcatcactg tctgcgacta caccaacccc    900

tgcaccaaat cttggttctg gactcgcctt gccaaggcct tgtccctgcc c             951
```

<210> SEQ ID NO 121
<211> LENGTH: 807
<212> TYPE: DNA
<213> ORGANISM: Homo sapiens
<220> FEATURE:
<223> OTHER INFORMATION: Interleukin 1-beta (IL-1beta)

<400> SEQUENCE: 121

```
atggcagaag tacctgagct cgccagtgaa atgatggctt attacagtgg caatgaggat     60

gacttgttct ttgaagctga tggccctaaa cagatgaagt gctccttcca ggacctggac    120

ctctgccctc tggatggcgg catccagcta cgaatctccg accaccacta cagcaagggc    180

ttcaggcagg ccgcgtcagt tgttgtggcc atggacaagc tgaggaagat gctggttccc    240

tgcccacaga ccttccagga gaatgacctg agcaccttct ttcccttcat ctttgaagaa    300

gaacctatct tcttcgacac atgggataac gaggcttatg tgcacgatgc acctgtacga    360

tcactgaact gcacgctccg ggactcacag caaaaaagct tggtgatgtc tggtccatat    420

gaactgaaag ctctccacct ccagggacag gatatggagc aacaagtggt gttctccatg    480

tcctttgtac aaggagaaga aagtaatgac aaaatacctg tggccttggg cctcaaggaa    540
```

aagaatctgt acctgtcctg cgtgttgaaa gatgataagc ccactctaca gctggagagt 600
gtagatccca aaaattaccc aaagaagaag atggaaaagc gatttgtctt caacaagata 660
gaaatcaata acaagctgga atttgagtct gcccagttcc ccaactggta catcagcacc 720
tctcaagcag aaaacatgcc cgtcttcctg ggagggacca aaggcggcca ggatataact 780
gacttcacca tgcaatttgt gtcttcc 807

<210> SEQ ID NO 122
<211> LENGTH: 3075
<212> TYPE: DNA
<213> ORGANISM: Homo sapiens
<220> FEATURE:
<223> OTHER INFORMATION: MDA5/IFIH1, isoform 1

<400> SEQUENCE: 122
atgtcgaatg ggtattccac agacgagaat ttccgctatc tcatctcgtg cttcagggcc 60
agggtgaaaa tgtacatcca ggtggagcct gtgctggact acctgacctt tctgcctgca 120
gaggtgaagg agcagattca gaggacagtc gccacctccg ggaacatgca ggcagttgaa 180
ctgctgctga gcaccttgga gaagggagtc tggcaccttg gttggactcg ggaattcgtg 240
gaggccctcc ggagaaccgg cagccctctg gccgcccgct acatgaaccc tgagctcacg 300
gacttgccct ctccatcgtt tgagaacgct catgatgaat atctccaact gctgaacctc 360
cttcagccca ctctggtgga caagcttcta gttagagacg tcttggataa gtgcatggag 420
gaggaactgt tgacaattga agacagaaac cggattgctg ctgcagaaaa caatggaaat 480
gaatcaggtg taagagagct actaaaaagg attgtgcaga aagaaaactg gttctctgca 540
tttctgaatg ttcttcgtca aacaggaaac aatgaacttg tccaagagtt aacaggctct 600
gattgctcag aaagcaatgc agagattgag aatttatcac aagttgatgg tcctcaagtg 660
gaagagcaac ttctttcaac cacagttcag ccaaatctgg agaaggaggt ctggggcatg 720
gagaataact catcagaatc atcttttgca gattcttctg tagtttcaga atcagacaca 780
agtttggcag aaggaagtgt cagctgctta gatgaaagtc ttggacataa cagcaacatg 840
ggcagtgatt caggcaccat gggaagtgat tcagatgaag agaatgtggc agcaagagca 900
tccccggagc cagaactcca gctcaggcct taccaaatgg aagttgccca gccagccttg 960
gaagggaaga atatcatcat ctgcctccct acagggagtg gaaaaaccag agtggctgtt 1020
tacattgcca aggatcactt agacaagaag aaaaaagcat ctgagcctgg aaaagttata 1080
gttcttgtca ataaggtact gctagttgaa cagctcttcc gcaaggagtt ccaaccattt 1140
ttgaagaaat ggtatcgtgt tattggatta agtggtgata cccaactgaa aatatcattt 1200
ccagaagttg tcaagtcctg tgatattatt atcagtacag ctcaaatcct tgaaaactcc 1260
ctcttaaact tggaaaatgg agaagatgct ggtgttcaat tgtcagactt ttccctcatt 1320
atcattgatg aatgtcatca caccaacaaa gaagcagtgt ataataacat catgaggcat 1380
tatttgatgc agaagttgaa aaacaataga ctcaagaaag aaaacaaacc agtgattccc 1440
cttcctcaga tactgggact aacagcttca cctggtgttg gaggggccac gaagcaagcc 1500
aaagctgaag aacacatttt aaaactatgt gccaatcttg atgcatttac tattaaaact 1560
gttaaagaaa accttgatca actgaaaaac caaatacagg agccatgcaa gaagtttgcc 1620
attgcagatg caaccagaga agatccattt aaagagaaac ttctagaaat aatgacaagg 1680
attcaaactt attgtcaaat gagtccaatg tcagattttg gaactcaacc ctatgaacaa 1740

```
tgggccattc aaatggaaaa aaaagctgca aaagaaggaa atcgcaaaga acgtgtttgt   1800
gcagaacatt tgaggaagta caatgaggcc ctacaaatta atgacacaat tcgaatgata   1860
gatgcgtata ctcatcttga aactttctat aatgaagaga aagataagaa gtttgcagtc   1920
atagaagatg atagtgatga gggtggtgat gatgagtatt gtgatggtga tgaagatgag   1980
gatgatttaa agaaaccttt gaaactggat gaaacagata gatttctcat gactttattt   2040
tttgaaaaca ataaaatgtt gaaaaggctg gctgaaaacc cagaatatga aaatgaaaag   2100
ctgaccaaat taagaaatac cataatggag caatatacta ggactgagga atcagcacga   2160
ggaataatct ttacaaaaac acgacagagt gcatatgcgc tttcccagtg gattactgaa   2220
aatgaaaaat ttgctgaagt aggagtcaaa gcccaccatc tgattggagc tggacacagc   2280
agtgagttca aacccatgac acagaatgaa caaaaagaag tcattagtaa atttcgcact   2340
ggaaaaataa atctgcttat cgctaccaca gtggcagaag aaggtctgga tattaaagaa   2400
tgtaacattg ttatccgtta tggtctcgtc accaatgaaa tagccatggt ccaggcccgt   2460
ggtcgagcca gagctgatga gagcacctac gtcctggttg ctcacagtgg ttcaggagtt   2520
atcgaacatg agacagttaa tgatttccga gagaagatga tgtataaagc tatacattgt   2580
gttcaaaata tgaaaccaga ggagtatgct cataagattt tggaattaca gatgcaaagt   2640
ataatggaaa agaaaatgaa aaccaagaga aatattgcca agcattacaa gaataaccca   2700
tcactaataa ctttcctttg caaaaactgc agtgtgctag cctgttctgg ggaagatatc   2760
catgtaattg agaaaatgca tcacgtcaat atgaccccag aattcaagga actttacatt   2820
gtaagagaaa acaaagcact gcaaaagaag tgtgccgact atcaaataaa tggtgaaatc   2880
atctgcaaat gtggccaggc ttggggaaca atgatggtgc acaaaggctt agatttgcct   2940
tgtctcaaaa taaggaattt tgtagtggtt ttcaaaaata attcaacaaa gaaacaatac   3000
aaaaagtggg tagaattacc tatcacattt cccaatcttg actattcaga atgctgttta   3060
tttagtgatg aggat                                                    3075
```

<210> SEQ ID NO 123
<211> LENGTH: 1620
<212> TYPE: DNA
<213> ORGANISM: Homo sapiens
<220> FEATURE:
<223> OTHER INFORMATION: IPS-1/MAVS, isoform 1

<400> SEQUENCE: 123

```
atgccgtttg ctgaagacaa gacctataag tatatctgcc gcaatttcag caatttttgc     60
aatgtggatg ttgtagagat tctgccttac ctgccctgcc tcacagcaag agaccaggat    120
cgactgcggg ccacctgcac actctcaggg aaccgggaca ccctctggca tctcttcaat    180
acccttcagc ggcggcccgg ctgggtggag tacttcattg cggcactgag ggctgtgag     240
ctagttgatc tcgcggacga agtggcctct gtctaccaga gctaccagcc tcggacctcg    300
gaccgtcccc cagacccact ggagccaccg tcacttcctg ctgagaggcc agggcccccc    360
acacctgctg cggcccacag catcccctac aacagctgca gagagaagga gccaagttac    420
cccatgcctg tccaggagac ccaggcgcca gagtccccag gagagaattc agagcaagcc    480
ctgcagacgc tcagccccag agccatccca aggaatccag atggtggccc cctggagtcc    540
tcctctgacc tggcagccct cagccctctg acctccagcg ggcatcagga gcaggacaca    600
gaactgggca gtacccacac agcaggtgcg acctccagcc tcacaccatc ccgtgggcct    660
gtgtctccat ctgtctcctt ccagcccctg gcccgttcca cccccagggc aagccgcttg    720
```

cctggaccca cagggtcagt tgtatctact ggcacctcct tctcctcctc atcccctggc 780
ttggcctctg caggggctgc agagggtaaa cagggtgcag agagtgacca ggccgagcct 840
atcatctgct ccagtggggc agaggcacct gccaactctc tgccctccaa agtgcctacc 900
accttgatgc ctgtgaacac agtggccctg aaagtgcctg ccaacccagc atctgtcagc 960
acagtgccct ccaagttgcc aactagctca aagccccctg gtgcagtgcc ttctaatgcg 1020
ctcaccaatc cagcaccatc caaattgccc atcaactcaa cccgtgctgg catggtgcca 1080
tccaaagtgc ctactagcat ggtgctcacc aaggtgtctg ccagcacagt ccccactgac 1140
gggagcagca gaaatgagga gaccccagca gctccaacac ccgccggcgc cactggaggc 1200
agctcagcct ggctagacag cagctctgag aataggggcc ttgggtcgga gctgagtaag 1260
cctggcgtgc tggcatccca ggtagacagc ccgttctcgg gctgcttcga ggatcttgcc 1320
atcagtgcca gcacctcctt gggcatgggg ccctgccatg gcccagagga gaatgagtat 1380
aagtccgagg gcacctttgg gatccacgtg gctgagaacc ccagcatcca gctcctggag 1440
ggcaaccctg ggccacctgc ggacccggat ggcggcccca ggccacaagc cgaccggaag 1500
ttccaggaga gggaggtgcc atgccacagg ccctcacctg ggctctgtg gctccaggtg 1560 gctgtgacag ggtgctggt agtcacactc ctggtggtgc tgtaccggcg gcgtctgcac 1620

<210> SEQ ID NO 124
<211> LENGTH: 2775
<212> TYPE: DNA
<213> ORGANISM: Homo sapiens
<220> FEATURE:
<223> OTHER INFORMATION: RIG-1/DDX58, isoform 1

<400> SEQUENCE: 124
atgaccaccg agcagcgacg cagcctgcaa gccttccagg attatatccg gaagaccctg 60
gaccctacct acatcctgag ctacatggcc ccctggttta gggaggaaga ggtgcagtat 120
attcaggctg agaaaaacaa caagggccca atggaggctg ccacactttt tctcaagttc 180
ctgttggagc tccaggagga aggctggttc cgtggctttt tggatgccct agaccatgca 240
ggttattctg gactttatga agccattgaa agttgggatt tcaaaaaaat tgaaaagttg 300
gaggagtata gattactttt aaaacgttta caaccagaat ttaaaaccag aattatccca 360
accgatatca tttctgatct gtctgaatgt ttaattaatc aggaatgtga agaaattcta 420
cagatttgct ctactaaggg gatgatggca ggtgcagaga aattggtgga atgccttctc 480
agatcagaca aggaaaactg gcccaaaact ttgaaacttg ctttggagaa agaaaggaac 540
aagttcagtg aactgtggat tgtagagaaa ggtataaaag atgttgaaac agaagatctt 600
gaggataaga tggaaacttc tgacatacag attttctacc aagaagatcc agaatgccag 660
aatcttagtg agaattcatg tccaccttca gaagtgtctg atacaaactt gtacagccca 720
tttaaaccaa gaaattacca attagagctt gctttgcctg ctatgaaagg aaaaaacaca 780
ataatatgtg ctcctacagg ttgtggaaaa acctttgttt cactgcttat atgtgaacat 840
catcttaaaa aattcccaca aggacaaaag gggaaagttg tctttttgc gaatcagatc 900 ccagtgtatg aacagcagaa atctgtattc tcaaaatact ttgaaagaca tgggtataga 960
gttacaggca tttctggagc aacagctgag aatgtcccag tggaacagat tgttgagaac 1020
aatgacatca tcattttaac tccacagatt cttgtgaaca accttaaaaa gggaacgatt 1080
ccatcactat ccatctttac tttgatgata tttgatgaat gccacaacac tagtaaacaa 1140

```
cacccgtaca atatgatcat gtttaattat ctagatcaga aacttggagg atcttcaggc   1200
ccactgcccc aggtcattgg gctgactgcc tcggttggtg ttggggatgc caaaaacaca   1260
gatgaagcct tggattatat ctgcaagctg tgtgcttctc ttgatgcgtc agtgatagca   1320
acagtcaaac acaatctgga ggaactggag caagttgttt ataagcccca gaagtttttc   1380
aggaaagtgg aatcacggat tagcgacaaa tttaaataca tcatagctca gctgatgagg   1440
gacacagaga gtctggcaaa gagaatctgc aaagacctcg aaaacttatc tcaaattcaa   1500
aatagggaat ttggaacaca gaaatatgaa caatggattg ttacagttca gaaagcatgc   1560
atggtgttcc agatgccaga caaagatgaa gagagcagga tttgtaaagc cctgttttta   1620
tacacttcac atttgcggaa atataatgat gccctcatta tcagtgagca tgcacgaatg   1680
aaagatgctc tggattactt gaaagacttc ttcagcaatg tccgagcagc aggattcgat   1740
gagattgagc aagatcttac tcagagattt gaagaaaagc tgcaggaact agaaagtgtt   1800
tccagggatc ccagcaatga gaatcctaaa cttgaagacc tctgcttcat cttacaagaa   1860
gagtaccact taaacccaga gacaataaca attctctttg tgaaaaccag agcacttgtg   1920
gacgctttaa aaaattggat tgaaggaaat cctaaactca gttttctaaa acctggcata   1980
ttgactggac gtggcaaaac aaatcagaac acaggaatga ccctcccggc acagaagtgt   2040
atattggatg cattcaaagc cagtggagat cacaatattc tgattgccac ctcagttgct   2100
gatgaaggca ttgacattgc acagtgcaat cttgtcatcc tttatgagta tgtgggcaat   2160
gtcatcaaaa tgatccaaac cagaggcaga ggaagagcaa gaggtagcaa gtgcttcctt   2220
ctgactagta atgctggtgt aattgaaaaa gaacaaataa acatgtacaa agaaaaaatg   2280
atgaatgact ctattttacg ccttcagaca tgggacgaag cagtatttag ggaaaagatt   2340
ctgcatatac agactcatga aaaattcatc agagatagtc aagaaaaacc aaaacctgta   2400
cctgataagg aaaataaaaa actgctctgc agaaaagtgca aagccttggc atgttacaca   2460
gctgacgtaa gagtgataga ggaatgccat tacactgtgc ttggagatgc ttttaaggaa   2520
tgctttgtga gtagaccaca tcccaagcca aagcagtttt caagttttga aaaaagagca   2580
aagatattct gtgcccgaca gaactgcagc catgactggg gaatccatgt gaagtacaag   2640
acatttgaga ttccagttat aaaaattgaa agttttgtgg tggaggatat tgcaactgga   2700
gttcagacac tgtactcgaa gtggaaggac tttcattttg agaagatacc atttgatcca   2760
gcagaaatgt ccaaa                                                     2775
```

```
<210> SEQ ID NO 125
<211> LENGTH: 1494
<212> TYPE: DNA
<213> ORGANISM: Homo sapiens
<220> FEATURE:
<223> OTHER INFORMATION: IRF5, transcript variant 2

<400> SEQUENCE: 125

atgaaccagt ccatcccagt ggctcccacc ccaccccgcc gcgtgcggct gaagccctgg     60
ctggtggccc aggtgaacag ctgccagtac ccagggcttc aatgggtcaa cggggaaaag    120
aaattattct gcatcccctg gaggcatgcc acaaggcatg gtcccagcca ggacggagat    180
aacaccatct tcaaggcctg ggccaaggag acagggaaat acaccgaagg cgtggatgaa    240
gccgatccgg ccaagtggaa ggccaacctg cgctgtgccc ttaacaagag ccgggacttc    300
cgcctcatct acgacgggcc ccgggacatg ccacctcagc cctacaagat ctacgaggtc    360
tgctccaatg gccctgctcc cacagactcc cagccccctg aggattactc ttttggtgca    420
```

ggagaggagg aggaagaaga ggaagagctg cagaggatgt tgccaagcct gagcctcaca 480
gaggatgtca agtggccgcc cactctgcag ccgcccactc tgcggccgcc tactctgcag 540
ccgcccactc tgcagccgcc cgtggtgctg ggtccccctg ctccagaccc cagccccctg 600
gctcctcccc ctggcaaccc tgctggcttc agggagcttc tctctgaggt cctggagcct 660
gggcccctgc ctgccagcct gccccctgca ggcgaacagc tcctgccaga cctgctgatc 720
agcccccaca tgctgcctct gaccgacctg gagatcaagt ttcagtaccg ggggcggcca 780
ccccgggccc tcaccatcag caacccccat ggctgccggc tcttctacag ccagctggag 840
gccacccagg agcaggtgga actcttcggc cccataagcc tggagcaagt gcgcttcccc 900
agccctgagg acatccccag tgacaagcag cgcttctaca cgaaccagct gctggatgtc 960
ctggaccgcg ggctcatcct ccagctacag ggccaggacc tttatgccat ccgcctgtgt 1020
cagtgcaagg tgttctggag cgggccttgt gcctcagccc atgactcatg ccccaacccc 1080
atccagcggg aggtcaagac caagcttttc agcctggagc attttctcaa tgagctcatc 1140
ctgttccaaa agggccagac caacacccca ccacccttcg agatcttctt ctgctttggg 1200
gaagaatggc ctgaccgcaa accccgagag aagaagctca ttactgtaca ggtggtgcct 1260
gtagcagctc gactgctgct ggagatgttc tcaggggagc tatcttggtc agctgatagt 1320
atccggctac agatctcaaa cccagacctc aaagaccgca tggtggagca attcaaggag 1380
ctccatcaca tctggcagtc ccagcagcgg ttgcagcctg tggcccaggc ccctcctgga 1440
gcaggccttg gtgttggcca ggggccctgg cctatgcacc cagctggcat gcaa 1494

<210> SEQ ID NO 126
<211> LENGTH: 1284
<212> TYPE: DNA
<213> ORGANISM: Homo sapiens
<220> FEATURE:
<223> OTHER INFORMATION: IRF3/TBK1, isoform 1

<400> SEQUENCE: 126
accatgggaa ccccaaagcc acggatcctg ccctggctgg tgtcgcagct ggacctgggg 60
caactggagg gcgtggcctg ggtgaacaag agccgcacgc gcttccgcat cccttggaag 120
cacggcctac ggcaggatgc acagcaggag gatttcggaa tcttccaggc ctgggccgag 180
gccactggtg catatgttcc cgggagggat aagccagacc tgccaacctg gaagaggaat 240
ttccgctctg ccctcaaccg caaagaaggg ttgcgtttag cagaggaccg gagcaaggac 300
cctcacgacc cacataaaat ctacgagttt gtgaactcag gagttgggga cttttcccag 360
ccagacacct ctccggacac caatggtgga ggcagtactt ctgataccca ggaagacatt 420
ctggatgagt tactgggtaa catggtgttg gccccactcc cagatccggg acccccaagc 480
ctggctgtag cccctgagcc ctgccctcag cccctgcgga gccccagctt ggacaatccc 540
actcccttcc caaacctggg gccctctgag aacccactga agcggctgtt ggtgccgggg 600
gaagagtggg agttcgaggt gacagccttc taccggggcc gccaagtctt ccagcagacc 660
atctcctgcc cggagggcct gcggctggtg gggtccgaag tgggagacag gacgctgcct 720
ggatggccag tcacactgcc agaccctggc atgtccctga cagacagggg agtgatgagc 780
tacgtgaggc atgtgctgag ctgcctgggt gggggactgg ctctctggcg ggccgggcag 840
tggctctggg cccagcggct ggggcactgc cacacatact gggcagtgag cgaggagctg 900
ctccccaaca gcgggcatgg gcctgatggc gaggtcccca aggacaagga aggaggcgtg 960

-continued

```
tttgacctgg ggcccttcat tgtagatctg attaccttca cggaaggaag cggacgctca   1020

ccacgctatg ccctctggtt ctgtgtgggg gagtcatggc cccaggacca gccgtggacc   1080

aagaggctcg tgatggtcaa ggttgtgccc acgtgcctca gggccttggt agaaatggcc   1140

cgggtagggg gtgcctcctc cctggagaat actgtggacc tgcacatttc caacagccac   1200

ccactctccc tcacctccga ccagtacaag gcctacctgc aggacttggt ggagggcatg   1260

gatttccagg gccctgggga gagc                                          1284
```

<210> SEQ ID NO 127
<211> LENGTH: 1275
<212> TYPE: DNA
<213> ORGANISM: Homo sapiens
<220> FEATURE:
<223> OTHER INFORMATION: TANK

<400> SEQUENCE: 127

```
atggataaaa acattggcga gcaactcaat aaagcgtatg aagccttccg gcaggcatgc     60

atggatagag attctgcagt aaaagaatta cagcaaaaga ctgagaacta tgagcagaga    120

atacgtgaac aacaggaaca gctgtcactt caacagacta ttattgacaa gctaaaatct    180

cagttacttc ttgtgaattc cactcaagat aacaattatg gctgtgttcc tctgcttgaa    240

gacagtgaaa caagaaagaa taatttgact cttgatcagc cacaagataa agtgatttca    300

ggaatagcaa gagaaaaact accaaaggta agaagacaag aggtttcttc tcctagaaaa    360

gaaacttcag caaggagtct tggcagtcct ttgctccatg aaaggggtaa tatagagaag    420

actttctggg atctgaaaga agaatttcat aaaatatgca tgctagcaaa agcacagaaa    480

gaccacttaa gcaaacttaa tataccagac actgcaactg aaacacagtg ctctgtgcct    540

atacagtgta cggataaaac agataaacaa gaagcgctgt ttaagcctca ggctaaagat    600

gatataaata gaggtgcacc atccatcaca tctgtcacac caagaggact gtgcagagat    660

gaggaagaca cctcttttga atcactttct aaattcaatg tcaagtttcc acctatggac    720

aatgactcaa ctttcttaca tagcactcca gagagacccg gcatccttag tcctgccacg    780

tctgaggcag tgtgccaaga gaaatttaat atggagttca gagacaaccc agggaacttt    840

gttaaaacag aagaaacttt atttgaaatt cagggaattg accccatagc ttcagctata    900

caaaacctta aaacaactga caaaacaaag ccctcaaatc tcgtaaacac ttgtatcagg    960

acaactctgg atagagctgc gtgtttgcca cctggagacc ataatgcatt atatgtaaat   1020

agcttcccac ttctggaccc atctgatgca ccttttccct cactcgattc cccgggaaaa   1080

gcaatccgag gaccacagca gcccatttgg aagccctttc ctaatcaaga cagtgactcg   1140

gtggtactaa gtggcacaga ctcagaactg catatacctc gagtatgtga attctgtcaa   1200

gcagttttcc caccatccat tacatccagg ggggatttcc ttcggcatct taattcacac   1260

ttcaatggag agact                                                    1275
```

<210> SEQ ID NO 128
<211> LENGTH: 2136
<212> TYPE: DNA
<213> ORGANISM: Homo sapiens
<220> FEATURE:
<223> OTHER INFORMATION: TRIF/TICAM1

<400> SEQUENCE: 128

```
atggcctgca caggcccatc acttcctagc gccttcgaca ttctaggtgc agcaggccag     60

gacaagctct tgtatctgaa gcacaaactg aagaccccac gcccaggctg ccaggggcag    120
```

gacctcctgc atgccatggt tctcctgaag ctgggccagg aaactgaggc caggatctct 180
ctagaggcat tgaaggccga tgcggtggcc cggctggtgg cccgccagtg ggctggcgtg 240
gacagcaccg aggacccaga ggagccccca gatgtgtcct gggctgtggc ccgcttgtac 300
cacctgctgg ctgaggagaa gctgtgcccc gcctcgctgc gggacgtggc ctaccaggaa 360
gccgtccgca ccctcagctc cagggacgac caccggctgg gggaacttca ggatgaggcc 420
cgaaaccggt gtgggtggga cattgctggg gatccaggga gcatccggac gctccagtcc 480
aatctgggct gcctcccacc atcctcggct ttgccctctg ggaccaggag cctcccacgc 540
cccattgacg gtgtttcgga ctggagccaa gggtgctccc tgcgatccac tggcagccct 600
gcctccctgg ccagcaactt ggaaatcagc cagtccccta ccatgccctt cctcagcctg 660
caccgcagcc cacatgggcc cagcaagctc tgtgacgacc cccaggccag cttggtgccc 720
gagcctgtcc ccggtggctg ccaggagcct gaggagatga gctggccgcc atcgggggag 780
attgccagcc caccagagct gccaagcagc ccacctcctg ggcttcccga agtggcccca 840
gatgcaacct ccactggcct ccctgatacc cccgcagctc cagaaaccag caccaactac 900
ccagtggagt gcaccgaggg gtctgcaggc ccccagtctc tccccttgcc tattctggag 960
ccggtcaaaa acccctgctc tgtcaaagac cagacgccac tccaactttc tgtagaagat 1020
accacctctc caaataccaa gccgtgccca cctactccca ccaccccaga aacatcccct 1080
cctcctcctc ctcctcctcc ttcatctact ccttgttcag ctcacctgac cccctcctcc 1140
ctgttccctt cctccctgga atcatcatcg gaacagaaat tctataactt tgtgatcctc 1200
cacgccaggg cagacgaaca catcgccctg cgggttcggg agaagctgga ggcccttggc 1260
gtgcccgacg gggccacctt ctgcgaggat ttccaggtgc cggggcgcgg ggagctgagc 1320
tgcctgcagg acgccataga ccactcagct ttcatcatcc tacttctcac ctccaacttc 1380
gactgtcgcc tgagcctgca ccaggtgaac caagccatga tgagcaacct cacgcgacag 1440
gggtcgccag actgtgtcat ccccttcctg cccctggaga gctccccggc ccagctcagc 1500
tccgacacgg ccagcctgct ctccgggctg gtgcggctgg acgaacactc ccagatcttc 1560
gccaggaagg tggccaacac cttcaagccc cacaggcttc aggcccgaaa ggccatgtgg 1620
aggaaggaac aggacacccg agccctgcgg gaacagagcc aacacctgga cggtgagcgg 1680
atgcaggcgg cggcactgaa cgcagcctac tcagcctacc tccagagcta cttgtcctac 1740
caggcacaga tggagcagct ccaggtggct tttgggagcc acatgtcatt tgggactggg 1800
gcgccctatg gggctcgaat gccctttggg ggccaggtgc ccctgggagc cccgccaccc 1860
tttcccactt ggccggggtg cccgcagccg ccacccctgc acgcatggca ggctggcacc 1920
cccccaccgc cctccccaca gccagcagcc tttccacagt cactgccctt cccgcagtcc 1980
ccagccttcc ctacggcctc acccgcaccc cctcagagcc cagggctgca accccctcatt 2040 atccaccacg cacagatggt acagctgggg ctgaacaacc acatgtggaa ccagagaggg 2100
tcccaggcgc ccgaggacaa gacgcaggag gcagaa 2136

<210> SEQ ID NO 129
<211> LENGTH: 381
<212> TYPE: DNA
<213> ORGANISM: Homo sapiens
<220> FEATURE:
<223> OTHER INFORMATION: Batf3

<400> SEQUENCE: 129

-continued

```
atgtcgcaag ggctcccggc cgccggcagc gtcctgcaga ggagcgtcgc ggcgcccggg     60

aaccagccgc agccgcagcc gcagcagcag agccctgagg atgatgacag gaaggtccga    120

aggagagaaa aaaaccgagt tgctgctcag agaagtcgga agaagcagac ccagaaggct    180

gacaagctcc atgaggaata tgagagcctg gagcaagaaa acaccatgct gcggagagag    240

atcgggaagc tgacagagga gctgaagcac ctgacagagg cactgaagga gcacgagaag    300

atgtgcccgc tgctgctctg ccctatgaac tttgtgccag tgcctccccg gccggaccct    360

gtggccggct gcttgccccg a                                              381
```

```
<210> SEQ ID NO 130
<211> LENGTH: 459
<212> TYPE: DNA
<213> ORGANISM: Homo sapiens
<220> FEATURE:
<223> OTHER INFORMATION: IL-4, isoform 1

<400> SEQUENCE: 130

atgggtctca cctcccaact gcttccccct ctgttcttcc tgctagcatg tgccggcaac     60

tttgtccacg gacacaagtg cgatatcacc ttacaggaga tcatcaaaac tttgaacagc    120

ctcacagagc agaagactct gtgcaccgag ttgaccgtaa cagacatctt tgctgcctcc    180

aagaacacaa ctgagaagga aaccttctgc agggctgcga ctgtgctccg gcagttctac    240

agccaccatg agaaggacac tcgctgcctg ggtgcgactg cacagcagtt ccacaggcac    300

aagcagctga tccgattcct gaaacggctc gacaggaacc tctggggcct ggcgggcttg    360

aattcctgtc ctgtgaagga agccaaccag agtacgttgg aaaacttctt ggaaaggcta    420

aagacgatca tgagagagaa atattcaaag tgttcgagc                           459
```

```
<210> SEQ ID NO 131
<211> LENGTH: 534
<212> TYPE: DNA
<213> ORGANISM: Homo sapiens
<220> FEATURE:
<223> OTHER INFORMATION: IL-10

<400> SEQUENCE: 131

atgcacagct cagcactgct ctgttgcctg gtcctcctga ctggggtgag ggccagccca     60

ggccagggca cccagtctga gaacagctgc acccacttcc caggcaacct gcctaacatg    120

cttcgagatc tccgagatgc cttcagcaga gtgaagactt tctttcaaat gaaggatcag    180

ctggacaact tgttgttaaa ggagtccttg ctggaggact ttaagggtta cctgggttgc    240

caagccttgt ctgagatgat ccagttttac ctggaggagg tgatgcccca agctgagaac    300

caagacccag acatcaaggc gcatgtgaac tccctggggg agaacctgaa gaccctcagg    360

ctgaggctac ggcgctgtca tcgatttctt ccctgtgaaa acaagagcaa ggccgtggag    420

caggtgaaga atgcctttaa taagctccaa gagaaaggca tctacaaagc catgagtgag    480

tttgacatct tcatcaacta catagaagcc tacatgacaa tgaagatacg aaac          534
```

```
<210> SEQ ID NO 132
<211> LENGTH: 759
<212> TYPE: DNA
<213> ORGANISM: Homo sapiens
<220> FEATURE:
<223> OTHER INFORMATION: IL-12 alpha

<400> SEQUENCE: 132

atgtggcccc ctgggtcagc ctcccagcca ccgccctcac ctgccgcggc cacaggtctg     60
```

```
catccagcgg ctcgccctgt gtccctgcag tgccggctca gcatgtgtcc agcgcgcagc    120

ctcctccttg tggctaccct ggtcctcctg gaccacctca gtttggccag aaacctcccc    180

gtggccactc cagacccagg aatgttccca tgccttcacc actcccaaaa cctgctgagg    240

gccgtcagca acatgctcca gaaggccaga caaactctag aattttaccc ttgcacttct    300

gaagagattg atcatgaaga tatcacaaaa gataaaacca gcacagtgga ggcctgttta    360

ccattggaat taaccaagaa tgagagttgc ctaaattcca gagagacctc tttcataact    420

aatgggagtt gcctggcctc cagaaagacc tcttttatga tggccctgtg ccttagtagt    480

atttatgaag acttgaagat gtaccaggtg gagttcaaga ccatgaatgc aaagcttctg    540

atggatccta agaggcagat ctttctagat caaaacatgc tggcagttat tgatgagctg    600

atgcaggccc tgaatttcaa cagtgagact gtgccacaaa aatcctccct tgaagaaccg    660

gatttttata aaactaaaat caagctctgc atacttcttc atgctttcag aattcgggca    720

gtgactattg atagagtgat gagctatctg aatgcttcc                           759
```

<210> SEQ ID NO 133
<211> LENGTH: 986
<212> TYPE: DNA
<213> ORGANISM: Homo sapiens
<220> FEATURE:
<223> OTHER INFORMATION: IL-12 beta

<400> SEQUENCE: 133

```
agatgtgtca ccagcagttg gtcatctctt ggttttccct ggtttttctg gcatctcccc     60

tcgtggccat atgggaactg aagaaagatg tttatgtcgt agaattggat tggtatccgg    120

atgcccctgg agaaatggtg gtcctcacct gtgacacccc tgaagaagat ggtatcacct    180

ggaccttgga ccagagcagt gaggtcttag gctctggcaa aaccctgacc atccaagtca    240

aagagtttgg agatgctggc cagtacacct gtcacaaagg aggcgaggtt ctaagccatt    300

cgctcctgct gcttcacaaa aaggaagatg gaatttggtc cactgatatt ttaaaggacc    360

agaaagaacc caaaaataag acctttctaa gatgcgaggc caagaattat tctggacgtt    420

tcacctgctg gtggctgacg acaatcagta ctgatttgac attcagtgtc aaaagcagca    480

gaggctcttc tgacccccaa ggggtgacgt gcggagctgc tacactctct gcagagagag    540

tcagagggga caacaaggag tatgagtact cagtggagtg ccaggaggac agtgcctgcc    600

cagctgctga ggagagtctg cccattgagg tcatggtgga tgccgttcac aagctcaagt    660

atgaaaacta caccagcagc ttcttcatca gggacatcat caaacctgac ccacccaaga    720

acttgcagct gaagccatta aagaattctc ggcaggtgga ggtcagctgg gagtaccctg    780

acacctggag tactccacat tcctacttct ccctgacatt ctgcgttcag gtccagggca    840

agagcaagag agaaaagaaa gatagagtct tcacggacaa gacctcagcc acggtcatct    900

gccgcaaaaa tgccagcatt agcgtgcggg cccaggaccg ctactatagc tcatcttgga    960

gcgaatgggc atctgtgccc tgcagt                                         986
```

<210> SEQ ID NO 134
<211> LENGTH: 276
<212> TYPE: DNA
<213> ORGANISM: Homo sapiens
<220> FEATURE:
<223> OTHER INFORMATION: MIP-1 alpha/ CCL3

<400> SEQUENCE: 134

-continued

```
atgcaggtct ccactgctgc ccttgctgtc ctcctctgca ccatggctct ctgcaaccag     60

ttctctgcat cacttgctgc tgacacgccg accgcctgct gcttcagcta cacctcccgg    120

cagattccac agaatttcat agctgactac tttgagacga gcagccagtg ctccaagccc    180

ggtgtcatct tcctaaccaa gcgaagccgg caggtctgtg ctgaccccag tgaggagtgg    240

gtccagaaat atgtcagcga cctggagctg agtgcc                              276
```

<210> SEQ ID NO 135
<211> LENGTH: 1530
<212> TYPE: DNA
<213> ORGANISM: Homo sapiens
<220> FEATURE:
<223> OTHER INFORMATION: CD39/ENTPD1, isoform 1

<400> SEQUENCE: 135

```
atggaagata caaaggagtc taacgtgaag acattttgct ccaagaatat cctagccatc     60

cttggcttct cctctatcat agctgtgata gctttgcttg ctgtggggtt gacccagaac    120

aaagcattgc cagaaaacgt taagtatggg attgtgctgg atgcgggttc ttctcacaca    180

agtttataca tctataagtg gccagcagaa aaggagaatg acacaggcgt ggtgcatcaa    240

gtagaagaat gcagggttaa aggtcctgga atctcaaaat ttgttcagaa agtaaatgaa    300

ataggcattt acctgactga ttgcatggaa agagctaggg aagtgattcc aaggtcccag    360

caccaagaga cacccgttta cctgggagcc acggcaggca tgcggttgct caggatggaa    420

agtgaagagt tggcagacag ggttctggat gtggtggaga ggagcctcag caactacccc    480

tttgacttcc agggtgccag gatcattact ggccaagagg aaggtgccta tggctggatt    540

actatcaact atctgctggg caaattcagt cagaaaacaa ggtggttcag catagtccca    600

tatgaaacca ataatcagga aacctttgga gctttggacc ttgggggagc ctctacacaa    660

gtcacttttg taccccaaaa ccagactatc gagtccccag ataatgctct gcaatttcgc    720

ctctatggca aggactacaa tgtctacaca catagcttct tgtgctatgg gaaggatcag    780

gcactctggc agaaactggc caaggacatt caggttgcaa gtaatgaaat tctcagggac    840

ccatgctttc atcctggata taagaaggta gtgaacgtaa gtgaccttta caagaccccc    900

tgcaccaaga gatttgagat gactcttcca ttccagcagt ttgaaatcca gggtattgga    960

aactatcaac aatgccatca aagcatcctg gagctcttca acaccagtta ctgcccttac   1020

tcccagtgtg ccttcaatgg gattttcttg ccaccactcc agggggattt tggggcattt   1080

tcagcttttt actttgtgat gaagttttta aacttgacat cagagaaagt ctctcaggaa   1140

aaggtgactg agatgatgaa aaagttctgt gctcagcctt gggaggagat aaaaacatct   1200

tacgctggag taaaggagaa gtacctgagt gaatactgct tttctggtac ctacattctc   1260

tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440

atggttctat tctccctggt ccttttcaca gtggccatca taggcttgct tatctttcac   1500

aagccttcat atttctggaa agatatggta                                    1530
```

<210> SEQ ID NO 136
<211> LENGTH: 1722
<212> TYPE: DNA
<213> ORGANISM: Homo sapiens
<220> FEATURE:
<223> OTHER INFORMATION: CD73/NT5E, isoform 1

<400> SEQUENCE: 136
atgtgtcccc gagccgcgcg ggcgcccgcg acgctactcc tcgccctggg cgcggtgctg 60
tggcctgcgg ctggcgcctg ggagcttacg attttgcaca ccaacgacgt gcacagccgg 120
ctggagcaga ccagcgagga ctccagcaag tgcgtcaacg ccagccgctg catgggtggc 180
gtggctcggc tcttcaccaa ggttcagcag atccgccgcg ccgaacccaa cgtgctgctg 240
ctggacgccg gcgaccagta ccagggcact atctggttca ccgtgtacaa gggcgccgag 300
gtggcgcact tcatgaacgc cctgcgctac gatgccatgg cactgggaaa tcatgaattt 360
gataatggtg tggaaggact gatcgagcca ctcctcaaag aggccaaatt tccaattctg 420
agtgcaaaca ttaaagcaaa ggggccacta gcatctcaaa tatcaggact ttatttgcca 480
tataaagttc ttcctgttgg tgatgaagtt gtgggaatcg ttggatacac ttccaaagaa 540
accccttttc tctcaaatcc agggacaaat ttagtgtttg aagatgaaat cactgcatta 600
caacctgaag tagataagtt aaaaactcta aatgtgaaca aaattattgc actgggacat 660
tcgggttttg aaatggataa actcatcgct cagaaagtga ggggtgtgga cgtcgtggtg 720
ggaggacact ccaacacatt tctttacaca ggcaatccac cttccaaaga ggtgcctgct 780
gggaagtacc cattcatagt cacttctgat gatgggcgga aggttcctgt agtccaggcc 840
tatgcttttg gcaaatacct aggctatctg aagatcgagt ttgatgaaag aggaaacgtc 900
atctcttccc atggaaatcc cattcttcta aacagcagca ttcctgaaga tccaagcata 960
aaagcagaca ttaacaaatg gaggataaaa ttggataatt attctaccca ggaattaggg 1020
aaaacaattg tctatctgga tggctcctct caatcatgcc gctttagaga atgcaacatg 1080
ggcaacctga tttgtgatgc aatgattaac aacaacctga gacacacgga tgaaatgttc 1140
tggaaccacg tatccatgtg cattttaaat ggaggtggta tccggtcgcc cattgatgaa 1200
cgcaacaatg gcacaattac ctgggagaac ctggctgctg tattgccctt tggaggcaca 1260
tttgacctag tccagttaaa aggttccacc ctgaagaagg cctttgagca tagcgtgcac 1320
cgctacggcc agtccactgg agagttcctg caggtgggcg gaatccatgt ggtgtatgat 1380
ctttcccgaa aacctggaga cagagtagtc aaattagatg ttctttgcac caagtgtcga 1440
gtgcccagtt atgaccctct caaaatggac gaggtatata aggtgatcct cccaaacttc 1500
ctggccaatg gtggagatgg gttccagatg ataaaagatg aattattaag acatgactct 1560
ggtgaccaag atatcaacgt ggtttctaca tatatctcca aaatgaaagt aatttatcca 1620
gcagttgaag gtcggatcaa gttttccaca ggaagtcact gccatggaag cttttcttta 1680
atatttcttt cactttgggc agtgatcttt gttttatacc aa 1722

<210> SEQ ID NO 137
<211> LENGTH: 297
<212> TYPE: DNA
<213> ORGANISM: Homo sapiens
<220> FEATURE:
<223> OTHER INFORMATION: IL-8 (CXCL8)

<400> SEQUENCE: 137
atgacttcca agctggccgt ggctctcttg gcagccttcc tgatttctgc agctctgtgt 60
gaaggtgcag ttttgccaag gagtgctaaa gaacttagat gtcagtgcat aaagacatac 120
tccaaacctt tccaccccaa atttatcaaa gaactgagag tgattgagag tggaccacac 180
tgcgccaaca cagaaattat tgtaaagctt tctgatggaa gagagctctg tctggacccc 240
aaggaaaact gggtgcagag ggttgtggag aagtttttga agagggctga gaattca 297

<210> SEQ ID NO 138
<211> LENGTH: 1596
<212> TYPE: DNA
<213> ORGANISM: Homo sapiens
<220> FEATURE:
<223> OTHER INFORMATION: ICAM1

<400> SEQUENCE: 138
atggctccca gcagccccg gcccgcgctg cccgcactcc tggtcctgct cggggctctg 60
ttcccaggac ctggcaatgc ccagacatct gtgtcccct caaaagtcat cctgcccgg 120 ggaggctccg tgctggtgac atgcagcacc tcctgtgacc agcccaagtt gttgggcata 180
gagaccccgt tgcctaaaaa ggagttgctc ctgcctggga acaaccggaa ggtgtatgaa 240
ctgagcaatg tgcaagaaga tagccaacca atgtgctatt caaactgccc tgatgggcag 300
tcaacagcta aaaccttcct caccgtgtac tggactccag aacgggtgga actggcaccc 360
ctcccctctt ggcagccagt gggcaagaac cttaccctac gctgccaggt ggagggtggg 420
gcaccccggg ccaacctcac cgtggtgctg ctccgtgggg agaaggagct gaaacgggag 480
ccagctgtgg gggagcccgc tgaggtcacg accacggtgc tggtgaggag agatcaccat 540
ggagccaatt tctcgtgccg cactgaactg gacctgcggc cccaagggct ggagctgttt 600
gagaacacct cggcccccta ccagctccag acctttgtcc tgccagcgac tcccccacaa 660
cttgtcagcc cccgggtcct agaggtggac acgcagggga ccgtggtctg ttccctggac 720
gggctgttcc cagtctcgga ggcccaggtc cacctggcac tgggggacca gaggttgaac 780
cccacagtca cctatggcaa cgactccttc tcggccaagg cctcagtcag tgtgaccgca 840
gaggacgagg gcacccagcg gctgacgtgt gcagtaatac tggggaacca gagccaggag 900
acactgcaga cagtgaccat ctacagcttt ccggcgccca acgtgattct gacgaagcca 960
gaggtctcag aagggaccga ggtgacagtg aagtgtgagg cccaccctag agccaaggtg 1020
acgctgaatg gggttccagc ccagccactg ggcccgaggg cccagctcct gctgaaggcc 1080
accccagagg acaacgggcg cagcttctcc tgctctgcaa ccctggaggt ggccggccag 1140
cttatacaca agaaccagac ccgggagctt cgtgtcctgt atggcccccg actggacgag 1200
agggattgtc cgggaaactg gacgtggcca gaaaattccc agcagactcc aatgtgccag 1260
gcttggggga acccattgcc cgagctcaag tgtctaaagg atggcacttt cccactgccc 1320
atcggggaat cagtgactgt cactcgagat cttgagggca cctacctctg tcgggccagg 1380
agcactcaag gggaggtcac ccgcaaggtg accgtgaatg tgctctcccc ccggtatgag 1440
attgtcatca tcactgtggt agcagccgca gtcataatgg gcactgcagg cctcagcacg 1500
tacctctata accgccagcg gaagatcaag aaatacagac tacaacaggc ccaaaaaggg 1560
acccccatga aaccgaacac acaagccacg cctccc 1596

<210> SEQ ID NO 139
<211> LENGTH: 1488
<212> TYPE: DNA
<213> ORGANISM: Homo sapiens
<220> FEATURE:
<223> OTHER INFORMATION: angiopoietin 2, isoform 1

<400> SEQUENCE: 139
atgtggcaga ttgttttctt tactctgagc tgtgatcttg tcttggccgc agcctataac 60
aactttcgga agagcatgga cagcatagga aagaagcaat atcaggtcca gcatgggtcc 120

```
tgcagctaca ctttcctcct gccagagatg gacaactgcc gctcttcctc cagcccctac    180
gtgtccaatg ctgtgcagag ggacgcgccg ctcgaatacg atgactcggt gcagaggctg    240
caagtgctgg agaacatcat ggaaaacaac actcagtggc taatgaagct tgagaattat    300
atccaggaca acatgaagaa agaaatggta gagatacagc agaatgcagt acagaaccag    360
acggctgtga tgatagaaat agggacaaac ctgttgaacc aaacagcgga gcaaacgcgg    420
aagttaactg atgtggaagc ccaagtatta aatcagacca cgagacttga acttcagctc    480
ttggaacact ccctctcgac aaacaaattg gaaaaacaga ttttggacca gaccagtgaa    540
ataaacaaat tgcaagataa gaacagtttc ctagaaaaga aggtgctagc tatggaagac    600
aagcacatca tccaactaca gtcaataaaa gaagagaaag atcagctaca ggtgttagta    660
tccaagcaaa attccatcat tgaagaacta gaaaaaaaaa tagtgactgc cacggtgaat    720
aattcagttc ttcagaagca gcaacatgat ctcatggaga cagttaataa cttactgact    780
atgatgtcca catcaaactc agctaaggac cccactgttg ctaaagaaga acaaatcagc    840
ttcagagact gtgctgaagt attcaaatca ggacacacca cgaatggcat ctacacgtta    900
acattcccta attctacaga agagatcaag gcctactgtg acatggaagc tggaggaggc    960
gggtggacaa ttattcagcg acgtgaggat ggcagcgttg attttcagag gacttggaaa   1020
gaatataaag tgggatttgg taacccttca ggagaatatt ggctgggaaa tgagtttgtt   1080
tcgcaactga ctaatcagca acgctatgtg cttaaaatac accttaaaga ctgggaaggg   1140
aatgaggctt actcattgta tgaacatttc tatctctcaa gtgaagaact caattatagg   1200
attcacctta aaggacttac agggacagcc ggcaaaataa gcagcatcag ccaaccagga   1260
aatgatttta gcacaaagga tggagacaac gacaaatgta tttgcaaatg ttcacaaatg   1320
ctaacaggag gctggtggtt tgatgcatgt ggtccttcca acttgaacgg aatgtactat   1380
ccacagaggc agaacacaaa taagttcaac ggcattaaat ggtactactg gaaaggctca   1440
ggctattcgc tcaaggccac aaccatgatg atccgaccag cagatttc                1488
```

```
<210> SEQ ID NO 140
<211> LENGTH: 2766
<212> TYPE: DNA
<213> ORGANISM: Homo sapiens
<220> FEATURE:
<223> OTHER INFORMATION: NLRP3, isoform 2

<400> SEQUENCE: 140

atgaagatgg caagcacccg ctgcaagctg gccaggtacc tggaggacct ggaggatgtg     60
gacttgaaga aatttaagat gcacttagag gactatcctc cccagaaggg ctgcatcccc    120
ctcccgaggg gtcagacaga gaaggcagac catgtggatc tagccacgct aatgatcgac    180
ttcaatgggg aggagaaggc gtgggccatg gccgtgtgga tcttcgctgc gatcaacagg    240
agagaccttt atgagaaagc aaaaagagat gagccgaagt ggggttcaga taatgcacgt    300
gtttcgaatc ccactgtgat atgccaggaa gacagcattg aagaggagtg gatgggttta    360
ctggagtacc tttcgagaat ctctatttgt aaaatgaaga aagattaccg taagaagtac    420
agaaagtacg tgagaagcag attccagtgc attgaagaca ggaatgcccg tctgggtgag    480
agtgtgagcc tcaacaaacg ctacacacga ctgcgtctca tcaaggagca ccggagccag    540
caggagaggg agcaggagct tctggccatc ggcaagacca agacgtgtga gagccccgtg    600
agtcccatta agatggagtt gctgtttgac cccgatgatg agcattctga gcctgtgcac    660
```

-continued

```
accgtggtgt tccagggggc ggcagggatt gggaaaacaa tcctggccag gaagatgatg    720
ttggactggg cgtcggggac actctaccaa gacaggtttg actatctgtt ctatatccac    780
tgtcgggagg tgagccttgt gacacagagg agcctggggg acctgatcat gagctgctgc    840
cccgacccaa acccacccat ccacaagatc gtgagaaaac cctccagaat cctcttcctc    900
atggacggct tcgatgagct gcaaggtgcc tttgacgagc acataggacc gctctgcact    960
gactggcaga aggccgagcg gggagacatt ctcctgagca gcctcatcag aaagaagctg   1020
cttcccgagg cctctctgct catcaccacg agacctgtgg ccctggagaa actgcagcac   1080
ttgctggacc atcctcggca tgtggagatc ctgggtttct ccgaggccaa aaggaaagag   1140
tacttcttca agtacttctc tgatgaggcc caagccaggg cagccttcag tctgattcag   1200
gagaacgagg tcctcttcac catgtgcttc atcccccctgg tctgctggat cgtgtgcact  1260
ggactgaaac agcagatgga gagtggcaag agccttgccc agacatccaa gaccaccacc   1320
gcggtgtacg tcttcttcct ttccagtttg ctgcagcccc ggggagggag ccaggagcac   1380
ggcctctgcg cccacctctg gggctctgc tctttggctg cagatggaat ctggaaccag    1440
aaaatcctgt ttgaggagtc cgacctcagg aatcatggac tgcagaaggc ggatgtgtct   1500
gctttcctga ggatgaacct gttccaaaag gaagtggact gcgagaagtt ctacagcttc   1560
atccacatga ctttccagga gttctttgcc gccatgtact acctgctgga agaggaaaag   1620
gaaggaagga cgaacgttcc agggagtcgt ttgaagcttc ccagccgaga cgtgacagtc   1680
cttctggaaa actatggcaa attcgaaaag ggggtatttga tttttgttgt acgtttcctc  1740
tttggcctgg taaaccagga gaggacctcc tacttggaga agaaattaag ttgcaagatc   1800
tctcagcaaa tcaggctgga gctgctgaaa tggattgaag tgaaagccaa agctaaaaag   1860
ctgcagatcc agcccagcca gctggaattg ttctactgtt tgtacgagat gcaggaggag   1920
gacttcgtgc aaagggccat ggactatttc cccaagattg agatcaatct ctccaccaga   1980
atggaccaca tggtttcttc cttttgcatt gagaactgtc atcgggtgga gtcactgtcc   2040
ctggggtttc tccataacat gcccaaggag gaagaggagg aggaaaagga aggccgacac   2100
cttgatatgg tgcagtgtgt cctcccaagc tcctctcatg ctgcctgttc tcatgggttg   2160
gggcgctgtg gcctctcgca tgagtgctgc ttcgacatct ccttggtcct cagcagcaac   2220
cagaagctgg tggagctgga cctgagtgac aacgccctcg gtgacttcgg aatcagactt   2280
ctgtgtgtgg gactgaagca cctgttgtgc aatctgaaga agctctggtt ggtgaattct   2340
ggccttacgt cagtctgttg ttcagctttg tcctcggtac tcagcactaa tcagaatctc   2400
acgcaccttt acctgcgagg caacactctc ggagacaagg ggatcaaact actctgtgag   2460
ggactcttgc accccgactg caagcttcag gtgttggaat tagacaactg caacctcacg   2520
tcacactgct gctgggatct ttccacactt ctgacctcca gccagagcct gcgaaagctg   2580
agcctgggca acaatgacct gggcgacctg ggggtcatga tgttctgtga agtgctgaaa   2640
cagcagagct gcctcctgca gaacctgggg ttgtctgaaa tgtatttcaa ttatgagaca   2700
aaaagtgcgt tagaaacact tcaagaagaa aagcctgagc tgaccgtcgt ctttgagcct   2760
tcttgg                                                              2766
```

<210> SEQ ID NO 141
<211> LENGTH: 831
<212> TYPE: DNA
<213> ORGANISM: Homo sapiens
<220> FEATURE:
<223> OTHER INFORMATION: CD40, isoform 1

<400> SEQUENCE: 141

```
atggttcgtc tgcctctgca gtgcgtcctc tggggctgct tgctgaccgc tgtccatcca      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
aaatactgcg accccaacct agggcttcgg gtccagcaga agggcacctc agaaacagac     300
accatctgca cctgtgaaga aggctggcac tgtacgagtg aggcctgtga gagctgtgtc     360
ctgcaccgct catgctcgcc cggctttggg gtcaagcaga ttgctacagg ggtttctgat     420
accatctgcg agccctgccc agtcggcttc ttctccaatg tgtcatctgc tttcgaaaaa     480
tgtcaccctt ggacaagctg tgagaccaaa gacctggttg tgcaacaggc aggcacaaac     540
aagactgatg ttgtctgtgg tccccaggat cggctgagag ccctggtggt gatccccatc     600
atcttcggga tcctgtttgc catcctcttg gtgctggtct ttatcaaaaa ggtggccaag     660
aagccaacca ataaggcccc ccaccccaag caggaacccc aggagatcaa ttttcccgac     720
gatcttcctg gctccaacac tgctgctcca gtgcaggaga ctttacatgg atgccaaccg     780
gtcacccagg aggatggcaa agagagtcgc atctcagtgc aggagagaca g              831
```

<210> SEQ ID NO 142
<211> LENGTH: 783
<212> TYPE: DNA
<213> ORGANISM: Homo sapiens
<220> FEATURE:
<223> OTHER INFORMATION: CD40 ligand (CD40L)

<400> SEQUENCE: 142

```
atgatcgaaa catacaacca aacttctccc cgatctgcgg ccactggact gcccatcagc      60
atgaaaattt ttatgtattt acttactgtt tttcttatca cccagatgat tgggtcagca     120
ctttttgctg tgtatcttca tagaaggttg gacaagatag aagatgaaag gaatcttcat     180
gaagattttg tattcatgaa aacgatacag agatgcaaca caggagaaag atccttatcc     240
ttactgaact gtgaggagat taaaagccag tttgaaggct ttgtgaagga tataatgtta     300
aacaaagagg agacgaagaa agaaaacagc tttgaaatgc aaaaaggtga tcagaatcct     360
caaattgcgg cacatgtcat aagtgaggcc agcagtaaaa caacatctgt gttacagtgg     420
gctgaaaaag gatactacac catgagcaac aacttggtaa ccctggaaaa tgggaaacag     480
ctgaccgtta aaagacaagg actctattat atctatgccc aagtcacctt ctgttccaat     540
cgggaagctt cgagtcaagc tccatttata gccagcctct gcctaaagtc ccccggtaga     600
ttcgagagaa tcttactcag agctgcaaat acccacagtt ccgccaaacc ttgcgggcaa     660
caatccattc acttgggagg agtatttgaa ttgcaaccag gtgcttcggt gtttgtcaat     720
gtgactgatc caagccaagt gagccatggc actggcttca cgtcctttgg cttactcaaa     780
ctc                                                                   783
```

<210> SEQ ID NO 143
<211> LENGTH: 579
<212> TYPE: DNA
<213> ORGANISM: Homo sapiens
<220> FEATURE:
<223> OTHER INFORMATION: CD-70 antigen, isoform 1

<400> SEQUENCE: 143

```
atgccggagg agggttcggg ctgctcggtg cggcgcaggc cctatgggtg cgtcctgcgg     60

gctgctttgg tcccattggt cgcgggcttg gtgatctgcc tcgtggtgtg catccagcgc    120

ttcgcacagg ctcagcagca gctgccgctc gagtcacttg ggtgggacgt agctgagctg    180

cagctgaatc acacaggacc tcagcaggac cccaggctat actggcaggg gggcccagca    240

ctgggccgct ccttcctgca tggaccagag ctggacaagg ggcagctacg tatccatcgt    300

gatggcatct acatggtaca catccaggtg acgctggcca tctgctcctc cacgacggcc    360

tccaggcacc accccaccac cctggccgtg ggaatctgct ctcccgcctc ccgtagcatc    420

agcctgctgc gtctcagctt ccaccaaggt tgtaccattg cctcccagcg cctgacgccc    480

ctggcccgag ggacacact ctgcaccaac ctcactggga cacttttgcc ttcccgaaac    540

actgatgaga ccttctttgg agtgcagtgg gtgcgcccc                           579
```

```
<210> SEQ ID NO 144
<211> LENGTH: 765
<212> TYPE: DNA
<213> ORGANISM: Homo sapiens
<220> FEATURE:
<223> OTHER INFORMATION: CD137 (TNFRSF9)

<400> SEQUENCE: 144

atgggaaaca gctgttacaa catagtagcc actctgttgc tggtcctcaa ctttgagagg     60

acaagatcat tgcaggatcc ttgtagtaac tgcccagctg gtacattctg tgataataac    120

aggaatcaga tttgcagtcc ctgtcctcca aatagtttct ccagcgcagg tggacaaagg    180

acctgtgaca tatgcaggca gtgtaaaggt gttttcagga ccaggaagga gtgttcctcc    240

accagcaatg cagagtgtga ctgcactcca gggtttcact gcctgggggc aggatgcagc    300

atgtgtgaac aggattgtaa acaaggtcaa gaactgacaa aaaaaggttg taaagactgt    360

tgctttggga catttaacga tcagaaacgt ggcatctgtc gaccctggac aaactgttct    420

ttggatggaa agtctgtgct tgtgaatggg acgaaggaga gggacgtggt ctgtggacca    480

tctccagccg acctctctcc gggagcatcc tctgtgaccc cgcctgcccc tgcgagagag    540

ccaggacact ctccgcagat catctccttc tttcttgcgc tgacgtcgac tgcgttgctc    600

ttcctgctgt tcttcctcac gctccgtttc tctgttgtta aacggggcag aaagaaactc    660

ctgtatatat tcaaacaacc atttatgaga ccagtacaaa ctactcaaga ggaagatggc    720

tgtagctgcc gatttccaga agaagaagaa ggaggatgtg aactg                    765
```

```
<210> SEQ ID NO 145
<211> LENGTH: 807
<212> TYPE: DNA
<213> ORGANISM: Homo sapiens
<220> FEATURE:
<223> OTHER INFORMATION: CD200, isoform 1

<400> SEQUENCE: 145

atggagaggc tggtgatcag gatgcccttc tctcatctgt ctacctacag cctggtttgg     60

gtcatggcag cagtggtgct gtgcacagca caagtgcaag tggtgaccca ggatgaaaga    120

gagcagctgt acacacctgc ttccttaaaa tgctctctgc aaaatgccca ggaagccctc    180

attgtgacat ggcagaaaaa gaaagctgta agcccagaaa acatggtcac cttcagcgag    240

aaccatgggg tggtgatcca gcctgcctat aaggacaaga taaacattac ccagctggga    300

ctccaaaact caaccatcac cttctggaat atcaccctgg aggatgaagg gtgttacatg    360

tgtctcttca ataccttggg ttttgggaag atctcaggaa cggcctgcct caccgtctat    420
```

```
gtacagccca tagtatccct tcactacaaa ttctctgaag accacctaaa tatcacttgc    480

tctgccactg cccgcccagc ccccatggtc ttctggaagg tccctcggtc agggattgaa    540

aatagtacag tgactctgtc tcacccaaat gggaccacgt ctgttaccag catcctccat    600

atcaaagacc ctaagaatca ggtggggaag gaggtgatct gccaggtgct gcacctgggg    660

actgtgaccg actttaagca aaccgtcaac aaaggctatt ggttttcagt tccgctattg    720

ctaagcattg tttccctggt aattcttctc gtcctaatct caatcttact gtactggaaa    780

cgtcaccgga atcaggaccg agagccc                                        807
```

```
<210> SEQ ID NO 146
<211> LENGTH: 1236
<212> TYPE: DNA
<213> ORGANISM: Homo sapiens
<220> FEATURE:
<223> OTHER INFORMATION: A2aR (ADORA2A)

<400> SEQUENCE: 146

atgcccatca tgggctcctc ggtgtacatc acggtggagc tggccattgc tgtgctggcc     60

atcctgggca atgtgctggt gtgctgggcc gtgtggctca acagcaacct gcagaacgtc    120

accaactact ttgtggtgtc actggcggcg gccgacatcg cagtgggtgt gctcgccatc    180

ccctttgcca tcaccatcag caccgggttc tgcgctgcct gccacggctg cctcttcatt    240

gcctgcttcg tcctggtcct cacgcagagc tccatcttca gtctcctggc catcgccatt    300

gaccgctaca ttgccatccg catcccgctc cggtacaatg gcttggtgac cggcacgagg    360

gctaagggca tcattgccat ctgctgggtg ctgtcgtttg ccatcggcct gactcccatg    420

ctaggttgga acaactgcgg tcagccaaag gagggcaaga accactccca gggctgcggg    480

gagggccaag tggcctgtct ctttgaggat gtggtcccca tgaactacat ggtgtacttc    540

aacttctttg cctgtgtgct ggtgcccctg ctgctcatgc tgggtgtcta tttgcggatc    600

ttcctggcgg cgcgacgaca gctgaagcag atggagagcc agcctctgcc gggggagcgg    660

gcacggtcca cactgcagaa ggaggtccat gctgccaagt cactggccat cattgtgggg    720

ctctttgccc tctgctggct gcccctacac atcatcaact gcttcacttt cttctgcccc    780

gactgcagcc acgcccctct ctggctcatg tacctggcca tcgtcctctc ccacaccaat    840

tcggttgtga atcccttcat ctacgcctac cgtatccgcg agttccgcca gaccttccgc    900

aagatcattc gcagccacgt cctgaggcag caagaacctt tcaaggcagc tggcaccagt    960

gcccgggtct tggcagctca tggcagtgac ggagagcagg tcagcctccg tctcaacggc   1020

cacccgccag gagtgtgggc caacggcagt gctccccacc ctgagcggag gcccaatggc   1080

tatgccctgg ggctggtgag tggagggagt gcccaagagt cccaggggaa cacgggcctc   1140

ccagacgtgg agctccttag ccatgagctc aagggagtgt gcccagagcc ccctggccta   1200

gatgaccccc tggcccagga tggagcagga gtgtcc                             1236
```

```
<210> SEQ ID NO 147
<211> LENGTH: 723
<212> TYPE: DNA
<213> ORGANISM: Homo sapiens
<220> FEATURE:
<223> OTHER INFORMATION: GITR/TNFRSF18, isoform 1

<400> SEQUENCE: 147

atggcacagc acggggcgat gggcgcgttt cgggccctgt gcggcctggc gctgctgtgc     60
```

-continued

```
gcgctcagcc tgggtcagcg ccccaccggg ggtcccgggt gcggccctgg gcgcctcctg    120

cttgggacgg gaacggacgc gcgctgctgc cgggttcaca cgacgcgctg ctgccgcgat    180

tacccgggcg aggagtgctg ttccgagtgg gactgcatgt gtgtccagcc tgaattccac    240

tgcggagacc cttgctgcac gacctgccgg caccaccctt gtcccccagg ccaggggta     300

cagtcccagg ggaaattcag ttttggcttc cagtgtatcg actgtgcctc ggggaccttc    360

tccgggggcc acgaaggcca ctgcaaacct tggacagact gcacccagtt cgggtttctc    420

actgtgttcc ctgggaacaa gacccacaac gctgtgtgcg tcccagggtc cccgccggca    480

gagccgcttg ggtggctgac cgtcgtcctc ctggccgtgg ccgcctgcgt cctcctcctg    540

acctcggccc agcttggact gcacatctgg cagctgagga gtcagtgcat gtggccccga    600

gagacccagc tgctgctgga ggtgccgccg tcgaccgaag acgccagaag ctgccagttc    660

cccgaggaag agcggggcga gcgatcggca gaggagaagg ggcggctggg agacctgtgg    720

gtg                                                                  723
```

<210> SEQ ID NO 148
<211> LENGTH: 1362
<212> TYPE: DNA
<213> ORGANISM: Homo sapiens
<220> FEATURE:
<223> OTHER INFORMATION: B7-H6 (NCR3LG1)

<400> SEQUENCE: 148

```
atgacgtgga gggctgccgc ctccacgtgc gcggcgctcc tgattctgct gtgggcgctg     60

acgaccgaag gtgatctgaa agtagagatg atggcagggg ggactcagat cacacccctg    120

aatgacaatg tcaccatatt ctgcaatatc ttttattccc aacccctcaa catcacgtct    180

atgggtatca cctggttttg gaagagtctg acgtttgaca aagaagtcaa agtctttgaa    240

ttttttggag atcaccaaga ggcattccga cctggagcca ttgtgtctcc atggaggctg    300

aagagtgggg acgcctcact gcggctgcct ggaatccagc tggaggaagc aggagagtac    360

cgatgtgagg tggtggtcac ccctctgaag gcacagggaa cagtccagct tgaagttgtg    420

gcttccccag ccagcagatt gttgctggat caagtgggca tgaaagagaa tgaagacaaa    480

tatatgtgtg agtcaagtgg gttctaccca gaggctatta atataacatg ggagaagcag    540

acccagaagt ttccccatcc catagagatt tctgaggatg tcatcactgg tcccaccatc    600

aagaatatgg atggcacatt taatgtcact agctgcttga agctgaactc ctctcaggaa    660

gaccctggga ctgtctacca gtgtgtggta cggcatgcgt ccttgcatac cccccttgagg   720

agcaacttta ccctgactgc tgctcggcac agtctttctg aaactgagaa gacagataat    780

ttttccattc attggtggcc tatttcattc attggtgttg gactggtttt attaattgtt    840

ttgattcctt ggaaaaagat atgtaacaaa tcatcttcag cctatactcc tctcaagtgc    900

attctgaaac actggaactc ctttgacact cagactctga agaaagagca cctcatattc    960

ttttgcactc gggcatggcc gtcttaccag ctgcaggatg gggaggcttg gcctcctgag   1020

ggaagtgtta atattaatac tattcaacaa ctagatgttt tctgcagaca ggagggcaaa   1080

tggtccgagg ttccttatgt gcaagccttc tttgccttgc gagacaaccc agatctttgt   1140

cagtgttgta gaattgaccc tgctctccta acagttacat caggcaagtc catagatgat   1200

aattccacaa agtctgagaa acaaacccct agggaacact cggatgcagt tccggatgcc   1260

ccaatccttc ctgtctcccc tatctgggaa cctcctccag ccacaacatc aacaactcca   1320

gttctatcct cccaaccccc aactttactg ttacccctac ag                      1362
```

<210> SEQ ID NO 149
<211> LENGTH: 597
<212> TYPE: DNA
<213> ORGANISM: Homo sapiens
<220> FEATURE:
<223> OTHER INFORMATION: ICOS, isoform 1

<400> SEQUENCE: 149
atgaagtcag gcctctggta tttctttctc ttctgcttgc gcattaaagt tttaacagga 60
gaaatcaatg gttctgccaa ttatgagatg tttatatttc acaacggagg tgtacaaatt 120
ttatgcaaat atcctgacat tgtccagcaa tttaaaatgc agttgctgaa agggggggcaa 180 atactctgcg atctcactaa gacaaaagga agtggaaaca cagtgtccat taagagtctg 240
aaattctgcc attctcagtt atccaacaac agtgtctctt tttttctata caacttggac 300
cattctcatg ccaactatta cttctgcaac ctatcaattt ttgatcctcc tccttttaaa 360
gtaactctta caggaggata tttgcatatt tatgaatcac aactttgttg ccagctgaag 420
ttctggttac ccataggatg tgcagccttt gttgtagtct gcattttggg atgcatactt 480
atttgttggc ttacaaaaaa gaagtattca tccagtgtgc acgaccctaa cggtgaatac 540
atgttcatga gagcagtgaa cacagccaaa aaatctagac tcacagatgt gaccta 597

<210> SEQ ID NO 150
<211> LENGTH: 906
<212> TYPE: DNA
<213> ORGANISM: Homo sapiens
<220> FEATURE:
<223> OTHER INFORMATION: ICOS ligand, isoform 1

<400> SEQUENCE: 150
atgcggctgg gcagtcctgg actgctcttc ctgctcttca gcagccttcg agctgatact 60
caggagaagg aagtcagagc gatggtaggc agcgacgtgg agctcagctg cgcttgccct 120
gaaggaagcc gttttgattt aaatgatgtt tacgtatatt ggcaaaccag tgagtcgaaa 180
accgtggtga cctaccacat cccacagaac agctccttgg aaaacgtgga cagccgctac 240
cggaaccgag ccctgatgtc accggccggc atgctgcggg gcgacttctc cctgcgcttg 300
ttcaacgtca ccccccagga cgagcagaag tttcactgcc tggtgttgag ccaatccctg 360
ggattccagg aggttttgag cgttgaggtt acactgcatg tggcagcaaa cttcagcgtg 420
cccgtcgtca gcgcccccca cagcccctcc caggatgagc tcaccttcac gtgtacatcc 480
ataaacggct accccaggcc caacgtgtac tggatcaata agacggacaa cagcctgctg 540
gaccaggctc tgcagaatga caccgtcttc ttgaacatgc ggggcttgta tgacgtggtc 600
agcgtgctga ggatcgcacg gacccccagc gtgaacattg gctgctgcat agagaacgtg 660
cttctgcagc agaacctgac tgtcggcagc cagacaggaa atgacatcgg agagagagac 720
aagatcacag agaatccagt cagtaccggc gagaaaaacg cggccacgtg gagcatcctg 780
gctgtcctgt gcctgcttgt ggtcgtggcg gtggccatag gctgggtgtg cagggaccga 840
tgcctccaac acagctatgc aggtgcctgg gctgtgagtc cggagacaga gctcactggc 900
cacgtt 906

<210> SEQ ID NO 151
<211> LENGTH: 1344
<212> TYPE: DNA
<213> ORGANISM: Homo sapiens
<220> FEATURE:

-continued

<223> OTHER INFORMATION: gp49B/LILRB4, isoform 1

<400> SEQUENCE: 151
atgatcccca ccttcacggc tctgctctgc ctcgggctga gtctgggccc caggacccac 60
atgcaggcag ggcccctccc caaacccacc ctctgggctg agccaggctc tgtgatcagc 120
tgggggaact ctgtgaccat ctggtgtcag gggaccctgg aggctcggga gtaccgtctg 180
gataaagagg aaagcccagc accctgggac agacagaacc cactggagcc caagaacaag 240
gccagattct ccatcccatc catgacagag gactatgcag ggagataccg ctgttactat 300
cgcagccctg taggctggtc acagcccagt gacccccctgg agctggtgat gacaggagcc 360
tacagtaaac ccaccctttc agccctgccg agtcctcttg tgacctcagg aaagagcgtg 420
accctgctgt gtcagtcacg gagcccaatg gacacttttc ttctgatcaa ggagcgggca 480
gcccatcccc tactgcatct gagatcagag cacggagctc agcagcacca ggctgaattc 540
cccatgagtc ctgtgacctc agtgcacggg gggacctaca ggtgcttcag ctcacacggc 600
ttctcccact acctgctgtc acaccccagt gacccccctgg agctcatagt ctcaggatcc 660
ttggagggtc ccaggccctc acccacaagg tccgtctcaa cagctgcagg ccctgaggac 720
cagcccctca tgcctacagg gtcagtcccc cacagtggtc tgagaaggca ctgggaggta 780
ctgatcgggg tcttggtggt ctccatcctg cttctctccc tcctcctctt cctcctcctc 840
caacactggc gtcagggaaa acacaggaca ttggcccaga gacaggctga tttccaacgt 900
cctccagggg ctgccgagcc agagcccaag gacgggggcc tacagaggag gtccagccca 960
gctgctgacg tccagggaga aaacttctgt gctgccgtga agaacacaca gcctgaggac 1020
ggggtggaaa tggacactcg gcagagccca cacgatgaag acccccaggc agtgacgtat 1080
gccaaggtga aacactccag acctaggaga gaaatggcct ctcctccctc cccactgtct 1140
ggggaattcc tggacacaaa ggacagacag gcagaagagg acagacagat ggacactgag 1200
gctgctgcat ctgaagcccc ccaggatgtg acctacgccc ggctgcacag ctttaccctc 1260
agacagaagg caactgagcc tcctccatcc caggaagggg cctctccagc tgagcccagt 1320
gtctatgcca ctctggccat ccac 1344

<210> SEQ ID NO 152
<211> LENGTH: 1896
<212> TYPE: DNA
<213> ORGANISM: Homo sapiens
<220> FEATURE:
<223> OTHER INFORMATION: PIR-B/LILRB3, isoform 1

<400> SEQUENCE: 152
atgacgcccg ccctcacagc cctgctctgc cttgggctga gtctgggccc caggacccgc 60
atgcaggcag ggcccttccc caaacccacc ctctgggctg agccaggctc tgtgatcagc 120
tgggggagcc ccgtgaccat ctggtgtcag gggagcctgg aggcccagga gtaccaactg 180
gataaagagg gaagcccaga gccctgggac agaaataacc cactggaacc caagaacaag 240
gccagattct ccatcccatc catgacacag caccatgcag ggagataccg ctgccactat 300
tacagctctg caggctggtc agagcccagc gacccccctgg agctggtgat gacaggattc 360
tacaacaaac ccaccctctc agccctgccc agccctgtgg tggcctcagg ggggaatatg 420
accctccgat gtggctcaca gaagggatat caccattttg ttctgatgaa ggaaggagaa 480
caccagctcc cccggaccct ggactcacag cagctccaca gtggggggtt ccaggccctg 540
ttccctgtgg gccccgtgac ccccagccac aggtggaggt tcacatgcta ttactattat 600
acaaacaccc cctgggtgtg gtcccacccc agtgaccccc tggagattct gccctcaggc 660
gtgtctagga agccctccct cctgaccctg cagggccctg tcctggcccc tgggcagagc 720
ctgaccctcc agtgtggctc tgatgtcggc tacgacagat ttgttctgta taaggagggg 780
gaacgtgact tcctccagcg ccctggccag cagccccagg ctgggctctc ccaggccaac 840
ttcaccctgg gccctgtgag ccgctcctac gggggccagt acaggtgcta tggtgcacac 900
aacctctcct ccgagtggtc ggcccccagt gacccccctgg acatcctgat cacaggacag 960
atctatgaca ccgtctccct gtcagcacag ccgggcccca cagtggcctc aggagagaac 1020
atgaccctgc tgtgtcagtc acgggggtat tttgacactt tccttctgac caaagaaggg 1080
gcagcccatc ccccactgcg tctgagatca atgtacggag ctcataagta ccaggctgaa 1140
ttccccatga gtcctgtgac ctcagcccac gcggggacct acaggtgcta cggctcacgc 1200
agctccaacc cccacctgct gtctttcccc agtgagcccc tggaactcat ggtctcagga 1260
cactctggag gctccagcct cccacccaca gggccgccct ccacacctgg tctgggaaga 1320
tacctggagg ttttgattgg ggtctcggtg gccttcgtcc tgctgctctt cctcctcctc 1380
ttcctcctcc tcctccgtca gcgtcacagc aaacacagga catctgacca gagaaagact 1440
gatttccagc gtcctgcagg ggctgcggag acagagccca aggacagggg cctgctgagg 1500
aggtccagcc cagctgctga cgtccaggaa gaaaacctct atgctgctgt gaaggacaca 1560
cagtctgagg acagggtgga gctggacagt cagcagagcc cacacgatga agacccccag 1620
gcagtgacgt atgccccggt gaaacactcc agtcctagga gagaaatggc ctctcctccc 1680
tcctcactgt ctggggaatt cctggacaca aaggacagac aggtggaaga ggacaggcag 1740
atggacactg aggctgctgc atctgaagcc tcccaggatg tgacctacgc ccagctgcac 1800
agcttgaccc ttagacggaa ggcaactgag cctcctccat cccaggaagg ggaacctcca 1860
gctgagccca gcatctacgc cactctggcc atccac 1896

<210> SEQ ID NO 153
<211> LENGTH: 1014
<212> TYPE: DNA
<213> ORGANISM: Homo sapiens
<220> FEATURE:
<223> OTHER INFORMATION: HLA-G alpha chain

<400> SEQUENCE: 153
atggtggtca tggcgccccg aaccctcttc ctgctgctct cgggggccct gaccctgacc 60
gagacctggg cgggctccca ctccatgagg tatttcagcg ccgccgtgtc ccggcccggc 120
cgcggggagc cccgcttcat cgccatgggc tacgtggacg acacgcagtt cgtgcggttc 180
gacagcgact cggcgtgtcc gaggatggag ccgcgggcgc cgtgggtgga gcaggagggg 240
ccggagtatt gggaagagga gacacggaac accaaggccc acgcacagac tgacagaatg 300
aacctgcaga ccctgcgcgg ctactacaac cagagcgagg ccagttctca caccctccag 360
tggatgattg gctgcgacct ggggtccgac ggacgcctcc tccgcgggta tgaacagtat 420
gcctacgatg gcaaggatta cctcgccctg aacgaggacc tgcgctcctg gaccgcagcg 480
gacactgcgg ctcagatctc caagcgcaag tgtgaggcgg ccaatgtggc tgaacaaagg 540
agagcctacc tggagggcac gtgcgtggag tggctccaca gatacctgga gaacgggaag 600
gagatgctgc agcgcgcgga cccccccaag acacacgtga cccaccaccc tgtctttgac 660
tatgaggcca ccctgaggtg ctgggccctg ggcttctacc ctgcggagat catactgacc 720

-continued

```
tggcagcggg atggggagga ccagacccag gacgtggagc tcgtggagac caggcctgca    780

ggggatggaa ccttccagaa gtgggcagct gtggtggtgc cttctggaga ggagcagaga    840

tacacgtgcc atgtgcagca tgaggggctg ccggagcccc tcatgctgag atggaagcag    900

tcttccctgc ccaccatccc catcatgggt atcgttgctg gcctggttgt ccttgcagct    960

gtagtcactg gagctgcggt cgctgctgtg ctgtggagaa agaagagctc agat         1014
```

<210> SEQ ID NO 154
<211> LENGTH: 1092
<212> TYPE: DNA
<213> ORGANISM: Homo sapiens
<220> FEATURE:
<223> OTHER INFORMATION: TIM1/HAVCR1

<400> SEQUENCE: 154

```
atgcatcctc aagtggtcat cttaagcctc atcctacatc tggcagattc tgtagctggt     60

tctgtaaagg ttggtggaga ggcaggtcca tctgtcacac taccctgcca ctacagtgga    120

gctgtcacat ccatgtgctg gaatagaggc tcatgttctc tattcacatg ccaaaatggc    180

attgtctgga ccaatggaac ccacgtcacc tatcggaagg acacacgcta taagctattg    240

ggggaccttt caagaaggga tgtctctttg accatagaaa atacagctgt gtctgacagt    300

ggcgtatatt gttgccgtgt tgagcaccgt gggtggttca atgacatgaa aatcaccgta    360

tcattggaga ttgtgccacc caaggtcacg actactccaa ttgtcacaac tgttccaacc    420

gtcacgactg ttcgaacgag caccactgtt ccaacgacaa cgactgttcc aatgacgact    480

gttccaacga caactgttcc aacaacaatg agcattccaa cgacaacgac tgttctgacg    540

acaatgactg tttcaacgac aacgagcgtt ccaacgacaa cgagcattcc aacaacaaca    600

agtgttccag tgacaacaac tgtctctacc tttgttcctc caatgccttt gcccaggcag    660

aaccatgaac cagtagccac ttcaccatct tcacctcagc cagcagaaac ccaccctacg    720

acactgcagg gagcaataag gagagaaccc accagctcac cattgtactc ttacacaaca    780

gatgggaatg acaccgtgac agagtcttca gatggccttt ggaataacaa tcaaactcaa    840

ctgttcctag aacatagtct actgacggcc aataccacta aaggaatcta tgctggagtc    900

tgtatttctg tcttggtgct tcttgctctt ttgggtgtca tcattgccaa aaagtatttc    960

ttcaaaaagg aggttcaaca actaagtgtt tcatttagca gccttcaaat taaagctttg   1020

caaaatgcag ttgaaaagga agtccaagca gaagacaata tctacattga gaatagtctt   1080

tatgccacgg ac                                                       1092
```

<210> SEQ ID NO 155
<211> LENGTH: 1134
<212> TYPE: DNA
<213> ORGANISM: Homo sapiens
<220> FEATURE:
<223> OTHER INFORMATION: TIM4/TIMD4, isoform 1

<400> SEQUENCE: 155

```
atgtccaaag aacctctcat tctctggctg atgattgagt tttggtggct ttacctgaca     60

ccagtcactt cagagactgt tgtgacggag gttttgggtc accgggtgac tttgccctgt    120

ctgtactcat cctggtctca caacagcaac agcatgtgct gggggaaaga ccagtgcccc    180

tactccggtt gcaaggaggc gctcatccgc actgatggaa tgagggtgac ctcaagaaag    240

tcagcaaaat atagacttca ggggactatc ccgagaggtg atgtctcctt gaccatctta    300

aaccccagtg aaagtgacag cggtgtgtac tgctgccgca tagaagtgcc tggctggttc    360
```

aacgatgtaa agataaacgt gcgcctgaat ctacagagag cctcaacaac cacgcacaga 420
acagcaacca ccaccacacg cagaacaaca acaacaagcc ccaccaccac ccgacaaatg 480
acaacaaccc cagctgcact tccaacaaca gtcgtgacca cacccgatct cacaaccgga 540
acaccactcc agatgacaac cattgccgtc ttcacaacag caaacacgtg cctttcacta 600
accccaagca cccttccgga ggaagccaca ggtcttctga ctcccgagcc ttctaaggaa 660
gggcccatcc tcactgcaga atcagaaact gtcctcccca gtgattcctg gagtagtgtt 720
gagtctactt ctgctgacac tgtcctgctg acatccaaag agtccaaagt ttgggatctc 780
ccatcaacat cccacgtgtc aatgtggaaa acgagtgatt ctgtgtcttc tcctcagcct 840
ggagcatctg atacagcagt tcctgagcag aacaaaaacaa caaaaaacagg acagatggat 900 ggaataccca tgtcaatgaa gaatgaaatg cccatctccc aactactgat gatcatcgcc 960
ccctccttgg gatttgtgct cttcgcattg tttgtggcgt ttctcctgag agggaaactc 1020
atggaaacct attgttcgca gaaacacaca aggctagact acattggaga tagtaaaaat 1080
gtcctcaatg acgtgcagca tggaagggaa gacgaagacg gccttttttac cctc 1134

<210> SEQ ID NO 156
<211> LENGTH: 831
<212> TYPE: DNA
<213> ORGANISM: Homo sapiens
<220> FEATURE:
<223> OTHER INFORMATION: OX-40/CD134/TNFRSF4

<400> SEQUENCE: 156
atgtgcgtgg gggctcggcg gctgggccgc gggccgtgtg cggctctgct cctcctgggc 60
ctggggctga gcaccgtgac ggggctccac tgtgtcgggg acacctaccc cagcaacgac 120
cggtgctgcc acgagtgcag gccaggcaac gggatggtga gccgctgcag ccgctcccag 180
aacacggtgt gccgtccgtg cgggccgggc ttctacaacg acgtggtcag ctccaagccg 240
tgcaagccct gcacgtggtg taacctcaga agtgggagtg agcggaagca gctgtgcacg 300
gccacacagg acacagtctg ccgctgccgg gcgggcaccc agcccctgga cagctacaag 360
cctggagttg actgtgcccc ctgccctcca gggcacttct ccccaggcga caaccaggcc 420
tgcaagccct ggaccaactg caccttggct gggaagcaca ccctgcagcc ggccagcaat 480
agctcggacg caatctgtga ggacagggac cccccagcca cgcagcccca ggagacccag 540 ggcccccgg ccaggcccat cactgtccag cccactgaag cctggcccag aacctcacag 600
ggaccctcca cccggcccgt ggaggtcccc gggggccgtg cggttgccgc catcctgggc 660
ctgggcctgg tgctggggct gctgggcccc ctggccatcc tgctggccct gtacctgctc 720
cggagggacc agaggctgcc ccccgatgcc cacaagcccc ctgggggagg cagtttccgg 780
acccccatcc aagaggagca ggccgacgcc cactccaccc tggccaagat c 831

<210> SEQ ID NO 157
<211> LENGTH: 549
<212> TYPE: DNA
<213> ORGANISM: Homo sapiens
<220> FEATURE:
<223> OTHER INFORMATION: OX-40L/CD252/TNFSF4, isoform 1

<400> SEQUENCE: 157
atggaaaggg tccaacccct ggaagagaat gtgggaaatg cagccaggcc aagattcgag 60
aggaacaagc tattgctggt ggcctctgta attcagggac tggggctgct cctgtgcttc 120

```
acctacatct gcctgcactt ctctgctctt caggtatcac atcggtatcc tcgaattcaa    180

agtatcaaag tacaatttac cgaatataag aaggagaaag gtttcatcct cacttcccaa    240

aaggaggatg aaatcatgaa ggtgcagaac aactcagtca tcatcaactg tgatgggttt    300

tatctcatct ccctgaaggg ctacttctcc caggaagtca acattagcct tcattaccag    360

aaggatgagg agcccctctt ccaactgaag aaggtcaggt ctgtcaactc cttgatggtg    420

gcctctctga cttacaaaga caaagtctac ttgaatgtga ccactgacaa tacctccctg    480

gatgacttcc atgtgaatgg cggagaactg attcttatcc atcaaaatcc tggtgaattc    540

tgtgtcctt                                                            549


<210> SEQ ID NO 158
<211> LENGTH: 1950
<212> TYPE: DNA
<213> ORGANISM: Homo sapiens
<220> FEATURE:
<223> OTHER INFORMATION: ILT-2/LILRB1, isoform 1

<400> SEQUENCE: 158

atgaccccca tcctcacggt cctgatctgt ctcgggctga gtctgggccc ccggacccac     60

gtgcaggcag ggcacctccc caagcccacc ctctgggctg aaccaggctc tgtgatcacc    120

caggggagtc ctgtgaccct caggtgtcag gggggccagg agacccagga gtaccgtcta    180

tatagagaaa agaaaacagc accctggatt acacggatcc cacaggagct tgtgaagaag    240

ggccagttcc ccatcccatc catcacctgg gaacacacag ggcggtatcg ctgttactat    300

ggtagcgaca ctgcaggccg ctcagagagc agtgaccccc tggagctggt ggtgacagga    360

gcctacatca aacccaccct ctcagcccag cccagccccg tggtgaactc aggagggaat    420

gtaaccctcc agtgtgactc acaggtggca tttgatggct tcattctgtg taaggaagga    480

gaagatgaac acccacaatg cctgaactcc cagccccatg cccgtgggtc gtcccgcgcc    540

atcttctccg tgggccccgt gagcccgagt cgcaggtggt ggtacaggtg ctatgcttat    600

gactcgaact ctccctatga gtggtctcta cccagtgatc tcctggagct cctggtccta    660

ggtgtttcta agaagccatc actctcagtg cagccaggtc ctatcgtggc ccctgaggag    720

accctgactc tgcagtgtgg ctctgatgct ggctacaaca gatttgttct gtataaggac    780

ggggaacgtg acttccttca gctcgctggc gcacagcccc aggctgggct ctcccaggcc    840

aacttcaccc tgggccctgt gagccgctcc tacgggggcc agtacagatg ctacggtgca    900

cacaacctct cctccgagtg gtcggccccc agcgaccccc tggacatcct gatcgcagga    960

cagttctatg acagagtctc cctctcggtg cagccgggcc ccacggtggc ctcaggagag   1020

aacgtgaccc tgctgtgtca gtcacaggga tggatgcaaa ctttccttct gaccaaggag   1080

ggggcagctg atgacccatg gcgtctaaga tcaacgtacc aatctcaaaa ataccaggct   1140

gaattcccca tgggtcctgt gacctcagcc catgcgggga cctacaggtg ctacggctca   1200

cagagctcca aaccctacct gctgactcac cccagtgacc ccctggagct cgtggtctca   1260

ggaccgtctg gggccccag ctccccgaca acaggcccca cctccacatc tggccctgag    1320

gaccagcccc tcacccccac cgggtcggat ccccagagtg gtctgggaag gcacctgggg   1380

gttgtgatcg gcatcttggt ggccgtcatc ctactgctcc tcctcctcct cctcctcttc   1440

ctcatcctcc gacatcgacg tcagggcaaa cactggacat cgacccagag aaaggctgat   1500

ttccaacatc ctgcaggggc tgtggggcca gagcccacag acagaggcct gcagtggagg   1560

tccagcccag ctgccgatgc ccaggaagaa aacctctatg ctgccgtgaa gcacacacag   1620
```

```
cctgaggatg gggtggagat ggacactcgg agcccacacg atgaagaccc ccaggcagtg   1680

acgtatgccg aggtgaaaca ctccagacct aggagagaaa tggcctctcc tccttcccca   1740

ctgtctgggg aattcctgga cacaaaggac agacaggcgg aagaggacag gcagatggac   1800

actgaggctg ctgcatctga agccccccag gatgtgacct acgcccagct gcacagcttg   1860

accctcagac gggaggcaac tgagcctcct ccatcccagg aagggccctc tccagctgtg   1920

cccagcatct acgccactct ggccatccac                                    1950
```

<210> SEQ ID NO 159
<211> LENGTH: 1794
<212> TYPE: DNA
<213> ORGANISM: Homo sapiens
<220> FEATURE:
<223> OTHER INFORMATION: ILT-4/LILRB2, isoform 1

<400> SEQUENCE: 159

```
atgaccccca tcgtcacagt cctgatctgt ctcgggctga gtctgggccc caggacccgc     60

gtgcagacag ggaccatccc caagcccacc ctgtgggctg agccagactc tgtgatcacc    120

caggggagtc ccgtcaccct cagttgtcag ggggagccttg aagcccagga gtaccgtcta    180

tatagggaga aaaaatcagc atcttggatt acacggatac gaccagagct tgtgaagaac    240

ggccagttcc acatcccatc catcacctgg gaacacacag ggcgatatgg ctgtcagtat    300

tacagccgcg ctcggtggtc tgagctcagt gaccccctgg tgctggtgat gacaggagcc    360

tacccaaaac ccaccctctc agcccagccc agccctgtgg tgacctcagg aggaagggtg    420

accctccagt gtgagtcaca ggtggcattt ggcggcttca ttctgtgtaa ggaaggagaa    480

gatgaacacc cacaatgcct gaactcccag ccccatgccc gtgggtcgtc ccgcgccatc    540

ttctccgtgg gccccgtgag cccgaatcgc aggtggtcgc acaggtgcta tggttatgac    600

ttgaactctc cctatgtgtg gtcttcaccc agtgatctcc tggagctcct ggtcccaggt    660

gtttctaaga agccatcact ctcagtgcag ccgggtcctg tcatggcccc tggggaaagc    720

ctgaccctcc agtgtgtctc tgatgtcggc tatgacagat ttgttctgta caaggagggg    780

gaacgtgacc ttcgccagct ccctggccgg cagccccagg ctgggctctc ccaggccaac    840

ttcaccctgg gccctgtgag ccgctcctac gggggccagt acagatgcta cggtgcacac    900

aacctctcct ctgagtgctc ggcccccagc gacccccctgg acatcctgat cacaggacag    960

atccgtggca caccctcat ctcagtgcag ccaggcccca cagtggcctc aggagagaac   1020

gtgaccctgc tgtgtcagtc atggcggcag ttccacactt tccttctgac caaggcggga   1080

gcagctgatg ccccactccg tctaagatca atacacgaat atcctaagta ccaggctgaa   1140

ttccccatga gtcctgtgac ctcagcccac gcggggacct acaggtgcta cggctcactc   1200

aactccgacc cctacctgct gtctcacccc agtgagcccc tggagctcgt ggtctcagga   1260

ccctccatgg gttccagccc cccacccacc ggtcccatct ccacacctgc aggccctgag   1320

gaccagcccc tcacccccac tgggtcggat ccccaaagtg gtctgggaag gcacctgggg   1380

gttgtgatcg gcatcttggt ggccgtcgtc ctactgctcc tcctcctcct cctcctcttc   1440

ctcatcctcc gacatcgacg tcagggcaaa cactggacat cgacccagag aaaggctgat   1500

ttccaacatc ctgcaggggc tgtggggcca gagcccacag acagaggcct gcagtggagg   1560

tccagcccag ctgccgacgc ccaggaagaa aacctctatg ctgccgtgaa ggacacacag   1620

cctgaagatg gggtggagat ggacactcgg gctgctgcat ctgaagcccc ccaggatgtg   1680
```

acctacgccc agctgcacag cttgaccctc agacggaagg caactgagcc tcctccatcc 1740
caggaaaggg aacctccagc tgagcccagc atctacgcca ccctggccat ccac 1794

<210> SEQ ID NO 160
<211> LENGTH: 717
<212> TYPE: DNA
<213> ORGANISM: Homo sapiens
<220> FEATURE:
<223> OTHER INFORMATION: BCL-2 isoform alpha

<400> SEQUENCE: 160
atggcgcacg ctgggagaac agggtacgat aaccgggaga tagtgatgaa gtacatccat 60
tataagctgt cgcagagggg ctacgagtgg gatgcgggag atgtgggcgc cgcgcccccg 120
ggggccgccc ccgcaccggg catcttctcc tcccagcccg ggcacacgcc ccatccagcc 180
gcatcccggg acccggtcgc caggacctcg ccgctgcaga ccccggctgc ccccggcgcc 240
gccgcggggc ctgcgctcag cccggtgcca cctgtggtcc acctgaccct ccgccaggcc 300
ggcgacgact tctcccgccg ctaccgccgc gacttcgccg agatgtccag ccagctgcac 360
ctgacgccct tcaccgcgcg gggacgcttt gccacggtgg tggaggagct cttcagggac 420
ggggtgaact gggggaggat tgtggccttc tttgagttcg gtggggtcat gtgtgtggag 480
agcgtcaacc gggagatgtc gcccctggtg gacaacatcg ccctgtggat gactgagtac 540
ctgaaccggc acctgcacac ctggatccag gataacggag gctgggatgc ctttgtggaa 600
ctgtacggcc ccagcatgcg gcctctgttt gatttctcct ggctgtctct gaagactctg 660
ctcagtttgg ccctggtggg agcttgcatc accctgggtg cctatctggg ccacaag 717

<210> SEQ ID NO 161
<211> LENGTH: 4050
<212> TYPE: DNA
<213> ORGANISM: Homo sapiens
<220> FEATURE:
<223> OTHER INFORMATION: MDR1/ABCB1, isoform 1

<400> SEQUENCE: 161
atgagtgtca acttgcaagg ggaccagaga ggtgcaacgg aagccagaac attcctcctg 60
gaaattcaac ctgtttcgca gtttctcgag gaatcagcat tcagtcaatc cgggccggga 120
gcagtcatct gtggtctttc cactaaagtc ggagtatctt cttccaaaat ttcacgtctt 180
ggtggccgtt ccaaggagcg cgaggtcgga atggatcttg aaggggaccg caatggagga 240
gcaaagaaga agaacttttt taaactgaac aataaaagtg aaaaagataa gaaggaaaag 300
aaaccaactg tcagtgtatt ttcaatgttt cgctattcaa attggcttga caagttgtat 360
atggtggtgg gaactttggc tgccatcatc catggggctg gacttcctct catgatgctg 420
gtgtttggag aaatgacaga tatctttgca aatgcaggaa atttagaaga tctgatgtca 480
aacatcacta atagaagtga tatcaatgat acagggttct tcatgaatct ggaggaagac 540
atgaccaggt atgcctatta ttacagtgga attggtgctg ggtgctggt tgctgcttac 600 attcaggttt cattttggtg cctggcagct ggaagacaaa tacacaaaat tagaaaacag 660
ttttttcatg ctataatgcg acaggagata ggctggtttg atgtgcacga tgttggggag 720
cttaacaccc gacttacaga tgatgtctcc aagattaatg aaggaattgg tgacaaaatt 780
ggaatgttct ttcagtcaat ggcaacattt ttcactgggt ttatagtagg atttacacgt 840
ggttggaagc taacccttgt gattttggcc atcagtcctg ttcttggact gtcagctgct 900
gtctgggcaa agatactatc ttcatttact gataaagaac tcttagcgta tgcaaaagct 960

-continued

```
ggagcagtag ctgaagaggt cttggcagca attagaactg tgattgcatt tggaggacaa   1020
aagaaagaac ttgaaaggta caacaaaaat ttagaagaag ctaaaagaat tgggataaag   1080
aaagctatta cagccaatat ttctataggt gctgctttcc tgctgatcta tgcatcttat   1140
gctctggcct tctggtatgg gaccaccttg gtcctctcag ggaatattc tattggacaa    1200
gtactcactg tattcttttc tgtattaatt ggggctttta gtgttggaca ggcatctcca   1260
agcattgaag catttgcaaa tgcaagagga gcagcttatg aaatcttcaa gataattgat   1320
aataagccaa gtattgacag ctattcgaag agtgggcaca aaccagataa tattaaggga   1380
aatttggaat tcagaaatgt tcacttcagt tacccatctc gaaaagaagt taagatcttg   1440
aagggtctga acctgaaggt gcagagtggg cagacggtgg ccctggttgg aaacagtggc   1500
tgtgggaaga gcacaacagt ccagctgatg cagaggctct atgaccccac agaggggatg   1560
gtcagtgttg atggacagga tattaggacc ataaatgtaa ggtttctacg ggaaatcatt   1620
ggtgtggtga gtcaggaacc tgtattgttt gccaccacga tagctgaaaa cattcgctat   1680
ggccgtgaaa atgtcaccat ggatgagatt gagaaagctg tcaaggaagc caatgcctat   1740
gactttatca tgaaactgcc tcataaattt gacaccctgg ttggagagag aggggcccag   1800
ttgagtggtg ggcagaagca gaggatcgcc attgcacgtg ccctggttcg caacccccaag  1860
atcctcctgc tggatgaggc cacgtcagcc ttggacacag aaagcgaagc agtggttcag   1920
gtggctctgg ataaggccag aaaaggtcgg accaccattg tgatagctca tcgtttgtct   1980
acagttcgta atgctgacgt catcgctggt ttcgatgatg gagtcattgt ggagaaagga   2040
aatcatgatg aactcatgaa agagaaaggc atttacttca aacttgtcac aatgcagaca   2100
gcaggaaatg aagttgaatt agaaaatgca gctgatgaat ccaaaagtga aattgatgcc   2160
ttggaaatgt cttcaaatga ttcaagatcc agtctaataa gaaaaagatc aactcgtagg   2220
agtgtccgtg gatcacaagc ccaagacaga aagcttagta ccaaagaggc tctggatgaa   2280
agtataccto cagtttcctt ttggaggatt atgaagctaa atttaactga atggccttat   2340
tttgttgttg gtgtattttg tgccattata aatggaggcc tgcaaccagc atttgcaata   2400
atattttcaa agattatagg ggtttttaca agaattgatg atcctgaaac aaaacgacag   2460
aatagtaact tgttttcact attgtttcta gcccttggaa ttatttcttt tattacattt   2520
ttccttcagg gtttcacatt tggcaaagct ggagagatcc tcaccaagcg gctccgatac   2580
atggttttcc gatccatgct cagacaggat gtgagttggt ttgatgaccc taaaaacacc   2640
actggagcat tgactaccag gctcgccaat gatgctgctc aagttaaagg ggctataggt   2700
tccaggcttg ctgtaattac ccagaatata gcaaatcttg ggacaggaat aattatatcc   2760
ttcatctatg gttggcaact aacactgtta ctcttagcaa ttgtacccat cattgcaata   2820
gcaggagttg ttgaaatgaa aatgttgtct ggacaagcac tgaaagataa gaaagaacta   2880
gaaggttctg ggaagatcgc tactgaagca atagaaaact tccgaaccgt tgtttctttg   2940
actcaggagc agaagtttga acatatgtat gctcagagtt tgcaggtacc atacagaaac   3000
tctttgagga aagcacacat ctttggaatt acattttcct tcacccaggc aatgatgtat   3060
ttttcctatg ctggatgttt ccggtttgga gcctacttgg tggcacataa actcatgagc   3120
tttgaggatg ttctgttagt attttcagct gttgtctttg gtgccatggc cgtggggcaa   3180
gtcagttcat ttgctcctga ctatgccaaa gccaaaatat cagcagccca catcatcatg   3240
atcattgaaa aaaccccttt gattgacagc tacagcacgg aaggcctaat gccgaacaca   3300
```

-continued

```
ttggaaggaa atgtcacatt tggtgaagtt gtattcaact atcccacccg accggacatc   3360

ccagtgcttc agggactgag cctggaggtg aagaagggcc agacgctggc tctggtgggc   3420

agcagtggct gtgggaagag cacagtggtc cagctcctgg agcggttcta cgaccccttg   3480

gcagggaaag tgctgcttga tggcaaagaa ataaagcgac tgaatgttca gtggctccga   3540

gcacacctgg gcatcgtgtc ccaggagccc atcctgtttg actgcagcat tgctgagaac   3600

attgcctatg gagacaacag ccgggtggtg tcacaggaag agattgtgag ggcagcaaag   3660

gaggccaaca tacatgcctt catcgagtca ctgcctaata aatatagcac taaagtagga   3720

gacaaaggaa ctcagctctc tggtggccag aaacaacgca ttgccatagc tcgtgccctt   3780

gttagacagc ctcatatttt gcttttggat gaagccacgt cagctctgga tacagaaagt   3840

gaaaaggttg tccaagaagc cctggacaaa gccagagaag gccgcacctg cattgtgatt   3900

gctcaccgcc tgtccaccat ccagaatgca gacttaatag tggtgtttca gaatggcaga   3960

gtcaaggagc atggcacgca tcagcagctg ctggcacaga aaggcatcta tttttcaatg   4020

gtcagtgtcc aggctggaac aaagcgccag                                    4050
```

<210> SEQ ID NO 162
<211> LENGTH: 990
<212> TYPE: DNA
<213> ORGANISM: Homo sapiens
<220> FEATURE:
<223> OTHER INFORMATION: Arginase1, isoform 1

<400> SEQUENCE: 162

```
atgagcgcca agtccagaac catagggatt attggagctc ctttctcaaa gggacagcca     60

cgaggagggg tggaagaagg ccctacagta ttgagaaagg ctggtctgct tgagaaactt    120

aaagaacaag taactcaaaa ctttttaatt ttagagtgtg atgtgaagga ttatggggac    180

ctgccctttg ctgacatccc taatgacagt ccctttcaaa ttgtgaagaa tccaaggtct    240

gtgggaaaag caagcgagca gctggctggc aaggtggcag aagtcaagaa gaacggaaga    300

atcagcctgg tgctgggcgg agaccacagt ttggcaattg gaagcatctc tggccatgcc    360

agggtccacc ctgatcttgg agtcatctgg gtggatgctc acactgatat caacactcca    420

ctgacaacca caagtggaaa cttgcatgga caacctgtat ctttcctcct gaaggaacta    480

aaaggaaaga ttcccgatgt gccaggattc tcctgggtga ctccctgtat atctgccaag    540

gatattgtgt atattggctt gagagacgtg gaccctgggg aacactacat tttgaaaact    600

ctaggcatta aatacttttc aatgactgaa gtggacagac taggaattgg caaggtgatg    660

gaagaaacac tcagctatct actaggaaga aagaaaaggc caattcatct aagttttgat    720

gttgacggac tggacccatc tttcacacca gctactggca caccagtcgt gggaggtctg    780

acatacagag aaggtctcta catcacagaa gaaatctaca aaacagggct actctcagga    840

ttagatataa tggaagtgaa cccatccctg ggaagacac cagaagaagt aactcgaaca    900

gtgaacacag cagttgcaat aaccttggct tgtttcggac ttgctcggga gggtaatcac    960

aagcctattg actaccttaa cccacctaag                                     990
```

<210> SEQ ID NO 163
<211> LENGTH: 3459
<212> TYPE: DNA
<213> ORGANISM: Homo sapiens
<220> FEATURE:
<223> OTHER INFORMATION: nitric oxide synthase, inducible (iNOS/NOS2),
      isoform 1

-continued

<400> SEQUENCE: 163

```
atggcctgtc cttggaaatt tctgttcaag accaaattcc accagtatgc aatgaatggg     60
gaaaaagaca tcaacaacaa tgtggagaaa gccccctgtg ccacctccag tccagtgaca    120
caggatgacc ttcagtatca caacctcagc aagcagcaga atgagtcccc gcagcccctc    180
gtggagacgg gaaagaagtc tccagaatct ctggtcaagc tggatgcaac cccattgtcc    240
tccccacggc atgtgaggat caaaaactgg ggcagcggga tgactttcca agacacactt    300
caccataagg ccaaagggat tttaacttgc aggtccaaat cttgcctggg gtccattatg    360
actcccaaaa gtttgaccag aggacccagg gacaagccta cccctccaga tgagcttcta    420
cctcaagcta tcgaatttgt caaccaatat tacggctcct tcaaagaggc aaaaatagag    480
gaacatctgg ccagggtgga agcggtaaca aaggagatag aaacaacagg aacctaccaa    540
ctgacgggag atgagctcat cttcgccacc aagcaggcct ggcgcaatgc cccacgctgc    600
attgggagga tccagtggtc caacctgcag gtcttcgatg cccgcagctg ttccactgcc    660
cgggaaatgt ttgaacacat ctgcagacac gtgcgttact ccaccaacaa tggcaacatc    720
aggtcggcca tcaccgtgtt cccccagcgg agtgatggca agcacgactt ccgggtgtgg    780
aatgctcagc tcatccgcta tgctggctac cagatgccag atggcagcat cagaggggac    840
cctgccaacg tggaattcac tcagctgtgc atcgacctgg gctggaagcc caagtacggc    900
cgcttcgatg tggtcccccct ggtcctgcag gccaatggcc gtgaccctga gctcttcgaa    960
atcccacctg accttgtgct tgaggtggcc atggaacatc ccaaatacga gtggtttcgg   1020
gaactggagc taaagtggta cgccctgcct gcagtggcca acatgctgct tgaggtgggc   1080
ggcctggagt tcccagggtg ccccttcaat ggctggtaca tgggcacaga gatcggagtc   1140
cgggacttct gtgacgtcca gcgctacaac atcctggagg aagtgggcag gagaatgggc   1200
ctggaaacgc acaagctggc ctcgctctgg aaagaccagg ctgtcgttga gatcaacatt   1260
gctgtgctcc atagtttcca gaagcagaat gtgaccatca tggaccacca ctcggctgca   1320
gaatccttca tgaagtacat gcagaatgaa taccggtccc gtgggggctg cccggcagac   1380
tggatttggc tggtccctcc catgtctggg agcatcaccc ccgtgtttca ccaggagatg   1440
ctgaactacg tcctgtcccc tttctactac tatcaggtag aggcctggaa aacccatgtc   1500
tggcaggacg agaagcggag acccaagaga agagagattc cattgaaagt cttggtcaaa   1560
gctgtgctct ttgcctgtat gctgatgcgc aagacaatgg cgtcccgagt cagagtcacc   1620
atcctctttg cgacagagac aggaaaatca gaggcgctgg cctgggacct gggggcctta   1680
ttcagctgtg ccttcaaccc caaggttgtc tgcatggata agtacaggct gagctgcctg   1740
gaggaggaac ggctgctgtt ggtggtgacc agtacgtttg gcaatggaga ctgccctggc   1800
aatggagaga aactgaagaa atcgctcttc atgctgaaag agctcaacaa caaattcagg   1860
tacgctgtgt ttggcctcgg ctccagcatg taccctcggt tctgcgcctt tgctcatgac   1920
attgatcaga agctgtccca cctgggggcc tctcagctca ccccgatggg agaaggggat   1980
gagctcagtg ggcaggagga cgccttccgc agctgggccg tgcaaacctt caaggcagcc   2040
tgtgagacgt ttgatgtccg aggcaaacag cacattcaga tccccaagct ctacacctcc   2100
aatgtgacct gggacccgca ccactacagg ctcgtgcagg actcacagcc tttggacctc   2160
agcaaagccc tcagcagcat gcatgccaag aacgtgttca ccatgaggct caaatctcgg   2220
cagaatctac aaagtccgac atccagccgt gccaccatcc tggtggaact ctcctgtgag   2280
gatggccaag gcctgaacta cctgccgggg gagcaccttg ggtttgccc aggcaaccag   2340
```

ccggccctgg tccaaggtat cctggagcga gtggtggatg gccccacacc ccaccagaca 2400
gtgcgcctgg aggccctgga tgagagtggc agctactggg tcagtgacaa gaggctgccc 2460
ccctgctcac tcagccaggc cctcacctac ttcctggaca tcaccacacc cccaacccag 2520
ctgctgctcc aaaagctggc ccaggtggcc acagaagagc ctgagagaca gaggctggag 2580
gccctgtgcc agccctcaga gtacagcaag tggaagttca ccaacagccc cacattcctg 2640
gaggtgctag aggagttccc gtccctgcgg gtgtctgctg gcttcctgct ttcccagctc 2700
cccattctga agcccaggtt ctactccatc agctcctccc gggatcacac gcccacagag 2760
atccacctga ctgtggccgt ggtcacctac cacacccgag atggccaggg tcccctgcac 2820
cacggcgtct gcagcacatg gctcaacagc ctgaagcccc aagacccagt gccctgcttt 2880
gtgcggaatg ccagcggctt ccacctcccc gaggatccct cccatccttg catcctcatc 2940
gggcctggca caggcatcgc gcccttccgc agtttctggc agcaacggct ccatgactcc 3000
cagcacaagg gagtgcgggg aggccgcatg accttggtgt ttgggtgccg ccgcccagat 3060
gaggaccaca tctaccagga ggagatgctg gagatggccc agaagggggt gctgcatgcg 3120
gtgcacacag cctattcccg cctgcctggc aagcccaagg tctatgttca ggacatcctg 3180
cggcagcagc tggccagcga ggtgctccgt gtgctccaca aggagccagg ccacctctat 3240
gtttgcgggg atgtgcgcat ggcccgggac gtggcccaca ccctgaagca gctggtggct 3300
gccaagctga aattgaatga ggagcaggtc gaggactatt tctttcagct caagagccag 3360
aagcgctatc acgaagatat ctttggtgct gtatttcctt acgaggcgaa gaaggacagg 3420
gtggcggtgc agcccagcag cctggagatg tcagcgctc 3459

<210> SEQ ID NO 164
<211> LENGTH: 3765
<212> TYPE: DNA
<213> ORGANISM: Homo sapiens
<220> FEATURE:
<223> OTHER INFORMATION: Her2

<400> SEQUENCE: 164
atggagctgg cggccttgtg ccgctggggg ctcctcctcg ccctcttgcc ccccggagcc 60
gcgagcaccc aagtgtgcac cggcacagac atgaagctgc ggctccctgc cagtcccgag 120
acccacctgg acatgctccg ccacctctac cagggctgcc aggtggtgca gggaaacctg 180
gaactcacct acctgcccac caatgccagc ctgtccttcc tgcaggatat ccaggaggtg 240
cagggctacg tgctcatcgc tcacaaccaa gtgaggcagg tcccactgca gaggctgcgg 300
attgtgcgag gcacccagct ctttgaggac aactatgccc tggccgtgct agacaatgga 360
gacccgctga acaataccac ccctgtcaca ggggcctccc caggaggcct gcgggagctg 420
cagcttcgaa gcctcacaga gatcttgaaa ggaggggtct tgatccagcg gaaccccccag 480 ctctgctacc aggacacgat tttgtggaag gacatcttcc acaagaacaa ccagctggct 540
ctcacactga tagacaccaa ccgctctcgg gcctgccacc cctgttctcc gatgtgtaag 600
ggctcccgct gctggggaga gagttctgag gattgtcaga gcctgacgcg cactgtctgt 660
gccggtggct gtgcccgctg caaggggcca ctgcccactg actgctgcca tgagcagtgt 720
gctgccggct gcacgggccc caagcactct gactgcctgg cctgcctcca cttcaaccac 780
agtggcatct gtgagctgca ctgcccagcc ctggtcacct acaacacaga cacgtttgag 840
tccatgccca atcccgaggg ccggtataca ttcggcgcca gctgtgtgac tgcctgtccc 900

-continued

```
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gcggagactg ctgcaggaaa cggagctggt ggagccgctg   2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca agagtcccaa ccatgtcaaa   2580
attacagact tcgggctggc tcggctgctg gacattgacg agacagagta ccatgcagat   2640
gggggcaagg tgcccatcaa gtggatggcg ctggagtcca ttctccgccg gcggttcacc   2700
caccagagtg atgtgtggag ttatggtgtg actgtgtggg agctgatgac ttttggggcc   2760
aaaccttacg atgggatccc agcccgggag atccctgacc tgctggaaaa gggggagcgg   2820
ctgccccagc cccccatctg caccattgat gtctacatga tcatggtcaa atgttggatg   2880
attgactctg aatgtcggcc aagattccgg gagttggtgt ctgaattctc ccgcatggcc   2940
agggaccccc agcgctttgt ggtcatccag aatgaggact tgggcccagc cagtcccttg   3000
gacagcacct tctaccgctc actgctggag gacgatgaca tgggggacct ggtggatgct   3060
gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300
```

ctccccacac atgaccccag ccctctacag cggtacagtg aggaccccac agtacccctg 3360
ccctctgaga ctgatggcta cgttgccccc ctgacctgca gcccccagcc tgaatatgtg 3420
aaccagccag atgttcggcc ccagcccccct tcgccccgag agggccctct gcctgctgcc 3480
cgacctgctg gtgccactct ggaaaggccc aagactctct ccccagggaa gaatggggtc 3540
gtcaaagacg tttttgcctt tgggggtgcc gtggagaacc ccgagtactt gacaccccag 3600
ggaggagctg cccctcagcc ccaccctcct cctgccttca gcccagcctt cgacaacctc 3660
tattactggg accaggaccc accagagcgg ggggctccac ccagcacctt caaagggaca 3720
cctacggcag agaacccaga gtacctgggt ctggacgtgc cagtg 3765

<210> SEQ ID NO 165
<211> LENGTH: 567
<212> TYPE: DNA
<213> ORGANISM: Homo sapiens
<220> FEATURE:
<223> OTHER INFORMATION: KRAS

<400> SEQUENCE: 165
atgactgaat ataaacttgt ggtagttgga gctggtggcg taggcaagag tgccttgacg 60
atacagctaa ttcagaatca ttttgtggac gaatatgatc caacaataga ggattcctac 120
aggaagcaag tagtaattga tggagaaacc tgtctcttgg atattctcga cacagcaggt 180
caagaggagt acagtgcaat gagggaccag tacatgagga ctggggaggg ctttctttgt 240
gtatttgcca taaataatac taaatcattt gaagatattc accattatag agaacaaatt 300
aaaagagtta aggactctga agatgtacct atggtcctag taggaaataa atgtgatttg 360
ccttctagaa cagtagacac aaaacaggct caggacttag caagaagtta tggaattcct 420
tttattgaaa catcagcaaa gacaagacag agagtggagg atgcttttta tacattggtg 480
agggagatcc gacaatacag attgaaaaaa atcagcaaag aagaaaagac tcctggctgt 540
gtgaaaatta aaaaatgcat tataatg 567

<210> SEQ ID NO 166
<211> LENGTH: 1809
<212> TYPE: DNA
<213> ORGANISM: Homo sapiens
<220> FEATURE:
<223> OTHER INFORMATION: PLK1

<400> SEQUENCE: 166
atgagtgctg cagtgactgc agggaagctg gcacgggcac cggccgaccc tgggaaagcc 60
ggggtccccg gagttgcagc tcccggagct ccggcggcgg ctccaccggc gaaagagatc 120
ccggaggtcc tagtggaccc acgcagccgg cggcgctatg tgcggggccg ctttttgggc 180
aagggcggct ttgccaagtg cttcgagatc tcggacgcgg acaccaagga ggtgttcgcg 240
ggcaagattg tgcctaagtc tctgctgctc aagccgcacc agagggagaa gatgtccatg 300
gaaatatcca ttcaccgcag cctcgcccac cagcacgtcg taggattcca cggctttttc 360
gaggacaacg acttcgtgtt cgtggtgttg gagctctgcc gccggaggtc tctcctggag 420
ctgcacaaga ggaggaaagc cctgactgag cctgaggccc gatactacct acggcaaatt 480
gtgcttggct gccagtacct gcaccgaaac cgagttattc atcgagacct caagctgggc 540
aaccttttcc tgaatgaaga tctggaggtg aaaatagggg attttggact ggcaaccaaa 600
gtcgaatatg acggggagag gaagaagacc ctgtgtggga ctcctaatta catagctccc 660

-continued

```
gaggtgctga gcaagaaagg gcacagtttc gaggtggatg tgtggtccat tgggtgtatc    720
atgtatacct tgttagtggg caaaccacct tttgagactt cttgcctaaa agagacctac    780
ctccggatca agaagaatga atacagtatt cccaagcaca tcaaccccgt ggccgcctcc    840
ctcatccaga agatgcttca gacagatccc actgcccgcc caaccattaa cgagctgctt    900
aatgacgagt tctttacttc tggctatatc cctgcccgtc tccccatcac ctgcctgacc    960
attccaccaa ggttttcgat tgctcccagc agcctggacc ccagcaaccg gaagcccctc   1020
acagtcctca ataaaggctt ggagaacccc ctgcctgagc gtccccggga aaaagaagaa   1080
ccagtggttc gagagacagg tgaggtggtc gactgccacc tcagtgacat gctgcagcag   1140
ctgcacagtg tcaatgcctc caagccctcg gagcgtgggc tggtcaggca agaggaggct   1200
gaggatcctg cctgcatccc catcttctgg gtcagcaagt gggtggacta ttcggacaag   1260
tacggccttg ggtatcagct ctgtgataac agcgtggggg tgctcttcaa tgactcaaca   1320
cgcctcatcc tctacaatga tggtgacagc ctgcagtaca tagagcgtga cggcactgag   1380
tcctacctca ccgtgagttc ccatcccaac tccttgatga agaagatcac cctccttaaa   1440
tatttccgca attacatgag cgagcacttg ctgaaggcag gtgccaacat cacgccgcgc   1500
gaaggtgatg agctcgcccg gctgccctac ctacggacct ggttccgcac ccgcagcgcc   1560
atcatcctgc acctcagcaa cggcagcgtg cagatcaact tcttccagga tcacaccaag   1620
ctcatcttgt gcccactgat ggcagccgtg acctacatcg acgagaagcg ggacttccgc   1680
acataccgcc tgagtctcct ggaggagtac ggctgctgca aggagctggc cagccggctc   1740
cgctacgccc gcactatggt ggacaagctg ctgagctcac gctcggccag caaccgtctc   1800
aaggcctcc                                                           1809
```

<210> SEQ ID NO 167
<211> LENGTH: 876
<212> TYPE: DNA
<213> ORGANISM: Salmonella typhimurium
<220> FEATURE:
<223> OTHER INFORMATION: dapA, strain LT2

<400> SEQUENCE: 167

```
atgttcacgg gaagtattgt cgcgcttgtt acgccgatgg atgagaaagg taacgtcagt     60
aggtcttgcc tgaaaaaact cattgattat catgtcgcca acggtacctc ggcgattgtt    120
tcggttggca ctaccggcga gtctgccacg ctaagccatg atgaacatgg cgatgtcgtg    180
atgatgacgc tggaactggc tgacggacgt attccggtta tcgccggcac gggcgcaaac    240
gcgaccgcgg aagcgattag cctgacgcag cgttttaacg atagcggtat tgtaggctgc    300
ctgacggtaa cgccgtacta caatcgcccc acgcaggaag gtttgttcca gcatttcaaa    360
gccatcgcgg aacacactga cttgccgcaa attctgtata atgtgccgtc ccgtaccggt    420
tgcgatatgt tgccggaaac cgtgggtcgt ctggcggaaa taaaaaatat tatcgctatc    480
aaagaggcga cagggaactt aacccgcgtt caccagatca aagagctggt ttcagacgat    540
tttattctgc ttagcggcga tgacgcgtct gcgctggact ttatgcaact gggtggtcat    600
ggcgtgattt ccgttacggc taacgtagcg gcgcgcgaga tggctgacat gtgcaaactg    660
gcggcggaag ggcaatttgc cgaggcgcgc gctatcaacc agcgtctgat gccgttacac    720
aacaaactat ttgtcgaacc caatcctatc ccggtgaaat gggcatgtaa ggcattgggt    780
cttgtggcga ccgacacgct gcgcctgcca atgacgccta tcacggacca tggtcgtgac    840
atcgtcaaag cagcgcttca gcatgctggc ctgctg                              876
```

<210> SEQ ID NO 168
<211> LENGTH: 819
<212> TYPE: DNA
<213> ORGANISM: Salmonella typhimurium
<220> FEATURE:
<223> OTHER INFORMATION: dapB, strain LT2

<400> SEQUENCE: 168

```
atgcatgaag cacaaatccg cgtcgccatt gccggcgccg gtggccgcat gggacggcag     60

ttaatccagg ccgccatggc gatggaaggt gttcagctgg gtgccgcgct ggagcgcgaa    120

ggctcttcct tgctgggcag cgatgctggc gaactggcag ggcgggaaaa gtccggcgtg    180

atcgttcaaa gcagccttga ggcggtaaaa gatgattttg acgttttcat cgattttacc    240

cgtccggaag gcacgttgac gcatctggcg ttttgccgcc agcatggtaa agggatggtg    300

attggtacta ccggctttga cgacgccggt aaacaagcca ttcgcgaggc gtcacaagag    360

attgcgatcg ttttcgccgc aaactttagc gtcggcgtta acgtcatgct caagctgctg    420

gagaaagccg cgaaggtaat gggcgactat agcgatattg aaattattga agcgcaccac    480

cgccataaag tggatgcacc gtcgggtacg gcgctggcaa tgggcgaggc aatcgccggg    540

gcgctggata aaaatctgaa ggactgcgcg gtctactcgc gtgaaggtta taccggcgag    600

cgcgtagcgg gcacgattgg ctttgcgacc gttcgggcgg gcgacatcgt cggcgaacat    660

accgcgatgt ttgccgatat tggcgagcgc gtagagatta cgcataaagc ttccagccgc    720

atgacgtttg caaatggcgc gttgcgatcg gcgttatggc taaaaacgaa gaaaaatggg    780

ctatttgaca tgcgggatgt gctggggctg gatgtatta                           819
```

<210> SEQ ID NO 169
<211> LENGTH: 876
<212> TYPE: DNA
<213> ORGANISM: E. coli
<220> FEATURE:
<223> OTHER INFORMATION: dapA

<400> SEQUENCE: 169

```
atgttcacgg gaagtattgt cgcgattgtt actccgatgg atgaaaaagg taatgtctgt     60

cgggctagct tgaaaaaact gattgattat catgtcgcca gcggtacttc ggcgatcgtt    120

tctgttggca ccactggcga gtccgctacc ttaaatcatg acgaacatgc tgatgtggtg    180

atgatgacgc tggatctggc tgatgggcgc attccggtaa ttgccgggac cggcgctaac    240

gctactgcgg aagccattag cctgacgcag cgcttcaatg acagtggtat cgtcggctgc    300

ctgacggtaa ccccttacta caatcgtccg tcgcaagaag gtttgtatca gcatttcaaa    360

gccatcgctg agcatactga cctgccgcaa attctgtata atgtgccgtc ccgtactggc    420

tgcgatctgc tcccggaaac ggtgggccgt ctggcgaaag taaaaaatat tatcggaatc    480

aaagaggcaa cagggaactt aacgcgtgta aaccagatca aagagctggt ttcagatgat    540

tttgttctgc tgagcggcga tgatgcgagc gcgctggact tcatgcaatt gggcggtcat    600

ggggttattt ccgttacgac taacgtcgca gcgcgtgata tggcccagat gtgcaaactg    660

gcagcagaag aacattttgc cgaggcacgc gttattaatc agcgtctgat gccattacac    720

aacaaactat ttgtcgaacc caatccaatc ccggtgaaat gggcatgtaa ggaactgggt    780

cttgtggcga ccgatacgct gcgcctgcca atgacaccaa tcaccgacag tggtcgtgag    840

acggtcagag cggcgcttaa gcatgccggt ttgctg                              876
```

<210> SEQ ID NO 170
<211> LENGTH: 819
<212> TYPE: DNA
<213> ORGANISM: E. coli
<220> FEATURE:
<223> OTHER INFORMATION: dapB

<400> SEQUENCE: 170
atgcatgatg caaacatccg cgttgccatc gcgggagccg gggggcgtat gggccgccag 60
ttgattcagg cggcgctggc attagagggc gtgcagttgg gcgctgcgct ggagcgtgaa 120
ggatcttctt tactgggcag cgacgccggt gagctggccg gagccgggaa aacaggcgtt 180
accgtgcaaa gcagcctcga tgcggtaaaa gatgattttg atgtgtttat cgattttacc 240
cgtccggaag gtacgctgaa ccatctcgct tttgtcgcc agcatggcaa agggatggtg 300
atcggcacta cggggtttga cgaagccggt aaacaagcaa ttcgtgacgc cgctgccgat 360
attgcgattg tctttgcggc caattttagc gttggcgtta acgtcatgct taagctgctg 420
gagaaagcag ccaaagtgat gggtgactac accgatatcg aaattattga agcacatcat 480
agacataaag ttgatgcgcc gtcaggcacc gcactggcaa tgggagaggc gatcgcccac 540
gcccttgata aagatctgaa agattgcgcg gtctacagtc gtgaaggcca caccggtgaa 600
cgtgtgcctg gcaccattgg ttttgccacc gtgcgtgcag gtgacatcgt tggtgaacat 660
accgcgatgt ttgccgatat tggcgagcgt ctggagatca cccataaggc gtccagccgt 720
atgacatttg ctaacggcgc ggtaagatcg gctttgtggt tgagtggtaa ggaaagcggt 780
ctttttgata tgcgagatgt acttgatctc aataatttg 819

<210> SEQ ID NO 171
<211> LENGTH: 1218
<212> TYPE: DNA
<213> ORGANISM: E. coli
<220> FEATURE:
<223> OTHER INFORMATION: dapC

<400> SEQUENCE: 171
atggcaattg aacaaacagc aattacacgc gcgactttcg atgaagtgat cctgccgatt 60
tatgctccgg cagagtttat tccggtaaaa ggtcagggca gccgaatctg ggatcagcaa 120
ggcaaggagt atgtcgattt cgcgggtggc attgcagtta cggcgttggg ccattgccat 180
cctgcgctgg tgaacgcgtt aaaaacccag ggcgaaactc tgtggcatat cagtaacgtt 240
ttcaccaatg aaccggcgct gcgtcttggg cgtaaactga ttgaggcaac gtttgccgaa 300
cgcgtggtgt ttatgaactc cggcacggaa gctaacgaaa ccgcctttaa actggcacgc 360
cattacgcct gtgtgcgtca tagcccgttc aaaaccaaaa ttattgcctt ccataacgct 420
tttcatggtc gctcgctgtt taccgtttcg gtgggtgggc agccaaaata ttccgacggc 480
tttgggccga aaccggcaga catcatccac gttcccttta acgatctcca tgcagtgaaa 540
gcggtgatgg atgatcacac ctgtgcggtg gtggttgagc cgatccaggg cgagggcggt 600
gtgacggcag cgacgccaga gtttttgcag ggcttgcgcg agctgtgcga tcaacatcag 660
gcattattgg tgtttgatga agtgcagtgc gggatggggc ggaccggcga tttgtttgct 720
tacatgcact acgcgttagc gccggatatt ctgacctctg cgaaagcgtt aggcggcggc 780
ttcccgatta gcgccatgct gaccacggcg gaaattgctt ctgcgtttca tcctggttct 840
cacggttcca cctacggcgg taatcctctg gcctgtgcag tagcgggggc ggcgtttgat 900
atcatcaata cccctgaagt gctggaaggc attcaggcga aacgccagcg ttttgttgac 960
catctgcaga agatcgatca gcagtacgat gtatttagcg atattcgcgg tatggggctg 1020
ttgattggcg cagagctgaa accacagtac aaaggtcggg cgcgtgattt cctgtatgcg 1080
ggcgcagagg ctggcgtaat ggtgctgaat gccggaccgg atgtgatgcg ttttgcaccg 1140
tcgctggtgg tggaagatgc ggatatcgat gaagggatgc aacgtttcgc ccacgcggtg 1200
gcgaaggtgg ttggggcg 1218

<210> SEQ ID NO 172
<211> LENGTH: 822
<212> TYPE: DNA
<213> ORGANISM: E. coli
<220> FEATURE:
<223> OTHER INFORMATION: dapD

<400> SEQUENCE: 172
atgcagcagt tacagaacat tattgaaacc gcttttgaac gccgtgccga gatcacgcca 60
gccaatgcag acaccgttac ccgcgaagcg gataatcagg tgatcgccct gctggattcc 120
ggcgcactgc gtgtagcgga aaaaattgac ggtcagtggg tgacgcatca gtggttgaaa 180
aaagcggtgc tgctctcttt ccgtattaat gataatcagg tgatcgaagg ggcagaaagc 240
cgctacttcg acaaagtgcc gatgaaattc gccgactacg acgaagcacg tttccagaaa 300
gaaggcttcc gcgttgtgcc accagcggcg gtacgtcagg gtgcgtttat tgcccgtaac 360
accgtgctga tgccgtctta cgtcaacatc ggcgcatatg ttgatgaagg caccatggtt 420
gatacctggg cgaccgtcgg ttcttgtgcg cagattggta aaaacgttca cctttccggt 480
ggcgtgcgca tcggcggcgt gctggaaccg ctgcaggcta acccaaccat gattgaagat 540
aattgcttca tcggcgcgcg ctctgaactg gttgaagggg tgattgtcga agaaggttcc 600
gtcatttcca tgggcgtata cattggtcag agcacccgta tttacgaccg tgaaaccggc 660
gaaatccact acggtcgcgt tccggcgggg tctgtggttg tttcaggtaa tctgccgtca 720
aaagatggca aatacagcct ctactgtgcg gttatcgtta agaaagttga cgcgaaaact 780
cgcggcaaag tcggcattaa cgaactgctg cgtaccatcg ac 822

<210> SEQ ID NO 173
<211> LENGTH: 1125
<212> TYPE: DNA
<213> ORGANISM: E. coli
<220> FEATURE:
<223> OTHER INFORMATION: dapE

<400> SEQUENCE: 173
atgtcgtgcc cggttattga gctgacacaa cagcttattc gccgcccttc cctgagtcct 60
gatgatgcag gatgccaggc tttgttgatt gaacgtttgc aggcgatcgg ttttaccgtt 120
gaacgcatgg actttgccga tacgcagaat ttttgggcat ggcgtgggca gggtgaaacg 180
ttagcctttg ccgggcatac cgacgtggtg ccgcctggcg acgccgatcg ttggatcaat 240
cccccgtttg aacccaccat tcgtgacggc atgttattcg ggcgcggtgc ggcagatatg 300
aaaggctcgc tggcggcgat ggtggtggcg gcagaacgtt ttgtcgcaca acatcccaac 360
catacggggc gactggcatt tctgatcacc tctgatgaag aagccagtgc ccacaacggt 420
acggtaaaag tcgtcgaagc gttaatggca cgtaatgagc gtctcgatta ctgcctggtt 480
ggcgaaccgt cgagtatcga agtggtaggt gatgtggtga aaaatggtcg tcgcggatca 540
ttaacctgca accttaccat tcatggcgtt caggggcatg ttgcctaccc acatctggct 600
gacaatccgg tacatcgcgc agcacctttc cttaatgaat tagtggctat tgagtgggat 660
cagggcaatg aattcttccc ggcgaccagt atgcagattg ccaatattca ggcgggaacg 720
ggcagtaaca acgttattcc gggtgaactg tttgtgcagt ttaacttccg cttcagcacc 780
gaactgactg atgagatgat caaagcgcag gtgcttgccc tgcttgaaaa acatcaactg 840
cgctatacgg tggattggtg gctttccggg cagccatttt tgaccgcgcg cggtaaactg 900
gtggatgcgg tcgttaacgc ggttgagcac tataatgaaa ttaaaccgca gctactgacc 960
acaggcggaa cgtccgacgg gcgctttatt gcccgcatgg gggcgcaggt ggtggaactc 1020
gggccggtca atgccactat tcataaaatt aatgaatgtg tgaacgctgc cgacctgcag 1080
ctacttgccc gtatgtatca acgtatcatg gaacagctcg tcgcc 1125

<210> SEQ ID NO 174
<211> LENGTH: 1179
<212> TYPE: DNA
<213> ORGANISM: Homo sapiens
<220> FEATURE:
<223> OTHER INFORMATION: p53

<400> SEQUENCE: 174
atggaggagc cgcagtcaga tcctagcgtc gagccccctc tgagtcagga aacattttca 60
gacctatgga aactacttcc tgaaaacaac gttctgtccc ccttgccgtc ccaagcaatg 120
gatgatttga tgctgtcccc ggacgatatt gaacaatggt tcactgaaga cccaggtcca 180
gatgaagctc ccagaatgcc agaggctgct ccccgcgtgg cccctgcacc agcagctcct 240
acaccggcgg cccctgcacc agccccctcc tggcccctgt catcttctgt cccttcccag 300
aaaacctacc agggcagcta cggtttccgt ctgggcttct tgcattctgg gacagccaag 360
tctgtgactt gcacgtactc ccctgccctc aacaagatgt tttgccaact ggccaagacc 420
tgccctgtgc agctgtgggt tgattccaca cccccgcccg gcacccgcgt ccgcgccatg 480
gccatctaca agcagtcaca gcacatgacg gaggttgtga ggcgctgccc ccaccatgag 540
cgctgctcag atagcgatgg tctggcccct cctcagcatc ttatccgagt ggaaggaaat 600
ttgcgtgtgg agtatttgga tgacagaaac acttttcgac atagtgtggt ggtgccctat 660
gagccgcctg aggttggctc tgactgtacc accatccact acaactacat gtgtaacagt 720
tcctgcatgg gcggcatgaa ccggaggccc atcctcacca tcatcacact ggaagactcc 780
agtggtaatc tactgggacg gaacagcttt gaggtgcatg tttgtgcctg tcctgggaga 840
gaccggcgca cagaggaaga gaatctccgc aagaaagggg agcctcacca cgagctgccc 900
ccagggagca ctaagcgagc actgtccaac aacaccagct cctctcccca gccaaagaag 960
aaaccactgg atggagaata tttcaccctt cagatccgtg ggcgtgagcg cttcgagatg 1020
ttccgagagc tgaatgaggc cttggaactc aaggatgccc aggctgggaa ggagccaggg 1080
gggagcaggg ctcactccag ccacctgaag tccaaaaagg gtcagtctac ctcccgccat 1140
aaaaaactca tgttcaagac agaagggcct gactcagac 1179

<210> SEQ ID NO 175
<211> LENGTH: 1470
<212> TYPE: DNA
<213> ORGANISM: Homo sapiens
<220> FEATURE:
<223> OTHER INFORMATION: ERBA

<400> SEQUENCE: 175
atggaacaga agccaagcaa ggtggagtgt gggtcagacc cagaggagaa cagtgccagg 60

```
tcaccagatg gaaagcgaaa aagaaagaac ggccaatgtt ccctgaaaac cagcatgtca    120

gggtatatcc ctagttacct ggacaaagac gagcagtgtg tcgtgtgtgg ggacaaggca    180

actggttatc actaccgctg tatcacttgt gagggctgca agggcttctt tcgccgcaca    240

atccagaaga acctccatcc cacctattcc tgcaaatatg acagctgctg tgtcattgac    300

aagatcaccc gcaatcagtg ccagctgtgc cgcttcaaga agtgcatcgc cgtgggcatg    360

gccatggact tggttctaga tgactcgaag cgggtggcca agcgtaagct gattgagcag    420

aaccgggagc ggcggcggaa ggaggagatg atccgatcac tgcagcagcg accagagccc    480

actcctgaag agtgggatct gatccacatt gccacagagg cccatcgcag caccaatgcc    540

cagggcagcc attggaaaca gaggcggaaa ttcctgcccg atgacattgg ccagtcaccc    600

attgtctcca tgccggacgg agacaaggtg gacctggaag ccttcagcga gtttaccaag    660

atcatcaccc cggccatcac ccgtgtggtg gactttgcca aaaaactgcc catgttctcc    720

gagctgcctt gcgaagacca gatcatcctc ctgaaggggt gctgcatgga gatcatgtcc    780

ctgcgggcgg ctgtccgcta cgaccctgag agcgacaccc tgacgctgag tggggagatg    840

gctgtcaagc gggagcagct caagaatggc ggcctgggcg tagtctccga cgccatcttt    900

gaactgggca agtcactctc tgcctttaac ctggatgaca cggaagtggc tctgctgcag    960

gctgtgctgc taatgtcaac agaccgctcg ggcctgctgt gtgtggacaa gatcgagaag   1020

agtcaggagg cgtacctgct ggcgttcgag cactacgtca accaccgcaa acacaacatt   1080

ccgcacttct ggcccaagct gctgatgaag gagagagaag tgcagagttc gattctgtac   1140

aagggggcag cggcagaagg ccggccgggc gggtcactgg gcgtccaccc ggaaggacag   1200

cagcttctcg gaatgcatgt tgttcagggt ccgcaggtcc ggcagcttga gcagcagctt   1260

ggtgaagcgg gaagtctcca agggccggtt cttcagcacc agagcccgaa gagcccgcag   1320

cagcgtctcc tggagctgct ccaccgaagc ggaattctcc atgcccgagc ggtctgtggg   1380

gaagacgaca gcagtgaggc ggactccccg agctcctctg aggaggaacc ggaggtctgc   1440

gaggacctgg caggcaatgc agcctctccc                                    1470
```

<210> SEQ ID NO 176
<211> LENGTH: 1317
<212> TYPE: DNA
<213> ORGANISM: Homo sapiens
<220> FEATURE:
<223> OTHER INFORMATION: myc

<400> SEQUENCE: 176

```
atgcccctca acgttagctt caccaacagg aactatgacc tcgactacga ctcggtgcag     60

ccgtatttct actgcgacga ggaggagaac ttctaccagc agcagcagca gagcgagctg    120

cagcccccgg cgcccagcga ggatatctgg aagaaattcg agctgctgcc caccccgccc    180

ctgtccccta gccgccgctc cgggctctgc tcgccctcct acgttgcggt cacacccttc    240

tcccttcggg gagacaacga cggcggtggc gggagcttct ccacggccga ccagctggag    300

atggtgaccg agctgctggg aggagacatg gtgaaccaga gtttcatctg cgacccggac    360

gacgagacct tcatcaaaaa catcatcatc caggactgta tgtggagcgg cttctcggcc    420

gccgccaagc tcgtctcaga gaagctggcc tcctaccagg ctgcgcgcaa agacagcggc    480

agcccgaacc ccgcccgcgg ccacagcgtc tgctccacct ccagcttgta cctgcaggat    540

ctgagcgccg ccgcctcaga gtgcatcgac ccctcggtgg tcttccccta ccctctcaac    600
```

```
gacagcagct cgcccaagtc ctgcgcctcg caagactcca gcgccttctc tccgtcctcg    660

gattctctgc tctcctcgac ggagtcctcc ccgcagggca gccccgagcc cctggtgctc    720

catgaggaga caccgcccac caccagcagc gactctgagg aggaacaaga agatgaggaa    780

gaaatcgatg ttgtttctgt ggaaaagagg caggctcctg gcaaaaggtc agagtctgga    840

tcaccttctg ctggaggcca cagcaaacct cctcacagcc cactggtcct caagaggtgc    900

cacgtctcca cacatcagca caactacgca gcgcctccct ccactcggaa ggactatcct    960

gctgccaaga gggtcaagtt ggacagtgtc agagtcctga gacagatcag caacaaccga   1020

aaatgcacca gccccaggtc ctcggacacc gaggagaatg tcaagaggcg aacacacaac   1080

gtcttggagc gccagaggag gaacgagcta aaacggagct tttttgccct gcgtgaccag   1140

atcccggagt tggaaaacaa tgaaaaggcc cccaaggtag ttatccttaa aaaagccaca   1200

gcatacatcc tgtccgtcca agcagaggag caaaagctca tttctgaaga ggacttgttg   1260

cggaaacgac gagaacagtt gaaacacaaa cttgaacagc tacggaactc ttgtgcg      1317
```

```
<210> SEQ ID NO 177
<211> LENGTH: 2283
<212> TYPE: DNA
<213> ORGANISM: Homo sapiens
<220> FEATURE:
<223> OTHER INFORMATION: MYB

<400> SEQUENCE: 177
```

```
atggcccgaa gaccccggca cagcatatat agcagtgacg aggatgatga ggactttgag     60

atgtgtgacc atgactatga tgggctgctt cccaagtctg gaaagcgtca cttggggaaa    120

acaaggtgga cccgggaaga ggatgaaaaa ctgaagaagc tggtggaaca gaatggaaca    180

gatgactgga aagttattgc caattatctc ccgaatcgaa cagatgtgca gtgccagcac    240

cgatggcaga aagtactaaa ccctgagctc atcaagggtc cttggaccaa agaagaagat    300

cagagagtga tagagcttgt acagaaatac ggtccgaaac gttggtctgt tattgccaag    360

cacttaaagg ggagaattgg aaaacaatgt agggagaggt ggcataacca cttgaatcca    420

gaagttaaga aaacctcctg gacagaagag gaagacagaa ttatttacca ggcacacaag    480

agactgggga acagatgggc agaaatcgca aagctactgc ctggacgaac tgataatgct    540

atcaagaacc actggaattc tacaatgcgt cggaaggtcg aacaggaagg ttatctgcag    600

gagtcttcaa aagccagcca gccagcagtg gccacaagct tccagaagaa cagtcatttg    660

atgggttttg ctcaggctcc gcctacagct caactccctg ccactggcca gcccactgtt    720

aacaacgact attcctatta ccacatttct gaagcacaaa atgtctccag tcatgttcca    780

taccctgtag cgttacatgt aaatatagtc aatgtccctc agccagctgc cgcagccatt    840

cagagacact ataatgatga agaccctgag aaggaaaagc gaataaagga attagaattg    900

ctcctaatgt caaccgagaa tgagctaaaa ggacagcagg tgctaccaac acagaaccac    960

acatgcagct accccgggtg gcacagcacc accattgccg accacaccag acctcatgga   1020

gacagtgcac ctgtttcctg tttgggagaa caccactcca ctccatctct gccagcggat   1080

cctggctccc tacctgaaga aagcgcctcg ccagcaaggt gcatgatcgt ccaccagggc   1140

accattctgg ataatgttaa gaacctctta gaatttgcag aaacactcca atttatagat   1200

tctgattctt catcatggtg tgatctcagc agttttgaat tctttgaaga agcagatttt   1260

tcacctagcc aacatcacac aggcaaagcc ctacagcttc agcaaagaga gggcaatggg   1320

actaaacctg caggagaacc tagcccaagg gtgaacaaac gtatgttgag tgagagttca   1380
```

cttgacccac ccaaggtctt acctcctgca aggcacagca caattccact ggtcatcctt 1440
cgaaaaaaac ggggccaggc cagcccctta gccactggag actgtagctc cttcatattt 1500
gctgacgtca gcagttcaac tcccaagcgt tcccctgtca aaagcctacc cttctctccc 1560
tcgcagttct taaacacttc cagtaaccat gaaaactcag acttggaaat gccttcttta 1620
acttccaccc ccctcattgg tcacaaattg actgttacaa caccatttca tagagaccag 1680
actgtgaaaa ctcaaaagga aaatactgtt tttagaaccc cagctatcaa aaggtcaatc 1740
ttagaaagct ctccaagaac tcctacacca ttcaaacatg cacttgcagc tcaagaaatt 1800
aaatacggtc ccctgaagat gctacctcag acaccctctc atctagtaga agatctgcag 1860
gatgtgatca aacaggaatc tgatgaatct ggaattgttg ctgagtttca agaaaatgga 1920
ccacccttac tgaagaaaat caaacaagag gtggaatctc caactgataa atcaggaaac 1980
ttcttctgct cacaccactg ggaaggggac agtctgaata cccaactgtt cacgcagacc 2040
tcgcctgtgg cagatgcacc gaatattctt acaagctccg ttttaatggc accagcatca 2100
gaagatgaag acaatgttct caaagcattt acagtaccta aaaacaggtc cctggcgagc 2160
cccttgcagc cttgtagcag tacctgggaa cctgcatcct gtggaaagat ggaggagcag 2220
atgacatctt ccagtcaagc tcgtaaatac gtgaatgcat tctcagcccg gacgctggtc 2280
atg 2283

<210> SEQ ID NO 178
<211> LENGTH: 993
<212> TYPE: DNA
<213> ORGANISM: Homo sapiens
<220> FEATURE:
<223> OTHER INFORMATION: JUN

<400> SEQUENCE: 178
atgactgcaa agatggaaac gaccttctat gacgatgccc tcaacgcctc gttcctcccg 60
tccgagagcg gaccttatgg ctacagtaac cccaagatcc tgaaacagag catgaccctg 120
aacctggccg acccagtggg gagcctgaag ccgcacctcc gcgccaagaa ctcggacctc 180
ctcacctcgc ccgacgtggg gctgctcaag ctggcgtcgc ccgagctgga gcgcctgata 240
atccagtcca gcaacgggca catcaccacc acgccgaccc ccacccagtt cctgtgcccc 300
aagaacgtga cagatgagca ggagggcttc gccgagggct tcgtgcgcgc cctggccgaa 360
ctgcacagcc agaacacgct gcccagcgtc acgtcggcgg cgcagccggt caacggggca 420
ggcatggtgg ctcccgcggt agcctcggtg gcagggggca gcggcagcgg cggcttcagc 480
gccagcctgc acagcgagcc gccggtctac gcaaacctca gcaacttcaa cccaggcgcg 540
ctgagcagcg gcggcggggc gccctcctac ggcgcggccg gcctggcctt tcccgcgcaa 600
ccccagcagc agcagcagcc gccgcaccac ctgccccagc agatgcccgt gcagcacccg 660
cggctgcagg ccctgaagga ggagcctcag acagtgcccg agatgcccgg cgagacaccg 720
cccctgtccc ccatcgacat ggagtcccag gagcggatca aggcggagag gaagcgcatg 780
aggaaccgca tcgctgcctc caagtgccga aaaaggaagc tggagagaat cgcccggctg 840
gaggaaaaag tgaaaacctt gaaagctcag aactcggagc tggcgtccac ggccaacatg 900
ctcagggaac aggtggcaca gcttaaacag aaagtcatga accacgttaa cagtgggtgc 960
caactcatgc taacgcagca gttgcaaaca ttt 993

<210> SEQ ID NO 179

<211> LENGTH: 3633
<212> TYPE: DNA
<213> ORGANISM: Homo sapiens
<220> FEATURE:
<223> OTHER INFORMATION: ERBB

<400> SEQUENCE: 179
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660
gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gccccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960
gacggcgtcc gcaagtgtaa gaagtgcgaa gggccttgcc gcaaagtgtg taacggaata 1020
ggtattggtg aatttaaaga ctcactctcc ataaatgcta cgaatattaa acacttcaaa 1080
aactgcacct ccatcagtgg cgatctccac atcctgccgg tggcatttag gggtgactcc 1140
ttcacacata ctcctcctct ggatccacag gaactggata ttctgaaaac cgtaaaggaa 1200
atcacagggt ttttgctgat tcaggcttgg cctgaaaaca ggacggacct ccatgccttt 1260
gagaacctag aaatcatacg cggcaggacc aagcaacatg gtcagttttc tcttgcagtc 1320
gtcagcctga acataacatc cttgggatta cgctccctca aggagataag tgatggagat 1380
gtgataattt caggaaacaa aaatttgtgc tatgcaaata caataaactg gaaaaaactg 1440
tttgggacct ccggtcagaa aaccaaaatt ataagcaaca gaggtgaaaa cagctgcaag 1500
gccacaggcc aggtctgcca tgccttgtgc tcccccgagg gctgctgggg cccggagccc 1560
agggactgcg tctcttgccg gaatgtcagc cgaggcaggg aatgcgtgga caagtgcaac 1620
cttctggagg gtgagccaag ggagtttgtg gagaactctg agtgcataca gtgccaccca 1680
gagtgcctgc ctcaggccat gaacatcacc tgcacaggac ggggaccaga caactgtatc 1740
cagtgtgccc actacattga cggcccccac tgcgtcaaga cctgcccggc aggagtcatg 1800
ggagaaaaca acaccctggt ctggaagtac gcagacgccg gccatgtgtg ccacctgtgc 1860
catccaaact gcacctacgg atgcactggg ccaggtcttg aaggctgtcc aacgaatggg 1920
cctaagatcc cgtccatcgc cactgggatg gtgggggccc tcctcttgct gctggtggtg 1980
gccctgggga tcggcctctt catgcgaagg cgccacatcg ttcggaagcg cacgctgcgg 2040
aggctgctgc aggagaggga gcttgtggag cctcttacac ccagtggaga agctcccaac 2100
caagctctct tgaggatctt gaaggaaact gaattcaaaa agatcaaagt gctgggctcc 2160

```
ggtgcgttcg gcacggtgta taagggactc tggatcccag aaggtgagaa agttaaaatt   2220

cccgtcgcta tcaaggaatt aagagaagca acatctccga aagccaacaa ggaaatcctc   2280

gatgaagcct acgtgatggc cagcgtggac aacccccacg tgtgccgcct gctgggcatc   2340

tgcctcacct ccaccgtgca gctcatcacg cagctcatgc ccttcggctg cctcctggac   2400

tatgtccggg aacacaaaga caatattggc tcccagtacc tgctcaactg gtgtgtgcag   2460

atcgcaaagg gcatgaacta cttggaggac cgtcgcttgg tgcaccgcga cctggcagcc   2520

aggaacgtac tggtgaaaac accgcagcat gtcaagatca cagattttgg gctggccaaa   2580

ctgctgggtg cggaagagaa agaataccat gcagaaggag gcaaagtgcc tatcaagtgg   2640

atggcattgg aatcaatttt acacagaatc tatacccacc agagtgatgt ctggagctac   2700

ggggtgactg tttgggagtt gatgaccttt ggatccaagc catatgacgg aatccctgcc   2760

agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 180
<211> LENGTH: 5589
<212> TYPE: DNA
<213> ORGANISM: Homo sapiens
<220> FEATURE:
<223> OTHER INFORMATION: BRCA1

<400> SEQUENCE: 180

```
atggatttat ctgctcttcg cgttgaagaa gtacaaaatg tcattaatgc tatgcagaaa     60

atcttagagt gtcccatctg tctggagttg atcaaggaac ctgtctccac aaagtgtgac    120

cacatatttt gcaaattttg catgctgaaa cttctcaacc agaagaaagg gccttcacag    180

tgtcctttat gtaagaatga tataaccaaa aggagcctac aagaaagtac gagatttagt    240

caacttgttg aagagctatt gaaaatcatt tgtgcttttc agcttgacac aggtttggag    300

tatgcaaaca gctataattt tgcaaaaaag gaaaataact ctcctgaaca tctaaaagat    360

gaagtttcta tcatccaaag tatgggctac agaaaccgtg ccaaaagact tctacagagt    420

gaacccgaaa atccttcctt gcaggaaacc agtctcagtg tccaactctc taaccttgga    480

actgtgagaa ctctgaggac aaagcagcgg atacaacctc aaaagacgtc tgtctacatt    540
```

-continued

```
gaattgggat ctgattcttc tgaagatacc gttaataagg caacttattg cagtgtggga    600
gatcaagaat tgttacaaat caccccctcaa ggaaccaggg atgaaatcag tttggattct    660
gcaaaaaagg ctgcttgtga attttctgag acggatgtaa caaatactga acatcatcaa    720
cccagtaata atgatttgaa caccactgag aagcgtgcag ctgagaggca tccagaaaag    780
tatcagggta gttctgtttc aaacttgcat gtggagccat gtggcacaaa tactcatgcc    840
agctcattac agcatgagaa cagcagttta ttactcacta aagacagaat gaatgtagaa    900
aaggctgaat tctgtaataa aagcaaacag cctggcttag caaggagcca acataacaga    960
tgggctggaa gtaaggaaac atgtaatgat aggcggactc ccagcacaga aaaaaaggta   1020
gatctgaatg ctgatcccct gtgtgagaga aaagaatgga ataagcagaa actgccatgc   1080
tcagagaatc ctagagatac tgaagatgtt ccttggataa cactaaatag cagcattcag   1140
aaagttaatg agtggttttc cagaagtgat gaactgttag gttctgatga ctcacatgat   1200
ggggagtctg aatcaaatgc caaagtagct gatgtattgg acgttctaaa tgaggtagat   1260
gaatattctg gttcttcaga gaaaatagac ttactggcca gtgatcctca tgaggcttta   1320
atatgtaaaa gtgaaagagt tcactccaaa tcagtagaga gtaatattga agacaaaata   1380
tttgggaaaa cctatcggaa gaaggcaagc ctccccaact taagccatgt aactgaaaat   1440
ctaattatag gagcatttgt tactgagcca cagataatac aagagcgtcc cctcacaaat   1500
aaattaaagc gtaaaaggag acctacatca ggccttcatc ctgaggattt tatcaagaaa   1560
gcagatttgg cagttcaaaa gactcctgaa atgataaatc agggaactaa ccaaacggag   1620
cagaatggtc aagtgatgaa tattactaat agtggtcatg agaataaaac aaaaggtgat   1680
tctattcaga atgagaaaaa tcctaaccca atagaatcac tcgaaaaaga atctgctttc   1740
aaaacgaaag ctgaacctat aagcagcagt ataagcaata tggaactcga attaaatatc   1800
cacaattcaa aagcacctaa aaagaatagg ctgaggagga agtcttctac caggcatatt   1860
catgcgcttg aactagtagt cagtagaaat ctaagcccac ctaattgtac tgaattgcaa   1920
attgatagtt gttctagcag tgaagagata aagaaaaaaa agtacaacca aatgccagtc   1980
aggcacagca gaaacctaca actcatggaa ggtaaagaac ctgcaactgg agccaagaag   2040
agtaacaagc caaatgaaca gacaagtaaa agacatgaca gcgatacttt cccagagctg   2100
aagttaacaa atgcacctgg ttcttttact aagtgttcaa ataccagtga acttaaagaa   2160
tttgtcaatc ctagccttcc aagagaagaa aaagaagaga aactagaaac agttaaagtg   2220
tctaataatg ctgaagaccc caaagatctc atgttaagtg gagaaagggt tttgcaaact   2280
gaaagatctg tagagagtag cagtatttca ttggtacctg gtactgatta tggcactcag   2340
gaaagtatct cgttactgga agttagcact ctagggaagg caaaaacaga accaaataaa   2400
tgtgtgagtc agtgtgcagc atttgaaaac cccaagggac taattcatgg ttgttccaaa   2460
gataatagaa atgacacaga aggctttaag tatccattgg gacatgaagt taaccacagt   2520
cgggaaacaa gcatagaaat ggaagaaagt gaacttgatg ctcagtattt gcagaataca   2580
ttcaaggttt caaagcgcca gtcatttgct ccgttttcaa atccaggaaa tgcagaagag   2640
gaatgtgcaa cattctctgc ccactctggg tccttaaaga aacaaagtcc aaaagtcact   2700
tttgaatgtg aacaaaagga agaaaatcaa ggaaagaatg agtctaatat caagcctgta   2760
cagacagtta atatcactgc aggctttcct gtggttggtc agaaagataa gccagttgat   2820
aatgccaaat gtagtatcaa aggaggctct aggttttgtc tatcatctca gttcagaggc   2880
aacgaaactg gactcattac tccaaataaa catggacttt tacaaaaccc atatcgtata   2940
```

```
ccaccacttt ttcccatcaa gtcatttgtt aaaactaaat gtaagaaaaa tctgctagag   3000
gaaaactttg aggaacattc aatgtcacct gaaagagaaa tgggaaatga gaacattcca   3060
agtacagtga gcacaattag ccgtaataac attagagaaa atgtttttaa agaagccagc   3120
tcaagcaata ttaatgaagt aggttccagt actaatgaag tgggctccag tattaatgaa   3180
ataggttcca gtgatgaaaa cattcaagca gaactaggta gaaacagagg gccaaaattg   3240
aatgctatgc ttagattagg ggttttgcaa cctgaggtct ataaacaaag tcttcctgga   3300
agtaattgta agcatcctga aataaaaaag caagaatatg aagaagtagt tcagactgtt   3360
aatacagatt tctctccata tctgatttca gataacttag aacagcctat gggaagtagt   3420
catgcatctc aggtttgttc tgagacacct gatgacctgt tagatgatgg tgaaataaag   3480
gaagatacta gttttgctga aaatgacatt aaggaaagtt ctgctgtttt tagcaaaagc   3540
gtccagaaag gagagcttag caggagtcct agccctttca cccatacaca tttggctcag   3600
ggttaccgaa gaggggccaa gaaattagag tcctcagaag agaacttatc tagtgaggat   3660
gaagagcttc cctgcttcca acacttgtta tttggtaaag taaacaatat accttctcag   3720
tctactaggc atagcaccgt tgctaccgag tgtctgtcta agaacacaga ggagaattta   3780
ttatcattga agaatagctt aaatgactgc agtaaccagg taatattggc aaaggcatct   3840
caggaacatc accttagtga ggaaacaaaa tgttctgcta gcttgttttc ttcacagtgc   3900
agtgaattgg aagacttgac tgcaaataca aacacccagg atcctttctt gattggttct   3960
tccaaacaaa tgaggcatca gtctgaaagc cagggagttg gtctgagtga caaggaattg   4020
gtttcagatg atgaagaaag aggaacgggc ttggaagaaa ataatcaaga agagcaaagc   4080
atggattcaa acttaggtga agcagcatct gggtgtgaga gtgaaacaag cgtctctgaa   4140
gactgctcag ggctatcctc tcagagtgac attttaacca ctcagcagag ggataccatg   4200
caacataacc tgataaagct ccagcaggaa atggctgaac tagaagctgt gttagaacag   4260
catgggagcc agccttctaa cagctaccct tccatcataa gtgactcttc tgcccttgag   4320
gacctgcgaa atccagaaca aagcacatca gaaaaagcag tattaacttc acagaaaagt   4380
agtgaatacc ctataagcca gaatccagaa ggcctttctg ctgacaagtt tgaggtgtct   4440
gcagatagtt ctaccagtaa aaataaagaa ccaggagtgg aaaggtcatc cccttctaaa   4500
tgcccatcat tagatgatag gtggtacatg cacagttgct ctgggagtct tcagaataga   4560
aactacccat ctcaagagga gctcattaag gttgttgatg tggaggagca acagctggaa   4620
gagtctgggc cacacgattt gacggaaaca tcttacttgc caaggcaaga tctagaggga   4680
accccttacc tggaatctgg aatcagcctc ttctctgatg accctgaatc tgatccttct   4740
gaagacagag ccccagagtc agctcgtgtt ggcaacatac catcttcaac ctctgcattg   4800
aaagttcccc aattgaaagt tgcagaatct gcccagagtc cagctgctgc tcatactact   4860
gatactgctg ggtataatgc aatggaagaa agtgtgagca gggagaagcc agaattgaca   4920
gcttcaacag aaagggtcaa caaaagaatg tccatggtgg tgtctggcct gaccccagaa   4980
gaatttatgc tcgtgtacaa gtttgccaga aaacaccaca tcactttaac taatctaatt   5040
actgaagaga ctactcatgt tgttatgaaa acagatgctg agtttgtgtg tgaacggaca   5100
ctgaaatatt ttctaggaat tgcgggagga aaatgggtag ttagctattt ctgggtgacc   5160
cagtctatta aagaaagaaa aatgctgaat gagcatgatt ttgaagtcag aggagatgtg   5220
gtcaatggaa gaaaccacca aggtccaaag cgagcaagag aatcccagga cagaaagatc   5280
```

ttcagggggc tagaaatctg ttgctatggg cccttcacca acatgcccac agatcaactg 5340
gaatggatgg tacagctgtg tggtgcttct gtggtgaagg agctttcatc attcaccctt 5400
ggcacaggtg tccacccaat tgtggttgtg cagccagatg cctggacaga ggacaatggc 5460
ttccatgcaa ttgggcagat gtgtgaggca cctgtggtga cccgagagtg ggtgttggac 5520
agtgtagcac tctaccagtg ccaggagctg gacacctacc tgatacccca gatcccccac 5580
agccactac 5589

<210> SEQ ID NO 181
<211> LENGTH: 10254
<212> TYPE: DNA
<213> ORGANISM: Homo sapiens
<220> FEATURE:
<223> OTHER INFORMATION: BRCA2

<400> SEQUENCE: 181
atgcctattg gatccaaaga gaggccaaca ttttttgaaa tttttaagac acgctgcaac 60
aaagcagatt taggaccaat aagtcttaat tggtttgaag aactttcttc agaagctcca 120
ccctataatt ctgaacctgc agaagaatct gaacataaaa acaacaatta cgaaccaaac 180
ctatttaaaa ctccacaaag gaaaccatct tataatcagc tggcttcaac tccaataata 240
ttcaaagagc aagggctgac tctgccgctg taccaatctc ctgtaaaaga attagataaa 300
ttcaaattag acttaggaag gaatgttccc aatagtagac ataaaagtct tcgcacagtg 360
aaaactaaaa tggatcaagc agatgatgtt tcctgtccac ttctaaattc ttgtcttagt 420
gaaagtcctg ttgttctaca atgtacacat gtaacaccac aaagagataa gtcagtggta 480
tgtgggagtt tgtttcatac accaaagttt gtgaagggtc gtcagacacc aaaacatatt 540
tctgaaagtc taggagctga ggtggatcct gatatgtctt ggtcaagttc tttagctaca 600
ccacccaccc ttagttctac tgtgctcata gtcagaaatg aagaagcatc tgaaactgta 660
tttcctcatg atactactgc taatgtgaaa agctattttt ccaatcatga tgaaagtctg 720
aagaaaaatg atagatttat cgcttctgtg acagacagtg aaaacacaaa tcaaagagaa 780
gctgcaagtc atggatttgg aaaaacatca gggaattcat ttaaagtaaa tagctgcaaa 840
gaccacattg gaaagtcaat gccaaatgtc ctagaagatg aagtatatga aacagttgta 900
gatacctctg aagaagatag tttttcatta tgtttttcta aatgtagaac aaaaaatcta 960
caaaaagtaa gaactagcaa gactaggaaa aaaattttcc atgaagcaaa cgctgatgaa 1020
tgtgaaaaat ctaaaaacca agtgaaagaa aaatactcat ttgtatctga agtggaacca 1080
aatgatactg atccattaga ttcaaatgta gcaaatcaga agccctttga gagtggaagt 1140
gacaaaatct ccaaggaagt tgtaccgtct ttggcctgtg aatggtctca actaaccctt 1200
tcaggtctaa atggagccca gatggagaaa ataccctat tgcatatttc ttcatgtgac 1260
caaaatattt cagaaaaaga cctattagac acagagaaca aaagaaagaa agattttctt 1320
acttcagaga attctttgcc acgtatttct agcctaccaa aatcagagaa gccattaaat 1380
gaggaaacag tggtaaataa gagagatgaa gagcagcatc ttgaatctca tacagactgc 1440
attcttgcag taaagcaggc aatatctgga acttctccag tggcttcttc atttcagggt 1500
atcaaaaagt ctatattcag aataagagaa tcacctaaag agactttcaa tgcaagtttt 1560
tcaggtcata tgactgatcc aaactttaaa aaagaaactg aagcctctga aagtggactg 1620
gaaatacata ctgtttgctc acagaaggag gactccttat gtccaaattt aattgataat 1680
ggaagctggc cagccaccac cacacagaat tctgtagctt tgaagaatgc aggtttaata 1740

-continued

```
tccactttga aaaagaaaac aaataagttt atttatgcta tacatgatga aacatcttat   1800
aaaggaaaaa aaataccgaa agaccaaaaa tcagaactaa ttaactgttc agcccagttt   1860
gaagcaaatg cttttgaagc accacttaca tttgcaaatg ctgattcagg tttattgcat   1920
tcttctgtga aaagaagctg ttcacagaat gattctgaag aaccaacttt gtccttaact   1980
agctcttttg ggacaattct gaggaaatgt tctagaaatg aaacatgttc taataataca   2040
gtaatctctc aggatcttga ttataaagaa gcaaaatgta ataaggaaaa actacagtta   2100
tttattaccc cagaagctga ttctctgtca tgcctgcagg aaggacagtg tgaaaatgat   2160
ccaaaaaagca aaaaagtttc agatataaaa gaagaggtct tggctgcagc atgtcaccca   2220
gtacaacatt caaaagtgga atacagtgat actgactttc aatcccagaa aagtctttta   2280
tatgatcatg aaaatgccag cactcttatt ttaactccta cttccaagga tgttctgtca   2340
aacctagtca tgatttctag aggcaaagaa tcatacaaaa tgtcagacaa gctcaaaggt   2400
aacaattatg aatctgatgt tgaattaacc aaaaatattc ccatggaaaa gaatcaagat   2460
gtatgtgctt taaatgaaaa ttataaaaac gttgagctgt tgccacctga aaaatacatg   2520
agagtagcat caccttcaag aaaggtacaa ttcaaccaaa acacaaatct aagagtaatc   2580
caaaaaaatc aagaagaaac tacttcaatt tcaaaaataa ctgtcaatcc agactctgaa   2640
gaacttttct cagacaatga gaataatttt gtcttccaag tagctaatga aaggaataat   2700
cttgctttag gaaatactaa ggaacttcat gaaacagact tgacttgtgt aaacgaaccc   2760
attttcaaga actctaccat ggttttatat ggagacacag gtgataaaca agcaacccaa   2820
gtgtcaatta aaaaagattt ggtttatgtt cttgcagagg agaacaaaaa tagtgtaaag   2880
cagcatataa aaatgactct aggtcaagat ttaaaatcgg acatctcctt gaatatagat   2940
aaaataccag aaaaaaataa tgattacatg aacaaatggg caggactctt aggtccaatt   3000
tcaaatcaca gttttggagg tagcttcaga acagcttcaa ataaggaaat caagctctct   3060
gaacataaca ttaagaagag caaaatgttc ttcaaagata ttgaagaaca atatcctact   3120
agtttagctt gtgttgaaat tgtaaatacc ttggcattag ataatcaaaa gaaactgagc   3180
aagcctcagt caattaatac tgtatctgca catttacaga gtagtgtagt tgtttctgat   3240
tgtaaaaata gtcatataac ccctcagatg ttattttcca agcaggattt taattcaaac   3300
cataatttaa cacctagcca aaaggcagaa attacagaac tttctactat attagaagaa   3360
tcaggaagtc agtttgaatt tactcagttt agaaaaccaa gctacatatt gcagaagagt   3420
acatttgaag tgcctgaaaa ccagatgact atcttaaaga ccacttctga ggaatgcaga   3480
gatgctgatc ttcatgtcat aatgaatgcc ccatcgattg gtcaggtaga cagcagcaag   3540
caatttgaag gtacagttga aattaaacgg aagtttgctg gcctgttgaa aaatgactgt   3600
aacaaaagtg cttctggtta tttaacagat gaaaatgaag tggggtttag gggcttttat   3660
tctgctcatg gcacaaaact gaatgtttct actgaagctc tgcaaaaagc tgtgaaactg   3720
tttagtgata ttgagaatat tagtgaggaa acttctgcag aggtacatcc aataagttta   3780
tcttcaagta aatgtcatga ttctgttgtt tcaatgttta agatagaaaa tcataatgat   3840
aaaactgtaa gtgaaaaaaa taataaatgc caactgatat tacaaaataa tattgaaatg   3900
actactggca cttttgttga agaaattact gaaaattaca agagaaatac tgaaaatgaa   3960
gataacaaat atactgctgc cagtagaaat tctcataact tagaatttga tggcagtgat   4020
tcaagtaaaa atgatactgt ttgtattcat aaagatgaaa cggacttgct atttactgat   4080
```

```
cagcacaaca tatgtcttaa attatctggc cagtttatga aggagggaaa cactcagatt   4140
aaagaagatt tgtcagattt aacttttttg gaagttgcga aagctcaaga agcatgtcat   4200
ggtaatactt caaataaaga acagttaact gctactaaaa cggagcaaaa tataaaagat   4260
tttgagactt ctgatacatt ttttcagact gcaagtggga aaaatattag tgtcgccaaa   4320
gagtcattta ataaaattgt aaatttcttt gatcagaaac cagaagaatt gcataacttt   4380
tccttaaatt ctgaattaca ttctgacata agaaagaaca aaatggacat tctaagttat   4440
gaggaaacag acatagttaa acacaaaata ctgaaagaaa gtgtcccagt tggtactgga   4500
aatcaactag tgaccttcca gggacaaccc gaacgtgatg aaaagatcaa agaacctact   4560
ctattgggtt ttcatacagc tagcgggaaa aaagttaaaa ttgcaaagga atctttggac   4620
aaagtgaaaa accttttga tgaaaaagag caaggtacta gtgaaatcac cagttttagc    4680
catcaatggg caaagaccct aaagtacaga gaggcctgta aagaccttga attagcatgt   4740
gagaccattg agatcacagc tgccccaaag tgtaaagaaa tgcagaattc tctcaataat   4800
gataaaaacc ttgtttctat tgagactgtg gtgccaccta agctcttaag tgataattta   4860
tgtagacaaa ctgaaaatct caaaacatca aaaagtatct tttgaaagt taaagtacat    4920
gaaaatgtag aaaaagaaac agcaaaaagt cctgcaactt gttacacaaa tcagtcccct   4980
tattcagtca ttgaaaattc agccttagct tttacacaa gttgtagtag aaaaacttct    5040
gtgagtcaga cttcattact tgaagcaaaa aaatggctta gagaaggaat atttgatggt   5100
caaccagaaa gaataaatac tgcagattat gtaggaaatt atttgtatga aaataattca   5160
aacagtacta tagctgaaaa tgacaaaaat catctctccg aaaaacaaga tacttattta   5220
agtaacagta gcatgtctaa cagctattcc taccattctg atgaggtata taatgattca   5280
ggatatctct caaaaaataa acttgattct ggtattgagc cagtattgaa gaatgttgaa   5340
gatcaaaaaa acactagttt ttccaaagta atatccaatg taaaagatgc aaatgcatac   5400
ccacaaactg taaatgaaga tatttgcgtt gaggaacttg tgactagctc ttcaccctgc   5460
aaaaataaaa atgcagccat taaattgtcc atatctaata gtaataattt tgaggtaggg   5520
ccacctgcat ttaggatagc cagtggtaaa atcgtttgtg tttcacatga aacaattaaa   5580
aaagtgaaag acatatttac agacagtttc agtaaagtaa ttaaggaaaa caacgagaat   5640
aaatcaaaaa tttgccaaac gaaaattatg gcaggttgtt acgaggcatt ggatgattca   5700
gaggatattc ttcataactc tctagataat gatgaatgta gcacgcattc acataaggtt   5760
tttgctgaca ttcagagtga agaaatttta caacataacc aaaatatgtc tggattggag   5820
aaagtttcta aaatatcacc ttgtgatgtt agtttggaaa cttcagatat atgtaaatgt   5880
agtataggga agcttcataa gtcagtctca tctgcaaata cttgtgggat tttagcaca    5940
gcaagtggaa aatctgtcca ggtatcagat gcttcattac aaaacgcaag acaagtgttt   6000
tctgaaatag aagatagtac caagcaagtc ttttccaaag tattgtttaa aagtaacgaa   6060
cattcagacc agctcacaag agaagaaaat actgctatac gtactccaga acatttaata   6120
tcccaaaaag gcttttcata taatgtggta aattcatctg ctttctctgg atttagtaca   6180
gcaagtggaa agcaagtttc cattttagaa agttccttac acaaagttaa gggagtgtta   6240
gaggaatttg atttaatcag aactgagcat agtcttcact attcacctac gtctagacaa   6300
aatgtatcaa aaatacttcc tcgtgttgat aagagaaacc cagagcactg tgtaaactca   6360
gaaatggaaa aaacctgcag taaagaattt aaattatcaa ataacttaaa tgttgaaggt   6420
ggttcttcag aaaataatca ctctattaaa gtttctccat atctctctca atttcaacaa   6480
```

-continued

```
gacaaacaac agttggtatt aggaaccaaa gtgtcacttg ttgagaacat tcatgttttg   6540
ggaaaagaac aggcttcacc taaaaacgta aaaatggaaa ttggtaaaac tgaaactttt   6600
tctgatgttc ctgtgaaaac aaatatagaa gtttgttcta cttactccaa agattcagaa   6660
aactactttg aaacagaagc agtagaaatt gctaaagctt ttatggaaga tgatgaactg   6720
acagattcta aactgccaag tcatgccaca cattctcttt ttacatgtcc cgaaaatgag   6780
gaaatggttt tgtcaaattc aagaattgga aaaagaagag gagagcccct tatcttagtg   6840
ggagaaccct caatcaaaag aaacttatta aatgaatttg acaggataat agaaaatcaa   6900
gaaaaatcct taaaggcttc aaaaagcact ccagatggca caataaaaga tcgaagattg   6960
tttatgcatc atgtttcttt agagccgatt acctgtgtac cctttcgcac aactaaggaa   7020
cgtcaagaga tacagaatcc aaattttacc gcacctggtc aagaatttct gtctaaatct   7080
catttgtatg aacatctgac tttggaaaaa tcttcaagca atttagcagt ttcaggacat   7140
ccattttatc aagtttctgc tacaagaaat gaaaaaatga gacacttgat tactacaggc   7200
agaccaacca aagtctttgt tccacctttt aaaactaaat cacattttca cagagttgaa   7260
cagtgtgtta ggaatattaa cttggaggaa aacagacaaa agcaaaacat tgatggacat   7320
ggctctgatg atagtaaaaa taagattaat gacaatgaga ttcatcagtt taacaaaaac   7380
aactccaatc aagcagcagc tgtaactttc acaaagtgtg aagaagaacc tttagattta   7440
attacaagtc ttcagaatgc cagagatata caggatatgc gaattaagaa gaaacaaagg   7500
caacgcgtct ttccacagcc aggcagtctg tatcttgcaa aaacatccac tctgcctcga   7560
atctctctga aagcagcagt aggaggccaa gttccctctg cgtgttctca taaacagctg   7620
tatacgtatg gcgtttctaa acattgcata aaaattaaca gcaaaaatgc agagtctttt   7680
cagtttcaca ctgaagatta ttttggtaag gaaagtttat ggactggaaa aggaatacag   7740
ttggctgatg gtggatggct cataccctcc aatgatggaa aggctggaaa agaagaattt   7800
tatagggctc tgtgtgacac tccaggtgtg gatccaaagc ttatttctag aatttgggtt   7860
tataatcact atagatggat catatggaaa ctggcagcta tggaatgtgc ctttcctaag   7920
gaatttgcta atagatgcct aagcccagaa agggtgcttc ttcaactaaa atacagatat   7980
gatacggaaa ttgatagaag cagaagatcg gctataaaaa agataatgga aagggatgac   8040
acagctgcaa aaacacttgt tctctgtgtt tctgacataa tttcattgag cgcaaatata   8100
tctgaaactt ctagcaataa aactagtagt gcagataccc aaaaagtggc cattattgaa   8160
cttacagatg ggtggtatgc tgttaaggcc cagttagatc ctcccctctt agctgtctta   8220
aagaatggca gactgacagt tggtcagaag attattcttc atggagcaga actggtgggc   8280
tctcctgatg cctgtacacc tcttgaagcc ccagaatctc ttatgttaaa gatttctgct   8340
aacagtactc ggcctgctcg ctggtatacc aaacttggat tctttcctga ccctagacct   8400
tttcctctgc ccttatcatc gcttttcagt gatggaggaa atgttggttg tgttgatgta   8460
attattcaaa gagcataccc tatacagtgg atggagaaga catcatctgg attatacata   8520
tttcgcaatg aaagagagga agaaaaggaa gcagcaaaat atgtggaggc ccaacaaaag   8580
agactagaag ccttattcac taaaattcag gaggaatttg aagaacatga agaaaacaca   8640
acaaaaccat atttaccatc acgtgcacta acaagacagc aagttcgtgc tttgcaagat   8700
ggtgcagagc tttatgaagc agtgaagaat gcagcagacc cagcttacct tgagggttat   8760
ttcagtgaag agcagttaag agccttgaat aatcacaggc aaatgttgaa tgataagaaa   8820
```

-continued caagctcaga tccagttgga aattaggaag gccatggaat ctgctgaaca aaaggaacaa 8880
ggtttatcaa gggatgtcac aaccgtgtgg aagttgcgta ttgtaagcta ttcaaaaaaa 8940
gaaaaagatt cagttatact gagtatttgg cgtccatcat cagatttata ttctctgtta 9000
acagaaggaa agagatacag aatttatcat cttgcaactt caaaatctaa aagtaaatct 9060
gaaagagcta acatacagtt agcagcgaca aaaaaaactc agtatcaaca actaccggtt 9120
tcagatgaaa ttttatttca gatttaccag ccacgggagc cccttcactt cagcaaattt 9180
ttagatccag actttcagcc atcttgttct gaggtggacc taataggatt tgtcgtttct 9240
gttgtgaaaa aaacaggact tgcccctttc gtctatttgt cagacgaatg ttacaattta 9300
ctggcaataa agttttggat agaccttaat gaggacatta ttaagcctca tatgttaatt 9360
gctgcaagca acctccagtg gcgaccagaa tccaaatcag gccttcttac tttatttgct 9420
ggagattttt ctgtgttttc tgctagtcca aaagagggcc actttcaaga gacattcaac 9480
aaaatgaaaa atactgttga gaatattgac atactttgca atgaagcaga aaacaagctt 9540
atgcatatac tgcatgcaaa tgatcccaag tggtccaccc caactaaaga ctgtacttca 9600
gggccgtaca ctgctcaaat cattcctggt acaggaaaca agcttctgat gtcttctcct 9660
aattgtgaga tatattatca aagtccttta tcactttgta tggccaaaag gaagtctgtt 9720
tccacacctg tctcagccca gatgacttca aagtcttgta aaggggagaa agagattgat 9780
gaccaaaaga actgcaaaaa gagaagagcc ttggatttct tgagtagact gcctttacct 9840
ccacctgtta gtcccatttg tacatttgtt tctccggctg cacagaaggc atttcagcca 9900
ccaaggagtt gtggcaccaa atacgaaaca cccataaaga aaaaagaact gaattctcct 9960
cagatgactc catttaaaaa attcaatgaa atttctcttt tggaaagtaa ttcaatagct 10020
gacgaagaac ttgcattgat aaatacccaa gctcttttgt ctggttcaac aggagaaaaa 10080
caatttatat ctgtcagtga atccactagg actgctccca ccagttcaga agattatctc 10140
agactgaaac gacgttgtac tacatctctg atcaaagaac aggagagttc ccaggccagt 10200
acggaagaat gtgagaaaaa taagcaggac acaattacaa ctaaaaaata tatc 10254

<210> SEQ ID NO 182
<211> LENGTH: 2487
<212> TYPE: DNA
<213> ORGANISM: Homo sapiens
<220> FEATURE:
<223> OTHER INFORMATION: MCC

<400> SEQUENCE: 182
atgaattccg gagttgccat gaaatatgga aacgactcct cggccgagct gagtgagctc 60
cattcagcag ccctggcatc actaaaggga gatatagtgg aacttaataa acgtctccag 120
caaacagaga gggaacggga ccttctggaa aagaaattgg ccaaggcaca gtgcgagcag 180
tcccacctca tgagagagca tgaggatgtc caggagcgaa cgacgcttcg ctatgaggaa 240
cgcatcacag agctccacag cgtcattgcg gagctcaaca agaagataga ccgtctgcaa 300
ggcaccacca tcagggagga agatgagtac tcagaactgc gatcagaact cagccagagc 360
caacacgagg tcaacgagga ctctcgaagc atggaccaag accagacctc tgtctctatc 420
cccgaaaacc agtctaccat ggttactgct gacatggaca actgcagtga cctgaactca 480
gaactgcaga gggtgctgac agggctggag aatgttgtct gcggcaggaa gaagagcagc 540
tgcagcctct ccgtggccga ggtggacagg cacattgagc agctcaccac agccagcgag 600
cactgtgacc tggctattaa gacagtcgag gagattgagg gggtgcttgg ccgggacctg 660
tatcccaacc tggctgaaga gaggtctcgg tgggagaagg agctggctgg gctgagggaa 720
gagaatgaga gcctgactgc catgctgtgc agcaaagagg aagaactgaa ccggactaag 780
gccaccatga atgccatccg ggaagagcgg gaccggctcc ggaggcgggt cagagagctt 840
caaactcgac tacagagcgt gcaggccaca ggtccctcca gccctggccg cctcacttcc 900
accaaccgcc cgattaaccc cagcactggg gagctgagca caagcagcag cagcaatgac 960
attcccatcg ccaagattgc tgagagggtg aagctatcaa agacaaggtc cgaatcgtca 1020
tcatctgatc ggccagtcct gggctcagaa atcagtagca taggggtatc cagcagtgtg 1080
gctgaacacc tggcccactc acttcaggac tgctccaata tccaagagat tttccaaaca 1140
ctctactcac acggatctgc catctcagaa agcaagatta gagagtttga ggtggaaaca 1200
gaacggctga atagccggat tgagcacctc aaatcccaaa atgacctcct gaccataacc 1260
ttggaggaat gtaaaagcaa tgctgagagg atgagcatgc tggtgggaaa atacgaatcc 1320
aatgccacag cgctgaggct ggccttgcag tacagcgagc agtgcatcga agcctacgaa 1380
ctcctcctgg cgctggcaga gagtgagcag agcctcatcc tggggcagtt ccgagcggcg 1440
ggcgtggggt cctcccctgg agaccagtcg ggggatgaaa acatcactca gatgctcaag 1500
cgagctcatg actgccggaa gacagctgag aacgctgcca aggccctgct catgaagctg 1560
gacggcagct gtgggggagc ctttgccgtg gccggctgca gcgtgcagcc ctgggagagc 1620
ctttcctcca acagccacac cagcacaacc agctccacag ccagtagttg cgacaccgag 1680
ttcactaaag aagacgagca gaggctgaag gattatatcc agcagctcaa gaatgacagg 1740
gctgcggtca agctgaccat gctggagctg gaaagcatcc acatcgatcc tctcagctat 1800
gacgtcaagc ctcggggaga cagccagagg ctggatctgg aaaacgcagt gcttatgcag 1860
gagctcatgg ccatgaagga ggagatggcc gagttgaagg cccagctcta cctactggag 1920
aaagagaaga aggccctgga gctgaagctg agcacgcggg aggcccagga gcaggcctac 1980
ctggtgcaca ttgagcacct gaagtccgag gtggaggagc agaaggagca gcggatgcga 2040
tccctcagct ccaccagcag cggcagcaaa gataaacctg gcaaggagtg tgctgatgct 2100
gcctccccag ctctgtccct agctgaactc aggacaacgt gcagcgagaa tgagctggct 2160
gcggagttca ccaacgccat tcgtcgagaa aagaagttga aggccagagt tcaagagctg 2220
gtgagtgcct tggagagact caccaagagc agtgaaatcc gacatcagca atctgcagag 2280
ttcgtgaatg atctaaagcg ggccaacagc aacctggtgg ctgcctatga gaaagcaaag 2340
aaaaagcatc aaaacaaact gaagaagtta gagtcgcaga tgatggccat ggtggagaga 2400
catgagaccc aagtgaggat gctcaagcaa agaatagctc tgctagagga ggagaactcc 2460
aggccacaca ccaatgaaac ttcgctt 2487

<210> SEQ ID NO 183
<211> LENGTH: 2253
<212> TYPE: DNA
<213> ORGANISM: Homo sapiens
<220> FEATURE:
<223> OTHER INFORMATION: EZH2, isoform 1

<400> SEQUENCE: 183
atgggccaga ctgggaagaa atctgagaag ggaccagttt gttggcggaa gcgtgtaaaa 60
tcagagtaca tgcgactgag acagctcaag aggttcagac gagctgatga agtaaagagt 120
atgtttagtt ccaatcgtca gaaaattttg gaaagaacgg aaatcttaaa ccaagaatgg 180

-continued

```
aaacagcgaa ggatacagcc tgtgcacatc ctgacttctg tgagctcatt gcgcgggact    240

agggagtgtt cggtgaccag tgacttggat tttccaacac aagtcatccc attaaagact    300

ctgaatgcag ttgcttcagt acccataatg tattcttggt ctcccctaca gcagaatttt    360

atggtggaag atgaaactgt tttacataac attccttata tgggagatga agttttagat    420

caggatggta ctttcattga agaactaata aaaaattatg atgggaaagt acacggggat    480

agagaatgtg ggtttataaa tgatgaaatt tttgtggagt tggtgaatgc ccttggtcaa    540

tataatgatg atgacgatga tgatgatgga gacgatcctg aagaaagaga agaaaagcag    600

aaagatctgg aggatcaccg agatgataaa gaaagccgcc cacctcggaa atttccttct    660

gataaaattt ttgaagccat ttcctcaatg tttccagata agggcacagc agaagaacta    720

aaggaaaaat ataaagaact caccgaacag cagctcccag gcgcacttcc tcctgaatgt    780

acccccaaca tagatggacc aaatgctaaa tctgttcaga gagagcaaag cttacactcc    840

tttcatacgc ttttctgtag gcgatgtttt aaatatgact gcttcctaca tcgtaagtgc    900

aattattctt ttcatgcaac acccaacact tataagcgga agaacacaga aacagctcta    960

gacaacaaac cttgtggacc acagtgttac cagcatttgg agggagcaaa ggagtttgct   1020

gctgctctca ccgctgagcg gataaagacc ccaccaaaac gtccaggagg ccgcagaaga   1080

ggacggcttc ccaataacag tagcaggccc agcaccccca ccattaatgt gctggaatca   1140

aaggatacag acagtgatag ggaagcaggg actgaaacgg ggggagagaa caatgataaa   1200

gaagaagaag agaagaaaga tgaaacttcg agctcctctg aagcaaattc tcggtgtcaa   1260

acaccaataa agatgaagcc aaatattgaa cctcctgaga atgtggagtg gagtggtgct   1320

gaagcctcaa tgtttagagt cctcattggc acttactatg acaatttctg tgccattgct   1380

aggttaattg ggaccaaaac atgtagacag gtgtatgagt ttagagtcaa agaatctagc   1440

atcatagctc cagctcccgc tgaggatgtg gatactcctc caaggaaaaa gaagaggaaa   1500

caccggttgt gggctgcaca ctgcagaaag atacagctga aaaaggacgg ctcctctaac   1560

catgtttaca actatcaacc ctgtgatcat ccacggcagc cttgtgacag ttcgtgccct   1620

tgtgtgatag cacaaaattt ttgtgaaaag ttttgtcaat gtagttcaga gtgtcaaaac   1680

cgctttccgg gatgccgctg caaagcacag tgcaacacca agcagtgccc gtgctacctg   1740

gctgtccgag agtgtgaccc tgacctctgt cttacttgtg gagccgctga ccattgggac   1800

agtaaaaatg tgtcctgcaa gaactgcagt attcagcggg gctccaaaaa gcatctattg   1860

ctggcaccat ctgacgtggc aggctggggg atttttatca aagatcctgt gcagaaaaat   1920

gaattcatct cagaatactg tggagagatt atttctcaag atgaagctga cagaagaggg   1980

aaagtgtatg ataaatacat gtgcagcttt ctgttcaact tgaacaatga ttttgtggtg   2040

gatgcaaccc gcaagggtaa caaaattcgt tttgcaaatc attcggtaaa tccaaactgc   2100

tatgcaaaag ttatgatggt taacggtgat cacaggatag gtatttttgc caagagagcc   2160

atccagactg gcgaagagct gttttttgat tacagataca gccaggctga tgccctgaag   2220

tatgtcggca tcgaaagaga aatggaaatc cct                                2253
```

<210> SEQ ID NO 184
<211> LENGTH: 1053
<212> TYPE: DNA
<213> ORGANISM: Homo sapiens
<220> FEATURE:
<223> OTHER INFORMATION: NIPP1/PPP1R8, isoform alpha

<400> SEQUENCE: 184

-continued

```
atggcggcag ccgcgaactc cggctctagc ctcccgctgt tcgactgccc aacctgggca     60

ggtaagcccc ctcccggttt acatctggat gtagtcaaag gagacaaact aattgagaaa    120

ctgattattg atgagaagaa gtattactta tttgggagaa accctgattt gtgtgacttt    180

accattgacc accagtcttg ctctcgggtc catgctgcac ttgtctacca caagcatctg    240

aagagagttt tcctgataga tctcaacagt acacacggca ctttcttggg tcacattcgg    300

ttggaacctc acaagcctca gcaaattccc atcgattcca cggtctcatt tggcgcatcc    360

acaagggcat acactctgcg cgagaagcct cagacattgc catcggctgt gaaaggagat    420

gagaagatgg gtggagagga tgatgaactc aagggcttac tggggcttcc agaggaggaa    480

actgagcttg ataacctgac agagttcaac actgcccaca acaagcggat ttctaccctt    540

accattgagg agggaaatct ggacattcaa agaccaaaga ggaagaggaa gaactcacgg    600

gtgacattca gtgaggatga tgagatcatc aacccagagg atgtggatcc ctcagttggt    660

cgattcagga acatggtgca aactgcagtg gtcccagtca agaagaagcg tgtggagggc    720

cctggctccc tgggcctgga ggaatcaggg agcaggcgca tgcagaactt tgccttcagc    780

ggaggactct acgggggcct gccccccaca cacagtgaag caggctccca gccacatggc    840

atccatggga cagcactcat cggtggcttg cccatgccat acccaaacct tgcccctgat    900

gtggacttga ctcctgttgt gccgtcagca gtgaacatga accctgcacc aaaccctgca    960

gtctataacc ctgaagctgt aaatgaaccc aagaagaaga aatatgcaaa agaggcttgg   1020

ccaggcaaga agcccacacc ttccttgctg att                                1053
```

```
<210> SEQ ID NO 185
<211> LENGTH: 990
<212> TYPE: DNA
<213> ORGANISM: Homo sapiens
<220> FEATURE:
<223> OTHER INFORMATION: PPP1CA, isoform 1

<400> SEQUENCE: 185
```

```
atgtccgaca gcgagaagct caacctggac tcgatcatcg ggcgcctgct ggaagtgcag     60

ggctcgcggc ctggcaagaa tgtacagctg acagagaacg agatccgcgg tctgtgcctg    120

aaatcccggg agatttttct gagccagccc attcttctgg agctggaggc acccctcaag    180

atctgcggtg acatacacgg ccagtactac gaccttctgc gactatttga gtatggcggt    240

ttccctcccg agagcaacta cctctttctg ggggactatg tggacagggg caagcagtcc    300

ttggagacca tctgcctgct gctggcctat aagatcaagt accccgagaa cttcttcctg    360

ctccgtggga accacgagtg tgccagcatc aaccgcatct atggtttcta cgatgagtgc    420

aagagacgct acaacatcaa actgtggaaa accttcactg actgcttcaa ctgcctgccc    480

atcgcggcca tagtggacga aaagatcttc tgctgccacg gaggcctgtc cccggacctg    540

cagtctatgg agcagattcg gcggatcatg cggcccacag atgtgcctga ccagggcctg    600

ctgtgtgacc tgctgtggtc tgaccctgac aaggacgtgc agggctgggg cgagaacgac    660

cgtggcgtct cttttacctt tggagccgag gtggtggcca agttcctcca caagcacgac    720

ttggacctca tctgccgagc acaccaggtg gtagaagacg gctacgagtt ctttgccaag    780

cggcagctgg tgacactttt ctcagctccc aactactgtg gcgagtttga caatgctggc    840

gccatgatga gtgtggacga gaccctcatg tgctctttcc agatcctcaa gcccgccgac    900

aagaacaagg ggaagtacgg gcagttcagt ggcctgaacc ctggaggccg acccatcacc    960
```

-continued

```
ccaccccgca attccgccaa agccaagaaa                                   990


<210> SEQ ID NO 186
<211> LENGTH: 1818
<212> TYPE: DNA
<213> ORGANISM: Homo sapiens
<220> FEATURE:
<223> OTHER INFORMATION: TAK1/MAP3K7, isoform 1B

<400> SEQUENCE: 186

atgtctacag cctctgccgc ctcctcctcc tcctcgtctt cggccggtga gatgatcgaa     60

gccccttccc aggtcctcaa ctttgaagag atcgactaca aggagatcga ggtggaagag    120

gttgttggaa gaggagcctt tggagttgtt tgcaaagcta agtggagagc aaaagatgtt    180

gctattaaac aaatagaaag tgaatctgag aggaaagcgt ttattgtaga gcttcggcag    240

ttatcccgtg tgaaccatcc taatattgta aagctttatg gagcctgctt gaatccagtg    300

tgtcttgtga tggaatatgc tgaaggggc tctttatata atgtgctgca tggtgctgaa    360

ccattgccat attatactgc tgcccacgca atgagttggt gtttacagtg ttcccaagga    420

gtggcttatc ttcacagcat gcaacccaaa gcgctaattc acagggacct gaaaccacca    480

aacttactgc tggttgcagg ggggacagtt ctaaaaattt gtgattttgg tacagcctgt    540

gacattcaga cacacatgac caataacaag gggagtgctg cttggatggc acctgaagtt    600

tttgaaggta gtaattacag tgaaaaatgt gacgtcttca gctggggtat tattctttgg    660

gaagtgataa cgcgtcggaa acccttttgat gagattggtg gcccagcttt ccgaatcatg    720

tgggctgttc ataatggtac tcgaccacca ctgataaaaa atttacctaa gcccattgag    780

agcctgatga ctcgttgttg gtctaaagat ccttcccagc gcccttcaat ggaggaaatt    840

gtgaaaataa tgactcactt gatgcggtac tttccaggag cagatgagcc attacagtat    900

ccttgtcagt attcagatga aggacagagc aactctgcca ccagtacagg ctcattcatg    960

gacattgctt ctacaaatac gagtaacaaa agtgacacta atatggagca agttcctgcc   1020

acaaatgata ctattaagcg cttagaatca aaattgttga aaaatcaggc aaagcaacag   1080

agtgaatctg gacgtttaag cttgggagcc tcccgtggga gcagtgtgga gagcttgccc   1140

ccaacctctg agggcaagag gatgagtgct gacatgtctg aaatagaagc taggatcgcc   1200

gcaaccacag cctattccaa gcctaaacgg ggccaccgta aaactgcttc atttggcaac   1260

attctggatg tccctgagat cgtcatatca ggcaacggac agccaagacg tagatccatc   1320

caagacttga ctgtaactgg aacagaacct ggtcaggtga gcagtaggtc atccagtccc   1380

agtgtcagaa tgattactac ctcaggacca acctcagaaa agccaactcg aagtcatcca   1440

tggacccctg atgattccac agataccaat ggatcagata actccatccc aatggcttat   1500

cttacactgg atcaccaact acagcctcta gcaccgtgcc caaactccaa agaatctatg   1560

gcagtgtttg aacagcattg taaaatggca caagaatata tgaaagttca aacagaaatt   1620

gcattgttat tacagagaaa gcaagaacta gttgcagaac tggaccagga tgaaaaggac   1680

cagcaaaata catctcgcct ggtacaggaa cataaaaagc ttttagatga aaacaaaagc   1740

ctttctactt actaccagca atgcaaaaaa caactagagg tcatcagaag tcagcagcag   1800

aaacgacaag gcacttca                                                1818


<210> SEQ ID NO 187
<211> LENGTH: 204
<212> TYPE: DNA
<213> ORGANISM: Unknown
```

<220> FEATURE:
<223> OTHER INFORMATION: CMV promoter

<400> SEQUENCE: 187
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agct 204

<210> SEQ ID NO 188
<211> LENGTH: 1212
<212> TYPE: DNA
<213> ORGANISM: Homo sapiens
<220> FEATURE:
<223> OTHER INFORMATION: Caspase-1, isoform alpha

<400> SEQUENCE: 188
atggccgaca aggtcctgaa ggagaagaga aagctgttta tccgttccat gggtgaaggt 60
acaataaatg gcttactgga tgaattatta cagacaaggg tgctgaacaa ggaagagatg 120
gagaaagtaa aacgtgaaaa tgctacagtt atggataaga cccgagcttt gattgactcc 180
gttattccga aaggggcaca ggcatgccaa atttgcatca catacatttg tgaagaagac 240
agttacctgg cagggacgct gggactctca gcagatcaaa catctggaaa ttaccttaat 300
atgcaagact ctcaaggagt actttcttcc tttccagctc ctcaggcagt gcaggacaac 360
ccagctatgc ccacatcctc aggctcagaa gggaatgtca agctttgctc cctagaagaa 420
gctcaaagga tatggaaaca aaagtcggca gagatttatc caataatgga caagtcaagc 480
cgcacacgtc ttgctctcat tatctgcaat gaagaatttg acagtattcc tagaagaact 540
ggagctgagg ttgacatcac aggcatgaca atgctgctac aaaatctggg gtacagcgta 600
gatgtgaaaa aaaatctcac tgcttcggac atgactacag agctggaggc atttgcacac 660
cgcccagagc acaagacctc tgacagcacg ttcctggtgt tcatgtctca tggtattcgg 720
gaaggcattt gtgggaagaa acactctgag caagtcccag atatactaca actcaatgca 780
atctttaaca tgttgaatac caagaactgc ccaagtttga aggacaaacc gaaggtgatc 840
atcatccagg cctgccgtgg tgacagccct ggtgtggtgt ggtttaaaga ttcagtagga 900
gtttctggaa acctatcttt accaactaca gaagagtttg aggatgatgc tattaagaaa 960
gcccacatag agaaggattt tatcgctttc tgctcttcca caccagataa tgtttcttgg 1020
agacatccca caatgggctc tgtttttatt ggaagactca ttgaacatat gcaagaatat 1080
gcctgttcct gtgatgtgga ggaaattttc cgcaaggttc gattttcatt tgagcagcca 1140
gatggtagag cgcagatgcc caccactgaa agagtgactt tgacaagatg tttctacctc 1200
ttcccaggac at 1212

<210> SEQ ID NO 189
<211> LENGTH: 885
<212> TYPE: DNA
<213> ORGANISM: Homo sapiens
<220> FEATURE:
<223> OTHER INFORMATION: cyclin-D1/CCND1

<400> SEQUENCE: 189
atggaacacc agctcctgtg ctgcgaagtg gaaaccatcc gccgcgcgta ccccgatgcc 60
aacctcctca acgaccgggt gctgcgggcc atgctgaagg cggaggagac ctgcgcgccc 120

-continued

```
tcggtgtcct acttcaaatg tgtgcagaag gaggtcctgc cgtccatgcg gaagatcgtc    180

gccacctgga tgctggaggt ctgcgaggaa cagaagtgcg aggaggaggt cttcccgctg    240

gccatgaact acctggaccg cttcctgtcg ctggagcccg tgaaaaagag ccgcctgcag    300

ctgctggggg ccacttgcat gttcgtggcc tctaagatga aggagaccat ccccctgacg    360

gccgagaagc tgtgcatcta caccgacaac tccatccggc ccgaggagct gctgcaaatg    420

gagctgctcc tggtgaacaa gctcaagtgg aacctggccg caatgacccc gcacgatttc    480

attgaacact tcctctccaa aatgccagag gcggaggaga acaaacagat catccgcaaa    540

cacgcgcaga ccttcgttgc cctctgtgcc acagatgtga agttcatttc caatccgccc    600

tccatggtgg cagcggggag cgtggtggcc gcagtgcaag gcctgaacct gaggagcccc    660

aacaacttcc tgtcctacta ccgcctcaca cgcttcctct ccagagtgat caagtgtgac    720

ccggactgcc tccgggcctg ccaggagcag atcgaagccc tgctggagtc aagcctgcgc    780

caggcccagc agaacatgga ccccaaggcc gccgaggagg aggaagagga ggaggaggag    840

gtggacctgg cttgcacacc caccgacgtg cgggacgtgg acatc                    885
```

<210> SEQ ID NO 190
<211> LENGTH: 996
<212> TYPE: DNA
<213> ORGANISM: Homo sapiens
<220> FEATURE:
<223> OTHER INFORMATION: A2b receptor (ADORA2B)

<400> SEQUENCE: 190

```
atgctgctgg agacacagga cgcgctgtac gtggcgctgg agctggtcat cgccgcgctt     60

tcggtggcgg gcaacgtgct ggtgtgcgcc gcggtgggca cggcgaacac tctgcagacg    120

cccaccaact acttcctggt gtccctggct gcggccgacg tggccgtggg gctcttcgcc    180

atcccctttg ccatcaccat cagcctgggc ttctgcactg acttctacgg ctgcctcttc    240

ctcgcctgct tcgtgctggt gctcacgcag agctccatct tcagccttct ggccgtggca    300

gtcgacagat acctggccat ctgtgtcccg ctcaggtata aagtttggt  cacggggacc    360

cgagcaagag gggtcattgc tgtcctctgg gtccttgcct ttggcatcgg attgactcca    420

ttcctggggt ggaacagtaa agacagtgcc accaacaact gcacagaacc ctgggatgga    480

accacgaatg aaagctgctg ccttgtgaag tgtctctttg agaatgtggt ccccatgagc    540

tacatggtat atttcaattt ctttgggtgt gttctgcccc cactgcttat aatgctggtg    600

atctacatta agatcttcct ggtggcctgc aggcagcttc agcgcactga gctgatggac    660

cactcgagga ccaccctcca gcgggagatc catgcagcca agtcactggc catgattgtg    720

gggatttttg ccctgtgctg gttacctgtg catgctgtta actgtgtcac tcttttccag    780

ccagctcagg gtaaaaataa gcccaagtgg gcaatgaata tggccattct tctgtcacat    840

gccaattcag ttgtcaatcc cattgtctat gcttaccgga accgagactt ccgctacact    900

tttcacaaaa ttatctccag gtatcttctc tgccaagcag atgtcaagag tgggaatggt    960

caggctgggg tacagcctgc tctcggtgtg ggccta                              996
```

<210> SEQ ID NO 191
<211> LENGTH: 1242
<212> TYPE: DNA
<213> ORGANISM: Homo sapiens
<220> FEATURE:
<223> OTHER INFORMATION: HHLA2, isoform 1

<400> SEQUENCE: 191

```
atgaaggcac agacagcact gtctttcttc ctcattctca taacatctct gagtggatct     60

caaggcatat tccctttggc tttcttcatt tatgttccta tgaatgaaca aatcgtcatt    120

ggaagacttg atgaagatat aattctccct tcttcatttg agaggggatc cgaagtcgta    180

atacactgga agtatcaaga tagctataag gttcacagtt actacaaagg cagtgaccat    240

ttggaaagcc aagatcccag atatgcaaac aggacatccc ttttctataa tgagattcaa    300

aatgggaatg cgtcgctatt tttcagaaga gtaagccttc tggacgaagg aatttacacc    360

tgctatgtag gaacagcaat tcaagtgatt acaaacaaag tggtgctaaa ggtgggagtt    420

tttctcacac ccgtgatgaa gtatgaaaag aggaacacaa acagcttctt aatatgcagc    480

gtgttaagtg tttatcctcg tccaattatc acgtggaaaa tggacaacac acctatctct    540

gaaaacaaca tggaagaaac agggtctttg gattcttttt ctattaacag cccactgaat    600

attacaggat caaattcatc ttatgaatgt acaattgaaa attcactgct gaagcaaaca    660

tggacagggc gctggacgat gaaagatggc cttcataaaa tgcaaagtga acacgtttca    720

ctctcatgtc aacctgtaaa tgattatttt tcaccaaacc aagacttcaa agttacttgg    780

tccagaatga aaagtgggac tttctctgtc ctggcttact atctgagctc ctcacaaaat    840

acaattatca atgaatcccg attctcatgg aacaaagagc tgataaacca gagtgacttc    900

tctatgaatt tgatggatct taatctttca gacagtgggg aatatttatg caatatttct    960

tcggatgaat atactttact taccatccac acagtgcatg tagaaccgag ccaagaaaca   1020

gcttcccata acaaaggctt atggattttg gtgccctctg cgattttggc agcttttctg   1080

ctgatttgga gcgtaaaatg ttgcagagcc cagctagaag ccaggaggag cagacaccct   1140

gctgatggag cccaacaaga aagatgttgt gtccctcctg gtgagcgctg tcccagtgca   1200

cccgataatg gcgaagaaaa tgtgcctctt tcaggaaaag ta                        1242
```

<210> SEQ ID NO 192
<211> LENGTH: 1128
<212> TYPE: DNA
<213> ORGANISM: Herpes simplex
<220> FEATURE:
<223> OTHER INFORMATION: herpes simplex virus thymidine kinase (HSV KT)

<400> SEQUENCE: 192

```
atggcttcgt acccctgcca tcaacacgcg tctgcgttcg accaggctgc gcgttctcgc     60

ggccatagca accgacgtac ggcgttgcgc cctcgccggc agcaagaagc cacggaagtc    120

cgcctggagc agaaaatgcc cacgctactg cgggtttata tagacggtcc tcacgggatg    180

gggaaaacca ccaccacgca actgctggtg gccctgggtt cgcgcgacga tatcgtctac    240

gtacccgagc cgatgactta ctggcaggtg ctgggggctt ccgagacaat cgcgaacatc    300

tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatgtcg gggggaggc tgggagttca catgccccgc ccccggccct caccctcatc    480

ttcgaccgcc atcccatcgc cgccctcctg tgctacccgg ccgcgcgata ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gcgagcggct tgacctggct atgctggccg cgattcgccg cgtttacggg    720

ctgcttgcca atacggtgcg gtatctgcag ggcggcgggt cgtggtggga ggattgggga    780
```

```
cagctttcgg ggacggccgt gccgccccag ggtgccgagc cccagagcaa cgcgggccca    840

cgaccccata tcggggacac gttatttacc ctgtttcggg cccccgagtt gctggccccc    900

aacggcgacc tgtataacgt gtttgcctgg gccttggacg tcttggccaa acgcctccgt    960

cccatgcacg tctttatcct ggattacgac caatcgcccg ccggctgccg ggacgccctg   1020

ctgcaactta cctccgggat ggtccagacc cacgtcacca ccccaggctc cataccgacg   1080

atctgcgacc tggcgcgcac gtttgcccgg gagatggggg aggctaac                1128
```

<210> SEQ ID NO 193
<211> LENGTH: 1173
<212> TYPE: DNA
<213> ORGANISM: Homo sapiens
<220> FEATURE:
<223> OTHER INFORMATION: Human TGF-beta isoform 1

<400> SEQUENCE: 193

```
atgccgccct ccgggctgcg gctgctgccg ctgctgctac cgctgctgtg gctactggtg     60

ctgacgcctg gccggccggc cgcgggacta tccacctgca agactatcga catggagctg    120

gtgaagcgga agcgcatcga ggccatccgc ggccagatcc tgtccaagct gcggctcgcc    180

agccccccga gccagggga ggtgccgccc ggcccgctgc ccgaggccgt gctcgccctg    240

tacaacagca cccgcgaccg ggtggccggg gagagtgcag aaccggagcc cgagcctgag    300

gccgactact acgccaagga ggtcacccgc gtgctaatgg tggaaaccca caacgaaatc    360

tatgacaagt tcaagcagag tacacacagc atatatatgt tcttcaacac atcagagctc    420

cgagaagcgg tacctgaacc cgtgttgctc tcccgggcag agctgcgtct gctgaggctc    480

aagttaaaag tggagcagca cgtggagctg taccagaaat acagcaacaa ttcctggcga    540

tacctcagca accggctgct ggcacccagc gactcgccag agtggttatc ttttgatgtc    600

accggagttg tgcggcagtg gttgagccgt ggaggggaaa ttgagggctt tcgccttagc    660

gcccactgct cctgtgacag cagggataac acactgcaag tggacatcaa cgggttcact    720

accggccgcc gaggtgacct ggccaccatt catggcatga accggccttt cctgcttctc    780

atggccaccc cgctggagag ggcccagcat ctgcaaagct cccggcaccg ccgagccctg    840

gacaccaact attgcttcag ctccacggag aagaactgct gcgtgcggca gctgtacatt    900

gacttccgca aggacctcgg ctggaagtgg atccacgagc ccaagggcta ccatgccaac    960

ttctgcctcg ggccctgccc ctacatttgg agcctggaca cgcagtacag caaggtcctg   1020

gccctgtaca accagcataa cccgggcgcc tcggcggcgc cgtgctgcgt gccgcaggcg   1080

ctggagccgc tgcccatcgt gtactacgtg ggccgcaagc ccaaggtgga gcagctgtcc   1140

aacatgatcg tgcgctcctg caagtgcagc tga                                1173
```

<210> SEQ ID NO 194
<211> LENGTH: 699
<212> TYPE: DNA
<213> ORGANISM: Homo sapiens
<220> FEATURE:
<223> OTHER INFORMATION: Human VEGF

<400> SEQUENCE: 194

```
atgaactttc tgctgtcttg ggtgcattgg agccttgcct tgctgctcta cctccaccat     60

gccaagtggt cccaggctgc acccatggca gaaggaggag ggcagaatca tcacgaagtg    120

gtgaagttca tggatgtcta tcagcgcagc tactgccatc caatcgagac cctggtggac    180

atcttccagg agtaccctga tgagatcgag tacatcttca agccatcctg tgtgcccctg    240
```

atgcgatgcg ggggctgctg caatgacgag ggcctggagt gtgtgcccac tgaggagtcc 300
aacatcacca tgcagattat gcggatcaaa cctcaccaag gccagcacat aggagagatg 360
agcttcctac agcacaacaa atgtgaatgc agaccaaaga aagatagagc aagacaagaa 420
aaaaaatcag ttcgaggaaa gggaaagggg caaaaacgaa agcgcaagaa atcccggtat 480
aagtcctgga gcgtgtacgt tggtgcccgc tgctgtctaa tgccctggag cctccctggc 540
ccccatccct gtgggccttg ctcagagcgg agaaagcatt tgtttgtaca agatccgcag 600
acgtgtaaat gttcctgcaa aaacacagac tcgcgttgca aggcgaggca gcttgagtta 660
aacgaacgta cttgcagatg tgacaagccg aggcggtga 699

<210> SEQ ID NO 195
<211> LENGTH: 19
<212> TYPE: DNA
<213> ORGANISM: Homo sapiens
<220> FEATURE:
<223> OTHER INFORMATION: Human TGF-beta isoform 1 shRNA target 1

<400> SEQUENCE: 195
gaaacccaca acgaaatct 19

<210> SEQ ID NO 196
<211> LENGTH: 19
<212> TYPE: DNA
<213> ORGANISM: Homo sapiens
<220> FEATURE:
<223> OTHER INFORMATION: Human TGF-beta isoform1 shRNA target 2

<400> SEQUENCE: 196
gtacacacag catatatat 19

<210> SEQ ID NO 197
<211> LENGTH: 19
<212> TYPE: DNA
<213> ORGANISM: Homo sapiens
<220> FEATURE:
<223> OTHER INFORMATION: Human TGF-beta isoform1 shRNA target 3

<400> SEQUENCE: 197
ctgctgaggc tcaagttaa 19

<210> SEQ ID NO 198
<211> LENGTH: 19
<212> TYPE: DNA
<213> ORGANISM: Homo sapiens
<220> FEATURE:
<223> OTHER INFORMATION: Human TGF-beta isoform1 shRNA target 4

<400> SEQUENCE: 198
gtggagctgt accagaaat 19

<210> SEQ ID NO 199
<211> LENGTH: 19
<212> TYPE: DNA
<213> ORGANISM: Homo sapiens
<220> FEATURE:
<223> OTHER INFORMATION: Human TGF-beta isoform1 shRNA target 5

<400> SEQUENCE: 199
gactcgccag agtggttat 19

<210> SEQ ID NO 200

<211> LENGTH: 19
<212> TYPE: DNA
<213> ORGANISM: Homo sapiens
<220> FEATURE:
<223> OTHER INFORMATION: Human TGF-beta isoform1 shRNA target 6

<400> SEQUENCE: 200
gagccgtgga ggggaaatt 19

<210> SEQ ID NO 201
<211> LENGTH: 19
<212> TYPE: DNA
<213> ORGANISM: Homo sapiens
<220> FEATURE:
<223> OTHER INFORMATION: Human TGF-beta isoform1 shRNA target 7

<400> SEQUENCE: 201
cctgtgacag cagggataa 19

<210> SEQ ID NO 202
<211> LENGTH: 19
<212> TYPE: DNA
<213> ORGANISM: Homo sapiens
<220> FEATURE:
<223> OTHER INFORMATION: Human TGF-beta isoform1 shRNA target 8

<400> SEQUENCE: 202
gccctggaca ccaactatt 19

<210> SEQ ID NO 203
<211> LENGTH: 19
<212> TYPE: DNA
<213> ORGANISM: Homo sapiens
<220> FEATURE:
<223> OTHER INFORMATION: Human TGF-beta isoform1 shRNA target 9

<400> SEQUENCE: 203
ccctgtacaa ccagcataa 19

<210> SEQ ID NO 204
<211> LENGTH: 19
<212> TYPE: DNA
<213> ORGANISM: Homo sapiens
<220> FEATURE:
<223> OTHER INFORMATION: Human VEGF shRNA target 1

<400> SEQUENCE: 204
gagatcgagt acatcttca 19

<210> SEQ ID NO 205
<211> LENGTH: 19
<212> TYPE: DNA
<213> ORGANISM: Homo sapiens
<220> FEATURE:
<223> OTHER INFORMATION: Human VEGF shRNA target 2

<400> SEQUENCE: 205
gcagattatg cggatcaaa 19

<210> SEQ ID NO 206
<211> LENGTH: 19
<212> TYPE: DNA
<213> ORGANISM: Homo sapiens
<220> FEATURE:
<223> OTHER INFORMATION: Human VEGF shRNA target 3

<400> SEQUENCE: 206
gatagagcaa gacaagaaa 19

<210> SEQ ID NO 207
<211> LENGTH: 19
<212> TYPE: DNA
<213> ORGANISM: Homo sapiens
<220> FEATURE:
<223> OTHER INFORMATION: Human VEGF shRNA target 4

<400> SEQUENCE: 207
ggagaaagca tttgtttgt 19

<210> SEQ ID NO 208
<211> LENGTH: 19
<212> TYPE: DNA
<213> ORGANISM: Homo sapiens
<220> FEATURE:
<223> OTHER INFORMATION: Human VEGF shRNA target 5

<400> SEQUENCE: 208
gatccgcaga cgtgtaaat 19

<210> SEQ ID NO 209
<211> LENGTH: 19
<212> TYPE: DNA
<213> ORGANISM: Homo sapiens
<220> FEATURE:
<223> OTHER INFORMATION: Human VEGF shRNA target 6

<400> SEQUENCE: 209
gcgaggcagc ttgagttaa 19

<210> SEQ ID NO 210
<211> LENGTH: 3888
<212> TYPE: DNA
<213> ORGANISM: Artificial Sequence
<220> FEATURE:
<223> OTHER INFORMATION: ARI-134

<400> SEQUENCE: 210
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg ccacactgta tggactattc tagagatagt ccatacagtg 840
tggctttttt cgacagatct ggcgcgccat agtggccagc ggccgcaggt aagccagccc 900

-continued aggcctcgcc ctccagctca aggcgggaca ggtgccctag agtagcctgc atccagggac 960
aggccccagc cgggtgctga cacgtccacc tccatctctt cctcaggtct gcccgggtgg 1020
catccctgtg accccctccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560
tatatcttgt ggaaaggacg aaactaggcc gactacaagc gaattatcta gagtaattcg 1620
cttgtagtcg gctttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800
actgccaagt gggcagttta ccgtaaatag tccacccatt gacgtcaatg gaaagtccct 1860
attggcgtta ctatgggaac atacgtcatt attgacgtca atgggcgggg gtcgttgggc 1920
ggtcagccag gcgggccatt taccgtaagt tatgtaacgc ggaactccat atatgggcta 1980
tgaactaatg accccgtaat tgattactat taataactag acccagcttt cttgtacaaa 2040
gttggcatta taagaaagca ttgcttatca atttgttgca acgaacaggt cactatcagt 2100
caaaataaaa tcattatttg ccatccagct gatatcccct atagtgagtc gtattacatg 2160
gtcatagctg tttcctggca gctctggccc gtgtctcaaa atctctgatg ttacattgca 2220
caagataaaa atatatcatc atgaacaata aaactgtctg cttacataaa cagtaataca 2280
aggggtgtta tgagccatat tcaacgggaa acgtcgaggc cgcgattaaa ttccaacatg 2340
gatgctgatt tatatgggta taaatgggct cgcgataatg tcgggcaatc aggtgcgaca 2400
atctatcgct tgtatgggaa gcccgatgcg ccagagttgt ttctgaaaca tggcaaaggt 2460
agcgttgcca atgatgttac agatgagatg gtcagactaa actggctgac ggaatttatg 2520
cctcttccga ccatcaagca ttttatccgt actcctgatg atgcatggtt actcaccact 2580
gcgatccccg gaaaaacagc attccaggta ttagaagaat atcctgattc aggtgaaaat 2640
attgttgatg cgctggcagt gttcctgcgc cggttgcatt cgattcctgt ttgtaattgt 2700
ccttttaaca gcgatcgcgt atttcgtctc gctcaggcgc aatcacgaat gaataacggt 2760
ttggttgatg cgagtgattt tgatgacgag cgtaatggct ggcctgttga acaagtctgg 2820
aaagaaatgc ataaactttt gccattctca ccggattcag tcgtcactca tggtgatttc 2880
tcacttgata accttatttt tgacgagggg aaattaatag gttgtattga tgttggacga 2940
gtcggaatcg cagaccgata ccaggatctt gccatcctat ggaactgcct cggtgagttt 3000
tctccttcat tacagaaacg gctttttcaa aaatatggta ttgataatcc tgatatgaat 3060
aaattgcagt ttcatttgat gctcgatgag tttttctaat cagaattggt taattggttg 3120
taacactggc agagcattac gctgacttga cgggacggcg caagctcatg accaaaatcc 3180
cttaacgtga gttacgcgtc gttccactga gcgtcagacc ccgtagaaaa gatcaaagga 3240
tcttcttgag atcctttttt tctgcgcgta atctgctgct tgcaaacaaa aaaaccaccg 3300

```
ctaccagcgg tggtttgttt gccggatcaa gagctaccaa ctctttttcc gaaggtaact   3360

ggcttcagca gagcgcagat accaaatact gtccttctag tgtagccgta gttaggccac   3420

cacttcaaga actctgtagc accgcctaca tacctcgctc tgctaatcct gttaccagtg   3480

gctgctgcca gtggcgataa gtcgtgtctt accgggttgg actcaagacg atagttaccg   3540

gataaggcgc agcggtcggg ctgaacgggg ggttcgtgca cacagcccag cttggagcga   3600

acgacctaca ccgaactgag atacctacag cgtgagcatt gagaaagcgc cacgcttccc   3660

gaagggagaa aggcggacag gtatccggta agcggcaggg tcggaacagg agagcgcacg   3720

agggagcttc cagggggaaa cgcctggtat ctttatagtc ctgtcgggtt tcgccacctc   3780

tgacttgagc gtcgattttt gtgatgctcg tcaggggggc ggagcctatg gaaaaacgcc   3840

agcaacgcgg cctttttacg gttcctggcc ttttgctggc cttttgct               3888


<210> SEQ ID NO 211
<211> LENGTH: 3888
<212> TYPE: DNA
<213> ORGANISM: Artificial Sequence
<220> FEATURE:
<223> OTHER INFORMATION: ARI-135

<400> SEQUENCE: 211

ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga gaattggtac catatttgca tgtcgctatg    720

tgttctggga aatcaccata aacgtgaaat gtctttggat ttgggaatct tataagttct    780

gtatgagacc actccctagg agctggctcc tggtgaattc tagagattca ccaggagcca    840

gctctttttt cgacagatct ggcgcgccat agtggccagc ggccgcaggt aagccagccc    900

aggcctcgcc ctccagctca aggcgggaca ggtgccctag agtagcctgc atccagggac    960

aggccccagc cgggtgctga cacgtccacc tccatctctt cctcaggtct gcccgggtgg   1020

catccctgtg accccctccc agtgcctctc ctggccctgg aagttgccac tccagtgccc   1080

accagccttg tcctaataaa attaagttgc atcattttgt ctgactaggt gtccttctat   1140

aatattatgg ggtggagggg ggtggtatgg agcaaggggc ccaagttaac ttgtttattg   1200

cagcttataa tggttacaaa taaagcaata gcatcacaaa tttcacaaat aaagcatttt   1260

tttcactgca ttctagttgt ggtttgtcca aactcatcaa tgtatcttat catgtctgga   1320

tccaaggtcg ggcaggaaga gggcctattt cccatgattc cttcatattt gcatatacga   1380

tacaaggctg ttagagagat aattagaatt aatttgactg taaacacaaa gatattagta   1440
```

-continued

```
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggcc gactacaagc gaattatcta gagtaattcg   1620
cttgtagtcg gctttttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc cagggggaaa cgcctggtat ctttatagtc ctgtcgggtt tcgccacctc   3780
tgacttgagc gtcgattttt gtgatgctcg tcaggggggc ggagcctatg gaaaaacgcc   3840
```

-continued agcaacgcgg cctttttacg gttcctggcc ttttgctggc cttttgct 3888

<210> SEQ ID NO 212
<211> LENGTH: 3888
<212> TYPE: DNA
<213> ORGANISM: Artificial Sequence
<220> FEATURE:
<223> OTHER INFORMATION: ARI-136

<400> SEQUENCE: 212
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg cagctggaat tctttctatc tagagtagaa agaattccag 840
ctgctttttt cgacagatct ggcgcgccat agtggccagc ggccgcaggt aagccagccc 900
aggcctcgcc ctccagctca aggcgggaca ggtgccctag agtagcctgc atccagggac 960
aggccccagc cgggtgctga cacgtccacc tccatctctt cctcaggtct gcccgggtgg 1020
catccctgtg acccctcccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560
tatatcttgt ggaaaggacg aaactaggcc gactacaagc gaattatcta gagtaattcg 1620
cttgtagtcg gctttttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800
actgccaagt gggcagttta ccgtaaatag tccacccatt gacgtcaatg gaaagtccct 1860
attggcgtta ctatgggaac atacgtcatt attgacgtca atgggcgggg gtcgttgggc 1920
ggtcagccag gcgggccatt taccgtaagt tatgtaacgc ggaactccat atatgggcta 1980

-continued

```
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct                3888
```

<210> SEQ ID NO 213
<211> LENGTH: 3890
<212> TYPE: DNA
<213> ORGANISM: Artificial Sequence
<220> FEATURE:
<223> OTHER INFORMATION: ARI-137

<400> SEQUENCE: 213

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
```

```
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg atgtgacctt ctacaagatt ctagagatct tgtagaaggt    840
cacatctttt ttcgacagat ctggcgcgcc atagtggcca gcggccgcag gtaagccagc    900
ccaggcctcg ccctccagct caaggcggga caggtgccct agagtagcct gcatccaggg    960
acaggcccca gccgggtgct gacacgtcca cctccatctc ttcctcaggt ctgcccgggt   1020
ggcatccctg tgacccctcc ccagtgcctc tcctggccct ggaagttgcc actccagtgc   1080
ccaccagcct tgtcctaata aaattaagtt gcatcatttt gtctgactag gtgtccttct   1140
ataatattat ggggtggagg ggggtggtat ggagcaaggg gcccaagtta acttgtttat   1200
tgcagcttat aatggttaca aataaagcaa tagcatcaca aatttcacaa ataaagcatt   1260
tttttcactg cattctagtt gtggtttgtc caaactcatc aatgtatctt atcatgtctg   1320
gatccaaggt cgggcaggaa gagggcctat ttcccatgat tccttcatat ttgcatatac   1380
gatacaaggc tgttagagag ataattagaa ttaatttgac tgtaaacaca aagatattag   1440
tacaaaatac gtgacgtaga aagtaataat ttcttgggta gtttgcagtt ttaaaattat   1500
gttttaaaat ggactatcat atgcttaccg taacttgaaa gtatttcgat ttcttggctt   1560
tatatatctt gtggaaagga cgaaactagg ccgactacaa gcgaattatc tagagtaatt   1620
cgcttgtagt cggctttttt cgagtagcta gagaattcat ggtaatagcg atgactaata   1680
cgtagatgta ctgccaagta ggaaagtccc ataaggtcat gtactgggca taatgccagg   1740
cgggccattt accgtcattg acgtcaatag gggcgtact tggcatatga tacacttgat   1800
gtactgccaa gtgggcagtt taccgtaaat agtccaccca ttgacgtcaa tggaaagtcc   1860
ctattggcgt tactatggga acatacgtca ttattgacgt caatgggcgg gggtcgttgg   1920
gcggtcagcc aggcgggcca tttaccgtaa gttatgtaac gcggaactcc atatatgggc   1980
tatgaactaa tgaccccgta attgattact attaataact agacccagct ttcttgtaca   2040
aagttggcat tataagaaag cattgcttat caatttgttg caacgaacag gtcactatca   2100
gtcaaaataa aatcattatt tgccatccag ctgatatccc ctatagtgag tcgtattaca   2160
tggtcatagc tgtttcctgg cagctctggc ccgtgtctca aaatctctga tgttacattg   2220
cacaagataa aaatatatca tcatgaacaa taaaactgtc tgcttacata aacagtaata   2280
caaggggtgt tatgagccat attcaacggg aaacgtcgag gccgcgatta aattccaaca   2340
tggatgctga tttatatggg tataaatggg ctcgcgataa tgtcgggcaa tcaggtgcga   2400
caatctatcg cttgtatggg aagcccgatg cgccagagtt gtttctgaaa catggcaaag   2460
gtagcgttgc caatgatgtt acagatgaga tggtcagact aaactggctg acggaattta   2520
```

tgcctcttcc gaccatcaag cattttatcc gtactcctga tgatgcatgg ttactcacca 2580
ctgcgatccc cggaaaaaca gcattccagg tattagaaga atatcctgat tcaggtgaaa 2640
atattgttga tgcgctggca gtgttcctgc gccggttgca ttcgattcct gtttgtaatt 2700
gtccttttaa cagcgatcgc gtatttcgtc tcgctcaggc gcaatcacga atgaataacg 2760
gtttggttga tgcgagtgat tttgatgacg agcgtaatgg ctggcctgtt gaacaagtct 2820
ggaaagaaat gcataaactt ttgccattct caccggattc agtcgtcact catggtgatt 2880
tctcacttga taaccttatt tttgacgagg ggaaattaat aggttgtatt gatgttggac 2940
gagtcggaat cgcagaccga taccaggatc ttgccatcct atggaactgc ctcggtgagt 3000
tttctccttc attacagaaa cggctttttc aaaaatatgg tattgataat cctgatatga 3060
ataaattgca gtttcatttg atgctcgatg agtttttcta atcagaattg gttaattggt 3120
tgtaacactg gcagagcatt acgctgactt gacgggacgg cgcaagctca tgaccaaaat 3180
cccttaacgt gagttacgcg tcgttccact gagcgtcaga ccccgtagaa aagatcaaag 3240
gatcttcttg agatcctttt tttctgcgcg taatctgctg cttgcaaaca aaaaaaccac 3300
cgctaccagc ggtggtttgt ttgccggatc aagagctacc aactcttttt ccgaaggtaa 3360
ctggcttcag cagagcgcag ataccaaata ctgtccttct agtgtagccg tagttaggcc 3420
accacttcaa gaactctgta gcaccgccta catacctcgc tctgctaatc ctgttaccag 3480
tggctgctgc cagtggcgat aagtcgtgtc ttaccgggtt ggactcaaga cgatagttac 3540
cggataaggc gcagcggtcg ggctgaacgg ggggttcgtg cacacagccc agcttggagc 3600
gaacgaccta caccgaactg agatacctac agcgtgagca ttgagaaagc gccacgcttc 3660
ccgaagggag aaaggcggac aggtatccgg taagcggcag ggtcggaaca ggagagcgca 3720
cgagggagct tccaggggga aacgcctggt atctttatag tcctgtcggg tttcgccacc 3780
tctgacttga gcgtcgattt ttgtgatgct cgtcaggggg gcggagccta tggaaaaacg 3840
ccagcaacgc ggccttttta cggttcctgg ccttttgctg gccttttgct 3890

<210> SEQ ID NO 214
<211> LENGTH: 3379
<212> TYPE: DNA
<213> ORGANISM: Artificial Sequence
<220> FEATURE:
<221> NAME/KEY: misc_feature
<222> LOCATION: (1018)...(1038)
<223> OTHER INFORMATION: n may be any nucleotide
<220> FEATURE:
<221> NAME/KEY: misc_feature
<222> LOCATION: (1060)...(1080)
<223> OTHER INFORMATION: n may be any nucleotide
<220> FEATURE:
<221> NAME/KEY: source
<222> LOCATION: (1)...(3379)
<223> OTHER INFORMATION: ARI-205

<400> SEQUENCE: 214
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420

```
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg ctttttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agtccggatc aacgccctag gtttatgttt ggatgaactg acatacgcgt atccgtcnnn   1020
nnnnnnnnnn nnnnnnnngt agtgaaatat atattaaacn nnnnnnnnnn nnnnnnnnnn   1080
tacggtaacg cggaattcgc aactatttta tcaatttttt gcgtcgactc gagtagctag   1140
agaattcatg gtaatagcga tgactaatac gtagatgtac tgccaagtag gaaagtccca   1200
taaggtcatg tactgggcat aatgccaggc gggccattta ccgtcattga cgtcaatagg   1260
gggcgtactt ggcatatgat acacttgatg tactgccaag tgggcagttt accgtaaata   1320
gtccacccat tgacgtcaat ggaaagtccc tattggcgtt actatgggaa catacgtcat   1380
tattgacgtc aatgggcggg ggtcgttggg cggtcagcca ggcgggccat ttaccgtaag   1440
ttatgtaacg cggaactcca tatatgggct atgaactaat gaccccgtaa ttgattacta   1500
ttaataacta gacccagctt tcttgtacaa agttggcatt ataagaaagc attgcttatc   1560
aatttgttgc aacgaacagg tcactatcag tcaaaataaa atcattattt gccatccagc   1620
tgatatcccc tatagtgagt cgtattacat ggtcatagct gtttcctggc agctctggcc   1680
cgtgtctcaa aatctctgat gttacattgc acaagataaa aatatatcat catgaacaat   1740
aaaactgtct gcttacataa acagtaatac aaggggtgtt atgagccata ttcaacggga   1800
aacgtcgagg ccgcgattaa attccaacat ggatgctgat ttatatgggt ataaatgggc   1860
tcgcgataat gtcgggcaat caggtgcgac aatctatcgc ttgtatggga agcccgatgc   1920
gccagagttg tttctgaaac atggcaaagg tagcgttgcc aatgatgtta cagatgagat   1980
ggtcagacta aactggctga cggaatttat gcctcttccg accatcaagc attttatccg   2040
tactcctgat gatgcatggt tactcaccac tgcgatcccc ggaaaaacag cattccaggt   2100
attagaagaa tatcctgatt caggtgaaaa tattgttgat gcgctggcag tgttcctgcg   2160
ccggttgcat tcgattcctg tttgtaattg tccttttaac agcgatcgcg tatttcgtct   2220
cgctcaggcg caatcacgaa tgaataacgg tttggttgat gcgagtgatt ttgatgacga   2280
gcgtaatggc tggcctgttg aacaagtctg gaaagaaatg cataaacttt tgccattctc   2340
accggattca gtcgtcactc atggtgattt ctcacttgat aaccttattt ttgacgaggg   2400
gaaattaata ggttgtattg atgttggacg agtcggaatc gcagaccgat accaggatct   2460
tgccatccta tggaactgcc tcggtgagtt ttctccttca ttacagaaac ggctttttca   2520
aaaatatggt attgataatc ctgatatgaa taaattgcag tttcatttga tgctcgatga   2580
gtttttctaa tcagaattgg ttaattggtt gtaacactgg cagagcatta cgctgacttg   2640
acgggacggc gcaagctcat gaccaaaatc ccttaacgtg agttacgcgt cgttccactg   2700
agcgtcagac cccgtagaaa agatcaaagg atcttcttga gatccttttt ttctgcgcgt   2760
```

```
aatctgctgc ttgcaaacaa aaaaaccacc gctaccagcg gtggtttgtt tgccggatca   2820

agagctacca actctttttc cgaaggtaac tggcttcagc agagcgcaga taccaaatac   2880

tgtccttcta gtgtagccgt agttaggcca ccacttcaag aactctgtag caccgcctac   2940

atacctcgct ctgctaatcc tgttaccagt ggctgctgcc agtggcgata agtcgtgtct   3000

taccgggttg gactcaagac gatagttacc ggataaggcg cagcggtcgg gctgaacggg   3060

gggttcgtgc acacagccca gcttggagcg aacgacctac accgaactga gatacctaca   3120

gcgtgagcat tgagaaagcg ccacgcttcc cgaagggaga aaggcggaca ggtatccggt   3180

aagcggcagg gtcggaacag gagagcgcac gagggagctt ccagggggaa acgcctggta   3240

tctttatagt cctgtcgggt ttcgccacct ctgacttgag cgtcgatttt tgtgatgctc   3300

gtcagggggg cggagcctat ggaaaaacgc cagcaacgcg gcctttttac ggttcctggc   3360

cttttgctgg ccttttgct                                                  3379
```

```
<210> SEQ ID NO 215
<211> LENGTH: 4744
<212> TYPE: DNA
<213> ORGANISM: Artificial Sequence
<220> FEATURE:
<221> NAME/KEY: misc_feature
<222> LOCATION: (3377)...(3398)
<223> OTHER INFORMATION: n may be any nucleotide
<220> FEATURE:
<221> NAME/KEY: misc_feature
<222> LOCATION: (3418)...(3439)
<223> OTHER INFORMATION: n may be any nucleotide
<220> FEATURE:
<221> NAME/KEY: source
<222> LOCATION: (1)...(4744)
<223> OTHER INFORMATION: ARI-206

<400> SEQUENCE: 215

aacatgtgag caaaaggcca gcaaaaggcc aggaaccgta aaaaggccgc gttgctggcg     60

tttttccata ggctccgccc ccctgacgag catcacaaaa atcgacgctc aagtcagagg    120

tggcgaaacc cgacaggact ataaagatac caggcgtttc cccctggaag ctccctcgtg    180

cgctctcctg ttccgaccct gccgcttacc ggatacctgt ccgcctttct cccttcggga    240

agcgtggcgc tttctcaatg ctcacgctgt aggtatctca gttcggtgta ggtcgttcgc    300

tccaagctgg gctgtgtgca cgaacccccc gttcagcccg accgctgcgc cttatccggt    360

aactatcgtc ttgagtccaa cccggtaaga cacgacttat cgccactggc agcagccact    420

ggtaacagga ttagcagagc gaggtatgta ggcggtgcta cagagttctt gaagtggtgg    480

cctaactacg gctacactag aaggacagta tttggtatct gcgctctgct gaagccagtt    540

accttcggaa aaagagttgg tagctcttga tccggcaaac aaaccaccgc tggtagcggt    600

ggtttttttg tttgcaagca gcagattacg cgcagaaaaa aaggatctca agaagatcct    660

ttgatctttt ctacggggtc tgacgctcag tggaacgacg cgtaactcac gttaagggat    720

tttggtcatg agcttgcgcc gtcccgtcaa gtcagcgtaa tgctctgcca gtgttacaac    780

caattaacca attctgatta gaaaaactca tcgagcatca aatgaaactg caatttattc    840

atatcaggat tatcaatacc atatttttga aaaagccgtt tctgtaatga aggagaaaac    900

tcaccgaggc agttccatag gatggcaaga tcctggtatc ggtctgcgat tccgactcgt    960

ccaacatcaa tacaacctat taatttcccc tcgtcaaaaa taaggttatc aagtgagaaa   1020

tcaccatgag tgacgactga atccggtgag aatggcaaaa gtttatgcat ttctttccag   1080

acttgttcaa caggccagcc attacgctcg tcatcaaaat cactcgcatc aaccaaaccg   1140
```

ttattcattc gtgattgcgc ctgagcgaga cgaaatacgc gatcgctgtt aaaaggacaa 1200
ttacaaacag gaatcgaatg caaccggcgc aggaacactg ccagcgcatc aacaatattt 1260
tcacctgaat caggatattc ttctaatacc tggaatgctg tttttccggg gatcgcagtg 1320
gtgagtaacc atgcatcatc aggagtacgg ataaaatgct tgatggtcgg aagaggcata 1380
aattccgtca gccagtttag tctgaccatc tcatctgtaa catcattggc aacgctacct 1440
ttgccatgtt tcagaaacaa ctctggcgca tcgggcttcc catacaagcg atagattgtc 1500
gcacctgatt gcccgacatt atcgcgagcc catttatacc catataaatc agcatccatg 1560
ttggaattta atcgcggcct cgacgtttcc cgttgaatat ggctcataac accccttgta 1620
ttactgttta tgtaagcaga cagttttatt gttcatgatg atatattttt atcttgtgca 1680
atgtaacatc agagattttg agacacgggc cagagctgcc aggaaacagc tatgaccatg 1740
taatacgact cactataggg gatatcagct ggatggcaaa taatgatttt attttgactg 1800
atagtgacct gttcgttgca acaaattgat aagcaatgct ttcttataat gccaactttg 1860
tacaagaaag ctgggtctag ttattaatag taatcaatta cggggtcatt agttcatagc 1920
ccatatatgg agttccgcgt tacataactt acggtaaatg gcccgcctgg ctgaccgccc 1980
aacgaccccc gcccattgac gtcaataatg acgtatgttc ccatagtaac gccaataggg 2040
actttccatt gacgtcaatg ggtggactat ttacggtaaa ctgcccactt ggcagtacat 2100
caagtgtatc atatgccaag tacgccccct attgacgtca atgacggtaa atggcccgcc 2160
tggcattatg cccagtacat gaccttatgg gactttccta cttggcagta catctacgta 2220
ttagtcatcg ctattaccat ggtgatgcgg ttttggcagt acatcaatgg gcgtggatag 2280
cggtttgact cacggggatt tccaagtctc caccccattg acgtcaatgg gagtttgttt 2340
tggcaccaaa atcaacggga ctttccaaaa tgtcgtaaca actccgcccc attgacgcaa 2400
atgggcggta ggcgtgtacg gtgggaggtc tatataagca gagctctctg gctaactaga 2460
gaacccactg cttactggct tatcgaaatt aatacgactc actataggga gacccaagct 2520
tagatctgtt tccggtcgcc accatgagcg agctgatcaa ggagaacatg cacatgaagc 2580
tgtacatgga gggcaccgtg aacaaccacc acttcaagtg cacatccgag ggcgaaggca 2640
agccctacga gggcacccag accatgaaga tcaaggtggt cgagggcggc cctctcccct 2700
tcgccttcga catcctggct accagcttca tgtacggcag caaagccttc atcaaccaca 2760
cccagggcat ccccgacttc tttaagcagt ccttccctga gggcttcaca tgggagagaa 2820
tcaccacata cgaagacggg ggcgtgctga ccgctaccca ggacaccagc ttccagaacg 2880
gctgcatcat ctacaacgtc aagatcaacg gggtgaactt cccatccaac ggccctgtga 2940
tgcagaagaa aacacgcggc tgggaggcca acaccgagat gctgtacccc gctgacggcg 3000
gcctgagagg ccacagccag atggccctga agctcgtggg cgggggctac ctgcactgct 3060
ccttcaagac cacatacaga tccaagaaac ccgctaagaa cctcaagatg cccggcttcc 3120
acttcgtgga ccacagactg gaaagaatca aggaggccga caaagagacc tacgtcgagc 3180
agcacgagat ggctgtggcc aagtactgcg acctccctag caaactgggg cacagataat 3240
cgatagtttg tttgaatgag gcttcagtac tttacagaat cgttgcctgc acatcttgga 3300
aacacttgct gggattactt cttcaggtta acccaacaga aggctcgaga aggtatattg 3360
ctgttgacag tgagcgnnnn nnnnnnnnnn nnnnnnnnta gtgaagccac agatgtannn 3420
nnnnnnnnnn nnnnnnnnnt gcctactgcc tcggaattca aggggctact ttaggagcaa 3480
ttatcttgtt tactaaaact gaataccttg ctatctcttt gatacatttt tacaaagctg 3540
aattaaaatg gtataaatta aatcactttt ttcaattctc tagaggtacc gcatgcgtac 3600
gtggccagcg gccgcaggta agccagccca ggcctcgccc tccagctcaa ggcgggacag 3660
gtgccctaga gtagcctgca tccagggaca ggccccagcc gggtgctgac acgtccacct 3720
ccatctcttc ctcaggtctg cccgggtggc atccctgtga cccctcccca gtgcctctcc 3780
tggccctgga agttgccact ccagtgccca ccagccttgt cctaataaaa ttaagttgca 3840
tcattttgtc tgactaggtg tccttctata atattatggg gtggaggggg gtggtatgga 3900
gcaaggggcc caagttaact tgtttattgc agcttataat ggttacaaat aaagcaatag 3960
catcacaaat ttcacaaata aagcattttt ttcactgcat tctagttgtg gtttgtccaa 4020
actcatcaat gtatcttatc atgtctggat ccagtcgact gaattggttc ctttaaagcc 4080
tgcttttttg tacaaagttg gcattataaa aaagcattgc tcatcaattt gttgcaacga 4140
acaggtcact atcagtcaaa ataaaatcat tatttggggc ccgagcttaa gactggccgt 4200
cgttttacaa cgtcgtgact gggaaaacat ccatgctagc gttaacgcga gagtagggaa 4260
ctgccaggca tcaaataaaa cgaaaggctc agtcggaaga ctgggccttt cgttttatct 4320
gttgtttgtc ggtgaacgct ctcctgagta ggacaaatcc gccgggagcg gatttgaacg 4380
ttgtgaagca acggcccgga gggtggcggg caggacgccc gccataaact gccaggcatc 4440
aaactaagca gaaggccatc ctgacggatg gcctttttgc gtttctacaa actcttcctg 4500
gctagcggta cgcgtattaa ttgcgttgcg ctcactgccc gctttccagt cgggaaacct 4560
gtcgtgccag ctgcattaat gaatcggcca acgcgcgggg agaggcggtt tgcgtattgg 4620
gcgctcttcc gcttcctcgc tcactgactc gctgcgctcg gtcgttcggc tgcggcgagc 4680
ggtatcagct cactcaaagg cggtaatacg gttatccaca gaatcagggg ataacgcagg 4740
aaag 4744

<210> SEQ ID NO 216
<211> LENGTH: 3377
<212> TYPE: DNA
<213> ORGANISM: Artificial Sequence
<220> FEATURE:
<221> NAME/KEY: misc_feature
<222> LOCATION: (1018)...(1036)
<223> OTHER INFORMATION: n may be any nucleotide
<220> FEATURE:
<221> NAME/KEY: misc_feature
<222> LOCATION: (1058)...(1078)
<223> OTHER INFORMATION: n may be any nucleotide
<220> FEATURE:
<221> NAME/KEY: source
<222> LOCATION: (1)...(3377)
<223> OTHER INFORMATION: ARI-207

<400> SEQUENCE: 216
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480

```
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agtccggatc aacgccctag gtttatgttt ggatgaactg acatacgcgt atccgtcnnn   1020
nnnnnnnnnn nnnnnngtag tgaaatatat attaaacnnn nnnnnnnnnn nnnnnnnnta   1080
cggtaacgcg gaattcgcaa ctattttatc aatttttgc gtcgactcga gtagctagag   1140
aattcatggt aatagcgatg actaatacgt agatgtactg ccaagtagga aagtcccata   1200
aggtcatgta ctgggcataa tgccaggcgg gccatttacc gtcattgacg tcaatagggg   1260
gcgtacttgg catatgatac acttgatgta ctgccaagtg ggcagtttac cgtaaatagt   1320
ccacccattg acgtcaatgg aaagtcccta ttggcgttac tatgggaaca tacgtcatta   1380
ttgacgtcaa tgggcggggg tcgttgggcg gtcagccagg cgggccattt accgtaagtt   1440
atgtaacgcg gaactccata tatgggctat gaactaatga ccccgtaatt gattactatt   1500
aataactaga cccagctttc ttgtacaaag ttggcattat aagaaagcat tgcttatcaa   1560
tttgttgcaa cgaacaggtc actatcagtc aaaataaaat cattatttgc catccagctg   1620
atatccccta tagtgagtcg tattacatgg tcatagctgt ttcctggcag ctctggcccg   1680
tgtctcaaaa tctctgatgt tacattgcac aagataaaaa tatatcatca tgaacaataa   1740
aactgtctgc ttacataaac agtaatacaa ggggtgttat gagccatatt caacgggaaa   1800
cgtcgaggcc gcgattaaat tccaacatgg atgctgattt atatgggtat aaatgggctc   1860
gcgataatgt cgggcaatca ggtgcgacaa tctatcgctt gtatgggaag cccgatgcgc   1920
cagagttgtt tctgaaacat ggcaaaggta gcgttgccaa tgatgttaca gatgagatgg   1980
tcagactaaa ctggctgacg gaatttatgc ctcttccgac catcaagcat tttatccgta   2040
ctcctgatga tgcatggtta ctcaccactg cgatccccgg aaaaacagca ttccaggtat   2100
tagaagaata tcctgattca ggtgaaaata ttgttgatgc gctggcagtg ttcctgcgcc   2160
ggttgcattc gattcctgtt tgtaattgtc cttttaacag cgatcgcgta tttcgtctcg   2220
ctcaggcgca atcacgaatg aataacggtt tggttgatgc gagtgatttt gatgacgagc   2280
gtaatggctg gcctgttgaa caagtctgga aagaaatgca taaacttttg ccattctcac   2340
cggattcagt cgtcactcat ggtgatttct cacttgataa ccttattttt gacgagggga   2400
aattaatagg ttgtattgat gttggacgag tcggaatcgc agaccgatac caggatcttg   2460
ccatcctatg gaactgcctc ggtgagtttt ctccttcatt acagaaacgg ctttttcaaa   2520
aatatggtat tgataatcct gatatgaata aattgcagtt tcatttgatg ctcgatgagt   2580
ttttctaatc agaattggtt aattggttgt aacactggca gagcattacg ctgacttgac   2640
gggacggcgc aagctcatga ccaaaatccc ttaacgtgag ttacgcgtcg ttccactgag   2700
cgtcagaccc cgtagaaaag atcaaaggat cttcttgaga tcctttttt ctgcgcgtaa   2760
tctgctgctt gcaaacaaaa aaaccaccgc taccagcggt ggtttgtttg ccggatcaag   2820
```

```
agctaccaac tctttttccg aaggtaactg gcttcagcag agcgcagata ccaaatactg   2880

tccttctagt gtagccgtag ttaggccacc acttcaagaa ctctgtagca ccgcctacat   2940

acctcgctct gctaatcctg ttaccagtgg ctgctgccag tggcgataag tcgtgtctta   3000

ccgggttgga ctcaagacga tagttaccgg ataaggcgca gcggtcgggc tgaacggggg   3060

gttcgtgcac acagcccagc ttggagcgaa cgacctacac cgaactgaga tacctacagc   3120

gtgagcattg agaaagcgcc acgcttcccg aagggagaaa ggcggacagg tatccggtaa   3180

gcggcagggt cggaacagga gagcgcacga gggagcttcc agggggaaac gcctggtatc   3240

tttatagtcc tgtcgggttt cgccacctct gacttgagcg tcgatttttg tgatgctcgt   3300

caggggggcg gagcctatgg aaaaacgcca gcaacgcggc ctttttacgg ttcctggcct   3360

tttgctggcc ttttgct                                                  3377
```

<210> SEQ ID NO 217
<211> LENGTH: 4738
<212> TYPE: DNA
<213> ORGANISM: Artificial Sequence
<220> FEATURE:
<221> NAME/KEY: misc_feature
<222> LOCATION: (3377)...(3395)
<223> OTHER INFORMATION: n may be any nucleotide
<220> FEATURE:
<221> NAME/KEY: misc_feature
<222> LOCATION: (3415)...(3433)
<223> OTHER INFORMATION: n may be any nucleotide
<220> FEATURE:
<221> NAME/KEY: source
<222> LOCATION: (1)...(4738)
<223> OTHER INFORMATION: ARI-208

<400> SEQUENCE: 217

```
aacatgtgag caaaaggcca gcaaaaggcc aggaaccgta aaaaggccgc gttgctggcg     60

tttttccata ggctccgccc ccctgacgag catcacaaaa atcgacgctc aagtcagagg    120

tggcgaaacc cgacaggact ataaagatac caggcgtttc cccctggaag ctccctcgtg    180

cgctctcctg ttccgaccct gccgcttacc ggatacctgt ccgcctttct cccttcggga    240

agcgtggcgc tttctcaatg ctcacgctgt aggtatctca gttcggtgta ggtcgttcgc    300

tccaagctgg gctgtgtgca cgaacccccc gttcagcccg accgctgcgc cttatccggt    360

aactatcgtc ttgagtccaa cccggtaaga cacgacttat cgccactggc agcagccact    420

ggtaacagga ttagcagagc gaggtatgta ggcggtgcta cagagttctt gaagtggtgg    480

cctaactacg gctacactag aaggacagta tttggtatct gcgctctgct gaagccagtt    540

accttcggaa aaagagttgg tagctcttga tccggcaaac aaaccaccgc tggtagcggt    600

ggtttttttg tttgcaagca gcagattacg cgcagaaaaa aaggatctca agaagatcct    660

ttgatctttt ctacggggtc tgacgctcag tggaacgacg cgtaactcac gttaagggat    720

tttggtcatg agcttgcgcc gtcccgtcaa gtcagcgtaa tgctctgcca gtgttacaac    780

caattaacca attctgatta gaaaaactca tcgagcatca aatgaaactg caatttattc    840

atatcaggat tatcaatacc atatttttga aaaagccgtt tctgtaatga aggagaaaac    900

tcaccgaggc agttccatag gatggcaaga tcctggtatc ggtctgcgat tccgactcgt    960

ccaacatcaa tacaacctat taatttcccc tcgtcaaaaa taaggttatc aagtgagaaa   1020

tcaccatgag tgacgactga atccggtgag aatggcaaaa gtttatgcat ttctttccag   1080

acttgttcaa caggccagcc attacgctcg tcatcaaaat cactcgcatc aaccaaaccg   1140

ttattcattc gtgattgcgc ctgagcgaga cgaaatacgc gatcgctgtt aaaaggacaa   1200
```

-continued

```
ttacaaacag gaatcgaatg caaccggcgc aggaacactg ccagcgcatc aacaatattt   1260
tcacctgaat caggatattc ttctaatacc tggaatgctg tttttccggg gatcgcagtg   1320
gtgagtaacc atgcatcatc aggagtacgg ataaaatgct tgatggtcgg aagaggcata   1380
aattccgtca gccagtttag tctgaccatc tcatctgtaa catcattggc aacgctacct   1440
ttgccatgtt tcagaaacaa ctctggcgca tcgggcttcc catacaagcg atagattgtc   1500
gcacctgatt gcccgacatt atcgcgagcc catttatacc catataaatc agcatccatg   1560
ttggaattta atcgcggcct cgacgtttcc cgttgaatat ggctcataac accccttgta   1620
ttactgttta tgtaagcaga cagttttatt gttcatgatg atatattttt atcttgtgca   1680
atgtaacatc agagattttg agacacgggc cagagctgcc aggaaacagc tatgaccatg   1740
taatacgact cactataggg gatatcagct ggatggcaaa taatgatttt attttgactg   1800
atagtgacct gttcgttgca acaaattgat aagcaatgct ttcttataat gccaactttg   1860
tacaagaaag ctgggtctag ttattaatag taatcaatta cggggtcatt agttcatagc   1920
ccatatatgg agttccgcgt tacataactt acggtaaatg gcccgcctgg ctgaccgccc   1980
aacgaccccc gcccattgac gtcaataatg acgtatgttc ccatagtaac gccaataggg   2040
actttccatt gacgtcaatg ggtggactat ttacggtaaa ctgcccactt ggcagtacat   2100
caagtgtatc atatgccaag tacgccccct attgacgtca atgacggtaa atggcccgcc   2160
tggcattatg cccagtacat gaccttatgg gactttccta cttggcagta catctacgta   2220
ttagtcatcg ctattaccat ggtgatgcgg ttttggcagt acatcaatgg gcgtggatag   2280
cggtttgact cacggggatt tccaagtctc caccccattg acgtcaatgg gagtttgttt   2340
tggcaccaaa atcaacggga ctttccaaaa tgtcgtaaca actccgcccc attgacgcaa   2400
atgggcggta ggcgtgtacg gtgggaggtc tatataagca gagctctctg gctaactaga   2460
gaacccactg cttactggct tatcgaaatt aatacgactc actataggga gacccaagct   2520
tagatctgtt tccggtcgcc accatgagcg agctgatcaa ggagaacatg cacatgaagc   2580
tgtacatgga gggcaccgtg aacaaccacc acttcaagtg cacatccgag ggcgaaggca   2640
agccctacga gggcacccag accatgaaga tcaaggtggt cgagggcggc cctctcccct   2700
tcgccttcga catcctggct accagcttca tgtacggcag caaagccttc atcaaccaca   2760
cccagggcat ccccgacttc tttaagcagt ccttccctga gggcttcaca tgggagagaa   2820
tcaccacata cgaagacggg ggcgtgctga ccgctaccca ggacaccagc ttccagaacg   2880
gctgcatcat ctacaacgtc aagatcaacg gggtgaactt cccatccaac ggccctgtga   2940
tgcagaagaa aacacgcggc tgggaggcca acaccgagat gctgtacccc gctgacggcg   3000
gcctgagagg ccacagccag atggccctga agctcgtggg cgggggctac ctgcactgct   3060
ccttcaagac cacatacaga tccaagaaac ccgctaagaa cctcaagatg cccggcttcc   3120
acttcgtgga ccacagactg gaaagaatca aggaggccga caaagagacc tacgtcgagc   3180
agcacgagat ggctgtggcc aagtactgcg acctccctag caaactgggg cacagataat   3240
cgatagtttg tttgaatgag gcttcagtac tttacagaat cgttgcctgc acatcttgga   3300
aacacttgct gggattactt cttcaggtta acccaacaga aggctcgaga aggtatattg   3360
ctgttgacag tgagcgnnnn nnnnnnnnnn nnnnntagtg aagccacaga tgtannnnnn   3420
nnnnnnnnnn nnntgcctac tgcctcggaa ttcaaggggc tactttagga gcaattatct   3480
tgtttactaa aactgaatac cttgctatct ctttgataca tttttacaaa gctgaattaa   3540
```

aatggtataa attaaatcac ttttttcaat tctctagagg taccgcatgc gtacgtggcc 3600
agcggccgca ggtaagccag cccaggcctc gccctccagc tcaaggcggg acaggtgccc 3660
tagagtagcc tgcatccagg gacaggcccc agccgggtgc tgacacgtcc acctccatct 3720
cttcctcagg tctgcccggg tggcatccct gtgacccctc cccagtgcct ctcctggccc 3780
tggaagttgc cactccagtg cccaccagcc ttgtcctaat aaaattaagt tgcatcattt 3840
tgtctgacta ggtgtccttc tataatatta tggggtggag gggggtggta tggagcaagg 3900
ggcccaagtt aacttgttta ttgcagctta taatggttac aaataaagca atagcatcac 3960
aaatttcaca aataaagcat ttttttcact gcattctagt tgtggtttgt ccaaactcat 4020
caatgtatct tatcatgtct ggatccagtc gactgaattg gttcctttaa agcctgcttt 4080
tttgtacaaa gttggcatta taaaaaagca ttgctcatca atttgttgca acgaacaggt 4140
cactatcagt caaaataaaa tcattatttg gggcccgagc ttaagactgg ccgtcgtttt 4200
acaacgtcgt gactgggaaa acatccatgc tagcgttaac gcgagagtag ggaactgcca 4260
ggcatcaaat aaaacgaaag gctcagtcgg aagactgggc ctttcgtttt atctgttgtt 4320
tgtcggtgaa cgctctcctg agtaggacaa atccgccggg agcggatttg aacgttgtga 4380
agcaacggcc cggagggtgg cgggcaggac gcccgccata aactgccagg catcaaacta 4440
agcagaaggc catcctgacg gatggccttt ttgcgtttct acaaactctt cctggctagc 4500
ggtacgcgta ttaattgcgt tgcgctcact gcccgctttc cagtcgggaa acctgtcgtg 4560
ccagctgcat taatgaatcg gccaacgcgc ggggagaggc ggtttgcgta ttgggcgctc 4620
ttccgcttcc tcgctcactg actcgctgcg ctcggtcgtt cggctgcggc gagcggtatc 4680
agctcactca aaggcggtaa tacggttatc cacagaatca ggggataacg caggaaag 4738

<210> SEQ ID NO 218
<211> LENGTH: 6329
<212> TYPE: DNA
<213> ORGANISM: Artificial Sequence
<220> FEATURE:
<223> OTHER INFORMATION: pKD46

<400> SEQUENCE: 218
catcgattta ttatgacaac ttgacggcta catcattcac tttttcttca caaccggcac 60
ggaactcgct cgggctggcc ccggtgcatt ttttaaatac ccgcgagaaa tagagttgat 120
cgtcaaaacc aacattgcga ccgacggtgg cgataggcat ccgggtggtg ctcaaaagca 180
gcttcgcctg gctgatacgt tggtcctcgc gccagcttaa gacgctaatc cctaactgct 240
ggcggaaaag atgtgacaga cgcgacggcg acaagcaaac atgctgtgcg acgctggcga 300
tatcaaaatt gctgtctgcc aggtgatcgc tgatgtactg acaagcctcg cgtacccgat 360
tatccatcgg tggatggagc gactcgttaa tcgcttccat gcgccgcagt aacaattgct 420
caagcagatt tatcgccagc agctccgaat agcgcccttc cccttgcccg gcgttaatga 480
tttgcccaaa caggtcgctg aaatgcggct ggtgcgcttc atccgggcga aagaaccccg 540
tattggcaaa tattgacggc cagttaagcc attcatgcca gtaggcgcgc ggacgaaagt 600
aaacccactg gtgataccat tcgcgagcct ccggatgacg accgtagtga tgaatctctc 660
ctggcgggaa cagcaaaata tcacccggtc ggcaaacaaa ttctcgtccc tgatttttca 720 ccacccccctg accgcgaatg gtgagattga gaatataacc tttcattccc agcggtcggt 780
cgataaaaaa atcgagataa ccgttggcct caatcggcgt taaacccgcc accagatggg 840
cattaaacga gtatcccggc agcaggggat cattttgcgc ttcagccata cttttcatac 900

-continued

```
tcccgccatt cagagaagaa accaattgtc catattgcat cagacattgc cgtcactgcg    960
tcttttactg gctcttctcg ctaaccaaac cggtaacccc gcttattaaa agcattctgt   1020
aacaaagcgg gaccaaagcc atgacaaaaa cgcgtaacaa aagtgtctat aatcacggca   1080
gaaaagtcca cattgattat ttgcacggcg tcacactttg ctatgccata gcatttttat   1140
ccataagatt agcggatcct acctgacgct ttttatcgca actctctact gtttctccat   1200
acccgttttt ttgggaattc gagctctaag gaggttataa aaaatggata ttaatactga   1260
aactgagatc aagcaaaagc attcactaac cccctttcct gttttcctaa tcagcccggc   1320
atttcgcggg cgatattttc acagctattt caggagttca gccatgaacg cttattacat   1380
tcaggatcgt cttgaggctc agagctgggc gcgtcactac cagcagctcg cccgtgaaga   1440
gaaagaggca gaactggcag acgacatgga aaaaggcctg ccccagcacc tgtttgaatc   1500
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acagggggat gatgcgtggc   2520
acaaattacg gctcggcgtc atcaccgctt cagaagttca caacgtgata gcaaaacccc   2580
gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgttta cctcccggga tttcatgaag ttccggctcg   2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaaatggac gaggcactgg ctgaaattgg ttttgtattt ggggagcaat   3120
ggcgatgacg catcctcacg ataatatccg ggtaggcgca atcactttcg tctactccgt   3180
tacaaagcga ggctgggtat ttcccggcct ttctgttatc cgaaatccac tgaaagcaca   3240
```

-continued

```
gcggctggct gaggagataa ataataaacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct acttttgttt gttagtcttg atgcttcact gatagataca   3480
agagccataa gaacctcaga tccttccgta tttagccagt atgttctcta gtgtggttcg   3540
ttgtttttgc gtgagccatg agaacgaacc attgagatca tacttacttt gcatgtcact   3600
caaaaatttt gcctcaaaac tggtgagctg aatttttgca gttaaagcat cgtgtagtgt   3660
ttttcttagt ccgttacgta ggtaggaatc tgatgtaatg gttgttggta ttttgtcacc   3720
attcattttt atctggttgt tctcaagttc ggttacgaga tccatttgtc tatctagttc   3780
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
ctcatggtag ttattttcaa gcattaacat gaacttaaat tcatcaaggc taatctctat   3960
atttgccttg tgagttttct tttgtgttag ttcttttaat aaccactcat aaatcctcat   4020
agagtatttg ttttcaaaag acttaacatg ttccagatta tattttatga atttttttaa   4080
ctggaaaaga taaggcaata tctcttcact aaaaactaat tctaattttt cgcttgagaa   4140
cttggcatag tttgtccact ggaaaatctc aaagccttta accaaaggat tcctgatttc   4200
cacagttctc gtcatcagct ctctggttgc tttagctaat acaccataag cattttccct   4260
actgatgttc atcatctgag cgtattggtt ataagtgaac gataccgtcc gttctttcct   4320
tgtagggttt tcaatcgtgg ggttgagtag tgccacacag cataaaatta gcttggtttc   4380
atgctccgtt aagtcatagc gactaatcgc tagttcattt gctttgaaaa caactaattc   4440
agacatacat ctcaattggt ctaggtgatt ttaatcacta taccaattga gatgggctag   4500
tcaatgataa ttactagtcc ttttcctttg agttgtgggt atctgtaaat tctgctagac   4560
ctttgctgga aaacttgtaa attctgctag accctctgta aattccgcta gacctttgtg   4620
tgtttttttt gtttatattc aagtggttat aatttataga ataaagaaag aataaaaaaa   4680
gataaaaaga atagatccca gccctgtgta taactcacta ctttagtcag ttccgcagta   4740
ttacaaaagg atgtcgcaaa cgctgtttgc tcctctacaa aacagacctt aaaaccctaa   4800
aggcttaagt agcaccctcg caagctcggt tgcggccgca atcgggcaaa tcgctgaata   4860
ttccttttgt ctccgaccat caggcacctg agtcgctgtc tttttcgtga cattcagttc   4920
gctgcgctca cggctctggc agtgaatggg ggtaaatggc actacaggcg cctttttatgg  4980
attcatgcaa ggaaactacc cataatacaa gaaaagcccg tcacgggctt ctcagggcgt   5040
tttatggcgg gtctgctatg tggtgctatc tgactttttg ctgttcagca gttcctgccc   5100
tctgattttc cagtctgacc acttcggatt atcccgtgac aggtcattca gactggctaa   5160
tgcacccagt aaggcagcgg tatcatcaac ggggtctgac gctcagtgga acgaaaactc   5220
acgttaaggg attttggtca tgagattatc aaaaaggatc ttcacctaga tccttttaaa   5280
ttaaaaatga agttttaaat caatctaaag tatatatgag taaacttggt ctgacagtta   5340
ccaatgctta atcagtgagg cacctatctc agcgatctgt ctatttcgtt catccatagt   5400
tgcctgactc cccgtcgtgt agataactac gatacgggag ggcttaccat ctggccccag   5460
tgctgcaatg ataccgcgag acccacgctc accggctcca gatttatcag caataaacca   5520
gccagccgga agggccgagc gcagaagtgg tcctgcaact ttatccgcct ccatccagtc   5580
tattaattgt tgccgggaag ctagagtaag tagttcgcca gttaatagtt tgcgcaacgt   5640
```

-continued tgttgccatt gctacaggca tcgtggtgtc acgctcgtcg tttggtatgg cttcattcag 5700
ctccggttcc caacgatcaa ggcgagttac atgatccccc atgttgtgca aaaaagcggt 5760
tagctccttc ggtcctccga tcgttgtcag aagtaagttg gccgcagtgt tatcactcat 5820
ggttatggca gcactgcata attctcttac tgtcatgcca tccgtaagat gcttttctgt 5880
gactggtgag tactcaacca agtcattctg agaatagtgt atgcggcgac cgagttgctc 5940
ttgcccggcg tcaatacggg ataataccgc gccacatagc agaactttaa aagtgctcat 6000
cattggaaaa cgttcttcgg ggcgaaaact ctcaaggatc ttaccgctgt tgagatccag 6060
ttcgatgtaa cccactcgtg cacccaactg atcttcagca tcttttactt tcaccagcgt 6120
ttctgggtga gcaaaaacag gaaggcaaaa tgccgcaaaa aagggaataa gggcgacacg 6180
gaaatgttga atactcatac tcttcctttt tcaatattat tgaagcattt atcagggtta 6240
ttgtctcatg agcggataca tatttgaatg tatttagaaa aataaacaaa taggggttcc 6300
gcgcacattt ccccgaaaag tgccacctg 6329

<210> SEQ ID NO 219
<211> LENGTH: 22
<212> TYPE: DNA
<213> ORGANISM: Artificial Sequence
<220> FEATURE:
<223> OTHER INFORMATION: asd-1 primer

<400> SEQUENCE: 219
ccttcctaac gcaaattccc tg 22

<210> SEQ ID NO 220
<211> LENGTH: 22
<212> TYPE: DNA
<213> ORGANISM: Artificial Sequence
<220> FEATURE:
<223> OTHER INFORMATION: asd-2 primer

<400> SEQUENCE: 220
ccaatgctct gcttaactcc tg 22

<210> SEQ ID NO 221
<211> LENGTH: 21
<212> TYPE: DNA
<213> ORGANISM: Artificial Sequence
<220> FEATURE:
<223> OTHER INFORMATION: asd-3 primer

<400> SEQUENCE: 221
gcctcgccat gtttcagtac g 21

<210> SEQ ID NO 222
<211> LENGTH: 21
<212> TYPE: DNA
<213> ORGANISM: Artificial Sequence
<220> FEATURE:
<223> OTHER INFORMATION: asd-4 primer

<400> SEQUENCE: 222
ggtctggtgc attccgagta c 21

<210> SEQ ID NO 223
<211> LENGTH: 23
<212> TYPE: DNA
<213> ORGANISM: Artificial Sequence
<220> FEATURE:

<223> OTHER INFORMATION: scFv-3 primer

<400> SEQUENCE: 223
cataatctgg gtccttggtc tgc     23

<210> SEQ ID NO 224
<211> LENGTH: 5728
<212> TYPE: DNA
<213> ORGANISM: Artificial Sequence
<220> FEATURE:
<223> OTHER INFORMATION: pJW168 plasmid

<400> SEQUENCE: 224

| | | | | | |
|---|---|---|---|---|---|
| ttactaatcg | ccatcttcca | gcaggcgcac | cattgcccct | gtttcactat | ccaggttacg | 60 |
| gatatagttc | atgacaatat | ttacattggt | ccagccacca | gcttgcatga | tctccggtat | 120 |
| tgaaactcca | gcgcgggcca | tatctcgcgc | ggctccgaca | cgggcactgt | gtccagacca | 180 |
| ggccaggtat | ctctgaccag | agtcatcctt | agcgccgtaa | atcaatcgat | gagttgcttc | 240 |
| aaaaatccct | tccagggcgc | gagttgatag | ctggctggtg | gcagatggcg | cggcaacacc | 300 |
| attttttctg | acccggcaaa | acaggtagtt | attcggatca | tcagctacac | cagagacgga | 360 |
| aatccatcgc | tcgaccagtt | tagttacccc | caggctaagt | gccttctcta | cacctgcggt | 420 |
| gctaaccagc | gttttcgttc | tgccaatatg | gattaacatt | ctcccaccgt | cagtacgtga | 480 |
| gatatcttta | accctgatcc | tggcaatttc | ggctatacgt | aacagggtgt | tataagcaat | 540 |
| ccccagaaat | gccagattac | gtatatcctg | gcagcgatcg | ctattttcca | tgagtgaacg | 600 |
| aacctggtcg | aaatcagtgc | gttcgaacgc | tagagcctgt | tttgcacgtt | caccggcatc | 660 |
| aacgttttct | tttcggatcc | gccgcataac | cagtgaaaca | gcattgctgt | cacttggtcg | 720 |
| tggcagcccg | gaccgacgat | gaagcatgtt | tagctggccc | aaatgttgct | ggatagtttt | 780 |
| tactgccaga | ccgcgcgcct | gaagatatag | aagataatcg | cgaacatctt | caggttctgc | 840 |
| gggaaaccat | ttccggttat | tcaacttgca | ccatgccgcc | cacgaccggc | aaacggacag | 900 |
| aagcattttc | caggtatgct | cagaaaacgc | ctggcgatcc | ctgaacatgt | ccatcaggtt | 960 |
| cttgcgaacc | tcatcactcg | ttgcatcgac | cggtaatgca | ggcaaatttt | ggtgtacggg | 1020 |
| cagtaaattg | gacatgtcaa | cggtacctgc | agtctagagt | cgaggcctgt | tcctgtgtg | 1080 |
| aaattgttat | ccgctcacaa | ttccacacat | tatacgagcc | ggaagcataa | agtgtaaagc | 1140 |
| ctggggtgcc | taatgagtga | gctgtttcct | gtgtgaaatt | gttatccgct | cacaattcca | 1200 |
| cacattatac | gagccggaag | cataaagtgt | aaagcctggg | gtgcctaatg | agtgagctgc | 1260 |
| ctcgcgcgtt | tcggtgatga | cggtgaaaac | ctctgacaca | tgcagctccc | ggagacggtc | 1320 |
| acagcttgtc | tgtaagcgga | tgccgggagc | agacaagccc | gtcagggcgc | gtcagcgggt | 1380 |
| gttggcgggt | gtcggggcgc | agccatgacc | cagtcacgta | gcgatagacg | gagtgtatcc | 1440 |
| gacaccatcg | aatggtgcaa | aacctttcgc | ggtatggcat | gatagcgccc | ggaagagagt | 1500 |
| caattcaggg | tggtgaatgt | gaaaccagta | acgttatacg | atgtcgcaga | gtatgccggt | 1560 |
| gtctcttatc | agaccgtttc | ccgcgtggtg | aaccaggcca | gccacgtttc | tgcgaaaacg | 1620 |
| cgggaaaaag | tggaagcggc | gatggcggag | ctgaattaca | ttcccaaccg | cgtggcacaa | 1680 |
| caactggcgg | gcaaacagtc | gttgctgatt | ggcgttgcca | cctccagtct | ggccctgcac | 1740 |
| gcgccgtcgc | aaattgtcgc | ggcgattaaa | tctcgcgccg | atcaactggg | tgccagcgtg | 1800 |
| gtggtgtcga | tggtagaacg | aagcggcgtc | gaagcctgta | aagcggcggt | gcacaatctt | 1860 |
| ctcgcgcaac | gcgtcagtgg | gctgatcatt | aactatccgc | tggatgacca | ggatgccatt | 1920 |

-continued

```
gctgtggaag ctgcctgcac taatgttccg gcgttatttc ttgatgtctc tgaccagaca   1980
cccatcaaca gtattatttt ctcccatgaa gacggtacgc gactgggcgt ggagcatctg   2040
gtcgcattgg gtcaccagca aatcgcgctg ttagcgggcc cattaagttc tgtctcggcg   2100
cgtctgcgtc tggctggctg gcataaatat ctcactcgca atcaaattca gccgatagcg   2160
gaacgggaag gcgactggag tgccatgtcc ggttttcaac aaaccatgca aatgctgaat   2220
gagggcatcg ttcccactgc gatgctggtt gccaacgatc agatggcgct gggcgcaatg   2280
cgcgccatta ccgagtccgg gctgcgcgtt ggtgcggata tctcggtagt gggatacgac   2340
gataccgaag acagctcatg ttatatcccg ccgttaacca ccatcaaaca ggattttcgc   2400
ctgctggggc aaaccagcgt ggaccgcttg ctgcaactct ctcagggcca ggcggtgaag   2460
ggcaatcagc tgttgcccgt ctcactggtg aaaagaaaaa ccaccctggc gcccaatacg   2520
caaaccgcct ctccccgcgc gttggccgat tcattaatgc agctggcacg acaggtttcc   2580
cgactggaaa gcgggcagtg agcgcaacgc aatcaatgtg agttagctca ctcattaggc   2640
accccaggct ttacacttta tgcttccgac catactggct taactatgcg gcatcagagc   2700
agattgtact gagagtgcac catcgatgca ggtggcactt ttcggggaaa tgtgcgcgga   2760
acccctattt gtttattttt ctaaatacat tcaaatatgt atccgctcat gagacaataa   2820
ccctgataaa tgcttcaata atattgaaaa aggaagagta tgagtattca acatttccgt   2880
gtcgccctta ttcccttttt tgcggcattt tgccttcctg tttttgctca cccagaaacg   2940
ctggtgaaag taaaagatgc tgaagatcag ttgggtgcac gagtgggtta catcgaactg   3000
gatctcaaca gcggtaagat ccttgagagt tttcgccccg aagaacgttt tccaatgatg   3060
agcactttta aagttctgct atgtggcgcg gtattatccc gtattgacgc cgggcaagag   3120
caactcggtc gccgcataca ctattctcag aatgacttgg ttgagtactc accagtcaca   3180
gaaaagcatc ttacggatgg catgacagta agagaattat gcagtgctgc cataaccatg   3240
agtgataaca ctgcggccaa cttacttctg acaacgatcg gaggaccgaa ggagctaacc   3300
gcttttttgc acaacatggg ggatcatgta actcgccttg atcgttggga accggagctg   3360
aatgaagcca taccaaacga cgagcgtgac accacgatgc ctgtagcaat ggcaacaacg   3420
ttgcgcaaac tattaactgg cgaactactt actctagctt cccggcaaca attaatagac   3480
tggatggagg cggataaagt tgcaggacca cttctgcgct cggcccttcc ggctggctgg   3540
tttattgctg ataaatctgg agccggtgag cgtgggtctc gcggtatcat tgcagcactg   3600
gggccagatg gtaagccctc ccgtatcgta gttatctaca cgacggggag tcaggcaact   3660
atggatgaac gaaatagaca gatcgctgag ataggtgcct cactgattaa gcattggtaa   3720
ctgtcagacc aagtttactc atatatactt tagattgatt taaaacttca tttttaattt   3780
aaaaggatct aggtgaagat cctttttgat aatctcatga ccaaaatccc ttaacgtgag   3840
ttttcgttcc actgagcgtc agaccccgtt gatgataccg ctgccttact gggtgcatta   3900
gccagtctga atgacctgtc acgggataat ccgaagtggt cagactggaa aatcagaggg   3960
caggaactgc tgaacagcaa aaagtcagat agcaccacat agcagacccg ccataaaacg   4020
ccctgagaag cccgtgacgg gcttttcttg tattatgggt agtttccttg catgaatcca   4080
taaaaggcgc ctgtagtgcc atttaccccc attcactgcc agagccgtga gcgcagcgaa   4140
ctgaatgtca cgaaaaagac agcgactcag gtgcctgatg gtcggagaca aaaggaatat   4200
tcagcgattt gcccgattgc ggccgcaacc gagcttgcga gggtgctact taagccttta   4260
```

gggttttaag gtctgttttg tagaggagca aacagcgttt gcgacatcct tttgtaatac 4320
tgcggaactg actaaagtag tgagttatac acagggctgg gatctattct ttttatcttt 4380
ttttattctt tctttattct ataaattata accacttgaa tataaacaaa aaaaacacac 4440
aaaggtctag cggaatttac agagggtcta gcagaattta caagttttcc agcaaaggtc 4500
tagcagaatt tacagatacc cacaactcaa aggaaaagga ctagtaatta tcattgacta 4560
gcccatctca attggtatag tgattaaaat cacctagacc aattgagatg tatgtctgaa 4620
ttagttgttt tcaaagcaaa tgaactagcg attagtcgct atgacttaac ggagcatgaa 4680
accaagctaa ttttatgctg tgtggcacta ctcaacccca cgattgaaaa ccctacaagg 4740
aaagaacgga cggtatcgtt cacttataac caatacgttc agatgatgaa catcagtagg 4800
gaaaatgctt atggtgtatt agctaaagca accagagagc tgatgacgag aactgtggaa 4860
atcaggaatc ctttggttaa aggctttgag attttccagt ggacaaacta tgccaagttc 4920
tcaagcgaaa aattagaatt agtttttagt gaagagatat tgccttatct tttccagtta 4980
aaaaaattca taaaatataa tctggaacat gttaagtctt ttgaaaacaa atactctatg 5040
aggatttatg agtggttatt aaaagaacta acacaaaaga aaactcacaa ggcaaatata 5100
gagattagcc ttgatgaatt taagttcatg ttaatgcttg aaaataacta ccatgagttt 5160
aaaaggctta accaatgggt tttgaaacca ataagtaaag atttaaacac ttacagcaat 5220
atgaaattgg tggttgataa gcgaggccgc ccgactgata cgttgatttt ccaagttgaa 5280
ctagatagac aaatggatct cgtaaccgaa cttgagaaca accagataaa aatgaatggt 5340
gacaaaatac caacaaccat tacatcagat tcctacctac ataacggact aagaaaaaca 5400
ctacacgatg ctttaactgc aaaaattcag ctcaccagtt ttgaggcaaa atttttgagt 5460
gacatgcaaa gtaagyatga tctcaatggt tcgttctcat ggctcacgca aaaacaacga 5520
accacactag agaacatact ggctaaatac ggaaggatct gaggttctta tggctcttgt 5580
atctatcagt gaagcatcaa gactaacaaa caaaagtaga acaactgttc accgttacat 5640
atcaaaggga aaactgtcca tacccatggg ctagctgatc agccagtgcc aagcttgctc 5700
aatcaatcac cggatccccc gggaattc 5728

<210> SEQ ID NO 225
<211> LENGTH: 3736
<212> TYPE: DNA
<213> ORGANISM: Artificial Sequence
<220> FEATURE:
<223> OTHER INFORMATION: pATIU6 plasmid

<400> SEQUENCE: 225
gcgcccaata cgcaaaccgc ctctccccgc gcgttggccg attcattaat gcagctggca 60
cgacaggttt cccgactgga aagcgggcag tgagcgcaac gcaatggatc caaggtcggg 120
caggaagagg gcctatttcc catgattcct tcatatttgc atatacgata caaggctgtt 180
agagagataa ttagaattaa tttgactgta aacacaaaga tattagtaca aaatacgtga 240
cgtagaaagt aataatttct tgggtagttt gcagttttaa aattatgttt taaaatggac 300
tatcatatgc ttaccgtaac ttgaaagtat ttcgatttct tggctttata tatcttgtgg 360
aaaggacgaa actagttttt tctcgagtag ctagagaatt cttaagccag ccccgacacc 420
cgccaacacc cgctgacgcg ccctgacggg cttgtctgct cccggcatcc gcttacagac 480
aagctgtgac cgtctccggg agctgcatgt gtcagaggtt ttcaccgtca tcaccgaaac 540
gcgcgagacg aaagggcctc gtgatacgcc tatttttata ggttaatgtc atgataataa 600

-continued

```
tggtttctta gacgtcaggt ggcacttttc ggggaaatgt gaagcttcgc ggaaccccta    660
tttgtttatt tttctaaata cattcaaata tgtatccgct catgagacaa taaccctgat    720
aaatgcttca ataatattga aaaaggaaga gtatgagtat tcaacatttc cgtgtcgccc    780
ttattccctt ttttgcggca ttttgccttc ctgtttttgc tcacccagaa acgctggtga    840
aagtaaaaga tgctgaagat cagttgggtg cacgagtggg ttacatcgaa ctggatctca    900
acagcggtaa gatccttgag agttttcgcc ccgaagaacg ttttccaatg atgagcactt    960
ttaaagttct gctatgtggc gcggtattat cccgtattga cgccgggcaa gagcaactcg   1020
gtcgccgcat acactattct cagaatgact tggttgagta ctcaccagtc acagaaaagc   1080
atcttacgga tggcatgaca gtaagagaat tatgcagtgc tgccataacc atgagtgata   1140
acactgcggc caacttactt ctgacaacga tcggaggacc gaaggagcta accgcttttt   1200
tgcacaacat gggggatcat gtaactcgcc ttgatcgttg ggaaccggag ctgaatgaag   1260
ccataccaaa cgacgagcgt gacaccacga tgcctgtagc aatggcaaca acgttgcgca   1320
aactattaac tggcgaacta cttactctag cttcccggca acaattaata gactggatgg   1380
aggcggataa agttgcagga ccacttctgc gctcggccct tccggctggc tggtttattg   1440
ctgataaatc tggagccggt gagcgtgggt ctcgcggtat cattgcagca ctggggccag   1500
atggtaagcc ctcccgtatc gtagttatct acacgacggg gagtcaggca actatggatg   1560
aacgaaatag acagatcgct gagataggtg cctcactgat taagcattgg taaaagcttc   1620
tgtcagacca agtttactca tatatacttt agattgattt aaaacttcat ttttaattta   1680
aaaggatcta ggtgaagatc ctttatggtg aaggatgcgc cacaggatac tggcgcgcat   1740
acacagcaca tctctttgca ggaaaaaaac gctatgaaaa atgttggttt tatcggctgg   1800
cgcggaatgg tcggctctgt tctcatgcaa cgcatggtag aggagcgcga tttcgacgct   1860
attcgccctg ttttcttttc tacctcccag tttggacagg cggcgcccac cttcggcgac   1920
acctccaccg gcacgctaca ggacgctttt gatctggatg cgctaaaagc gctcgatatc   1980
atcgtgacct gccagggcgg cgattatacc aacgaaattt atccaaagct gcgcgaaagc   2040
ggatggcagg gttactggat tgatgcggct tctacgctgc gcatgaaaga tgatgccatt   2100
attattctcg acccggtcaa ccaggacgtg attaccgacg gcctgaacaa tggcgtgaag   2160
acctttgtgg gcggtaactg taccgttagc ctgatgttga tgtcgctggg cggtctcttt   2220
gcccataatc tcgttgactg ggtatccgtc gcgacctatc aggccgcctc cggcggcggc   2280
gcgcgccata tgcgcgagct gttaacccag atgggtcagt tgtatggcca tgtcgccgat   2340
gaactggcga cgccgtcttc cgcaattctt gatattgaac gcaaagttac ggcattgacc   2400
cgcagcggcg agctgccggt tgataacttt ggcgtaccgc tggcgggaag cctgatcccc   2460
tggatcgaca aacagctcga taacggccag agccgcgaag agtggaaagg ccaggcggaa   2520
accaacaaga ttctcaatac tgcctctgtg attccggttg atggtttgtg tgtgcgcgtc   2580
ggcgcgctgc gctgtcacag ccaggcgttc accatcaagc tgaaaaaaga ggtatccatt   2640
ccgacggtgg aagaactgct ggcggcacat aatccgtggg cgaaagtggt gccgaacgat   2700
cgtgatatca ctatgcgcga attaaccccg gcggcggtga ccggcacgtt gactacgccg   2760
gttggtcgtc tgcgtaagct gaacatgggg ccagagttct tgtcggcgtt taccgtaggc   2820
gaccagttgt tatggggcgc cgccgagccg ctgcgtcgaa tgctgcgcca gttggcgtag   2880
ttgataatct catgaccaaa atcccttaac gtgagttttc gttccactga gcgtcagacc   2940
```

```
ccgtagaaaa gatcaaagga tcttcttgag atcctttttt tctgcgcgta atctgctgct   3000

tgcaaacaaa aaaaccaccg ctaccagcgg tggtttgttt gccggatcaa gagctaccaa   3060

ctctttttcc gaaggtaact ggcttcagca gagcgcagat accaaatact gttcttctag   3120

tgtagccgta gttaggccac cacttcaaga actctgtagc accgcctaca tacctcgctc   3180

tgctaatcct gttaccagtg gctgctgcca gtggcgataa gtcgtgtctt accgggttgg   3240

actcaagacg atagttaccg gataaggcgc agcggtcggg ctgaacgggg ggttcgtgca   3300

cacagcccag cttggagcga acgacctaca ccgaactgag atacctacag cgtgagctat   3360

gagaaagcgc cacgcttccc gaagggagaa aggcggacag gtatccggta agcggcaggg   3420

tcggaacagg agagcgcacg agggagcttc caggggggaaa cgcctggtat ctttatagtc  3480

ctgtcgggtt tcgccacctc tgacttgagc gtcgattttt gtgatgctcg tcaggggggc   3540

ggagcctatg gaaaaacgcc agcaacgcgg cctttttacg gttcctggcc ttttgctggc   3600

cttttgctca catgttcttt cctgcgttat cccctgattc tgtggataac cgtattaccg   3660

cctttgagtg agctgatacc gctcgccgca gccgaacgac cgagcgcagc gagtcagtga   3720

gcgaggaagc ggaaga                                                    3736
```

<210> SEQ ID NO 226
<211> LENGTH: 26
<212> TYPE: DNA
<213> ORGANISM: Artificial Sequence
<220> FEATURE:
<223> OTHER INFORMATION: APR-001 Kan PrimerF

<400> SEQUENCE: 226
aaaaaagctt gcagctctgg cccgtg 26

<210> SEQ ID NO 227
<211> LENGTH: 38
<212> TYPE: DNA
<213> ORGANISM: Artificial Sequence
<220> FEATURE:
<223> OTHER INFORMATION: APR-002 Kan PrimerR

<400> SEQUENCE: 227
aaaaaagctt ttagaaaaac tcatcgagca tcaaatga 38

<210> SEQ ID NO 228
<211> LENGTH: 28
<212> TYPE: DNA
<213> ORGANISM: Artificial Sequence
<220> FEATURE:
<223> OTHER INFORMATION: APR-003 pATI ori T148CF

<400> SEQUENCE: 228
acactagaag gacagtattt ggtatctg 28

<210> SEQ ID NO 229
<211> LENGTH: 18
<212> TYPE: DNA
<213> ORGANISM: Artificial Sequence
<220> FEATURE:
<223> OTHER INFORMATION: APR-004 pATI ori T148CR

<400> SEQUENCE: 229
agccgtagtt aggccacc 18

<210> SEQ ID NO 230
<211> LENGTH: 3203

<212> TYPE: DNA
<213> ORGANISM: Artificial Sequence
<220> FEATURE:
<223> OTHER INFORMATION: pSL0147 plasmid

<400> SEQUENCE: 230

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
```

cggctcgtat gttgtgtgga attgtgagcg gataacaatt tcacacagga aacagctatg 2220
accatgatta cgccaagctc ggcgcgccat tgggatggaa cgcgttatcg gcaatctgga 2280
ggcaaagttt aatgataatt ttgcaaaaat aatgcgcgga ataatgatgc ataaagcggc 2340
tatttcgccg cctaagaaaa agatcggggg aagtgaaaaa ttttctaaag ttcgaaattc 2400
aggtgccgat acaagggtta cggtgagaaa ccgtgggcaa cagcccaata acatcaagtt 2460
gtaattgata aggaaaagat catgggctag cctcaataag cttcttgcct ttctgcagac 2520
caaggaccca gattatgttg cagcaggccg gtacctccgt tctggcgcag gcgaaccagg 2580
ttccgcaaaa cgtcctctct ttactgcgtt aatccggcga ttgattcacc gacacgtggt 2640
acacaatcaa ggcagcgaaa gctgcctttt ttaattccgg agcctgtgta atgaaagaaa 2700
tcaccgtcac tgaacctgcc tttgtcaccc gcttttcctg ttctggctcg gcctgtcgcg 2760
accactgttg taagggctgg aaagttccat cccaatacgc gtcaattcac tggccgtcgt 2820
tttacaacgt cgtgactggg aaaaccctgg cgttacccaa cttaatcgcc ttgcagcaca 2880
tccccctttc gccagctggc gtaatagcga agaggcccgc accgatcgcc cttcccaaca 2940
gttgcgcagc ctgaatggcg aatggcgcct gatgcggtat tttctcctta cgcatctgtg 3000
cggtatttca caccgcatat ggtgcactct cagtacaatc tgctctgatg ccgcatagtt 3060
aagccagccc cgacacccgc caacacccgc tgacgcgccc tgacgggctt gtctgctccc 3120
ggcatccgct tacagacaag ctgtgaccgt ctccgggagc tgcatgtgtc agaggttttc 3180
accgtcatca ccgaaacgcg cga 3203

<210> SEQ ID NO 231
<211> LENGTH: 3196
<212> TYPE: DNA
<213> ORGANISM: Artificial Sequence
<220> FEATURE:
<223> OTHER INFORMATION: pSL0148 plasmid

<400> SEQUENCE: 231
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggga gtcaggcaac tatggatgaa cgaaatagac 1020
agatcgctga gataggtgcc tcactgatta agcattggta actgtcagac caagtttact 1080
catatatact ttagattgat ttaaaacttc atttttaatt taaaaggatc taggtgaaga 1140
tcctttttga taatctcatg accaaaatcc cttaacgtga gttttcgttc cactgagcgt 1200
cagaccccgt agaaaagatc aaaggatctt cttgagatcc tttttttctg cgcgtaatct 1260
gctgcttgca aacaaaaaaa ccaccgctac cagcggtggt ttgtttgccg gatcaagagc 1320
taccaactct ttttccgaag gtaactggct tcagcagagc gcagatacca aatactgttc 1380
ttctagtgta gccgtagtta ggccaccact tcaagaactc tgtagcaccg cctacatacc 1440
tcgctctgct aatcctgtta ccagtggctg ctgccagtgg cgataagtcg tgtcttaccg 1500
ggttggactc aagacgatag ttaccggata aggcgcagcg gtcgggctga acggggggtt 1560
cgtgcacaca gcccagcttg gagcgaacga cctacaccga actgagatac ctacagcgtg 1620
agctatgaga aagcgccacg cttcccgaag ggagaaaggc ggacaggtat ccggtaagcg 1680
gcagggtcgg aacaggagag cgcacgaggg agcttccagg gggaaacgcc tggtatcttt 1740
atagtcctgt cgggtttcgc cacctctgac ttgagcgtcg atttttgtga tgctcgtcag 1800
gggggcggag cctatggaaa aacgccagca acgcggcctt tttacggttc ctggcctttt 1860
gctggccttt tgctcacatg ttctttcctg cgttatcccc tgattctgtg gataaccgta 1920
ttaccgcctt tgagtgagct gataccgctc gccgcagccg aacgaccgag cgcagcgagt 1980
cagtgagcga ggaagcggaa gagcgcccaa tacgcaaacc gcctctcccc gcgcgttggc 2040
cgattcatta atgcagctgg cacgacaggt ttcccgactg gaaagcgggc agtgagcgca 2100
acgcaattaa tgtgagttag ctcactcatt aggcacccca ggctttacac tttatgcttc 2160
cggctcgtat gttgtgtgga attgtgagcg gataacaatt tcacacagga aacagctatg 2220
accatgatta cgccaagctc ggcgcgccat tgggatggaa cttccagacg acaagagtat 2280
cgcctttatt tacatacttt aacgctcgtt tcaggccggg gcggtttgca atcttgccac 2340
tgatacggtc ctcaaaaatg cggtcacaat ttgcactagt aagcgcatta cgctgtaaat 2400
cgatattttg gtcaattgtt gacacccgaa tatacccaat agtagccatg attttctcct 2460
ttacatcaga taaggaagaa ttttagtcgc ttttctcatg gaggattgct gctagcctca 2520
ataagcttct tgcctttctg cagaccaagg acccagatta tgtatggaat gtatggctgt 2580
aaatgatatt tcctacgggc gagaagctga aatatggccg cgggattatt ctatgcttgc 2640
tcgtcgagtt caatttctac gttttaatga tatccctgtt cgattggtga gtaataatgc 2700
ccggataatc acaggctaca ttgcgaagtt taatccgaag gaaaatttga ttctggcttc 2760
ggataaacct aaaggagttc catcccaata cgcgtcaatt cactggccgt cgttttacaa 2820
cgtcgtgact gggaaaaccc tggcgttacc caacttaatc gccttgcagc acatccccct 2880
ttcgccagct ggcgtaatag cgaagaggcc cgcaccgatc gcccttccca acagttgcgc 2940
agcctgaatg gcgaatggcg cctgatgcgg tattttctcc ttacgcatct gtgcggtatt 3000
tcacaccgca tatggtgcac tctcagtaca atctgctctg atgccgcata gttaagccag 3060
ccccgacacc cgccaacacc cgctgacgcg ccctgacggg cttgtctgct cccggcatcc 3120
gcttacagac aagctgtgac cgtctccggg agctgcatgt gtcagaggtt ttcaccgtca 3180
tcaccgaaac gcgcga 3196

<210> SEQ ID NO 232
<211> LENGTH: 21
<212> TYPE: DNA

<213> ORGANISM: Artificial Sequence
<220> FEATURE:
<223> OTHER INFORMATION: flic-1 primer

<400> SEQUENCE: 232
cgttatcggc aatctggagg c 21

<210> SEQ ID NO 233
<211> LENGTH: 21
<212> TYPE: DNA
<213> ORGANISM: Artificial Sequence
<220> FEATURE:
<223> OTHER INFORMATION: flic-2 primer

<400> SEQUENCE: 233
ccagccctta caacagtggt c 21

<210> SEQ ID NO 234
<211> LENGTH: 24
<212> TYPE: DNA
<213> ORGANISM: Artificial Sequence
<220> FEATURE:
<223> OTHER INFORMATION: flic-3 primer

<400> SEQUENCE: 234
gtctgtcaac aactggtcta acgg 24

<210> SEQ ID NO 235
<211> LENGTH: 23
<212> TYPE: DNA
<213> ORGANISM: Artificial Sequence
<220> FEATURE:
<223> OTHER INFORMATION: flic-4 primer

<400> SEQUENCE: 235
agacggtcct catccagata agg 23

<210> SEQ ID NO 236
<211> LENGTH: 22
<212> TYPE: DNA
<213> ORGANISM: Artificial Sequence
<220> FEATURE:
<223> OTHER INFORMATION: fljb-1 primer sequence

<400> SEQUENCE: 236
ttccagacga caagagtatc gc 22

<210> SEQ ID NO 237
<211> LENGTH: 27
<212> TYPE: DNA
<213> ORGANISM: Artificial Sequence
<220> FEATURE:
<223> OTHER INFORMATION: fljb-2 primer

<400> SEQUENCE: 237
cctttaggtt tatccgaagc cagaatc 27

<210> SEQ ID NO 238
<211> LENGTH: 20
<212> TYPE: DNA
<213> ORGANISM: Artificial Sequence
<220> FEATURE:
<223> OTHER INFORMATION: fljb-3 primer

<400> SEQUENCE: 238
caccaggttt ttcacgctgc 20

<210> SEQ ID NO 239
<211> LENGTH: 20
<212> TYPE: DNA
<213> ORGANISM: Artificial Sequence
<220> FEATURE:
<223> OTHER INFORMATION: fljb-4 primer

<400> SEQUENCE: 239
acacgcattt acgcctgtcg 20

<210> SEQ ID NO 240
<211> LENGTH: 1518
<212> TYPE: DNA
<213> ORGANISM: Artificial Sequence
<220> FEATURE:
<223> OTHER INFORMATION: cytoLLO ORF

<400> SEQUENCE: 240
atgaaagacg cctccgcgtt taacaaggag aactccatca gctccatggc cccgcccgct 60
tccccgccgg cgagccctaa aaccccgatc gagaaaaagc acgccgacga gattgacaaa 120
tatattcaag gtttagacta caataagaac aacgtgctgg tgtatcacgg cgatgcggtg 180
accaatgttc cgccgcgcaa gggctacaaa gatggtaacg aatatatcgt ggttgagaaa 240
aagaaaaaaa gcatcaacca gaacaacgcc gatatccaag ttgtgaacgc catcagctct 300
ttaacctatc cgggcgcgct ggtgaaagcc aacagcgaac tggtggaaaa ccagcccgat 360
gtgctgccgg tgaaacgcga ttctttaacg ctgagcattg atttaccggg catgacgaac 420
caagataaca aaatcgtggt gaagaacgcg accaagtcca acgtgaacaa cgcggtgaac 480
acgctggtgg aacgctggaa cgaaaaatac gcccaagctt acccgaacgt gagcgcgaag 540
attgactacg acgacgaaat ggcctacagc gagagccagc tgatcgcgaa attcggcacc 600
gcgttcaaag cggtgaacaa ctctttaaac gtgaactttg gcgcgatcag cgaaggcaaa 660
atgcaagaag aggtgatcag ctttaaacaa atctattata acgtgaatgt taacgagccg 720
acgcgtccga gccgcttttt cggcaaagcg gtgacgaagg aacagctgca agcgcttggc 780
gtgaacgcgg aaaaccctcc ggcctatatt tccagcgtgg cgtatggccg ccaagtttat 840
ctgaagctga gcacgaacag ccacagcacc aaagttaagg cggcctttga tgcggcggtg 900
agcggcaaaa gcgttagcgg cgacgttgag ctgacgaaca tcatcaagaa cagctccttt 960
aaagcggtga tctatggcgg tagcgcgaaa gacgaagtgc agatcatcga cggcaattta 1020
ggtgatctgc gcgatatttt aaaaaagggc gccaccttca accgtgagac gcccggtgtg 1080
ccgatcgcct acaccaccaa ctttttaaag gataacgagc tggccgtgat caaaaacaat 1140
tccgaatata tcgaaaccac gagcaaggcg tataccgatg gcaagatcaa cattgaccac 1200
agcggtggct atgtggcgca gttcaacatc agctgggatg aagtgaacta tgatccggag 1260
ggcaacgaga tcgtgcagca caagaactgg tccgagaaca acaaatccaa gctggcgcat 1320
ttcaccagca gcatctatct gccgggcaac gcgcgcaaca ttaatgtgta cgcgaaagag 1380
tgcacgggtc ttgcgtggga atggtggcgc accgtgatcg atgatcgcaa tttaccgctg 1440
gtgaaaaacc gcaacatctc catctggggc accactttat acccgaaata ttccaacaaa 1500
gttgataacc ctattgag 1518

<210> SEQ ID NO 241
<211> LENGTH: 45
<212> TYPE: DNA

-continued

<213> ORGANISM: Artificial Sequence
<220> FEATURE:
<223> OTHER INFORMATION: LLO promoter

<400> SEQUENCE: 241
attatgtctt gacatgtagt gagtgggctg gtataatgca gcaag 45

<210> SEQ ID NO 242
<211> LENGTH: 1176
<212> TYPE: DNA
<213> ORGANISM: Artificial Sequence
<220> FEATURE:
<223> OTHER INFORMATION: Asd Gene ORF

<400> SEQUENCE: 242
ctacgccaac tggcgcagca ttcgacgcag cggctcggcg gcgccccata acaactggtc 60
gcctacggta aacgccgaca agaactctgg ccccatgttc agcttacgca gacgaccaac 120
cggcgtagtc aacgtgccgg tcaccgccgc cggggttaat tcgcgcatag tgatatcacg 180
atcgttcggc accactttcg cccacggatt atgtgccgcc agcagttctt ccaccgtcgg 240
aatggatacc tctttttca gcttgatggt gaacgcctgg ctgtgacagc gcagcgcgcc 300
gacgcgcaca cacaaaccat caaccggaat cacagaggca gtattgagaa tcttgttggt 360
ttccgcctgg cctttccact cttcgcggct ctggccgtta tcgagctgtt tgtcgatcca 420
ggggatcagg cttcccgcca gcggtacgcc aaagttatca accggcagct cgccgctgcg 480
ggtcaatgcc gtaactttgc gttcaatatc aagaattgcg gaagacggcg tcgccagttc 540
atcggcgaca tggccataca actgacccat ctgggttaac agctcgcgca tatggcgcgc 600
gccgccgccg gaggcggcct gataggtcgc gacggatacc cagtcaacga gattatgggc 660
aaagagaccg cccagcgaca tcaacatcag gctaacggta cagttaccgc ccacaaaggt 720
cttcacgcca ttgttcaggc cgtcggtaat cacgtcctgg ttgaccgggt cgagaataat 780
aatggcatca tctttcatgc gcagcgtaga agccgcatca atccagtaac cctgccatcc 840
gctttcgcgc agctttggat aaatttcgtt ggtataatcg ccgccctggc aggtcacgat 900
gatatcgagc gcttttagcg catccagatc aaaagcgtcc tgtagcgtgc cggtggaggt 960
gtcgccgaag gtgggcgccg cctgtccaaa ctgggaggta gaaaagaaaa cagggcgaat 1020
agcgtcgaaa tcgcgctcct ctaccatgcg ttgcatgaga acagagccga ccattccgcg 1080
ccagccgata aaaccaacat ttttcatagc gttttttttcc tgcaaagaga tgtgctgtgt 1140
atgcgcgcca gtatcctgtg gcgcatcctt caccat 1176

<210> SEQ ID NO 243
<211> LENGTH: 589
<212> TYPE: DNA
<213> ORGANISM: Artificial Sequence
<220> FEATURE:
<223> OTHER INFORMATION: pBR322 Origin

<400> SEQUENCE: 243
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgtcct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360

```
ctacaccgaa ctgagatacc tacagcgtga gctatgagaa agcgccacgc ttcccgaagg    420

gagaaaggcg gacaggtatc cggtaagcgg cagggtcgga acaggagagc gcacgaggga    480

gcttccaggg ggaaacgcct ggtatcttta tagtcctgtc gggtttcgcc acctctgact    540

tgagcgtcga tttttgtgat gctcgtcagg ggggcggagc ctatggaaa                589


<210> SEQ ID NO 244
<211> LENGTH: 3269
<212> TYPE: DNA
<213> ORGANISM: Artificial Sequence
<220> FEATURE:
<223> OTHER INFORMATION: pEQU6 shSCR

<400> SEQUENCE: 244

ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga ctggatccaa ggtcgggcag gaagagggcc    720

tatttcccat gattccttca tatttgcata tacgatacaa ggctgttaga gagataatta    780

gaattaattt gactgtaaac acaaagatat tagtacaaaa tacgtgacgt agaaagtaat    840

aatttcttgg gtagtttgca gttttaaaat tatgttttaa aatggactat catatgctta    900

ccgtaacttg aaagtatttc gatttcttgg ctttatatat cttgtggaaa ggacgaaact    960

agcaacaaga tgaagagcac caattctaga gattggtgct cttcatcttg ttgttttttc   1020

gagtagctag agaattcatg gtaatagcga tgactaatac gtagatgtac tgccaagtag   1080

gaaagtccca taaggtcatg tactgggcat aatgccaggc gggccattta ccgtcattga   1140

cgtcaatagg gggcgtactt ggcatatgat acacttgatg tactgccaag tgggcagttt   1200

accgtaaata gtccacccat tgacgtcaat ggaaagtccc tattggcgtt actatgggaa   1260

catacgtcat tattgacgtc aatgggcggg ggtcgttggg cggtcagcca ggcgggccat   1320

ttaccgtaag ttatgtaacg cggaactcca tatatgggct atgaactaat gaccccgtaa   1380

ttgattacta ttaataacta gacccagctt tcttgtacaa agttggcatt ataagaaagc   1440

attgcttatc aatttgttgc aacgaacagg tcactatcag tcaaaataaa atcattattt   1500

gccatccagc tgatatcccc tatagtgagt cgtattacat ggtcatagct gtttcctggc   1560

agctctggcc cgtgtctcaa aatctctgat gttacattgc acaagataaa aatatatcat   1620

catgaacaat aaaactgtct gcttacataa acagtaatac aaggggtgtt atgagccata   1680

ttcaacggga aacgtcgagg ccgcgattaa attccaacat ggatgctgat ttatatgggt   1740

ataaatgggc tcgcgataat gtcgggcaat caggtgcgac aatctatcgc ttgtatggga   1800
```

agcccgatgc gccagagttg tttctgaaac atggcaaagg tagcgttgcc aatgatgtta 1860
cagatgagat ggtcagacta aactggctga cggaatttat gcctcttccg accatcaagc 1920
attttatccg tactcctgat gatgcatggt tactcaccac tgcgatcccc ggaaaaacag 1980
cattccaggt attagaagaa tatcctgatt caggtgaaaa tattgttgat gcgctggcag 2040
tgttcctgcg ccggttgcat tcgattcctg tttgtaattg tccttttaac agcgatcgcg 2100
tatttcgtct cgctcaggcg caatcacgaa tgaataacgg tttggttgat gcgagtgatt 2160
ttgatgacga gcgtaatggc tggcctgttg aacaagtctg gaaagaaatg cataaacttt 2220
tgccattctc accggattca gtcgtcactc atggtgattt ctcacttgat aaccttattt 2280
ttgacgaggg gaaattaata ggttgtattg atgttggacg agtcggaatc gcagaccgat 2340
accaggatct tgccatccta tggaactgcc tcggtgagtt ttctccttca ttacagaaac 2400
ggctttttca aaaatatggt attgataatc ctgatatgaa taaattgcag tttcatttga 2460
tgctcgatga gtttttctaa tcagaattgg ttaattggtt gtaacactgg cagagcatta 2520
cgctgacttg acgggacggc gcaagctcat gaccaaaatc ccttaacgtg agttacgcgt 2580
cgttccactg agcgtcagac cccgtagaaa agatcaaagg atcttcttga gatccttttt 2640
ttctgcgcgt aatctgctgc ttgcaaacaa aaaaaccacc gctaccagcg gtggtttgtt 2700
tgccggatca agagctacca actctttttc cgaaggtaac tggcttcagc agagcgcaga 2760
taccaaatac tgtccttcta gtgtagccgt agttaggcca ccacttcaag aactctgtag 2820
caccgcctac atacctcgct ctgctaatcc tgttaccagt ggctgctgcc agtggcgata 2880
agtcgtgtct taccgggttg gactcaagac gatagttacc ggataaggcg cagcggtcgg 2940
gctgaacggg gggttcgtgc acacagccca gcttggagcg aacgacctac accgaactga 3000
gatacctaca gcgtgagcat tgagaaagcg ccacgcttcc cgaagggaga aaggcggaca 3060
ggtatccggt aagcggcagg gtcggaacag gagagcgcac gagggagctt ccagggggaa 3120
acgcctggta tctttatagt cctgtcgggt ttcgccacct ctgacttgag cgtcgatttt 3180
tgtgatgctc gtcagggggg cggagcctat ggaaaaacgc cagcaacgcg gcctttttac 3240
ggttcctggc cttttgctgg ccttttgct 3269

<210> SEQ ID NO 245
<211> LENGTH: 4642
<212> TYPE: DNA
<213> ORGANISM: Artificial Sequence
<220> FEATURE:
<223> OTHER INFORMATION: pATI2.0 U6-H1 Plasmid

<400> SEQUENCE: 245
accggtctgt ggaatgtgtg tcagttaggg tgtggaaagt ccccaggctc cccagcaggc 60
agaagtatgc aaagcatgca tctcaattag tcagcaacca accggtcttg cacctcagca 120
aaaggccatc cgtcaggatg gccttctgct tagtttgatg cctggcagtt tatggcgggc 180
gtcctgcccg ccaccctccg ggccgttgct tcacaacgtt caaatccgct cccggcggat 240
ttgtcctact caggagagcg ttcaccgaca aacaacagat aaaacgaaag gcccagtctt 300
ccgactgagc ctttcgtttt atttgggccg gccatgcctg gcagttccct actctcgcgt 360
taacgctagc atggatgttt tcccagtcac gacgttctta agctcgggcc cttaaaggaa 420
ccaattcagt cgagaattac tagtggtacc atatttgcat gtcgctatgt gttctgggaa 480
atcaccataa acgtgaaatg tctttggatt tgggaatctt ataagttctg tatgagacca 540
ctccctaggt ttttgtcgac agatctggcg cgccgactac caaaatgact tcggatatga 600

```
ccattatggt gcccgacttc gtaatttacg cgtacccatt tggatgacgg tgcgtccatg    660
tttgttctgc atgcctgaga tagtaaggcc gacccccaac aatccacaag gccacgattg    720
acacatgagg ttcctttttt aaacctgaac ctttagttca cacaggtggc tgcgccgccg    780
tgaatggtgg cagtagttac ttctaatcaa gctcaatccc tcggctctga agaggacata    840
gtagacctca tctggtcttt cgactacggg ggtaacaga tgtcggtggt ataacaatcc    900
tccacgagat catttcacgt aagcatgact tttacaccta tcggaatcat ataactgtta    960
ggcaatggtt tatgattggg cgacagacgt cagatcggcg aacctttacg tagcccccg   1020
ttcatctaga caggaagagg gcctatttcc catgattcct tcatatttgc atatacgata   1080
caaggctgtt agagagataa ttagaattaa tttgactgta aacacaaaga tattagtaca   1140
aaatacgtga cgtagaaagt aataatttct tgggtagttt gcagttttaa aattatgttt   1200
taaaatggac tatcatatgc ttaccgtaac ttgaaagtat ttcgatttct tggctttata   1260
tatcttgtgg aaaggacgaa acttgttttt tctcgagtag ctagagaatt cgtcgacgga   1320
actccatata tgggctatga actaatgacc ccgtaattga ttactattaa taactagcca   1380
tccagctgat atccgccggc gctgcagcta cgccaactgg cgcagcattc gacgcagcgg   1440
ctcggcggcg ccccataaca actggtcgcc tacggtaaac gccgacaaga actctggccc   1500
catgttcagc ttacgcagac gaccaaccgg cgtagtcaac gtgccggtca ccgccgccgg   1560
ggttaattcg cgcatagtga tatcacgatc gttcggcacc actttcgccc acggattatg   1620
tgccgccagc agttcttcca ccgtcggaat ggatacctct tttttcagct tgatggtgaa   1680
cgcctggctg tgacagcgca gcgcgccgac gcgcacacac aaaccatcaa ccggaatcac   1740
agaggcagta ttgagaatct tgttggtttc cgcctggcct ttccactctt cgcggctctg   1800
gccgttatcg agctgtttgt cgatccaggg gatcaggctt cccgccagcg gtacgccaaa   1860
gttatcaacc ggcagctcgc cgctgcgggt caatgccgta actttgcgtt caatatcaag   1920
aattgcggaa gacggcgtcg ccagttcatc ggcgacatgg ccatacaact gacccatctg   1980
ggttaacagc tcgcgcatat ggcgcgcgcc gccgccggag gcggcctgat aggtcgcgac   2040
ggatacccag tcaacgagat tatgggcaaa gagaccgccc agcgacatca acatcaggct   2100
aacggtacag ttaccgccca caaaggtctt cacgccattg ttcaggccgt cggtaatcac   2160
gtcctggttg accgggtcga gaataataat ggcatcatct ttcatgcgca gcgtagaagc   2220
cgcatcaatc cagtaaccct gccatccgct ttcgcgcagc tttggataaa tttcgttggt   2280
ataatcgccg ccctggcagg tcacgatgat atcgagcgct tttagcgcat ccagatcaaa   2340
agcgtcctgt agcgtgccgg tggaggtgtc gccgaaggtg ggcgccgcct gtccaaactg   2400
ggaggtagaa aagaaaacag ggcgaatagc gtcgaaatcg cgctcctcta ccatgcgttg   2460
catgagaaca gagccgacca ttccgcgcca gccgataaaa ccaacatttt tcatagcgtt   2520
tttttcctgc aaagagatgt gctgtgtatg cgcgccagta tcctgtggcg catccttcac   2580
cataaaggat cttcacctag atccttttaa attaaaaatg aagttttaaa tcaatctaaa   2640
gtatatatga gtaaacttgg tctgacagtc tgcaggatat cccatgggca ttggcgcaga   2700
aaaaaatgcc tgatgcgacg ctgcgcgtct tatactccca catatgccag attcagcaac   2760
ggatacggct tccccaactt gcccacttcc atacgtgtcc tccttaccag aaatttatcc   2820
ttaaccatgg aagctttgca gctctggccc gtgtctcaaa atctctgatg ttacattgca   2880
caagataaaa atatatcatc atgaacaata aaactgtctg cttacataaa cagtaataca   2940
```

```
aggggtgtta tgagccatat tcaacgggaa acgtcgaggc cgcgattaaa ttccaacatg   3000
gatgctgatt tatatgggta taaatgggct cgcgataatg tcgggcaatc aggtgcgaca   3060
atctatcgct tgtatgggaa gcccgatgcg ccagagttgt ttctgaaaca tggcaaaggt   3120
agcgttgcca atgatgttac agatgagatg gtcagactaa actggctgac ggaatttatg   3180
cctcttccga ccatcaagca ttttatccgt actcctgatg atgcatggtt actcaccact   3240
gcgatccccg gaaaaacagc attccaggta ttagaagaat atcctgattc aggtgaaaat   3300
attgttgatg cgctggcagt gttcctgcgc cggttgcatt cgattcctgt ttgtaattgt   3360
ccttttaaca gcgatcgcgt atttcgtctc gctcaggcgc aatcacgaat gaataacggt   3420
ttggttgatg cgagtgattt tgatgacgag cgtaatggct ggcctgttga acaagtctgg   3480
aaagaaatgc ataaactttt gccattctca ccggattcag tcgtcactca tggtgatttc   3540
tcacttgata accttatttt tgacgagggg aaattaatag gttgtattga tgttggacga   3600
gtcggaatcg cagaccgata ccaggatctt gccatcctat ggaactgcct cggtgagttt   3660
tctccttcat tacagaaacg gctttttcaa aaatatggta ttgataatcc tgatatgaat   3720
aaattgcagt ttcatttgat gctcgatgag tttttctaaa gctttcagaa ttggttaatt   3780
ggttgtaaca ctggcagagc attacgctga cttgacggga cggcgcaagc tcatggatcc   3840
caattggcgg ccgcttaatt aaacatgtga gctcgatgta cattcgaagg accccaaaat   3900
cccttaacgt gagttacgcg tcgttccact gagcgtcaga ccccgtagaa aagatcaaag   3960
gatcttcatc gatttgagat cctttttttc tgcgcgtaat ctgctgcttg caaacaaaaa   4020
aaccaccgct accagcggtg gtttgtttgc cggatcaaga gctaccaact ctttttccga   4080
aggtaactgg cttcagcaga gcgcagatac caaatactgt ccttctagtg tagccgtagt   4140
taggccacca cttcaagaac tctgtagcac cgcctacata cctcgctctg ctaatcctgt   4200
taccagtggc tgctgccagt ggcgataagt cgtgtcttac cgggttggac tcaagacgat   4260
agttaccgga taaggcgcag cggtcgggct gaacgggggg ttcgtgcaca cagcccagct   4320
tggagcgaac gacctacacc gaactgagat acctacagcg tgagctatga gaaagcgcca   4380
cgcttcccga agggagaaag gcggacaggt atccggtaag cggcagggtc ggaacaggag   4440
agcgcacgag ggagcttcca gggggaaacg cctggtatct ttatagtcct gtcgggtttc   4500
gccacctctg acttgagcgt cgatttttgt gatgctcgtc aggggggcgg agcctatgga   4560
aaatcgattc cggaaacgcc aggctcttcc aacgcggcct tttacggtt gaagagccct    4620
ggccttttgc tggccttttg ct                                            4642
```

```
<210> SEQ ID NO 246
<211> LENGTH: 1261
<212> TYPE: DNA
<213> ORGANISM: Artificial Sequence
<220> FEATURE:
<223> OTHER INFORMATION: ASD gene orf + 85 bp upstream

<400> SEQUENCE: 246
```

```
ctgtcagacc aagtttactc atatatactt tagattgatt taaaacttca tttttaattt     60
aaaaggatct aggtgaagat cctttatggt gaaggatgcg ccacaggata ctggcgcgca    120
tacacagcac atctctttgc aggaaaaaaa cgctatgaaa aatgttggtt ttatcggctg    180
gcgcggaatg gtcggctctg ttctcatgca acgcatggta gaggagcgcg atttcgacgc    240
tattcgccct gttttctttt ctacctccca gtttggacag gcggcgccca ccttcggcga    300
cacctccacc ggcacgctac aggacgcttt tgatctggat gcgctaaaag cgctcgatat    360
```

catcgtgacc tgccagggcg gcgattatac caacgaaatt tatccaaagc tgcgcgaaag 420
cggatggcag ggttactgga ttgatgcggc ttctacgctg cgcatgaaag atgatgccat 480
tattattctc gacccggtca accaggacgt gattaccgac ggcctgaaca atggcgtgaa 540
gacctttgtg ggcggtaact gtaccgttag cctgatgttg atgtcgctgg gcggtctctt 600
tgcccataat ctcgttgact gggtatccgt cgcgacctat caggccgcct ccggcggcgg 660
cgcgcgccat atgcgcgagc tgttaaccca gatgggtcag ttgtatggcc atgtcgccga 720
tgaactggcg acgccgtctt ccgcaattct tgatattgaa cgcaaagtta cggcattgac 780
ccgcagcggc gagctgccgg ttgataactt tggcgtaccg ctggcgggaa gcctgatccc 840
ctggatcgac aaacagctcg ataacggcca gagccgcgaa gagtggaaag gccaggcgga 900
aaccaacaag attctcaata ctgcctctgt gattccggtt gatggtttgt gtgtgcgcgt 960
cggcgcgctg cgctgtcaca gccaggcgtt caccatcaag ctgaaaaaag aggtatccat 1020
tccgacggtg gaagaactgc tggcggcaca taatccgtgg gcgaaagtgg tgccgaacga 1080
tcgtgatatc actatgcgcg aattaacccc ggcggcggtg accggcacgt tgactacgcc 1140
ggttggtcgt ctgcgtaagc tgaacatggg gccagagttc ttgtcggcgt ttaccgtagg 1200
cgaccagttg ttatggggcg ccgccgagcc gctgcgtcga atgctgcgcc agttggcgta 1260
g 1261

<210> SEQ ID NO 247
<211> LENGTH: 4112
<212> TYPE: DNA
<213> ORGANISM: Artificial Sequence
<220> FEATURE:
<223> OTHER INFORMATION: pATI2.0 synthetic v26 scramble pBR322ori.dna

<400> SEQUENCE: 247
accggtctgt ggaatgtgtg tcagttaggg tgtggaaagt ccccaggctc cccagcaggc 60
agaagtatgc aaagcatgca tctcaattag tcagcaacca accggtcttg cacctcagca 120
aaaggccatc cgtcaggatg gccttctgct tagtttgatg cctggcagtt tatggcgggc 180
gtcctgcccg ccaccctccg ggccgttgct tcacaacgtt caaatccgct cccggcggat 240
ttgtcctact caggagagcg ttcaccgaca aacaacagat aaaacgaaag gcccagtctt 300
ccgactgagc ctttcgtttt atttgggccg gccatgcctg gcagttccct actctcgcgt 360
taacgctagc atggatgttt tcccagtcac gacgttctta agctcgggcc cttaaaggaa 420
ccaattcagt cgagaattac tagtggtacc caggaagagg gcctatttcc catgattcct 480
tcatatttgc atatacgata caaggctgtt agagagataa ttagaattaa tttgactgta 540
aacacaaaga tattagtaca aaatacgtga cgtagaaagt aataatttct tgggtagttt 600
gcagttttaa aattatgttt taaaatggac tatcatatgc ttaccgtaac ttgaaagtat 660
ttcgatttct tggctttata tatcttgtgg aaaggacgaa actagcaaca agatgaagag 720
caccaattct agagattggt gctcttcatc ttgttgtttt tctcgagtag ctagagaatt 780
cgtcgacgga actccatata tgggctatga actaatgacc ccgtaattga ttactattaa 840
taactagcca tccagctgat atccgccggc gctgcagcta cgccaactgg cgcagcattc 900
gacgcagcgg ctcggcggcg ccccataaca actggtcgcc tacggtaaac gccgacaaga 960
actctggccc catgttcagc ttacgcagac gaccaaccgg cgtagtcaac gtgccggtca 1020
ccgccgccgg ggttaattcg cgcatagtga tatcacgatc gttcggcacc actttcgccc 1080

-continued acggattatg tgccgccagc agttcttcca ccgtcggaat ggatacctct tttttcagct 1140
tgatggtgaa cgcctggctg tgacagcgca gcgcgccgac gcgcacacac aaaccatcaa 1200
ccggaatcac agaggcagta ttgagaatct tgttggtttc cgcctggcct ttccactctt 1260
cgcggctctg gccgttatcg agctgtttgt cgatccaggg gatcaggctt cccgccagcg 1320
gtacgccaaa gttatcaacc ggcagctcgc cgctgcgggt caatgccgta actttgcgtt 1380
caatatcaag aattgcggaa gacggcgtcg ccagttcatc ggcgacatgg ccatacaact 1440
gacccatctg ggttaacagc tcgcgcatat ggcgcgcgcc gccgccggag gcggcctgat 1500
aggtcgcgac ggatacccag tcaacgagat tatgggcaaa gagaccgccc agcgacatca 1560
acatcaggct aacggtacag ttaccgccca caaaggtctt cacgccattg ttcaggccgt 1620
cggtaatcac gtcctggttg accgggtcga gaataataat ggcatcatct ttcatgcgca 1680
gcgtagaagc cgcatcaatc cagtaaccct gccatccgct ttcgcgcagc tttggataaa 1740
tttcgttggt ataatcgccg ccctggcagg tcacgatgat atcgagcgct tttagcgcat 1800
ccagatcaaa agcgtcctgt agcgtgccgg tggaggtgtc gccgaaggtg ggcgccgcct 1860
gtccaaactg ggaggtagaa aagaaaacag ggcgaatagc gtcgaaatcg cgctcctcta 1920
ccatgcgttg catgagaaca gagccgacca ttccgcgcca gccgataaaa ccaacatttt 1980
tcatagcgtt tttttcctgc aaagagatgt gctgtgtatg cgcgccagta tcctgtggcg 2040
catccttcac cataaaggat cttcacctag atccttttaa attaaaaatg aagttttaaa 2100
tcaatctaaa gtatatatga gtaaacttgg tctgacagtc tgcaggatat cccatgggca 2160
ttggcgcaga aaaaaatgcc tgatgcgacg ctgcgcgtct tatactccca catatgccag 2220
attcagcaac ggatacggct tccccaactt gcccacttcc atacgtgtcc tccttaccag 2280
aaatttatcc ttaaccatgg aagctttgca gctctggccc gtgtctcaaa atctctgatg 2340
ttacattgca caagataaaa atatatcatc atgaacaata aaactgtctg cttacataaa 2400
cagtaataca aggggtgtta tgagccatat tcaacgggaa acgtcgaggc cgcgattaaa 2460
ttccaacatg gatgctgatt tatatgggta taaatgggct cgcgataatg tcgggcaatc 2520
aggtgcgaca atctatcgct tgtatgggaa gcccgatgcg ccagagttgt ttctgaaaca 2580
tggcaaaggt agcgttgcca atgatgttac agatgagatg gtcagactaa actggctgac 2640
ggaatttatg cctcttccga ccatcaagca ttttatccgt actcctgatg atgcatggtt 2700
actcaccact gcgatccccg gaaaaacagc attccaggta ttagaagaat atcctgattc 2760
aggtgaaaat attgttgatg cgctggcagt gttcctgcgc cggttgcatt cgattcctgt 2820
ttgtaattgt ccttttaaca gcgatcgcgt atttcgtctc gctcaggcgc aatcacgaat 2880
gaataacggt ttggttgatg cgagtgattt tgatgacgag cgtaatggct ggcctgttga 2940
acaagtctgg aaagaaatgc ataaactttt gccattctca ccggattcag tcgtcactca 3000
tggtgatttc tcacttgata accttatttt tgacgagggg aaattaatag gttgtattga 3060
tgttggacga gtcggaatcg cagaccgata ccaggatctt gccatcctat ggaactgcct 3120
cggtgagttt tctccttcat tacagaaacg gctttttcaa aaatatggta ttgataatcc 3180
tgatatgaat aaattgcagt ttcatttgat gctcgatgag tttttctaaa gctttcagaa 3240
ttggttaatt ggttgtaaca ctggcagagc attacgctga cttgacggga cggcgcaagc 3300
tcatggatcc caattggcgg ccgcttaatt aaacatgtga gctcgatgta cattcgaagg 3360
accccaaaat cccttaacgt gagttacgcg tcgttccact gagcgtcaga ccccgtagaa 3420
aagatcaaag gatcttcatc gatttgagat cctttttttc tgcgcgtaat ctgctgcttg 3480

```
caaacaaaaa aaccaccgct accagcggtg gtttgtttgc cggatcaaga gctaccaact   3540

ctttttccga aggtaactgg cttcagcaga gcgcagatac caaatactgt ccttctagtg   3600

tagccgtagt taggccacca cttcaagaac tctgtagcac cgcctacata cctcgctctg   3660

ctaatcctgt taccagtggc tgctgccagt ggcgataagt cgtgtcttac cgggttggac   3720

tcaagacgat agttaccgga taaggcgcag cggtcgggct gaacgggggg ttcgtgcaca   3780

cagcccagct tggagcgaac gacctacacc gaactgagat acctacagcg tgagctatga   3840

gaaagcgcca cgcttcccga agggagaaag gcggacaggt atccggtaag cggcagggtc   3900

ggaacaggag agcgcacgag ggagcttcca gggggaaacg cctggtatct ttatagtcct   3960

gtcgggtttc gccacctctg acttgagcgt cgatttttgt gatgctcgtc aggggggcgg   4020

agcctatgga aaatcgattc cggaaacgcc aggctcttcc aacgcggcct ttttacggtt   4080

gaagagccct ggccttttgc tggccttttg ct                                 4112
```

<210> SEQ ID NO 248
<211> LENGTH: 165
<212> TYPE: DNA
<213> ORGANISM: Artificial Sequence
<220> FEATURE:
<223> OTHER INFORMATION: miR-16-2

<400> SEQUENCE: 248

```
ccggatcaac gccctaggtt tatgtttgga tgaactgaca tacttgttcc actctagcag     60

cacgtaaata ttggcgtagt gaaatatata ttaaacacca atattactgt gctgctttag    120

tgtgacaggg atacagcaac tattttatca attgtttgcg tcgac                    165
```

<210> SEQ ID NO 249
<211> LENGTH: 165
<212> TYPE: DNA
<213> ORGANISM: Artificial Sequence
<220> FEATURE:
<221> NAME/KEY: misc_feature
<222> LOCATION: (55)...(75)
<223> OTHER INFORMATION: n may be any nucleotide
<220> FEATURE:
<221> NAME/KEY: misc_feature
<222> LOCATION: (97)...(117)
<223> OTHER INFORMATION: n may be any nucleotide
<220> FEATURE:
<221> NAME/KEY: source
<222> LOCATION: (1)...(165)
<223> OTHER INFORMATION: microRNA backbone where Ns represent inserted
anti-sense and sense microRNAs

<400> SEQUENCE: 249

```
ccggatcaac gccctaggtt tatgtttgga tgaactgaca tacgcgtatc cgtcnnnnnn     60

nnnnnnnnnn nnnnngtagt gaaatatata ttaaacnnnn nnnnnnnnnn nnnnnnntac    120

ggtaacgcgg aattcgcaac tattttatca attttttgcg tcgac                    165
```

<210> SEQ ID NO 250
<211> LENGTH: 708
<212> TYPE: DNA
<213> ORGANISM: Salmonella typhimurium
<220> FEATURE:
<223> OTHER INFORMATION: endA

<400> SEQUENCE: 250

```
atgtaccgta atttctcttt tgccgctgtg ttgctggccg cagcgttttc aggccaggcc     60

ctggccgatg gcattaacaa tttttctcag gccaaagcgg cgagcgtcaa agtcaatgct    120
```

```
gacgcgcccg gcagctttta ctgcgggtgc caaatccgct ggcagggtaa aaaaggcgtc    180

gtagacctgg agtcctgcgg ctataaggtg cgtaaaaacg agaatcgcgc cagacgcatt    240

gagtgggagc acgttgtccc cgcctggcaa ttcggtcatc agcgccagtg ctggcaggac    300

ggcgggcgaa aaaactgcgc taaagacccg gtctaccgca aaatggaaag cgatatgcat    360

aacctgcaac ccgcgattgg cgaagtgaat ggcgatcgcg gcaactttat gtatagccag    420

tggaacggcg gcgaaggtca gtacgggcag tgcgccatga aagtagattt caaagcgaag    480

ctcgccgagc cgcccgcccg cgcccgtggc gcaatcgccc gcacttattt ttatatgcgc    540

gaccaatacc aactgaaact ttcccgccaa caaacgcagc tttttaacgt ctgggataag    600

cagtaccccg ttaccgcctg ggagtgcgag cgcgatgcgc gtatcgcgaa ggtccagggt    660

aatcataatc cctatgtgca acgcgcttgc caggcgcgaa agagctaa                 708
```

```
<210> SEQ ID NO 251
<211> LENGTH: 235
<212> TYPE: PRT
<213> ORGANISM: Salmonella typhimurium
<220> FEATURE:
<223> OTHER INFORMATION: endA

<400> SEQUENCE: 251

Met Tyr Arg Asn Phe Ser Phe Ala Ala Ala Leu Leu Ala Ala Ala Phe
1               5                   10                  15

Ser Gly Gln Ala Leu Ala Asp Gly Ile Asn Asn Phe Ser Gln Ala Lys
            20                  25                  30

Ala Ala Ser Val Lys Val Asn Ala Asp Ala Pro Gly Ser Phe Tyr Cys
        35                  40                  45

Gly Cys Gln Ile Arg Trp Gln Gly Lys Lys Gly Val Val Asp Leu Glu
    50                  55                  60

Ser Cys Gly Tyr Lys Val Arg Lys Asn Glu Asn Arg Ala Arg Arg Ile
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Ala Lys Asp Pro Val Tyr
            100                 105                 110

Arg Lys Met Glu Ser Asp Met His Asn Leu Gln Pro Ala Ile Gly Glu
        115                 120                 125

Val Asn Gly Asp Arg Gly Asn Phe Met Tyr Ser Gln Trp Asn Gly Gly
    130                 135                 140

Glu Gly Gln Tyr Gly Gln Cys Ala Met Lys Val Asp Phe Lys Ala Lys
145                 150                 155                 160

Ile Ala Glu Pro Pro Ala Arg Ala Arg Gly Ala Ile Ala Arg Ile Tyr
                165                 170                 175

Phe Tyr Met Arg Asp Gln Tyr Gln Leu Lys Leu Ser Arg Gln Gln Thr
            180                 185                 190

Gln Leu Phe Asn Val Trp Asp Lys Gln Tyr Pro Val Thr Ala Trp Glu
        195                 200                 205

Cys Glu Arg Asp Ala Arg Ile Ala Lys Val Gln Gly Asn His Asn Pro
    210                 215                 220

Tyr Val Gln Arg Ala Cys Gln Ala Arg Lys Ser
225                 230                 235


<210> SEQ ID NO 252
<211> LENGTH: 78
```

<212> TYPE: DNA
<213> ORGANISM: Homo sapiens
<220> FEATURE:
<223> OTHER INFORMATION: microRNA-103a1 (miR-103a1)

<400> SEQUENCE: 252
tactgccctc ggcttcttta cagtgctgcc ttgttgcata tggatcaagc agcattgtac 60
agggctatga aggcattg 78

<210> SEQ ID NO 253
<211> LENGTH: 71
<212> TYPE: DNA
<213> ORGANISM: Homo sapiens
<220> FEATURE:
<223> OTHER INFORMATION: microRNA-30a (miR-30a)

<400> SEQUENCE: 253
gcgactgtaa acatcctcga ctggaagctg tgaagccaca gatgggcttt cagtcggatg 60
tttgcagctg c 71

<210> SEQ ID NO 254
<211> LENGTH: 615
<212> TYPE: DNA
<213> ORGANISM: Artificial Sequence
<220> FEATURE:
<223> OTHER INFORMATION: pMB1 origin of replication

<400> SEQUENCE: 254
aaaggatctt cttgagatcc tttttttctg cgcgtaatct gctgcttgca aacaaaaaaa 60
ccaccgctac cagcggtggt ttgtttgccg gatcaagagc taccaactct ttttccgaag 120
gtaactggct tcagcagagc gcagatacca aatactgttc ttctagtgta gccgtagtta 180
ggccaccact tcaagaactc tgtagcaccg cctacatacc tcgctctgct aatcctgtta 240
ccagtggctg ctgccagtgg cgataagtcg tgtcttaccg ggttggactc aagacgatag 300
ttaccggata aggcgcagcg gtcgggctga acggggggtt cgtgcacaca gcccagcttg 360
gagcgaacga cctacaccga actgagatac ctacagcgtg agctatgaga aagcgccacg 420
cttcccgaag ggagaaaggc ggacaggtat ccggtaagcg gcagggtcgg aacaggagag 480
cgcacgaggg agcttccagg gggaaacgcc tggtatcttt atagtcctgt cgggtttcgc 540
cacctctgac ttgagcgtcg atttttgtga tgctcgtcag gggggcggag cctatggaaa 600
aacgccagca acgcg 615

<210> SEQ ID NO 255
<211> LENGTH: 913
<212> TYPE: DNA
<213> ORGANISM: Artificial Sequence
<220> FEATURE:
<223> OTHER INFORMATION: p15A origin of replication

<400> SEQUENCE: 255
gcgctagcgg agtgtatact ggcttactat gttggcactg atgagggtgt cagtgaagtg 60
cttcatgtgg caggagaaaa aaggctgcac cggtgcgtca gcagaatatg tgatacagga 120
tatattccgc ttcctcgctc actgactcgc tacgctcggt cgttcgactg cggcgagcgg 180
aaatggctta cgaacggggc ggagatttcc tggaagatgc caggaagata cttaacaggg 240
aagtgagagg gccgcggcaa agccgttttt ccataggctc cgcccccctg acaagcatca 300
cgaaatctga cgctcaaatc agtggtggcg aaacccgaca ggactataaa gataccaggc 360

```
gtttccccct ggcggctccc tcgtgcgctc tcctgttcct gcctttcggt ttaccggtgt    420

cattccgctg ttatggccgc gtttgtctca ttccacgcct gacactcagt tccgggtagg    480

cagttcgctc caagctggac tgtatgcacg aaccccccgt tcagtccgac cgctgcgcct    540

tatccggtaa ctatcgtctt gagtccaacc cggaaagaca tgcaaaagca ccactggcag    600

cagccactgg taattgattt agaggagtta gtcttgaagt catgcgccgg ttaaggctaa    660

actgaaagga caagttttgg tgactgcgct cctccaagcc agttacctcg gttcaaagag    720

ttggtagctc agagaacctt cgaaaaaccg ccctgcaagg cggttttttc gttttcagag    780

caagagatta cgcgcagacc aaaacgatct caagaagatc atcttattaa tcagataaaa    840

tatttctaga tttcagtgca atttatctct tcaaatgtag cacctgaagt cagccccata    900

cgatataagt tgt                                                       913
```

<210> SEQ ID NO 256
<211> LENGTH: 223
<212> TYPE: DNA
<213> ORGANISM: Artificial Sequence
<220> FEATURE:
<223> OTHER INFORMATION: pSC101 origin of replication

<400> SEQUENCE: 256

```
gagttataca cagggctggg atctattctt tttatctttt tttattcttt ctttattcta    60

taaattataa ccacttgaat ataaacaaaa aaaacacaca aaggtctagc ggaatttaca    120

gagggtctag cagaatttac aagttttcca gcaaaggtct agcagaattt acagataccc    180

acaactcaaa ggaaaaggac tagtaattat cattgactag ccc                      223
```

<210> SEQ ID NO 257
<211> LENGTH: 602
<212> TYPE: DNA
<213> ORGANISM: E. coli
<220> FEATURE:
<223> OTHER INFORMATION: ColE1 origin of replication

<400> SEQUENCE: 257

```
aggatcttct tgagatcctt tttttctgcg cgtaatctgc tgcttgcaaa caaaaaaacc    60

accgctacca acggtggttt gtttgccgga tcaagagcta ccaactcttt ttccgaaggt    120

aactggcttc agcagagcgc agataccaaa tactgtcctt ctagtgtagc cgtagtcggg    180

ccactacttc aagaactctg tagcaccgtt tgtgccatca tcgctctgct aatccggtta    240

ccagtggctg ctgccagtgg cgttaaggcg tgccttaccg ggttggactc aagacgatag    300

ttaccggata aggcgcagcg gtcgggctga acggggggtt cgtgcacaca gcccagcttg    360

gagcgaacga cctacaccga actgagatac aacagcgtg agctatgaga aagcgccacg    420

cttcccgaag ggagaaaggc ggacaggtat ccggtaagcg gcagggtcgg aacaggagag    480

cgcacgaggg agcttccagg gggaaacgcc tggtatcttt atagtcctgt cgggtttcgc    540

cacctctgac ttgagcgtct atttttgtga tgctcgtcag ggggcggag cctatggaaa    600

aa                                                                    602
```

<210> SEQ ID NO 258
<211> LENGTH: 201
<212> TYPE: DNA
<213> ORGANISM: Pseudomonas syringae
<220> FEATURE:
<223> OTHER INFORMATION: pPS10 origin of replication

<400> SEQUENCE: 258

```
acctgaccgg cgcggaagcg ctcttgatct ttttttcttg tttttacttg ttgttccttg     60

ttttcgtaat tttaactata tgatttataa gaaaaaaaag ggtttaaagg ggacagattc    120

agggtttaaa ggggacagat tcagggttta aaggggacag attcagggtt taaaggggac    180

agattcaggc tgatatccac a                                              201


<210> SEQ ID NO 259
<211> LENGTH: 617
<212> TYPE: DNA
<213> ORGANISM: E. coli
<220> FEATURE:
<223> OTHER INFORMATION: RK2 origin of replication

<400> SEQUENCE: 259

ccgggctggt tgccctcgcc gctgggctgg cggccgtcta tggccctgca aacgcgccag     60

aaacgccgtc gaagccgtgt gcgagacacc gcggccgccg gcgttgtgga taccacgcgg    120

aaaacttggc cctcactgac agatgagggg cggacgttga cacttgaggg gccgactcac    180

ccggcgcggc gttgacagat gaggggcagg ctcgatttcg gccggcgacg tggagctggc    240

cagcctcgca aatcggcgaa aacgcctgat tttacgcgag tttcccacag atgatgtgga    300

caagcctggg gataagtgcc ctgcggtatt gacacttgag gggcgcgact actgacagat    360

gaggggcgcg atccttgaca cttgaggggc agagtgatga cagatgaggg gcgcacctat    420

tgacatttga ggggctgtcc acaggcagaa aatccagcat ttgcaagggt ttccgcccgt    480

ttttcggcca ccgctaacct gtcttttaac ctgcttttaa accaatattt ataaaccttg    540

tttttaacca gggctgcgcc ctggcgcgtg accgcgcacg ccgaaggggg gtgccccccc    600

ttctcgaacc ctcccgg                                                   617


<210> SEQ ID NO 260
<211> LENGTH: 639
<212> TYPE: DNA
<213> ORGANISM: E. coli
<220> FEATURE:
<223> OTHER INFORMATION: R6K alpha origin of replication

<400> SEQUENCE: 260

tcttacttct ttgcgtagct gttaaataca gcgttgtttt gataaaatca tcattatcat     60

cgataatgct ttcttcaatt tttttatcct tactctttaa taaagcactt gctaataact    120

tcatacctt tgcaactgtc aaatttggtt catcagggta aatgctttta aggcatacta    180

acaaataatc atggtcttca tcttcaactc taaactgaat ttttttcatc ataactccca    240

acaagaaccg actgtaggtc accgggcaaa cgctgaaaaa taacgtcgaa tgacgtcatt    300

ttgcggcgtt tgccctatcc tgcatcgcag tagaaaatgc cacaactgaa attgtgcttc    360

agtatgtaca gaaatgcaaa atctgaggga tttcgtagct gaaagatcgc cagtcttcga    420

ccgtaaggat aggagttgct gtaagacctg tgcggggcgt tcgcttcgcg aacgggtctg    480

gcagggggca caagcgctgt gctgtgatat atgcaaaaga agccacccac gaacgggagg    540

gcttcggcga atcgactata gtgatctatt tacccggctg attgtcgcct tctagccctc    600

gcgggcatca tgcaaccagt gcctgaattt agttatatg                           639


<210> SEQ ID NO 261
<211> LENGTH: 1027
<212> TYPE: DNA
<213> ORGANISM: E. coli
<220> FEATURE:
```

<223> OTHER INFORMATION: R6K beta origin of replication

<400> SEQUENCE: 261
tgaagctttt tttatgaatt tatctgaagc tgatgcagct tttctcaagg tatttgatga 60
aaccgtacct cccaaaaaag ctaaggggtg atatatggct aaaatttacg atttccctca 120
aggagccgaa cgccgcagga tgcaccgcaa aatccagtgg aacaacgctg taaaattatc 180
taaaaatggc tggagtaagc cagaggttaa acgctggtct tttttagcat tcatctcaac 240
tggctggtat tactttcgcc tttcggtagc agtcattttc catatcatta ctatttgtgg 300
tttagctgtg ctcgcggcgt taagcaatac gatattctgg attggtggcg cgatatgtct 360
tgtaacctgg tatacaaatg accatcaaat ttggagtact aacaatctta ctatccctat 420
tgttttcgga ctttgggtgt taagtttagt agctgcacca ctcatagatt ttttcagtca 480
aaaattgccc ttttatcgtc ttcttgtgcc tgatgcgaag cgtgaggaag tgggcgaaga 540
tgattcttaa agccctgccc tgtacggctt taacgccttc tcgcggtaga tctatggatg 600
ttgagaatgt agtatggtta tactgcgatg caggataggg caaacgccgt aaaatgacgt 660
ctttgacgtt atttttcagc gcttgcccgg tgacctacag tcggtgcttg ttgggagatt 720
ttatgaagtt tactagtaaa ggattttatc agtgataaat atgcaaaggc tattaacatt 780
ttaaatgata accttaaaga aaactactat gtttttatg gtgtaaggtt aagtgaaatt 840
ctttttcctg caagtgatta tggtacagat gattttttta aggagtttga ggaaataaac 900
aacgttacct tgcctttagt tgtttttgaa ataaatgaac gtgaacctgt gattgtaatt 960
ggttttgatg aaataaatcc tgcgattctt atagagaaat ccggtataaa ggttttagta 1020
atcggac 1027

<210> SEQ ID NO 262
<211> LENGTH: 442
<212> TYPE: DNA
<213> ORGANISM: E. coli
<220> FEATURE:
<223> OTHER INFORMATION: R6K gamma origin of replication

<400> SEQUENCE: 262
gatcgctagt ttgttttgac tccatccatt agggcttcta aaacgccttc taaggccatg 60
tcagccgtta agtgttcctg tgtcactgaa aattgctttg agaggctcta agggcttctc 120
agtgcgttac atccctggct tgttgtccac aaccgttaaa ccttaaaagc tttaaaagcc 180
ttatatattc ttttttttct tataaaactt aaaaccttag aggctattta agttgctgat 240
ttatattaat tttattgttc aaacatgaga gcttagtacg tgaaacatga gagcttagta 300
cgttagccat gagagcttag tacgttagcc atgagggttt agttcgttaa acatgagagc 360
ttagtacgtt aaacatgaga gcttagtacg tgaaacatga gagcttagta cgtactatca 420
acaggttgaa ctgctgatct tc 442

<210> SEQ ID NO 263
<211> LENGTH: 242
<212> TYPE: DNA
<213> ORGANISM: Enterobacteria phage P1
<220> FEATURE:
<223> OTHER INFORMATION: P1 origin of plasmid replication oriR

<400> SEQUENCE: 263
tttcccgtca acacacatcc tatatcccgc cagcacacat tagcaacccg tcagcacaca 60
tttttatccc tccagcacac atcgttttcc ctccagcaca catcgcgata cacttctaag 120
ccagacgtgg cgcggcctgc aacgatcagg gatctatatg gatctaattg ggatctgtat 180
ggacctgatt attggatcta tccagtggat aatgtggata agtgaaaaac cggccaacgt 240
ag 242

<210> SEQ ID NO 264
<211> LENGTH: 792
<212> TYPE: DNA
<213> ORGANISM: Artificial Sequence
<220> FEATURE:
<223> OTHER INFORMATION: R1 origin of replication

<400> SEQUENCE: 264
ttatccacat ttaactgcaa gggacttccc cataaggtta caaccgttca tgtcataaag 60
cgccagccgc cagtcttaca gggtgcaatg tatcttttaa acacctgttt atatctcctt 120
taaactactt aattacattc atttaaaaag aaaacctatt cactgcctgt cctgtggaca 180
gacagatatg cacctcccac cgcaagcggc gggccccgac cggagccact ttagttacaa 240
cacacaaaaa caacctccag aaaaaccccg gtccagcgca gaaccgaaac cacaaagccc 300
ctccctcata actgaaaagc ggccccgccc cggcccaaag ggccggaaca gagtcgcttt 360
taattatgaa tgttgtaact acatcttcat cgctgtcagt cttctcgctg gaagttctca 420
gtacacgctc gtaagcggcc ctcacggccc gctaacgcgg agatacgccc cgacttcggg 480
taaaccctcg tcgggaccac tccgaccgcg cacagaagct ctctcatggc tgaaagcggg 540
tatggtctgg cagggctggg gatgggtaag gtgaaatcta tcaatcagta ccggcttacg 600
ccgggcttcg gcggttttac tcctgtatca tatgaaacaa cagagtgccg ccttccatgc 660
cgctgatgcg gcatatcctg gtaacgatat ctgaattgtt atacatgtgt atatacgtgg 720
taatgacaaa aataggacaa gttaaaaatt tacaggcgat gcaatgattc aaacacgtaa 780
tcaatatctg ca 792

<210> SEQ ID NO 265
<211> LENGTH: 2920
<212> TYPE: DNA
<213> ORGANISM: Artificial Sequence
<220> FEATURE:
<223> OTHER INFORMATION: pWSK origin of replication

<400> SEQUENCE: 265
ccgatgccct tgagagcctt caacccagtc agctccttcc ggtgggcgcg gggcatgact 60
atcgtcgccg cacttatgac tgtcttcttt atcatgcaac tcgtaggaca gggtgccggc 120
agcgctctgg gtcattttcg gcgaggaccg ctttcgctgg agcgcgacga tgatcggcct 180
gtcgcttgcg gtattcggaa tcttgcacgc cctcgctcaa gccttcgtca ctggtcccgc 240
caccaaacgt ttcggcgaga agcaggccat tatcgccggc atggcggccg acgcgctggg 300
ctacgtcttg ctggcgttcg cgacgcgagg ctggatggcc ttccccatta tgattcttct 360
cgcttccggc ggcatcggga tgcccgcgtt gcaggccatg ctgtccaggc aggtagatga 420
cgaccatcag ggacagcttc aaggatcgct cgcggctctt accagcctaa cttcgatcat 480
tggaccgctg atcgtcacgg cgatttatgc cgcctcggcg agcacatgga acgggttggc 540
atggattgta ggcgccgccc tataccttgt ctgcctcccc gcgttgcgtc gcggtgcatg 600
gagccgggcc acctcgacct gaatggaagc cggcggcacc tcgctaacgg attcaccact 660
ccgcagaccc gccataaaac gccctgagaa gcccgtgacg ggcttttctt gtattatggg 720

-continued

```
tagtttcctt gcatgaatcc ataaaaggcg cctgtagtgc catttacccc cattcactgc    780
cagagccgtg agcgcagcga actgaatgtc acgaaaaaga cagcgactca ggtgcctgat    840
ggtcggagac aaaaggaata ttcagcgatt tgcccgagct tgcgagggtg ctacttaagc    900
ctttagggtt ttaaggtctg ttttgtagag gagcaaacag cgtttgcgac atccttttgt    960
aatactgcgg aactgactaa agtagtgagt tatacacagg gctgggatct attcttttta   1020
tcttttttta ttctttcttt attctataaa ttataaccac ttgaatataa acaaaaaaaa   1080
cacacaaagg tctagcggaa tttacagagg gtctagcaga atttacaagt tttccagcaa   1140
aggtctagca gaatttacag atacccacaa ctcaaaggaa aaggactagt aattatcatt   1200
gactagccca tctcaattgg tatagtgatt aaaatcacct agaccaattg agatgtatgt   1260
ctgaattagt tgttttcaaa gcaaatgaac tagcgattag tcgctatgac ttaacggagc   1320
atgaaaccaa gctaatttta tgctgtgtgg cactactcaa ccccacgatt gaaaacccta   1380
caaggaaaga acggacggta tcgttcactt ataaccaata cgctcagatg atgaacatca   1440
gtagggaaaa tgcttatggt gtattagcta aagcaaccag agagctgatg acgagaactg   1500
tggaaatcag gaatcctttg gttaaaggct ttgagatttt ccagtggaca aactatgcca   1560
agttctcaag cgaaaaatta gaattagttt ttagtgaaga gatattgcct tatcttttcc   1620
agttaaaaaa attcataaaa tataatctgg aacatgttaa gtcttttgaa aacaaatact   1680
ctatgaggat ttatgagtgg ttattaaaag aactaacaca aaagaaaact cacaaggcaa   1740
atatagagat tagccttgat gaatttaagt tcatgttaat gcttgaaaat aactaccatg   1800
agtttaaaag gcttaaccaa tgggttttga aaccaataag taaagattta aacacttaca   1860
gcaatatgaa attggtggtt gataagcgag gccgcccgac tgatacgttg attttccaag   1920
ttgaactaga tagacaaatg gatctcgtaa ccgaacttga gaacaaccag ataaaaatga   1980
atggtgacaa aataccaaca accattacat cagattccta cctacataac ggactaagaa   2040
aaacactaca cgatgcttta actgcaaaaa ttcagctcac cagttttgag gcaaaatttt   2100
tgagtgacat gcaaagtaag tatgatctca atggttcgtt ctcatggctc acgcaaaaac   2160
aacgaaccac actagagaac atactggcta aatacggaag gatctgaggt tcttatggct   2220
cttgtatcta tcagtgaagc atcaagacta acaaacaaaa gtagaacaac tgttcaccgt   2280
tacatatcaa agggaaaact gtccatatgc acagatgaaa acggtgtaaa aaagatagat   2340
acatcagagc ttttacgagt ttttggtgca ttcaaagctg ttcaccatga acagatcgac   2400
aatgtaacag atgaacagca tgtaacacct aatagaacag gtgaaaccag taaaacaaag   2460
caactagaac atgaaattga acacctgaga caacttgtta cagctcaaca gtcacacata   2520
gacagcctga aacaggcgat gctgcttatc gaatcaaagc tgccgacaac acgggagcca   2580
gtgacgcctc ccgtggggaa aaaatcatgg caattctgga agaaatagcg ctttcagccg   2640
gcaaaccggc tgaagccgga tctgcgattc tgataacaaa ctagcaacac cagaacagcc   2700
cgtttgcggg cagcaaaacc cgtacttttg gacgttccgg cggttttttg tggcgagtgg   2760
tgttcgggcg gtgcgcgcaa gatccattat gttaaacggg cgagtttaca tctcaaaacc   2820
gcccgcttaa caccatcaga aatcctcagc gcgattttaa gcaccaaccc ccccccgtaa   2880
cacccaaatc catactgaaa gtggctttgt tgaataaatc                          2920
```

<210> SEQ ID NO 266
<211> LENGTH: 37
<212> TYPE: DNA
<213> ORGANISM: E. coli

```
<220> FEATURE:
<223> OTHER INFORMATION: ColE2 origin of replication

<400> SEQUENCE: 266

aaaatgagac cagataagcc ttatcagata acagcgc                              37


<210> SEQ ID NO 267
<211> LENGTH: 668
<212> TYPE: DNA
<213> ORGANISM: Artificial Sequence
<220> FEATURE:
<223> OTHER INFORMATION: pUC origin of replication

<400> SEQUENCE: 267

tgagcaaaag gccagcaaaa ggccaggaac cgtaaaaagg ccgcgttgct ggcgtttttc      60

cataggctcc gcccccctga cgagcatcac aaaaatcgac gctcaagtca gaggtggcga     120

aacccgacag gactataaag ataccaggcg tttccccctg gaagctccct cgtgcgctct     180

cctgttccga ccctgccgct taccggatac ctgtccgcct ttctcccttc gggaagcgtg     240

gcgctttctc atagctcacg ctgtaggtat ctcagttcgg tgtaggtcgt tcgctccaag     300

ctgggctgtg tgcacgaacc ccccgttcag cccgaccgct gcgccttatc cggtaactat     360

cgtcttgagt ccaacccggt aagacacgac ttatcgccac tggcagcagc cactggtaac     420

aggattagca gagcgaggta tgtaggcggt gctacagagt tcttgaagtg gtggcctaac     480

tacggctaca ctagaagaac agtatttggt atctgcgctc tgctgaagcc agttaccttc     540

ggaaaaagag ttggtagctc ttgatccggc aaacaaacca ccgctggtag cggtggtttt     600

tttgtttgca agcagcagat tacgcgcaga aaaaaaggat ctcaagaaga tcctttgatc     660

ttttctac                                                              668


<210> SEQ ID NO 268
<211> LENGTH: 457
<212> TYPE: DNA
<213> ORGANISM: Bacteriophage F1
<220> FEATURE:
<223> OTHER INFORMATION: F1 origin of replication

<400> SEQUENCE: 268

gacgcgccct gtagcggcgc attaagcgcg gcgggtgtgg tggttacgcg cagcgtgacc      60

gctacacttg ccagcgccct agcgcccgct cctttcgctt tcttcccttc ctttctcgcc     120

acgttcgccg gctttccccg tcaagctcta aatcgggggc tccctttagg gttccgattt     180

agtgctttac ggcacctcga ccccaaaaaa cttgattagg gtgatggttc acgtagtggg     240

ccatcgccct gatagacggt ttttcgccct ttgacgttgg agtccacgtt ctttaatagt     300

ggactcttgt tccaaactgg aacaacactc aaccctatct cggtctattc ttttgattta     360

taagggattt tgccgatttc ggcctattgg ttaaaaaatg agctgattta acaaaaattt     420

aacgcgaatt ttaacaaaat attaacgctt acaattt                              457
```